US012534734B2

(12) United States Patent
Erickson et al.

(10) Patent No.: US 12,534,734 B2
(45) Date of Patent: Jan. 27, 2026

(54) STEM-LOOP COMPOSITIONS AND METHODS FOR INHIBITING INTERLEUKIN-8

(71) Applicant: DRIVE THERAPEUTICS LLC, Chapel Hill, NC (US)

(72) Inventors: Carl Erickson, Corte Madera, CA (US); Christopher P. Rusconi, Durham, NC (US); Arijit Bhowmick, Astoria, NY (US); Matthew Levy, Cary, NC (US); Matthew Walker, Chapel Hill, NC (US); Kevin G. McLure, Oakland, CA (US)

(73) Assignee: DRIVE THERAPEUTICS LLC, Chapel Hill, NC (US)

( * ) Notice: Subject to any disclaimer, the term of this patent is extended or adjusted under 35 U.S.C. 154(b) by 1393 days.

(21) Appl. No.: 17/055,429

(22) PCT Filed: May 15, 2019

(86) PCT No.: PCT/US2019/032411
§ 371 (c)(1),
(2) Date: Nov. 13, 2020

(87) PCT Pub. No.: WO2019/222344
PCT Pub. Date: Nov. 21, 2019

(65) Prior Publication Data

US 2021/0230599 A1 Jul. 29, 2021

Related U.S. Application Data

(60) Provisional application No. 62/671,765, filed on May 15, 2018.

(51) Int. Cl.

| | |
|---|---|
| ***G01N 31/00*** | (2006.01) |
| ***A61K 31/7105*** | (2006.01) |
| ***A61K 45/06*** | (2006.01) |
| ***A61K 47/54*** | (2017.01) |
| ***A61K 47/60*** | (2017.01) |
| ***A61P 27/02*** | (2006.01) |
| ***C12N 15/115*** | (2010.01) |
| ***G01N 33/53*** | (2006.01) |

(52) U.S. Cl.
CPC ........ *C12N 15/115* (2013.01); *A61K 31/7105* (2013.01); *A61K 45/06* (2013.01); *A61K 47/549* (2017.08); *A61K 47/60* (2017.08); *A61P 27/02* (2018.01); *C12N 2310/16* (2013.01); *C12N 2310/321* (2013.01); *C12N 2310/351* (2013.01); *C12N 2310/531* (2013.01); *C12N 2320/31* (2013.01)

(58) Field of Classification Search
None
See application file for complete search history.

(56) References Cited

U.S. PATENT DOCUMENTS

| | | | | |
|---|---|---|---|---|
| 7,709,616 | B2 * | 5/2010 | Bentwich | C12Q 1/6876 435/375 |
| 7,795,419 | B2 * | 9/2010 | Bentwich | C12Q 1/701 536/24.32 |
| 9,328,346 | B2 * | 5/2016 | Lee | A61P 29/00 |
| 9,958,448 | B2 * | 5/2018 | Halbert | C12N 15/115 |
| 10,669,337 | B2 * | 6/2020 | Irving | A61K 39/395 |
| 11,472,889 | B2 * | 10/2022 | Boustany | C07K 16/2809 |
| 11,512,113 | B2 * | 11/2022 | Campbell | C07K 16/2863 |
| 11,859,010 | B2 * | 1/2024 | Boustany | C12N 15/62 |

FOREIGN PATENT DOCUMENTS

| | | | | |
|---|---|---|---|---|
| WO | WO-2014080997 | A1 * | 5/2014 | A61K 47/549 |
| WO | 2014137141 | A1 | 9/2014 | |
| WO | 2016029139 | A1 | 2/2016 | |
| WO | 2017139417 | A1 | 8/2017 | |

OTHER PUBLICATIONS

Sung, H. J., et al., "Inhibition of human neutrophil activity by an RNA aptamer bound to interleukin-8", Biomaterials, 2014, vol. 35, pp. 578-589. (Year: 2014).*
Sung, H.J. et al., ("Inhibition of human neutrophil activity by an RNA aptamer bound to interleukin-8", Biomaterials, 2014, vol. 35, pp. 578-589—IDS dated Nov. 13, 2020) (Year: 2014).*
Zhang, W. et al., ("A dual-functional microfluidic chip for on-line detection of interleukin-8 based on rolling circle amplification", Biosensors and Bioelectronics, Apr. 15, 2018, vol. 102, pp. 652-660—IDS dated Nov. 13, 2020) (Year: 2018).*
International Search Report issued for PCT/US2019/032411 dated Aug. 27, 2019, 5 pages.
Kozlov, D. G., et al., "The Use of SELEX Procedure for the Preparation of Single—Stranded DNA Aptamers Specifically Interacting with Human Recombinant Interleukin-8", Biotechnology in Russia, 2002, No. 4, pp. 38-47.

(Continued)

*Primary Examiner* — Lisa V Cook
(74) *Attorney, Agent, or Firm* — Rothwell, Figg, Ernst & Manbeck, P.C.

(57) ABSTRACT

The application discloses methods and compositions for inhibiting functions associated with Interleukin-8 (IL8). The methods and compositions may involve the use of aptamers for binding to IL8 and preventing or reducing association of IL8 with CXCR1, CXCR2, or both. The methods and compositions may include one or more aptamers that bind to an N-terminal domain of IL8. The methods and compositions may include one or more aptamers that bind to a hydrophobic pocket of IL8. The methods and compositions may include one or more aptamers that bind to an N-loop of IL8. The methods and compositions may include one or more aptamers that bind to a GAG binding site of IL8. The application further provides anti-IL8 aptamers for the treatment of ocular diseases or disorders. In some cases, the anti-IL8 aptamers may have a stem-loop secondary structure.

11 Claims, 45 Drawing Sheets

Specification includes a Sequence Listing.

(56) References Cited

OTHER PUBLICATIONS

Sung, H. J., et al., "Inhibition of human neutrophil activity by an RNA aptamer bound to interleukin-8", Biomaterials, 2014, vol. 35, pp. 578-589.

Zhang, W., et al., "A dual-functional microfluidic chip for on-line detection of interleukin-8 based on rolling circle amplification", Biosensors and Bioelectronics, Apr. 15, 2018, vol. 102, pp. 652-660.

* cited by examiner

FIG. 2A

TCTTAATACGACTCACTATA*GGGAGAGTCGGTAGCAGTCT*-N35-TCTATGTGGAAATGGCGCTGT

*GGGAGAGUCGGUAGCAGUCU*-N35-UCUAUGUGGAAAUGGCGCUGU

*ACAGCGCCATTTCCACATAG*

SEQ ID NO:81

FIG. 2B

| | | S1 | | | | L1 | S2 | | | | L2 | | S3 | | L3 | | | | | | | | | |
|---|---|---|---|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 |
| | U | G | A | U | G | A | C | G | G | U | A | G | A | U | U | A | C | G | G | G | U | A | G | A |
| A | 0.0% | 0.2% | 98.8% | 0.0% | 0.0% | 100.0% | 0.1% | 1.9% | 3.9% | 0.2% | 99.9% | 0.0% | 98.3% | 1.3% | 14.3% | 57.4% | 7.6% | 0.6% | 0.0% | 0.0% | 10.5% | 94.9% | 0.0% | 27.8% |
| C | 0.0% | 8.2% | 0.1% | 0.0% | 1.2% | 0.0% | 99.7% | 0.0% | 0.0% | 0.1% | 0.1% | 0.0% | 0.0% | 0.0% | 0.0% | 5.9% | 65.4% | 0.0% | 0.0% | 0.0% | 14.3% | 0.4% | 0.0% | 0.8% |
| G | 0.0% | 90.2% | 0.4% | 0.0% | 98.8% | 0.0% | 0.1% | 98.0% | 95.9% | 0.5% | 0.0% | 100.0% | 0.0% | 80.0% | 1.4% | 1.7% | 1.3% | 99.6% | 100.0% | 100.0% | 7.2% | 0.0% | 100.0% | 0.0% |
| U | 100.0% | 1.3% | 0.7% | 99.9% | 0.0% | 0.0% | 0.1% | 0.1% | 0.2% | 99.2% | 0.0% | 0.0% | 1.7% | 97.9% | 84.3% | 35.0% | 25.7% | 0.0% | 0.0% | 0.0% | 67.9% | 4.6% | 0.0% | 71.3% |

| | S3 | | L4 | S2 | | | | S1 | | | | |
|---|---|---|---|---|---|---|---|---|---|---|---|---|
| | 25 | 26 | 27 | 28 | 29 | 30 | 31 | 32 | 33 | 34 | 35 | 36 |
| | G | U | G | A | C | C | G | C | A | U | C | U |
| A | 0.0% | 0.0% | 0.0% | 99.8% | 0.2% | 0.1% | 0.1% | 0.0% | 99.9% | 0.6% | 1.5% | 0.4% |
| C | 0.0% | 0.0% | 0.0% | 0.0% | 95.9% | 97.9% | 0.1% | 98.8% | 0.0% | 0.4% | 90.1% | 0.0% |
| G | 100.0% | 0.0% | 100.0% | 0.1% | 0.0% | 0.0% | 99.7% | 1.2% | 0.0% | 0.1% | 8.0% | 0.1% |
| U | 0.0% | 100.0% | 0.0% | 0.2% | 3.9% | 2.1% | 0.1% | 0.0% | 0.0% | 98.9% | 0.4% | 99.5% |

FIG. 12

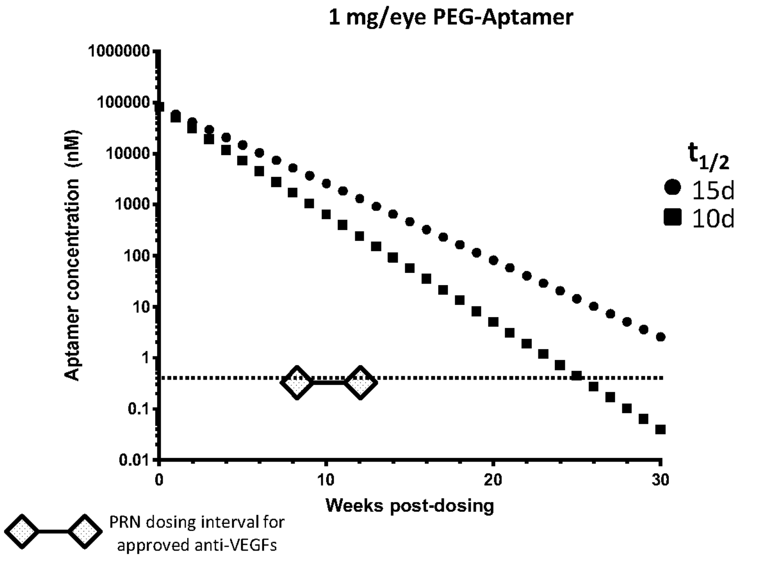

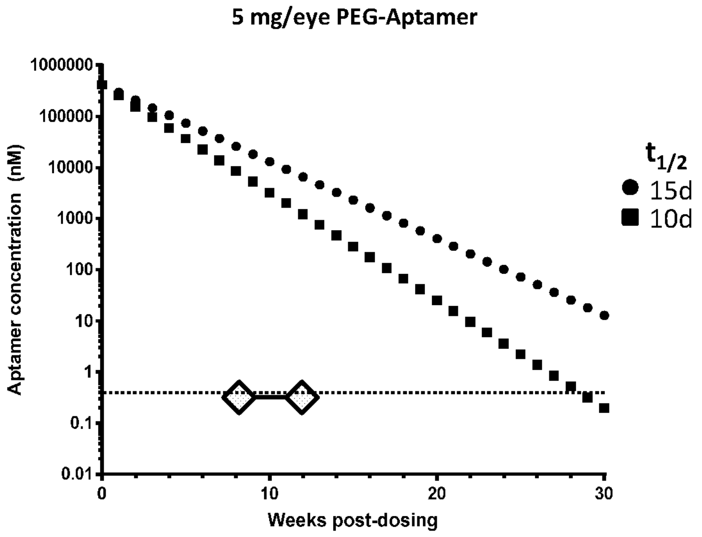

Assumptions

- Dosing based on MW of aptamer (-PEG) of 11,900 Da
- Vitreous volume = 4.5 mL
- Retina $C_{max}$ is half of vitreous,
- 10 day $t_{1/2}$ based on $t_{1/2}$ of Macugen in humans
- 15 day $t_{1/2}$ estimate based on performance of metabolically optimized candidate aptamers in 8 wk rabbit IVT PK studies

| Weeks to 90% Target Occupancy | | |
|---|---|---|
| Aptamer $K_d$ 20pM | 10 day $t_{1/2}$ | 15 day $t_{1/2}$ |
| 1mg/eye | 22.4 | 25 |
| 5mg/eye | 26.6 | 37.4 |

0.4 nM drug concentration provides 90% IL8 engagement when IL8 is 200 pM and inhibitor affinity is 20 pM

FIG. 29

| | STEM 1 | | | | | | LOOP L1 | | | | STEM S2 | | | | | LOOP S2 | | | | |
|---|---|---|---|---|---|---|---|---|---|---|---|---|---|---|---|---|---|---|---|---|
| position | **1** | 2 | 3 | 4 | 5 | 6 | **7** | 8 | 9 | 10 | **11** | 12 | 13 | 14 | 15 | **16** | 17 | 18 | 19 | 20 |
| | U | A | C | G | G | U | G | G | G | A | A | A | U | G | U | G | A | G | A | U |
| **A** | 0.8% | 95.7% | 0.2% | 0.2% | 3.3% | 0.2% | 0.0% | 0.0% | 0.0% | 100.0% | 99.7% | 100.0% | 4.2% | 0.0% | 1.3% | 0.0% | 100.0% | 0.0% | 100.0% | 4.8% |
| **C** | 1.6% | 0.0% | 99.7% | 0.1% | 2.2% | 6.0% | 0.0% | 0.0% | 0.0% | 0.0% | 0.0% | 0.0% | 2.9% | 0.0% | 2.1% | 0.0% | 0.0% | 0.0% | 0.0% | 5.6% |
| **G** | 0.7% | 3.7% | 0.0% | 99.0% | 93.7% | 0.0% | 100.0% | 100.0% | 100.0% | 0.0% | 0.3% | 0.0% | 0.2% | 100.0% | 0.6% | 100.0% | 0.0% | 100.0% | 0.0% | 0.0% |
| **U** | 96.9% | 0.7% | 0.1% | 0.7% | 0.7% | 93.8% | 0.0% | 0.0% | 0.0% | 0.0% | 0.0% | 0.0% | 92.7% | 0.0% | 96.1% | 0.0% | 0.0% | 0.0% | 0.0% | 89.6% |

| | STEM S2 | | | | | STEM S1 | | | | | | | | | | |
|---|---|---|---|---|---|---|---|---|---|---|---|---|---|---|---|---|
| position | **21** | 22 | 23 | 24 | 25 | **26** | 27 | 28 | 29 | 30 | 31 | 32 | 33 | 34 | 35 | 36 |
| | G | G | G | U | U | G | C | C | G | U | A | U | U | U | U | U |
| **A** | 0.0% | 0.0% | 0.0% | 0.0% | 0.1% | 4.4% | 0.7% | 0.7% | 0.1% | 0.3% | 93.8% | 7.2% | 4.6% | 3.4% | 0.0% | 0.0% |
| **C** | 0.0% | 0.0% | 0.0% | 0.0% | 0.0% | 0.0% | 93.5% | 99.0% | 0.0% | 2.2% | 0.5% | 12.9% | 5.2% | 6.0% | 0.2% | 1.9% |
| **G** | 100.0% | 100.0% | 100.0% | 0.0% | 0.2% | 95.4% | 2.2% | 0.1% | 99.7% | 0.1% | 4.0% | 1.0% | 3.4% | 4.8% | 0.0% | 0.0% |
| **U** | 0.0% | 0.0% | 0.0% | 100.0% | 99.4% | 0.2% | 3.6% | 0.2% | 0.2% | 97.4% | 1.7% | 79.0% | 86.7% | 85.8% | 99.8% | 98.1% |

FIG. 31

Loop L1

GGGA

Stem S1

UACGGU/GCCGUA  UACGGU/GCCGCA
UACGAU/GUCGUA  UACCGU/GCGGUA
UACGGC/GCCGUA  UACGGU/GUCGUA
UGCGGU/GCCGCA  UACGGC/GUCGUA
UACGCU/GGCGUA  UACGGC/GCCGUG
UACGGU/ACCGUA  UAUGGU/GCCAUA
UACGGU/GCCGUG  AACGGU/GCCGUU
CACGGU/GCCGUG  ACGGC/GCCGU
UGCGGU/GCCGUA  CACGAU/GUCGUG
UACUGU/GCAGUA  UGCGGU/GCCGCG
GACGGU/GCCGUC  UGCGGC/GCCGUA
ACGGU/GCCGU  UACGGU/ACCGUG
UACGUU/GACGUA  UACGAC/GUCGUA
UUCGGU/GCCGUA  UUCGGC/GCCGUA
UACGAU/AUCGUA  UGCGGU/ACCGCA
UUCGGU/GCCGAA  UACGGA/GCCGUA
UACAGU/GCUGUA  UGCGCU/GGCGUA
UGCGAU/GUCGCA  UACGCU/GCCGUA
UACGAU/GCCGUA  UAGGGU/GCCCUA
UACGUU/AACGUA  UGCGUU/GACGCA
UAAGGU/GCCUUA

Stem S2

AAUGU/GGGUU  AAUGG/GGGUU
AAAGU/GGGUU  AAUGU/GGGUG
AACGU/GGGUU  AAGGU/GGGUU
AAUGC/GGGUU  GAUGU/GGGUU
AAUGA/GGGUU  AAUGU/GGGUA

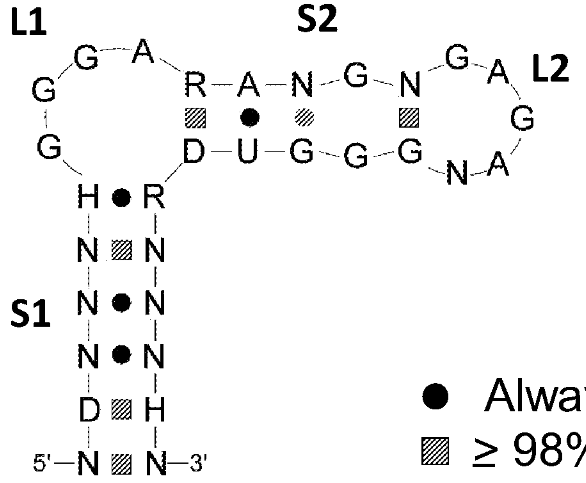

Loop L2

GAGAU
GAGAC
GAGAA
GAGAG

● Always paired
≥ 98% paired
≥ 96% paired

FIG. 32

SEQUENCE LISTING

<160> NUMBER OF SEQ ID NOS: 1313

<210> SEQ ID NO 1

<400> SEQUENCE: 1

000

<210> SEQ ID NO 2
<211> LENGTH: 72
<212> TYPE: PRT
<213> ORGANISM: Homo sapiens

<400> SEQUENCE: 2

```
Ser Ala Lys Glu Leu Arg Cys Gln Cys Ile Lys Thr Tyr Ser Lys Pro
1               5                   10                  15

Phe His Pro Lys Phe Ile Lys Glu Leu Arg Val Ile Glu Ser Gly Pro
            20                  25                  30

His Cys Ala Asn Thr Glu Ile Ile Val Lys Leu Ser Asp Gly Arg Glu
        35                  40                  45
```

```
Leu Cys Leu Asp Pro Lys Glu Asn Trp Val Gln Arg Val Val Glu Lys
    50                  55                  60

Phe Leu Lys Arg Ala Glu Asn Ser
65                  70


<210> SEQ ID NO 3
<211> LENGTH: 75
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3

gggagagucg guagcagucu agcggccgaa guuagcguac guuugccggg uacgucuaug     60

uggaaauggc gcugu                                                      75


<210> SEQ ID NO 4
<211> LENGTH: 75
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4

gggagagucg guagcagucu gaugacggua gauuacgggu agagugaccg caucucuaug     60

uggaaauggc gcugu                                                      75


<210> SEQ ID NO 5
<211> LENGTH: 75
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5

gggagagucg guagcagucu aauugcgguc uaccuugaau gacuugccgc ccauucuaug     60

uggaaauggc gcugu                                                      75


<210> SEQ ID NO 6
<211> LENGTH: 75
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6

gggagagucg guagcagucu cgugaagggc gauucuggug cguguucccu cgcgucuaug     60

uggaaauggc gcugu                                                      75


<210> SEQ ID NO 7
<211> LENGTH: 75
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7

gggagagucg guagcagucu caggcugaaa agugagcuau aauguccuga uugaucuaug     60
```

uggaaauggc gcugu 75

<210> SEQ ID NO 8
<211> LENGTH: 75
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 8
gggagagucg guagcagucu uauugcggcc cgauuuaccg aauuugccgu ccggucuaug 60
uggaaauggc gcugu 75

<210> SEQ ID NO 9
<211> LENGTH: 74
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 9
gggagagucg guagcagucu acggugggaa augugagaug gguugccgua uuuucuaugu 60
ggaaauggcg cugu 74

<210> SEQ ID NO 10
<211> LENGTH: 75
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 10
gggagagucg guagcagucu gccgacucac gaaauccucg cguagacugc cuuaucuaug 60
uggaaauggc gcugu 75

<210> SEQ ID NO 11
<211> LENGTH: 75
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 11
gggagagucg guagcagucu gaugauuugc ggcaauaccg uaccugccgc ccggucuaug 60
uggaaauggc gcugu 75

<210> SEQ ID NO 12
<211> LENGTH: 75
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 12
gggagagucg guagcagucu ccgguugcug agaugugaga uuaaugucca ccguucuaug 60
uggaaauggc gcugu 75

<210> SEQ ID NO 13
<211> LENGTH: 75
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 13
gggagagucg guagcagucu uggccacagu agauuucggu gcgugugacu gggcucuaug 60
uggaaauggc gcugu 75

<210> SEQ ID NO 14
<211> LENGTH: 75
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 14
gggagagucg guagcagucu cgcuuguacc ucugagaugu gagacuaaug uaggucuaug 60
uggaaauggc gcugu 75

<210> SEQ ID NO 15
<211> LENGTH: 75
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 15
gggagagucg guagcagucu gcggccuccg uugacuguug uaaugccggg acagucuaug 60
uggaaauggc gcugu 75

<210> SEQ ID NO 16
<211> LENGTH: 75
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 16
gggagagucg guagcagucu caguugcggc cccugauacc gauuugccgc ccggucuaug 60
uggaaauggc gcugu 75

<210> SEQ ID NO 17
<211> LENGTH: 75
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 17
gggagagucg guagcagucu gcuggcgacu cgcacggugu auuugucccg caccucuaug 60
uggaaauggc gcugu 75

<210> SEQ ID NO 18
<211> LENGTH: 74
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 18
gggagagucg guagcagucu ggaugacauu cgggggcacc aaucaucguc ugcucuaugu 60
ggaaauggcg cugu 74

<210> SEQ ID NO 19
<211> LENGTH: 75
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 19
gggagagucg guagcagucu gucgcccuac guaaaccgcu auuugcgacu gcggucuaug 60
uggaaauggc gcugu 75

<210> SEQ ID NO 20
<211> LENGTH: 75
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 20
gggagagucg guagcagucu gacugcgguc gcaaguuacg gauuugccgc cccgucuaug 60
uggaaauggc gcugu 75

<210> SEQ ID NO 21
<211> LENGTH: 75
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 21
gggagagucg guagcagucu uaagcgcuga gacgagagau uaaugccgcu ugccucuaug 60
uggaaauggc gcugu 75

<210> SEQ ID NO 22
<211> LENGTH: 75
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 22
gggagagucg guagcagucu cugaaucggc ugaaacggga gcauuaaugu ccggucuaug 60
uggaaauggc gcugu 75

<210> SEQ ID NO 23
<211> LENGTH: 74
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 23
gggagagucg guagcagucu uagcccugcc auuggggcau acuuuggccg cacucuaugu 60
ggaaauggcg cugu 74

<210> SEQ ID NO 24
<211> LENGTH: 75
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 24
gggagagucg guagcagucu ugcccuuuga ucguaccgag gcggggaagu acgaucuaug 60
uggaaauggc gcugu 75

<210> SEQ ID NO 25
<211> LENGTH: 75
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 25
gggagagucg guagcagucu caugguugc caaccggccg uguauguacg uacaucuaug 60
uggaaauggc gcugu 75

<210> SEQ ID NO 26
<211> LENGTH: 75
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 26
gggagagucg guagcagucu agcggccgaa guuagcguac guuugccggg uacgucuaug 60
uggaaauggc gcugu 75

<210> SEQ ID NO 27

<400> SEQUENCE: 27

000

<210> SEQ ID NO 28

<400> SEQUENCE: 28

000

<210> SEQ ID NO 29

<400> SEQUENCE: 29

000

<210> SEQ ID NO 30

<400> SEQUENCE: 30

000

<210> SEQ ID NO 31

<400> SEQUENCE: 31

000

<210> SEQ ID NO 32

<400> SEQUENCE: 32

000

<210> SEQ ID NO 33

<400> SEQUENCE: 33

000

<210> SEQ ID NO 34

<400> SEQUENCE: 34

000

<210> SEQ ID NO 35

<400> SEQUENCE: 35

000

<210> SEQ ID NO 36

<400> SEQUENCE: 36

000

<210> SEQ ID NO 37

<400> SEQUENCE: 37

000

<210> SEQ ID NO 38

<400> SEQUENCE: 38

000

<210> SEQ ID NO 39

<400> SEQUENCE: 39

000

<210> SEQ ID NO 40

<400> SEQUENCE: 40

000

<210> SEQ ID NO 41

<400> SEQUENCE: 41

000

<210> SEQ ID NO 42

-continued

<400> SEQUENCE: 42

000

<210> SEQ ID NO 43

<400> SEQUENCE: 43

000

<210> SEQ ID NO 44

<400> SEQUENCE: 44

000

<210> SEQ ID NO 45

<400> SEQUENCE: 45

000

<210> SEQ ID NO 46

<400> SEQUENCE: 46

000

<210> SEQ ID NO 47

<400> SEQUENCE: 47

000

<210> SEQ ID NO 48

<400> SEQUENCE: 48

000

<210> SEQ ID NO 49

<400> SEQUENCE: 49

000

<210> SEQ ID NO 50
<211> LENGTH: 37
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 50
uagcggccga aguuagcgua cguuugccgg guacgut 37

<210> SEQ ID NO 51
<211> LENGTH: 37
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:

<223> OTHER INFORMATION: Description of Combined DNA/RNA Molecule:
      Synthetic oligonucleotide

<400> SEQUENCE: 51
ugaugacggu agauuacggg uagagugacc gcaucut 37

<210> SEQ ID NO 52
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 52
uaauugcggu cuaccuugaa ugacuugccg cccauut 37

<210> SEQ ID NO 53
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 53
ucgugaaggg cgauucuggu gcguguuccc ucgcgut 37

<210> SEQ ID NO 54
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 54
ucaggcugaa aagugagcua uaauguccug auugaut 37

<210> SEQ ID NO 55
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 55
uuauugcggc ccgauuuacc gaauuugccg uccggut 37

<210> SEQ ID NO 56
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

```
<220> FEATURE:
<223> OTHER INFORMATION: Description of Combined DNA/RNA Molecule:
      Synthetic oligonucleotide

<400> SEQUENCE: 56

uacgguggga aaugugagau ggguugccgu auuuut                              36


<210> SEQ ID NO 57
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 57

ugccgacuca cgaaauccuc gcguagacug ccuuaut                             37


<210> SEQ ID NO 58
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 58

ugaugauuug cggcaauacc guaccugccg cccggut                             37


<210> SEQ ID NO 59
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 59

uccgguugcu gagaugugag auuaaugucc accguut                             37


<210> SEQ ID NO 60
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 60

uuggccacag uagauuucgg ugcgugugac ugggcut                             37


<210> SEQ ID NO 61
<211> LENGTH: 37
<212> TYPE: DNA
<213> ORGANISM: Artificial Sequence
<220> FEATURE:
<223> OTHER INFORMATION: Description of Artificial Sequence: Synthetic
```

oligonucleotide
<220> FEATURE:
<223> OTHER INFORMATION: Description of Combined DNA/RNA Molecule: Synthetic oligonucleotide

<400> SEQUENCE: 61
ucgcuuguac cucugagaug ugagacuaau guaggut 37

<210> SEQ ID NO 62
<211> LENGTH: 37
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 62
ugcggccucc guugacuguu guaaugccgg gacagut 37

<210> SEQ ID NO 63
<211> LENGTH: 37
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 63
ucaguugcgg ccccugauac cgauuugccg cccggut 37

<210> SEQ ID NO 64
<211> LENGTH: 37
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 64
ugcuggcgac ucgcacggug uauuugucccc gcaccut 37

<210> SEQ ID NO 65
<211> LENGTH: 36
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 65
uggaugacau ucgggggcac caaucaucgu cugcut 36

<210> SEQ ID NO 66
<211> LENGTH: 37
<212> TYPE: DNA
<213> ORGANISM: Artificial Sequence
<220> FEATURE:

<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 66
ugucgcccua cguaaaccgc uauuugcgac ugcggut 37

<210> SEQ ID NO 67
<211> LENGTH: 37
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 67
ugacugcggu cgcaaguuac ggauuugccg ccccgut 37

<210> SEQ ID NO 68
<211> LENGTH: 37
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 68
uuaagcgcug agacgagaga uuaaugccgc uugccut 37

<210> SEQ ID NO 69
<211> LENGTH: 37
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 69
ucugaaucgg cugaaacggg agcauuaaug uccggut 37

<210> SEQ ID NO 70
<211> LENGTH: 36
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 70
uuagcccugc cauuggggca uacuuuggcc gcacut 36

<210> SEQ ID NO 71
<211> LENGTH: 37
<212> TYPE: DNA
<213> ORGANISM: Artificial Sequence -continued
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 71
uugcccuuug aucguaccga ggcggggaag uacgaut 37

<210> SEQ ID NO 72
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 72 ucaugggguug ccaaccggcc guguauguac guacaut 37

<210> SEQ ID NO 73

<400> SEQUENCE: 73

000

<210> SEQ ID NO 74

<400> SEQUENCE: 74

000

<210> SEQ ID NO 75
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 75
gggggcuuau cauuccauuu aguguuauga uaacct 36

<210> SEQ ID NO 76

<400> SEQUENCE: 76

000

<210> SEQ ID NO 77

<400> SEQUENCE: 77

000

<210> SEQ ID NO 78

<400> SEQUENCE: 78

000

<210> SEQ ID NO 79

<400> SEQUENCE: 79

000

<210> SEQ ID NO 80

<400> SEQUENCE: 80

000

<210> SEQ ID NO 81
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 81
acagcgccat ttccacatag 20

<210> SEQ ID NO 82
<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 82
uacggguaga 10

<210> SEQ ID NO 83
<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 83
uacggguaga 10

<210> SEQ ID NO 84
<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 84
uacggguagu 10

<210> SEQ ID NO 85
<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (7)..(7)
<223> OTHER INFORMATION: a, c, u, g, unknown or other

<400> SEQUENCE: 85 uwyggkndga 10

<210> SEQ ID NO 86
<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (7)..(7)
<223> OTHER INFORMATION: a, c, u, g, unknown or other

<400> SEQUENCE: 86 uwyggkndgu 10

<210> SEQ ID NO 87
<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (2)..(3)
<223> OTHER INFORMATION: a, c, u, g, unknown or other
<220> FEATURE:
<221> NAME/KEY: modified_base
<222> LOCATION: (7)..(7)
<223> OTHER INFORMATION: a, c, u, g, unknown or other

<400> SEQUENCE: 87 dnnrggnwgh 10

<210> SEQ ID NO 88
<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (2)..(3)
<223> OTHER INFORMATION: a, c, u, g, unknown or other
<220> FEATURE:
<221> NAME/KEY: modified_base
<222> LOCATION: (7)..(7)
<223> OTHER INFORMATION: a, c, u, g, unknown or other

<400> SEQUENCE: 88 dnngggnwgh 10

<210> SEQ ID NO 89
<211> LENGTH: 34
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(2)
<223> OTHER INFORMATION: a, c, u, g, unknown or other
<220> FEATURE:
<221> NAME/KEY: modified_base
<222> LOCATION: (6)..(6)
<223> OTHER INFORMATION: a, c, u, g, unknown or other
<220> FEATURE:

<221> NAME/KEY: modified_base
<222> LOCATION: (9)..(9)
<223> OTHER INFORMATION: a, c, u, g, unknown or other
<220> FEATURE:
<221> NAME/KEY: modified_base
<222> LOCATION: (15)..(16)
<223> OTHER INFORMATION: a, c, u, g, unknown or other
<220> FEATURE:
<221> NAME/KEY: modified_base
<222> LOCATION: (20)..(20)
<223> OTHER INFORMATION: a, c, u, g, unknown or other
<220> FEATURE:
<221> NAME/KEY: modified_base
<222> LOCATION: (30)..(30)
<223> OTHER INFORMATION: a, c, u, g, unknown or other
<220> FEATURE:
<221> NAME/KEY: modified_base
<222> LOCATION: (33)..(34)
<223> OTHER INFORMATION: a, c, u, g, unknown or other

<400> SEQUENCE: 89
nnusanddna gwddnnrggn wghgugdhhn sann 34

<210> SEQ ID NO 90
<211> LENGTH: 34
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(2)
<223> OTHER INFORMATION: a, c, u, g, unknown or other
<220> FEATURE:
<221> NAME/KEY: modified_base
<222> LOCATION: (6)..(6)
<223> OTHER INFORMATION: a, c, u, g, unknown or other
<220> FEATURE:
<221> NAME/KEY: modified_base
<222> LOCATION: (9)..(9)
<223> OTHER INFORMATION: a, c, u, g, unknown or other
<220> FEATURE:
<221> NAME/KEY: modified_base
<222> LOCATION: (15)..(16)
<223> OTHER INFORMATION: a, c, u, g, unknown or other
<220> FEATURE:
<221> NAME/KEY: modified_base
<222> LOCATION: (20)..(20)
<223> OTHER INFORMATION: a, c, u, g, unknown or other
<220> FEATURE:
<221> NAME/KEY: modified_base
<222> LOCATION: (30)..(30)
<223> OTHER INFORMATION: a, c, u, g, unknown or other
<220> FEATURE:
<221> NAME/KEY: modified_base
<222> LOCATION: (33)..(34)
<223> OTHER INFORMATION: a, c, u, g, unknown or other

<400> SEQUENCE: 90
nnusanddna gwddnngggn wghgugdhhn sann 34

<210> SEQ ID NO 91
<211> LENGTH: 33
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(2)
<223> OTHER INFORMATION: a, c, u, g, unknown or other
<220> FEATURE:
<221> NAME/KEY: modified_base
<222> LOCATION: (6)..(6)
<223> OTHER INFORMATION: a, c, u, g, unknown or other
<220> FEATURE:
<221> NAME/KEY: modified_base
<222> LOCATION: (9)..(9)
<223> OTHER INFORMATION: a, c, u, g, unknown or other
<220> FEATURE:
<221> NAME/KEY: modified_base
<222> LOCATION: (15)..(15)
<223> OTHER INFORMATION: a, c, u, g, unknown or other
<220> FEATURE:
<221> NAME/KEY: modified_base
<222> LOCATION: (19)..(19)
<223> OTHER INFORMATION: a, c, u, g, unknown or other
<220> FEATURE:
<221> NAME/KEY: modified_base
<222> LOCATION: (29)..(29)
<223> OTHER INFORMATION: a, c, u, g, unknown or other
<220> FEATURE:
<221> NAME/KEY: modified_base
<222> LOCATION: (32)..(33)
<223> OTHER INFORMATION: a, c, u, g, unknown or other

<400> SEQUENCE: 91
nnusanddna gwdhngggna gwgugdhhns ann 33

<210> SEQ ID NO 92
<211> LENGTH: 34
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(2)
<223> OTHER INFORMATION: a, c, u, g, unknown or other
<220> FEATURE:
<221> NAME/KEY: modified_base
<222> LOCATION: (6)..(6)
<223> OTHER INFORMATION: a, c, u, g, unknown or other
<220> FEATURE:
<221> NAME/KEY: modified_base
<222> LOCATION: (9)..(9)
<223> OTHER INFORMATION: a, c, u, g, unknown or other
<220> FEATURE:
<221> NAME/KEY: modified_base
<222> LOCATION: (15)..(16)
<223> OTHER INFORMATION: a, c, u, g, unknown or other
<220> FEATURE:
<221> NAME/KEY: modified_base
<222> LOCATION: (20)..(21)
<223> OTHER INFORMATION: a, c, u, g, unknown or other
<220> FEATURE:
<221> NAME/KEY: modified_base
<222> LOCATION: (27)..(27)
<223> OTHER INFORMATION: a, c, u, g, unknown or other
<220> FEATURE:
<221> NAME/KEY: modified_base
<222> LOCATION: (30)..(30)
<223> OTHER INFORMATION: a, c, u, g, unknown or other
<220> FEATURE:
<221> NAME/KEY: modified_base
<222> LOCATION: (33)..(34)
<223> OTHER INFORMATION: a, c, u, g, unknown or other

<400> SEQUENCE: 92
nnyvanddnw gwddnnrgkn nghgugnhhn vrnn 34

<210> SEQ ID NO 93
<211> LENGTH: 31
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (2)..(6)
<223> OTHER INFORMATION: a, c, u, g, unknown or other
<220> FEATURE:
<221> NAME/KEY: modified_base
<222> LOCATION: (13)..(13)
<223> OTHER INFORMATION: a, c, u, g, unknown or other
<220> FEATURE:
<221> NAME/KEY: modified_base
<222> LOCATION: (15)..(15)
<223> OTHER INFORMATION: a, c, u, g, unknown or other
<220> FEATURE:
<221> NAME/KEY: modified_base
<222> LOCATION: (20)..(20)
<223> OTHER INFORMATION: a, c, u, g, unknown or other
<220> FEATURE:
<221> NAME/KEY: modified_base
<222> LOCATION: (26)..(31)
<223> OTHER INFORMATION: a, c, u, g, unknown or other

<400> SEQUENCE: 93
hnnnnngggd ddngngdgdn ggguknnnnn n 31

<210> SEQ ID NO 94
<211> LENGTH: 32
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (2)..(6)
<223> OTHER INFORMATION: a, c, u, g, unknown or other
<220> FEATURE:
<221> NAME/KEY: modified_base
<222> LOCATION: (14)..(14)
<223> OTHER INFORMATION: a, c, u, g, unknown or other
<220> FEATURE:
<221> NAME/KEY: modified_base
<222> LOCATION: (16)..(16)
<223> OTHER INFORMATION: a, c, u, g, unknown or other
<220> FEATURE:
<221> NAME/KEY: modified_base
<222> LOCATION: (21)..(21)
<223> OTHER INFORMATION: a, c, u, g, unknown or other
<220> FEATURE:
<221> NAME/KEY: modified_base
<222> LOCATION: (27)..(32)
<223> OTHER INFORMATION: a, c, u, g, unknown or other

<400> SEQUENCE: 94
hnnnnncggg addngngdgd ngggguknnnn nn 32

<210> SEQ ID NO 95
<211> LENGTH: 31
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(1)
<223> OTHER INFORMATION: a, c, u, g, unknown or other
<220> FEATURE:
<221> NAME/KEY: modified_base
<222> LOCATION: (3)..(5)
<223> OTHER INFORMATION: a, c, u, g, unknown or other
<220> FEATURE:
<221> NAME/KEY: modified_base
<222> LOCATION: (13)..(13)
<223> OTHER INFORMATION: a, c, u, g, unknown or other
<220> FEATURE:
<221> NAME/KEY: modified_base
<222> LOCATION: (15)..(15)
<223> OTHER INFORMATION: a, c, u, g, unknown or other
<220> FEATURE:
<221> NAME/KEY: modified_base
<222> LOCATION: (20)..(20)
<223> OTHER INFORMATION: a, c, u, g, unknown or other
<220> FEATURE:
<221> NAME/KEY: modified_base
<222> LOCATION: (27)..(29)
<223> OTHER INFORMATION: a, c, u, g, unknown or other
<220> FEATURE:
<221> NAME/KEY: modified_base
<222> LOCATION: (31)..(31)
<223> OTHER INFORMATION: a, c, u, g, unknown or other

<400> SEQUENCE: 95
ndnnnhggga rangngagan gggudrnnnh n 31

<210> SEQ ID NO 96
<211> LENGTH: 31
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(6)
<223> OTHER INFORMATION: a, c, u, g, unknown or other
<220> FEATURE:
<221> NAME/KEY: modified_base
<222> LOCATION: (13)..(13)
<223> OTHER INFORMATION: a, c, u, g, unknown or other
<220> FEATURE:
<221> NAME/KEY: modified_base
<222> LOCATION: (15)..(15)
<223> OTHER INFORMATION: a, c, u, g, unknown or other
<220> FEATURE:
<221> NAME/KEY: modified_base
<222> LOCATION: (20)..(20)
<223> OTHER INFORMATION: a, c, u, g, unknown or other
<220> FEATURE:
<221> NAME/KEY: modified_base
<222> LOCATION: (26)..(31)
<223> OTHER INFORMATION: a, c, u, g, unknown or other

<400> SEQUENCE: 96
nnnnnngggd ddngngdgdn gggudnnnnn n 31

<210> SEQ ID NO 97
<211> LENGTH: 77
<212> TYPE: PRT
<213> ORGANISM: Homo sapiens

<400> SEQUENCE: 97

Ala Val Leu Pro Arg Ser Ala Lys Glu Leu Arg Cys Gln Cys Ile Lys
1 5 10 15

Thr Tyr Ser Lys Pro Phe His Pro Lys Phe Ile Lys Glu Leu Arg Val
20 25 30

Ile Glu Ser Gly Pro His Cys Ala Asn Thr Glu Ile Ile Val Lys Leu
35 40 45

Ser Asp Gly Arg Glu Leu Cys Leu Asp Pro Lys Glu Asn Trp Val Gln
50 55 60

Arg Val Val Glu Lys Phe Leu Lys Arg Ala Glu Asn Ser
65 70 75

<210> SEQ ID NO 98

<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 98
uagcggccga aguuagcgua cguuugccgg guacgu 36

<210> SEQ ID NO 99
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 99
ugaugacggu agauuacggg uagagugacc gcaucu 36

<210> SEQ ID NO 100
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 100
uaauugcggu cuaccuugaa ugacuugccg cccauu 36

<210> SEQ ID NO 101
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 101
ucgugaaggg cgauucuggu gcguguuccc ucgcgu 36

<210> SEQ ID NO 102
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 102
ucaggcugaa aagugagcua uaauguccug auugau 36

<210> SEQ ID NO 103
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 103
uuauugcggc ccgauuuacc gaauuugccg uccggu 36

<210> SEQ ID NO 104
<211> LENGTH: 35

<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 104 uacggauggga aaugugagau ggguugccgu auuuu 35

<210> SEQ ID NO 105
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 105
ugccgacuca cgaaauccuc gcguagacug ccuuau 36

<210> SEQ ID NO 106
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 106
ugaugauuug cggcaauacc guaccugccg cccggu 36

<210> SEQ ID NO 107
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 107
uccgguugcu gagaugugag auuaaugucc accguu 36

<210> SEQ ID NO 108
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 108
uuggccacag uagauuucgg ugcgugugac ugggcu 36

<210> SEQ ID NO 109
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 109
ucgcuuguac cucugagaug ugagacuaau guaggu 36

<210> SEQ ID NO 110
<211> LENGTH: 36
<212> TYPE: RNA

<213> ORGANISM: Artificial Sequence
<220> FEATURE:
<223> OTHER INFORMATION: Description of Artificial Sequence: Synthetic oligonucleotide

<400> SEQUENCE: 110
ugcggccucc guugacuguu guaaugccgg gacagu 36

<210> SEQ ID NO 111
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 111
ucaguugcgg ccccugauac cgauuugccg cccggu 36

<210> SEQ ID NO 112
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 112
ugcuggcgac ucgcacggug uauuuguccc gcaccu 36

<210> SEQ ID NO 113
<211> LENGTH: 35
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 113
uggaugacau ucgggggcac caaucaucgu cugcu 35

<210> SEQ ID NO 114
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 114
ugucgcccua cguaaaccgc uauuugcgac ugcggu 36

<210> SEQ ID NO 115
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 115
ugacugcggu cgcaaguuac ggauuugccg ccccgu 36

<210> SEQ ID NO 116
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 116
uuaagcgcug agacgagaga uuaaugccgc uugccu 36

<210> SEQ ID NO 117
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 117
ucugaaucgg cugaaacggg agcauuaaug uccggu 36

<210> SEQ ID NO 118
<211> LENGTH: 35
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 118
uuagcccugc cauuggggca uacuuuggcc gcacu 35

<210> SEQ ID NO 119
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 119
uugcccuuug aucguaccga ggcggggaag uacgau 36

<210> SEQ ID NO 120
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 120 ucaugggulug ccaaccggcc guguauguac guacau 36

<210> SEQ ID NO 121
<211> LENGTH: 74
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 121
gggagggcaa gagacagaug augacgguag auuucgggua gugugaccgc aucucuaugu 60
ggaaauggcg cugu 74

<210> SEQ ID NO 122
<211> LENGTH: 74
<212> TYPE: RNA

<213> ORGANISM: Artificial Sequence
<220> FEATURE:
<223> OTHER INFORMATION: Description of Artificial Sequence: Synthetic
      oligonucleotide

<400> SEQUENCE: 122
gggagggcaa gagacagaug augacgguag auuacgggua gugugaccgc aucucuaugu     60
ggaaauggcg cugu                                                       74

<210> SEQ ID NO 123
<211> LENGTH: 74
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 123
gggagggcaa gagacagaug augacgguag auuaugggua gugugaccgc aucucuaugu     60
ggaaauggcg cugu                                                       74

<210> SEQ ID NO 124
<211> LENGTH: 74
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 124
gggagggcaa gagacagaug augacgguag auuccgggua gugugaccgc aucucuaugu     60
ggaaauggcg cugu                                                       74

<210> SEQ ID NO 125
<211> LENGTH: 73
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 125
gggagggcaa gagacagaug augacgguag auuuggguag agugaccgca ucucuaugug     60
gaaauggcgc ugu                                                        73

<210> SEQ ID NO 126
<211> LENGTH: 74
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 126
gggagggcaa gagacagaug augacgguag auaacgggua gagugaccgc aucucuaugu     60
ggaaauggcg cugu                                                       74

<210> SEQ ID NO 127
<211> LENGTH: 74
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 127
gggagggcaa gagacagaug augacgguag auuaagggua gugugaccgc aucucuaugu 60
ggaaauggcg cugu 74

<210> SEQ ID NO 128
<211> LENGTH: 74
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 128
gggagggcaa gagacagaug augacgguag auuacgggaa gugugaccgc aucucuaugu 60
ggaaauggcg cugu 74

<210> SEQ ID NO 129
<211> LENGTH: 74
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 129
gggagggcaa gagacagaug augacgguag auuacgggaa gagugaccgc aucucuaugu 60
ggaaauggcg cugu 74

<210> SEQ ID NO 130
<211> LENGTH: 74
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 130
gggagggcaa gagacagaug augacgguag auaacgggua gugugaccgc aucucuaugu 60
ggaaauggcg cugu 74

<210> SEQ ID NO 131
<211> LENGTH: 74
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 131
gggagggcaa gagacagaug augacgguag auuacgggga gugugaccgc aucucuaugu 60
ggaaauggcg cugu 74

<210> SEQ ID NO 132
<211> LENGTH: 74
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 132
gggagggcaa gagacagaug augacgguag auuucgggaa gugugaccgc aucucuaugu 60
ggaaauggcg cugu 74

<210> SEQ ID NO 133
<211> LENGTH: 74
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 133
gggagggcaa gagacagaug augacgguag auuacgggca gugugaccgc aucucuaugu 60
ggaaauggcg cugu 74

<210> SEQ ID NO 134
<211> LENGTH: 74
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 134
gggagggcaa gagacagaug augacgguag auuaugggaa gugugaccgc aucucuaugu 60
ggaaauggcg cugu 74

<210> SEQ ID NO 135
<211> LENGTH: 74
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 135
gggagggcaa gagacagauc augacgguag auuucgggua gugugaccgc augucuaugu 60
ggaaauggcg cugu 74

<210> SEQ ID NO 136
<211> LENGTH: 74
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 136
gggagggcaa gagacagaug augacgguag auuaugggca gugugaccgc aucucuaugu 60
ggaaauggcg cugu 74

<210> SEQ ID NO 137
<211> LENGTH: 74
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 137
gggagggcaa gagacagauc augacgguag auuaugggua gugugaccgc augucuaugu 60
ggaaauggcg cugu 74

<210> SEQ ID NO 138
<211> LENGTH: 74
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 138
gggagggcaa gagacagaug augacgguag auuuugggua gugugaccgc aucucuaugu 60
ggaaauggcg cugu 74

<210> SEQ ID NO 139
<211> LENGTH: 74
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 139
gggagggcaa gagacagaug augacgguag auuacgggca gagugaccgc aucucuaugu 60
ggaaauggcg cugu 74

<210> SEQ ID NO 140
<211> LENGTH: 74
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 140
gggagggcaa gagacagaug augacgauag auuucgggua gugugaucgc aucucuaugu 60
ggaaauggcg cugu 74

<210> SEQ ID NO 141
<211> LENGTH: 74
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 141
gggagggcaa gagacagaug augacgguag auaucgggua gugugaccgc aucucuaugu 60
ggaaauggcg cugu 74

<210> SEQ ID NO 142
<211> LENGTH: 74
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 142
gggagggcaa gagacagaug augacgguag auaaugggua gugugaccgc aucucuaugu 60
ggaaauggcg cugu 74

<210> SEQ ID NO 143
<211> LENGTH: 74
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 143
gggagggcaa gagacagaug augacgguag auuucgggca gugugaccgc aucucuaugu 60
ggaaauggcg cugu 74

<210> SEQ ID NO 144
<211> LENGTH: 74
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 144
gggagggcaa gagacagaug augacgguag auuacggguu gugugaccgc aucucuaugu 60
ggaaauggcg cugu 74

<210> SEQ ID NO 145
<211> LENGTH: 74
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 145
gggagggcaa gagacagaug augacgguag auuucgggga gugugaccgc aucucuaugu 60
ggaaauggcg cugu 74

<210> SEQ ID NO 146
<211> LENGTH: 74
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 146
gggagggcaa gagacagaug augacaguag auuucgggua gugugacugc aucucuaugu 60
ggaaauggcg cugu 74

<210> SEQ ID NO 147
<211> LENGTH: 74
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 147
gggagggcaa gagacagaug augacgguag auuucggguu gugugaccgc aucucuaugu 60
ggaaauggcg cugu 74

<210> SEQ ID NO 148
<211> LENGTH: 74
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 148
gggagggcaa gagacagaug augacgguag auuaugggca gagugaccgc aucucuaugu 60
ggaaauggcg cugu 74

<210> SEQ ID NO 149
<211> LENGTH: 74
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 149
gggagggcaa gagacagaug augacgguag auuaagggua gagugaccgc aucucuaugu 60
ggaaauggcg cugu 74

<210> SEQ ID NO 150
<211> LENGTH: 74
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 150
gggagggcaa gagacagaug augacgguag auuucgggua gagugaccgc aucucuaugu 60
ggaaauggcg cugu 74

<210> SEQ ID NO 151
<211> LENGTH: 74
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 151
gggagggcaa gagacagaug augacgguag auuaagggca gugugaccgc aucucuaugu 60
ggaaauggcg cugu 74

<210> SEQ ID NO 152
<211> LENGTH: 74
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 152
gggagggcaa gagacagaug augacgguag auuacgggga gagugaccgc aucucuaugu 60
ggaaauggcg cugu 74

<210> SEQ ID NO 153
<211> LENGTH: 74
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 153
gggagggcaa gagacagauu augacgguag auuucgggua gugugaccgc auaucuaugu 60
ggaaauggcg cugu 74

<210> SEQ ID NO 154
<211> LENGTH: 74
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 154
gggagggcaa gagacagaug augacgguag auuauggguu gugugaccgc aucucuaugu 60
ggaaauggcg cugu 74

<210> SEQ ID NO 155
<211> LENGTH: 74
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 155
gggagggcaa gagacagaug augacgguag auaacgggaa gagugaccgc aucucuaugu 60
ggaaauggcg cugu 74

<210> SEQ ID NO 156
<211> LENGTH: 74
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 156
gggagggcaa gagacagaug augacgguag auuuagggua gugugaccgc aucucuaugu 60
ggaaauggcg cugu 74

<210> SEQ ID NO 157
<211> LENGTH: 74
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 157
gggagggcaa gagacagaug augacgguag auucugggua gugugaccgc aucucuaugu 60
ggaaauggcg cugu 74

<210> SEQ ID NO 158
<211> LENGTH: 74
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 158
gggagggcaa gagacagaug augacgguag auuaugggga gugugaccgc aucucuaugu 60
ggaaauggcg cugu 74

<210> SEQ ID NO 159

<211> LENGTH: 74
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 159
gggagggcaa gagacagaug augacgguag auuuugggua gagugaccgc aucucuaugu 60
ggaaauggcg cugu 74

<210> SEQ ID NO 160
<211> LENGTH: 74
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 160
gggagggcaa gagacagaug augacgguag auuaugggaa gagugaccgc aucucuaugu 60
ggaaauggcg cugu 74

<210> SEQ ID NO 161
<211> LENGTH: 73
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 161
gggagggcaa gagacagaug augacgguag auuagggaag ugugaccgca ucucuaugug 60
gaaauggcgc ugu 73

<210> SEQ ID NO 162
<211> LENGTH: 74
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 162
gggagggcaa gagacagaug aucacgguag auuaugggua gugugaccgg aucucuaugu 60
ggaaauggcg cugu 74

<210> SEQ ID NO 163
<211> LENGTH: 74
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 163
gggagggcaa gagacagaug augacgguag auuacggguu gagugaccgc aucucuaugu 60
ggaaauggcg cugu 74

<210> SEQ ID NO 164
<211> LENGTH: 74
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 164
gggagggcaa gagacagaug uugacgguag auuucgggua gugugaccgc aacucuaugu     60
ggaaauggcg cugu                                                       74

<210> SEQ ID NO 165
<211> LENGTH: 73
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 165
gggagggcaa gagacagaug augacgguag auaugggguag agugaccgca ucucuaugug     60
gaaauggcgc ugu                                                        73

<210> SEQ ID NO 166
<211> LENGTH: 73
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 166
gggagggcaa gagacagaug augacgguag auucgggaag ugugaccgca ucucuaugug     60
gaaauggcgc ugu                                                        73

<210> SEQ ID NO 167
<211> LENGTH: 74
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 167
gggagggcaa gagacagaug augacgauag auuaugggua gagugaucgc aucucuaugu     60
ggaaauggcg cugu                                                       74

<210> SEQ ID NO 168
<211> LENGTH: 73
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 168
gggagggcaa gagacagaug augacgguag aaucggguag ugugaccgca ucucuaugug     60
gaaauggcgc ugu                                                        73

<210> SEQ ID NO 169
<211> LENGTH: 74
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 169
gggagggcaa gagacagaug augacgguag auaacgggaa gugugaccgc aucucuaugu 60
ggaaauggcg cugu 74

<210> SEQ ID NO 170
<211> LENGTH: 74
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 170
gggagggcaa gagacagaug augacgguag auucagggua gugugaccgc aucucuaugu 60
ggaaauggcg cugu 74

<210> SEQ ID NO 171
<211> LENGTH: 74
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 171
gggagggcaa gagacagauc aucacgguag auuucgggua gugugaccgg augucuaugu 60
ggaaauggcg cugu 74

<210> SEQ ID NO 172
<211> LENGTH: 74
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 172
gggagggcaa gagacagauc augacgguag auaacgggca gagugaccgc augucuaugu 60
ggaaauggcg cugu 74

<210> SEQ ID NO 173
<211> LENGTH: 74
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 173
gggagggcaa gagacagaug augacgguag aguucgggua gugugaccgc aucucuaugu 60
ggaaauggcg cugu 74

<210> SEQ ID NO 174
<211> LENGTH: 73
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 174
gggagggcaa gagacagaug augacgguag auucggguag agugaccgca ucucuaugug 60
gaaauggcgc ugu 73

<210> SEQ ID NO 175
<211> LENGTH: 74
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 175
gggagggcaa gagacagaug augacgguag auaaagggua gugugaccgc aucucuaugu 60
ggaaauggcg cugu 74

<210> SEQ ID NO 176
<211> LENGTH: 74
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 176
gggagggcaa gagacagaug augacgguag auaacgggga gugugaccgc aucucuaugu 60
ggaaauggcg cugu 74

<210> SEQ ID NO 177
<211> LENGTH: 73
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 177
gggagggcaa gagacagauc augacgguag auaugggguag ugugaccgca ugucuaugug 60
gaaauggcgc ugu 73

<210> SEQ ID NO 178
<211> LENGTH: 74
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 178
gggagggcaa gagacagaug gugacgguag auuacgggua gagugaccgc accucuaugu 60
ggaaauggcg cugu 74

<210> SEQ ID NO 179
<211> LENGTH: 74
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 179
gggagggcaa gagacagaug augacgguag auugugggua gugugaccgc aucucuaugu 60
ggaaauggcg cugu 74

<210> SEQ ID NO 180
<211> LENGTH: 74

<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 180
gggagggcaa gagacagaug augacgguag auuaggggua gugugaccgc aucucuaugu 60
ggaaauggcg cugu 74

<210> SEQ ID NO 181
<211> LENGTH: 74
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 181
gggagggcaa gagacagaug augacgguag auuaugggua gcgugaccgc aucucuaugu 60
ggaaauggcg cugu 74

<210> SEQ ID NO 182
<211> LENGTH: 74
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 182
gggagggcaa gagacagaug augacggaag auuucgggua guguguccgc aucucuaugu 60
ggaaauggcg cugu 74

<210> SEQ ID NO 183
<211> LENGTH: 74
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 183
gggagggcaa gagacagaug augacgguag auaacgggca gugugaccgc aucucuaugu 60
ggaaauggcg cugu 74

<210> SEQ ID NO 184
<211> LENGTH: 73
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 184
gggagggcaa gagacagaug augacgguag uuucggguag ugugaccgca ucucuaugug 60
gaaauggcgc ugu 73

<210> SEQ ID NO 185
<211> LENGTH: 74
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 185
gggagggcaa gagacagaug augaugguag auuucgggua gugugaccac aucucuaugu 60
ggaaauggcg cugu 74

<210> SEQ ID NO 186
<211> LENGTH: 74
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 186
gggagggcaa gagacagaug augacgguag auuuugggca gugugaccgc aucucuaugu 60
ggaaauggcg cugu 74

<210> SEQ ID NO 187
<211> LENGTH: 74
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 187
gggagggcaa gagacagaug augacgguag auugcgggua gugugaccgc aucucuaugu 60
ggaaauggcg cugu 74

<210> SEQ ID NO 188
<211> LENGTH: 74
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 188
gggagggcaa gagacagaug augacgguag auuucgggga gagugaccgc aucucuaugu 60
ggaaauggcg cugu 74

<210> SEQ ID NO 189
<211> LENGTH: 74
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 189
gggagggcaa gagacagauc augacgguag auaaugggca gugugaccgc augucuaugu 60
ggaaauggcg cugu 74

<210> SEQ ID NO 190
<211> LENGTH: 74
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 190

-continued gggagggcaa gagacagaug augacgguag auuucgggua gcgugaccgc aucucuaugu 60
ggaaauggcg cugu 74

<210> SEQ ID NO 191
<211> LENGTH: 74
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 191
gggagggcaa gagacagaug augacgguag auaaugggaa gugugaccgc aucucuaugu 60
ggaaauggcg cugu 74

<210> SEQ ID NO 192
<211> LENGTH: 73
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 192
gggagggcaa gagacagaug augacgauag auuaggguag ugugaucgca ucucuaugug 60
gaaauggcgc ugu 73

<210> SEQ ID NO 193
<211> LENGTH: 73
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 193
gggagggcaa gagacagaug augacgguag auaugggaag ugugaccgca ucucuaugug 60
gaaauggcgc ugu 73

<210> SEQ ID NO 194
<211> LENGTH: 73
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 194
gggagggcaa gagacagaug augacgguag auuugggaag ugugaccgca ucucuaugug 60
gaaauggcgc ugu 73

<210> SEQ ID NO 195
<211> LENGTH: 73
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 195
gggagggcaa gagacagaug augacgguag auuagggcag agugaccgca ucucuaugug 60
gaaauggcgc ugu 73

<210> SEQ ID NO 196
<211> LENGTH: 73
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 196
gggagggcaa gagacagaug augacgguag auuggggu ag ugugaccgca ucucuaugug 60
gaaauggcgc ugu 73

<210> SEQ ID NO 197
<211> LENGTH: 74
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 197
gggagggcaa gagacagaug augacguuag auuacgggua gagugaacgc aucucuaugu 60
ggaaauggcg cugu 74

<210> SEQ ID NO 198
<211> LENGTH: 73
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 198
gggagggcaa gagacagaug augacgguag auucgggcag agugaccgca ucucuaugug 60
gaaauggcgc ugu 73

<210> SEQ ID NO 199
<211> LENGTH: 74
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 199
gggagggcaa gagacagaug augacgguag auuccgggca gugugaccgc aucucuaugu 60
ggaaauggcg cugu 74

<210> SEQ ID NO 200
<211> LENGTH: 74
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 200
gggagggcaa gagacagaug augacgguag auuccggguu gugugaccgc aucucuaugu 60
ggaaauggcg cugu 74

<210> SEQ ID NO 201
<211> LENGTH: 74
<212> TYPE: RNA

<213> ORGANISM: Artificial Sequence
<220> FEATURE:
<223> OTHER INFORMATION: Description of Artificial Sequence: Synthetic
oligonucleotide

<400> SEQUENCE: 201
gggagggcaa gagacagaug augacgguag augacgggua gagugaccgc aucucuaugu 60
ggaaauggcg cugu 74

<210> SEQ ID NO 202
<211> LENGTH: 73
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 202
gggagggcaa gagacagaug augacgguag aucaggguag ugugaccgca ucucuaugug 60
gaaauggcgc ugu 73

<210> SEQ ID NO 203
<211> LENGTH: 74
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 203
gggagggcaa gagacagaug augacgguag auugcgggua gagugaccgc aucucuaugu 60
ggaaauggcg cugu 74

<210> SEQ ID NO 204
<211> LENGTH: 74
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 204
gggagggcaa gagacagaug augaggguag auuucgggua gugugacccc aucucuaugu 60
ggaaauggcg cugu 74

<210> SEQ ID NO 205
<211> LENGTH: 73
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 205
gggagggcaa gagacagaug augacgguag auuaggggag ugugaccgca ucucuaugug 60
gaaauggcgc ugu 73

<210> SEQ ID NO 206
<211> LENGTH: 74
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 206
gggagggcaa gagacagaug augaagguag auuucgggua gugugaccuc aucucuaugu 60
ggaaauggcg cugu 74

<210> SEQ ID NO 207
<211> LENGTH: 74
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 207
gggagggcaa gagacagaug augacgguag auuaugggUu gagugaccgc aucucuaugu 60
ggaaauggcg cugu 74

<210> SEQ ID NO 208
<211> LENGTH: 74
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 208
gggagggcaa gagacagaug cugacgguag auuacgggua gagugaccgc agcucuaugu 60
ggaaauggcg cugu 74

<210> SEQ ID NO 209
<211> LENGTH: 74
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 209
gggagggcaa gagacagaug augacgguag auuaaggguu gugugaccgc aucucuaugu 60
ggaaauggcg cugu 74

<210> SEQ ID NO 210
<211> LENGTH: 74
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 210
gggagggcaa gagacagaug augacgguag augacgggua gugugaccgc aucucuaugu 60
ggaaauggcg cugu 74

<210> SEQ ID NO 211
<211> LENGTH: 74
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 211
gggagggcaa gagacagaug augacgguag augucgggua gugugaccgc aucucuaugu 60
ggaaauggcg cugu 74

<210> SEQ ID NO 212
<211> LENGTH: 74
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 212
gggagggcaa gagacagaug augacuguag auuucgggua gugugacagc aucucuaugu 60
ggaaauggcg cugu 74

<210> SEQ ID NO 213
<211> LENGTH: 74
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 213
gggagggcaa gagacagaug augacgguag auuuagggua gagugaccgc aucucuaugu 60
ggaaauggcg cugu 74

<210> SEQ ID NO 214
<211> LENGTH: 74
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 214
gggagggcaa gagacagaug augacggcag auuucgggua guguggccgc aucucuaugu 60
ggaaauggcg cugu 74

<210> SEQ ID NO 215
<211> LENGTH: 74
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 215
gggagggcaa gagacagaug augacgguag auuuggggua gugugaccgc aucucuaugu 60
ggaaauggcg cugu 74

<210> SEQ ID NO 216
<211> LENGTH: 74
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 216
gggagggcaa gagacagaug augacgguag auuucaggua gugugaccgc aucucuaugu 60
ggaaauggcg cugu 74

<210> SEQ ID NO 217
<211> LENGTH: 74
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 217
gggagggcaa gagacagaug augacgguag auuuugggca gagugaccgc aucucuaugu 60
ggaaauggcg cugu 74

<210> SEQ ID NO 218
<211> LENGTH: 74
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 218
gggagggcaa gagacagaug augacgguag auuacggggc gugugaccgc aucucuaugu 60
ggaaauggcg cugu 74

<210> SEQ ID NO 219
<211> LENGTH: 74
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 219
gggagggcaa gagacagaug augacgguag auaacgggga gagugaccgc aucucuaugu 60
ggaaauggcg cugu 74

<210> SEQ ID NO 220
<211> LENGTH: 74
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 220
gggagggcaa gagacagauc augacgguag auuaugggcu gugugaccgc augucuaugu 60
ggaaauggcg cugu 74

<210> SEQ ID NO 221
<211> LENGTH: 73
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 221
gggagggcaa gagacagaug augacgguag auacggguag agugaccgca ucucuaugug 60
gaaauggcgc ugu 73

<210> SEQ ID NO 222
<211> LENGTH: 74
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 222
gggagggcaa gagacagaug augacgguag auaacggguu gugugaccgc aucucuaugu 60
ggaaauggcg cugu 74

<210> SEQ ID NO 223
<211> LENGTH: 75
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 223
gggagagucg guagcagucu gaugacggua gauuaugggu agagugaccg caucucuaug 60
uggaaauggc gcugu 75

<210> SEQ ID NO 224
<211> LENGTH: 75
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 224
gggagagucg guagcagucu gaugacggua gauuacgggu agugugaccg caucucuaug 60
uggaaauggc gcugu 75

<210> SEQ ID NO 225
<211> LENGTH: 75
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 225
gggagagucg guagcagucu uaaacaaagg agauuucggu gcgugugccu uguuucuaug 60
uggaaauggc gcugu 75

<210> SEQ ID NO 226
<211> LENGTH: 76
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 226
gggagagucg guagcagucu cuaguuacgg gagauuaugg ugugugugcc cgaacucuau 60
guggaaaugg cgcugu 76

<210> SEQ ID NO 227
<211> LENGTH: 75
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 227
gggagagucg guagcagucu gaugacggua gauuaugggu agugugaccg caucucuaug 60
uggaaauggc gcugu 75

<210> SEQ ID NO 228
<211> LENGTH: 75
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 228
gggagagucg guagcagucu gaugacggua gauuacgggu ugagugaccg caucucuaug 60
uggaaauggc gcugu 75

<210> SEQ ID NO 229
<211> LENGTH: 75
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 229
gggagagucg guagcagucu gaugacggua gauuacgggu agagugaccg caucccuaug 60
uggaaauggc gcugu 75

<210> SEQ ID NO 230
<211> LENGTH: 75
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 230
gggagagucg guagcagucc gaugacggua gauuacgggu agagugaccg caucucuaug 60
uggaaauggc gcugu 75

<210> SEQ ID NO 231
<211> LENGTH: 75
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 231
gggagagucg guagcagucu uggccacagu agauuucggu gcgugugacu gggcccuaug 60
uggaaauggc gcugu 75

<210> SEQ ID NO 232
<211> LENGTH: 75
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 232
gggagagucg guagcagucu uggccacugu agauuucggu gcgugugacu gggcucuaug 60

-continued

```
uggaaauggc gcugu                                                        75


<210> SEQ ID NO 233
<211> LENGTH: 75
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 233

gggagagucg guagcagucu gaugacggua gauuacgggu agagugaccg caucgcuaug     60

uggaaauggc gcugu                                                      75


<210> SEQ ID NO 234
<211> LENGTH: 75
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 234

gggagagucg guagcagucu gaugacggua gauuacgggg agagugaccg caucucuaug     60

uggaaauggc gcugu                                                      75


<210> SEQ ID NO 235
<211> LENGTH: 75
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 235

gggagagucg guagcagucu gaugacggua gauuacgggu agagugaccg caucacuaug     60

uggaaauggc gcugu                                                      75


<210> SEQ ID NO 236
<211> LENGTH: 75
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 236

gggagagucg guagcagucu gggccacagu agauuucggu gcgugugacu gggcucuaug     60

uggaaauggc gcugu                                                      75


<210> SEQ ID NO 237
<211> LENGTH: 75
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 237

gggagagucg guagcagucu gaugacggua gauuucgggu agagugaccg caucucuaug     60

uggaaauggc gcugu                                                      75


<210> SEQ ID NO 238
```

<211> LENGTH: 75
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 238
gggagagucg guagcagucu gaugacggua gauuacgggc agagugaccg caucucuaug 60
uggaaauggc gcugu 75

<210> SEQ ID NO 239
<211> LENGTH: 75
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 239
gggagagucg guagcagucu ugaccacagu agauuucggu gcgugugacu gggcucuaug 60
uggaaauggc gcugu 75

<210> SEQ ID NO 240
<211> LENGTH: 75
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 240
gggagagucg guagcaguca gaugacggua gauuacgggu agagugaccg caucucuaug 60
uggaaauggc gcugu 75

<210> SEQ ID NO 241
<211> LENGTH: 75
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 241
gggagagucg guagcagucu gaugacggua gauuacgggu agagugaccg caccucuaug 60
uggaaauggc gcugu 75

<210> SEQ ID NO 242
<211> LENGTH: 75
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 242
gggagagucg guagcagucu uggccacagu agauuucggu gcgugugacg gggcucuaug 60
uggaaauggc gcugu 75

<210> SEQ ID NO 243
<211> LENGTH: 75
<212> TYPE: RNA
<213> ORGANISM: Artificial Sequence
<220> FEATURE:

<223> OTHER INFORMATION: Description of Artificial Sequence: Synthetic
oligonucleotide

<400> SEQUENCE: 243
gggagagucg guagcagucu uggccacagu agauuucggu gugugugacu gggcucuaug 60
uggaaauggc gcugu 75

<210> SEQ ID NO 244
<211> LENGTH: 75
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 244
gggagagucg guagcagucu uggccacagu agauuucggu gcgugugacu ggguucuaug 60
uggaaauggc gcugu 75

<210> SEQ ID NO 245
<211> LENGTH: 75
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 245
gggagagucg guagcagucu uggccacggu agauuucggu gcgugugacu gggcucuaug 60
uggaaauggc gcugu 75

<210> SEQ ID NO 246
<211> LENGTH: 75
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 246
gggagagucg guagcagucu gaugacggua gauuacgggu agagugacug caucucuaug 60
uggaaauggc gcugu 75

<210> SEQ ID NO 247
<211> LENGTH: 75
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 247
gggagagucg guagcagucu gaugacggua gauaacgggu agagugaccg caucucuaug 60
uggaaauggc gcugu 75

<210> SEQ ID NO 248
<211> LENGTH: 75
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 248
gggagagucg guagcagucu gaugacgguu gauuacgggu agagugaccg caucucuaug 60
uggaaauggc gcugu 75

<210> SEQ ID NO 249
<211> LENGTH: 75
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 249
gggagagucg guagcagucu gaugacggua gauuacgggu agaguggccg caucucuaug 60
uggaaauggc gcugu 75

<210> SEQ ID NO 250
<211> LENGTH: 75
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 250
gggagagucg guagcagucu gaugacggua guuuacgggu agagugaccg caucucuaug 60
uggaaauggc gcugu 75

<210> SEQ ID NO 251
<211> LENGTH: 75
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 251
gggagagucg guagcagucu gaugacggua gauuacggga agagugaccg caucucuaug 60
uggaaauggc gcugu 75

<210> SEQ ID NO 252
<211> LENGTH: 75
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 252
gggagagucg guagcagucu gacgacggua gauuacgggu agagugaccg caucucuaug 60
uggaaauggc gcugu 75

<210> SEQ ID NO 253
<211> LENGTH: 34
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 253
gaugacggua gauuacgggu agagugaccg cauc 34

-continued

<210> SEQ ID NO 254
<211> LENGTH: 33
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 254
gaugcgguag auuacgggua gagugaccgc auc 33

<210> SEQ ID NO 255
<211> LENGTH: 34
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 255
gaugucggua gauuacgggu agagugaccg cauc 34

<210> SEQ ID NO 256
<211> LENGTH: 32
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 256
gcgacgguag auuacgggua gagugaccgc gc 32

<210> SEQ ID NO 257
<211> LENGTH: 32
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 257
gcgacggcag auuacgggua gaguggccgc gc 32

<210> SEQ ID NO 258
<211> LENGTH: 30
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 258
gcgacguaga uuacggguag agugacgcgc 30

<210> SEQ ID NO 259
<211> LENGTH: 30
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 259
gcgacgcaga uuacggguag aguggcgcgc 30

<210> SEQ ID NO 260

<211> LENGTH: 11
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 260
cugaugacgg u 11

<210> SEQ ID NO 261
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 261
gauuacgggu agagugaccg caucu 25

<210> SEQ ID NO 262
<211> LENGTH: 11
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 262
ugaugacggu a 11

<210> SEQ ID NO 263
<211> LENGTH: 24
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 263
auuacgggua gagugaccgc aucu 24

<210> SEQ ID NO 264
<211> LENGTH: 12
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 264
ugaugacggu ag 12

<210> SEQ ID NO 265
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 265
uuacggguag agugaccgca ucu 23

<210> SEQ ID NO 266
<211> LENGTH: 13

<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 266
ugaugacggu aga 13

<210> SEQ ID NO 267
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 267
uacggguaga gugaccgcau cut 23

<210> SEQ ID NO 268
<211> LENGTH: 14
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 268
ugaugacggu agau 14

<210> SEQ ID NO 269
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 269
acggguagag ugaccgcauc u 21

<210> SEQ ID NO 270
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 270
ugaugacggu agauu 15

<210> SEQ ID NO 271
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 271
cggguagagu gaccgcaucu 20

-continued

<210> SEQ ID NO 272
<211> LENGTH: 16
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 272
ugaugacggu agauua 16

<210> SEQ ID NO 273
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 273
ggguagagug accgcaucu 19

<210> SEQ ID NO 274
<211> LENGTH: 17
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 274
ugaugacggu agauuac 17

<210> SEQ ID NO 275
<211> LENGTH: 18
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 275
gguagaguga ccgcaucu 18

<210> SEQ ID NO 276
<211> LENGTH: 18
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 276
ugaugacggu agauuacg 18

<210> SEQ ID NO 277
<211> LENGTH: 17
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 277
guagagugac cgcaucu 17

<210> SEQ ID NO 278

<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 278
ugaugacggu agauuacgg 19

<210> SEQ ID NO 279
<211> LENGTH: 16
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 279
uagagugacc gcaucu 16

<210> SEQ ID NO 280
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 280
ugaugacggu agauuacggg 20

<210> SEQ ID NO 281
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 281
agagugaccg caucu 15

<210> SEQ ID NO 282
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 282
ugaugacggu agauuacggg u 21

<210> SEQ ID NO 283
<211> LENGTH: 14
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 283
gagugaccgc aucu 14

<210> SEQ ID NO 284
<211> LENGTH: 22

<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 284
ugaugacggu agauuacggg ua 22

<210> SEQ ID NO 285
<211> LENGTH: 13
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 285
agugaccgca ucu 13

<210> SEQ ID NO 286
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 286
ugaugacggu agauuacggg uag 23

<210> SEQ ID NO 287
<211> LENGTH: 12
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 287
gugaccgcau cu 12

<210> SEQ ID NO 288
<211> LENGTH: 24
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 288
ugaugacggu agauuacggg uaga 24

<210> SEQ ID NO 289
<211> LENGTH: 11
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 289
ugaccgcauc u 11

<210> SEQ ID NO 290
<211> LENGTH: 25
<212> TYPE: RNA

<213> ORGANISM: Artificial Sequence
<220> FEATURE:
<223> OTHER INFORMATION: Description of Artificial Sequence: Synthetic
oligonucleotide

<400> SEQUENCE: 290
ugaugacggu agauuacggg uagag 25

<210> SEQ ID NO 291
<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 291
gaccgcaucu 10

<210> SEQ ID NO 292
<211> LENGTH: 26
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 292
ugaugacggu agauuacggg uagagu 26

<210> SEQ ID NO 293
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 293
gcgacgguag auuac 15

<210> SEQ ID NO 294
<211> LENGTH: 16
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 294
gguagaguga ccgcgc 16

<210> SEQ ID NO 295
<211> LENGTH: 34
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 295
ggcgacggua gacuacgggu agagugaccg cgcc 34

<210> SEQ ID NO 296
<211> LENGTH: 34
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 296
ggcgacggua gaucacgggu agggugaccg cgcc 34

<210> SEQ ID NO 297
<211> LENGTH: 34
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 297
ggcgacggua gauuacgggu agagugaccg cgcc 34

<210> SEQ ID NO 298
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 298
ugaugacggu agauuucggg uagugugacc gcaucu 36

<210> SEQ ID NO 299
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 299
ugaugacggu agauuccggg uagugugacc gcaucu 36

<210> SEQ ID NO 300
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 300
ugaugacggu agauuacggg cagugugacc gcaucu 36

<210> SEQ ID NO 301
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 301
ugaugacggu agauuacggg gagugugacc gcaucu 36

<210> SEQ ID NO 302
<211> LENGTH: 36
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 302
ugaugacggu agauuacggg aagugugacc gcaucu 36

<210> SEQ ID NO 303
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 303
ugaugacggu agauuauggg cagugugacc gcaucu 36

<210> SEQ ID NO 304
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 304
ugaugacggu agauuauggg aagugugacc gcaucu 36

<210> SEQ ID NO 305
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 305
ucaugacggu agauuucggg uagugugacc gcaugu 36

<210> SEQ ID NO 306
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 306
ucaugacggu agauuacggg uagagugacc gcaugu 36

<210> SEQ ID NO 307
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 307
ugaugacggu agauuacggg aagagugacc gcaucu 36

<210> SEQ ID NO 308
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 308
ugaugacggu agauuaaggg uagugugacc gcaucu 36

<210> SEQ ID NO 309
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 309
ugaugacggu agauuacggg uugugugacc gcaucu 36

<210> SEQ ID NO 310
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 310
ugaugacgau agauuucggg uagugugauc gcaucu 36

<210> SEQ ID NO 311
<211> LENGTH: 35
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 311
ugaugacggu agauuugggu agagugaccg caucu 35

<210> SEQ ID NO 312
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 312
ugaugacggu agauaacggg uagagugacc gcaucu 36

<210> SEQ ID NO 313
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 313
ugaugacggu agauaacggg uagugugacc gcaucu 36

<210> SEQ ID NO 314
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 314
ugaugacggu agauuucggg aagugugacc gcaucu 36

<210> SEQ ID NO 315
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 315
ugaugacggu agauuauggg uagugugacc gcaucu 36

<210> SEQ ID NO 316
<211> LENGTH: 13
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 316
gaugacggua gau 13

<210> SEQ ID NO 317
<211> LENGTH: 17
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 317
gguagaguga ccgcauc 17

<210> SEQ ID NO 318
<211> LENGTH: 13
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 318
ggcgacggua gau 13

<210> SEQ ID NO 319
<211> LENGTH: 17
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 319
gguagaguga ccgcgcc 17

<210> SEQ ID NO 320
<211> LENGTH: 13
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 320
gaugacggua gau 13

<210> SEQ ID NO 321
<211> LENGTH: 17
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 321
gguagaguga ccgcauc 17

<210> SEQ ID NO 322
<211> LENGTH: 13
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 322
gaugacggua gau 13

<210> SEQ ID NO 323
<211> LENGTH: 17
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 323
gguagaguga ccgcauc 17

<210> SEQ ID NO 324
<211> LENGTH: 13
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 324
gaugacggua gau 13

<210> SEQ ID NO 325
<211> LENGTH: 17
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 325
gguagaguga ccgcauc 17

<210> SEQ ID NO 326
<211> LENGTH: 13
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 326
gaugacggua gau 13

<210> SEQ ID NO 327
<211> LENGTH: 17
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 327
gguagaguga ccgcauc 17

<210> SEQ ID NO 328
<211> LENGTH: 13
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 328
gaugacggua gau 13

<210> SEQ ID NO 329
<211> LENGTH: 17
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 329
gguagaguga ccgcauc 17

<210> SEQ ID NO 330
<211> LENGTH: 13
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 330
gaugacggua gau 13

<210> SEQ ID NO 331
<211> LENGTH: 17
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 331
gguagaguga ccgcauc 17

<210> SEQ ID NO 332
<211> LENGTH: 34
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 332

-continued gaugacggua gauuucgggu agugugaccg cauc 34

<210> SEQ ID NO 333
<211> LENGTH: 34
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 333
ggcgacggua gauuucgggu agugugaccg cgcc 34

<210> SEQ ID NO 334
<211> LENGTH: 32
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 334
gcgacgguag auuucgggua gugugaccgc gc 32

<210> SEQ ID NO 335
<211> LENGTH: 16
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 335
gaugacggua gauuuc 16

<210> SEQ ID NO 336
<211> LENGTH: 17
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 336
gguaguguga ccgcauc 17

<210> SEQ ID NO 337
<211> LENGTH: 34
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 337
gaugacggua gauuaugggc agugugaccg cauc 34

<210> SEQ ID NO 338
<211> LENGTH: 34
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 338
ggcgacggua gauuaugggc agugugaccg cgcc 34

<210> SEQ ID NO 339
<211> LENGTH: 32
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 339
gcgacgguag auuaugggca gugugaccgc gc 32

<210> SEQ ID NO 340
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 340
gaugacggua gauuau 16

<210> SEQ ID NO 341
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 341
ggcaguguga ccgcauc 17

<210> SEQ ID NO 342
<211> LENGTH: 34
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 342
gaugacggua gauuauggga agugugaccg cauc 34

<210> SEQ ID NO 343
<211> LENGTH: 34
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 343
ggcgacggua gauuauggga agugugaccg cgcc 34

<210> SEQ ID NO 344
<211> LENGTH: 32
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 344
gcgacgguag auuaugggaa gugugaccgc gc 32

<210> SEQ ID NO 345
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 345
gaugacggua gauuau 16

<210> SEQ ID NO 346
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 346
ggaaguguga ccgcauc 17

<210> SEQ ID NO 347
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 347
ucaugacggu agauuacggg uagagugacc gcaugu 36

<210> SEQ ID NO 348
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 348
ugaucacggu agauuacggg uagagugacc ggaucu 36

<210> SEQ ID NO 349
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 349
ugaugacagu agauuacggg uagagugacu gcaucu 36

<210> SEQ ID NO 350
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 350
ugaugacgau agauuacggg uagagugauc gcaucu 36

<210> SEQ ID NO 351
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 351
ucuugacggu agauuacggg uagagugacc gcaucu 36

<210> SEQ ID NO 352
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 352
ugaugacccu agauuacggg uagagugacc gcaucu 36

<210> SEQ ID NO 353
<211> LENGTH: 13
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 353
gaugacggua gau 13

<210> SEQ ID NO 354
<211> LENGTH: 17
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 354
gguagaguga ccgcauc 17

<210> SEQ ID NO 355
<211> LENGTH: 13
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 355
gaugacggua gau 13

<210> SEQ ID NO 356
<211> LENGTH: 17
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 356
gguagaguga ccgcauc 17

<210> SEQ ID NO 357

<211> LENGTH: 34
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 357
ggcgacggua gauuuugggu agugugaccg cgcc 34

<210> SEQ ID NO 358
<211> LENGTH: 34
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 358
ggcgacggua gauuuugggc agugugaccg cgcc 34

<210> SEQ ID NO 359
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 359
ugaugacggu agauuacugg uagagugacc gcaucu 36

<210> SEQ ID NO 360
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 360
ugaugacggu agauuaccgg uagagugacc gcaucu 36

<210> SEQ ID NO 361
<211> LENGTH: 37
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 361
ugaugacggu agauuacagg uagagugacc gcaucut 37

<210> SEQ ID NO 362
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 362
ugcggacggu agauuacggg uagagugacc gccgcu 36

<210> SEQ ID NO 363
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 363
uggagacggu agauuacggg uagagugacc gcuccu 36

<210> SEQ ID NO 364
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 364
ugccgacggu agauuacggg uagagugacc gcggcu 36

<210> SEQ ID NO 365
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 365
ugcugacggu agauuacggg uagagugacc gcagcu 36

<210> SEQ ID NO 366
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 366
uggcgacggu agauuacggg uagagugacc gcgccu 36

<210> SEQ ID NO 367
<211> LENGTH: 34
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 367
ggcgacggua gauuaugggc agugugaccg cgcc 34

<210> SEQ ID NO 368
<211> LENGTH: 34
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 368
ggcgacggua gauuaugggc agugugaccg cgcc 34

<210> SEQ ID NO 369
<211> LENGTH: 34
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 369
ggcgacggua gauuaugggc agugugaccg cgcc 34

<210> SEQ ID NO 370
<211> LENGTH: 34
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 370
ggcgacggua gauuaugggc agugugaccg cgcc 34

<210> SEQ ID NO 371
<211> LENGTH: 34
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 371
ggcgacggua gauuaugggc agugugaccg cgcc 34

<210> SEQ ID NO 372
<211> LENGTH: 34
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 372
ggcgacggua gauuaugggc agugugaccg cgcc 34

<210> SEQ ID NO 373
<211> LENGTH: 34
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 373
ggcgacggua gauuaugggc agugugaccg cgcc 34

<210> SEQ ID NO 374
<211> LENGTH: 34
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 374
ggcgacggua gauuaugggc agugugaccg cgcc 34

<210> SEQ ID NO 375

<211> LENGTH: 34
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 375
ggcgacggua gauuaugggc agugugaccg cgcc 34

<210> SEQ ID NO 376
<211> LENGTH: 34
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 376
ggcgacggua gauuaugggc agugugaccg cgcc 34

<210> SEQ ID NO 377
<211> LENGTH: 34
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 377
ggcgacggua gauuaugggc agugugaccg cgcc 34

<210> SEQ ID NO 378
<211> LENGTH: 34
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 378
ggcgacggua gauuaugggc agugugaccg cgcc 34

<210> SEQ ID NO 379
<211> LENGTH: 34
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 379
ggcgacggua gauuaugggc agugugaccg cgcc 34

<210> SEQ ID NO 380
<211> LENGTH: 34
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 380
ggcgacggua gauuaugggc agugugaccg cgcc 34

<210> SEQ ID NO 381
<211> LENGTH: 34

<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 381
ggcgacggua gauuaugggc agugugaccg cgcc 34

<210> SEQ ID NO 382
<211> LENGTH: 34
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 382
ggcgacggua gauuaugggc agugugaccg cgcc 34

<210> SEQ ID NO 383
<211> LENGTH: 34
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 383
ggcgacggua gauuaugggc agugugaccg cgcc 34

<210> SEQ ID NO 384
<211> LENGTH: 34
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 384
ggcgacggua gauuaugggc agugugaccg cgcc 34

<210> SEQ ID NO 385
<211> LENGTH: 34
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 385
ggcgacggua gauuaugggc agugugaccg cgcc 34

<210> SEQ ID NO 386
<211> LENGTH: 34
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 386
ggcgacggua gauuaugggc agugugaccg cgcc 34

<210> SEQ ID NO 387
<211> LENGTH: 34
<212> TYPE: RNA

<213> ORGANISM: Artificial Sequence
<220> FEATURE:
<223> OTHER INFORMATION: Description of Artificial Sequence: Synthetic
oligonucleotide

<400> SEQUENCE: 387
ggcgacggua gauuaugggc agugugaccg cgcc 34

<210> SEQ ID NO 388
<211> LENGTH: 34
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 388
ggcgacggua gauuaugggc agugugaccg cgcc 34

<210> SEQ ID NO 389
<211> LENGTH: 34
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 389
ggcgacggua gauuaugggc agugugaccg cgcc 34

<210> SEQ ID NO 390
<211> LENGTH: 34
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 390
ggcgacggua gauuaugggc agugugaccg cgcc 34

<210> SEQ ID NO 391
<211> LENGTH: 32
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 391
gcgacgguag auuaugggca gugugaccgc gc 32

<210> SEQ ID NO 392
<211> LENGTH: 32
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 392
gcgacgguag auuaugggca gugugaccgc gc 32

<210> SEQ ID NO 393
<211> LENGTH: 34
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 393
ggcgacggua gauuucgggu agugugaccg cgcc 34

<210> SEQ ID NO 394
<211> LENGTH: 34
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 394
ggcgacggua gauuucgggu agugugaccg cgcc 34

<210> SEQ ID NO 395
<211> LENGTH: 34
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 395
ggcgacggua gauuucgggu agugugaccg cgcc 34

<210> SEQ ID NO 396
<211> LENGTH: 34
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 396
ggcgacggua gauuucgggu agugugaccg cgcc 34

<210> SEQ ID NO 397
<211> LENGTH: 32
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 397
gcgacgguag auuucgggua gugugaccgc gc 32

<210> SEQ ID NO 398
<211> LENGTH: 32
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 398
gcgacgguag auuucgggua gugugaccgc gc 32

<210> SEQ ID NO 399
<211> LENGTH: 35
<212> TYPE: DNA
<213> ORGANISM: Artificial Sequence
<220> FEATURE:

<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 399
gaugacggua gauuacgggu agagugaccg cauct 35

<210> SEQ ID NO 400
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 400
gaugcgguag auuacgggua gagugaccgc auct 34

<210> SEQ ID NO 401
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 401
gaugucggua gauuacgggu agagugaccg cauct 35

<210> SEQ ID NO 402
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 402
gcgacgguag auuacgggua gagugaccgc gct 33

<210> SEQ ID NO 403
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 403
gcgacggcag auuacgggua gaguggccgc gct 33

<210> SEQ ID NO 404
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 404
gcgacguaga uuacggguag agugacgcgc t 31

<210> SEQ ID NO 405
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 405
gcgacgcaga uuacggguag aguggcgcgc t 31

<210> SEQ ID NO 406
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 406
ugaugacggu 10

<210> SEQ ID NO 407
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 407
gauuacgggu agagugaccg caucut 26

<210> SEQ ID NO 408
<211> LENGTH: 11
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 408
ugaugacggu a 11

<210> SEQ ID NO 409
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:

Synthetic oligonucleotide

<400> SEQUENCE: 409
auuacgggua gagugaccgc aucut 25

<210> SEQ ID NO 410
<211> LENGTH: 12
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 410
ugaugacggu ag 12

<210> SEQ ID NO 411
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 411
uuacggguag agugaccgca ucut 24

<210> SEQ ID NO 412
<211> LENGTH: 13
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 412
ugaugacggu aga 13

<210> SEQ ID NO 413
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 413
uacggguaga gugaccgcau cut 23

<210> SEQ ID NO 414
<211> LENGTH: 14
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 414
ugaugacggu agau 14

<210> SEQ ID NO 415

<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 415
acggguagag ugaccgcauc ut 22

<210> SEQ ID NO 416
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 416
ugaugacggu agauu 15

<210> SEQ ID NO 417
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 417
cggguagagu gaccgcaucu t 21

<210> SEQ ID NO 418
<211> LENGTH: 16
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 418
ugaugacggu agauua 16

<210> SEQ ID NO 419
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 419
ggguagagug accgcaucut 20

<210> SEQ ID NO 420
<211> LENGTH: 17
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 420
ugaugacggu agauuac 17

<210> SEQ ID NO 421
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 421
gguagaguga ccgcaucut 19

<210> SEQ ID NO 422
<211> LENGTH: 18
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 422
ugaugacggu agauuacg 18

<210> SEQ ID NO 423
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 423
guagagugac cgcaucut 18

<210> SEQ ID NO 424
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 424
ugaugacggu agauuacgg 19

<210> SEQ ID NO 425
<211> LENGTH: 17
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 425
uagagugacc gcaucut 17

<210> SEQ ID NO 426
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 426
ugaugacggu agauuacggg 20

<210> SEQ ID NO 427
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 427
agagugaccg caucut 16

<210> SEQ ID NO 428
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 428
ugaugacggu agauuacggg u 21

<210> SEQ ID NO 429
<211> LENGTH: 15
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 429
gagugaccgc aucut 15

<210> SEQ ID NO 430
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 430
ugaugacggu agauuacggg ua 22

<210> SEQ ID NO 431
<211> LENGTH: 14
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 431
agugaccgca ucut 14

<210> SEQ ID NO 432
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 432
ugaugacggu agauuacggg uag 23

<210> SEQ ID NO 433
<211> LENGTH: 13
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 433
gugaccgcau cut 13

<210> SEQ ID NO 434
<211> LENGTH: 24
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 434
ugaugacggu agauuacggg uaga 24

<210> SEQ ID NO 435
<211> LENGTH: 12
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 435
ugaccgcauc ut 12

<210> SEQ ID NO 436
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 436
ugaugacggu agauuacggg uagag 25

<210> SEQ ID NO 437
<211> LENGTH: 11
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 437
gaccgcaucu t 11

<210> SEQ ID NO 438
<211> LENGTH: 26
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 438
ugaugacggu agauuacggg uagagu 26

<210> SEQ ID NO 439
<211> LENGTH: 10
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 439
accgcaucut 10

<210> SEQ ID NO 440
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 440
gcgacgguag auuac 15

<210> SEQ ID NO 441
<211> LENGTH: 17
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 441
gguagaguga ccgcgct 17

<210> SEQ ID NO 442
<211> LENGTH: 35
<212> TYPE: DNA

<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 442
ggcgacggua gacuacgggu agagugaccg cgcct 35

<210> SEQ ID NO 443
<211> LENGTH: 35
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 443
ggcgacggua gaucacgggu agggugaccg cgcct 35

<210> SEQ ID NO 444
<211> LENGTH: 35
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 444
ggcgacggua gauuacgggu agagugaccg cgcct 35

<210> SEQ ID NO 445
<211> LENGTH: 37
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 445
ugaugacggu agauuucggg uagugugacc gcaucut 37

<210> SEQ ID NO 446
<211> LENGTH: 37
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 446
ugaugacggu agauuccggg uagugugacc gcaucut 37

<210> SEQ ID NO 447
<211> LENGTH: 37

<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 447
ugaugacggu agauuacggg cagugugacc gcaucut 37

<210> SEQ ID NO 448
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 448
ugaugacggu agauuacggg gagugugacc gcaucut 37

<210> SEQ ID NO 449
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 449
ugaugacggu agauuacggg aagugugacc gcaucut 37

<210> SEQ ID NO 450
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 450
ugaugacggu agauuauggg cagugugacc gcaucut 37

<210> SEQ ID NO 451
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 451
ugaugacggu agauuauggg aagugugacc gcaucut 37

<210> SEQ ID NO 452

<211> LENGTH: 37
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 452
ucaugacggu agauuucggg uagugugacc gcaugut 37

<210> SEQ ID NO 453
<211> LENGTH: 37
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 453
ucaugacggu agauuacggg uagagugacc gcaugut 37

<210> SEQ ID NO 454
<211> LENGTH: 37
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 454
ugaugacggu agauuacggg aagagugacc gcaucut 37

<210> SEQ ID NO 455
<211> LENGTH: 37
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 455
ugaugacggu agauuaaggg uagugugacc gcaucut 37

<210> SEQ ID NO 456
<211> LENGTH: 37
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 456
ugaugacggu agauuacggg uugugugacc gcaucut 37

<210> SEQ ID NO 457
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 457
ugaugacgau agauuucggg uagugugauc gcaucut 37

<210> SEQ ID NO 458
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 458
ugaugacggu agauuugggu agagugaccg caucut 36

<210> SEQ ID NO 459
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 459
ugaugacggu agauaacggg uagagugacc gcaucut 37

<210> SEQ ID NO 460
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 460
ugaugacggu agauaacggg uagugugacc gcaucut 37

<210> SEQ ID NO 461
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 461
ugaugacggu agauuucggg aagugugacc gcaucut 37

<210> SEQ ID NO 462
<211> LENGTH: 37
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 462
ugaugacggu agauuauggg uagugugacc gcaucut 37

<210> SEQ ID NO 463
<211> LENGTH: 13
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 463
gaugacggua gau 13

<210> SEQ ID NO 464
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 464
gguagaguga ccgcauct 18

<210> SEQ ID NO 465
<211> LENGTH: 13
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 465
ggcgacggua gau 13

<210> SEQ ID NO 466
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 466
gguagaguga ccgcgcct 18

<210> SEQ ID NO 467
<211> LENGTH: 13
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 467
gaugacggua gau 13

<210> SEQ ID NO 468
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 468
gguagaguga ccgcauct 18

<210> SEQ ID NO 469
<211> LENGTH: 13
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 469
gaugacggua gau 13

<210> SEQ ID NO 470
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 470
gguagaguga ccgcauct 18

<210> SEQ ID NO 471
<211> LENGTH: 13
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 471
gaugacggua gau 13

<210> SEQ ID NO 472
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 472
gguagaguga ccgcauct 18

<210> SEQ ID NO 473
<211> LENGTH: 13
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 473
gaugacggua gau 13

<210> SEQ ID NO 474
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 474
gguagaguga ccgcauct 18

<210> SEQ ID NO 475
<211> LENGTH: 13
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 475
gaugacggua gau 13

<210> SEQ ID NO 476
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 476
gguagaguga ccgcauct 18

<210> SEQ ID NO 477
<211> LENGTH: 13
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 477
gaugacggua gau 13

<210> SEQ ID NO 478
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 478
gguagaguga ccgcauct 18

<210> SEQ ID NO 479
<211> LENGTH: 35
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 479
gaugacggua gauuucgggu agugugaccg cauct 35

<210> SEQ ID NO 480
<211> LENGTH: 35
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 480
ggcgacggua gauuucgggu agugugaccg cgcct 35

<210> SEQ ID NO 481
<211> LENGTH: 33
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 481
gcgacgguag auuucgggua gugugaccgc gct 33

<210> SEQ ID NO 482
<211> LENGTH: 16
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 482
gaugacggua gauuuc 16

<210> SEQ ID NO 483
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule:
Synthetic oligonucleotide

<400> SEQUENCE: 483
gguaguguga ccgcauct 18

<210> SEQ ID NO 484
<211> LENGTH: 35
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 484
gaugacggua gauuaugggc agugugaccg cauct 35

<210> SEQ ID NO 485
<211> LENGTH: 35
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 485
ggcgacggua gauuaugggc agugugaccg cgcct 35

<210> SEQ ID NO 486
<211> LENGTH: 33
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 486
gcgacgguag auuaugggca gugugaccgc gct 33

<210> SEQ ID NO 487
<211> LENGTH: 16
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 487
gaugacggua gauuau 16

<210> SEQ ID NO 488
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:

<223> OTHER INFORMATION: Description of Combined DNA/RNA Molecule: Synthetic oligonucleotide

<400> SEQUENCE: 488
ggcaguguga ccgcauct 18

<210> SEQ ID NO 489
<211> LENGTH: 35
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 489
gaugacggua gauuauggga agugugaccg cauct 35

<210> SEQ ID NO 490
<211> LENGTH: 35
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 490
ggcgacggua gauuauggga agugugaccg cgcct 35

<210> SEQ ID NO 491
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 491
gcgacgguag auuaugggaa gugugaccgc gct 33

<210> SEQ ID NO 492
<211> LENGTH: 16
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 492
gaugacggua gauuau 16

<210> SEQ ID NO 493
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 493
ggaaguguga ccgcauct 18

<210> SEQ ID NO 494
<211> LENGTH: 37
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 494
ucaugacggu agauuacggg uagagugacc gcaugut 37

<210> SEQ ID NO 495
<211> LENGTH: 37
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 495
ugaucacggu agauuacggg uagagugacc ggaucut 37

<210> SEQ ID NO 496
<211> LENGTH: 37
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 496
ugaugacagu agauuacggg uagagugacu gcaucut 37

<210> SEQ ID NO 497
<211> LENGTH: 37
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 497
ugaugacgau agauuacggg uagagugauc gcaucut 37

<210> SEQ ID NO 498
<211> LENGTH: 37
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule:

Synthetic oligonucleotide

<400> SEQUENCE: 498
ucuugacggu agauuacggg uagagugacc gcaucut 37

<210> SEQ ID NO 499
<211> LENGTH: 37
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 499
ugaugacccu agauuacggg uagagugacc gcaucut 37

<210> SEQ ID NO 500
<211> LENGTH: 13
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 500
gaugacggua gau 13

<210> SEQ ID NO 501
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 501
gguagaguga ccgcauct 18

<210> SEQ ID NO 502
<211> LENGTH: 13
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 502
gaugacggua gau 13

<210> SEQ ID NO 503
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 503
gguagaguga ccgcauct 18

<210> SEQ ID NO 504
<211> LENGTH: 35
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 504
ggcgacggua gauuuugggu agugugaccg cgcct 35

<210> SEQ ID NO 505
<211> LENGTH: 35
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 505
ggcgacggua gauuuugggc agugugaccg cgcct 35

<210> SEQ ID NO 506
<211> LENGTH: 37
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 506
ugaugacggu agauuacugg uagagugacc gcaucut 37

<210> SEQ ID NO 507
<211> LENGTH: 37
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 507
ugaugacggu agauuaccgg uagagugacc gcaucut 37

<210> SEQ ID NO 508
<211> LENGTH: 37
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 508
ugaugacggu agauuacagg uagagugacc gcaucut 37

<210> SEQ ID NO 509
<211> LENGTH: 37
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 509
ugcggacggu agauuacggg uagagugacc gccgcut 37

<210> SEQ ID NO 510
<211> LENGTH: 37
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 510
uggagacggu agauuacggg uagagugacc gcuccut 37

<210> SEQ ID NO 511
<211> LENGTH: 37
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 511
ugccgacggu agauuacggg uagagugacc gcggcut 37

<210> SEQ ID NO 512
<211> LENGTH: 37
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 512
ugcugacggu agauuacggg uagagugacc gcagcut 37

<210> SEQ ID NO 513
<211> LENGTH: 37
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 513
uggcgacggu agauuacggg uagagugacc gcgccut 37

<210> SEQ ID NO 514
<211> LENGTH: 35
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 514
ggcgacggua gauuaugggc agugugaccg cgcct 35

<210> SEQ ID NO 515
<211> LENGTH: 35
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 515
ggcgacggua gauuaugggc agugugaccg cgcct 35

<210> SEQ ID NO 516
<211> LENGTH: 35
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 516
ggcgacggua gauuaugggc agugugaccg cgcct 35

<210> SEQ ID NO 517
<211> LENGTH: 35
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 517
ggcgacggua gauuaugggc agugugaccg cgcct 35

<210> SEQ ID NO 518
<211> LENGTH: 35
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 518
ggcgacggua gauuaugggc agugugaccg cgcct 35

<210> SEQ ID NO 519
<211> LENGTH: 35
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 519
ggcgacggua gauuaugggc agugugaccg cgcct 35

<210> SEQ ID NO 520
<211> LENGTH: 35
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 520
ggcgacggua gauuaugggc agugugaccg cgcct 35

<210> SEQ ID NO 521
<211> LENGTH: 35
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 521
ggcgacggua gauuaugggc agugugaccg cgcct 35

<210> SEQ ID NO 522
<211> LENGTH: 35
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 522
ggcgacggua gauuaugggc agugugaccg cgcct 35

<210> SEQ ID NO 523
<211> LENGTH: 35
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 523
ggcgacggua gauuaugggc agugugaccg cgcct 35

<210> SEQ ID NO 524
<211> LENGTH: 35
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 524
ggcgacggua gauuaugggc agugugaccg cgcct 35

<210> SEQ ID NO 525
<211> LENGTH: 35
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 525
ggcgacggua gauuaugggc agugugaccg cgcct 35

<210> SEQ ID NO 526
<211> LENGTH: 35
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 526
ggcgacggua gauuaugggc agugugaccg cgcct 35

<210> SEQ ID NO 527
<211> LENGTH: 35
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 527
ggcgacggua gauuaugggc agugugaccg cgcct 35

<210> SEQ ID NO 528
<211> LENGTH: 35
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule:

Synthetic oligonucleotide

<400> SEQUENCE: 528
ggcgacggua gauuaugggc agugugaccg cgcct 35

<210> SEQ ID NO 529
<211> LENGTH: 35
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 529
ggcgacggua gauuaugggc agugugaccg cgcct 35

<210> SEQ ID NO 530
<211> LENGTH: 35
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 530
ggcgacggua gauuaugggc agugugaccg cgcct 35

<210> SEQ ID NO 531
<211> LENGTH: 35
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 531
ggcgacggua gauuaugggc agugugaccg cgcct 35

<210> SEQ ID NO 532
<211> LENGTH: 35
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 532
ggcgacggua gauuaugggc agugugaccg cgcct 35

<210> SEQ ID NO 533
<211> LENGTH: 35
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:

<223> OTHER INFORMATION: Description of Combined DNA/RNA Molecule:
Synthetic oligonucleotide

<400> SEQUENCE: 533
ggcgacggua gauuaugggc agugugaccg cgcct 35

<210> SEQ ID NO 534
<211> LENGTH: 35
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 534
ggcgacggua gauuaugggc agugugaccg cgcct 35

<210> SEQ ID NO 535
<211> LENGTH: 35
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 535
ggcgacggua gauuaugggc agugugaccg cgcct 35

<210> SEQ ID NO 536
<211> LENGTH: 35
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 536
ggcgacggua gauuaugggc agugugaccg cgcct 35

<210> SEQ ID NO 537
<211> LENGTH: 35
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 537
ggcgacggua gauuaugggc agugugaccg cgcct 35

<210> SEQ ID NO 538
<211> LENGTH: 33
<212> TYPE: DNA
<213> ORGANISM: Artificial Sequence
<220> FEATURE:
<223> OTHER INFORMATION: Description of Artificial Sequence: Synthetic
oligonucleotide <220> FEATURE:
<223> OTHER INFORMATION: Description of Combined DNA/RNA Molecule:
      Synthetic oligonucleotide

<400> SEQUENCE: 538
gcgacgguag auuaugggca gugugaccgc gct                                   33

<210> SEQ ID NO 539
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 539
gcgacgguag auuaugggca gugugaccgc gct                                   33

<210> SEQ ID NO 540
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 540
ggcgacggua gauuucgggu agugugaccg cgcct                                 35

<210> SEQ ID NO 541
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 541
ggcgacggua gauuucgggu agugugaccg cgcct                                 35

<210> SEQ ID NO 542
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 542
ggcgacggua gauuucgggu agugugaccg cgcct                                 35

<210> SEQ ID NO 543
<211> LENGTH: 35
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule:
Synthetic oligonucleotide

<400> SEQUENCE: 543
ggcgacggua gauuucgggu agugugaccg cgcct 35

<210> SEQ ID NO 544
<211> LENGTH: 33
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 544
gcgacgguag auuucgggua gugugaccgc gct 33

<210> SEQ ID NO 545
<211> LENGTH: 33
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 545
gcgacgguag auuucgggua gugugaccgc gct 33

<210> SEQ ID NO 546
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 546
uaaucgcugg gaaaugggag augguuggc gauuau 36

<210> SEQ ID NO 547
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 547
ugggcauggg aaaugugaga uggguugugc ucaagu 36

<210> SEQ ID NO 548
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 548
ugauagcaag ugggaaaugu gagaugggguu acuugu 36

<210> SEQ ID NO 549
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 549
uagucacggg aaaagugaga ugggugugac guguuu 36

<210> SEQ ID NO 550
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 550
uaaucaccgg ugggaaaugu gagaagggug gccggu 36

<210> SEQ ID NO 551
<211> LENGTH: 36
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 551
uacgguggga aaugugagau ggguugccgt attttt 36

<210> SEQ ID NO 552
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 552
uugugccaug ggaaauguga gaugggguuau gucacu 36

<210> SEQ ID NO 553
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 553
ugaccgggaa augugagaug gguggucagc auaaau 36

<210> SEQ ID NO 554
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 554
uaauuagcug cgggaaaugg gagaugggu gcggcu 36

<210> SEQ ID NO 555
<211> LENGTH: 35
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 555
uacgguggga uaugugagau ggguugccgu auuuu 35

<210> SEQ ID NO 556
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 556
uaacauacgg gaaacgugag aagggguguau guuauu 36

<210> SEQ ID NO 557
<211> LENGTH: 35
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 557
uacgguggga aaugugagau ggguugccgu uuuuu 35

<210> SEQ ID NO 558
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 558
uuugagagca gcgggaaaug ugagaugggu guugcu 36

<210> SEQ ID NO 559
<211> LENGTH: 35
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 559
uacgguggga aaugugagau ggguugccgu auuuc 35

<210> SEQ ID NO 560
<211> LENGTH: 35
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 560
uacgguggga aaugcgagau ggguugccgu auuuu 35

<210> SEQ ID NO 561
<211> LENGTH: 35
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 561
uacggcggga aaugugagau ggguugccgu auuuu 35

<210> SEQ ID NO 562
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 562
uuggccuggg aaaugugaga aggguuaggc uauuau 36

<210> SEQ ID NO 563
<211> LENGTH: 35
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 563
uacgguggga aaugugagau ggguugccgu auucu 35

<210> SEQ ID NO 564
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 564
ucguuucggg aaaugugaga ugggugaagc gauaau 36

<210> SEQ ID NO 565
<211> LENGTH: 35
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 565
uacgguggga aaugugaggu ggguugccgu auuuu 35

<210> SEQ ID NO 566
<211> LENGTH: 35
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 566
uacgguggga aacgugagau ggguugccgu auuuu 35

<210> SEQ ID NO 567
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 567
ucuuugggug ggaaauguga gacggguugc ccaaau 36

<210> SEQ ID NO 568
<211> LENGTH: 35
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 568
uucgguggga aaugugagau ggguugccgu auuuu 35

<210> SEQ ID NO 569
<211> LENGTH: 35
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 569
uacgguggga aaugugggau ggguugccgu auuuu 35

<210> SEQ ID NO 570
<211> LENGTH: 35
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 570
uacgguggga auugugagau ggguugccgu auuuu 35

<210> SEQ ID NO 571
<211> LENGTH: 35
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 571
uacgguggga aaugugugau ggguugccgu auuuu 35

<210> SEQ ID NO 572
<211> LENGTH: 35
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 572
ugcgguggga aaugugagau ggguugccgu auuuu 35

<210> SEQ ID NO 573
<211> LENGTH: 37
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 573
uacgguggga aaugugagau ggguugccgu auuuuuu 37

<210> SEQ ID NO 574
<211> LENGTH: 35
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 574
uacgguggga aaugugagau ggguugccgu auuug 35

<210> SEQ ID NO 575
<211> LENGTH: 35
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 575
uacgguggga aaggugagau ggguugccgu auuuu 35

<210> SEQ ID NO 576
<211> LENGTH: 35
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 576
uacgguggga aaugggagau ggguugccgu auuuu 35

<210> SEQ ID NO 577
<211> LENGTH: 35
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 577
uacgguggga aaugugagau ggguugccgu auuau 35

<210> SEQ ID NO 578
<211> LENGTH: 35
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 578
uacgggggga aaugugagau ggguugccgu auuuu 35

<210> SEQ ID NO 579
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 579
uuccagcggg aaaugugaga uggguugcug ggucua 36

<210> SEQ ID NO 580
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 580
ugagcauggg aaaugugaga uggguugugc ucaagu 36

<210> SEQ ID NO 581
<211> LENGTH: 35
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 581
uaugguggga aaugugagau ggguugccgu auuuu 35

<210> SEQ ID NO 582
<211> LENGTH: 35
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 582
uacgguggga aaugugagau ggguugccgu aucuu 35

<210> SEQ ID NO 583
<211> LENGTH: 35
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 583
uacgguggga aaugugagau ggguugccgu auugu 35

<210> SEQ ID NO 584
<211> LENGTH: 35
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 584
uacgguggga aaugugagau ggguugccgu acuuu 35

<210> SEQ ID NO 585

<211> LENGTH: 35
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 585
uacgguggga aaugugaguu ggguugccgu auuuu 35

<210> SEQ ID NO 586
<211> LENGTH: 35
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 586
uacgauggga aaugugagau ggguugccgu auuuu 35

<210> SEQ ID NO 587
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 587
uuucguucgg cgggaaaagu gagaugggug ccgauu 36

<210> SEQ ID NO 588
<211> LENGTH: 35
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 588
uacggugggg aaugugagau ggguugccgu auuuu 35

<210> SEQ ID NO 589
<211> LENGTH: 35
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 589
uacgguggga agugugagau ggguugccgu auuuu 35

<210> SEQ ID NO 590
<211> LENGTH: 35
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 590 uacgguggguu aaugugagau ggguugccgu auuuu 35

<210> SEQ ID NO 591
<211> LENGTH: 35

<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 591
uacaguggga aaugugagau ggguugccgu auuuu 35

<210> SEQ ID NO 592
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 592
ugcccgggaa augugagaug gguugggcaa aucauu 36

<210> SEQ ID NO 593
<211> LENGTH: 35
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 593
uacgguggga aaugugagau ggguugccgu guuuu 35

<210> SEQ ID NO 594
<211> LENGTH: 35
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 594
uacgguggga aaugugagag ggguugccgu auuuu 35

<210> SEQ ID NO 595
<211> LENGTH: 35
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 595
uacgguggga gaugugagau ggguugccgu auuuu 35

<210> SEQ ID NO 596
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 596
ugggcauggg aaaugugaga uggguugugc ucaugu 36

<210> SEQ ID NO 597
<211> LENGTH: 35
<212> TYPE: RNA

<213> ORGANISM: Artificial Sequence
<220> FEATURE:
<223> OTHER INFORMATION: Description of Artificial Sequence: Synthetic
oligonucleotide

<400> SEQUENCE: 597
uacgguggga aaugugagac ggguugccgu auuuu 35

<210> SEQ ID NO 598
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 598
uuucuucaag cgggaaauga gagaugggug cuugau 36

<210> SEQ ID NO 599
<211> LENGTH: 35
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 599
uacgguggga aaugugagau ggguggccgu auuuu 35

<210> SEQ ID NO 600
<211> LENGTH: 35
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 600
uacgguggga aaugugagau ggguugccgc auuuu 35

<210> SEQ ID NO 601
<211> LENGTH: 35
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 601
uacgguggga aaagugagau ggguugccgu auuuu 35

<210> SEQ ID NO 602
<211> LENGTH: 35
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 602
uacgguggga aaugugagau ggguugccau auuuu 35

<210> SEQ ID NO 603
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 603
cggugggaaa ugugagaugg guugccg 27

<210> SEQ ID NO 604
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 604
cggugggaaa ugugagacgg guugccg 27

<210> SEQ ID NO 605
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 605
cggugggaaa ugugagaagg guugccg 27

<210> SEQ ID NO 606
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 606
cggugggaaa agugagaugg guugccg 27

<210> SEQ ID NO 607
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 607
cggugggaaa ucugagaugg guugccg 27

<210> SEQ ID NO 608
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 608
cggugggaaa uaugagaugg guugccg 27

<210> SEQ ID NO 609
<211> LENGTH: 27
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 609
cggugggaaa uuugagaugg guugccg 27

<210> SEQ ID NO 610
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 610
cggugggaaa ugcgagaugg guugccg 27

<210> SEQ ID NO 611
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 611
cggugggaaa cgugagaugg guugccg 27

<210> SEQ ID NO 612
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 612
cggugggaaa cgcgagaugg guugccg 27

<210> SEQ ID NO 613
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 613
cggugggaca cgcgagaugg guggccg 27

<210> SEQ ID NO 614
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 614
cggugggaaa ccugagaugg guugccg 27

<210> SEQ ID NO 615
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 615
cggugggaaa cccgagaugg guugccg 27

<210> SEQ ID NO 616
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 616
cggugggaca cccgagaugg guggccg 27

<210> SEQ ID NO 617
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 617
cggcgggaaa ugugagaugg guugccg 27

<210> SEQ ID NO 618
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 618
cggugggaac ugugagaugg ggugccg 27

<210> SEQ ID NO 619
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 619
cggugggaac cgugagaugg ggugccg 27

<210> SEQ ID NO 620
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 620
cggucggaaa ugugagaugg guugccg 27

<210> SEQ ID NO 621
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 621
cgguaggaaa ugugagaugg guugccg 27

<210> SEQ ID NO 622
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 622
cgguuggaaa ugugagaugg guugccg 27

<210> SEQ ID NO 623
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 623
cggugcgaaa ugugagaugg guugccg 27

<210> SEQ ID NO 624
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 624
cggugagaaa ugugagaugg guugccg 27

<210> SEQ ID NO 625
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 625
cggugugaaa ugugagaugg guugccg 27

<210> SEQ ID NO 626
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 626
cgguggcaaa ugugagaugg guugccg 27

<210> SEQ ID NO 627
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 627
cgguggaaaa ugugagaugg guugccg 27

<210> SEQ ID NO 628
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 628
cggugguaaa ugugagaugg guugccg 27

<210> SEQ ID NO 629
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 629 cgguggcaa ugugagaugg guugccg 27

<210> SEQ ID NO 630
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 630
cgguggggaa ugugagaugg guugccg 27

<210> SEQ ID NO 631
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 631
cgguggguaa ugugagaugg guugccg 27

<210> SEQ ID NO 632
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 632 cgguggaaa ugucagaugg guugccg 27

<210> SEQ ID NO 633
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 633
cggugggaaa uguaagaugg guugccg 27

<210> SEQ ID NO 634
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 634
cggugggaaa uguuagaugg guugccg 27

<210> SEQ ID NO 635
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 635
cggugggaaa ugugcgaugg guugccg 27

<210> SEQ ID NO 636
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 636
cggugggaaa ugugggaugg guugccg 27

<210> SEQ ID NO 637
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 637
cggugggaaa ugugugaugg guugccg 27

<210> SEQ ID NO 638
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 638
cggugggaaa ugugacaugg guugccg 27

<210> SEQ ID NO 639
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 639

-continued cggugggaaa ugugaaaugg guugccg 27

<210> SEQ ID NO 640
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 640
cggugggaaa ugugauaugg guugccg 27

<210> SEQ ID NO 641
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 641
cggugggaaa ugugagcugg guu 23

<210> SEQ ID NO 642
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 642
cggugggaaa ugugaggugg guugccg 27

<210> SEQ ID NO 643
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 643
cggugggaaa ugugaguugg guugccg 27

<210> SEQ ID NO 644
<211> LENGTH: 27
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 644
cggugggaaa ugugagaggg guugccg 27

<210> SEQ ID NO 645
<211> LENGTH: 29
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 645
gcggugggaa augugagaug gguugccgc 29

<210> SEQ ID NO 646
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 646
caaugggaaa ugugagaugg guugccg 27

<210> SEQ ID NO 647
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 647
cggugggaaa ugugagaugg gaugccg 27

<210> SEQ ID NO 648
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 648
cugugggaaa ugugagaugg guugcag 27

<210> SEQ ID NO 649
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 649
cgcugggaaa ugugagaugg guuggcg 27

<210> SEQ ID NO 650
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 650
cgaugggaaa ugugagaugg guugucg 27

<210> SEQ ID NO 651
<211> LENGTH: 27
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 651
cggugggaaa ugugagaugg guuaccg 27

<210> SEQ ID NO 652
<211> LENGTH: 29
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 652
gcggugggaa augugagaug gguugccgc 29

<210> SEQ ID NO 653
<211> LENGTH: 29
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 653
gcggugggaa augugagaug gguugccgc 29

<210> SEQ ID NO 654
<211> LENGTH: 29
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 654
gcggugggaa augugagaug gguugccgc 29

<210> SEQ ID NO 655
<211> LENGTH: 29
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 655
gcggugggaa augugagaug gguugccgc 29

<210> SEQ ID NO 656
<211> LENGTH: 29
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 656
gcggugggaa augugagaug gguugccgc 29

<210> SEQ ID NO 657
<211> LENGTH: 29
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 657
gcggugggaa augugagaug gguugccgc 29

<210> SEQ ID NO 658
<211> LENGTH: 29
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 658
gcggugggaa augugagaug gguugccgc 29

<210> SEQ ID NO 659
<211> LENGTH: 29
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 659
gcggugggaa augugagaug gguugccgc 29

<210> SEQ ID NO 660
<211> LENGTH: 29
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 660
gcggugggaa augugagaug gguugccgc 29

<210> SEQ ID NO 661
<211> LENGTH: 29
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 661
gcggugggaa augugagaug gguugccgc 29

<210> SEQ ID NO 662
<211> LENGTH: 29
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 662
gcggugggaa augugagaug gguugccgc 29

<210> SEQ ID NO 663
<211> LENGTH: 29
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 663
gcggugggaa augugagaug gguugccgc 29

<210> SEQ ID NO 664

<211> LENGTH: 29
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 664
gcggugggaa augugagaug gguugccgc 29

<210> SEQ ID NO 665
<211> LENGTH: 29
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 665
gcggugggaa augugagaug gguugccgc 29

<210> SEQ ID NO 666
<211> LENGTH: 29
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 666
gcggugggaa augugagaug gguugccgc 29

<210> SEQ ID NO 667
<211> LENGTH: 29
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 667
gcggugggaa augugagaug gguugccgc 29

<210> SEQ ID NO 668
<211> LENGTH: 29
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 668
gcggugggaa augugagaug gguugccgc 29

<210> SEQ ID NO 669
<211> LENGTH: 29
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 669
gcggugggaa augugagaug gguugccgc 29

<210> SEQ ID NO 670
<211> LENGTH: 29

<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 670
gcggugggaa augugagaug gguugccgc 29

<210> SEQ ID NO 671
<211> LENGTH: 29
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 671
gcggugggaa augugagaug gguugccgc 29

<210> SEQ ID NO 672
<211> LENGTH: 29
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 672
gcggugggaa augugagaug gguugccgc 29

<210> SEQ ID NO 673
<211> LENGTH: 29
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 673
gcggugggaa augugagaug gguugccgc 29

<210> SEQ ID NO 674
<211> LENGTH: 29
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 674
gcggugggaa augugagaug gguugccgc 29

<210> SEQ ID NO 675
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 675
cggugggaaa cgugagaugg guugccg 27

<210> SEQ ID NO 676
<211> LENGTH: 27
<212> TYPE: RNA

-continued

<213> ORGANISM: Artificial Sequence
<220> FEATURE:
<223> OTHER INFORMATION: Description of Artificial Sequence: Synthetic
      oligonucleotide

<400> SEQUENCE: 676
cggugggaaa cgugagaugg guugccg 27

<210> SEQ ID NO 677
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 677
cggugggaaa cgugagaugg guugccg 27

<210> SEQ ID NO 678
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 678
cggugggaaa cgugagaugg guugccg 27

<210> SEQ ID NO 679
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 679
cggugggaaa ugugagaugg guugccgt 28

<210> SEQ ID NO 680
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 680
cggugggaaa ugugagacgg guugccgt 28

<210> SEQ ID NO 681
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 681
cggugggaaa ugugagaagg guugccgt 28

<210> SEQ ID NO 682
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 682
cggugggaaa agugagaugg guugccgt 28

<210> SEQ ID NO 683
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 683
cggugggaaa ucugagaugg guugccgt 28

<210> SEQ ID NO 684
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 684
cggugggaaa uaugagaugg guugccgt 28

<210> SEQ ID NO 685
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 685
cggugggaaa uuugagaugg guugccgt 28

<210> SEQ ID NO 686
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 686
cggugggaaa ugcgagaugg guugccgt 28

<210> SEQ ID NO 687
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 687
cggugggaaa cgugagaugg guugccgt 28

<210> SEQ ID NO 688
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 688
cggugggaaa cgcgagaugg guugccgt 28

<210> SEQ ID NO 689
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 689
cggugggaca cgcgagaugg guggccgt 28

<210> SEQ ID NO 690
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 690
cggugggaaa ccugagaugg guugccgt 28

<210> SEQ ID NO 691
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule:

Synthetic oligonucleotide

<400> SEQUENCE: 691
cggugggaaa cccgagaugg guugccgt 28

<210> SEQ ID NO 692
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 692
cggugggaca cccgagaugg guggccgt 28

<210> SEQ ID NO 693
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 693
cggcgggaaa ugugagaugg guugccgt 28

<210> SEQ ID NO 694
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 694
cggugggaac ugugagaugg ggugccgt 28

<210> SEQ ID NO 695
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 695
cggugggaac cgugagaugg ggugccgt 28

<210> SEQ ID NO 696
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:

<223> OTHER INFORMATION: Description of Combined DNA/RNA Molecule:
      Synthetic oligonucleotide

<400> SEQUENCE: 696
cggucggaaa ugugagaugg guugccgt 28

<210> SEQ ID NO 697
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 697
cgguaggaaa ugugagaugg guugccgt 28

<210> SEQ ID NO 698
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 698
cgguuggaaa ugugagaugg guugccgt 28

<210> SEQ ID NO 699
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 699
cggugcgaaa ugugagaugg guugccgt 28

<210> SEQ ID NO 700
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 700
cggugagaaa ugugagaugg guugccgt 28

<210> SEQ ID NO 701
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide <220> FEATURE:
<223> OTHER INFORMATION: Description of Combined DNA/RNA Molecule:
Synthetic oligonucleotide

<400> SEQUENCE: 701
cggugugaaa ugugagaugg guugccgt 28

<210> SEQ ID NO 702
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 702
cgguggcaaa ugugagaugg guugccgt 28

<210> SEQ ID NO 703
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 703
cgguggaaaa ugugagaugg guugccgt 28

<210> SEQ ID NO 704
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 704
cggugguaaa ugugagaugg guugccgt 28

<210> SEQ ID NO 705
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 705
cggugggcaa ugugagaugg guugccgt 28

<210> SEQ ID NO 706
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 706
cggyggggaa ugugagaugg guugccgt 28

<210> SEQ ID NO 707
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 707
cggugggyaa ugugagaugg guugccgt 28

<210> SEQ ID NO 708
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 708
cggugggaaa ugucagaugg guugccgt 28

<210> SEQ ID NO 709
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 709
cggugggaaa uguaagaugg guugccgt 28

<210> SEQ ID NO 710
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 710
cggugggaaa uguuagaugg guugccgt 28

<210> SEQ ID NO 711
<211> LENGTH: 28
<212> TYPE: DNA
<213> ORGANISM: Artificial Sequence
<220> FEATURE:

<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 711
cggugggaaa ugugcgaugg guugccgt 28

<210> SEQ ID NO 712
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 712
cggugggaaa ugugggaugg guugccgt 28

<210> SEQ ID NO 713
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 713
cggugggaaa ugugugaugg guugccgt 28

<210> SEQ ID NO 714
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 714
cggugggaaa ugugacaugg guugccgt 28

<210> SEQ ID NO 715
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 715
cggugggaaa ugugaaaugg guugccgt 28

<210> SEQ ID NO 716
<211> LENGTH: 28
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 716

cggugggaaa ugugauaugg guugccgt                                        28


<210> SEQ ID NO 717
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 717

cggugggaaa ugugagcugg guut                                            24


<210> SEQ ID NO 718
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 718

cggugggaaa ugugaggugg guugccgt                                        28


<210> SEQ ID NO 719
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 719

cggugggaaa ugugaguugg guugccgt                                        28


<210> SEQ ID NO 720
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 720

cggugggaaa ugugagaggg guugccgt                                        28


<210> SEQ ID NO 721
<211> LENGTH: 30
<212> TYPE: DNA
```

<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 721
gcggugggaa augugagaug gguugccgct 30

<210> SEQ ID NO 722
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 722
caaugggaaa ugugagaugg guugccgt 28

<210> SEQ ID NO 723
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 723
cggugggaaa ugugagaugg gaugccgt 28

<210> SEQ ID NO 724
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 724
cugugggaaa ugugagaugg guugcagt 28

<210> SEQ ID NO 725
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 725
cgcugggaaa ugugagaugg guuggcgt 28

<210> SEQ ID NO 726
<211> LENGTH: 28

<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 726
cgaugggaaa ugugagaugg guugucgt 28

<210> SEQ ID NO 727
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 727
cggugggaaa ugugagaugg guuaccgt 28

<210> SEQ ID NO 728
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 728
gcggugggaa augugagaug gguugccgct 30

<210> SEQ ID NO 729
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 729
gcggugggaa augugagaug gguugccgct 30

<210> SEQ ID NO 730
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 730
gcggugggaa augugagaug gguugccgct 30

<210> SEQ ID NO 731

<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 731
gcggugggaa augugagaug gguugccgct 30

<210> SEQ ID NO 732
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 732
gcggugggaa augugagaug gguugccgct 30

<210> SEQ ID NO 733
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 733
gcggugggaa augugagaug gguugccgct 30

<210> SEQ ID NO 734
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 734
gcggugggaa augugagaug gguugccgct 30

<210> SEQ ID NO 735
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 735
gcggugggaa augugagaug gguugccgct 30

<210> SEQ ID NO 736
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 736
gcggugggaa augugagaug gguugccgct 30

<210> SEQ ID NO 737
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 737
gcggugggaa augugagaug gguugccgct 30

<210> SEQ ID NO 738
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 738
gcggugggaa augugagaug gguugccgct 30

<210> SEQ ID NO 739
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 739
gcggugggaa augugagaug gguugccgct 30

<210> SEQ ID NO 740
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 740
gcggugggaa augugagaug gguugccgct 30

<210> SEQ ID NO 741
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 741
gcggugggaa augugagaug gguugccgct 30

<210> SEQ ID NO 742
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 742
gcggugggaa augugagaug gguugccgct 30

<210> SEQ ID NO 743
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 743
gcggugggaa augugagaug gguugccgct 30

<210> SEQ ID NO 744
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 744
gcggugggaa augugagaug gguugccgct 30

<210> SEQ ID NO 745
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 745
gcggugggaa augugagaug gguugccgct 30

<210> SEQ ID NO 746
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 746
gcggugggaa augugagaug gguugccgct 30

<210> SEQ ID NO 747
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 747
gcggugggaa augugagaug gguugccgct 30

<210> SEQ ID NO 748
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 748
gcggugggaa augugagaug gguugccgct 30

<210> SEQ ID NO 749
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 749
gcggugggaa augugagaug gguugccgct 30

<210> SEQ ID NO 750
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 750
gcggugggaa augugagaug gguugccgct 30

<210> SEQ ID NO 751
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 751
cggugggaaa cgugagaugg guugccgt 28

<210> SEQ ID NO 752
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 752
cggugggaaa cgugagaugg guugccgt 28

<210> SEQ ID NO 753
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 753
cggugggaaa cgugagaugg guugccgt 28

<210> SEQ ID NO 754
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 754
cggugggaaa cgugagaugg guugccgt 28

<210> SEQ ID NO 755
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 755
gggagagucg guagcaguc 19

<210> SEQ ID NO 756
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 756
cuauguggaa auggcgcugu 20

<210> SEQ ID NO 757
<211> LENGTH: 18
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 757
gggagggcaa gagacaga 18

<210> SEQ ID NO 758
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 758
cuauguggaa auggcgcugu 20

<210> SEQ ID NO 759
<211> LENGTH: 91
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 759
gggagagcgg aagcgugcug ggcuuaucau uccauuuagu guuaugauaa ccuucccauc 60
agacauaacc cagaggucga uggaucccgg g 91

<210> SEQ ID NO 760
<211> LENGTH: 44
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 760
gggggcuuau cauuccauuu aguguuauga uaaccuuccc auca 44

<210> SEQ ID NO 761
<211> LENGTH: 35
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 761
gggggcuuau cauuccauuu aguguuauga uaacc 35

<210> SEQ ID NO 762
<211> LENGTH: 30
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 762
ggguuaucau uccauuuagu guuaugauaa 30

<210> SEQ ID NO 763
<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 763
uacggguaga 10

<210> SEQ ID NO 764
<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (7)..(7)
<223> OTHER INFORMATION: a, c, u, g, unknown or other

<400> SEQUENCE: 764 uwyggkndga 10

<210> SEQ ID NO 765
<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 765
uacggguagu 10

<210> SEQ ID NO 766
<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (7)..(7)
<223> OTHER INFORMATION: a, c, u, g, unknown or other

<400> SEQUENCE: 766 uwyggkndgu 10

<210> SEQ ID NO 767
<211> LENGTH: 10
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (2)..(3)
<223> OTHER INFORMATION: a, c, u, g, unknown or other
<220> FEATURE:
<221> NAME/KEY: modified_base
<222> LOCATION: (7)..(7)
<223> OTHER INFORMATION: a, c, u, g, unknown or other

<400> SEQUENCE: 767 dnnrggnwgh 10

<210> SEQ ID NO 768
<211> LENGTH: 10
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (2)..(3)
<223> OTHER INFORMATION: a, c, u, g, unknown or other
<220> FEATURE:
<221> NAME/KEY: modified_base
<222> LOCATION: (7)..(7)
<223> OTHER INFORMATION: a, c, u, g, unknown or other

<400> SEQUENCE: 768 dnngggnwgh 10

<210> SEQ ID NO 769
<211> LENGTH: 34
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(2)
<223> OTHER INFORMATION: a, c, u, g, unknown or other
<220> FEATURE:
<221> NAME/KEY: modified_base
<222> LOCATION: (6)..(6)
<223> OTHER INFORMATION: a, c, u, g, unknown or other
<220> FEATURE:
<221> NAME/KEY: modified_base
<222> LOCATION: (9)..(9)
<223> OTHER INFORMATION: a, c, u, g, unknown or other
<220> FEATURE:
<221> NAME/KEY: modified_base
<222> LOCATION: (15)..(16)
<223> OTHER INFORMATION: a, c, u, g, unknown or other
<220> FEATURE:
<221> NAME/KEY: modified_base
<222> LOCATION: (20)..(20)
<223> OTHER INFORMATION: a, c, u, g, unknown or other
<220> FEATURE:
<221> NAME/KEY: modified_base
<222> LOCATION: (30)..(30)
<223> OTHER INFORMATION: a, c, u, g, unknown or other
<220> FEATURE:
<221> NAME/KEY: modified_base
<222> LOCATION: (33)..(34)
<223> OTHER INFORMATION: a, c, u, g, unknown or other

<400> SEQUENCE: 769
nnusanddna gwddnnrggn wghgugdhhn sann 34

<210> SEQ ID NO 770
<211> LENGTH: 34
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(2)
<223> OTHER INFORMATION: a, c, u, g, unknown or other
<220> FEATURE:
<221> NAME/KEY: modified_base
<222> LOCATION: (6)..(6)
<223> OTHER INFORMATION: a, c, u, g, unknown or other
<220> FEATURE:
<221> NAME/KEY: modified_base
<222> LOCATION: (9)..(9)
<223> OTHER INFORMATION: a, c, u, g, unknown or other
<220> FEATURE:
<221> NAME/KEY: modified_base
<222> LOCATION: (15)..(16)
<223> OTHER INFORMATION: a, c, u, g, unknown or other
<220> FEATURE:
<221> NAME/KEY: modified_base
<222> LOCATION: (20)..(20)
<223> OTHER INFORMATION: a, c, u, g, unknown or other
<220> FEATURE:
<221> NAME/KEY: modified_base
<222> LOCATION: (30)..(30)
<223> OTHER INFORMATION: a, c, u, g, unknown or other
<220> FEATURE:
<221> NAME/KEY: modified_base
<222> LOCATION: (33)..(34)
<223> OTHER INFORMATION: a, c, u, g, unknown or other

<400> SEQUENCE: 770
nnusanddna gwddnngggn wghgugdhhn sann 34

<210> SEQ ID NO 771
<211> LENGTH: 33
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(2)
<223> OTHER INFORMATION: a, c, u, g, unknown or other
<220> FEATURE:
<221> NAME/KEY: modified_base
<222> LOCATION: (6)..(6)
<223> OTHER INFORMATION: a, c, u, g, unknown or other
<220> FEATURE:
<221> NAME/KEY: modified_base
<222> LOCATION: (9)..(9)
<223> OTHER INFORMATION: a, c, u, g, unknown or other
<220> FEATURE:
<221> NAME/KEY: modified_base
<222> LOCATION: (15)..(15)
<223> OTHER INFORMATION: a, c, u, g, unknown or other
<220> FEATURE:
<221> NAME/KEY: modified_base
<222> LOCATION: (19)..(19)
<223> OTHER INFORMATION: a, c, u, g, unknown or other
<220> FEATURE:
<221> NAME/KEY: modified_base
<222> LOCATION: (29)..(29)
<223> OTHER INFORMATION: a, c, u, g, unknown or other
<220> FEATURE:
<221> NAME/KEY: modified_base
<222> LOCATION: (32)..(33)
<223> OTHER INFORMATION: a, c, u, g, unknown or other

<400> SEQUENCE: 771
nnusanddna gwdhngggna gwgugdhhns ann 33

<210> SEQ ID NO 772
<211> LENGTH: 34
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(2)
<223> OTHER INFORMATION: a, c, u, g, unknown or other
<220> FEATURE:
<221> NAME/KEY: modified_base
<222> LOCATION: (6)..(6)
<223> OTHER INFORMATION: a, c, u, g, unknown or other
<220> FEATURE:
<221> NAME/KEY: modified_base
<222> LOCATION: (9)..(9)
<223> OTHER INFORMATION: a, c, u, g, unknown or other
<220> FEATURE:
<221> NAME/KEY: modified_base
<222> LOCATION: (15)..(16)
<223> OTHER INFORMATION: a, c, u, g, unknown or other
<220> FEATURE:
<221> NAME/KEY: modified_base
<222> LOCATION: (20)..(21)
<223> OTHER INFORMATION: a, c, u, g, unknown or other
<220> FEATURE:
<221> NAME/KEY: modified_base
<222> LOCATION: (27)..(27)
<223> OTHER INFORMATION: a, c, u, g, unknown or other
<220> FEATURE:
<221> NAME/KEY: modified_base
<222> LOCATION: (30)..(30)
<223> OTHER INFORMATION: a, c, u, g, unknown or other
<220> FEATURE:
<221> NAME/KEY: modified_base
<222> LOCATION: (33)..(34)
<223> OTHER INFORMATION: a, c, u, g, unknown or other

<400> SEQUENCE: 772
nnyvanddnw gwddnnrgkn nghgugnhhn vrnn 34

<210> SEQ ID NO 773
<211> LENGTH: 31
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (2)..(6)
<223> OTHER INFORMATION: a, c, u, g, unknown or other
<220> FEATURE:
<221> NAME/KEY: modified_base
<222> LOCATION: (13)..(13)
<223> OTHER INFORMATION: a, c, u, g, unknown or other
<220> FEATURE:
<221> NAME/KEY: modified_base
<222> LOCATION: (15)..(15)
<223> OTHER INFORMATION: a, c, u, g, unknown or other
<220> FEATURE:
<221> NAME/KEY: modified_base
<222> LOCATION: (20)..(20)
<223> OTHER INFORMATION: a, c, u, g, unknown or other
<220> FEATURE:
<221> NAME/KEY: modified_base
<222> LOCATION: (26)..(31)
<223> OTHER INFORMATION: a, c, u, g, unknown or other

<400> SEQUENCE: 773
hnnnnngggd ddngngdgdn ggguknnnnn n 31

<210> SEQ ID NO 774
<211> LENGTH: 32
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (2)..(6)
<223> OTHER INFORMATION: a, c, u, g, unknown or other
<220> FEATURE:
<221> NAME/KEY: modified_base
<222> LOCATION: (14)..(14)
<223> OTHER INFORMATION: a, c, u, g, unknown or other
<220> FEATURE:
<221> NAME/KEY: modified_base
<222> LOCATION: (16)..(16)
<223> OTHER INFORMATION: a, c, u, g, unknown or other
<220> FEATURE:
<221> NAME/KEY: modified_base
<222> LOCATION: (21)..(21)
<223> OTHER INFORMATION: a, c, u, g, unknown or other
<220> FEATURE:
<221> NAME/KEY: modified_base
<222> LOCATION: (27)..(32)
<223> OTHER INFORMATION: a, c, u, g, unknown or other

<400> SEQUENCE: 774
hnnnnncggg addngngdgd ngggukn nnn nn 32

<210> SEQ ID NO 775
<211> LENGTH: 31
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(1)
<223> OTHER INFORMATION: a, c, u, g, unknown or other
<220> FEATURE:
<221> NAME/KEY: modified_base
<222> LOCATION: (3)..(5)
<223> OTHER INFORMATION: a, c, u, g, unknown or other
<220> FEATURE:
<221> NAME/KEY: modified_base
<222> LOCATION: (13)..(13)
<223> OTHER INFORMATION: a, c, u, g, unknown or other
<220> FEATURE:
<221> NAME/KEY: modified_base
<222> LOCATION: (15)..(15)
<223> OTHER INFORMATION: a, c, u, g, unknown or other
<220> FEATURE:
<221> NAME/KEY: modified_base
<222> LOCATION: (20)..(20)
<223> OTHER INFORMATION: a, c, u, g, unknown or other
<220> FEATURE:
<221> NAME/KEY: modified_base
<222> LOCATION: (27)..(29)
<223> OTHER INFORMATION: a, c, u, g, unknown or other
<220> FEATURE:
<221> NAME/KEY: modified_base
<222> LOCATION: (31)..(31)
<223> OTHER INFORMATION: a, c, u, g, unknown or other

<400> SEQUENCE: 775
ndnnnhggga rangngagan gggudrnnnh n 31

<210> SEQ ID NO 776
<211> LENGTH: 31
<212> TYPE: RNA

<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(6)
<223> OTHER INFORMATION: a, c, u, g, unknown or other
<220> FEATURE:
<221> NAME/KEY: modified_base
<222> LOCATION: (13)..(13)
<223> OTHER INFORMATION: a, c, u, g, unknown or other
<220> FEATURE:
<221> NAME/KEY: modified_base
<222> LOCATION: (15)..(15)
<223> OTHER INFORMATION: a, c, u, g, unknown or other
<220> FEATURE:
<221> NAME/KEY: modified_base
<222> LOCATION: (20)..(20)
<223> OTHER INFORMATION: a, c, u, g, unknown or other
<220> FEATURE:
<221> NAME/KEY: modified_base
<222> LOCATION: (26)..(31)
<223> OTHER INFORMATION: a, c, u, g, unknown or other

<400> SEQUENCE: 776
nnnnnngggd ddngngdgdn gggudnnnnn n 31

<210> SEQ ID NO 777
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 777
uacggguaga 10

<210> SEQ ID NO 778
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 778
uacggguaga 10

<210> SEQ ID NO 779
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 779
uacggguagu 10

<210> SEQ ID NO 780
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(7)

<223> OTHER INFORMATION: a, c, u, g, unknown or other

<400> SEQUENCE: 780 uwyggkndga 10

<210> SEQ ID NO 781
<211> LENGTH: 10
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (7)..(7)
<223> OTHER INFORMATION: a, c, u, g, unknown or other

<400> SEQUENCE: 781 uwyggkndgu 10

<210> SEQ ID NO 782
<211> LENGTH: 10
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (2)..(3)
<223> OTHER INFORMATION: a, c, u, g, unknown or other
<220> FEATURE:
<221> NAME/KEY: modified_base
<222> LOCATION: (7)..(7)
<223> OTHER INFORMATION: a, c, u, g, unknown or other

<400> SEQUENCE: 782 dnnrggnwgh 10

<210> SEQ ID NO 783
<211> LENGTH: 10
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (2)..(3)
<223> OTHER INFORMATION: a, c, u, g, unknown or other
<220> FEATURE:
<221> NAME/KEY: modified_base
<222> LOCATION: (7)..(7)
<223> OTHER INFORMATION: a, c, u, g, unknown or other

<400> SEQUENCE: 783 dnngggnwgh 10

<210> SEQ ID NO 784
<211> LENGTH: 34
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(2)
<223> OTHER INFORMATION: a, c, u, g, unknown or other
<220> FEATURE:
<221> NAME/KEY: modified_base
<222> LOCATION: (6)..(6)
<223> OTHER INFORMATION: a, c, u, g, unknown or other
<220> FEATURE:
<221> NAME/KEY: modified_base
<222> LOCATION: (9)..(9)
<223> OTHER INFORMATION: a, c, u, g, unknown or other
<220> FEATURE:
<221> NAME/KEY: modified_base
<222> LOCATION: (15)..(16)
<223> OTHER INFORMATION: a, c, u, g, unknown or other
<220> FEATURE:
<221> NAME/KEY: modified_base
<222> LOCATION: (20)..(20)
<223> OTHER INFORMATION: a, c, u, g, unknown or other
<220> FEATURE:
<221> NAME/KEY: modified_base
<222> LOCATION: (30)..(30)
<223> OTHER INFORMATION: a, c, u, g, unknown or other
<220> FEATURE:
<221> NAME/KEY: modified_base
<222> LOCATION: (33)..(34)
<223> OTHER INFORMATION: a, c, u, g, unknown or other

<400> SEQUENCE: 784
nnusanddna gwddnnrggn wghgugdhhn sann 34

<210> SEQ ID NO 785
<211> LENGTH: 33
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(2)
<223> OTHER INFORMATION: a, c, u, g, unknown or other
<220> FEATURE:
<221> NAME/KEY: modified_base
<222> LOCATION: (6)..(6)
<223> OTHER INFORMATION: a, c, u, g, unknown or other
<220> FEATURE:
<221> NAME/KEY: modified_base
<222> LOCATION: (9)..(9)
<223> OTHER INFORMATION: a, c, u, g, unknown or other
<220> FEATURE:
<221> NAME/KEY: modified_base
<222> LOCATION: (15)..(15)
<223> OTHER INFORMATION: a, c, u, g, unknown or other
<220> FEATURE:
<221> NAME/KEY: modified_base
<222> LOCATION: (19)..(19)
<223> OTHER INFORMATION: a, c, u, g, unknown or other
<220> FEATURE:
<221> NAME/KEY: modified_base
<222> LOCATION: (29)..(29)
<223> OTHER INFORMATION: a, c, u, g, unknown or other
<220> FEATURE:
<221> NAME/KEY: modified_base
<222> LOCATION: (32)..(33)
<223> OTHER INFORMATION: a, c, u, g, unknown or other

<400> SEQUENCE: 785
nnusanddna gwdhngggna gwgugdhhns ann 33

<210> SEQ ID NO 786
<211> LENGTH: 34
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(2)

<223> OTHER INFORMATION: a, c, u, g, unknown or other
<220> FEATURE:
<221> NAME/KEY: modified_base
<222> LOCATION: (6)..(6)
<223> OTHER INFORMATION: a, c, u, g, unknown or other
<220> FEATURE:
<221> NAME/KEY: modified_base
<222> LOCATION: (9)..(9)
<223> OTHER INFORMATION: a, c, u, g, unknown or other
<220> FEATURE:
<221> NAME/KEY: modified_base
<222> LOCATION: (15)..(16)
<223> OTHER INFORMATION: a, c, u, g, unknown or other
<220> FEATURE:
<221> NAME/KEY: modified_base
<222> LOCATION: (20)..(21)
<223> OTHER INFORMATION: a, c, u, g, unknown or other
<220> FEATURE:
<221> NAME/KEY: modified_base
<222> LOCATION: (27)..(27)
<223> OTHER INFORMATION: a, c, u, g, unknown or other
<220> FEATURE:
<221> NAME/KEY: modified_base
<222> LOCATION: (30)..(30)
<223> OTHER INFORMATION: a, c, u, g, unknown or other
<220> FEATURE:
<221> NAME/KEY: modified_base
<222> LOCATION: (33)..(34)
<223> OTHER INFORMATION: a, c, u, g, unknown or other

<400> SEQUENCE: 786
nnyvanddnw gwddnnrgkn nghgugnhhn vrnn 34

<210> SEQ ID NO 787
<211> LENGTH: 31
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (2)..(6)
<223> OTHER INFORMATION: a, c, u, g, unknown or other
<220> FEATURE:
<221> NAME/KEY: modified_base
<222> LOCATION: (13)..(13)
<223> OTHER INFORMATION: a, c, u, g, unknown or other
<220> FEATURE:
<221> NAME/KEY: modified_base
<222> LOCATION: (15)..(15)
<223> OTHER INFORMATION: a, c, u, g, unknown or other
<220> FEATURE:
<221> NAME/KEY: modified_base
<222> LOCATION: (20)..(20)
<223> OTHER INFORMATION: a, c, u, g, unknown or other
<220> FEATURE:
<221> NAME/KEY: modified_base
<222> LOCATION: (26)..(29)
<223> OTHER INFORMATION: a, c, u, g, unknown or other
<220> FEATURE:
<221> NAME/KEY: modified_base
<222> LOCATION: (31)..(31)
<223> OTHER INFORMATION: a, c, u, g, unknown or other

<400> SEQUENCE: 787
hnnnnngggd ddngngdgdn ggguknnnnh n 31

<210> SEQ ID NO 788
<211> LENGTH: 32
<212> TYPE: RNA
<213> ORGANISM: Artificial Sequence
<220> FEATURE:
<223> OTHER INFORMATION: Description of Artificial Sequence: Synthetic
oligonucleotide <220> FEATURE:
<221> NAME/KEY: modified_base
<222> LOCATION: (2)..(6)
<223> OTHER INFORMATION: a, c, u, g, unknown or other
<220> FEATURE:
<221> NAME/KEY: modified_base
<222> LOCATION: (14)..(14)
<223> OTHER INFORMATION: a, c, u, g, unknown or other
<220> FEATURE:
<221> NAME/KEY: modified_base
<222> LOCATION: (16)..(16)
<223> OTHER INFORMATION: a, c, u, g, unknown or other
<220> FEATURE:
<221> NAME/KEY: modified_base
<222> LOCATION: (21)..(21)
<223> OTHER INFORMATION: a, c, u, g, unknown or other
<220> FEATURE:
<221> NAME/KEY: modified_base
<222> LOCATION: (27)..(30)
<223> OTHER INFORMATION: a, c, u, g, unknown or other
<220> FEATURE:
<221> NAME/KEY: modified_base
<222> LOCATION: (32)..(32)
<223> OTHER INFORMATION: a, c, u, g, unknown or other

<400> SEQUENCE: 788
hnnnnncggg addngngdgd ngggukmnnn hn 32

<210> SEQ ID NO 789
<211> LENGTH: 31
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(1)
<223> OTHER INFORMATION: a, c, u, g, unknown or other
<220> FEATURE:
<221> NAME/KEY: modified_base
<222> LOCATION: (3)..(5)
<223> OTHER INFORMATION: a, c, u, g, unknown or other
<220> FEATURE:
<221> NAME/KEY: modified_base
<222> LOCATION: (13)..(13)
<223> OTHER INFORMATION: a, c, u, g, unknown or other
<220> FEATURE:
<221> NAME/KEY: modified_base
<222> LOCATION: (15)..(15)
<223> OTHER INFORMATION: a, c, u, g, unknown or other
<220> FEATURE:
<221> NAME/KEY: modified_base
<222> LOCATION: (20)..(20)
<223> OTHER INFORMATION: a, c, u, g, unknown or other
<220> FEATURE:
<221> NAME/KEY: modified_base
<222> LOCATION: (27)..(29)
<223> OTHER INFORMATION: a, c, u, g, unknown or other
<220> FEATURE:
<221> NAME/KEY: modified_base
<222> LOCATION: (31)..(31)
<223> OTHER INFORMATION: a, c, u, g, unknown or other

<400> SEQUENCE: 789
ndnnnhggga rangngagan gggudrnnnh n 31

<210> SEQ ID NO 790
<211> LENGTH: 31
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:

<221> NAME/KEY: modified_base
<222> LOCATION: (1)..(6)
<223> OTHER INFORMATION: a, c, u, g, unknown or other
<220> FEATURE:
<221> NAME/KEY: modified_base
<222> LOCATION: (13)..(13)
<223> OTHER INFORMATION: a, c, u, g, unknown or other
<220> FEATURE:
<221> NAME/KEY: modified_base
<222> LOCATION: (15)..(15)
<223> OTHER INFORMATION: a, c, u, g, unknown or other
<220> FEATURE:
<221> NAME/KEY: modified_base
<222> LOCATION: (20)..(20)
<223> OTHER INFORMATION: a, c, u, g, unknown or other
<220> FEATURE:
<221> NAME/KEY: modified_base
<222> LOCATION: (26)..(31)
<223> OTHER INFORMATION: a, c, u, g, unknown or other

<400> SEQUENCE: 790
nnnnnngggd ddngngdgdn gggudnnnnn n 31

<210> SEQ ID NO 791
<211> LENGTH: 39
<212> TYPE: PRT
<213> ORGANISM: Unknown
<220> FEATURE:
<223> OTHER INFORMATION: Description of Unknown:
CXCR1 sequence

<400> SEQUENCE: 791

Met Ser Asn Ile Thr Asp Pro Gln Met Trp Asp Phe Asp Asp Leu Asn
1 5 10 15

Phe Thr Gly Met Pro Pro Ala Asp Glu Asp Tyr Ser Pro Cys Met Leu
20 25 30

Glu Thr Glu Thr Leu Asn Lys
35

<210> SEQ ID NO 792
<211> LENGTH: 37
<212> TYPE: PRT
<213> ORGANISM: Unknown
<220> FEATURE:
<223> OTHER INFORMATION: Description of Unknown:
CXCR2 sequence

<400> SEQUENCE: 792

Met Glu Ser Asp Ser Phe Glu Asp Phe Trp Lys Gly Glu Asp Leu Ser
1 5 10 15

Asn Tyr Ser Tyr Ser Ser Thr Leu Pro Pro Phe Leu Leu Asp Ala Ala
20 25 30

Pro Cys Glu Pro Glu
35

<210> SEQ ID NO 793
<211> LENGTH: 76
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (21)..(55)
<223> OTHER INFORMATION: a, c, t, g, unknown or other

<400> SEQUENCE: 793

-continued gggagagtcg gtagcagtct nnnnnnnnnn nnnnnnnnnn nnnnnnnnnn nnnnntctat 60
gtggaaatgg cgctgt 76

<210> SEQ ID NO 794
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 794
gggagagtcg gtagcagtc 19

<210> SEQ ID NO 795
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 795
acagcgccat ttccacatag 20

<210> SEQ ID NO 796
<211> LENGTH: 6
<212> TYPE: PRT
<213> ORGANISM: Artificial Sequence
<220> FEATURE:
<223> OTHER INFORMATION: Description of Artificial Sequence: Synthetic 6xHis tag

<400> SEQUENCE: 796

His His His His His His
1 5

<210> SEQ ID NO 797
<211> LENGTH: 466
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 797

Met Gly Trp Ser Cys Ile Ile Leu Phe Leu Val Ala Thr Ala Thr Gly
1 5 10 15

Val His Ser Gln Val Gln Leu Val Glu Ser Gly Gly Gly Val Val Gln
20 25 30

Pro Gly Arg Ser Leu Arg Leu Ser Cys Thr Ala Ser Gly Phe Thr Phe
35 40 45

Ser His Tyr Gly Met Tyr Trp Val Arg Gln Ala Pro Gly Lys Gly Leu
50 55 60

Glu Trp Val Ala Val Ile Trp Tyr Asp Gly Ser Tyr Glu Tyr Asn Ala
65 70 75 80

Asp Ser Val Lys Gly Arg Phe Thr Ile Ser Arg Asp Asn Ser Lys Asn
85 90 95

Thr Leu Tyr Leu Gln Met Asn Ser Leu Arg Ala Glu Asp Thr Ala Val
100 105 110

Tyr Tyr Cys Ala Arg Asp Arg Val Gly Leu Phe Asp Tyr Trp Gly Gln
115 120 125

-continued

```
Gly Thr Leu Val Thr Val Ser Ser Ala Ser Thr Lys Gly Pro Ser Val
    130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Ser Leu Gly Thr Gln Thr Tyr Ile Cys Asn Val Asn His Lys
    210                 215                 220

Pro Ser Asn Thr Lys Val Asp Lys Lys Val Glu Pro Lys Ser Cys Asp
225                 230                 235                 240

Lys Thr His Thr Cys Pro Pro Cys Pro Ala Pro Glu Leu Leu Gly Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Lys Phe Asn Trp Tyr Val Asp Gly Val Glu Val His
    290                 295                 300

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
                325                 330                 335

Glu Tyr Lys Cys Lys Val Ser Asn Lys Ala Leu Pro Ala Pro Ile Glu
            340                 345                 350

Lys Thr Ile Ser Lys Ala Lys Gly Gln Pro Arg Glu Pro Gln Val Tyr
        355                 360                 365

Thr Leu Pro Pro Ser Arg Asp Glu Leu Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
    450                 455                 460

Gly Lys
465


<210> SEQ ID NO 798
<211> LENGTH: 233
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 798

Met Gly Trp Ser Cys Ile Ile Leu Phe Leu Val Ala Thr Ala Thr Gly
1               5                   10                  15
```

```
Val His Ser Glu Ile Val Leu Thr Gln Ser Pro Gly Thr Leu Ser Leu
            20                  25                  30

Ser Pro Gly Glu Arg Ala Thr Leu Ser Cys Arg Ala Ser Gln Ser Ile
        35                  40                  45

Ser Ser Ser Tyr Leu Ala Trp Tyr Gln Gln Lys Pro Gly Gln Ala Pro
    50                  55                  60

Arg Leu Leu Ile Tyr Gly Pro Ser Ser Arg Ala Thr Gly Ile Pro Asp
65                  70                  75                  80

Arg Phe Ser Gly Ser Gly Ser Gly Thr Asp Phe Thr Leu Thr Ile Ser
                85                  90                  95

Arg Leu Glu Pro Glu Asp Phe Ala Val Tyr Tyr Cys Gln Gln Tyr Ala
            100                 105                 110

Gly Ser Leu Thr Phe Gly Pro Gly Thr Lys Val Asp Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230
```

<210> SEQ ID NO 799
<211> LENGTH: 10
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 799
uacggguaga 10

<210> SEQ ID NO 800
<211> LENGTH: 10
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 800
uacggguagu 10

<210> SEQ ID NO 801
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 801
cgguagauua cggguagagu gaccg 25

<210> SEQ ID NO 802
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 802
ugaugacggu agauuacggg uagagugacc gcaucu 36

<210> SEQ ID NO 803
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 803
uuggccacag uagauuucgg ugcgugugac ugggcu 36

<210> SEQ ID NO 804
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 804
ugaugacggu agauuauggg uagagugacc gcaucu 36

<210> SEQ ID NO 805
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 805
ugaugacggu agauuacggg uagugugacc gcaucu 36

<210> SEQ ID NO 806
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 806
uuaaacaaag gagauuucgg ugcgugugcc uuguuu 36

<210> SEQ ID NO 807
<211> LENGTH: 37
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 807
ucuaguuacg ggagauuaug gugugugugc ccgaacu 37

<210> SEQ ID NO 808
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 808
ugaugacggu agauuauggg uagugugacc gcaucu 36

<210> SEQ ID NO 809
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 809
ugaugacggu agauuacggg uugagugacc gcaucu 36

<210> SEQ ID NO 810
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 810
ugaugacggu agauuacggg uagagugacc gcaucc 36

<210> SEQ ID NO 811
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 811
cgaugacggu agauuacggg uagagugacc gcaucu 36

<210> SEQ ID NO 812
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 812
uuggccacag uagauuucgg ugcgugugac ugggcc 36

<210> SEQ ID NO 813
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 813
uuggccacug uagauuucgg ugcgugugac ugggcu 36

<210> SEQ ID NO 814
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 814
ugaugacggu agauuacggg uagagugacc gcaucg 36

<210> SEQ ID NO 815
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 815
ugaugacggu agauuacggg gagagugacc gcaucu 36

<210> SEQ ID NO 816
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 816
ugaugacggu agauuacggg uagagugacc gcauca 36

<210> SEQ ID NO 817
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 817
ugggccacag uagauuucgg ugcgugugac ugggcu 36

<210> SEQ ID NO 818
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 818
ugaugacggu agauuucggg uagagugacc gcaucu 36

<210> SEQ ID NO 819
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 819
ugaugacggu agauuacggg cagagugacc gcaucu 36

<210> SEQ ID NO 820
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 820
uugaccacag uagauuucgg ugcgugugac ugggcu 36

<210> SEQ ID NO 821
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 821
agaugacggu agauuacggg uagagugacc gcaucu 36

<210> SEQ ID NO 822
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 822
ugaugacggu agauuacggg uagagugacc gcaccu 36

<210> SEQ ID NO 823
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 823
uuggccacag uagauuucgg ugcgugugac ggggcu 36

<210> SEQ ID NO 824
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 824
uuggccacag uagauuucgg ugugugugac ugggcu 36

<210> SEQ ID NO 825
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 825
uuggccacgg uagauuucgg ugcgugugac ugggcu 36

<210> SEQ ID NO 826
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 826
uuggccacag uagauuucgg ugcgugugac ugggu u 36

<210> SEQ ID NO 827
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 827
ugaugacggu agauaacggg uagagugacc gcaucu 36

<210> SEQ ID NO 828
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 828
ugaugacggu agauuacggg uagagugacu gcaucu 36

<210> SEQ ID NO 829
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 829
ugaugacggu ugauuacggg uagagugacc gcaucu 36

<210> SEQ ID NO 830
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 830
ugaugacggu agauuacggg uagaguggcc gcaucu 36

<210> SEQ ID NO 831
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 831
ugaugacggu aguuuacggg uagagugacc gcaucu 36

<210> SEQ ID NO 832

<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 832
ugaugacggu agauuacggg aagagugacc gcaucu 36

<210> SEQ ID NO 833
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 833
ugacgacggu agauuacggg uagagugacc gcaucu 36

<210> SEQ ID NO 834
<211> LENGTH: 10
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (7)..(7)
<223> OTHER INFORMATION: a, c, u, g, unknown or other

<400> SEQUENCE: 834 uwyggknwga 10

<210> SEQ ID NO 835
<211> LENGTH: 10
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (7)..(7)
<223> OTHER INFORMATION: a, c, u, g, unknown or other

<400> SEQUENCE: 835 wwyggknhgw 10

<210> SEQ ID NO 836
<211> LENGTH: 10
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 836
uacggguaga 10

<210> SEQ ID NO 837
<211> LENGTH: 10
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 837
uucggugcgu 10

<210> SEQ ID NO 838
<211> LENGTH: 10
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 838
uaugguaga 10

<210> SEQ ID NO 839
<211> LENGTH: 10
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 839
uacggguagu 10

<210> SEQ ID NO 840
<211> LENGTH: 10
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 840
uauggugugu 10

<210> SEQ ID NO 841
<211> LENGTH: 10
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 841
uacggguuga 10

<210> SEQ ID NO 842
<211> LENGTH: 10
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 842
uucggguaga 10

<210> SEQ ID NO 843
<211> LENGTH: 10
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 843
uacgggcaga 10

<210> SEQ ID NO 844
<211> LENGTH: 10
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 844
uucggugugu 10

<210> SEQ ID NO 845
<211> LENGTH: 10
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 845
aacggguaga 10

<210> SEQ ID NO 846
<211> LENGTH: 10
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 846
uacgggaaga 10

<210> SEQ ID NO 847
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 847
gggagggcaa gagacaga 18

<210> SEQ ID NO 848
<211> LENGTH: 38
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 848
tcttaatacg actcactata gggagggcaa gagacaga 38

<210> SEQ ID NO 849
<211> LENGTH: 10
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (2)..(3)
<223> OTHER INFORMATION: a, c, u, g, unknown or other
<220> FEATURE:
<221> NAME/KEY: modified_base
<222> LOCATION: (7)..(7)
<223> OTHER INFORMATION: a, c, u, g, unknown or other

<400> SEQUENCE: 849 dnnrggnwgh 10

<210> SEQ ID NO 850
<211> LENGTH: 10
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (2)..(3)
<223> OTHER INFORMATION: a, c, u, g, unknown or other
<220> FEATURE:
<221> NAME/KEY: modified_base
<222> LOCATION: (7)..(7)
<223> OTHER INFORMATION: a, c, u, g, unknown or other

<400> SEQUENCE: 850 dnngggnwgh 10

<210> SEQ ID NO 851
<211> LENGTH: 10
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 851
uacggguaga 10

<210> SEQ ID NO 852
<211> LENGTH: 10
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 852
uucggguagu 10

<210> SEQ ID NO 853
<211> LENGTH: 10
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 853
uacggguagu 10

<210> SEQ ID NO 854
<211> LENGTH: 10
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 854 uaugggguagu 10

<210> SEQ ID NO 855
<211> LENGTH: 10
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 855
uccggguagu 10

<210> SEQ ID NO 856
<211> LENGTH: 10
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 856
aacggguaga 10

<210> SEQ ID NO 857
<211> LENGTH: 10
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 857
uaaggguagu 10

<210> SEQ ID NO 858
<211> LENGTH: 10
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 858
uacgggaagu 10

<210> SEQ ID NO 859
<211> LENGTH: 10
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 859
uacgggaaga 10

<210> SEQ ID NO 860
<211> LENGTH: 10
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 860
aacggguagu 10

<210> SEQ ID NO 861
<211> LENGTH: 10
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 861
uacggggagu 10

<210> SEQ ID NO 862
<211> LENGTH: 10
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 862
uucgggaagu 10

<210> SEQ ID NO 863
<211> LENGTH: 10
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 863
uacgggcagu 10

<210> SEQ ID NO 864
<211> LENGTH: 10
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 864
uaugggaagu 10

<210> SEQ ID NO 865
<211> LENGTH: 10
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 865
uaugggcagu 10

<210> SEQ ID NO 866
<211> LENGTH: 10
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 866 uuugggguagu 10

<210> SEQ ID NO 867
<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 867
uacgggcaga 10

<210> SEQ ID NO 868
<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 868
aucggguagu 10

<210> SEQ ID NO 869
<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 869
aauggguagu 10

<210> SEQ ID NO 870
<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 870
uucgggcagu 10

<210> SEQ ID NO 871
<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 871
uacggguugu 10

<210> SEQ ID NO 872
<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 872

-continued uucggggagu 10

<210> SEQ ID NO 873
<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 873
uucggguugu 10

<210> SEQ ID NO 874
<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 874
uaugggcaga 10

<210> SEQ ID NO 875
<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 875
uaaggguaga 10

<210> SEQ ID NO 876
<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 876
uucggguaga 10

<210> SEQ ID NO 877
<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 877
uaagggcagu 10

<210> SEQ ID NO 878
<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 878
uacggggaga 10

<210> SEQ ID NO 879
<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 879 uaugggu ugu 10

<210> SEQ ID NO 880
<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 880
aacgggaaga 10

<210> SEQ ID NO 881
<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 881
uuaggguagu 10

<210> SEQ ID NO 882
<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 882
ucuggguagu 10

<210> SEQ ID NO 883
<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 883
uauggggagu 10

<210> SEQ ID NO 884
<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 884
uuuggguaga 10

<210> SEQ ID NO 885
<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 885
uaugggaaga 10

<210> SEQ ID NO 886
<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 886
uacggguuga 10

<210> SEQ ID NO 887
<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 887 uaugggtuaga 10

<210> SEQ ID NO 888
<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 888
aacgggaagu 10

<210> SEQ ID NO 889
<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 889
ucaggguagu 10

<210> SEQ ID NO 890
<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 890
aacgggcaga 10

<210> SEQ ID NO 891
<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 891
aaaggguagu 10

<210> SEQ ID NO 892
<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 892
aacggggagu 10

<210> SEQ ID NO 893
<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 893 ugugggguagu 10

<210> SEQ ID NO 894
<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 894
uaggguagu 10

<210> SEQ ID NO 895
<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 895
uaugguagc 10

<210> SEQ ID NO 896
<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 896
aacgggcagu 10

<210> SEQ ID NO 897

<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 897
uuugggcagu 10

<210> SEQ ID NO 898
<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 898
ugcggguagu 10

<210> SEQ ID NO 899
<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 899
uucggggaga 10

<210> SEQ ID NO 900
<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 900
aaugggcagu 10

<210> SEQ ID NO 901
<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 901
uucggguagc 10

<210> SEQ ID NO 902
<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 902
aaugggaagu 10

<210> SEQ ID NO 903
<211> LENGTH: 10

<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 903
uccgggcagu 10

<210> SEQ ID NO 904
<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 904
uccggguugu 10

<210> SEQ ID NO 905
<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 905
gacggguaga 10

<210> SEQ ID NO 906
<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 906
ugcggguaga 10

<210> SEQ ID NO 907
<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 907
uauggguuga 10

<210> SEQ ID NO 908
<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 908
uaaggguugu 10

<210> SEQ ID NO 909
<211> LENGTH: 10
<212> TYPE: RNA

<213> ORGANISM: Artificial Sequence
<220> FEATURE:
<223> OTHER INFORMATION: Description of Artificial Sequence: Synthetic
oligonucleotide

<400> SEQUENCE: 909
gacggguagu 10

<210> SEQ ID NO 910
<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 910
gucggguagu 10

<210> SEQ ID NO 911
<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 911
uuaggguaga 10

<210> SEQ ID NO 912
<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 912 uuggggguagu 10

<210> SEQ ID NO 913
<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 913
uucagguagu 10

<210> SEQ ID NO 914
<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 914
uuugggcaga 10

<210> SEQ ID NO 915
<211> LENGTH: 10
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 915
uacggggcgu 10

<210> SEQ ID NO 916
<211> LENGTH: 10
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 916
aacggggaga 10

<210> SEQ ID NO 917
<211> LENGTH: 10
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 917
uaugggcugu 10

<210> SEQ ID NO 918
<211> LENGTH: 10
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 918
aacggguugu 10

<210> SEQ ID NO 919
<211> LENGTH: 34
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(2)
<223> OTHER INFORMATION: a, c, u, g, unknown or other
<220> FEATURE:
<221> NAME/KEY: modified_base
<222> LOCATION: (6)..(6)
<223> OTHER INFORMATION: a, c, u, g, unknown or other
<220> FEATURE:
<221> NAME/KEY: modified_base
<222> LOCATION: (9)..(9)
<223> OTHER INFORMATION: a, c, u, g, unknown or other
<220> FEATURE:
<221> NAME/KEY: modified_base
<222> LOCATION: (15)..(16)
<223> OTHER INFORMATION: a, c, u, g, unknown or other
<220> FEATURE:
<221> NAME/KEY: modified_base
<222> LOCATION: (20)..(20)
<223> OTHER INFORMATION: a, c, u, g, unknown or other
<220> FEATURE:
<221> NAME/KEY: modified_base
<222> LOCATION: (30)..(30)
<223> OTHER INFORMATION: a, c, u, g, unknown or other
<220> FEATURE:
<221> NAME/KEY: modified_base
<222> LOCATION: (33)..(34)
<223> OTHER INFORMATION: a, c, u, g, unknown or other

<400> SEQUENCE: 919
nnusanddna gwddnnrggn wghgugdhhn sann 34

<210> SEQ ID NO 920
<211> LENGTH: 33
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(2)
<223> OTHER INFORMATION: a, c, u, g, unknown or other
<220> FEATURE:
<221> NAME/KEY: modified_base
<222> LOCATION: (6)..(6)
<223> OTHER INFORMATION: a, c, u, g, unknown or other
<220> FEATURE:
<221> NAME/KEY: modified_base
<222> LOCATION: (9)..(9)
<223> OTHER INFORMATION: a, c, u, g, unknown or other
<220> FEATURE:
<221> NAME/KEY: modified_base
<222> LOCATION: (15)..(15)
<223> OTHER INFORMATION: a, c, u, g, unknown or other
<220> FEATURE:
<221> NAME/KEY: modified_base
<222> LOCATION: (19)..(19)
<223> OTHER INFORMATION: a, c, u, g, unknown or other
<220> FEATURE:
<221> NAME/KEY: modified_base
<222> LOCATION: (29)..(29)
<223> OTHER INFORMATION: a, c, u, g, unknown or other
<220> FEATURE:
<221> NAME/KEY: modified_base
<222> LOCATION: (32)..(33)
<223> OTHER INFORMATION: a, c, u, g, unknown or other

<400> SEQUENCE: 920
nnusanddna gwdhngggna gwgugdhhns ann 33

<210> SEQ ID NO 921
<211> LENGTH: 34
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(2)
<223> OTHER INFORMATION: a, c, u, g, unknown or other
<220> FEATURE:
<221> NAME/KEY: modified_base
<222> LOCATION: (6)..(6)
<223> OTHER INFORMATION: a, c, u, g, unknown or other
<220> FEATURE:
<221> NAME/KEY: modified_base
<222> LOCATION: (9)..(9)
<223> OTHER INFORMATION: a, c, u, g, unknown or other
<220> FEATURE:
<221> NAME/KEY: modified_base
<222> LOCATION: (15)..(16)
<223> OTHER INFORMATION: a, c, u, g, unknown or other
<220> FEATURE:
<221> NAME/KEY: modified_base
<222> LOCATION: (20)..(21)
<223> OTHER INFORMATION: a, c, u, g, unknown or other
<220> FEATURE:

<221> NAME/KEY: modified_base
<222> LOCATION: (27)..(27)
<223> OTHER INFORMATION: a, c, u, g, unknown or other
<220> FEATURE:
<221> NAME/KEY: modified_base
<222> LOCATION: (30)..(30)
<223> OTHER INFORMATION: a, c, u, g, unknown or other
<220> FEATURE:
<221> NAME/KEY: modified_base
<222> LOCATION: (33)..(34)
<223> OTHER INFORMATION: a, c, u, g, unknown or other

<400> SEQUENCE: 921
nnyvanddnw gwddnnrgkn nghgugnhhn vrnn 34

<210> SEQ ID NO 922
<211> LENGTH: 37
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 922
ugaugacggu agauuacggg uagagugacc gcaucut 37

<210> SEQ ID NO 923
<211> LENGTH: 35
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 923
gaugacggua gauuacgggu agagugaccg cauct 35

<210> SEQ ID NO 924
<211> LENGTH: 35
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 924
ggcgacggua gauuacgggu agagugaccg cgcct 35

<210> SEQ ID NO 925
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 925
gcgacgguag auuacgggua gagugaccgc gct 33

<210> SEQ ID NO 926
<211> LENGTH: 37
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 926
ucaugacggu agauuacggg uagagugacc gcaugut 37

<210> SEQ ID NO 927
<211> LENGTH: 37
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 927
ugaucacggu agauuacggg uagagugacc ggaucut 37

<210> SEQ ID NO 928
<211> LENGTH: 37
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 928
ugcggacggu agauuacggg uagagugacc gccgcut 37

<210> SEQ ID NO 929
<211> LENGTH: 37
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 929
uggagacggu agauuacggg uagagugacc gcuccut 37

<210> SEQ ID NO 930
<211> LENGTH: 37
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 930
ugccgacggu agauuacggg uagagugacc gcggcut 37

<210> SEQ ID NO 931
<211> LENGTH: 37
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 931
ugcugacggu agauuacggg uagagugacc gcagcut 37

<210> SEQ ID NO 932
<211> LENGTH: 37
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 932
uggcgacggu agauuacggg uagagugacc gcgccut 37

<210> SEQ ID NO 933
<211> LENGTH: 37
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 933
ugaugacagu agauuacggg uagagugacu gcaucut 37

<210> SEQ ID NO 934
<211> LENGTH: 37
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 934
ugaugacgau agauuacggg uagagugauc gcaucut 37

<210> SEQ ID NO 935
<211> LENGTH: 37
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 935

```
ucuugacggu agauuacggg uagagugacc gcaucut                            37


<210> SEQ ID NO 936
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 936

ugaugacccu agauuacggg uagagugacc gcaucut                            37


<210> SEQ ID NO 937
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 937

gcgacguaga uuacggguag agugacgcgc t                                  31


<210> SEQ ID NO 938
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 938

gcgacggcag auuacgggua gaguggccgc gct                                33


<210> SEQ ID NO 939
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 939

gcgacgcaga uuacggguag aguggcgcgc t                                  31


<210> SEQ ID NO 940
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

<400> SEQUENCE: 940
ggcgacggua gacuacgggu agagugaccg cgcct 35

<210> SEQ ID NO 941
<211> LENGTH: 35
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 941
ggcgacggua gaucacgggu agggugaccg cgcct 35

<210> SEQ ID NO 942
<211> LENGTH: 37
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 942
ugaugacggu agauuacggg uagagugacc gcaucut 37

<210> SEQ ID NO 943
<211> LENGTH: 34
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 943
gaugcgguag auuacgggua gagugaccgc auct 34

<210> SEQ ID NO 944
<211> LENGTH: 35
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 944
gaugucggua gauuacgggu agagugaccg cauct 35

<210> SEQ ID NO 945
<211> LENGTH: 37
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 945
ugaugacggu agauuacggg uagagugacc gcaucut 37

<210> SEQ ID NO 946
<211> LENGTH: 37
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 946
ugaugacggu agauuucggg uagugugacc gcaucut 37

<210> SEQ ID NO 947
<211> LENGTH: 37
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 947
ugaugacggu agauuccggg uagugugacc gcaucut 37

<210> SEQ ID NO 948
<211> LENGTH: 37
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 948
ugaugacggu agauuacggg cagugugacc gcaucut 37

<210> SEQ ID NO 949
<211> LENGTH: 37
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 949
ugaugacggu agauuacggg gagugugacc gcaucut 37

<210> SEQ ID NO 950
<211> LENGTH: 37
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule:

Synthetic oligonucleotide

<400> SEQUENCE: 950
ugaugacggu agauuacggg aagugugacc gcaucut 37

<210> SEQ ID NO 951
<211> LENGTH: 37
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 951
ugaugacggu agauuauggg cagugugacc gcaucut 37

<210> SEQ ID NO 952
<211> LENGTH: 37
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 952
ugaugacggu agauuauggg aagugugacc gcaucut 37

<210> SEQ ID NO 953
<211> LENGTH: 37
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 953
ucaugacggu agauuucggg uagugugacc gcaugut 37

<210> SEQ ID NO 954
<211> LENGTH: 37
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 954
ucaugacggu agauuacggg uagagugacc gcaugut 37

<210> SEQ ID NO 955
<211> LENGTH: 37
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:

<223> OTHER INFORMATION: Description of Combined DNA/RNA Molecule: Synthetic oligonucleotide

<400> SEQUENCE: 955
ugaugacggu agauuacggg aagagugacc gcaucut 37

<210> SEQ ID NO 956
<211> LENGTH: 37
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 956
ugaugacggu agauuaaggg uagugugacc gcaucut 37

<210> SEQ ID NO 957
<211> LENGTH: 37
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 957
ugaugacggu agauuacggg uugugugacc gcaucut 37

<210> SEQ ID NO 958
<211> LENGTH: 37
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 958
ugaugacgau agauuucggg uagugugauc gcaucut 37

<210> SEQ ID NO 959
<211> LENGTH: 36
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 959
ugaugacggu agauuugggu agagugaccg caucut 36

<210> SEQ ID NO 960
<211> LENGTH: 37
<212> TYPE: DNA
<213> ORGANISM: Artificial Sequence
<220> FEATURE:
<223> OTHER INFORMATION: Description of Artificial Sequence: Synthetic oligonucleotide -continued
<220> FEATURE:
<223> OTHER INFORMATION: Description of Combined DNA/RNA Molecule:
Synthetic oligonucleotide

<400> SEQUENCE: 960
ugaugacggu agauaacggg uagagugacc gcaucut 37

<210> SEQ ID NO 961
<211> LENGTH: 37
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 961
ugaugacggu agauaacggg uagugugacc gcaucut 37

<210> SEQ ID NO 962
<211> LENGTH: 37
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 962
ugaugacggu agauuucggg aagugugacc gcaucut 37

<210> SEQ ID NO 963
<211> LENGTH: 37
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 963
ugaugacggu agauuauggg uagugugacc gcaucut 37

<210> SEQ ID NO 964
<211> LENGTH: 37
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 964
ugaugacggu agauuacggg uagagugacc gcaucut 37

<210> SEQ ID NO 965
<211> LENGTH: 10
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 965
ugaugacggu 10

<210> SEQ ID NO 966
<211> LENGTH: 26
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 966
gauuacgggu agagugaccg caucut 26

<210> SEQ ID NO 967
<211> LENGTH: 11
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 967
ugaugacggu a 11

<210> SEQ ID NO 968
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 968
auuacgggua gagugaccgc aucut 25

<210> SEQ ID NO 969
<211> LENGTH: 12
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 969
ugaugacggu ag 12

<210> SEQ ID NO 970
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 970
uuacggguag agugaccgca ucut 24

<210> SEQ ID NO 971
<211> LENGTH: 13
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 971
ugaugacggu aga 13

<210> SEQ ID NO 972
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 972
uacggguaga gugaccgcau cut 23

<210> SEQ ID NO 973
<211> LENGTH: 14
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 973
ugaugacggu agau 14

<210> SEQ ID NO 974
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 974
acggguagag ugaccgcauc ut 22

<210> SEQ ID NO 975
<211> LENGTH: 15
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 975
ugaugacggu agauu 15

<210> SEQ ID NO 976
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule:
Synthetic oligonucleotide

<400> SEQUENCE: 976
cggguagagu gaccgcaucu t 21

<210> SEQ ID NO 977
<211> LENGTH: 16
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 977
ugaugacggu agauua 16

<210> SEQ ID NO 978
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 978
ggguagagug accgcaucut 20

<210> SEQ ID NO 979
<211> LENGTH: 17
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 979
ugaugacggu agauuac 17

<210> SEQ ID NO 980
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 980
gguagaguga ccgcaucut 19

<210> SEQ ID NO 981
<211> LENGTH: 18
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 981
ugaugacggu agauuacg 18

<210> SEQ ID NO 982
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 982
guagagugac cgcaucut 18

<210> SEQ ID NO 983
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 983
ugaugacggu agauuacgg 19

<210> SEQ ID NO 984
<211> LENGTH: 17
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 984
uagagugacc gcaucut 17

<210> SEQ ID NO 985
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 985
ugaugacggu agauuacggg 20

<210> SEQ ID NO 986
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 986
agagugaccg caucut 16

<210> SEQ ID NO 987
<211> LENGTH: 21
<212> TYPE: RNA

<213> ORGANISM: Artificial Sequence
<220> FEATURE:
<223> OTHER INFORMATION: Description of Artificial Sequence: Synthetic
oligonucleotide

<400> SEQUENCE: 987
ugaugacggu agauuacggg u 21

<210> SEQ ID NO 988
<211> LENGTH: 15
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 988
gagugaccgc aucut 15

<210> SEQ ID NO 989
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 989
ugaugacggu agauuacggg ua 22

<210> SEQ ID NO 990
<211> LENGTH: 14
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 990
agugaccgca ucut 14

<210> SEQ ID NO 991
<211> LENGTH: 23
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 991
ugaugacggu agauuacggg uag 23

<210> SEQ ID NO 992
<211> LENGTH: 13
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 992
gugaccgcau cut 13

<210> SEQ ID NO 993
<211> LENGTH: 24
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 993
ugaugacggu agauuacggg uaga 24

<210> SEQ ID NO 994
<211> LENGTH: 12
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 994
ugaccgcauc ut 12

<210> SEQ ID NO 995
<211> LENGTH: 25
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 995
ugaugacggu agauuacggg uagag 25

<210> SEQ ID NO 996
<211> LENGTH: 11
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 996
gaccgcaucu t 11

<210> SEQ ID NO 997
<211> LENGTH: 26
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 997
ugaugacggu agauuacggg uagagu 26

<210> SEQ ID NO 998
<211> LENGTH: 10
<212> TYPE: DNA

<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 998
accgcaucut 10

<210> SEQ ID NO 999
<211> LENGTH: 15
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 999
gcgacgguag auuac 15

<210> SEQ ID NO 1000
<211> LENGTH: 17
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1000
gguagaguga ccgcgct 17

<210> SEQ ID NO 1001
<211> LENGTH: 37
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1001
ugaugacggu agauuacggg uagagugacc gcaucut 37

<210> SEQ ID NO 1002
<211> LENGTH: 37
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1002
ugaugacggu agauuacugg uagagugacc gcaucut 37

<210> SEQ ID NO 1003
<211> LENGTH: 37
<212> TYPE: DNA
<213> ORGANISM: Artificial Sequence
<220> FEATURE:

-continued

<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1003
ugaugacggu agauuaccgg uagagugacc gcaucut 37

<210> SEQ ID NO 1004
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1004
ugaugacggu agauuacagg uagagugacc gcaucut 37

<210> SEQ ID NO 1005
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1005
ugaugacggu agauuacggg uagagugacc gcaucut 37

<210> SEQ ID NO 1006
<211> LENGTH: 17
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1006
ugaugacggu agauuac 17

<210> SEQ ID NO 1007
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1007
gguagaguga ccgcaucut 19

<210> SEQ ID NO 1008
<211> LENGTH: 15
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1008
gcgacgguag auuac 15

<210> SEQ ID NO 1009
<211> LENGTH: 17
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1009
gguagaguga ccgcgct 17

<210> SEQ ID NO 1010
<211> LENGTH: 13
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1010
gaugacggua gau 13

<210> SEQ ID NO 1011
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1011
gguagaguga ccgcauct 18

<210> SEQ ID NO 1012
<211> LENGTH: 13
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1012
ggcgacggua gau 13

<210> SEQ ID NO 1013
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1013
gguagaguga ccgcgcct 18

-continued

<210> SEQ ID NO 1014
<211> LENGTH: 13
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1014
gaugacggua gau 13

<210> SEQ ID NO 1015
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1015
gguagaguga ccgcauct 18

<210> SEQ ID NO 1016
<211> LENGTH: 13
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1016
gaugacggua gau 13

<210> SEQ ID NO 1017
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1017
gguagaguga ccgcauct 18

<210> SEQ ID NO 1018
<211> LENGTH: 13
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1018
gaugacggua gau 13

<210> SEQ ID NO 1019
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide <220> FEATURE:
<223> OTHER INFORMATION: Description of Combined DNA/RNA Molecule:
Synthetic oligonucleotide

<400> SEQUENCE: 1019
gguagaguga ccgcauct 18

<210> SEQ ID NO 1020
<211> LENGTH: 13
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1020
gaugacggua gau 13

<210> SEQ ID NO 1021
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1021
gguagaguga ccgcauct 18

<210> SEQ ID NO 1022
<211> LENGTH: 13
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1022
gaugacggua gau 13

<210> SEQ ID NO 1023
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1023
gguagaguga ccgcauct 18

<210> SEQ ID NO 1024
<211> LENGTH: 13
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1024
gaugacggua gau 13

<210> SEQ ID NO 1025
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1025
gguagaguga ccgcauct 18

<210> SEQ ID NO 1026
<211> LENGTH: 13
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1026
gaugacggua gau 13

<210> SEQ ID NO 1027
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1027
gguagaguga ccgcauct 18

<210> SEQ ID NO 1028
<211> LENGTH: 13
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1028
gaugacggua gau 13

<210> SEQ ID NO 1029
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1029
gguagaguga ccgcauct 18

<210> SEQ ID NO 1030
<211> LENGTH: 37
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1030
ugaugacggu agauuacggg uagagugacc gcaucut 37

<210> SEQ ID NO 1031
<211> LENGTH: 37
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1031
ugaugacggu agauuucggg uagugugacc gcaucut 37

<210> SEQ ID NO 1032
<211> LENGTH: 35
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1032
gaugacggua gauuucgggu agugugaccg cauct 35

<210> SEQ ID NO 1033
<211> LENGTH: 35
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1033
ggcgacggua gauuucgggu agugugaccg cgcct 35

<210> SEQ ID NO 1034
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1034
gcgacgguag auuucgggua gugugaccgc gct 33

<210> SEQ ID NO 1035
<211> LENGTH: 16
<212> TYPE: RNA

<213> ORGANISM: Artificial Sequence
<220> FEATURE:
<223> OTHER INFORMATION: Description of Artificial Sequence: Synthetic
oligonucleotide

<400> SEQUENCE: 1035
gaugacggua gauuuc 16

<210> SEQ ID NO 1036
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1036
gguaguguga ccgcauct 18

<210> SEQ ID NO 1037
<211> LENGTH: 37
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1037
ugaugacggu agauuauggg cagugugacc gcaucut 37

<210> SEQ ID NO 1038
<211> LENGTH: 35
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1038
gaugacggua gauuaugggc agugugaccg cauct 35

<210> SEQ ID NO 1039
<211> LENGTH: 35
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1039
ggcgacggua gauuaugggc agugugaccg cgcct 35

<210> SEQ ID NO 1040
<211> LENGTH: 33
<212> TYPE: DNA
<213> ORGANISM: Artificial Sequence
<220> FEATURE:

<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1040
gcgacgguag auuaugggca gugugaccgc gct 33

<210> SEQ ID NO 1041
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1041
gaugacggua gauuau 16

<210> SEQ ID NO 1042
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1042
ggcaguguga ccgcauct 18

<210> SEQ ID NO 1043
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1043
ugaugacggu agauuauggg aagugugacc gcaucut 37

<210> SEQ ID NO 1044
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1044
gaugacggua gauuauggga agugugaccg cauct 35

<210> SEQ ID NO 1045
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide <220> FEATURE:
<223> OTHER INFORMATION: Description of Combined DNA/RNA Molecule:
Synthetic oligonucleotide

<400> SEQUENCE: 1045
ggcgacggua gauuauggga agugugaccg cgcct 35

<210> SEQ ID NO 1046
<211> LENGTH: 33
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1046 gcgacggua g auuaugggaa gugugaccgc gct 33

<210> SEQ ID NO 1047
<211> LENGTH: 16
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1047
gaugacggua gauuau 16

<210> SEQ ID NO 1048
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1048
ggaaguguga ccgcauct 18

<210> SEQ ID NO 1049
<211> LENGTH: 37
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1049
ugaugacggu agauuacggg uagagugacc gcaucut 37

<210> SEQ ID NO 1050
<211> LENGTH: 35
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:

Synthetic oligonucleotide

<400> SEQUENCE: 1050
ggcgacggua gauuucgggu agugugaccg cgcct 35

<210> SEQ ID NO 1051
<211> LENGTH: 35
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1051
ggcgacggua gauuuugggu agugugaccg cgcct 35

<210> SEQ ID NO 1052
<211> LENGTH: 35
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1052
ggcgacggua gauuaugggc agugugaccg cgcct 35

<210> SEQ ID NO 1053
<211> LENGTH: 35
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1053
ggcgacggua gauuuugggc agugugaccg cgcct 35

<210> SEQ ID NO 1054
<211> LENGTH: 35
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1054
ggcgacggua gauuaugggc agugugaccg cgcct 35

<210> SEQ ID NO 1055
<211> LENGTH: 35
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:

<223> OTHER INFORMATION: Description of Combined DNA/RNA Molecule:
Synthetic oligonucleotide

<400> SEQUENCE: 1055
ggcgacggua gauuaugggc agugugaccg cgcct 35

<210> SEQ ID NO 1056
<211> LENGTH: 35
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1056
ggcgacggua gauuaugggc agugugaccg cgcct 35

<210> SEQ ID NO 1057
<211> LENGTH: 35
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1057
ggcgacggua gauuaugggc agugugaccg cgcct 35

<210> SEQ ID NO 1058
<211> LENGTH: 35
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1058
ggcgacggua gauuaugggc agugugaccg cgcct 35

<210> SEQ ID NO 1059
<211> LENGTH: 35
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1059
ggcgacggua gauuaugggc agugugaccg cgcct 35

<210> SEQ ID NO 1060
<211> LENGTH: 35
<212> TYPE: DNA
<213> ORGANISM: Artificial Sequence
<220> FEATURE:
<223> OTHER INFORMATION: Description of Artificial Sequence: Synthetic
oligonucleotide <220> FEATURE:
<223> OTHER INFORMATION: Description of Combined DNA/RNA Molecule:
Synthetic oligonucleotide

<400> SEQUENCE: 1060
ggcgacggua gauuaugggc agugugaccg cgcct 35

<210> SEQ ID NO 1061
<211> LENGTH: 35
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1061
ggcgacggua gauuaugggc agugugaccg cgcct 35

<210> SEQ ID NO 1062
<211> LENGTH: 35
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1062
ggcgacggua gauuaugggc agugugaccg cgcct 35

<210> SEQ ID NO 1063
<211> LENGTH: 35
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1063
ggcgacggua gauuaugggc agugugaccg cgcct 35

<210> SEQ ID NO 1064
<211> LENGTH: 35
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1064
ggcgacggua gauuaugggc agugugaccg cgcct 35

<210> SEQ ID NO 1065
<211> LENGTH: 35
<212> TYPE: DNA
<213> ORGANISM: Artificial Sequence
<220> FEATURE:
<223> OTHER INFORMATION: Description of Artificial Sequence: Synthetic

```
      oligonucleotide
<220> FEATURE:
<223> OTHER INFORMATION: Description of Combined DNA/RNA Molecule:
      Synthetic oligonucleotide

<400> SEQUENCE: 1065

ggcgacggua gauuaugggc agugugaccg cgcct                            35


<210> SEQ ID NO 1066
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1066

ggcgacggua gauuaugggc agugugaccg cgcct                            35


<210> SEQ ID NO 1067
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1067

ggcgacggua gauuaugggc agugugaccg cgcct                            35


<210> SEQ ID NO 1068
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1068

ggcgacggua gauuaugggc agugugaccg cgcct                            35


<210> SEQ ID NO 1069
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1069

ggcgacggua gauuaugggc agugugaccg cgcct                            35


<210> SEQ ID NO 1070
<211> LENGTH: 35
<212> TYPE: DNA
<213> ORGANISM: Artificial Sequence
<220> FEATURE:
```

<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1070
ggcgacggua gauuaugggc agugugaccg cgcct 35

<210> SEQ ID NO 1071
<211> LENGTH: 35
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1071
ggcgacggua gauuaugggc agugugaccg cgcct 35

<210> SEQ ID NO 1072
<211> LENGTH: 35
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1072
ggcgacggua gauuaugggc agugugaccg cgcct 35

<210> SEQ ID NO 1073
<211> LENGTH: 35
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1073
ggcgacggua gauuaugggc agugugaccg cgcct 35

<210> SEQ ID NO 1074
<211> LENGTH: 35
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1074
ggcgacggua gauuaugggc agugugaccg cgcct 35

<210> SEQ ID NO 1075
<211> LENGTH: 35
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1075
ggcgacggua gauuaugggc agugugaccg cgcct 35

<210> SEQ ID NO 1076
<211> LENGTH: 35
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1076
ggcgacggua gauuaugggc agugugaccg cgcct 35

<210> SEQ ID NO 1077
<211> LENGTH: 35
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1077
ggcgacggua gauuaugggc agugugaccg cgcct 35

<210> SEQ ID NO 1078
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1078
gcgacgguag auuaugggca gugugaccgc gct 33

<210> SEQ ID NO 1079
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1079
gcgacgguag auuaugggca gugugaccgc gct 33

<210> SEQ ID NO 1080
<211> LENGTH: 35
<212> TYPE: DNA

<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1080
ggcgacggua gauuucgggu agugugaccg cgcct 35

<210> SEQ ID NO 1081
<211> LENGTH: 35
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1081
ggcgacggua gauuucgggu agugugaccg cgcct 35

<210> SEQ ID NO 1082
<211> LENGTH: 35
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1082
ggcgacggua gauuucgggu agugugaccg cgcct 35

<210> SEQ ID NO 1083
<211> LENGTH: 35
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1083
ggcgacggua gauuucgggu agugugaccg cgcct 35

<210> SEQ ID NO 1084
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1084
gcgacgguag auuucgggua gugugaccgc gct 33

<210> SEQ ID NO 1085
<211> LENGTH: 33

<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1085
gcgacgguag auuucgggua gugugaccgc gct 33

<210> SEQ ID NO 1086
<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1086
aacggguugu 10

<210> SEQ ID NO 1087
<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1087
uaaggguugu 10

<210> SEQ ID NO 1088
<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1088
uucggguugu 10

<210> SEQ ID NO 1089
<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1089
uccggguugu 10

<210> SEQ ID NO 1090
<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1090
uacggggcgu 10

<210> SEQ ID NO 1091
<211> LENGTH: 10
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1091
uauggguagc 10

<210> SEQ ID NO 1092
<211> LENGTH: 34
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(2)
<223> OTHER INFORMATION: a, c, u, g, unknown or other
<220> FEATURE:
<221> NAME/KEY: modified_base
<222> LOCATION: (6)..(6)
<223> OTHER INFORMATION: a, c, u, g, unknown or other
<220> FEATURE:
<221> NAME/KEY: modified_base
<222> LOCATION: (9)..(9)
<223> OTHER INFORMATION: a, c, u, g, unknown or other
<220> FEATURE:
<221> NAME/KEY: modified_base
<222> LOCATION: (15)..(16)
<223> OTHER INFORMATION: a, c, u, g, unknown or other
<220> FEATURE:
<221> NAME/KEY: modified_base
<222> LOCATION: (20)..(21)
<223> OTHER INFORMATION: a, c, u, g, unknown or other
<220> FEATURE:
<221> NAME/KEY: modified_base
<222> LOCATION: (27)..(27)
<223> OTHER INFORMATION: a, c, u, g, unknown or other
<220> FEATURE:
<221> NAME/KEY: modified_base
<222> LOCATION: (30)..(30)
<223> OTHER INFORMATION: a, c, u, g, unknown or other
<220> FEATURE:
<221> NAME/KEY: modified_base
<222> LOCATION: (33)..(34)
<223> OTHER INFORMATION: a, c, u, g, unknown or other

<400> SEQUENCE: 1092
nnyvanddnw gwddnnrgkn nghgugnhhn vrnn 34

<210> SEQ ID NO 1093
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1093
gggaaaugug agaugggguu 19

<210> SEQ ID NO 1094
<211> LENGTH: 35
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1094
uacgguggga aaugugagau ggguugccgu auuuu 35

<210> SEQ ID NO 1095
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1095
uaaucgcugg gaaaugggag augguuggc gauuau 36

<210> SEQ ID NO 1096
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1096
ugggcauggg aaaugugaga uggguugugc ucaagu 36

<210> SEQ ID NO 1097
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1097
ugauagcaag ugggaaaugu gagaugggcuu acuugu 36

<210> SEQ ID NO 1098
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1098
uagucacggg aaaagugaga uggguguggac guguuu 36

<210> SEQ ID NO 1099
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1099
uaaucaccgg ugggaaaugu gagaagggug gccggu 36

<210> SEQ ID NO 1100
<211> LENGTH: 36
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:

Synthetic oligonucleotide

<400> SEQUENCE: 1100
uacgguggga aaugugagau ggguugccgt attttt 36

<210> SEQ ID NO 1101
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1101
uugugccaug ggaaauguga gaugggguuau gucacu 36

<210> SEQ ID NO 1102
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1102
ugaccgggaa augugagaug gguggucagc auaaau 36

<210> SEQ ID NO 1103
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1103
uaauuagcug cgggaaaugg gagaugggguu gcggcu 36

<210> SEQ ID NO 1104
<211> LENGTH: 35
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1104
uacgguggga uaugugagau ggguugccgu auuuu 35

<210> SEQ ID NO 1105
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1105
uaacauacgg gaaacgugag aaggguguau guuauu 36

<210> SEQ ID NO 1106
<211> LENGTH: 35
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1106
uacgguggga aaugugagau ggguugccgu uuuuu 35

<210> SEQ ID NO 1107
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1107
uuugagagca gcgggaaaug ugagaugggu guugcu 36

<210> SEQ ID NO 1108
<211> LENGTH: 35
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1108
uacgguggga aaugugagau ggguugccgu auuuc 35

<210> SEQ ID NO 1109
<211> LENGTH: 35
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1109
uacgguggga aaugcgagau ggguugccgu auuuu 35

<210> SEQ ID NO 1110
<211> LENGTH: 35
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1110
uacggcggga aaugugagau ggguugccgu auuuu 35

<210> SEQ ID NO 1111
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1111
uuggccuggg aaaugugaga aggguuaggc uauuau 36

<210> SEQ ID NO 1112
<211> LENGTH: 35
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1112
uacgguggga aaugugagau ggguugccgu auucu 35

<210> SEQ ID NO 1113
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1113
ucguuucggg aaaugugaga ugggugaagc gauaau 36

<210> SEQ ID NO 1114
<211> LENGTH: 35
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1114
uacgguggga aaugugaggu ggguugccgu auuuu 35

<210> SEQ ID NO 1115
<211> LENGTH: 35
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1115
uacgguggga aacgugagau ggguugccgu auuuu 35

<210> SEQ ID NO 1116
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1116
ucuuugggug ggaaauguga gacggguugc ccaaau 36

<210> SEQ ID NO 1117
<211> LENGTH: 35
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1117
uucgguggga aaugugagau ggguugccgu auuuu 35

<210> SEQ ID NO 1118
<211> LENGTH: 35
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1118
uacgguggga aaugugggau ggguugccgu auuuu 35

<210> SEQ ID NO 1119
<211> LENGTH: 35
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1119
uacgguggga auugugagau ggguugccgu auuuu 35

<210> SEQ ID NO 1120
<211> LENGTH: 35
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1120
uacgguggga aaugugugau ggguugccgu auuuu 35

<210> SEQ ID NO 1121
<211> LENGTH: 35
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1121
ugcgguggga aaugugagau ggguugccgu auuuu 35

<210> SEQ ID NO 1122
<211> LENGTH: 37
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1122
uacgguggga aaugugagau ggguugccgu auuuuuu 37

<210> SEQ ID NO 1123
<211> LENGTH: 35
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1123
uacgguggga aaugugagau ggguugccgu auuug 35

<210> SEQ ID NO 1124
<211> LENGTH: 35
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1124
uacgguggga aaggugagau ggguugccgu auuuu 35

<210> SEQ ID NO 1125
<211> LENGTH: 35
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1125
uacgguggga aaugggagau ggguugccgu auuuu 35

<210> SEQ ID NO 1126
<211> LENGTH: 35
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1126
uacgguggga aaugugagau ggguugccgu auuau 35

<210> SEQ ID NO 1127
<211> LENGTH: 35
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1127
uacgggggga aaugugagau ggguugccgu auuuu 35

<210> SEQ ID NO 1128
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1128
uuccagcggg aaaugugaga uggguugcug ggucua 36

<210> SEQ ID NO 1129
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1129
ugagcauggg aaaugugaga uggguugugc ucaagu 36

<210> SEQ ID NO 1130
<211> LENGTH: 35
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1130
uaugguggga aaugugagau ggguugccgu auuuu 35

<210> SEQ ID NO 1131
<211> LENGTH: 35
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1131
uacgguggga aaugugagau ggguugccgu aucuu 35

<210> SEQ ID NO 1132
<211> LENGTH: 35
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1132
uacgguggga aaugugagau ggguugccgu auugu 35

<210> SEQ ID NO 1133
<211> LENGTH: 35
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1133
uacgguggga aaugugagau ggguugccgu acuuu 35

<210> SEQ ID NO 1134
<211> LENGTH: 35
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1134
uacgguggga aaugugaguu ggguugccgu auuuu 35

<210> SEQ ID NO 1135
<211> LENGTH: 35
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1135
uacgauggga aaugugagau ggguugccgu auuuu 35

<210> SEQ ID NO 1136
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1136
uuucguucgg cgggaaaagu gagaugggug ccgauu 36

<210> SEQ ID NO 1137
<211> LENGTH: 35
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1137
uacggugggg aaugugagau ggguugccgu auuuu 35

<210> SEQ ID NO 1138
<211> LENGTH: 35
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1138
uacgguggga agugugagau ggguugccgu auuuu 35

<210> SEQ ID NO 1139
<211> LENGTH: 35
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1139
uacggugggu aaugugagau ggguugccgu auuuu 35

<210> SEQ ID NO 1140
<211> LENGTH: 35
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1140
uacaguggga aaugugagau ggguugccgu auuuu 35

<210> SEQ ID NO 1141
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1141
ugcccgggaa augugagaug gguugggcaa aucauu 36

<210> SEQ ID NO 1142
<211> LENGTH: 35
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1142
uacgguggga aaugugagau ggguugccgu guuuu 35

<210> SEQ ID NO 1143
<211> LENGTH: 35
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1143
uacgguggga aaugugagag ggguugccgu auuuu 35

<210> SEQ ID NO 1144
<211> LENGTH: 35
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1144
uacgguggga gaugugagau ggguugccgu auuuu 35

<210> SEQ ID NO 1145
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1145
ugggcauggg aaaugugaga uggguugugc ucaugu 36

<210> SEQ ID NO 1146
<211> LENGTH: 35
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1146
uacgguggga aaugugagac ggguugccgu auuuu 35

<210> SEQ ID NO 1147
<211> LENGTH: 36
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1147
uuucuucaag cgggaaauga gagaugggug cuugau 36

<210> SEQ ID NO 1148
<211> LENGTH: 35
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1148
uacgguggga aaugugagau ggguggccgu auuuu 35

<210> SEQ ID NO 1149

<211> LENGTH: 35
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1149
uacgguggga aaugugagau ggguugccgc auuuu 35

<210> SEQ ID NO 1150
<211> LENGTH: 35
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1150
uacgguggga aaagugagau ggguugccgu auuuu 35

<210> SEQ ID NO 1151
<211> LENGTH: 35
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1151
uacgguggga aaugugagau ggguugccau auuuu 35

<210> SEQ ID NO 1152
<211> LENGTH: 31
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(1)
<223> OTHER INFORMATION: a, c, u, g, unknown or other
<220> FEATURE:
<221> NAME/KEY: modified_base
<222> LOCATION: (3)..(5)
<223> OTHER INFORMATION: a, c, u, g, unknown or other
<220> FEATURE:
<221> NAME/KEY: modified_base
<222> LOCATION: (13)..(13)
<223> OTHER INFORMATION: a, c, u, g, unknown or other
<220> FEATURE:
<221> NAME/KEY: modified_base
<222> LOCATION: (15)..(15)
<223> OTHER INFORMATION: a, c, u, g, unknown or other
<220> FEATURE:
<221> NAME/KEY: modified_base
<222> LOCATION: (20)..(20)
<223> OTHER INFORMATION: a, c, u, g, unknown or other
<220> FEATURE:
<221> NAME/KEY: modified_base
<222> LOCATION: (27)..(29)
<223> OTHER INFORMATION: a, c, u, g, unknown or other
<220> FEATURE:
<221> NAME/KEY: modified_base
<222> LOCATION: (31)..(31)
<223> OTHER INFORMATION: a, c, u, g, unknown or other

<400> SEQUENCE: 1152
ndnnnhggga rangngagan gggudrnnnh n 31

<210> SEQ ID NO 1153
<211> LENGTH: 31
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (1)..(6)
<223> OTHER INFORMATION: a, c, u, g, unknown or other
<220> FEATURE:
<221> NAME/KEY: modified_base
<222> LOCATION: (13)..(13)
<223> OTHER INFORMATION: a, c, u, g, unknown or other
<220> FEATURE:
<221> NAME/KEY: modified_base
<222> LOCATION: (15)..(15)
<223> OTHER INFORMATION: a, c, u, g, unknown or other
<220> FEATURE:
<221> NAME/KEY: modified_base
<222> LOCATION: (20)..(20)
<223> OTHER INFORMATION: a, c, u, g, unknown or other
<220> FEATURE:
<221> NAME/KEY: modified_base
<222> LOCATION: (26)..(31)
<223> OTHER INFORMATION: a, c, u, g, unknown or other

<400> SEQUENCE: 1153
nnnnnngggd ddngngdgdn gggudnnnnn n 31

<210> SEQ ID NO 1154
<211> LENGTH: 36
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1154
uacgguggga aaugugagau ggguugccgu auuuut 36

<210> SEQ ID NO 1155
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1155
gcggugggaa atgtgagatg ggttgccgct 30

<210> SEQ ID NO 1156
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1156
cggugggaaa ugugagaugg guugccgt 28

<210> SEQ ID NO 1157
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1157
cugugggaaa ugugagaugg guugcagt 28

<210> SEQ ID NO 1158
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1158
cgcugggaaa ugugagaugg guuggcgt 28

<210> SEQ ID NO 1159
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1159
cgaugggaaa ugugagaugg guugucgt 28

<210> SEQ ID NO 1160
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1160
cggcgggaaa ugugagaugg guugccgt 28

<210> SEQ ID NO 1161
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1161
cggugggaaa ugugagaugg guuaccgt 28

<210> SEQ ID NO 1162
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1162
caaugggaaa ugugagaugg guugccgt 28

<210> SEQ ID NO 1163
<211> LENGTH: 36
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1163
uacgguggga aaugugagau ggguugccgu auuuut 36

<210> SEQ ID NO 1164
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1164
cggugggaaa ugugagaugg guugccgt 28

<210> SEQ ID NO 1165
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1165
cggugggaaa ucugagaugg guugccgt 28

<210> SEQ ID NO 1166
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1166
cggugggaaa uaugagaugg guugccgt 28

<210> SEQ ID NO 1167
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1167
cggugggaaa uuugagaugg guugccgt 28

<210> SEQ ID NO 1168
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1168
cggugggaaa ugcgagaugg guugccgt 28

<210> SEQ ID NO 1169
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1169
cggugggaaa cgugagaugg guugccgt 28

<210> SEQ ID NO 1170
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1170
cggugggaaa agugagaugg guugccgt 28

<210> SEQ ID NO 1171
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1171
cggugggaaa cgcgagaugg guugccgt 28

<210> SEQ ID NO 1172
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1172
cggugggaca cgcgagaugg guggccgt 28

<210> SEQ ID NO 1173
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1173
cggugggaaa ccugagaugg guugccgt 28

<210> SEQ ID NO 1174
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1174
cggugggaaa cccgagaugg guugccgt 28

<210> SEQ ID NO 1175
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1175
cggugggaca cccgagaugg guggccgt 28

<210> SEQ ID NO 1176
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1176
cggugggaac ugugagaugg ggugccgt 28

<210> SEQ ID NO 1177
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1177
cggugggaac cgugagaugg ggugccgt 28

<210> SEQ ID NO 1178
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1178
cggugggaaa ugugagaugg gaugccgt 28

<210> SEQ ID NO 1179
<211> LENGTH: 36
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1179
uacgguggga aaugugagau ggguugccgu auuuut 36

<210> SEQ ID NO 1180
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1180
cggugggaaa ugugagaugg guugccgt 28

<210> SEQ ID NO 1181
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule:

Synthetic oligonucleotide

<400> SEQUENCE: 1181
cggucggaaa ugugagaugg guugccgt 28

<210> SEQ ID NO 1182
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1182
cgguaggaaa ugugagaugg guugccgt 28

<210> SEQ ID NO 1183
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1183
cgguuggaaa ugugagaugg guugccgt 28

<210> SEQ ID NO 1184
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1184
cggugcgaaa ugugagaugg guugccgt 28

<210> SEQ ID NO 1185
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1185
cggugagaaa ugugagaugg guugccgt 28

<210> SEQ ID NO 1186
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:

<223> OTHER INFORMATION: Description of Combined DNA/RNA Molecule: Synthetic oligonucleotide

<400> SEQUENCE: 1186
cggugugaaa ugugagaugg guugccgt 28

<210> SEQ ID NO 1187
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1187
cgguggcaaa ugugagaugg guugccgt 28

<210> SEQ ID NO 1188
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1188
cgguggaaaa ugugagaugg guugccgt 28

<210> SEQ ID NO 1189
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1189
cggugguaaa ugugagaugg guugccgt 28

<210> SEQ ID NO 1190
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1190 cgguggcaa ugugagaugg guugccgt 28

<210> SEQ ID NO 1191
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule:
Synthetic oligonucleotide

<400> SEQUENCE: 1191
cgguggggaa ugugagaugg guugccgt 28

<210> SEQ ID NO 1192
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1192 cggugggua ugugagaugg guugccgt 28

<210> SEQ ID NO 1193
<211> LENGTH: 36
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1193
uacgguggga aaugugagau ggguugccgu auuuut 36

<210> SEQ ID NO 1194
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1194
cggugggaaa ugugagaugg guugccgt 28

<210> SEQ ID NO 1195
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1195
cggugggaaa ugucagaugg guugccgt 28

<210> SEQ ID NO 1196
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule:
Synthetic oligonucleotide

<400> SEQUENCE: 1196
cggugggaaa uguaagaugg guugccgt 28

<210> SEQ ID NO 1197
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1197
cggugggaaa uguuagaugg guugccgt 28

<210> SEQ ID NO 1198
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1198
cggugggaaa ugugcgaugg guugccgt 28

<210> SEQ ID NO 1199
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1199
cggugggaaa ugugggaugg guugccgt 28

<210> SEQ ID NO 1200
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1200
cggugggaaa ugugugaugg guugccgt 28

<210> SEQ ID NO 1201
<211> LENGTH: 28
<212> TYPE: DNA
<213> ORGANISM: Artificial Sequence
<220> FEATURE:

<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1201
cggugggaaa ugugacaugg guugccgt 28

<210> SEQ ID NO 1202
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1202
cggugggaaa ugugaaaugg guugccgt 28

<210> SEQ ID NO 1203
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1203
cggugggaaa ugugauaugg guugccgt 28

<210> SEQ ID NO 1204
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1204
cggugggaaa ugugagcugg guut 24

<210> SEQ ID NO 1205
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1205
cggugggaaa ugugaggugg guugccgt 28

<210> SEQ ID NO 1206
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1206
cggugggaaa ugugaguugg guugccgt 28

<210> SEQ ID NO 1207
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1207
cggugggaaa ugugagaggg guugccgt 28

<210> SEQ ID NO 1208
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1208
cggugggaaa ugugagacgg guugccgt 28

<210> SEQ ID NO 1209
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1209
cggugggaaa ugugagaagg guugccgt 28

<210> SEQ ID NO 1210
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1210
gcggugggaa atgtgagatg ggttgccgct 30

<210> SEQ ID NO 1211
<211> LENGTH: 30
<212> TYPE: DNA

<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1211
gcggugggaa augugagaug gguugccgct 30

<210> SEQ ID NO 1212
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1212
gcggugggaa augugagaug gguugccgct 30

<210> SEQ ID NO 1213
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1213
gcggugggaa augugagaug gguugccgct 30

<210> SEQ ID NO 1214
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1214
gcggugggaa augugagaug gguugccgct 30

<210> SEQ ID NO 1215
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 1215
gcggugggaa augugagaug gguugccgct 30

<210> SEQ ID NO 1216
<211> LENGTH: 30

<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1216
gcggugggaa augugagaug gguugccgct 30

<210> SEQ ID NO 1217
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1217
gcggugggaa augugagaug gguugccgct 30

<210> SEQ ID NO 1218
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1218
gcggugggaa augugagaug gguugccgct 30

<210> SEQ ID NO 1219
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1219
gcggugggaa augugagaug gguugccgct 30

<210> SEQ ID NO 1220
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1220
gcggugggaa augugagaug gguugccgct 30

<210> SEQ ID NO 1221

<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1221
gcggugggaa augugagaug gguugccgct 30

<210> SEQ ID NO 1222
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1222
gcggugggaa augugagaug gguugccgct 30

<210> SEQ ID NO 1223
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1223
gcggugggaa augugagaug gguugccgct 30

<210> SEQ ID NO 1224
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1224
gcggugggaa augugagaug gguugccgct 30

<210> SEQ ID NO 1225
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1225
gcggugggaa augugagaug gguugccgct 30

<210> SEQ ID NO 1226
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1226
gcggugggaa augugagaug gguugccgct 30

<210> SEQ ID NO 1227
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1227
gcggugggaa augugagaug gguugccgct 30

<210> SEQ ID NO 1228
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1228
gcggugggaa augugagaug gguugccgct 30

<210> SEQ ID NO 1229
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1229
gcggugggaa augugagaug gguugccgct 30

<210> SEQ ID NO 1230
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1230
gcggugggaa augugagaug gguugccgct 30

-continued

<210> SEQ ID NO 1231
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1231
gcggugggaa augugagaug gguugccgct 30

<210> SEQ ID NO 1232
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1232
gcggugggaa augugagaug gguugccgct 30

<210> SEQ ID NO 1233
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1233
gcggugggaa augugagaug gguugccgct 30

<210> SEQ ID NO 1234
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1234
cggugggaaa cgugagaugg guugccgt 28

<210> SEQ ID NO 1235
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 1235
cggugggaaa cgugagaugg guugccgt 28

<210> SEQ ID NO 1236
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1236
cggugggaaa cgugagaugg guugccgt 28

<210> SEQ ID NO 1237
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1237
cggugggaaa cgugagaugg guugccgt 28

<210> SEQ ID NO 1238
<211> LENGTH: 35
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1238
uacgguggga aaugugagau ggguugccgu auuuu 35

<210> SEQ ID NO 1239
<211> LENGTH: 32
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(6)
<223> OTHER INFORMATION: a, c, u, g, unknown or other
<220> FEATURE:
<221> NAME/KEY: modified_base
<222> LOCATION: (14)..(14)
<223> OTHER INFORMATION: a, c, u, g, unknown or other
<220> FEATURE:
<221> NAME/KEY: modified_base
<222> LOCATION: (16)..(16)
<223> OTHER INFORMATION: a, c, u, g, unknown or other
<220> FEATURE:
<221> NAME/KEY: modified_base
<222> LOCATION: (21)..(21)
<223> OTHER INFORMATION: a, c, u, g, unknown or other
<220> FEATURE:
<221> NAME/KEY: modified_base
<222> LOCATION: (27)..(32)
<223> OTHER INFORMATION: a, c, u, g, unknown or other

<400> SEQUENCE: 1239
hnnnnncggg dddngngdgd ngggukmnnn nn 32

<210> SEQ ID NO 1240
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1240
uacgguggga aaugugagau ggguugccgu auuuuu 36

<210> SEQ ID NO 1241
<211> LENGTH: 31
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(1)
<223> OTHER INFORMATION: a, c, u, g, unknown or other
<220> FEATURE:
<221> NAME/KEY: modified_base
<222> LOCATION: (3)..(5)
<223> OTHER INFORMATION: a, c, u, g, unknown or other
<220> FEATURE:
<221> NAME/KEY: modified_base
<222> LOCATION: (13)..(13)
<223> OTHER INFORMATION: a, c, u, g, unknown or other
<220> FEATURE:
<221> NAME/KEY: modified_base
<222> LOCATION: (15)..(15)
<223> OTHER INFORMATION: a, c, u, g, unknown or other
<220> FEATURE:
<221> NAME/KEY: modified_base
<222> LOCATION: (20)..(20)
<223> OTHER INFORMATION: a, c, u, g, unknown or other
<220> FEATURE:
<221> NAME/KEY: modified_base
<222> LOCATION: (27)..(29)
<223> OTHER INFORMATION: a, c, u, g, unknown or other
<220> FEATURE:
<221> NAME/KEY: modified_base
<222> LOCATION: (31)..(31)
<223> OTHER INFORMATION: a, c, u, g, unknown or other

<400> SEQUENCE: 1241
ndnnnhggga rangngagan gggudrnnnh n 31

<210> SEQ ID NO 1242
<211> LENGTH: 32
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(6)
<223> OTHER INFORMATION: a, c, u, g, unknown or other
<220> FEATURE:
<221> NAME/KEY: modified_base
<222> LOCATION: (14)..(14)
<223> OTHER INFORMATION: a, c, u, g, unknown or other
<220> FEATURE:
<221> NAME/KEY: modified_base
<222> LOCATION: (16)..(16)
<223> OTHER INFORMATION: a, c, u, g, unknown or other
<220> FEATURE:
<221> NAME/KEY: modified_base
<222> LOCATION: (21)..(21)
<223> OTHER INFORMATION: a, c, u, g, unknown or other
<220> FEATURE:

<221> NAME/KEY: modified_base
<222> LOCATION: (27)..(32)
<223> OTHER INFORMATION: a, c, u, g, unknown or other

<400> SEQUENCE: 1242
nnnnnncggg dddngngdgd ngggudnnnn nn 32

<210> SEQ ID NO 1243
<211> LENGTH: 96
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (41)..(75)
<223> OTHER INFORMATION: a, c, t, g, unknown or other

<400> SEQUENCE: 1243
tcttaatacg actcactata gggagagtcg gtagcagtct nnnnnnnnnn nnnnnnnnnn 60
nnnnnnnnnn nnnnntctat gtggaaatgg cgctgt 96

<210> SEQ ID NO 1244
<211> LENGTH: 76
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (21)..(55)
<223> OTHER INFORMATION: a, c, u, g, unknown or other

<400> SEQUENCE: 1244
gggagagucg guagcagucu nnnnnnnnnn nnnnnnnnnn nnnnnnnnnn nnnnnucuau 60
guggaaaugg cgcugu 76

<210> SEQ ID NO 1245
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1245
ugaugacggu agauuacggg uagagugacc gcaucu 36

<210> SEQ ID NO 1246
<211> LENGTH: 36
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1246
uuggccacag uagauuacgg guagugugac ugggcu 36

<210> SEQ ID NO 1247
<211> LENGTH: 34
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1247
grysacrgua gauuacgggu agwgugacyg sryy 34

<210> SEQ ID NO 1248
<211> LENGTH: 34
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (20)..(20)
<223> OTHER INFORMATION: a, c, u, g, unknown or other

<400> SEQUENCE: 1248
rrhbamdgkw gwuwwyggkn hgwgugvcbk vdyy 34

<210> SEQ ID NO 1249
<211> LENGTH: 34
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (1)..(2)
<223> OTHER INFORMATION: a, c, u, g, unknown or other
<220> FEATURE:
<221> NAME/KEY: modified_base
<222> LOCATION: (6)..(6)
<223> OTHER INFORMATION: a, c, u, g, unknown or other
<220> FEATURE:
<221> NAME/KEY: modified_base
<222> LOCATION: (9)..(9)
<223> OTHER INFORMATION: a, c, u, g, unknown or other
<220> FEATURE:
<221> NAME/KEY: modified_base
<222> LOCATION: (15)..(16)
<223> OTHER INFORMATION: a, c, u, g, unknown or other
<220> FEATURE:
<221> NAME/KEY: modified_base
<222> LOCATION: (20)..(20)
<223> OTHER INFORMATION: a, c, u, g, unknown or other
<220> FEATURE:
<221> NAME/KEY: modified_base
<222> LOCATION: (30)..(30)
<223> OTHER INFORMATION: a, c, u, g, unknown or other
<220> FEATURE:
<221> NAME/KEY: modified_base
<222> LOCATION: (33)..(34)
<223> OTHER INFORMATION: a, c, u, g, unknown or other

<400> SEQUENCE: 1249
nnusanddna gwddnnrggn wghgugdhhn sann 34

<210> SEQ ID NO 1250
<211> LENGTH: 10
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1250
uacggguaga 10

<210> SEQ ID NO 1251

<211> LENGTH: 10
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1251
aacggguaga 10

<210> SEQ ID NO 1252
<211> LENGTH: 10
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1252
gacggguaga 10

<210> SEQ ID NO 1253
<211> LENGTH: 10
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1253 uaugggugaga 10

<210> SEQ ID NO 1254
<211> LENGTH: 10
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1254
uacgggcaga 10

<210> SEQ ID NO 1255
<211> LENGTH: 10
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1255
uaugggcaga 10

<210> SEQ ID NO 1256
<211> LENGTH: 10
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1256
aacgggcaga 10

<210> SEQ ID NO 1257
<211> LENGTH: 10

<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1257
aaugggcaga 10

<210> SEQ ID NO 1258
<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1258 uaugggguagu 10

<210> SEQ ID NO 1259
<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1259 aaugggguagu 10

<210> SEQ ID NO 1260
<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1260
aaugggcagu 10

<210> SEQ ID NO 1261
<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1261
aacggguagu 10

<210> SEQ ID NO 1262
<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1262
aacgggcagu 10

<210> SEQ ID NO 1263
<211> LENGTH: 10
<212> TYPE: RNA

<213> ORGANISM: Artificial Sequence
<220> FEATURE:
<223> OTHER INFORMATION: Description of Artificial Sequence: Synthetic oligonucleotide

<400> SEQUENCE: 1263
gacggguagu 10

<210> SEQ ID NO 1264
<211> LENGTH: 10
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1264
uacggguagu 10

<210> SEQ ID NO 1265
<211> LENGTH: 10
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1265
uacgggcagu 10

<210> SEQ ID NO 1266
<211> LENGTH: 10
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1266
uaugggcagu 10

<210> SEQ ID NO 1267
<211> LENGTH: 10
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1267
ugugguagu 10

<210> SEQ ID NO 1268
<211> LENGTH: 10
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1268
ugcggguagu 10

<210> SEQ ID NO 1269
<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1269
ugcggguaga 10

<210> SEQ ID NO 1270
<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1270
uucggguagu 10

<210> SEQ ID NO 1271
<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1271
aucggguagu 10

<210> SEQ ID NO 1272
<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1272
gucggguagu 10

<210> SEQ ID NO 1273
<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1273
uuuggguagu 10

<210> SEQ ID NO 1274
<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1274
uucgggcagu 10

<210> SEQ ID NO 1275
<211> LENGTH: 10
<212> TYPE: RNA
<213> ORGANISM: Artificial Sequence
<220> FEATURE:

<223> OTHER INFORMATION: Description of Artificial Sequence: Synthetic
      oligonucleotide

<400> SEQUENCE: 1275
uuugggcagu 10

<210> SEQ ID NO 1276
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1276
uccggguagu 10

<210> SEQ ID NO 1277
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1277
ucuggguagu 10

<210> SEQ ID NO 1278
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1278
uccgggcagu 10

<210> SEQ ID NO 1279
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1279
uucggguagc 10

<210> SEQ ID NO 1280
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1280
uucggguaga 10

<210> SEQ ID NO 1281
<211> LENGTH: 10
<212> TYPE: RNA
<213> ORGANISM: Artificial Sequence
<220> FEATURE:
<223> OTHER INFORMATION: Description of Artificial Sequence: Synthetic -continued oligonucleotide

<400> SEQUENCE: 1281
uuuggguaga 10

<210> SEQ ID NO 1282
<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1282
uuugggcaga 10

<210> SEQ ID NO 1283
<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1283
uucagguagu 10

<210> SEQ ID NO 1284
<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1284
uaaggguagu 10

<210> SEQ ID NO 1285
<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1285
uaagggcagu 10

<210> SEQ ID NO 1286
<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1286
uaggguagu 10

<210> SEQ ID NO 1287
<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1287
uaaggguaga 10

<210> SEQ ID NO 1288
<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1288
aaaggguagu 10

<210> SEQ ID NO 1289
<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1289
uuaggguaga 10

<210> SEQ ID NO 1290
<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1290
uugggguagu 10

<210> SEQ ID NO 1291
<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1291
uuaggguagu 10

<210> SEQ ID NO 1292
<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1292
ucaggguagu 10

<210> SEQ ID NO 1293
<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1293
uacggggagu 10

<210> SEQ ID NO 1294
<211> LENGTH: 10
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1294
uacgggaagu 10

<210> SEQ ID NO 1295
<211> LENGTH: 10
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1295
uauggggagu 10

<210> SEQ ID NO 1296
<211> LENGTH: 10
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1296
uaugggaagu 10

<210> SEQ ID NO 1297
<211> LENGTH: 10
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1297
aaugggaagu 10

<210> SEQ ID NO 1298
<211> LENGTH: 10
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1298
aacgggaagu 10

<210> SEQ ID NO 1299
<211> LENGTH: 10
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1299
aacggggagu 10

<210> SEQ ID NO 1300
<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1300
uacgggaaga 10

<210> SEQ ID NO 1301
<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1301
uacggggaga 10

<210> SEQ ID NO 1302
<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1302
uaugggaaga 10

<210> SEQ ID NO 1303
<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1303
aacgggaaga 10

<210> SEQ ID NO 1304
<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1304
aacggggaga 10

<210> SEQ ID NO 1305
<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1305

-continued uucgggaagu 10

<210> SEQ ID NO 1306
<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1306
uucggggagu 10

<210> SEQ ID NO 1307
<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1307
uucggggaga 10

<210> SEQ ID NO 1308
<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1308 uaugggguugu 10

<210> SEQ ID NO 1309
<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1309
uacggguugu 10

<210> SEQ ID NO 1310
<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1310
uaugggcugu 10

<210> SEQ ID NO 1311
<211> LENGTH: 10
<212> TYPE: RNA
<213> ORGANISM: Artificial Sequence
<220> FEATURE:
<223> OTHER INFORMATION: Description of Artificial Sequence: Synthetic
oligonucleotide

<400> SEQUENCE: 1311
uauggguuga 10

-continued

```
<210> SEQ ID NO 1312
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1312

uacggguuga                                                            10


<210> SEQ ID NO 1313
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1313

Arg Arg Arg Arg Arg Arg Arg Arg
1               5
```

STEM-LOOP COMPOSITIONS AND METHODS FOR INHIBITING INTERLEUKIN-8

CROSS-REFERENCE

This application is a 35 U.S.C. 371 National Phase Entry Application from PCT/US2019/032411, filed May 15, 2019, which claims priority to U.S. provisional Application No. 62/671,765, filed May 15, 2018, the disclosures of which are incorporated herein by reference in their entireties, and priority is claimed to each of the foregoing.

SEQUENCE LISTING

The instant application contains a Sequence Listing which has been submitted electronically via EFS-Web in ASCII format and is hereby incorporated by reference in its entirety. Said ASCII copy, created on Nov. 12, 2020, is named 4790-104_SL and is 384,953 bytes in size.

BACKGROUND OF THE INVENTION

Visual impairment is a national and global health concern that has a negative impact on physical and mental health. The number of people with visual impairment and blindness is increasing due to an overall aging population. Visual impairment and blindness can be caused by any one of a large number of eye diseases and disorders affecting people of all ages.

Interleukin-8 (IL8) is thought to be involved in angiogenesis, inflammation, hypoxia, immunity, and cell senescence. IL8 may have two primary functions: induction of chemotaxis of inflammatory target cells including neutrophils, granulocytes, and macrophages, and promotion of angiogenesis. IL8 may play a role in various ocular disease and disorders, including, diabetic eye disease (e.g., diabetic macular edema, diabetic retinopathy). In addition, IL8 levels may be elevated in certain eye diseases such as, for example, Behçet's disease, uveitis, proliferative diabetic retinopathy (PDR), retinal vein occlusion (RVO), central retinal vein occlusion (CRVO), retinopathy of prematurity (ROP), wet age-related macular degeneration, geographic atrophy (GA), open angle glaucoma, neovascular glaucoma, and dry eye, among others. There is an un-met need in the art for inhibitors demonstrating high specificity and potency towards IL8. Additionally, there is an un-met need in the art for anti-IL8 therapeutics that are effective in the eye. These needs may be met by the aptamers provided in the present disclosure.

SUMMARY OF THE INVENTION

In one aspect, an aptamer is provided that inhibits Interleukin-8 (IL8) comprising a nucleic acid sequence that selectively binds to an epitope of IL8, wherein the epitope is not a GAG-binding site. In another aspect, an aptamer is provided that inhibits Interleukin-8 (IL8) comprising a nucleic acid sequence that selectively binds to an N-terminal domain of Interleukin-8 (IL8), a hydrophobic pocket of IL8, an N-loop of IL8, or any combination thereof. In another aspect, an aptamer is provided that inhibits Interleukin-8 (IL8) comprising a nucleic acid sequence that selectively binds to a GAG binding site of IL8, wherein said nucleic acid sequence does not comprise any one of SEQ ID NOS: 759-762. In another aspect, an aptamer is provided comprising a nucleic acid sequence that selectively binds to and inhibits Interleukin-8 (IL8), wherein at least 75% of said aptamer remains bound to IL8 in a presence of 10 μM heparan sulphate. In yet another aspect, an aptamer is provided comprising a nucleic acid sequence that binds to and inhibits Interleukin-8 (IL8), wherein said aptamer has a $K_d$ for IL8 of less than about 0.5 nM as measured by a flow cytometry assay, a time resolved-fluorescence energy transfer (TR-FRET) assay, or a competition TR-FRET assay.

In yet another aspect, an aptamer is provided that binds to and inhibits Interleukin-8 (IL8), comprising a secondary structure comprising at least one terminal loop comprising greater than three nucleotides, wherein said at least one terminal loop participates in binding of said aptamer to IL8. In yet another aspect, an aptamer is provided that binds to and inhibits Interleukin-8 (IL8), comprising a secondary structure comprising more than one loop, each loop of said more than one loop having at least four nucleotides. In yet another aspect, an aptamer is provided that binds to and inhibits Interleukin-8 (IL8), comprising a secondary structure comprising a terminal stem comprising from four to six base pairs. In yet another aspect, an aptamer that binds to and inhibits Interleukin-8 (IL8), comprising a secondary structure comprising a single internal loop, wherein said single internal loop comprises at least four nucleotides. In yet another aspect, an aptamer is provided that binds to and inhibits Interleukin-8 (IL8), comprising a secondary structure comprising at least one internal stem having no more than one internal mismatch. In yet another aspect, an aptamer is provided that binds to and inhibits Interleukin-8 (IL8) comprising an internal stem having exactly one internal mismatch. In yet another aspect, an aptamer is provided that binds to and inhibits Interleukin-8 (IL8) comprising, in a 5' to 3' direction, a first base-paired stem, a first loop, and a second base-paired stem, wherein a 3' side of said first base-paired stem is adjacent to a 3' side of said second base-paired stem, and wherein said first loop comprises more than two nucleotides.

In some cases, any aptamer of the preceding comprises a secondary structure comprising, in a 5' to 3' direction: (i) a first base paired stem; (ii) a first loop; (iii) a second base paired stem; and (iv) a second loop. In some cases, the first loop joins a 5' side of said first base paired stem with a 5' side of said second base paired stem. In some cases, the second base paired stem joins said first loop with said second loop. In some cases, the second loop joins said 5' side of said second base paired stem with a 3' side of said second base paired stem. In some cases, the 3' side of said second base paired stem joins said second loop with a 3' side of said first base paired stem. In some cases, the first base paired stem is a terminal stem. In some cases, the second loop is a terminal loop. In some cases, the first loop is an internal loop. In some cases, the second base paired stem is an internal stem. In some cases, the first base paired stem comprises from four to six base pairs. In some cases, the first base paired stem comprises more than three base pairs. In some cases, the first base paired stem comprises less than seven base pairs. In some cases, the first base paired stem comprises one or more internal mismatches. In some cases, the first base paired stem comprises a mismatch at the 3' terminal nucleotide of a 5' side of said first base paired stem, and the 5' terminal nucleotide of a 3' side of said first base paired stem. In some cases, the first base paired stem comprises a mismatch at positions 6 and 26 according to the numbering scheme in FIG. 31. In some cases, the first base paired stem comprises a single nucleotide bulge. In some cases, the first base paired stem comprises six base pairs. In some cases, a 5' side of said first base paired stem comprises a consensus nucleic acid sequence of 5'-HNNNNN-3', and/or a 3' side of said first base paired stem comprises a consensus nucleic acid sequence of 5'-NNNNNN-3', where His A, C, or U; and N is A, C, G, or U. In some cases, a 5' side of said first base paired stem comprises a consensus nucleic acid sequence of 5'-NDNNNH-3', and/or a 3' side of said first base paired stem comprises a consensus nucleic acid sequence of 5'-RNNNHN-3', where N is A, C, G, or U; D is A, G, or U; His A, C, or U; and R is A or G. In some cases, a 5' side of said first base paired stem comprises a consensus nucleic acid sequence of 5'-NNNNNN-3', and/or a 3' side of said first base paired stem comprises a consensus nucleic acid sequence of 5'-NNNNNN-3', where N is A, C, G, or U. In some cases, the first base paired stem comprises five base pairs. In some cases, a 5' side of said first base paired stem comprises a consensus nucleic acid sequence of 5'-WSVVB-3', and/or a 3' side of said first base paired stem comprises a consensus nucleic acid sequence of 5'-BBBSW-3', where W is A or U; S is G or C; V is A, C, or G; and B is C, G, or U. In some cases, a 5' side of said first base paired stem comprises a consensus nucleic acid sequence of 5'-DSVVB-3', and/or a 3' side of said first base paired stem comprises a consensus nucleic acid sequence of 5'-BBBSW-3', where D is A, G, or U; S is G or C; V is A, C, or G; B is C, G, or U; and W is A or U. In some cases, a 5' side of said first base paired stem comprises a consensus nucleic acid sequence of 5'-ACGGY-3', and/or a 3' side of said first base paired stem comprises a consensus nucleic acid sequence of 5'-GCCGU-3', where Y is C or U. In some cases, the first base paired stem comprises four base pairs. In some cases, a 5' side of said first base paired stem comprises a consensus nucleic acid sequence of 5'-UGAC-3', and/or a 3' side of said first base paired stem comprises a consensus nucleic acid sequence of 5'-GUCA-3'. In some cases, the first base paired stem comprises any sequence configuration described in Table 38 or Table 42. In some cases, the aptamer comprises one or more unpaired nucleotides at a 5' terminal end of said aptamer, one or more unpaired nucleotides at a 3' terminal end of said aptamer, or both. In some cases, the aptamer comprises one or more U nucleotides at a 3' terminal end of said aptamer. In some cases, the aptamer does not comprise any unpaired nucleotides at a 5' terminal end or a 3' terminal end of said aptamer. In some cases, the first loop comprises four or five nucleotides. In some cases, the first loop comprises more than three nucleotides. In some cases, the first loop comprises less than six nucleotides. In some cases, the first loop comprises four nucleotides. In some cases, the first loop comprises a consensus nucleic acid sequence of 5'-GGGD-3', where D is A, G, or U. In some cases, the first loop comprises a consensus nucleic acid sequence of 5'-GGGA-3'. In some cases, the first loop comprises five nucleotides. In some cases, the first loop comprises a consensus nucleic acid sequence of 5'-CGGGA-3'. In some cases, the first loop comprises any sequence configuration described in Table 39. In some cases, the first loop is a bulge. In some cases, the second base paired stem comprises five base pairs. In some cases, the second base paired stem comprises more than four base pairs. In some cases, the second base paired stem comprises less than six base pairs. In some cases, the second base paired stem comprises a G·G mismatch at positions 14 and 22, according to the numbering scheme in FIG. 31. In some cases, the second base paired stem comprises a mismatch at the terminal base pair of positions 15 and 21, according to the numbering scheme in FIG. 31. In some cases, a 5' side of said second base paired stem comprises a consensus nucleic acid sequence of 5'-DDNGN-3', and/or a 3' side of said second base paired stem comprises a consensus nucleic acid sequence of 5'-GGGUK-3', where D is A, G, or U; N is A, C, G, or U; K is G or U. In some cases, a 5' side of said second base paired stem comprises a consensus nucleic acid sequence of 5'-AAUGU-3', and/or a 3' side of said second base paired stem comprises a consensus nucleic acid sequence of 5'-GGGUU-3'. In some cases, a 5' side of said second base paired stem comprises a consensus nucleic acid sequence of 5'-RANGN-3', and/or a 3' side of said second base paired stem comprises a consensus nucleic acid sequence of 5'-GGGUD-3', where R is A or G; N is A, C, G, or U; and D is A, G, or U. In some cases, the second base paired stem comprises any sequence configuration described in Table 40 or Table 43. In some cases, the second loop comprises five nucleotides. In some cases, the second loop comprises more than four nucleotides. In some cases, the second loop comprises less than six nucleotides. In some cases, the second loop comprises a consensus nucleic acid sequence of 5'-GDGDN-3', where D is A, G, or U; and N is A, C, G, or U. In some cases, the second loop comprises a consensus nucleic acid sequence of 5'-GAGAU-3'. In some cases, the second loop comprises a consensus nucleic acid sequence of 5'-GAGAH-3', where H is A, C, or U. In some cases, the second loop comprises a consensus nucleic acid sequence of 5'-GAGAN-3', where N is A, C, G, or U. In some cases, the second loop comprises any sequence configuration described in Table 41 or Table 44. In some cases, the aptamer comprises a consensus nucleic acid sequence of 5'-HNNNNNGGGDDDNGNGDGDNGGGUKNNNNNN-3' (SEQ ID NO: 93), where H is A, C, or U; N is A, C, G, or U; D is A, G, or U; and K is G or U. In some cases, the aptamer comprises a consensus nucleic acid sequence of 5'-HNNNNNCGGGADDNGNGDGDNGGGUKNNNNNN-3' (SEQ ID NO: 94), where H is A, C, or U; Nis A, C, G, or U; D is A, G, or U; and K is G or U. In some cases, the aptamer comprises a consensus nucleic acid sequence of 5'-NDNNNHGGGARANGNGAGANGGGUDRNNNHN-3' (SEQ ID NO: 95), where N is A, C, G, or U; D is A, G, or U; H is A, C, or U; and R is A or G. In some cases, the aptamer comprises a consensus nucleic acid sequence of 5'-NNNNNNGGGDDDNGNGDGDNGGGUDNNNNNN-3' (SEQ ID NO: 96), where N is A, C, G, or U; and D is A, G, or U. In some cases, the first base paired stem, said second base paired stem, or both, are perfectly complementary. In some cases, the first base paired stem, said second base paired stem, or both, comprise a single base pair mismatch.

In another aspect, an aptamer is provided that binds to and inhibits Interleukin-8 (IL8) and comprises a consensus nucleic acid sequence selected from the group consisting of: (a) 5'-HNNNNNGGGDDDNGNGDGDNGGGUKNNNNNN-3' (SEQ ID NO: 93), where H is A, C, or U; Nis A, C, G, or U; D is A, G, or U; and K is G or U; (b) 5'-HNNNNNCGGGADDNGNGDGDNGGGUKNNNNNN-3' (SEQ ID NO: 94), where H is A, C, or U; Nis A, C, G, or U; D is A, G, or U; and K is G or U; (c) 5'-NDNNNHGGGARANGNGAGANGGGUDRNNNHN-3' (SEQ ID NO: 95), where N is A, C, G, or U; D is A, G, or U; H is A, C, or U; and R is A or G; (d) 5'-NNNNNNGGGDDDNGNGDGDNGGGUDNNNNNN-3' (SEQ ID NO: 96), where N is A, C, G, or U; and D is A, G, or U.

In another aspect, an aptamer is provided that binds to and inhibits Interleukin-8 (IL8) and comprises one or more sequence configurations according to any one of Tables 38-42. In some cases, any aptamer of the preceding comprises a nucleic acid sequence comprising any nucleic acid sequence described in Table 1 or Table 3. In another aspect, an aptamer is provided having a nucleic acid sequence comprising any nucleic acid sequence described in Table 1 or Table 3, or a nucleic acid sequence having at least 80% sequence identity to any nucleic acid sequence described in Table 1 or Table 3, wherein said aptamer selectively binds to Interleukin-8 (IL8).

In another aspect, an aptamer is provided that selectively binds to Interleukin-8 (IL8), selected from the group consisting of: Aptamer 32 as described in Table 3, Aptamer 54 as described in Table 3, Aptamer 59 as described in Table 3, Aptamer 61 as described in Table 3, Aptamer 112 as described in Table 3, Aptamer 113 as described in Table 3, Aptamer 114 as described in Table 3, Aptamer 115 as described in Table 3, Aptamer 116 as described in Table 3, Aptamer 117 as described in Table 3, Aptamer 118 as described in Table 3, Aptamer 119 as described in Table 3, Aptamer 120 as described in Table 3, Aptamer 121 as described in Table 3, Aptamer 122 as described in Table 3, Aptamer 154 as described in Table 3, Aptamer 155 as described in Table 3, Aptamer 156 as described in Table 3, Aptamer 157 as described in Table 3, Aptamer 158 as described in Table 3, Aptamer 159 as described in Table 3, Aptamer 160 as described in Table 3, Aptamer 161 as described in Table 3, Aptamer 162 as described in Table 3, Aptamer 163 as described in Table 3, Aptamer 164 as described in Table 3, Aptamer 165 as described in Table 3, Aptamer 166 as described in Table 3, Aptamer 167 as described in Table 3, Aptamer 168 as described in Table 3, Aptamer 169 as described in Table 3, Aptamer 170 as described in Table 3, Aptamer 171 as described in Table 3, Aptamer 172 as described in Table 3, Aptamer 173 as described in Table 3, Aptamer 174 as described in Table 3, Aptamer 175 as described in Table 3, Aptamer 176 as described in Table 3, Aptamer 177 as described in Table 3, Aptamer 178 as described in Table 3, Aptamer 179 as described in Table 3, Aptamer 180 as described in Table 3, Aptamer 212 as described in Table 3, Aptamer 214 as described in Table 3, Aptamer 215 as described in Table 3, Aptamer 216 as described in Table 3, Aptamer 217 as described in Table 3, Aptamer 218 as described in Table 3, Aptamer 219 as described in Table 3, Aptamer 242 as described in Table 3, Aptamer 243 as described in Table 3, Aptamer 244 as described in Table 3, Aptamer 245 as described in Table 3, Aptamer 246 as described in Table 3, Aptamer 247 as described in Table 3, Aptamer 248 as described in Table 3, Aptamer 249 as described in Table 3, Aptamer 250 as described in Table 3, Aptamer 251 as described in Table 3, Aptamer 252 as described in Table 3, Aptamer 253 as described in Table 3, Aptamer 254 as described in Table 3, Aptamer 255 as described in Table 3, Aptamer 256 as described in Table 3, Aptamer 257 as described in Table 3, Aptamer 258 as described in Table 3, Aptamer 259 as described in Table 3, Aptamer 260 as described in Table 3, Aptamer 261 as described in Table 3, Aptamer 262 as described in Table 3, Aptamer 263 as described in Table 3, Aptamer 264 as described in Table 3, Aptamer 265 as described in Table 3, Aptamer 266 as described in Table 3, Aptamer 267 as described in Table 3, and Aptamer 268 as described in Table 3.

In another aspect, an aptamer is provided that binds to and inhibits Interleukin-8 (IL8) comprising a secondary structure comprising at least one asymmetric internal loop pair connected to exactly two stems. In some cases, a first loop sequence of said at least one asymmetric internal loop pair is connected at a 5' end to a first stem sequence and is connected at a 3' end to a second stem sequence, and wherein a second loop sequence of said at least one asymmetric internal loop pair is connected at a 5' end to a third stem sequence that is complementary to said second stem sequence and is connected at a 3' end to a fourth stem sequence that is complementary to said first stem sequence.

In another aspect, an aptamer is provided that binds to and inhibits Interleukin-8 (IL8) comprising a secondary structure comprising at least two loops, wherein at least two of said at least two loops do not comprise a pyrimidine. In another aspect, an aptamer is provided that binds to and inhibits Interleukin-8 (IL8) comprising a secondary structure comprising at least one terminal loop comprising from six to ten nucleotides. In yet another aspect, an aptamer is provided that inhibits Interleukin-8 (IL8) comprising a secondary structure comprising more than one internal stem, wherein each internal stem of said more than one internal stem has less than six contiguous base pairs.

In some cases, any aptamer of the preceding comprises a secondary structure further comprising, in a 5' to 3' direction: (i) a first base paired stem; (ii) a first loop; (iii) a second base paired stem; (iv) a second loop; (v) a third base paired stem; (vi) a third loop; and (vii) a fourth loop. In some cases, the first loop joins a 5' side of said first base paired stem with a 5' side of said second base paired stem. In some cases, the second base paired stem joins said first loop with said second loop. In some cases, the second loop joins a 5' side of said second base paired stem with a 5' side of said third base paired stem. In some cases, the third base paired stem joins said second loop with said third loop. In some cases, the third loop joins a 5' side of said third base paired stem with a 3' side of said third base paired stem. In some cases, a 3' side of said third base paired stem joins said third loop with said fourth loop. In some cases, a 3' side of said second base paired stem joins said fourth loop with a 3' side of said first base paired stem. In some cases, the first base paired stem is a terminal stem. In some cases, the third loop is a terminal loop. In some cases, the first base paired stem comprises from two to four base pairs. In some cases, the first base paired stem comprises less than five base pairs. In some cases, the first base paired stem comprises more than one base pair. In some cases, the first base paired stem comprises one or more internal mismatches. In some cases, the first loop comprises no more than one nucleotide. In some cases, the loop comprises less than two nucleotides. In some cases, the first loop comprises exactly one nucleotide. In some cases, a nucleic acid sequence of said first loop is 5'-A-3'. In some cases, the first loop is a bulge. In some cases, the second base paired stem comprises less than five base pairs. In some cases, the second base paired stem comprises more than three base pairs. In some cases, the second base paired stem comprises exactly four base pairs. In some cases, a terminal base pair of said second base paired stem is A·U. In some cases, the second loop comprises more than one nucleotide. In some cases, the second loop comprises less than three nucleotides. In some cases, the second loop comprises exactly two nucleotides. In some cases, a nucleic acid sequence of said second loop is 5'-AG-3'. In some cases, a nucleic acid sequence of said second loop is 5'-WG-3', where W is A or U. In some cases, the third base paired stem comprises from one to three base pairs. In some cases, the third base paired stem comprises less than four base pairs. In some cases, a 5' side of said third base paired stem comprises a nucleic acid sequence of 5'-WU-3', where W is A or U; and/or a 3' side of said third base paired stem comprises a nucleic acid sequence of 5'-GU-3'. In some cases, a 5' side of said third base paired stem comprises a nucleic acid sequence of 5'-WD-3', where W is A or U; and D is A, G, or U; and/or a 3' side of said third base paired stem comprises a nucleic acid sequence of 5'-GU-3'. In some cases, a 5' side of said third base paired stem comprises a nucleic acid sequence of 5'-AAU-3'; and/or a 3' side of said third base paired stem comprises a nucleic acid sequence of 5'-AGU-3'. In some cases, a 5' side of said third base paired stem comprises a nucleic acid sequence of 5'-AU-3'; and/or a 3' side of said third base paired stem comprises a nucleic acid sequence of 5'-GU-3'. In some cases, a 5' side of said third base paired stem comprises a nucleic acid sequence of 5'-UU-3'; and/or a 3' side of said third base paired stem comprises a nucleic acid sequence of 5'-GU-3'. In some cases, a 5' side of said third base paired stem comprises a nucleic acid sequence of 5'-AA-3'; and/or a 3' side of said third base paired stem comprises a nucleic acid sequence of 5'-GU-3'. In some cases, a 5' side of said third base paired stem comprises a nucleic acid sequence of 5'-AG-3'; and/or a 3' side of said third base paired stem comprises a nucleic acid sequence of 5'-GU-3'. In some cases, the third base paired stem comprises exactly three base pairs, and said third loop comprises exactly eight nucleotides. In some cases, the third loop comprises nine or ten nucleotides. In some cases, the third loop comprises less than 11 nucleotides. In some cases, the third loop comprises more than eight nucleotides. In some cases, the third loop comprises a nucleic acid sequence of 5'-ACGGGUAG-3'. In some cases, the third loop comprises a nucleic acid sequence of 5'-WYGGKNDG-3', where W is A or U; Y is C or U; K is G or U; N is A, C, G, or U; and D is A, G, or U. In some cases, the third loop comprises a nucleic acid sequence of 5'-UACGGGUAGA-3' (SEQ ID NO: 82). In some cases, the third loop comprises a nucleic acid sequence of 5'-UWYGGKNDGA-3' (SEQ ID NO: 85), where W is A or U; Y is C or U; K is G or U; N is A, C, G, or U; and D is A, G, or U. In some cases, the third loop comprises a nucleic acid sequence of 5'-UACGGGUAGU-3' (SEQ ID NO: 84). In some cases, the third loop comprises a nucleic acid sequence of 5'-UWYGGKNDGU-3' (SEQ ID NO: 86), where W is A or U; Y is Cor U: K is G or U; Nis A, C, G, or U; and Dis A, G, or U. In some cases, the third loop comprises a nucleic acid sequence of 5'-DNNRGGNWGH-3 (SEQ ID NO: 87), where D is A, G, or U; N is A, C, G, or U; R is A or G; W is A or U; and His A, C, or U. In some cases, the third loop comprises a nucleic acid sequence of 5'-DNNGGGNWGH-3' (SEQ ID NO: 88), where D is A, G, or U; N is A, C, G, or U; W is A or U; and His A, C, or U. In some cases, the third loop comprises a nucleic acid sequence of 5'-HNGGGNAGW-3', where H is A, C, or U; N is A, C, G, or U; and W is A or U. In some cases, a 5' terminal nucleotide of said third loop and a 3' terminal nucleotide of said third loop form a single base pair. In some cases, a 5' terminal nucleotide of said third loop and a 3' terminal nucleotide of said third loop do not form a base pair. In some cases, the third loop comprises one or more non-nucleotidyl linkers. In some cases, the fourth loop comprises exactly one nucleotide. In some cases, the fourth loop comprises less than two nucleotides. In some cases, the fourth loop has a nucleic acid sequence of 5'-G-3'. In some cases, the first base paired stem comprises a nucleic acid sequence selected from Table 14. In some cases, the second base paired stem comprises a nucleic acid sequence selected from Table 15. In some cases, the third base paired stem comprises a nucleic acid sequence selected from Table 16. In some cases, the third loop comprises a nucleic acid sequence selected from Table 17. In some cases, the first loop comprises a nucleic acid sequence of 5'-A-3'. In some cases, the second loop comprises a nucleic acid sequence of 5'-AG-3'. In some cases, the fourth loop comprises a nucleic acid sequence of 5'-G-3'. In some cases, the first base paired stem, said second base paired stem, said third base paired stem, or any combination thereof, is perfectly complementary. In some cases, the first base paired stem, said second base paired stem, said third base paired stem, or any combination thereof, comprises a single base pair mismatch. In some cases, the aptamer comprises a consensus nucleic acid sequence of 5'-NNUSANDDNAGWDDNNRGGNWGHGUGDHHNSANN-3' (SEQ ID NO: 89), where N is A, C, G, or U; S is G or C; D is A, G, or U; W is A or U; R is A or G; and His A, C, or U. In some cases, the aptamer comprises a consensus nucleic acid sequence of 5'-NNUSANDDNAGWDDNNGGGNWGHGUGDHHNSANN-3' (SEQ ID NO: 90), where N is A, C, G, or U; S is G or C; D is A, G, or U; W is A or U; R is A or G; and His A, C, or U. In some cases, the aptamer comprises a consensus nucleic acid sequence of 5'-NNUSANDDNAGWDHNGGGNAGWGUGDHHNSANN-3' (SEQ ID NO: 91), where N is A, C, G, or U; S is G or C; D is A, G, or U; W is A or U; His A, C, or U; and S is G or C; or a consensus nucleic acid sequence of 5'-NNYVANDDNWGWDDNNRGKNNGHGUGNHHNVRNN-3' (SEQ ID NO: 92), where N is A, C, G, or U; Y is C or U; Vis A, C, or G; D is A, G, or U; W is A or U; R is A or G; Kis Gor U; and His A, C, or U.

In another aspect, an aptamer is provided that inhibits Interleukin-8 (IL8) and comprises one or more consensus nucleic acid sequences selected from the group consisting of: (a) 5'-ACGGGUAG-3'; (b) 5'-UACGGGUAGA-3' (SEQ ID NO: 82); (c) 5'-UACGGGUAGU-3' (SEQ ID NO: 84); (d) 5'-WYGGKNDG-3', where W is A or U; Y is C or U; K is Gor U; N is A, C, G, or U; and D is A, G, or U; (e) 5'-UWYGGKNDGA-3' (SEQ ID NO: 85), where W is A or U; Y is C or U; K is G or U; N is A, C, G, or U; and D is A, G, or U; (f) 5'-UWYGGKNDGU-3' (SEQ ID NO: 86), where W is A or U; Y is C or U; K is Gor U; N is A, C, G, or U; and D is A, G, or U; (g) 5'-DNNRGGNWGH-3' (SEQ ID NO: 87), where D is A, G, or U; N is A, C, G, or U; R is A or G; W is A or U; and H is A, C, or U; (h) 5'-DNNGGGNWGH-3' (SEQ ID NO: 88), where D is A, G, or U; N is A, C, G, or U; W is A or U; and His A, C, or U; (i) 5'-HNGGGNAGW-3', where His A, C, or U; N is A, C, G, or U; and W is A or U; (j) 5'-NNUSANDDNAGWDDNNRGGNWGHGUGDHHNSANN-3' (SEQ ID NO: 89), where Nis A, C, G, or U; S is G or C; D is A, G, or U; W is A or U; R is A or G; and H is A, C, or U; 5'-NNUSANDDNAGWDDNNGGGNWGHGUGDHHNSANN-3' (SEQ ID NO: 90), where Nis A, C, G, or U; S is G or C; D is A, G, or U; W is A or U; R is A or G; and H is A, C, or U; (1) 5'-NNUSANDDNAGWDHNGGGNAGWGUGDHHNSANN-3' (SEQ ID NO: 91), where Nis A, C, G, or U; S is G or C; D is A, G, or U; W is A or U; H is A, C, or U; and S is G or C; and (m) 5'-NNYVANDDNWGWDDNNRGKNNGHGUGNHHNVRNN-3' (SEQ ID NO: 92), where Nis A, C, G, or U; Y is C or U; V is A, C, or G; D is A, G, or U; W is A or U; R is A or G; K is G or U; and His A, C, or U. In some cases, the nucleic acid sequence comprises any nucleic acid sequence described in Table 2.

In another aspect, an aptamer is provided having a nucleic acid sequence comprising any nucleic acid sequence described in Table 2, or a nucleic acid sequence having at least 80% sequence identity to any nucleic acid sequence described in Table 2, wherein said aptamer selectively binds to Interleukin-8 (IL8).

In another aspect, an aptamer is provided that selectively binds to Interleukin-8 (IL8), selected from the group consisting of: Aptamer 2 as described in Table 1, Aptamer 3 as described in Table 1, Aptamer 4 as described in Table 1, Aptamer 5 as described in Table 1, Aptamer 6 as described in Table 1, Aptamer 7 as described in Table 1, Aptamer 8 as described in Table 1, Aptamer 9 as described in Table 1, Aptamer 10 as described in Table 1, Aptamer 11 as described in Table 1, Aptamer 12 as described in Table 1, Aptamer 13 as described in Table 1, Aptamer 14 as described in Table 1, Aptamer 15 as described in Table 1, Aptamer 16 as described in Table 1, Aptamer 18 as described in Table 1, Aptamer 19 as described in Table 1, Aptamer 20 as described in Table 1, Aptamer 21 as described in Table 1, Aptamer 22 as described in Table 1, Aptamer 23 as described in Table 1, Aptamer 24 as described in Table 1, Aptamer 25 as described in Table 1, Aptamer 38 as described in Table 2, Aptamer 40 as described in Table 2, Aptamer 41 as described in Table 2, Aptamer 42 as described in Table 2, Aptamer 43 as described in Table 2, Aptamer 44 as described in Table 2, Aptamer 45 as described in Table 2, Aptamer 69 as described in Table 2, Aptamer 70 as described in Table 2, Aptamer 71 as described in Table 2, Aptamer 72 as described in Table 2, Aptamer 73 as described in Table 2, Aptamer 74 as described in Table 2, Aptamer 75 as described in Table 2, Aptamer 76 as described in Table 2, Aptamer 77 as described in Table 2, Aptamer 78 as described in Table 2, Aptamer 79 as described in Table 2, Aptamer 80 as described in Table 2, Aptamer 81 as described in Table 2, Aptamer 82 as described in Table 2, Aptamer 83 as described in Table 2, Aptamer 84 as described in Table 2, Aptamer 85 as described in Table 2, Aptamer 87 as described in Table 2, Aptamer 89 as described in Table 2, Aptamer 90 as described in Table 2, Aptamer 92 as described in Table 2, Aptamer 94 as described in Table 2, Aptamer 95 as described in Table 2, Aptamer 96 as described in Table 2, Aptamer 97 as described in Table 2, Aptamer 98 as described in Table 2, Aptamer 99 as described in Table 2, Aptamer 100 as described in Table 2, Aptamer 101 as described in Table 2, Aptamer 102 as described in Table 2, Aptamer 103 as described in Table 2, Aptamer 104 as described in Table 2, Aptamer 105 as described in Table 2, Aptamer 106 as described in Table 2, Aptamer 107 as described in Table 2, Aptamer 108 as described in Table 2, Aptamer 109 as described in Table 2, Aptamer 110 as described in Table 2, Aptamer 111 as described in Table 2, Aptamer 134 as described in Table 2, Aptamer 135 as described in Table 2, Aptamer 136 as described in Table 2, Aptamer 137 as described in Table 2, Aptamer 138 as described in Table 2, Aptamer 139 as described in Table 2, Aptamer 140 as described in Table 2, Aptamer 141 as described in Table 2, Aptamer 142 as described in Table 2, Aptamer 143 as described in Table 2, Aptamer 144 as described in Table 2, Aptamer 145 as described in Table 2, Aptamer 146 as described in Table 2, Aptamer 147 as described in Table 2, Aptamer 148 as described in Table 2, Aptamer 149 as described in Table 2, Aptamer 150 as described in Table 2, Aptamer 151 as described in Table 2, Aptamer 152 as described in Table 2, Aptamer 153 as described in Table 2, Aptamer 183 as described in Table 2, Aptamer 184 as described in Table 2, Aptamer 185 as described in Table 2, Aptamer 186 as described in Table 2, Aptamer 187 as described in Table 2, Aptamer 188 as described in Table 2, Aptamer 189 as described in Table 2, Aptamer 190 as described in Table 2, Aptamer 193 as described in Table 2, Aptamer 197 as described in Table 2, Aptamer 199 as described in Table 2, Aptamer 200 as described in Table 2, Aptamer 201 as described in Table 2, Aptamer 206 as described in Table 2, Aptamer 207 as described in Table 2, Aptamer 208 as described in Table 2, Aptamer 209 as described in Table 2, and Aptamer 210 as described in Table 2.

In some cases, any aptamer of the preceding selectively binds to an N-terminal domain of Interleukin-8 (IL8), a hydrophobic pocket of IL8, an N-loop of IL8, a GAG binding site of IL8, or any combination thereof. In some cases, the N-loop includes at least one of residues 7-11 of IL8-72 (SEQ ID NO: 2). In some cases, the N-terminal domain includes at least one of residues 2-6 of IL8-72 (SEQ ID NO: 2). In some cases, the hydrophobic pocket includes at least one of residues 12-18, 21, 22, 40, 43, 47, and 49 of IL8-72 (SEQ ID NO: 2). In some cases, the GAG binding site includes at least one of residues 18, 20, 60, 64, 67, and 68 of IL8-72 (SEQ ID NO: 2).

In some cases, any aptamer of the preceding comprises a nucleic acid sequence comprising nucleotides having ribose in a β-D-ribofuranose configuration. In some cases, at least 50% of said nucleic acid sequence comprises nucleotides having ribose in a β-D-ribofuranose configuration. In some cases, any aptamer of the preceding comprises RNA, modified RNA, or both. In some cases, any aptamer of the preceding comprises DNA, modified DNA, or both. In some cases, any aptamer of the preceding comprises one or more modified nucleotides. In some cases, at least 50% of said nucleic acid sequence comprises one or more modified nucleotides. In some cases, the one or more modified nucleotides comprises a 2'F-modified nucleotide, a 2'OMe-modified nucleotide, or a combination thereof. In some cases, the one or more modified nucleotides are selected from the group consisting of: 2'F-G, 2'OMe-G, 2'OMe-U, 2'OMe-A, 2'OMe-C, a 3' terminal inverted deoxythymidine, and any combination thereof. In some cases, any aptamer of the preceding comprises a nuclease-stabilized nucleic acid backbone. In some cases, any aptamer of the preceding inhibits IL8 with an $IC_{50}$ of less than about 5 nM as measured by an IL8/CXCR1 competition assay, an IL8-mediated intracellular calcium signaling assay, an IL8-mediated neutrophil migration assay, or an IL8-mediated endothelial cell tube formation assay. In some cases, any aptamer of the preceding inhibits IL8 with an $IC_{50}$ of less than about 1 nM as measured by an IL8/CXCR1 competition assay, an IL8-mediated intracellular calcium signaling assay, an IL8-mediated neutrophil migration assay, or an IL8-mediated endothelial cell tube formation assay. In some cases, any aptamer of the preceding inhibits IL8 with an $IC_{50}$ of less than about 0.5 nM as measured by an IL8/CXCR1 competition assay, an IL8-mediated intracellular calcium signaling assay, an IL8-mediated neutrophil migration assay, or an IL8-mediated endothelial cell tube formation assay. In some cases, any aptamer of the preceding inhibits IL8 with an $IC_{50}$ of less than about 0.1 nM as measured by an IL8/CXCR1 competition assay, an IL8-mediated intracellular calcium signaling assay, an IL8-mediated neutrophil migration assay, or an IL8-mediated endothelial cell tube formation assay. In some cases, any aptamer of the preceding binds to IL8 with a $K_d$ of less than about 5 nM as measured by a flow cytometry assay, a TR-FRET assay, or a competition TR-FRET assay. In some cases, any aptamer of the preceding binds to IL8 with a $K_d$ of less than about 1 nM as measured by a flow cytometry assay, a TR-FRET assay, or a competition TR-FRET assay. In some cases, any aptamer of the preceding binds to IL8 with a $K_d$ of less than about 0.5 nM as measured by a flow cytometry assay, a TR-FRET assay, or a competition TR-FRET assay. In some cases, any aptamer of the preceding aptamer binds to IL8 with a $K_d$ of less than about 0.1 nM as measured by a flow cytometry assay, a TR-FRET assay, or a competition TR- FRET assay. In some cases, any aptamer of the preceding prevents or reduces association of IL8 with CXCR1, CXCR2, or both. In some cases, any aptamer of the preceding comprises a nucleic acid sequence comprising from about 30 to about 90 nucleotides, wherein said nucleotides are unmodified nucleotides, modified nucleotides, or a combination of modified nucleotides and unmodified nucleotides. In some cases, any aptamer of the preceding is conjugated to a polyethylene glycol (PEG) molecule. In some cases, the PEG molecule has a molecular weight of about 40 kDa or less. In some cases, any aptamer of the preceding has an intraocular half-life of at least about 4.5 days in a rabbit.

In another aspect, an aptamer of the preceding is provided for use in treating an ocular disease or disorder in a subject in need thereof. In some cases, one or more symptoms of said ocular disease or disorder are treated.

In another aspect, a method of treating an ocular disease or disorder in a subject in need thereof is provided, comprising administering to said subject an aptamer of any one of the preceding, thereby treating said ocular disease or disorder. In some cases, the ocular disease or disorder is selected from the group consisting of: wet age-related macular degeneration, dry age-related macular degeneration, geographic atrophy, proliferative diabetic retinopathy, retinal vein occlusion, diabetic retinopathy, diabetic macular edema, nonarteritic anterior ischemic optic neuropathy, infectious uveitis, non-infectious uveitis, iritis (anterior uveitis), cyclitis (intermediate uveitis), choroiditis and retinitis (posterior uveitis), diffuse uveitis (panuveitis), Behçet's disease, Coats' disease, retinopathy of prematurity, dry eye, allergic conjunctivitis, pterygium, branch retinal vein occlusion, central retinal vein occlusion, adenovirus keratitis, corneal ulcers, vernal keratoconjunctivitis, Stevens-Johnson syndrome, corneal herpetic keratitis, rhegmatogenous retinal detachment, pseudo-exfoliation syndrome, proliferative vitreoretinopathy, infectious conjunctivitis, Stargardt disease, retinitis pigmentosa, Contact Lens-Induced Acute Red Eye (CLARE), conjunctivochalasis. In some cases, the ocular disease or disorder is a diabetic eye disease. In some cases, the ocular disease or disorder is an inherited retinal disease. In some cases, the ocular disease or disorder is a retinal degenerative disease. In some cases, the ocular disease or disorder exhibits elevated levels of IL8. In some cases, the ocular disease or disorder exhibits elevated levels of bis-retinoids.

In another aspect, use of any aptamer of the preceding is provided, in a formulation of a medicament for treatment of an ocular disease or disorder.

In another aspect, use of any aptamer of the preceding is provided for treatment of an ocular disease or disorder.

In another aspect, a method is provided for modulating Interleukin-8 (IL8) in a biological system, said method comprising: administering to said biological system any aptamer of the preceding, thereby modulating IL8 in said biological system. In some cases, the biological system comprises a biological tissue or biological cells. In some cases, the biological system is a subject. In some cases, the subject is a human. In some cases, the modulating comprises inhibiting a function associated with IL8. In some cases, the modulating comprises preventing or reducing an association of IL8 with CXCR1, CXCR2, or both. In some cases, the method further comprises administering to said biological system a therapeutically effective amount of an anti-VEGF composition. In some cases, the anti-VEGF composition comprises bevacizumab. ranibizumab, pegaptanib, brolucizumab, abicipar pegol, conbercept, or aflibercept. In some cases, the aptamer and said anti-VEGF composition are administered to said biological system at the same time. In some cases, the aptamer and said anti-VEGF composition are administered to said biological system sequentially or separately.

In another aspect, a method is provided for selecting for aptamers which selectively bind to Interleukin-8 (IL8), the method comprising: (a) incubating an aptamer library with an IL8 protein, wherein a C-terminus of said IL8 protein is blocked or occluded; and (b) selecting one or more aptamers that are bound to said IL8 protein, thereby selecting aptamers which bind to IL8. In some cases, the incubating further comprises the presence of heparin sulfate. In some cases, the IL8 protein comprises a different protein attached to said C-terminus of said IL8 protein. In some cases, the different protein is a mucin stalk.

INCORPORATION BY REFERENCE

All publications, patents, and patent applications mentioned in this specification are herein incorporated by reference in their entireties to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 2A depicts a non-limiting example of an aptamer library suitable for screening for aptamers that target Interleukin-8 according to embodiments of the disclosure. FIG. 2A discloses SEQ ID NOS: 1243-1244 and 81, respectively, in order of appearance.

FIG. 2B depicts a non-limiting example of a reverse oligonucleotide hybridized to a portion of the aptamer library sequence depicted in FIG. 2A according to embodiments of the disclosure.

FIG. 12 depicts a representation of nucleotide conservation within the top 250 stacks of sequences from round 5 of a secondary selection conducted on the Aptamer 3 family, according to embodiments of the disclosure. FIG. 12 discloses SEQ ID NO: 1245.

FIG. 29 depicts a non-limiting example of PK and target engagement models for IL8 aptamers following IVT administration to humans.

FIG. 31 depicts a representation of nucleotide conservation within the top 250 stacks of sequences from round 5 of a secondary selection conducted on the Aptamer 8 family, according to embodiments of the disclosure. FIG. 31 discloses SEQ ID NO: 1240.

FIG. 32 depicts a representation of an anti-IL8 aptamer secondary structure (SEQ ID NO: 1241) with consensus and motif variations observed during the secondary selection. The percent base pairing is based on the fraction of sequence stacks, not the total sequence numbers.

DETAILED DESCRIPTION OF THE INVENTION

Figure 1:
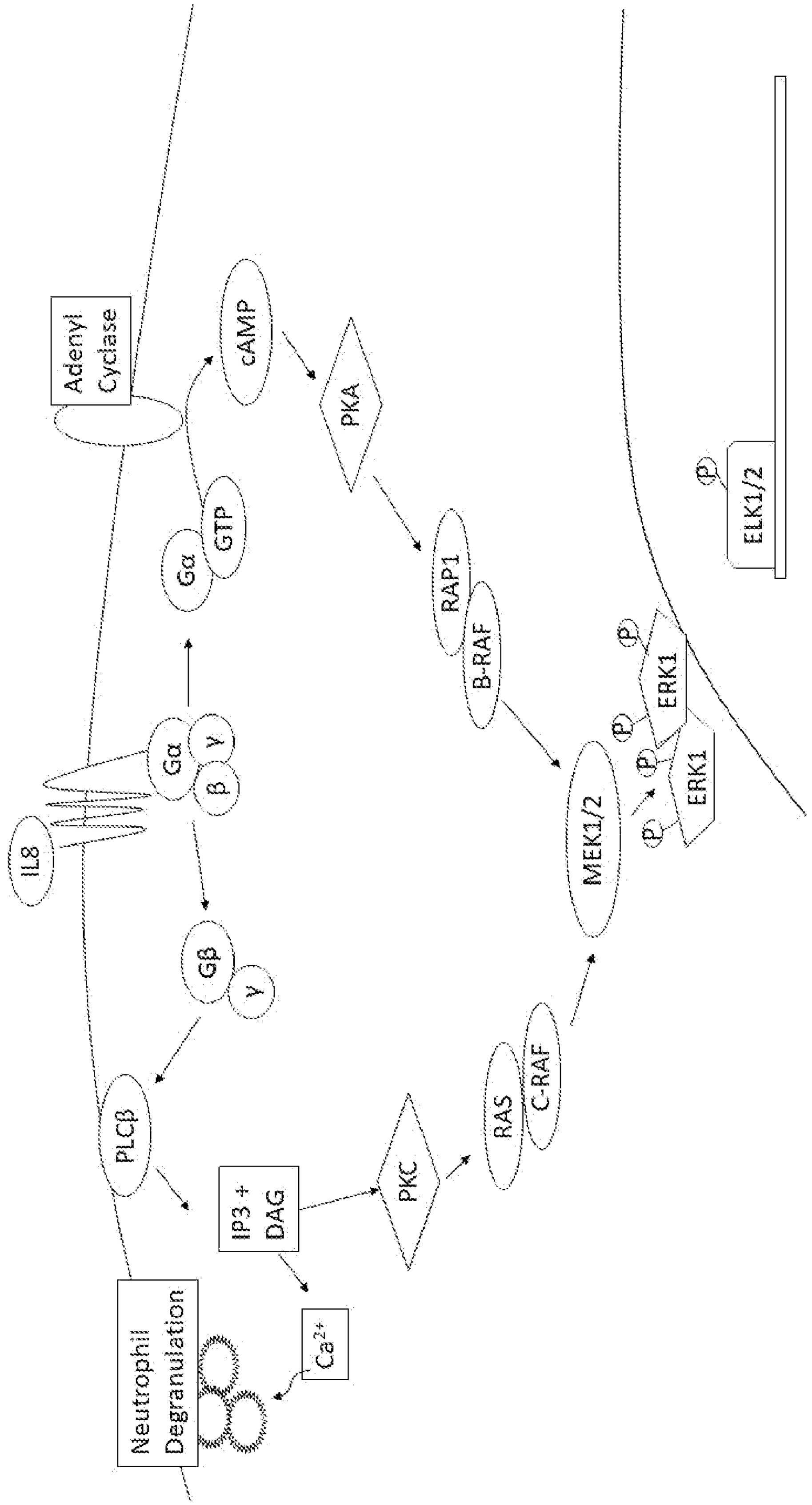
FIG. 1 depicts a non-limiting example of a model of intracellular IL8 signaling induced by interaction of IL8 with its cognate receptors according to embodiments of the disclosure.

The disclosure herein provides aptamer compositions that selectively bind to and/or inhibit a function associated with Interleukin-8 (IL8) and methods of using such aptamer compositions. In some cases, the anti-IL8 aptamers may bind to the N-terminal domain of IL8, or a portion thereof. In some cases, the anti-IL8 aptamers may bind to the hydrophobic pocket of IL8, or a portion thereof, such as the ELR residues. In some cases, the anti-IL8 aptamers may bind to the N-loop of IL8, or a portion thereof. In some cases, the anti-IL8 aptamers may bind to the GAG binding site of IL8, or a portion thereof. Without wishing to be bound by theory, anti-IL8 aptamers of the disclosure may prevent or reduce binding of IL8 to the C-X-C motif chemokine receptor 1 (CXCR1), the C-X-C motif chemokine receptor 2 (CXCR2), or both. In some cases, the disclosure provides anti-IL8 compositions that may inhibit signaling pathways downstream of CXCR1, CXCR2, or both. Additionally or alternatively, in some cases, the anti-IL8 aptamers may bind to a region of IL8 such that a molecule conjugated to the anti-IL8 aptamer (e.g., a polyethylene glycol (PEG) polymer) is positioned in a manner such that the conjugate itself may prevent or reduce interaction with CXCR1, CXCR2, or both. In such cases, the anti-IL8 aptamer may bind to IL8 at a region that is not itself important for interaction with CXCR1, CXCR2, or both.

The disclosure herein further provides aptamer compositions having unique stem-loop secondary structures that selectively bind to and inhibit a function associated with IL8 and methods of using such aptamer compositions. In one aspect, a first structural family of aptamers is provided (hereinafter referred to as the "Aptamer 3 structural family" or "Aptamer 3 family"). The Aptamer 3 structural family of aptamers may comprise the parent aptamer, Aptamer 3, as disclosed herein, as well as additional aptamers that share common structural features with Aptamer 3. The Aptamer 3 structural family of aptamers generally comprise aptamers that selectively bind to and inhibit functions associated with IL8. In some cases, the Aptamer 3 structural family may comprise aptamers having, in a 5' to 3' direction, a first side of a first base paired stem (e.g., S1); a first loop (e.g., L1); a first side of a second base paired stem (e.g., S2); a second loop (e.g., L2); a first side of a third base paired stem (e.g., S3); a third loop (e.g., L3); a second, complementary side of the third base paired stem (e.g., S3'); a fourth loop (e.g., L4); a second, complementary side of the second base paired stem (e.g., S2'); and a second, complementary side of the first base paired stem (e.g., S1'). Put another way, aptamers of the Aptamer 3 structural family may have the following stem and loop structure: 5'-S1-L1-S2-L2-S3-L3-S3'-L4-S2'-S1'-3'. The Aptamer 3 structural family of aptamers disclosed herein may also include one or more further elements (e.g., additional stem(s) or loop(s)). In some cases, additional elements (e.g., additional stem(s), loop(s), one or more nucleotides, etc.) may be located before (e.g., 5' side) the first side of the first base paired stem, after (e.g., 3' side) the second, complementary side of the first base paired stem, or both. In some cases, additional elements may be located interspersed between other elements of the aptamer. Additional elements may include additional stem structures, loop structures, non-nucleotidyl linkers, or any number of overhanging, unpaired nucleotides.

In some aspects, each element may be adjacent to each other. For example, the Aptamer 3 structural family may comprise aptamers having, in a 5' to 3' direction, a first side of a first base paired stem. The 3' terminal end of the first side of the first base paired stem may be connected to the 5' terminal end of the first loop. The first loop may be connected at its 5' terminal end to the 3' terminal end of the first side of the first base paired stem, and the first loop may be connected at its 3' terminal end to the 5' terminal end of the first side of the second base paired stem. The first side of the second base paired stem may be connected at its 5' terminal end to the 3' terminal end of the first loop, and the first side of the second base paired stem may be connected at its 3' terminal end to the 5' terminal end of the second loop. The second loop may be connected at its 5' terminal end to the 3' terminal end of the first side of the second base paired stem, and the second loop may be connected at its 3' terminal end to the 5' terminal end of the first side of the third base paired stem. The first side of the third base paired stem may be connected at its 5' terminal end to the 3' terminal end of the second loop, and the first side of the third base paired stem may be connected at its 3' terminal end to the 5' terminal end of the third loop. The third loop may be connected at its 5' terminal end to the 3' terminal end of the first side of the third base paired stem, and the third loop may be connected at its 3' terminal end to the 5' terminal end of the second, complementary side of the third base paired stem. The second, complementary side of the third base paired stem may be connected at its 5' terminal end to the 3' terminal end of the third loop, and the second, complementary side of the third base paired stem may be connected at its 3' terminal end to the 5' terminal end of the fourth loop. The fourth loop may be connected at its 5' terminal end to the 3' terminal end of the second, complementary side of the third base paired stem, and the fourth loop may be connected at its 3' terminal end to the 5' terminal end of the second, complementary side of the second base paired stem. The second, complementary side of the second base paired stem may be connected at its 5' terminal end to the 3' terminal end of the fourth loop, and the second, complementary side of the second based paired stem may be connected at its 3' terminal end to the 5' terminal end of the second, complementary side of the first base paired stem. The second, complementary side of the first base paired stem may be connected at its 5' terminal end to the 3' terminal end of the second, complementary side of the second base paired stem. In some cases, the Aptamer 3 structural family may include aptamers comprising a terminal stem. In some cases, the terminal stem may be the first base paired stem. In some cases, the Aptamer 3 structural family may include aptamers comprising a terminal loop. In some cases, the terminal loop may be the third loop. Non-limiting examples of Aptamer 3 structural family aptamers that may be used to inhibit IL8 are described throughout.

As described above, in some cases, the Aptamer 3 structural family may comprise anti-IL8 aptamers that have the following stem and loop structure: 5'-S1-L1-S2-L2-S3-L3-S3'-L4-S2'-S1'-3'. In some cases, S1/S1', S2/S2', S3/S3', and/or L3 may comprise any combination of nucleotide sequences provided in Tables 15-18. Additionally, such aptamers may include one or more of the following: L1 may be 5'-A-3', L2 may be 5'-AG-3', and L4 may be 5'-G-3'.

The disclosure further provides anti-IL8 aptamers comprising consensus nucleic acid sequences. In some cases, an anti-IL8 aptamer of the disclosure may comprise a consensus nucleic acid sequence of 5'-ACGGGUAG-3'. In some cases, an anti-IL8 aptamer of the disclosure may comprise a consensus nucleic acid sequence of 5'-UACGGGUAGA-3' (SEQ ID NO: 82). In some cases, an anti-IL8 aptamer of the disclosure may comprise a consensus nucleic acid sequence of 5'-UACGGGUAGA-3' (SEQ ID NO: 83). In some cases, an anti-IL8 aptamer of the disclosure may comprise a consensus nucleic acid sequence of 5'-UACGGGUAGU-3' (SEQ ID NO: 84). In some cases, an anti-IL8 aptamer of the disclosure may comprise a consensus nucleic acid sequence of 5'-WYGGKNDG-3', where W is A or U; Y is C or U; K is Gor U; N is A, C, G, or U; and D is A, G, or U. In some cases, an anti-IL8 aptamer of the disclosure may comprise a consensus nucleic acid sequence of 5'-UWYGGKNDGA-3' (SEQ ID NO: 85), where W is A or U; Y is C or U; K is Gor U; N is A, C, G, or U; and D is A, G, or U. In some cases, an anti-IL8 aptamer of the disclosure may comprise a consensus nucleic acid sequence of 5'-UWYGGKNDGU-3' (SEQ ID NO: 86), where W is A or U; Y is C or U; K is G or U; N is A, C, G, or U; and D is A, G, or U. In some cases, an anti-IL8 aptamer of the disclosure may comprise a consensus nucleic acid sequence of 5'-DNNRGGNWGH-3' (SEQ ID NO: 87), where D is A, G, or U; N is A, C, G, or U; R is A or G; W is A or U; and H is A, C, or U. In some cases, an anti-IL8 aptamer of the disclosure may comprise a consensus nucleic acid sequence of 5'-DNNGGGNWGH-3' (SEQ ID NO: 88), where D is A, G, or U; N is A, C, G, or U; W is A or U; and His A, C, or U. In some cases, an anti-IL8 aptamer of the disclosure may comprise a consensus nucleic acid sequence of 5'-HNGGGNAGW-3', where His A, C, or U; N is A, C, G, or U; and W is A or U. In some cases, an anti-IL8 aptamer of the disclosure may comprise a consensus nucleic acid sequence of 5'-NNUSANDD-NAGWDDNNRGGNWGHGUGDHHNSANN-3' (SEQ ID NO: 89), where N is A, C, G, or U; S is Gor C; D is A, G, or U; W is A or U; R is A or G; and H is A, C, or U. In some cases, an anti-IL8 aptamer of the disclosure may comprise a consensus nucleic acid sequence of 5' NNUSANDD-NAGWDDNNGGGNWGHGUGDHHNSANN-3' (SEQ ID NO: 90), where N is A, C, G, or U; S is G or C; D is A, G, or U; W is A or U; R is A or G; and His A, C, or U. In some cases, an anti-IL8 aptamer of the disclosure may comprise a consensus nucleic acid sequence of 5'-NNUSANDD-NAGWDHNGGGNAGWGUGDHHNSANN-3' (SEQ ID NO: 91), where N is A, C, G, or U; S is G or C; D is A, G, or U; W is A or U; His A, C, or U; and S is Gor C. In some cases, an anti-IL8 aptamer of the disclosure may comprise a consensus nucleic acid sequence of 5'-NNY-VANDDNWGWDDNNRGKNNGHGUGNHHNVRNN-3' (SEQ ID NO: 92), where N is A, C, G, or U; Y is C or U; V is A, C, or G; D is A, G, or U; W is A or U; R is A or G; K is G or U; and H is A, C, or U.

In another aspect, a second structural family of aptamers is provided (hereinafter referred to as the "Aptamer 8 structural family" or the "Aptamer 8 family"). The Aptamer 8 structural family of aptamers may comprise the parent aptamer, Aptamer 8, as disclosed herein, as well as additional aptamers that share common structural features with Aptamer 8. The Aptamer 8 structural family of aptamers generally comprise aptamers that selectively bind to and inhibit functions associated with IL8. In some cases, the Aptamer 8 structural family may comprise aptamers having, in a 5' to 3' direction, a first side of a first base paired stem (e.g., S1); a first loop (e.g., L1); a first side of a second base paired stem (e.g., S2); a second loop (e.g., L2); a second, complementary side of the second base paired stem (e.g., S2'); and a second, complementary side of the first base paired stem (e.g., S1'). Put another way, aptamers of the Aptamer 8 structural family may have the following stem and loop structure: 5'-S1-L1-S2-L2-S2'-S1'-3'. The Aptamer 8 structural family of aptamers disclosed herein may also include one or more further elements (e.g., additional stem(s) or loop(s)). In some cases, additional elements (e.g., additional stem(s), loop(s), one or more nucleotides, etc.) may be located before (e.g., 5' side) the first side of the first base paired stem, after (e.g., 3' side) the second, complementary side of the first base paired stem, or both. In some cases, additional elements may be located interspersed between other elements of the aptamer. Additional elements may include additional stem structures, loop structures, non-nucleotidyl linkers, or any number of overhanging, unpaired nucleotides.

In some aspects, each element may be adjacent to each other. For example, the Aptamer 8 structural family may comprise aptamers having, in a 5' to 3' direction, a first side of a first base paired stem. The 3' terminal end of the first side of the first base paired stem may be connected to the 5' terminal end of the first loop. The first loop may be connected at its 5' terminal end to the 3' terminal end of the first side of the first base paired stem, and the first loop may be connected at its 3' terminal end to the 5' terminal end of the first side of the second base paired stem. The first side of the second base paired stem may be connected at its 5' terminal end to the 3' terminal end of the first loop, and the first side of the second base paired stem may be connected at its 3' terminal end to the 5' terminal end of the second loop. The second loop may be connected at its 5' terminal end to the 3' terminal end of the first side of the second base paired stem, and the second loop may be connected at its 3' terminal end to the 5' terminal end of the second, complementary side of the second base paired stem. The second, complementary side of the second base paired stem may be connected at its 5' terminal end to the 3' terminal end of the second loop, and the second, complementary side of the second base paired stem may be connected at its 3' terminal end to the 5' terminal end of the second, complementary side of the first paired stem. The second, complementary side of the first base paired stem may be connected at its 5' terminal end to the 3' terminal end of the second, complementary side of the second base paired stem. In some cases, the Aptamer 8 structural family may include aptamers comprising a terminal stem. In some cases, the terminal stem may be the first base paired stem. In some cases, the Aptamer 8 structural family may include aptamers comprising a terminal loop. In some cases, the terminal loop may be the second loop. Non-limiting examples of Aptamer 8 structural family aptamers that may be used to inhibit IL8 are described throughout.

As described above, in some cases, the Aptamer 8 structural family may comprise anti-IL8 aptamers that have the following stem and loop structure: 5'-S1-L1-S2-L2-S2'-S1'-3'. In some cases, S1/S1', S2/S2', L1, and/or L2 may comprise any combination of nucleotide sequences provided in Tables 38-44.

The disclosure further provides anti-IL8 aptamers comprising consensus nucleic acid sequences. In some cases, an anti-IL8 aptamer of the disclosure may comprise consensus nucleic acid sequence of 5'-HNNNNNGGGDDDNG-NGDGDNGGGUKNNNNNN-3' (SEQ ID NO: 93), where His A, C, or U; N is A, C, G, or U; D is A, G, or U; and K is G or U. In some cases, an anti-IL8 aptamer of the disclosure may comprise a consensus nucleic acid sequence of 5'-HNNNNNCGGGADDNGNGDGDNGGGUKN-NNNNN-3' (SEQ ID NO: 94), where H is A, C, or U; Nis A, C, G, or U; D is A, G, or U; and K is G or U. In some cases, an anti-IL8 aptamer of the disclosure may comprise a consensus nucleic acid sequence of 5'-NDNNNHGGGA-RANGNGAGANGGGUDRNNNHN-3' (SEQ ID NO: 95), where N is A, C, G, or U; D is A, G, or U; H is A, C, or U; and R is A or G. In some cases, an anti-IL8 aptamer of the disclosure may comprise a consensus nucleic acid sequence of 5'-NNNNNNGGGDDDNGNGDGDNGGGUDNN-NNNN-3' (SEQ ID NO: 96), where N is A, C, G, or U; and D is A, G, or U.

The disclosure herein further provides methods and compositions for the treatment of ocular diseases or disorders. In some cases, the methods and compositions may include the use of an anti-IL8 aptamer for, e.g., the treatment of ocular diseases or disorders. In some cases, the methods and compositions may include the use of anti-IL8 aptamer having a stem-loop secondary structure as described herein for the treatment of ocular diseases or disorders. In some cases, the anti-IL8 aptamer may have a stem-loop secondary structure as described herein for the Aptamer 3 structural family of aptamers. In some cases, the anti-IL8 aptamer may have a stem-loop secondary structure as described herein for the Aptamer 8 structural family of aptamers. Additionally or alternatively, the methods and compositions may include the use of an anti-IL8 aptamer of the disclosure, in combination with an anti-vascular endothelial growth factor (VEGF) inhibitor, for the treatment of an ocular disease or disorder. In some cases, the ocular disease or disorder may be age-related macular degeneration. In some cases, macular degeneration may be wet age-related macular degeneration. In some cases, macular degeneration may be dry age-related macular degeneration. In some cases, the ocular disease or disorder may be geographic atrophy. In some cases, the ocular disease or disorder may be proliferative diabetic retinopathy. In some cases, the ocular disease or disorder may be diabetic retinopathy. In some cases, the ocular disease or disorder may be diabetic macular edema. In some cases, the ocular disease or disorder may be nonarteritic anterior ischemic optic neuropathy. In some cases, the ocular disease or disorder may be uveitis. Uveitis can be, for example, infectious uveitis or non-infectious uveitis. Uveitis can be, for example, Iritis (anterior uveitis); Cyclitis (intermediate uveitis); Choroiditis and retinitis (posterior uveitis); and/or Diffuse uveitis (panuveitis). In some cases, the ocular disease or disorder may be Behçet's disease. In some cases, the ocular disease or disorder may be Coats' disease. In some cases, the ocular disease or disorder may be retinopathy of prematurity. In some cases, the ocular disease or disorder may be dry eye. In some cases, the ocular disease or disorder may be allergic conjunctivitis. In some cases, the ocular disease or disorder may be pterygium. In some cases, the ocular disease or disorder may be branch retinal vein occlusion. In some cases, the ocular disease or disorder may be central retinal vein occlusion. In some cases, the ocular disease or disorder may be adenovirus keratitis. In some cases, the ocular disease or disorder may be corneal ulcers. In some cases, the ocular disease or disorder may be vernal keratoconjunctivitis. In some cases, the ocular disease or disorder may be Stevens-Johnson syndrome. In some cases, the ocular disease or disorder may be corneal herpetic keratitis. In some cases, the ocular disease or disorder may be rhegmatogenous retinal detachment. In some cases, the ocular disease or disorder may be pseudo-exfoliation syndrome. In some cases, the ocular disease or disorder may be proliferative vitreoretinopathy. In some cases, the ocular disease or disorder may be infectious conjunctivitis. In some cases, the ocular disease or disorder may be Stargardt disease. In some cases, the ocular disease or disorder may be retinitis pigmentosa. In some cases, the ocular disease or disorder may be Contact Lens-Induced Acute Red Eye (CLARE). In some cases, the methods and compositions may include the use of an anti-IL8 aptamer for the treatment of symptoms associated with conjunctivochalasis. In some cases, the ocular disease or disorder may be an inherited retinal disease. In some cases, the ocular disease or disorder may be a retinal degenerative disease. In some cases, a subject having an ocular disease or disorder may exhibit elevated levels of IL8. In some cases, a subject having an ocular disease or disorder may exhibit elevated bisretinoids such as, for example, N-retinylidene-N-retinylethanolamine (A2E).

In some aspects of the disclosure, the methods and compositions may involve the inhibition of a function associated with IL8. In some cases, the methods and compositions may involve preventing or reducing IL8 binding to CXCR1, CXCR2, or both. In some cases, the methods and compositions may involve preventing or reducing downstream signaling associated with CXCR1, CXCR2, or both. In some cases, the methods and compositions may involve the inhibition of a function associated with IL8 for the treatment of ocular diseases or disorders. In some aspects of the disclosure, the methods and compositions may involve partial or complete inhibition of a function associated with IL8. In some cases, the methods and compositions may involve partial or complete inhibition of a function associated with IL8 for the treatment of ocular diseases. Additionally or alternatively, the methods and compositions may involve partial or complete inhibition of a function associated with IL8, in combination with partial or complete inhibition of a function associated with VEGF, for the treatment of an ocular disease or disorder. In some cases, the methods and compositions may involve the inhibition of a function associated with IL8 for the treatment of wet age-related macular degeneration. In some cases, the methods and compositions may involve the inhibition of a function associated with IL8 for the treatment of dry age-related macular degeneration. In some cases, the methods and compositions may involve the inhibition of a function associated with IL8 for the treatment of geographic atrophy. In some cases, the methods and compositions may involve the inhibition of a function associated with IL8 for the treatment of proliferative diabetic retinopathy. In some cases, the methods and compositions may involve the inhibition of a function associated with IL8 for the treatment of retinal vein occlusion. In some cases, the method and compositions may involve the inhibition of a function associated with IL8 for the treatment of central retinal vein occlusion. In some cases, the methods and compositions may involve the inhibition of a function associated with IL8 for the treatment of diabetic retinopathy. In some cases, the methods and compositions may involve the inhibition of a function associated with IL8 for the treatment of diabetic macular edema. In some cases, the methods and compositions may involve the inhibition of a function associated with IL8 for the treatment of nonarteritic anterior ischemic optic neuropathy. In some cases, the methods and compositions may involve the inhibition of a function associated with IL8 for the treatment of uveitis. Uveitis can be, for example, infectious uveitis or non-infectious uveitis. Uveitis can be, for example, Iritis (anterior uveitis); Cyclitis (intermediate uveitis); Choroiditis and retinitis (posterior uveitis); and/or Diffuse uveitis (panuveitis). In some cases, the methods and compositions may involve the inhibition of a function associated with IL8 for the treatment of Behçet's disease. In some cases, the methods and compositions may involve the inhibition of a function associated with IL8 for the treatment of Coats' disease. In some cases, the methods and compositions may involve the inhibition of a function associated with IL8 for the treatment of retinopathy of prematurity. In some cases, the methods and compositions may involve the inhibition of a function associated with IL8 for the treatment of dry eye. In some cases, the methods and compositions may involve the inhibition of a function associated with IL8 for the treatment of allergic conjunctivitis. In some cases, the methods and compositions may involve the inhibition of a function associated with IL8 for the treatment of pterygium. In some cases, the methods and compositions may involve the inhibition of a function associated with IL8 for the treatment of branch retinal vein occlusion. In some cases, the methods and compositions may involve the inhibition of a function associated with IL8 for the treatment of central retinal vein occlusion. In some cases, the methods and compositions may involve the inhibition of a function associated with IL8 for the treatment of adenovirus keratitis. In some cases, the methods and compositions may involve the inhibition of a function associated with IL8 for the treatment of corneal ulcers. In some cases, the methods and compositions may involve the inhibition of a function associated with IL8 for the treatment of vernal keratoconjunctivitis. In some cases, the methods and compositions may involve the inhibition of a function associated with IL8 for the treatment of Stevens-Johnson syndrome. In some cases, the methods and compositions may involve the inhibition of a function associated with IL8 for the treatment of corneal herpetic keratitis. In some cases, the methods and compositions may involve the inhibition of a function associated with IL8 for the treatment of rhegmatogenous retinal detachment. In some cases, the methods and compositions may involve the inhibition of a function associated with IL8 for the treatment of pseudo-exfoliation syndrome. In some cases, the methods and compositions may involve the inhibition of a function associated with IL8 for the treatment of proliferative vitreoretinopathy. In some cases, the methods and compositions may involve the inhibition of a function associated with IL8 for the treatment of infectious conjunctivitis. In some cases, the methods and compositions may involve the inhibition of a function associated with IL8 for the treatment of Stargardt disease. In some cases, the methods and compositions may involve the inhibition of a function associated with IL8 for the treatment of retinitis pigmentosa. In some cases, the methods and compositions may involve the inhibition of a function associated with IL8 for the treatment of Contact Lens-Induced Acute Red Eye (CLARE). In some cases, the methods and compositions may involve the inhibition of a function associated with IL8 for the treatment of symptoms associated with conjunctivochalasis. In some cases, the methods and compositions may involve the inhibition of a function associated with IL8 for the treatment of an inherited retinal disease. In some cases, the methods and compositions may involve the inhibition of a function associated with IL8 for the treatment of a retinal degenerative disease. In some cases, the methods and compositions may involve the inhibition of a function associated with IL8 for the treatment of an ocular disease or disorder exhibiting elevated levels of IL8. In some cases, the methods and compositions may involve the inhibition of a function associated with IL8 for the treatment an ocular disease or disorder exhibiting elevated levels of bisretinoids, such as, for example, N-retinylidene-N-retinylethanoloamine (A2E).

Additionally or alternatively, the methods and compositions may involve the inhibition of a function associated with IL8, in combination with inhibition of a function associated with VEGF, for the treatment of any one of the following: wet age-related macular degeneration, dry age-related macular degeneration, geographic atrophy, proliferative diabetic retinopathy, retinal vein occlusion, central retinal vein occlusion, diabetic retinopathy, diabetic macular edema, central serous chorioretinopathy, X-linked retinitis pigmentosa, X-linked retinoschisis, nonarteritic anterior ischemic optic neuropathy, uveitis (including infectious uveitis, non-infectious uveitis, iritis (anterior uveitis), cyclitis (intermediate uveitis), choroiditis and retinitis (posterior uveitis), diffuse uveitis (panuveitis)), scleritis, optic neuritis, optic neuritis secondary to multiple sclerosis, macular pucker, Behçet's disease, Coats' disease, retinopathy of prematurity, open angle glaucoma, neovascular glaucoma, dry eye, allergic conjunctivitis, pterygium, branch retinal vein occlusion, adenovirus keratitis, corneal ulcers, vernal keratoconjunctivitis, blepharitis, epithelial basement membrane dystrophy, Stevens-Johnson syndrome, achromatophasia, corneal herpetic keratitis, keratoconus, rhegmatogenous retinal detachment, pseudo-exfoliation syndrome, proliferative vitreoretinopathy, infectious conjunctivitis, Stargardt disease, retinitis pigmentosa, Contact Lens-Induced Acute Red Eye (CLARE), conjunctivochalasis, inherited retinal disease, a retinal degenerative disease, an ocular disease or disorder exhibiting elevated levels of IL8, and an ocular disease or disorder exhibiting elevated levels of bisretinoids, such as, for example, N-retinylidene-N-retinylethanoloamine (A2E).

In various aspects, the compositions may include oligonucleotides that selectively bind to and inhibit a function associated with IL8. In some aspects, the oligonucleotide compositions may bind directly to IL8 and inhibit a function thereof. In some cases, the oligonucleotide compositions of the disclosure may bind to the N-terminal domain of IL8, or a portion thereof. In some cases, the oligonucleotide compositions of the disclosure may bind to the hydrophobic pocket of IL8, or a portion thereof. In some cases, the oligonucleotide compositions of the disclosure may bind to the N-loop of IL8, or a portion thereof. In some cases, the oligonucleotide compositions of the disclosure may bind to the GAG binding site of IL8, or a portion thereof. In some cases, the oligonucleotide compositions of the disclosure may prevent or reduce binding of IL8 to CXCR1, CXCR2, or both. In some cases, the oligonucleotide compositions of the disclosure may prevent or reduce downstream signaling associated with CXCR1, CXCR2, or both. Additionally or alternatively, the oligonucleotide compositions of the disclosure may include an anti-IL8 aptamer that binds to a region of IL8 such that a molecule conjugated to the anti-IL8 aptamer (e.g., a polyethylene glycol polymer) is positioned in a manner such that the conjugate itself may prevent or reduce interaction with CXCR1, CXCR2, or both. In such cases, the anti-IL8 aptamer may bind to IL8 at a region that is not itself important for interaction with CXCR1, CXCR2, or both. In some cases, the oligonucleotides may be aptamers, such as RNA aptamers, DNA aptamers, modified RNA aptamers, or modified DNA aptamers. In particular examples, the aptamers of the disclosure may have secondary structures. The secondary structures may include a stem-loop structure which may include one or more loops and one or more stems. Various examples of anti-IL8 aptamers having stem-loop secondary structures for modulating IL8 are described herein. In some cases, an anti-IL8 aptamer of the disclosure may have a stem-loop secondary structure as described herein for the Aptamer 3 structural family of aptamers. In some cases, an anti-IL8 aptamer of the disclosure may have a stem-loop secondary structure as described herein for the Aptamer 8 structural family of aptamers.

In general, "sequence identity" refers to an exact nucleotide-to-nucleotide or amino acid-to-amino acid correspondence of two polynucleotides or polypeptide sequences, respectively. Typically, techniques for determining sequence identity include determining the nucleotide sequence of a polynucleotide and/or determining the amino acid sequence encoded thereby, and comparing these sequences to a second nucleotide or amino acid sequence. Two or more sequences (polynucleotide or amino acid) can be compared by determining their "percent identity." The percent identity of two sequences, whether nucleic acid or amino acid sequences, is the number of exact matches between two aligned sequences divided by the length of the longer sequence and multiplied by 100. Percent identity may also be determined, for example, by comparing sequence information using the advanced BLAST computer program, including version 2.2.9, available from the National Institutes of Health. The BLAST program is based on the alignment method of Karlin and Altschul, Proc. Natl. Acad. Sci. USA, 87:2264-2268 (1990) and as discussed in Altschul, et al., J. Mol. Biol., 215:403-410 (1990); Karlin And Altschul, Proc. Natl. Acad. Sci. USA, 90:5873-5877 (1993); and Altschul et al., Nucleic Acids Res., 25:3389-3402 (1997). The program may be used to determine percent identity over the entire length of the proteins being compared. Default parameters are provided to optimize searches with short query sequences in, for example, with the blastp program. The program also allows use of an SEG filter to mask-off segments of the query sequences as determined by the SEG program of Wootton and Federhen, Computers and Chemistry 17:149-163 (1993). Ranges of desired degrees of sequence identity are approximately 50% to 100% and integer values therebetween. In general, this disclosure encompasses sequences with at least 50%, at least 55%, at least 60%, at least 65%, at least 70%, at least 75%, at least 80%, at least 85%, at least 90%, at least 95%, or at least 98% sequence identity with any sequence provided herein.

In general, "modification identity" refers to two polynucleotides with identical patterns of modifications on a nucleotide-to-nucleotide level. Techniques for determining modification identity may include determining the modifications of a polynucleotide and comparing these modifications to modifications of a second polynucleotide. The percent modification identity of two sequences is the number of exact modification matches between two aligned sequences divided by the length of the longer sequence and multiplied by 100. Ranges of desired degrees of modification identity are generally approximately 50% to 100%. In general, this disclosure encompasses sequences with at least 50%, at least 55%, at least 60%, at least 65%, at least 70%, at least 75%, at least 80%, at least 85%, at least 90%, at least 95%, or at least 98% modification identity with any sequence provided herein.

As used herein, "consensus sequence", when used in reference to a group or series of related nucleic acids, refers to a nucleotide sequence that reflects the most common choice of base at each position in the sequence where the series of related nucleic acids has been subjected to mathematical and/or sequence analysis. Unless otherwise indicated, nucleotide sequences provided herein are represented by standard nucleotide notation, as set forth by the International Union of Pure and Applied Chemistry (IUPAC). For example, the nucleotides typically found in DNA are represented by "A", "C", "G", "T"; and the nucleotides typically found in RNA are represented by "A", "C", "G", "U". Nucleotide sequences provided herein may include one or more degenerate bases. A "degenerate base" generally refers to a position on a nucleotide sequence that can have more than one possible alternative. Degenerate bases are generally represented by a Roman character as set forth by the International Union of Pure and Applied Chemistry (IUPAC). For example, the Roman character "D", when used in relation to a nucleotide sequence, represents a degenerate base of A, G, or U.

The term "aptamer" as used herein refers to oligonucleotide and/or nucleic acid analogues that can bind to a specific target molecule. Aptamers can include RNA, DNA, modified RNA, modified DNA, any nucleic acid analogue, and/or combinations thereof. Aptamers can be single-stranded oligonucleotides. In some cases, aptamers may comprise more than one nucleic acid strand (e.g., two or more nucleic acid strands). Aptamers may bind to a target (e.g., a protein) with high affinity and specificity through non-Watson-Crick base pairing interactions. Generally, the aptamers described herein are non-naturally occurring oligonucleotides (e.g., synthetically produced) that are isolated and used for the treatment of a disorder or a disease. Aptamers can bind to essentially any target molecule including, without limitation, proteins, oligonucleotides, carbohydrates, lipids, small molecules, and even bacterial cells. Aptamers may be monomeric (composed of a single unit) or multimeric (composed of multiple units). Multimeric aptamers can be homomeric (composed of multiple identical units) or heteromeric (composed of multiple non-identical units). Aptamers herein may be described by their primary structures, meaning the linear nucleotide sequence of the aptamer. Aptamer sequences herein are generally described from the 5' end to the 3' end, unless otherwise stated. Additionally or alternatively, aptamers herein may be described by their secondary structures which may refer to the combination of single-stranded regions and base-pairing interactions within the aptamer. Whereas many naturally occurring oligonucleotides, such as mRNA, encode information in their linear base sequences, aptamers generally do not encode information in their linear base sequences. Further, aptamers can be distinguished from naturally occurring oligonucleotides in that binding of aptamers to target molecules is dependent upon secondary and tertiary structures of the aptamer. Aptamers may be suitable as therapeutic agents and may be preferable to other therapeutic agents because: 1) aptamers may be fast and economical to produce because aptamers can be developed entirely by in vitro processes; 2) aptamers may have low toxicity and may lack an immunogenic response; 3) aptamers may have high specificity and affinity for their targets; 4) aptamers may have good solubility; 5) aptamers may have tunable pharmacokinetic properties; 6) aptamers may be amenable to site-specific conjugation of PEG and other carriers; and 7) aptamers may be stable at ambient temperatures.

An aptamer may have a secondary structure having at least two complementary regions of the same nucleic acid strand that base-pair to form a double helix (referred to herein as a “stem”). Generally, these complementary regions are complementary when read in the opposite direction. The term “stem” as used herein may refer to either of the complementary nucleotide regions individually or may encompass a base-paired region containing both complementary regions, or a portion thereof. For example, the term “stem” may refer to the 5' side of the stem, that is, the stem sequence that is closer to the 5' end of the aptamer; additionally or alternatively, the term “stem” may refer to the 3' side of the stem, that is, the stem sequence that is closer to the 3' end of the aptamer. In some cases, the term “stem” may refer to the 5' side of the stem and the 3' side of the stem, collectively. The term “base-paired stem” is generally used herein to refer to both complementary stem regions collectively. A base-paired stem may be perfectly complementary meaning that 100% of its base pairs are Watson-Crick base pairs. A base-paired stem may also be “partially complementary.” As used herein, the term “partially complementary stem” refers to a base-paired stem that is not entirely made up of Watson-Crick base pairs but does contain base pairs (either Watson-Crick base pairs or G-U/U-G wobble base pairs) at each terminus. In some cases, a partially complementary stem contains both Watson-Crick base-pairs and G-U/U-G wobble base pairs. In other cases, a partially complementary stem is exclusively made up of G-U/U-G wobble base pairs. A partially complementary stem may contain mis-matched base pairs and/or unpaired bases in the region between the base pairs at each terminus of the stem; but in such cases, the mis-matched base pairs and/or unpaired bases make up at most 50% of the positions between the base pairs at each terminus of the stem.

A stem as described herein may be referred to by the position, in a 5' to 3' direction on the aptamer, of the 5' side of the stem (e.g., the stem sequence closer to the 5' terminus of the aptamer), relative to the 5' side of additional stems present on the aptamer. For example, stem 1 (S1) may refer to the stem sequence that is closest to the 5' terminus of the aptamer, its complementary stem sequence, or both stem sequences collectively. Similarly, stem 2 (S2) may refer to the next stem sequence that is positioned 3' relative to S1, its complementary stem sequence, or both stem sequences collectively. Each additional stem may be referred to by its position, in a 5' to 3' direction, on the aptamer, as described above. For example, S3 may be positioned 3' relative to S2 on the aptamer, S4 may be positioned 3' relative to S3 on the aptamer, and so on. In some cases, the term “first stem” may be used to refer to a stem in the aptamer, irrespective of its location. For example, a first stem may be S1, S2, S3, S4 or any other stem in the aptamer. A stem may be adjacent to an unpaired region. An unpaired region may be present at a terminus of the aptamer or at an internal region of the aptamer.

Figures 11A, 11B, 11C, 11D:
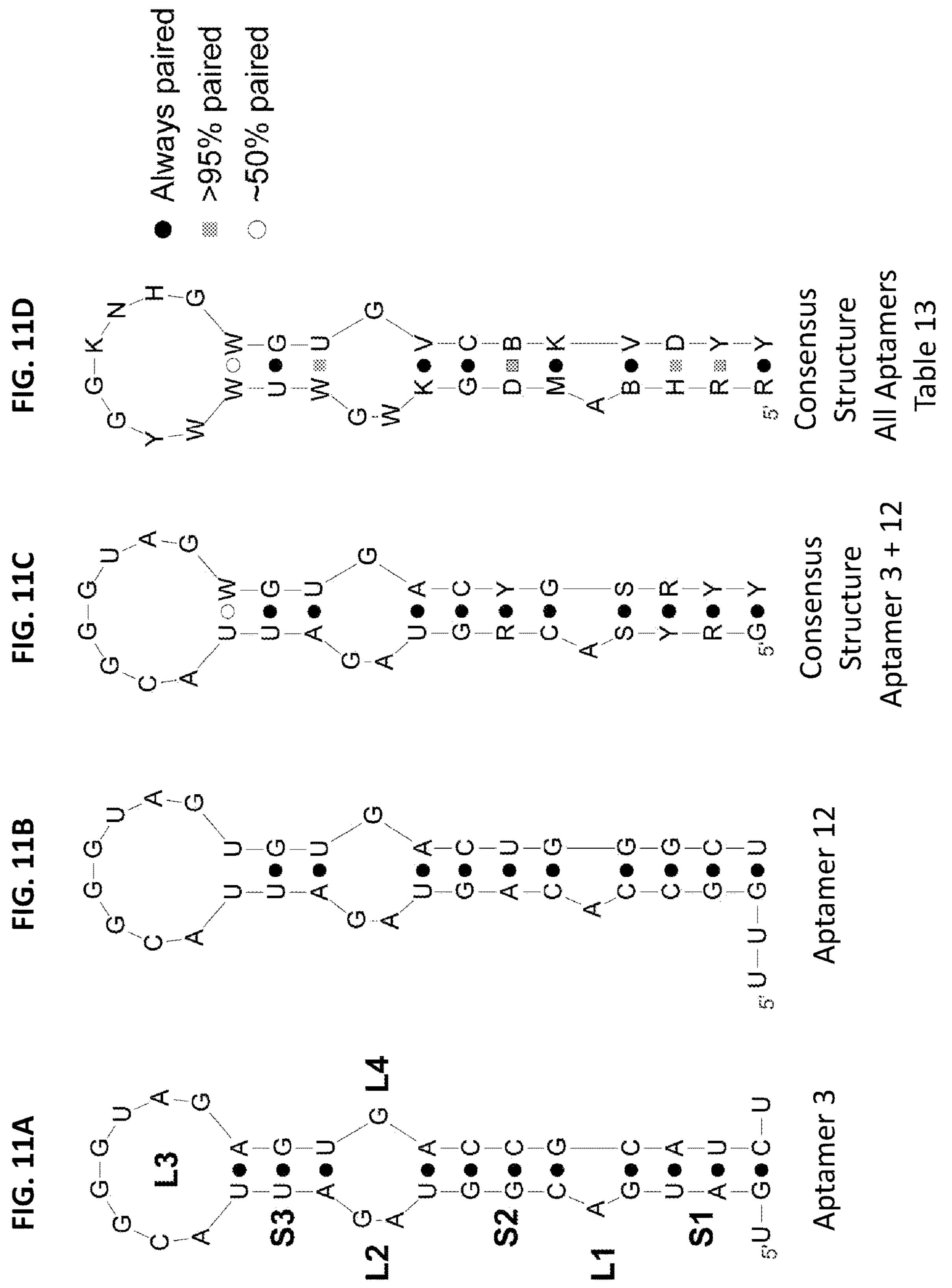
FIG. 11A depicts a secondary structure of an exemplary anti-IL8 aptamer of the disclosure (SEQ ID NO: 1245).
FIG. 11B depicts a secondary structure of an exemplary anti-IL8 aptamer of the disclosure (SEQ ID NO: 1246).
FIG. 11C depicts a non-limiting example of a consensus structure of anti-IL8 aptamers according to embodiments of the disclosure (SEQ ID NO: 1247).
FIG. 11D depicts a non-limiting example of a consensus structure of anti-IL8 aptamers according to embodiments of the disclosure (SEQ ID NO: 1248).

As used herein, the term “loop” generally refers to an internal unpaired region of an aptamer. The term “loop” generally refers to any unpaired region of an aptamer that is flanked on both the 5' end and the 3' end by a stem region. In some cases, a loop sequence may be adjacent to a single base-paired stem, such that the loop and stem structure together resemble a hairpin. In such cases, generally the primary sequence of the aptamer contains a first stem sequence adjacent to the 5' end of the loop sequence and a second stem sequence adjacent to the 3' end of the loop sequence; and the first and second stem sequences are complementary to each other. In some cases, each terminus of a loop is adjacent to first and second stem sequences that are not complementary. In such cases, the primary sequence of the aptamer may contain an additional loop sequence that is bordered at one or both ends by stem sequences that are complementary to the first and/or second stem sequences. In cases where the two loops have different number of nucleotides, and where each of the two loops comprises at least one nucleotide, the two loops are referred to jointly herein as an “asymmetric loop”, an “asymmetric loop pair,”, or an “asymmetric internal loop”, terms that are used herein interchangeably. In cases where the two loops have the same number of nucleotides, they are referred to jointly as a “symmetric loop”, a “symmetric loop pair,” or a “symmetric internal loop”, terms that are used interchangeably herein. The term “loop” as used herein encompasses a “bulge.” As used herein, a “bulge” refers to an internal loop that comprises a single loop that is not paired with a second loop. For example, L1 of Aptamer 3 in FIG. 11A is a bulge.

A loop as described herein may be referred to by its position, in a 5' to 3' direction, on the aptamer. For example, loop 1 (L1) may refer to a loop sequence that is positioned most 5' on the aptamer. Similarly, loop 2 (L2) may refer to a loop sequence that is positioned 3' relative to L1, and loop 3 (L3) may refer to a loop sequence that is positioned 3' relative to L2. Each additional loop may be referred to by its position, in a 5' to 3' direction, on the aptamer, as described above. For example, L4 may be positioned 3' relative to L3 on the aptamer, L5 may be positioned 3' relative to L4 on the aptamer, and so on. In some cases, the term “first loop” is used to refer to a loop in the aptamer, irrespective of its location. For example, a first loop may be L1, L2, L3, L4 or any other loop in the aptamer.

The term “stem-loop” as used herein generally refers to the secondary structure of an aptamer of the disclosure having at least one stem and at least one loop. In some cases, a stem-loop secondary structure may include a terminal stem and a terminal loop. In some cases, a stem-loop secondary structure includes structures having more than one stem, and more than one loop, which may include a terminal stem, at least one internal loop, at least one internal stem, and a terminal loop. A “terminal stem” as used herein generally refers to a stem that encompasses both the 5' and/or 3' terminus of the aptamer. In some cases, a “terminal stem” is bordered at one or both termini by a “tail” comprising one or more unpaired nucleotides. For example, a terminal stem present in the aptamer may be bordered by a tail of one or more unpaired nucleotides (or other structures) at its 5' end. Similarly, a terminal stem present in the aptamer may be bordered by a tail of one or more unpaired nucleotides (or other structures) at its 3' end. In some cases, a terminal stem present in the aptamer may be bordered by a tail of one or more unpaired nucleotides (or other structures) at both its 5' end and its 3' end. A terminal stem may be adjacent to a loop; for example, the 5' side of a terminal stem (e.g., the terminal stem sequence closest to the 5' end of the molecule) may be bordered at its 3' terminus by the 5' terminus of a loop. Similarly, the 3' side of a terminal stem (e.g., the terminal stem sequence closest to the 3' end of the molecule) may be bordered at its 5' terminus by the 3' terminus of a loop. In some cases, the 5' side of a terminal stem (e.g., the terminal stem sequence closest to the 5' end of the molecule) may be bordered at its 3' terminus by the 5' terminus of a loop, and the 3' side of the terminal stem (e.g., the terminal stem sequence closest to the 3' end of the molecule) may be bordered at its 5' terminus by the 3' terminus of an internal stem. An "internal stem" as used herein may refer to a stem that is bordered at both termini by a loop sequence, or may refer to a stem that is bordered at one terminus by a loop sequence and bordered at the other terminus by a stem sequence. In some cases, a stem-loop secondary structure of the disclosure may include more than one internal stem. A "terminal loop" as used herein generally refers to a loop that is bordered by the same stem at both termini of the loop. For example, a terminal loop may be bordered at its 5' end by a stem sequence, and may be bordered at its 3' end by the complementary stem sequence. An "internal loop" as used herein generally refers to a loop that is bordered at both termini by different stems. For example, an internal loop may be bordered at its 5' end by a first stem sequence, and may be bordered at its 3' end by a second stem sequence that is not complementary to the first stem sequence. In some cases, a stem-loop secondary structure of the disclosure may include more than one internal loop. In some cases, a stem-loop secondary structure of the disclosure may include more than one terminal loop. In some cases, a stem-loop secondary structure includes structures having more than two stems. Unless otherwise stated, when an aptamer includes more than one stem and/or more than one loop, the stems and loops are numbered consecutively in ascending order from the 5' end to the 3' end of the primary nucleotide sequence.

In some aspects, an aptamer of the disclosure may have a stem-loop secondary structure as described herein for the Aptamer 3 structural family of aptamers. In some cases, an aptamer of the Aptamer 3 structural family of aptamers may have, in a 5' to 3' direction, a first stem, a first loop, a second stem, a second loop, a third stem, a third loop, and a fourth loop. In some cases, an aptamer of the Aptamer 3 structural family of aptamers may have the general structure, in a 5' to 3' direction, S1-L1-S2-L2-S3-L3-S3'-L4-S2'-S1'.

In some aspects, an aptamer of the disclosure may have a stem-loop secondary structure as described herein for the Aptamer 8 structural family of aptamers. In some cases, an aptamer of the Aptamer 8 structural family of aptamers may have, in a 5' to 3' direction, a first stem, a first loop, a second stem, and a second loop. In some cases, an aptamer of the Aptamer 8 structural family of aptamers may have the general structure, in a 5' to 3' direction, S1-L1-S2-L2-S2'-S1'.

The term "about," as used herein, generally refers to a range that is 15% greater than or less than a stated numerical value within the context of the particular usage. For example, "about 10" would include a range from 8.5 to 11.5.

As used herein, the term "or" is used nonexclusively to encompass "or" and "and." For example, "A or B" includes "A but not B," "B but not A," and "A and B" unless otherwise indicated.

"A", "an", and "the", as used herein, can include plural referents unless expressly and unequivocally limited to one referent Interleukin-8

This disclosure generally provides compositions that bind to interleukins, particularly interleukin-8 (IL8; also known as chemokine (C-X-C motif) ligand 8 (CXCL8)), and methods of using such compositions to modulate interleukin signaling pathways. IL8 is a chemokine that may be involved in chronic inflammation as well as various human malignancies. IL8 may function by being secreted into the extracellular space and by binding to membrane-bound receptors; as such, the compositions and methods of the disclosure may prevent or reduce binding of IL8 to such membrane-bound receptors. IL8 may be secreted by a number of different cell types, including, but not limited to, monocytes, macrophages, neutrophils, epithelial cells, endothelial cells, tumors cells, melanocytes, and hepatocytes. In the eye, IL8 may be secreted by, for example, retinal pigment epithelial cells, corneal epithelial cells, corneal fibroblasts, conjunctival epithelial cells, and uveal melanocytes. Accordingly, the compositions of the disclosure may bind to IL8 after it has been secreted by various cell types.

IL8 is a member of the CXC family of chemokines and may be closely related to GRO-α (also known as CXCL1) and GRO-β (also known as CXCL2). In some cases, the compositions may include anti-IL8 inhibitors that selectively bind to IL8. In some cases, such anti-IL8 inhibitors may have little to no binding affinity for GRO-α, GRO-β, or both. In other cases, such anti-IL8 aptamers may also bind to GRO-α, GRO-β, or both. IL8 may signal through both the C-X-C motif chemokine receptor 1 (CXCR1) and the C-X-C motif chemokine receptor 2 (CXCR2); as such, the compositions and methods disclosed herein may prevent or reduce the ability of IL8 to signal through CXCR1, CXCR2, or both. There are thought to be two major isoforms of IL8: IL8-72 and IL8-77. IL8-77 may have a decreased affinity for receptor binding. In some cases, the compositions may include anti-IL8 inhibitors that bind to an isoform of IL8. For example, the compositions may include anti-IL8 inhibitors that bind to IL8-72. Additionally or alternatively, the compositions may include anti-IL8 inhibitors that bind to IL8-77. In addition, IL8 may exist as both a monomer and dimer, both of which may bind to CXCR1, CXCR2, or both. In some cases, the compositions may include anti-IL8 inhibitors that bind to a monomer of IL8. In some cases, the compositions may include anti-IL8 inhibitors that bind to a dimer of IL8.

CXCR1 and CXCR2 are seven-transmembrane-domain containing G-coupled protein receptors (GPCRs) which may signal through intracellular G-proteins. As depicted in FIG. 1, upon IL8 binding, G protein subunits may be released into the cells leading to an increase in intracellular cAMP or phospholipase that may activate MAPK signaling. IL8 binding may cause an increase in 3,4,5-inosital triphosphate which may lead to a rapid increase in free calcium and subsequently to neutrophil degranulation (FIG. 1). Neutrophil degranulation may be an important step in the infiltration process that may allow for bacterial clearance. Glycosaminoglycans (GAGs), in particular heparin, may bind to the C-terminus of IL8; such binding is thought to increase the activity of IL8 by allowing for binding to the surface of neutrophils. In some cases, the anti-IL8 compositions of the disclosure may prevent or reduce binding of IL8 to GAGs (e.g., heparin); without wishing to be bound by theory, such compositions may prevent or reduce binding of IL8 to the surface of neutrophils. In addition to the role of IL8 in neutrophil migration, IL8 may affect neovascularization and angiogenesis, thus, anti-IL8 compositions of the disclosure may affect neovascularization, angiogenesis, or both. In some cases, the compositions described herein may affect a signaling pathway associated with IL8 signaling through CXCR1, CXCR2, or both, as described in FIG. 1. For example, the anti-IL8 compositions of the disclosure may prevent or reduce IL8-induced G protein signaling; without wishing to be bound by theory, such inhibitors may prevent an increase in intracellular cAMP or phospholipase, thereby preventing or reducing IL8-induced MAPK signaling. In some examples, the anti-IL8 compositions of the disclosure may prevent or reduce IL8-induced increases in 3,4,5-inositol triphosphate and increases in intracellular free calcium. In some cases, the anti-IL8 compositions of the disclosure may prevent or reduce IL8-induced neutrophil degranulation.

In one instance, an amino acid sequence of human IL8 comprises the following sequence:

AVLPRSAKELRCQCIKTYSKPFHPKFIKELRVIES-GPHCANTEIIVKLSDGRELCLDPKEN WVQRVVEKF-LKRAENS (SEQ ID NO: 97).

In one instance, an amino acid sequence of human IL8-72 may comprise the following sequence: SAKELRCQCIK-TYSKPFHPKFIKELRVIESGPHCANTEIIVKLSDGREL-CLDPKENWVQRV VEKFLKRAENS (SEQ ID NO: 2)

Aptamers

In some cases, the methods and compositions described herein use one or more aptamers for the treatment of an ocular disease. In some cases, the methods and compositions described herein may use one or more anti-IL8 aptamers having a stem-loop secondary structure for the treatment of an ocular disease. In some cases, the stem-loop secondary structure may be as described herein for the Aptamer 3 structural family of aptamers. In some cases, the stem-loop secondary structure may be as described herein for the Aptamer 8 structural family of aptamers. In some cases, the methods and compositions described herein utilize one or more aptamers for inhibiting an activity associated with IL8. In some cases, the methods and compositions may include the use of one or more anti-IL8 aptamers having a stem-loop secondary structure for inhibiting an activity associated with IL8. In some cases, the stem-loop secondary structure may be as described herein for the Aptamer 3 structural family of aptamers. In some cases, the stem-loop secondary structure may be as described herein for the Aptamer 8 structural family of aptamers.

Aptamers as described herein may include any number of modifications that can affect the function or affinity of the aptamer. For example, aptamers may be unmodified or they may contain modified nucleotides to improve stability, nuclease resistance or delivery characteristics. Examples of such modifications may include chemical substitutions at the sugar and/or phosphate and/or base positions, for example, at the 2' position of ribose, the 5 position of pyrimidines, and the 8 position of purines, various 2'-modified pyrimidines and purines and modifications with 2'-amino (2'-$NH_2$), 2'-fluoro (2'-F), and/or 2'-O-methyl (2'-OMe) substituents. In some cases, aptamers described herein comprise a 2'-OMe and/or a 2'F modification to increase in vivo stability. In some cases, the aptamers described herein contain modified nucleotides to improve the affinity and specificity of the aptamers for a target. Examples of modified nucleotides include those modified with guanidine, indole, amine, phenol, hydroxymethyl, or boronic acid. In other cases, pyrimidine nucleotide triphosphate analogs or CE-phosphoramidites may be modified at the 5 position to generate, for example, 5-benzylaminocarbonyl-2'-deoxyuridine (BndU); 5-[N-(phenyl-3-propyl) carboxamide]-2'-deoxyuridine (PPdU); 5-(N-thiophenylmethylcarboxyamide)-2'-deoxyuridine (ThdU); 5-(N-4-fluorobenzylcarboxyamide)-2'-deoxyuridine (FBndU); 5-(N-(1-naphthylmethyl) carboxamide)-2'-deoxyuridine (NapdU); 5-(N-2-naphthylmethylcarboxyamide)-2'-deoxyuridine (2NapdU); 5-(N-1-naphthylethylcarboxyamide)-2'-deoxyuridine (NEdU); 5-(N-2-naphthylethylcarboxyamide)-2'-deoxyuridine (2NEdU); 5-(N-tryptaminocarboxyamide)-2'-deoxyuridine (TrpdU); 5-isobutylaminocarbonyl-2'-deoxyuridine (IbdU); 5-(N-tyrosylcarboxyamide)-2'-deoxyuridine (TyrdU); 5-(N-isobutylaminocarbonyl-2'-deoxyuridine (iBudU); 5-(N-benzylcarboxyamide)-2'-O-methyluridine, 5-(N-benzylcarboxyamide)-2'-fluorouridine, 5-(N-phenethylcarboxyamide)-2'-deoxyuridine (PEdU), 5-(N-3,4-methylenedioxybenzylcarboxyamide)-2'-deoxyuridine (MBndU), 5-(N-imidizolylethylcarboxyamide)-2'-deoxyuridine (ImdU), 5-(N-isobutylcarboxyamide)-2'-O-methyluridine, 5-(N-isobutylcarboxyamide)-2'-fluorouridine, 5-(N—R-threoninylcarboxyamide)-2'-deoxyuridine (ThrdU), 5-(N-tryptaminocarboxyamide)-2'-O-methyluridine, 5-(N-tryptaminocarboxyamide)-2'-fluorouridine, 5-(N-[1-(3-trimethylamonium) propyl]carboxyamide)-2'-deoxyuridine chloride, 5-(N-naphthylmethylcarboxyamide)-2'-O-methyluridine, 5-(N-naphthylmethylcarboxyamide)-2'-fluorouridine, 5-(N-[1-(2,3-dihydroxypropyl)]carboxyamide)-2'-deoxyuridine), 5-(N-2-naphthylmethylcarboxyamide)-2'-O-methyluridine, 5-(N-2-naphthylmethylcarboxyamide)-2'-fluorouridine, 5-(N-1-naphthylethylcarboxyamide)-2'-O-methyluridine, 5-(N-1-naphthylethylcarboxyamide)-2'-fluorouridine, 5-(N-2-naphthylethylcarboxyamide)-2'-O-methyluridine, 5-(N-2-naphthylethylcarboxyamide)-2'-fluorouridine, 5-(N-3-benzofuranylethylcarboxyamide)-2'-deoxyuridine (BFdU), 5-(N-3-benzofuranylethylcarboxyamide)-2'-O-methyluridine, 5-(N-3-benzofuranylethylcarboxyamide)-2'-fluorouridine, 5-(N-3-benzothiophenylethylcarboxyamide)-2'-deoxyuridine (BTdU), 5-(N-3-benzothiophenylethylcarboxyamide)-2'-O-methyluridine, 5-(N-3-benzothiophenylethylcarboxyamide)-2'-fluorouridine; 5-[N-(1-morpholino-2-ethyl) carboxamide]-2'-deoxyuridine (MOEdu); R-tetrahydrofuranylmethyl-2'-deoxyuridine (RTMdU); 3-methoxybenzyl-2'-deoxyuridine (3MBndU); 4-methoxybenzyl-2'-deoxyuridine (4MBndU); 3,4-dimethoxybenzyl-2'-deoxyuridine (3,4DMBndU); S-tetrahydrofuranylmethyl-2'-deoxyuridine (STMdU); 3,4-methylenedioxyphenyl-2-ethyl-2'-deoxyuridine (MPEdU); 4-pyridinylmethyl-2'-deoxyuridine (PyrdU); or 1-benzimidazol-2-ethyl-2'-deoxyuridine (BidU); 5-(amino-1-propenyl)-2'-deoxyuridine; 5-(indole-3-acetamido-1-propenyl)-2'-deoxyuridine; or 5-(4-pivaloylbenzamido-1-propenyl)-2'-deoxyuridine.

Modifications of the aptamers contemplated in this disclosure include, without limitation, those which provide other chemical groups that incorporate additional charge, polarizability, hydrophobicity, hydrogen bonding, electrostatic interaction, and functionality to the nucleic acid aptamer bases or to the nucleic acid aptamer as a whole. Modifications to generate oligonucleotide populations that are resistant to nucleases can also include one or more substitute internucleotide linkages, altered sugars, altered bases, or combinations thereof. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, phosphorothioate, phosphorodithioate, or alkyl phosphate modifications, methylations, and unusual base-pairing combinations such as the isobases isocytidine and isoguanosine. Modifications can also include 3' and 5' modifications such as capping, e.g., addition of a 3'-3'-dT cap to increase exonuclease resistance.

Aptamers of the disclosure may generally comprise nucleotides having ribose in the β-D-ribofuranose configuration. In some cases, 100% of the nucleotides present in the aptamer have ribose in the β-D-ribofuranose configuration. In some cases, at least 50% of the nucleotides present in the aptamer have ribose in the β-D-ribofuranose configuration. In some cases, at least 10%, at least 20%, at least 30%, at least 40%, at least 50%, at least 60%, at least 70%, at least 80%, at least 90%, or 100% of the nucleotides present in the aptamer have ribose in the β-D-ribofuranose configuration.

The length of the aptamer can be variable. In some cases, the length of the aptamer is less than 100 nucleotides. In some cases, the length of the aptamer is greater than 10 nucleotides. In some cases, the length of the aptamer is between 10 and 90 nucleotides. The aptamer can be, without limitation, about 10, about 15, about 20, about 25, about 30, about 35, about 40, about 45, about 50, about 55, about 60, about 65, about 70, about 75, about 80, about 85, or about 90 nucleotides in length.

In some instances, a polyethylene glycol (PEG) polymer chain is covalently bound to the aptamer, referred to herein as PEGylation. Without wishing to be bound by theory, PEGylation may increase the half-life and stability of the aptamer in physiological conditions. In some cases, the PEG polymer is covalently bound to the 5' end of the aptamer. In some cases, the PEG polymer is covalently bound to the 3' end of the aptamer. In some cases, the PEG polymer is covalently bound to both the 5' end and the 3' end of the aptamer. In some cases, the PEG polymer is covalently bound to a specific site on a nucleobase within the aptamer, including the 5-position of a pyrimidine or 8-position of a purine. In some cases, the PEG polymer is covalently bound to an abasic site within the aptamer.

In some cases, an aptamer described herein may be conjugated to a PEG having the general formula, $H—(O—CH_2—CH_2)$ n-OH. In some cases, an aptamer described herein may be conjugated to a methoxy-PEG (mPEG) of the general formula, $CH_3O—(CH_2—CH_2—O)_n—H$. In some cases, the aptamer is conjugated to a linear chain PEG or mPEG. The linear chain PEG or mPEG may have an average molecular weight of up to about 30 kD. Multiple linear chain PEGs or mPEGs can be linked to a common reactive group to form multi-arm or branched PEGs or mPEGs. For example, more than one PEG or mPEG can be linked together through an amino acid linker (e.g., lysine) or another linker, such as glycerine. In some cases, the aptamer is conjugated to a branched PEG or branched mPEG. Branched PEGs or mPEGs may be referred to by their total mass (e.g., two linked 20 kD mPEGs have a total molecular weight of 40 kD). Branched PEGs or mPEGs may have more than two arms. Multi-arm branched PEGs or mPEGs may be referred to by their total mass (e.g., four linked 10 kD mPEGs have a total molecular weight of 40 kD). In some cases, an aptamer of the present disclosure is conjugated to a PEG polymer having a total molecular weight from about 5 kD to about 200 kD, for example, about 5 kD, about 10 kD, about 20 kD, about 30 kD, about 40 kD, about 50 kD, about 60 kD, about 70 kD, about 80 kD, about 90 kD, about 100 kD, about 110 kD, about 120 kD, about 130 kD, about 140 kD, about 150 kD, about 160 kD, about 170 kD, about 180 kD, about 190 kD, or about 200 kD. In one non-limiting example, the aptamer is conjugated to a PEG having a total molecular weight of about 40 kD.

In some cases, the reagent that may be used to generate PEGylated aptamers is a branched PEG N-Hydroxysuccinimide (mPEG-NHS) having the general formula:

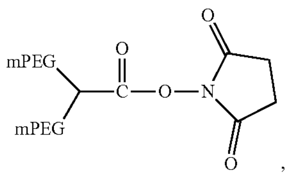

with a 20 kD, 40 kD or 60 kD total molecular weight (e.g., where each mPEG is about 10 kD, 20 kD or about 30 kD). As described above, the branched PEGs can be linked through any appropriate reagent, such as an amino acid (e.g., lysine or glycine residues).

In one non-limiting example, the reagent used to generate PEGylated aptamers is [$N^2$-(monomethoxy 20K polyethylene glycol carbamoyl)-$N^6$-(monomethoxy 20K polyethylene glycol carbamoyl)]-lysine N-hydroxysuccinimide having the formula:

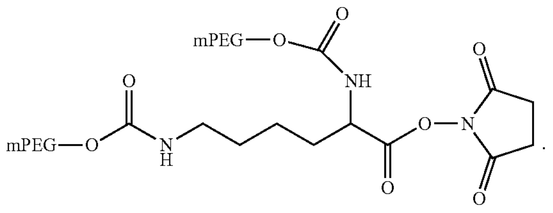

In yet another non-limiting example, the reagent used to generate PEGylated aptamers has the formula:

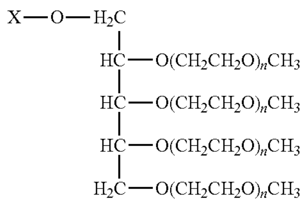

where X is N-hydroxysuccinimide and the PEG arms are of approximately equivalent molecular weight. Such PEG architecture may provide a compound with reduced viscosity compared to a similar aptamer conjugated to a two-armed or single-arm linear PEG.

In some examples, the reagent used to generate PEGylated aptamers has the formula:

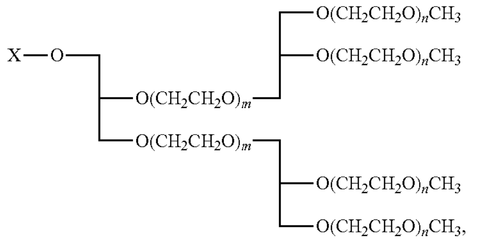

where X is N-hydroxysuccinimide and the PEG arms are of different molecular weights, for example, a 40 kD PEG of this architecture may be composed of 2 arms of 5 kD and 4 arms of 7.5 kD. Such PEG architecture may provide a compound with reduced viscosity compared to a similar aptamer conjugated to a two-armed PEG or a single-arm linear PEG.

In some cases, the reagent that may be used to generate PEGylated aptamers is a non-branched mPEG-Succinimidyl Propionate (mPEG-SPA), having the general formula:

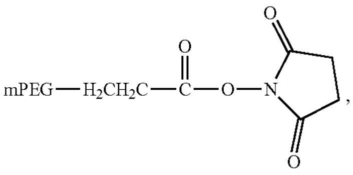

where mPEG is about 20 kD or about 30 kD. In one example, the reactive ester may be —O—$CH_2$—$CH_2$—$CO_2$—NHS.

In some instances, the reagent that may be used to generate PEGylated aptamers may include a branched PEG linked through glycerol, such as the SUNBRIGHT® series from NOF Corporation, Japan. Non-limiting examples of these reagents include:

(SUNBRIGHT® GL2-400GS2)

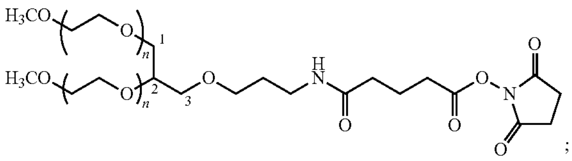

;

(SUNBRIGHT® GL2-400HS)

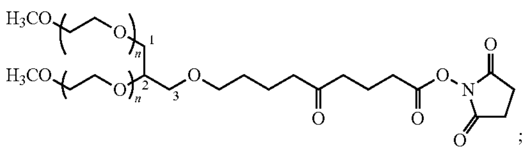

; and (SUNBRIGHT® GL2-400TS)

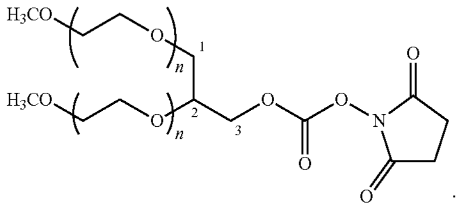

.

In another example, the reagents may include a non-branched mPEG Succinimidyl alpha-methylbutanoate (mPEG-SMB) having the general formula:

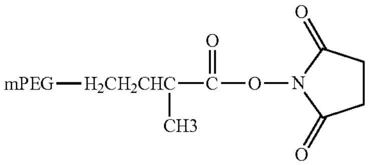

, where mPEG is between 10 and 30 kD. In one example, the reactive ester may be —O—$CH_2$—$CH_2$—$CH(CH_3)$—$CO_2$—NHS.

In other instances, the PEG reagents may include nitrophenyl carbonate-linked PEGs, having the general formula:

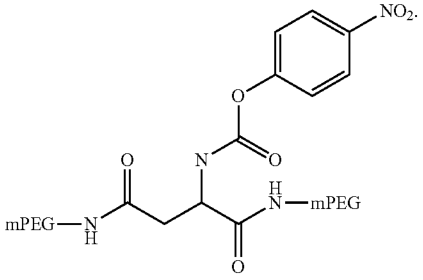

Compounds including nitrophenyl carbonate can be conjugated to primary amine containing linkers.

In some cases, the reagents used to generate PEGylated aptamers may include PEG with thiol-reactive groups that can be used with a thiol-modified linker. One non-limiting example may include reagents having the following general structure:

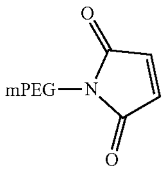

, where mPEG is about 10 kD, about 20 kD or about 30 kD.

Another non-limiting example may include reagents having the following general structure:

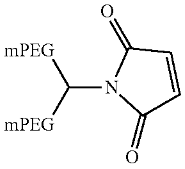

, where each mPEG is about 10 kD, about 20 kD, or about 30 kD and the total molecular weight is about 20 kD, about 40 kD, or about 60 kD, respectively. Branched PEGs with thiol reactive groups that can be used with a thiol-modified linker, as described above, may include reagents in which the branched PEG has a total molecular weight of about 40 kD or about 60 kD (e.g., where each mPEG is about 20 kD or about 30 kD).

In some cases, the reagents used to generated PEGylated aptamers may include reagents having the following structure:

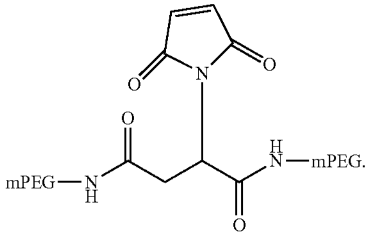

In some cases, the reaction to conjugate the PEG to the aptamer is carried out between about pH 6 and about pH 10, or between about pH 7 and pH 9 or about pH 8.

In some cases, the reagents used to generate PEGylated aptamers may include reagents having the following structure:

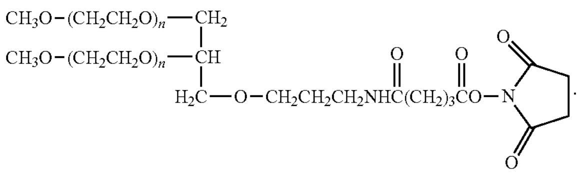

In some cases, the reagents used to generate PEGylated aptamers may include reagents having the following structure:

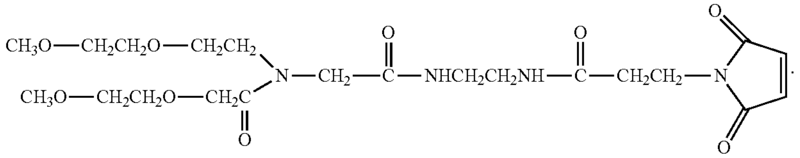

In some cases, the aptamer is associated with a single PEG molecule. In other cases, the aptamer is associated with two or more PEG molecules.

In some cases, the aptamers described herein may be bound or conjugated to one or more molecules having desired biological properties. Any number of molecules can be bound or conjugated to aptamers, non-limiting examples including antibodies, peptides, proteins, carbohydrates, enzymes, polymers, drugs, small molecules, gold nanoparticles, radiolabels, fluorescent labels, dyes, haptens (e.g., biotin), other aptamers, or nucleic acids (e.g., siRNA). In some cases, aptamers may be conjugated to molecules that increase the stability, the solubility or the bioavailability of the aptamer. Non-limiting examples include polyethylene glycol (PEG) polymers, carbohydrates and fatty acids. In some cases, molecules that improve the transport or delivery of the aptamer may be used, such as cell penetrating peptides. Non-limiting examples of cell penetrating peptides can include peptides derived from Tat, penetratin, polyarginine peptide Args sequence (SEQ ID NO: 1313), Transportan, VP22 protein from Herpes Simplex Virus (HSV), antimicrobial peptides such as Buforin I and SynB, polyproline sweet arrow peptide molecules, Pep-1 and MPG. In some embodiments, the aptamer is conjugated to a lipophilic compound such as cholesterol, dialkyl glycerol, diacyl glycerol, or a non-immunogenic, high molecular weight compound or polymer such as polyethylene glycol (PEG) or other water-soluble pharmaceutically acceptable polymers including, but not limited to, polyaminoamines (PAMAM) and polysaccharides such as dextran, or polyoxazolines (POZ).

The molecule to be conjugated can be covalently bonded or can be associated through non-covalent interactions with the aptamer of interest. In one example, the molecule to be conjugated is covalently attached to the aptamer. The covalent attachment may occur at a variety of positions on the aptamer, for example, to the exocyclic amino group on the base, the 5-position of a pyrimidine nucleotide, the 8-position of a purine nucleotide, the hydroxyl group of the phosphate, or a hydroxyl group or other group at the 5' or 3' terminus. In one example, the covalent attachment is to the 5' or 3' hydroxyl group of the aptamer.

In some cases, the aptamer can be attached to another molecule directly or with the use of a spacer or linker. For example, a lipophilic compound or a non-immunogenic, high molecular weight compound can be attached to the aptamer using a linker or a spacer. Various linkers and attachment chemistries are known in the art. In a non-limiting example, 6-(trifluoroacetamido) hexanol (2-cyanoethyl-N,N-diisopropyl)phosphoramidite can be used to add a hexylamino linker to the 5' end of the synthesized aptamer. This linker, as with the other amino linkers provided herein, once the group protecting the amine has been removed, can be reacted with PEG-NHS esters to produce covalently linked PEG-aptamers. Other non-limiting examples of linker phosphoramidites may include: TFA-amino C4 CED phosphoramidite having the structure:

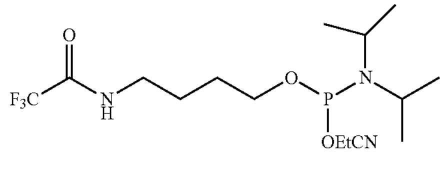

;

5'-amino modifier C3 TFA having the structure:

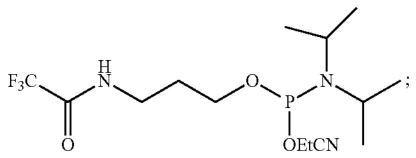

MMT amino modifier C6 CED phosphoramidite having the structure:

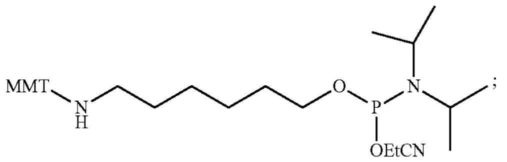

5'-amino modifier 5 having the structure:

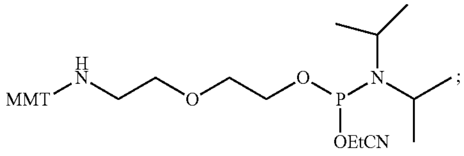

MMT: 4-Monomethoxytrityl

5'-amino modifier C12 having the structure:

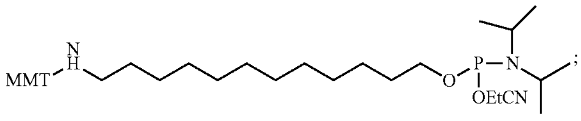

MMT: 4-Monomethoxytrityl

5' thiol-modifier C6 having the structure:

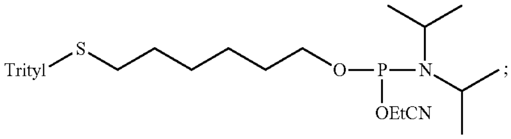

5' thiol-modifier C6 having the structure:

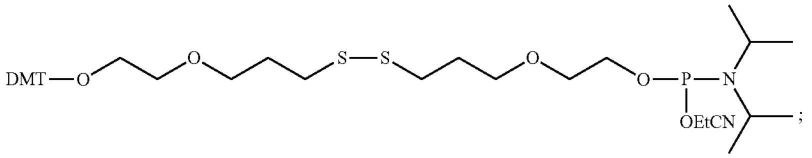

DMT: 4,4'-Dimethoxytrityl and 5' thiol-modifier C6 having the structure:

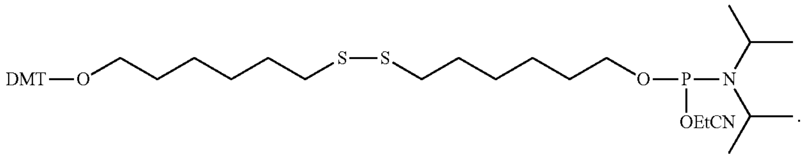

DMT: 4,4'-Dimethoxytrityl

The 5'-thiol modified linker may be used, for example, with PEG-maleimides, PEG-vinylsulfone, PEG-iodoacetamide and PEG-orthopyridyl-disulfide. In one example, the aptamer may be bonded to the 5'-thiol through a maleimide or vinyl sulfone functionality.

In some cases, the aptamer formulated according to the present disclosure may also be modified by encapsulation within or displayed on the surface of a liposome. In other cases, the aptamer formulated according to the present disclosure may also be modified by encapsulation within or displayed on the surface of a micelle. Liposomes and micelles may be comprised of any lipids, and in some cases the lipids may be phospholipids, including phosphatidylcholine. Liposomes and micelles may also contain or be comprised in part or in total of other polymers and amphipathic molecules including PEG conjugates of poly lactic acid (PLA), poly DL-lactic-co-glycolic acid (PLGA), or poly caprolactone (PCL).

In some cases, the aptamers described herein may be designed to inhibit a function associated with IL8. In some cases, the aptamers described herein may be designed to bind the N-terminal domain of IL8, or a portion thereof. The N-terminal domain of IL8 may include any one or more of residues 2-6 of IL8-72 (SEQ ID NO: 2). In some cases, the aptamers described herein may be designed to bind to the hydrophobic pocket of IL8, or a portion thereof. The hydrophobic pocket of IL8 may include any one or more of residues 12-18, F21, 122, 140, L43, R47, and L49, of IL8-72 (SEQ ID NO: 2). In some cases, the aptamers described herein may be designed to bind to the N-loop of IL8, or a portion thereof. The N-loop of IL8 may include any one or more of residues 7-11 of IL8-72 (SEQ ID NO: 2). In some cases, the aptamers described herein may be designed to bind to the GAG binding site of IL8, or a portion thereof. The GAG binding site may include any one or more of residues H18, K20, R60, K64, K67 and R68 of IL8-72 (SEQ ID NO: 2). In some cases, the aptamers described herein may block or reduce binding of IL8 to CXCR1, CXCR2, or both.

In some instances, an aptamer is isolated or purified. “Isolated” (used interchangeably with “substantially pure” or “purified”) as used herein means that an aptamer that is synthesized chemically; or has been separated from other aptamers.

In some cases, an aptamer of the disclosure may comprise one of the following sequences described in Tables 1-3.

TABLE 1

| Anti-IL8 Aptamer Sequences | | | |
|---|---|---|---|
| Compound Name | Backbone | Primary Sequence (5' to 3') | Modified Sequence (5' to 3') |
| Rd8-3 | RNA | GGGAGAGUCGGUAGCAGUC UAGCGGCCGAAGUUAGCGU ACGUUUGCCGGGUACGUCU AUGUGGAAAUGGCGCUGU (SEQ ID NO: 3) | GGGAGAGUCGGUAGCAGUCUAGC GGCCGAAGUUAGCGUACGUUUGC CGGGUACGUCUAUGUGGAAAUGG CGCUGU (SEQ ID NO: 3), where G is 2'F; and A, C, and U are 2'OMe modified RNA. |
| Rd6-6 | RNA | GGGAGAGUCGGUAGCAGUC UGAUGACGGUAGAUUACGG GUAGAGUGACCGCAUCUCU AUGUGGAAAUGGCGCUGU (SEQ ID NO: 4) | GGGAGAGUCGGUAGCAGUCUGAU GACGGUAGAUUACGGGUAGAGU GACCGCAUCUCUAUGUGGAAAUG GCGCUGU (SEQ ID NO: 4), where G is 2'F; and A, C, and U are 2'OMe modified RNA. |
| Rd6-11 | RNA | GGGAGAGUCGGUAGCAGUC UAAUUGCGGUCUACCUUGA AUGACUUGCCGCCCAUUCU AUGUGGAAAUGGCGCUGU (SEQ ID NO: 5) | GGGAGAGUCGGUAGCAGUCUAAU UGCGGUCUACCUUGAAUGACUUG CCGCCCAUUCUAUGUGGAAAUGG CGCUGU (SEQ ID NO: 5), where G is 2'F; and A, C, and U are 2'OMe modified RNA. |
| Rd6-4 | RNA | GGGAGAGUCGGUAGCAGUC UCGUGAAGGGCGAUUCUGG UGCGUGUUCCCUCGCGUCU AUGUGGAAAUGGCGCUGU (SEQ ID NO: 6) | GGGAGAGUCGGUAGCAGUCUCGU GAAGGGCGAUUCUGGUGCGUGUU CCCUCGCGUCUAUGUGGAAAUGG CGCUGU (SEQ ID NO: 6), where G is 2'F; and A, C, and U are 2'OMe modified RNA. |
| Rd8-4 | RNA | GGGAGAGUCGGUAGCAGUC UCAGGCUGAAAAGUGAGCU AUAAUGUCCUGAUUGAUCU AUGUGGAAAUGGCGCUGU (SEQ ID NO: 7) | GGGAGAGUCGGUAGCAGUCUCAG GCUGAAAAGUGAGCUAUAAUGUC CUGAUUGAUCUAUGUGGAAAUG GCGCUGU (SEQ ID NO: 7), where G is 2'F; and A, C, and U are 2'OMe modified RNA. |
| Rd6-10 | RNA | GGGAGAGUCGGUAGCAGUC UUAUUGCGGCCCGAUUUAC CGAAUUUGCCGUCCGGUCU AUGUGGAAAUGGCGCUGU (SEQ ID NO: 8) | GGGAGAGUCGGUAGCAGUCUUAU UGCGGCCCGAUUUACCGAAUUUG CCGUCCGGUCUAUGUGGAAAUGG CGCUGU (SEQ ID NO: 8), where G is 2'F; and A, C, and U are 2'OMe modified RNA. |
| Rd6-1 | RNA | GGGAGAGUCGGUAGCAGUC UACGGUGGGAAAUGUGAGA UGGGUUGCCGUAUUUUCUA UGUGGAAAUGGCGCUGU (SEQ ID NO: 9) | GGGAGAGUCGGUAGCAGUCUACG GUGGGAAAUGUGAGAUGGGUUG CCGUAUUUUCUAUGUGGAAAUGG CGCUGU (SEQ ID NO: 9), where G is 2'F; and A, C, and U are 2'OMe modified RNA. |
| Rd6-3 | RNA | GGGAGAGUCGGUAGCAGUC UGCCGACUCACGAAAUCCU CGCGUAGACUGCCUUAUCU AUGUGGAAAUGGCGCUGU (SEQ ID NO: 10) | GGGAGAGUCGGUAGCAGUCUGCC GACUCACGAAAUCCUCGCGUAGA CUGCCUUAUCUAUGUGGAAAUGG CGCUGU (SEQ ID NO: 10), where G is 2'F; and A, C, and U are 2'OMe modified RNA. |
| Rd6-19 | RNA | GGGAGAGUCGGUAGCAGUC UGAUGAUUUGCGGCAAUAC CGUACCUGCCGCCCGGUCU AUGUGGAAAUGGCGCUGU (SEQ ID NO: 11) | GGGAGAGUCGGUAGCAGUCUGAU GAUUUGCGGCAAUACCGUACCUG CCGCCCGGUCUAUGUGGAAAUGG CGCUGU (SEQ ID NO: 11), where G is 2'F; and A, C, and U are 2'OMe modified RNA. |
| Rd6-8 | RNA | GGGAGAGUCGGUAGCAGUC UCCGGUUGCUGAGAUGUGA GAUUAAUGUCCACCGUUCU AUGUGGAAAUGGCGCUGU (SEQ ID NO: 12) | GGGAGAGUCGGUAGCAGUCUCCG GUUGCUGAGAUGUGAGAUUAAU GUCCACCGUUCUAUGUGGAAAUG GCGCUGU (SEQ ID NO: 12), where G is 2'F; and A, C, and U are 2'OMe modified RNA. |

TABLE 1-continued

| Anti-IL8 Aptamer Sequences | | | |
|---|---|---|---|
| Compound Name | Backbone | Primary Sequence (5' to 3') | Modified Sequence (5' to 3') |
| Rd6-9 | RNA | GGGAGAGUCGGUAGCAGUC UUGGCCACAGUAGAUUUCG GUGCGUGUGACUGGGCUCU AUGUGGAAAUGGCGCUGU (SEQ ID NO: 13) | GGGAGAGUCGGUAGCAGUCUUGG CCACAGUAGAUUUCGGUGCGUGU GACUGGGCUCUAUGUGGAAAUGG CGCUGU (SEQ ID NO: 13), where G is 2'F; and A, C, and U are 2'OMe modified RNA. |
| Rd6-12 | RNA | GGGAGAGUCGGUAGCAGUC UCGCUUGUACCUCUGAGAU GUGAGACUAAUGUAGGUCU AUGUGGAAAUGGCGCUGU (SEQ ID NO: 14) | GGGAGAGUCGGUAGCAGUCUCGC UUGUACCUCUGAGAUGUGAGACU AAUGUAGGUCUAUGUGGAAAUG GCGCUGU (SEQ ID NO: 14), where G is 2'F; and A, C, and U are 2'OMe modified RNA. |
| Rd8-7 | RNA | GGGAGAGUCGGUAGCAGUC UGCGGCCUCCGUUGACUGU UGUAAUGCCGGGACAGUCU AUGUGGAAAUGGCGCUGU (SEQ ID NO: 15) | GGGAGAGUCGGUAGCAGUCUGCG GCCUCCGUUGACUGUUGUAAUGC CGGGACAGUCUAUGUGGAAAUGG CGCUGU (SEQ ID NO: 15), where G is 2'F; and A, C, and U are 2'OMe modified RNA. |
| Rd6-15 | RNA | GGGAGAGUCGGUAGCAGUC UCAGUUGCGGCCCCUGAUA CCGAUUUGCCGCCCGGUCU AUGUGGAAAUGGCGCUGU (SEQ ID NO: 16) | GGGAGAGUCGGUAGCAGUCUCAG UUGCGGCCCCUGAUACCGAUUUG CCGCCCGGUCUAUGUGGAAAUGG CGCUGU (SEQ ID NO: 16), where G is 2'F; and A, C, and U are 2'OMe modified RNA. |
| Rd6-17 | RNA | GGGAGAGUCGGUAGCAGUC UGCUGGCGACUCGCACGGU GUAUUUGUCCCGCACCUCU AUGUGGAAAUGGCGCUGU (SEQ ID NO: 17) | GGGAGAGUCGGUAGCAGUCUGCU GGCGACUCGCACGGUGUAUUUGU CCCGCACCUCUAUGUGGAAAUGG CGCUGU (SEQ ID NO: 17), where G is 2'F; and A, C, and U are 2'OMe modified RNA. |
| Rd6-24 | RNA | GGGAGAGUCGGUAGCAGUC UGGAUGACAUUCGGGGGCA CCAAUCAUCGUCUGCUCUA UGUGGAAAUGGCGCUGU (SEQ ID NO: 18) | GGGAGAGUCGGUAGCAGUCUGGA UGACAUUCGGGGGCACCAAUCAU CGUCUGCUCUAUGUGGAAAUGGC GCUGU (SEQ ID NO: 18), where G is 2'F; and A, C, and U are 2'OMe modified RNA. |
| Rd6-29 | RNA | GGGAGAGUCGGUAGCAGUC UGUCGCCCUACGUAAACCG CUAUUUGCGACUGCGGUCU AUGUGGAAAUGGCGCUGU (SEQ ID NO: 19) | GGGAGAGUCGGUAGCAGUCUGUC GCCCUACGUAAACCGCUAUUUGC GACUGCGGUCUAUGUGGAAAUGG CGCUGU (SEQ ID NO: 19), where G is 2'F; and A, C, and U are 2'OMe modified RNA. |
| Rd6-30 | RNA | GGGAGAGUCGGUAGCAGUC UGACUGCGGUCGCAAGUUA CGGAUUUGCCGCCCCGUCU AUGUGGAAAUGGCGCUGU (SEQ ID NO: 20) | GGGAGAGUCGGUAGCAGUCUGAC UGCGGUCGCAAGUUACGGAUUUG CCGCCCCGUCUAUGUGGAAAUGG CGCUGU (SEQ ID NO: 20), where G is 2'F; and A, C, and U are 2'OMe modified RNA. |
| Rd6-31 | RNA | GGGAGAGUCGGUAGCAGUC UUAAGCGCUGAGACGAGAG AUUAAUGCCGCUUGCCUCU AUGUGGAAAUGGCGCUGU (SEQ ID NO: 21) | GGGAGAGUCGGUAGCAGUCUUAA GCGCUGAGACGAGAGAUUAAUGC CGCUUGCCUCUAUGUGGAAAUGG CGCUGU (SEQ ID NO: 21), where G is 2'F; and A, C, and U are 2'OMe modified RNA. |
| Rd8-15 | RNA | GGGAGAGUCGGUAGCAGUC UCUGAAUCGGCUGAAACGG GAGCAUUAAUGUCCGGUCU AUGUGGAAAUGGCGCUGU (SEQ ID NO: 22) | GGGAGAGUCGGUAGCAGUCUCUG AAUCGGCUGAAACGGGAGCAUUA AUGUCCGGUCUAUGUGGAAAUGG CGCUGU (SEQ ID NO: 22), where G is 2'F; and A, C, and U are 2'OMe modified RNA. |

TABLE 1-continued

Anti-IL8 Aptamer Sequences

| Compound Name | Backbone | Primary Sequence (5' to 3') | Modified Sequence (5' to 3') |
|---|---|---|---|
| Rd6-40 | RNA | GGGAGAGUCGGUAGCAGUC UUAGCCCUGCCAUUGGGGC AUACUUUGGCCGCACUCUA UGUGGAAAUGGCGCUGU (SEQ ID NO: 23) | GGGAGAGUCGGUAGCAGUCUUAG CCCUGCCAUUGGGGCAUACUUUG GCCGCACUCUAUGUGGAAAUGGC GCUGU (SEQ ID NO: 23), where G is 2'F; and A, C, and U are 2'OMe modified RNA. |
| Rd6-63 | RNA | GGGAGAGUCGGUAGCAGUC UUGCCCUUUGAUCGUACCG AGGCGGGGAAGUACGAUCU AUGUGGAAAUGGCGCUGU (SEQ ID NO: 24) | GGGAGAGUCGGUAGCAGUCUUGC CCUUUGAUCGUACCGAGGCGGGG AAGUACGAUCUAUGUGGAAAUG GCGCUGU (SEQ ID NO: 24), where G is 2'F; and A, C, and U are 2'OMe modified RNA. |
| Rd6-94 | RNA | GGGAGAGUCGGUAGCAGUC UCAUGGGUUGCCAACCGGC CGUGUAUGUACGUACAUCU AUGUGGAAAUGGCGCUGU (SEQ ID NO: 25) | GGGAGAGUCGGUAGCAGUCUCAU GGGUUGCCAACCGGCCGUGUAUG UACGUACAUCUAUGUGGAAAUGG CGCUGU (SEQ ID NO: 25), where G is 2'F; and A, C, and U are 2'OMe modified RNA. |
| Rd8-3 | RNA | GGGAGAGUCGGUAGCAGUC UAGCGGCCGAAGUUAGCGU ACGUUUGCCGGGUACGUCU AUGUGGAAAUGGCGCUGU (SEQ ID NO: 26) | GGGAGAGUCGGUAGCAGUCUAGC GGCCGAAGUUAGCGUACGUUUGC CGGGUACGUCUAUGUGGAAAUGG CGCUGU (SEQ ID NO: 26), where G is 2'F; and A, C, and U are 2'OMe modified RNA. |
| Aptamer 2 | RNA | UAGCGGCCGAAGUUAGCGU ACGUUUGCCGGGUACGU (SEQ ID NO: 98) | $C6NH_2$- UAGCGGCCGAAGUUAGCGUACGU UUGCCGGGUACGU-idT (SEQ ID NO: 50), where G is 2'F; A, C, and U are 2'OMe modified RNA; $C6NH_2$ is a hexylamine linker; and idT is an inverted deoxythymidine residue. |
| Aptamer 3 | RNA | UGAUGACGGUAGAUUACGG GUAGAGUGACCGCAUCU (SEQ ID NO: 99) | $C6NH_2$- UGAUGACGGUAGAUUACGGGUA GAGUGACCGCAUCU-idT (SEQ ID NO: 51), where G is 2'F; A, C, and U are 2'OMe modified RNA; $C6NH_2$ is a hexylamine linker; and idT is an inverted deoxythymidine residue. |
| Aptamer 4 | RNA | UAAUUGCGGUCUACCUUGA AUGACUUGCCGCCCAUU (SEQ ID NO: 100) | $C6NH_2$- UAAUUGCGGUCUACCUUGAAUGA CUUGCCGCCCAUU-idT (SEQ ID NO: 52), where G is 2'F; A, C, and U are 2'OMe modified RNA; $C6NH_2$ is a hexylamine linker; and idT is an inverted deoxythymidine residue. |
| Aptamer 5 | RNA | UCGUGAAGGGCGAUUCUGG UGCGUGUUCCCUCGCGU (SEQ ID NO: 101) | $C6NH_2$- UCGUGAAGGGCGAUUCUGGUGCG UGUUCCCUCGCGU-idT (SEQ ID NO: 53), where G is 2'F; A, C, and U are 2'OMe modified RNA; $C6NH_2$ is a hexylamine linker; and idT is an inverted deoxythymidine residue. |
| Aptamer 6 | RNA | UCAGGCUGAAAAGUGAGCU AUAAUGUCCUGAUUGAU (SEQ ID NO: 102) | $C6NH_2$- UCAGGCUGAAAAGUGAGCUAUAA UGUCCUGAUUGAU-idT (SEQ ID NO: 54), where G is 2'F; A, C, and U are 2'OMe modified RNA; $C6NH_2$ is a hexylamine linker; and idT is an inverted deoxythymidine residue. |

TABLE 1-continued

Anti-IL8 Aptamer Sequences

| Compound Name | Backbone | Primary Sequence (5' to 3') | Modified Sequence (5' to 3') |
|---|---|---|---|
| Aptamer 7 | RNA | UUAUUGCGGCCCGAUUUAC CGAAUUUGCCGUCCGGU (SEQ ID NO: 103) | $C6NH_2$-UUAUUGCGGCCCGAUUUACCGAAUUUGCCGUCCGGU-idT (SEQ ID NO: 55), where G is 2'F; A, C, and U are 2'OMe modified RNA; $C6NH_2$ is a hexylamine linker; and idT is an inverted deoxythymidine residue. |
| Aptamer 8 | RNA | UACGGUGGGAAAUGUGAGA UGGGUUGCCGUAUUUU (SEQ ID NO: 104) | $C6NH_2$-UACGGUGGGAAAUGUGAGAUGGGUUGCCGUAUUUU-idT (SEQ ID NO: 56), where G is 2'F; A, C, and U are 2'OMe modified RNA; $C6NH_2$ is a hexylamine linker; and idT is an inverted deoxythymidine residue. |
| Aptamer 9 | RNA | UGCCGACUCACGAAAUCCU CGCGUAGACUGCCUUAU (SEQ ID NO: 105) | $C6NH_2$-UGCCGACUCACGAAAUCCUCGCGUAGACUGCCUUAU-idT (SEQ ID NO: 57), where G is 2'F; A, C, and U are 2'OMe modified RNA; $C6NH_2$ is a hexylamine linker; and idT is an inverted deoxythymidine residue. |
| Aptamer 10 | RNA | UGAUGAUUUGCGGCAAUAC CGUACCUGCCGCCCGGU (SEQ ID NO: 106) | $C6NH_2$-UGAUGAUUUGCGGCAAUACCGUACCUGCCGCCCGGU-idT (SEQ ID NO: 58), where G is 2'F; and A, C, and U are 2'OMe modified RNA; $C6NH_2$ is a hexylamine linker; and idT is an inverted deoxythymidine residue. |
| Aptamer 11 | RNA | UCCGGUUGCUGAGAUGUGA GAUUAAUGUCCACCGUU (SEQ ID NO: 107) | $C6NH_2$-UCCGGUUGCUGAGAUGUGAGAUUAAUGUCCACCGUU-idT (SEQ ID NO: 59), where G is 2'F; A, C, and U are 2'OMe modified RNA; $C6NH_2$ is a hexylamine linker; and idT is an inverted deoxythymidine residue. |
| Aptamer 12 | RNA | UUGGCCACAGUAGAUUUCG GUGCGUGUGACUGGGCU (SEQ ID NO: 108) | $C6NH_2$-UUGGCCACAGUAGAUUUCGGUGCGUGUGACUGGGCU-idT (SEQ ID NO: 60), where G is 2'F; A, C, and U are 2'OMe modified RNA; $C6NH_2$ is a hexylamine linker; and idT is an inverted deoxythymidine residue. |
| Aptamer 13 | RNA | UCGCUUGUACCUCUGAGAU GUGAGACUAAUGUAGGU (SEQ ID NO: 109) | $C6NH_2$-UCGCUUGUACCUCUGAGAUGUGAGACUAAUGUAGGU-idT (SEQ ID NO: 61), where G is 2'F; A, C, and U are 2'OMe modified RNA; $C6NH_2$ is a hexylamine linker; and idT is an inverted deoxythymidine residue. |
| Aptamer 14 | RNA | UGCGGCCUCCGUUGACUGU UGUAAUGCCGGGACAGU (SEQ ID NO: 110) | $C6NH_2$-UGCGGCCUCCGUUGACUGUUGUAAUGCCGGGACAGU-idT (SEQ ID NO: 62), where G is 2'F; A, C, and U are 2'OMe modified RNA; $C6NH_2$ is a hexylamine linker; and idT is an inverted deoxythymidine residue. |

TABLE 1-continued

| Anti-IL8 Aptamer Sequences | | | |
|---|---|---|---|
| Compound Name | Backbone | Primary Sequence (5' to 3') | Modified Sequence (5' to 3') |
| Aptamer 15 | RNA | UCAGUUGCGGCCCCUGAUA CCGAUUUGCCGCCCGGU (SEQ ID NO: 111) | $C6NH_2$-UCAGUUGCGGCCCCUGAUACCGA UUUGCCGCCCGGU-idT (SEQ ID NO: 63), where G is 2'F; A, C, and U are 2'OMe modified RNA; $C6NH_2$ is a hexylamine linker; and idT is an inverted deoxythymidine residue. |
| Aptamer 16 | RNA | UGCUGGCGACUCGCACGGU GUAUUUGUCCCGCACCU (SEQ ID NO: 112) | $C6NH_2$-UGCUGGCGACUCGCACGGUGUAU UUGUCCCGCACCU-idT (SEQ ID NO: 64), where G is 2'F; A, C, and U are 2'OMe modified RNA; $C6NH_2$ is a hexylamine linker; and idT is an inverted deoxythymidine residue. |
| Aptamer 18 | RNA | UGGAUGACAUUCGGGGGCA CCAAUCAUCGUCUGCU (SEQ ID NO: 113) | $C6NH_2$-UGGAUGACAUUCGGGGGCACCAA UCAUCGUCUGCU-idT (SEQ ID NO: 65), where G is 2'F; A, C, and U are 2'OMe modified RNA; $C6NH_2$ is a hexylamine linker; and idT is an inverted deoxythymidine residue. |
| Aptamer 19 | RNA | UGUCGCCCUACGUAAACCG CUAUUUGCGACUGCGGU (SEQ ID NO: 114) | $C6NH_2$-UGUCGCCCUACGUAAACCGCUAU UUGCGACUGCGGU-idT (SEQ ID NO: 66), where G is 2'F; A, C, and U are 2'OMe modified RNA; $C6NH_2$ is a hexylamine linker; and idT is an inverted deoxythymidine residue. |
| Aptamer 20 | RNA | UGACUGCGGUCGCAAGUUA CGGAUUUGCCGCCCCGU (SEQ ID NO: 115) | $C6NH_2$-UGACUGCGGUCGCAAGUUACGGA UUUGCCGCCCCGU-idT (SEQ ID NO: 67), where G is 2'F; A, C, and U are 2'OMe modified RNA; $C6NH_2$ is a hexylamine linker; and idT is an inverted deoxythymidine residue. |
| Aptamer 21 | RNA | UUAAGCGCUGAGACGAGAG AUUAAUGCCGCUUGCCU (SEQ ID NO: 116) | $C6NH_2$-UUAAGCGCUGAGACGAGAGAUUA AUGCCGCUUGCCU-idT (SEQ ID NO: 68), where G is 2'F; A, C, and U are 2'OMe modified RNA; $C6NH_2$ is a hexylamine linker; and idT is an inverted deoxythymidine residue. |
| Aptamer 22 | RNA | UCUGAAUCGGCUGAAACGG GAGCAUUAAUGUCCGGU (SEQ ID NO: 117) | $C6NH_2$-UCUGAAUCGGCUGAAACGGGAGC AUUAAUGUCCGGU-idT (SEQ ID NO: 69), where G is 2'F; A, C, and U are 2'OMe modified RNA; $C6NH_2$ is a hexylamine linker; and idT is an inverted deoxythymidine residue. |
| Aptamer 23 | RNA | UUAGCCCUGCCAUUGGGGC AUACUUUGGCCGCACU (SEQ ID NO: 118) | $C6NH_2$-UUAGCCCUGCCAUUGGGGCAUAC UUUGGCCGCACU-idT (SEQ ID NO: 70), where G is 2'F; A, C, and U are 2'OMe modified RNA; $C6NH_2$ is a hexylamine linker; and idT is an inverted deoxythymidine residue. |

TABLE 1-continued

| Anti-IL8 Aptamer Sequences | | | |
|---|---|---|---|
| Compound Name | Backbone | Primary Sequence (5' to 3') | Modified Sequence (5' to 3') |
| Aptamer 24 | RNA | UUGCCCUUUGAUCGUACCG AGGCGGGGAAGUACGAU (SEQ ID NO: 119) | $C6NH_2$- UUGCCCUUUGAUCGUACCGAGGC GGGGAAGUACGAU-idT (SEQ ID NO: 71), where G is 2'F; A, C, and U are 2'OMe modified RNA; $C6NH_2$ is a hexylamine linker; and idT is an inverted deoxythymidine residue. |
| Aptamer 25 | RNA | UCAUGGGUUGCCAACCGGC CGUGUAUGUACGUACAU (SEQ ID NO: 120) | $C6NH_2$- UCAUGGGUUGCCAACCGGCCGUG UAUGUACGUACAU-idT (SEQ ID NO: 72), where G is 2'F; A, C, and U are 2'OMe modified RNA; $C6NH_2$ is a hexylamine linker; and idT is an inverted deoxythymidine residue. |

TABLE 2

| Aptamer 3 Family | | | |
|---|---|---|---|
| Compound Name | Backbone | Primary Sequence (5' to 3') | Modified Sequence (5' to 3') |
| R5-2 | RNA | GGGAGGGCAAGAGACAGAU GAUGACGGUAGAUUUCGGG UAGUGUGACCGCAUCUCUA UGUGGAAAUGGCGCUGU (SEQ ID NO: 121) | GGGAGGGCAAGAGACAGAUGAU GACGGUAGAUUUCGGGUAGUGU GACCGCAUCUCUAUGUGGAAAUG GCGCUGU (SEQ ID NO: 121), where G is 2'F' and A, C, and U are 2'OMe modified RNA. |
| R5-3 | RNA | GGGAGGGCAAGAGACAGAU GAUGACGGUAGAUUACGGG UAGUGUGACCGCAUCUCUA UGUGGAAAUGGCGCUGU (SEQ ID NO: 122) | GGGAGGGCAAGAGACAGAUGAU GACGGUAGAUUACGGGUAGUGU GACCGCAUCUCUAUGUGGAAAUG GCGCUGU (SEQ ID NO: 122), where G is 2'F; and A, C, and U are 2'OMe modified RNA. |
| R5-4 | RNA | GGGAGGGCAAGAGACAGAU GAUGACGGUAGAUUAUGGG UAGUGUGACCGCAUCUCUA UGUGGAAAUGGCGCUGU (SEQ ID NO: 123) | GGGAGGGCAAGAGACAGAUGAU GACGGUAGAUUAUGGGUAGUGU GACCGCAUCUCUAUGUGGAAAUG GCGCUGU (SEQ ID NO: 123), where G is 2'F; and A, C, and U are 2'OMe modified RNA. |
| R5-5 | RNA | GGGAGGGCAAGAGACAGAU GAUGACGGUAGAUUCCGGG UAGUGUGACCGCAUCUCUA UGUGGAAAUGGCGCUGU (SEQ ID NO: 124) | GGGAGGGCAAGAGACAGAUGAU GACGGUAGAUUCCGGGUAGUGUG ACCGCAUCUCUAUGUGGAAAUGG CGCUGU (SEQ ID NO: 124), where G is 2'F; and A, C, and U are 2'OMe modified RNA. |
| R5-6 | RNA | GGGAGGGCAAGAGACAGAU GAUGACGGUAGAUUUGGGU AGAGUGACCGCAUCUCUAU GUGGAAAUGGCGCUGU (SEQ ID NO: 125) | GGGAGGGCAAGAGACAGAUGAU GACGGUAGAUUUGGGUAGAGUG ACCGCAUCUCUAUGUGGAAAUGG CGCUGU (SEQ ID NO: 125), where G is 2'F; and A, C, and U are 2'OMe modified RNA. |
| R5-7 | RNA | GGGAGGGCAAGAGACAGAU GAUGACGGUAGAUAACGGG UAGAGUGACCGCAUCUCUA UGUGGAAAUGGCGCUGU (SEQ ID NO: 126) | GGGAGGGCAAGAGACAGAUGAU GACGGUAGAUAACGGGUAGAGU GACCGCAUCUCUAUGUGGAAAUG GCGCUGU (SEQ ID NO: 126), where G is 2'F; and A, C, and U are 2'OMe modified RNA. |

TABLE 2-continued

| Aptamer 3 Family | | | |
|---|---|---|---|
| Compound Name | Backbone | Primary Sequence (5' to 3') | Modified Sequence (5' to 3') |
| R5-8 | RNA | GGGAGGGCAAGAGACAGAU GAUGACGGUAGAUUAAGGG UAGUGUGACCGCAUCUCUA UGUGGAAAUGGCGCUGU (SEQ ID NO: 127) | GGGAGGGCAAGAGACAGAUGAU GACGGUAGAUUAAGGGUAGUGU GACCGCAUCUCUAUGUGGAAAUG GCGCUGU (SEQ ID NO: 127), where G is 2'F; and A, C, and U are 2'OMe modified RNA. |
| R5-9 | RNA | GGGAGGGCAAGAGACAGAU GAUGACGGUAGAUUACGGG AAGUGUGACCGCAUCUCUA UGUGGAAAUGGCGCUGU (SEQ ID NO: 128) | GGGAGGGCAAGAGACAGAUGAU GACGGUAGAUUACGGGAAGUGU GACCGCAUCUCUAUGUGGAAAUG GCGCUGU (SEQ ID NO: 128), where G is 2'F; and A, C, and U are 2'OMe modified RNA. |
| R5-10 | RNA | GGGAGGGCAAGAGACAGAU GAUGACGGUAGAUUACGGG AAGAGUGACCGCAUCUCUA UGUGGAAAUGGCGCUGU (SEQ ID NO: 129) | GGGAGGGCAAGAGACAGAUGAU GACGGUAGAUUACGGGAAGAGU GACCGCAUCUCUAUGUGGAAAUG GCGCUGU (SEQ ID NO: 129), where G is 2'F; and A, C, and U are 2'OMe modified RNA. |
| R5-11 | RNA | GGGAGGGCAAGAGACAGAU GAUGACGGUAGAUAACGGG UAGUGUGACCGCAUCUCUA UGUGGAAAUGGCGCUGU (SEQ ID NO: 130) | GGGAGGGCAAGAGACAGAUGAU GACGGUAGAUAACGGGUAGUGU GACCGCAUCUCUAUGUGGAAAUG GCGCUGU (SEQ ID NO: 130), where G is 2'F; and A, C, and U are 2'OMe modified RNA. |
| R5-12 | RNA | GGGAGGGCAAGAGACAGAU GAUGACGGUAGAUUACGGG GAGUGUGACCGCAUCUCUA UGUGGAAAUGGCGCUGU (SEQ ID NO: 131) | GGGAGGGCAAGAGACAGAUGAU GACGGUAGAUUACGGGGAGUGU GACCGCAUCUCUAUGUGGAAAUG GCGCUGU (SEQ ID NO: 131), where G is 2'F; and A, C, and U are 2'OMe modified RNA. |
| R5-13 | RNA | GGGAGGGCAAGAGACAGAU GAUGACGGUAGAUUUCGGG AAGUGUGACCGCAUCUCUA UGUGGAAAUGGCGCUGU (SEQ ID NO: 132) | GGGAGGGCAAGAGACAGAUGAU GACGGUAGAUUUCGGGAAGUGU GACCGCAUCUCUAUGUGGAAAUG GCGCUGU (SEQ ID NO: 132), where G is 2'F; and A, C, and U are 2'OMe modified RNA. |
| R5-14 | RNA | GGGAGGGCAAGAGACAGAU GAUGACGGUAGAUUACGGG CAGUGUGACCGCAUCUCUA UGUGGAAAUGGCGCUGU (SEQ ID NO: 133) | GGGAGGGCAAGAGACAGAUGAU GACGGUAGAUUACGGGCAGUGUG ACCGCAUCUCUAUGUGGAAAUGG CGCUGU (SEQ ID NO: 133), where G is 2'F; and A, C, and U are 2'OMe modified RNA. |
| R5-15 | RNA | GGGAGGGCAAGAGACAGAU GAUGACGGUAGAUUAUGGG AAGUGUGACCGCAUCUCUA UGUGGAAAUGGCGCUGU (SEQ ID NO: 134) | GGGAGGGCAAGAGACAGAUGAU GACGGUAGAUUAUGGGAAGUGU GACCGCAUCUCUAUGUGGAAAUG GCGCUGU (SEQ ID NO: 134), where G is 2'F; and A, C, and U are 2'OMe modified RNA. |
| R5-16 | RNA | GGGAGGGCAAGAGACAGAU CAUGACGGUAGAUUUCGGG UAGUGUGACCGCAUGUCUA UGUGGAAAUGGCGCUGU (SEQ ID NO: 135) | GGGAGGGCAAGAGACAGAUCAUG ACGGUAGAUUUCGGGUAGUGUG ACCGCAUGUCUAUGUGGAAAUGG CGCUGU (SEQ ID NO: 135), where G is 2'F; and A, C, and U are 2'OMe modified RNA. |
| R5-18 | RNA | GGGAGGGCAAGAGACAGAU GAUGACGGUAGAUUAUGGG CAGUGUGACCGCAUCUCUA UGUGGAAAUGGCGCUGU (SEQ ID NO: 136) | GGGAGGGCAAGAGACAGAUGAU GACGGUAGAUUAUGGGCAGUGU GACCGCAUCUCUAUGUGGAAAUG GCGCUGU (SEQ ID NO: 136), where G is 2'F; and A, C, and U are 2'OMe modified RNA. |

TABLE 2-continued

| Aptamer 3 Family | | | |
|---|---|---|---|
| Compound Name | Backbone | Primary Sequence (5' to 3') | Modified Sequence (5' to 3') |
| R5-19 | RNA | GGGAGGGCAAGAGACAGAU CAUGACGGUAGAUUAUGGG UAGUGUGACCGCAUGUCUA UGUGGAAAUGGCGCUGU (SEQ ID NO: 137) | GGGAGGGCAAGAGACAGAUCAUG ACGGUAGAUUAUGGGUAGUGUG ACCGCAUGUCUAUGUGGAAAUGG CGCUGU (SEQ ID NO: 137), where G is 2'F; and A, C, and U are 2'OMe modified RNA. |
| R5-20 | RNA | GGGAGGGCAAGAGACAGAU GAUGACGGUAGAUUUUGGG UAGUGUGACCGCAUCUCUA UGUGGAAAUGGCGCUGU (SEQ ID NO: 138) | GGGAGGGCAAGAGACAGAUGAU GACGGUAGAUUUUGGGUAGUGU GACCGCAUCUCUAUGUGGAAAUG GCGCUGU (SEQ ID NO: 138), where G is 2'F; and A, C, and U are 2'OMe modified RNA. |
| R5-21 | RNA | GGGAGGGCAAGAGACAGAU GAUGACGGUAGAUUACGGG CAGAGUGACCGCAUCUCUA UGUGGAAAUGGCGCUGU (SEQ ID NO: 139) | GGGAGGGCAAGAGACAGAUGAU GACGGUAGAUUACGGGCAGAGUG ACCGCAUCUCUAUGUGGAAAUGG CGCUGU (SEQ ID NO: 139), where G is 2'F; and A, C, and U are 2'OMe modified RNA. |
| R5-22 | RNA | GGGAGGGCAAGAGACAGAU GAUGACGAUAGAUUUCGGG UAGUGUGAUCGCAUCUCUA UGUGGAAAUGGCGCUGU (SEQ ID NO: 140) | GGGAGGGCAAGAGACAGAUGAU GACGAUAGAUUUCGGGUAGUGU GAUCGCAUCUCUAUGUGGAAAUG GCGCUGU (SEQ ID NO: 140), where G is 2'F; and A, C, and U are 2'OMe modified RNA. |
| R5-23 | RNA | GGGAGGGCAAGAGACAGAU GAUGACGGUAGAUAUCGGG UAGUGUGACCGCAUCUCUA UGUGGAAAUGGCGCUGU (SEQ ID NO: 141) | GGGAGGGCAAGAGACAGAUGAU GACGGUAGAUAUCGGGUAGUGU GACCGCAUCUCUAUGUGGAAAUG GCGCUGU (SEQ ID NO: 141), where G is 2'F; and A, C, and U are 2'OMe modified RNA. |
| R5-24 | RNA | GGGAGGGCAAGAGACAGAU GAUGACGGUAGAUAAUGGG UAGUGUGACCGCAUCUCUA UGUGGAAAUGGCGCUGU (SEQ ID NO: 142) | GGGAGGGCAAGAGACAGAUGAU GACGGUAGAUAAUGGGUAGUGU GACCGCAUCUCUAUGUGGAAAUG GCGCUGU (SEQ ID NO: 142), where G is 2'F; and A, C, and U are 2'OMe modified RNA. |
| R5-25 | RNA | GGGAGGGCAAGAGACAGAU GAUGACGGUAGAUUUCGGG CAGUGUGACCGCAUCUCUA UGUGGAAAUGGCGCUGU (SEQ ID NO: 143) | GGGAGGGCAAGAGACAGAUGAU GACGGUAGAUUUCGGGCAGUGUG ACCGCAUCUCUAUGUGGAAAUGG CGCUGU (SEQ ID NO: 143), where G is 2'F; and A, C, and U are 2'OMe modified RNA. |
| R5-27 | RNA | GGGAGGGCAAGAGACAGAU GAUGACGGUAGAUUACGGG UUGUGUGACCGCAUCUCUA UGUGGAAAUGGCGCUGU (SEQ ID NO: 144) | GGGAGGGCAAGAGACAGAUGAU GACGGUAGAUUACGGGUUGUGU GACCGCAUCUCUAUGUGGAAAUG GCGCUGU (SEQ ID NO: 144), where G is 2'F; and A, C, and U are 2'OMe modified RNA. |
| R5-28 | RNA | GGGAGGGCAAGAGACAGAU GAUGACGGUAGAUUUCGGG GAGUGUGACCGCAUCUCUA UGUGGAAAUGGCGCUGU (SEQ ID NO: 145) | GGGAGGGCAAGAGACAGAUGAU GACGGUAGAUUUCGGGGAGUGU GACCGCAUCUCUAUGUGGAAAUG GCGCUGU (SEQ ID NO: 145), where G is 2'F; and A, C, and U are 2'OMe modified RNA. |
| R5-29 | RNA | GGGAGGGCAAGAGACAGAU GAUGACAGUAGAUUUCGGG UAGUGUGACUGCAUCUCUA UGUGGAAAUGGCGCUGU (SEQ ID NO: 146) | GGGAGGGCAAGAGACAGAUGAU GACAGUAGAUUUCGGGUAGUGU GACUGCAUCUCUAUGUGGAAAUG GCGCUGU (SEQ ID NO: 146), where G is 2'F; and A, C, and U are 2'OMe modified RNA. |

TABLE 2-continued

| Aptamer 3 Family | | | |
|---|---|---|---|
| Compound Name | Backbone | Primary Sequence (5' to 3') | Modified Sequence (5' to 3') |
| R5-30 | RNA | GGGAGGGCAAGAGACAGAU GAUGACGGUAGAUUUCGGG UUGUGUGACCGCAUCUCUA UGUGGAAAUGGCGCUGU (SEQ ID NO: 147) | GGGAGGGCAAGAGACAGAUGAU GACGGUAGAUUUCGGGUUGUGU GACCGCAUCUCUAUGUGGAAAUG GCGCUGU (SEQ ID NO: 147), where G is 2'F; and A, C, and U are 2'OMe modified RNA. |
| R5-31 | RNA | GGGAGGGCAAGAGACAGAU GAUGACGGUAGAUUAUGGG CAGAGUGACCGCAUCUCUA UGUGGAAAUGGCGCUGU (SEQ ID NO: 148) | GGGAGGGCAAGAGACAGAUGAU GACGGUAGAUUAUGGGCAGAGU GACCGCAUCUCUAUGUGGAAAUG GCGCUGU (SEQ ID NO: 148), where G is 2'F; and A, C, and U are 2'OMe modified RNA. |
| R5-32 | RNA | GGGAGGGCAAGAGACAGAU GAUGACGGUAGAUUAAGGG UAGAGUGACCGCAUCUCUA UGUGGAAAUGGCGCUGU (SEQ ID NO: 149) | GGGAGGGCAAGAGACAGAUGAU GACGGUAGAUUAAGGGUAGAGU GACCGCAUCUCUAUGUGGAAAUG GCGCUGU (SEQ ID NO: 149), where G is 2'F; and A, C, and U are 2'OMe modified RNA. |
| R5-33 | RNA | GGGAGGGCAAGAGACAGAU GAUGACGGUAGAUUUCGGG UAGAGUGACCGCAUCUCUA UGUGGAAAUGGCGCUGU (SEQ ID NO: 150) | GGGAGGGCAAGAGACAGAUGAU GACGGUAGAUUUCGGGUAGAGU GACCGCAUCUCUAUGUGGAAAUG GCGCUGU (SEQ ID NO: 150), where G is 2'F; and A, C, and U are 2'OMe modified RNA. |
| R5-35 | RNA | GGGAGGGCAAGAGACAGAU GAUGACGGUAGAUUAAGGG CAGUGUGACCGCAUCUCUA UGUGGAAAUGGCGCUGU (SEQ ID NO: 151) | GGGAGGGCAAGAGACAGAUGAU GACGGUAGAUUAAGGGCAGUGU GACCGCAUCUCUAUGUGGAAAUG GCGCUGU (SEQ ID NO: 151), where G is 2'F; and A, C, and U are 2'OMe modified RNA. |
| R5-36 | RNA | GGGAGGGCAAGAGACAGAU GAUGACGGUAGAUUACGGG GAGAGUGACCGCAUCUCUA UGUGGAAAUGGCGCUGU (SEQ ID NO: 152) | GGGAGGGCAAGAGACAGAUGAU GACGGUAGAUUACGGGGAGAGU GACCGCAUCUCUAUGUGGAAAUG GCGCUGU (SEQ ID NO: 152), where G is 2'F; and A, C, and U are 2'OMe modified RNA. |
| R5-39 | RNA | GGGAGGGCAAGAGACAGAU UAUGACGGUAGAUUUCGGG UAGUGUGACCGCAUAUCUA UGUGGAAAUGGCGCUGU (SEQ ID NO: 153) | GGGAGGGCAAGAGACAGAUUAU GACGGUAGAUUUCGGGUAGUGU GACCGCAUAUCUAUGUGGAAAUG GCGCUGU (SEQ ID NO: 153), where G is 2'F; and A, C, and U are 2'OMe modified RNA. |
| R5-40 | RNA | GGGAGGGCAAGAGACAGAU GAUGACGGUAGAUUAUGGG UUGUGUGACCGCAUCUCUA UGUGGAAAUGGCGCUGU (SEQ ID NO: 154) | GGGAGGGCAAGAGACAGAUGAU GACGGUAGAUUAUGGGUUGUGU GACCGCAUCUCUAUGUGGAAAUG GCGCUGU (SEQ ID NO: 154), where G is 2'F; and A, C, and U are 2'OMe modified RNA. |
| R5-47 | RNA | GGGAGGGCAAGAGACAGAU GAUGACGGUAGAUAACGGG AAGAGUGACCGCAUCUCUA UGUGGAAAUGGCGCUGU (SEQ ID NO: 155) | GGGAGGGCAAGAGACAGAUGAU GACGGUAGAUAACGGGAAGAGU GACCGCAUCUCUAUGUGGAAAUG GCGCUGU (SEQ ID NO: 155), where G is 2'F; and A, C, and U are 2'OMe modified RNA. |
| R5-48 | RNA | GGGAGGGCAAGAGACAGAU GAUGACGGUAGAUUUAGGG UAGUGUGACCGCAUCUCUA UGUGGAAAUGGCGCUGU (SEQ ID NO: 156) | GGGAGGGCAAGAGACAGAUGAU GACGGUAGAUUUAGGGUAGUGU GACCGCAUCUCUAUGUGGAAAUG GCGCUGU (SEQ ID NO: 156), where G is 2'F; and A, C, and U are 2'OMe modified RNA. |

TABLE 2-continued

| Aptamer 3 Family | | | |
|---|---|---|---|
| Compound Name | Backbone | Primary Sequence (5' to 3') | Modified Sequence (5' to 3') |
| R5-50 | RNA | GGGAGGGCAAGAGACAGAU GAUGACGGUAGAUUCUGGG UAGUGUGACCGCAUCUCUA UGUGGAAAUGGCGCUGU (SEQ ID NO: 157) | GGGAGGGCAAGAGACAGAUGAU GACGGUAGAUUCUGGGUAGUGU GACCGCAUCUCUAUGUGGAAAUG GCGCUGU (SEQ ID NO: 157), where G is 2'F; and A, C, and U are 2'OMe modified RNA. |
| R5-52 | RNA | GGGAGGGCAAGAGACAGAU GAUGACGGUAGAUUAUGGG GAGUGUGACCGCAUCUCUA UGUGGAAAUGGCGCUGU (SEQ ID NO: 158) | GGGAGGGCAAGAGACAGAUGAU GACGGUAGAUUAUGGGGAGUGU GACCGCAUCUCUAUGUGGAAAUG GCGCUGU (SEQ ID NO: 158), where G is 2'F; and A, C, and U are 2'OMe modified RNA. |
| R5-54 | RNA | GGGAGGGCAAGAGACAGAU GAUGACGGUAGAUUUUGGG UAGAGUGACCGCAUCUCUA UGUGGAAAUGGCGCUGU (SEQ ID NO: 159) | GGGAGGGCAAGAGACAGAUGAU GACGGUAGAUUUUGGGUAGAGU GACCGCAUCUCUAUGUGGAAAUG GCGCUGU (SEQ ID NO: 159), where G is 2'F; and A, C, and U are 2'OMe modified RNA. |
| R5-55 | RNA | GGGAGGGCAAGAGACAGAU GAUGACGGUAGAUUAUGGG AAGAGUGACCGCAUCUCUA UGUGGAAAUGGCGCUGU (SEQ ID NO: 160) | GGGAGGGCAAGAGACAGAUGAU GACGGUAGAUUAUGGGAAGAGU GACCGCAUCUCUAUGUGGAAAUG GCGCUGU (SEQ ID NO: 160), where G is 2'F; and A, C, and U are 2'OMe modified RNA. |
| R5-56 | RNA | GGGAGGGCAAGAGACAGAU GAUGACGGUAGAUUAGGGA AGUGUGACCGCAUCUCUAU GUGGAAAUGGCGCUGU (SEQ ID NO: 161) | GGGAGGGCAAGAGACAGAUGAU GACGGUAGAUUAGGGAAGUGUG ACCGCAUCUCUAUGUGGAAAUGG CGCUGU (SEQ ID NO: 161), where G is 2'F; and A, C, and U are 2'OMe modified RNA. |
| R5-57 | RNA | GGGAGGGCAAGAGACAGAU GAUCACGGUAGAUUAUGGG UAGUGUGACCGGAUCUCUA UGUGGAAAUGGCGCUGU (SEQ ID NO: 162) | GGGAGGGCAAGAGACAGAUGAUC ACGGUAGAUUAUGGGUAGUGUG ACCGGAUCUCUAUGUGGAAAUGG CGCUGU (SEQ ID NO: 162), where G is 2'F; and A, C, and U are 2'OMe modified RNA. |
| R5-59 | RNA | GGGAGGGCAAGAGACAGAU GAUGACGGUAGAUUACGGG UUGAGUGACCGCAUCUCUA UGUGGAAAUGGCGCUGU (SEQ ID NO: 163) | GGGAGGGCAAGAGACAGAUGAU GACGGUAGAUUACGGGUUGAGU GACCGCAUCUCUAUGUGGAAAUG GCGCUGU (SEQ ID NO: 163), where G is 2'F; and A, C, and U are 2'OMe modified RNA. |
| R5-60 | RNA | GGGAGGGCAAGAGACAGAU GUUGACGGUAGAUUUCGGG UAGUGUGACCGCAACUCUA UGUGGAAAUGGCGCUGU (SEQ ID NO: 164) | GGGAGGGCAAGAGACAGAUGUU GACGGUAGAUUUCGGGUAGUGU GACCGCAACUCUAUGUGGAAAUG GCGCUGU (SEQ ID NO: 164), where G is 2'F; and A, C, and U are 2'OMe modified RNA. |
| R5-62 | RNA | GGGAGGGCAAGAGACAGAU GAUGACGGUAGAUAUGGGU AGAGUGACCGCAUCUCUAU GUGGAAAUGGCGCUGU (SEQ ID NO: 165) | GGGAGGGCAAGAGACAGAUGAU GACGGUAGAUAUGGGUAGAGUG ACCGCAUCUCUAUGUGGAAAUGG CGCUGU (SEQ ID NO: 165), where G is 2'F; and A, C, and U are 2'OMe modified RNA. |
| R5-65 | RNA | GGGAGGGCAAGAGACAGAU GAUGACGGUAGAUUCGGGA AGUGUGACCGCAUCUCUAU GUGGAAAUGGCGCUGU (SEQ ID NO: 166) | GGGAGGGCAAGAGACAGAUGAU GACGGUAGAUUCGGGAAGUGUG ACCGCAUCUCUAUGUGGAAAUGG CGCUGU (SEQ ID NO: 166), where G is 2'F; and A, C, and U are 2'OMe modified RNA. |

TABLE 2-continued

| Aptamer 3 Family | | | |
|---|---|---|---|
| Compound Name | Backbone | Primary Sequence (5' to 3') | Modified Sequence (5' to 3') |
| R5-69 | RNA | GGGAGGGCAAGAGACAGAU GAUGACGAUAGAUUAUGGG UAGAGUGAUCGCAUCUCUA UGUGGAAAUGGCGCUGU (SEQ ID NO: 167) | GGGAGGGCAAGAGACAGAUGAU GACGAUAGAUUAUGGGUAGAGU GAUCGCAUCUCUAUGUGGAAAUG GCGCUGU (SEQ ID NO: 167), where G is 2'F; and A, C, and U are 2'OMe modified RNA. |
| R5-75 | RNA | GGGAGGGCAAGAGACAGAU GAUGACGGUAGAAUCGGGU AGUGUGACCGCAUCUCUAU GUGGAAAUGGCGCUGU (SEQ ID NO: 168) | GGGAGGGCAAGAGACAGAUGAU GACGGUAGAAUCGGGUAGUGUG ACCGCAUCUCUAUGUGGAAAUGG CGCUGU (SEQ ID NO: 168), where G is 2'F; and A, C, and U are 2'OMe modified RNA. |
| R5-77 | RNA | GGGAGGGCAAGAGACAGAU GAUGACGGUAGAUAACGGG AAGUGUGACCGCAUCUCUA UGUGGAAAUGGCGCUGU (SEQ ID NO: 169) | GGGAGGGCAAGAGACAGAUGAU GACGGUAGAUAACGGGAAGUGU GACCGCAUCUCUAUGUGGAAAUG GCGCUGU (SEQ ID NO: 169), where G is 2'F; and A, C, and U are 2'OMe modified RNA. |
| R5-78 | RNA | GGGAGGGCAAGAGACAGAU GAUGACGGUAGAUUCAGGG UAGUGUGACCGCAUCUCUA UGUGGAAAUGGCGCUGU (SEQ ID NO: 170) | GGGAGGGCAAGAGACAGAUGAU GACGGUAGAUUCAGGGUAGUGU GACCGCAUCUCUAUGUGGAAAUG GCGCUGU (SEQ ID NO: 170), where G is 2'F; and A, C, and U are 2'OMe modified RNA. |
| R5-80 | RNA | GGGAGGGCAAGAGACAGAU CAUCACGGUAGAUUUCGGG UAGUGUGACCGGAUGUCUA UGUGGAAAUGGCGCUGU (SEQ ID NO: 171) | GGGAGGGCAAGAGACAGAUCAUC ACGGUAGAUUUCGGGUAGUGUG ACCGGAUGUCUAUGUGGAAAUGG CGCUGU (SEQ ID NO: 171), where G is 2'F; and A, C, and U are 2'OMe modified RNA. |
| R5-81 | RNA | GGGAGGGCAAGAGACAGAU CAUGACGGUAGAUAACGGG CAGAGUGACCGCAUGUCUA UGUGGAAAUGGCGCUGU (SEQ ID NO: 172) | GGGAGGGCAAGAGACAGAUCAUG ACGGUAGAUAACGGGCAGAGUGA CCGCAUGUCUAUGUGGAAAUGGC GCUGU (SEQ ID NO: 172), where G is 2'F; and A, C, and U are 2'OMe modified RNA. |
| R5-82 | RNA | GGGAGGGCAAGAGACAGAU GAUGACGGUAGAGUUCGGG UAGUGUGACCGCAUCUCUA UGUGGAAAUGGCGCUGU (SEQ ID NO: 173) | GGGAGGGCAAGAGACAGAUGAU GACGGUAGAGUUCGGGUAGUGU GACCGCAUCUCUAUGUGGAAAUG GCGCUGU (SEQ ID NO: 173), where G is 2'F; and A, C, and U are 2'OMe modified RNA. |
| R5-85 | RNA | GGGAGGGCAAGAGACAGAU GAUGACGGUAGAUUCGGGU AGAGUGACCGCAUCUCUAU GUGGAAAUGGCGCUGU (SEQ ID NO: 174) | GGGAGGGCAAGAGACAGAUGAU GACGGUAGAUUCGGGUAGAGUG ACCGCAUCUCUAUGUGGAAAUGG CGCUGU (SEQ ID NO: 174), where G is 2'F; and A, C, and U are 2'OMe modified RNA. |
| R5-90 | RNA | GGGAGGGCAAGAGACAGAU GAUGACGGUAGAUAAAGGG UAGUGUGACCGCAUCUCUA UGUGGAAAUGGCGCUGU (SEQ ID NO: 175) | GGGAGGGCAAGAGACAGAUGAU GACGGUAGAUAAAGGGUAGUGU GACCGCAUCUCUAUGUGGAAAUG GCGCUGU (SEQ ID NO: 175), where G is 2'F; and A, C, and U are 2'OMe modified RNA. |
| R5-95 | RNA | GGGAGGGCAAGAGACAGAU GAUGACGGUAGAUAACGGG GAGUGUGACCGCAUCUCUA UGUGGAAAUGGCGCUGU (SEQ ID NO: 176) | GGGAGGGCAAGAGACAGAUGAU GACGGUAGAUAACGGGGAGUGU GACCGCAUCUCUAUGUGGAAAUG GCGCUGU (SEQ ID NO: 176), where G is 2'F; and A, C, and U are 2'OMe modified RNA. |

TABLE 2-continued

| Aptamer 3 Family | | | |
|---|---|---|---|
| Compound Name | Backbone | Primary Sequence (5' to 3') | Modified Sequence (5' to 3') |
| R5-96 | RNA | GGGAGGGCAAGAGACAGAU CAUGACGGUAGAUAUGGGU AGUGUGACCGCAUGUCUAU GUGGAAAUGGCGCUGU (SEQ ID NO: 177) | GGGAGGGCAAGAGACAGAUCAUG ACGGUAGAUAUGGGUAGUGUGA CCGCAUGUCUAUGUGGAAAUGGC GCUGU (SEQ ID NO: 177), where G is 2'F; and A, C, and U are 2'OMe modified RNA. |
| R5-97 | RNA | GGGAGGGCAAGAGACAGAU GGUGACGGUAGAUUACGGG UAGAGUGACCGCACCUCUA UGUGGAAAUGGCGCUGU (SEQ ID NO: 178) | GGGAGGGCAAGAGACAGAUGGU GACGGUAGAUUACGGGUAGAGU GACCGCACCUCUAUGUGGAAAUG GCGCUGU (SEQ ID NO: 178), where G is 2'F; and A, C, and U are 2'OMe modified RNA. |
| R5-100 | RNA | GGGAGGGCAAGAGACAGAU GAUGACGGUAGAUUGUGGG UAGUGUGACCGCAUCUCUA UGUGGAAAUGGCGCUGU (SEQ ID NO: 179) | GGGAGGGCAAGAGACAGAUGAU GACGGUAGAUUGUGGGUAGUGU GACCGCAUCUCUAUGUGGAAAUG GCGCUGU (SEQ ID NO: 179), where G is 2'F; and A, C, and U are 2'OMe modified RNA. |
| R5-101 | RNA | GGGAGGGCAAGAGACAGAU GAUGACGGUAGAUUAGGGG UAGUGUGACCGCAUCUCUA UGUGGAAAUGGCGCUGU (SEQ ID NO: 180) | GGGAGGGCAAGAGACAGAUGAU GACGGUAGAUUAGGGGUAGUGU GACCGCAUCUCUAUGUGGAAAUG GCGCUGU (SEQ ID NO: 180), where G is 2'F; and A, C, and U are 2'OMe modified RNA. |
| R5-103 | RNA | GGGAGGGCAAGAGACAGAU GAUGACGGUAGAUUAUGGG UAGCGUGACCGCAUCUCUA UGUGGAAAUGGCGCUGU (SEQ ID NO: 181) | GGGAGGGCAAGAGACAGAUGAU GACGGUAGAUUAUGGGUAGCGU GACCGCAUCUCUAUGUGGAAAUG GCGCUGU (SEQ ID NO: 181), where G is 2'F; and A, C, and U are 2'OMe modified RNA. |
| R5-104 | RNA | GGGAGGGCAAGAGACAGAU GAUGACGGAAGAUUUCGGG UAGUGUGUCCGCAUCUCUA UGUGGAAAUGGCGCUGU (SEQ ID NO: 182) | GGGAGGGCAAGAGACAGAUGAU GACGGAAGAUUUCGGGUAGUGU GUCCGCAUCUCUAUGUGGAAAUG GCGCUGU (SEQ ID NO: 182), where G is 2'F; and A, C, and U are 2'OMe modified RNA. |
| R5-106 | RNA | GGGAGGGCAAGAGACAGAU GAUGACGGUAGAUAACGGG CAGUGUGACCGCAUCUCUA UGUGGAAAUGGCGCUGU (SEQ ID NO: 183) | GGGAGGGCAAGAGACAGAUGAU GACGGUAGAUAACGGGCAGUGUG ACCGCAUCUCUAUGUGGAAAUGG CGCUGU (SEQ ID NO: 183), where G is 2'F; and A, C, and U are 2'OMe modified RNA. |
| R5-112 | RNA | GGGAGGGCAAGAGACAGAU GAUGACGGUAGUUUCGGGU AGUGUGACCGCAUCUCUAU GUGGAAAUGGCGCUGU (SEQ ID NO: 184) | GGGAGGGCAAGAGACAGAUGAU GACGGUAGUUUCGGGUAGUGUG ACCGCAUCUCUAUGUGGAAAUGG CGCUGU (SEQ ID NO: 184), where G is 2'F; and A, C, and U are 2'OMe modified RNA. |
| R5-113 | RNA | GGGAGGGCAAGAGACAGAU GAUGAUGGUAGAUUUCGGG UAGUGUGACCACAUCUCUA UGUGGAAAUGGCGCUGU (SEQ ID NO: 185) | GGGAGGGCAAGAGACAGAUGAU GAUGGUAGAUUUCGGGUAGUGU GACCACAUCUCUAUGUGGAAAUG GCGCUGU (SEQ ID NO: 185), where G is 2'F; and A, C, and U are 2'OMe modified RNA. |
| R5-115 | RNA | GGGAGGGCAAGAGACAGAU GAUGACGGUAGAUUUUGGG CAGUGUGACCGCAUCUCUA UGUGGAAAUGGCGCUGU (SEQ ID NO: 186) | GGGAGGGCAAGAGACAGAUGAU GACGGUAGAUUUUGGGCAGUGU GACCGCAUCUCUAUGUGGAAAUG GCGCUGU (SEQ ID NO: 186), where G is 2'F; and A, C, and U are 2'OMe modified RNA. |

TABLE 2-continued

| Aptamer 3 Family | | | |
|---|---|---|---|
| Compound Name | Backbone | Primary Sequence (5' to 3') | Modified Sequence (5' to 3') |
| R5-116 | RNA | GGGAGGGCAAGAGACAGAU GAUGACGGUAGAUUGCGGG UAGUGUGACCGCAUCUCUA UGUGGAAAUGGCGCUGU (SEQ ID NO: 187) | GGGAGGGCAAGAGACAGAUGAU GACGGUAGAUUGCGGGUAGUGU GACCGCAUCUCUAUGUGGAAAUG GCGCUGU (SEQ ID NO: 187), where G is 2'F; and A, C, and U are 2'OMe modified RNA. |
| R5-119 | RNA | GGGAGGGCAAGAGACAGAU GAUGACGGUAGAUUUCGGG GAGAGUGACCGCAUCUCUA UGUGGAAAUGGCGCUGU (SEQ ID NO: 188) | GGGAGGGCAAGAGACAGAUGAU GACGGUAGAUUUCGGGGAGAGU GACCGCAUCUCUAUGUGGAAAUG GCGCUGU (SEQ ID NO: 188), where G is 2'F; and A, C, and U are 2'OMe modified RNA. |
| R5-127 | RNA | GGGAGGGCAAGAGACAGAU CAUGACGGUAGAUAAUGGG CAGUGUGACCGCAUGUCUA UGUGGAAAUGGCGCUGU (SEQ ID NO: 189) | GGGAGGGCAAGAGACAGAUCAUG ACGGUAGAUAAUGGGCAGUGUG ACCGCAUGUCUAUGUGGAAAUGG CGCUGU (SEQ ID NO: 189), where G is 2'F; and A, C, and U are 2'OMe modified RNA. |
| R5-131 | RNA | GGGAGGGCAAGAGACAGAU GAUGACGGUAGAUUUCGGG UAGCGUGACCGCAUCUCUA UGUGGAAAUGGCGCUGU (SEQ ID NO: 190) | GGGAGGGCAAGAGACAGAUGAU GACGGUAGAUUUCGGGUAGCGUG ACCGCAUCUCUAUGUGGAAAUGG CGCUGU (SEQ ID NO: 190), where G is 2'F; and A, C, and U are 2'OMe modified RNA. |
| R5-132 | RNA | GGGAGGGCAAGAGACAGAU GAUGACGGUAGAUAAUGGG AAGUGUGACCGCAUCUCUA UGUGGAAAUGGCGCUGU (SEQ ID NO: 191) | GGGAGGGCAAGAGACAGAUGAU GACGGUAGAUAAUGGGAAGUGU GACCGCAUCUCUAUGUGGAAAUG GCGCUGU (SEQ ID NO: 191), where G is 2'F; and A, C, and U are 2'OMe modified RNA. |
| R5-133 | RNA | GGGAGGGCAAGAGACAGAU GAUGACGAUAGAUUAGGGU AGUGUGAUCGCAUCUCUAU GUGGAAAUGGCGCUGU (SEQ ID NO: 192) | GGGAGGGCAAGAGACAGAUGAU GACGAUAGAUUAGGGUAGUGUG AUCGCAUCUCUAUGUGGAAAUGG CGCUGU (SEQ ID NO: 192), where G is 2'F; and A, C, and U are 2'OMe modified RNA. |
| R5-135 | RNA | GGGAGGGCAAGAGACAGAU GAUGACGGUAGAUAUGGGA AGUGUGACCGCAUCUCUAU GUGGAAAUGGCGCUGU (SEQ ID NO: 193) | GGGAGGGCAAGAGACAGAUGAU GACGGUAGAUAUGGGAAGUGUG ACCGCAUCUCUAUGUGGAAAUGG CGCUGU (SEQ ID NO: 193), where G is 2'F; and A, C, and U are 2'OMe modified RNA. |
| R5-137 | RNA | GGGAGGGCAAGAGACAGAU GAUGACGGUAGAUUUGGGA AGUGUGACCGCAUCUCUAU GUGGAAAUGGCGCUGU (SEQ ID NO: 194) | GGGAGGGCAAGAGACAGAUGAU GACGGUAGAUUUGGGAAGUGUG ACCGCAUCUCUAUGUGGAAAUGG CGCUGU (SEQ ID NO: 194), where G is 2'F; and A, C, and U are 2'OMe modified RNA. |
| R5-139 | RNA | GGGAGGGCAAGAGACAGAU GAUGACGGUAGAUUAGGGC AGAGUGACCGCAUCUCUAU GUGGAAAUGGCGCUGU (SEQ ID NO: 195) | GGGAGGGCAAGAGACAGAUGAU GACGGUAGAUUAGGGCAGAGUG ACCGCAUCUCUAUGUGGAAAUGG CGCUGU (SEQ ID NO: 195), where G is 2'F; and A, C, and U are 2'OMe modified RNA. |
| R5-140 | RNA | GGGAGGGCAAGAGACAGAU GAUGACGGUAGAUUGGGGU AGUGUGACCGCAUCUCUAU GUGGAAAUGGCGCUGU (SEQ ID NO: 196) | GGGAGGGCAAGAGACAGAUGAU GACGGUAGAUUGGGGUAGUGUG ACCGCAUCUCUAUGUGGAAAUGG CGCUGU (SEQ ID NO: 196), where G is 2'F; and A, C, and U are 2'OMe modified RNA. |

TABLE 2-continued

| Aptamer 3 Family | | | |
|---|---|---|---|
| Compound Name | Backbone | Primary Sequence (5' to 3') | Modified Sequence (5' to 3') |
| R5-141 | RNA | GGGAGGGCAAGAGACAGAU GAUGACGUUAGAUUACGGG UAGAGUGAACGCAUCUCUA UGUGGAAAUGGCGCUGU (SEQ ID NO: 197) | GGGAGGGCAAGAGACAGAUGAU GACGUUAGAUUACGGGUAGAGU GAACGCAUCUCUAUGUGGAAAUG GCGCUGU (SEQ ID NO: 197), where G is 2'F; and A, C, and U are 2'OMe modified RNA. |
| R5-145 | RNA | GGGAGGGCAAGAGACAGAU GAUGACGGUAGAUUCGGGC AGAGUGACCGCAUCUCUAU GUGGAAAUGGCGCUGU (SEQ ID NO: 198) | GGGAGGGCAAGAGACAGAUGAU GACGGUAGAUUCGGGCAGAGUGA CCGCAUCUCUAUGUGGAAAUGGC GCUGU (SEQ ID NO: 198), where G is 2'F; and A, C, and U are 2'OMe modified RNA. |
| R5-151 | RNA | GGGAGGGCAAGAGACAGAU GAUGACGGUAGAUUCCGGG CAGUGUGACCGCAUCUCUA UGUGGAAAUGGCGCUGU (SEQ ID NO: 199) | GGGAGGGCAAGAGACAGAUGAU GACGGUAGAUUCCGGGCAGUGUG ACCGCAUCUCUAUGUGGAAAUGG CGCUGU (SEQ ID NO: 199), where G is 2'F; and A, C, and U are 2'OMe modified RNA. |
| R5-160 | RNA | GGGAGGGCAAGAGACAGAU GAUGACGGUAGAUUCCGGG UUGUGUGACCGCAUCUCUA UGUGGAAAUGGCGCUGU (SEQ ID NO: 200) | GGGAGGGCAAGAGACAGAUGAU GACGGUAGAUUCCGGGUUGUGUG ACCGCAUCUCUAUGUGGAAAUGG CGCUGU (SEQ ID NO: 200), where G is 2'F; and A, C, and U are 2'OMe modified RNA. |
| R5-162 | RNA | GGGAGGGCAAGAGACAGAU GAUGACGGUAGAUGACGGG UAGAGUGACCGCAUCUCUA UGUGGAAAUGGCGCUGU (SEQ ID NO: 201) | GGGAGGGCAAGAGACAGAUGAU GACGGUAGAUGACGGGUAGAGU GACCGCAUCUCUAUGUGGAAAUG GCGCUGU (SEQ ID NO: 201), where G is 2'F; and A, C, and U are 2'OMe modified RNA. |
| R5-169 | RNA | GGGAGGGCAAGAGACAGAU GAUGACGGUAGAUCAGGGU AGUGUGACCGCAUCUCUAU GUGGAAAUGGCGCUGU (SEQ ID NO: 202) | GGGAGGGCAAGAGACAGAUGAU GACGGUAGAUCAGGGUAGUGUG ACCGCAUCUCUAUGUGGAAAUGG CGCUGU (SEQ ID NO: 202), where G is 2'F; and A, C, and U are 2'OMe modified RNA. |
| R5-173 | RNA | GGGAGGGCAAGAGACAGAU GAUGACGGUAGAUUGCGGG UAGAGUGACCGCAUCUCUA UGUGGAAAUGGCGCUGU (SEQ ID NO: 203) | GGGAGGGCAAGAGACAGAUGAU GACGGUAGAUUGCGGGUAGAGU GACCGCAUCUCUAUGUGGAAAUG GCGCUGU (SEQ ID NO: 203), where G is 2'F; and A, C, and U are 2'OMe modified RNA. |
| R5-181 | RNA | GGGAGGGCAAGAGACAGAU GAUGAGGGUAGAUUUCGGG UAGUGUGACCCCAUCUCUA UGUGGAAAUGGCGCUGU (SEQ ID NO: 204) | GGGAGGGCAAGAGACAGAUGAU GAGGGUAGAUUUCGGGUAGUGU GACCCCAUCUCUAUGUGGAAAUG GCGCUGU (SEQ ID NO: 204), where G is 2'F; and A, C, and U are 2'OMe modified RNA. |
| R5-183 | RNA | GGGAGGGCAAGAGACAGAU GAUGACGGUAGAUUAGGGG AGUGUGACCGCAUCUCUAU GUGGAAAUGGCGCUGU (SEQ ID NO: 205) | GGGAGGGCAAGAGACAGAUGAU GACGGUAGAUUAGGGGAGUGUG ACCGCAUCUCUAUGUGGAAAUGG CGCUGU (SEQ ID NO: 205), where G is 2'F; and A, C, and U are 2'OMe modified RNA. |
| R5-185 | RNA | GGGAGGGCAAGAGACAGAU GAUGAAGGUAGAUUUCGGG UAGUGUGACCUCAUCUCUA UGUGGAAAUGGCGCUGU (SEQ ID NO: 206) | GGGAGGGCAAGAGACAGAUGAU GAAGGUAGAUUUCGGGUAGUGU GACCUCAUCUCUAUGUGGAAAUG GCGCUGU (SEQ ID NO: 206), where G is 2'F; and A, C, and U are 2'OMe modified RNA. |

TABLE 2-continued

| Aptamer 3 Family | | | |
|---|---|---|---|
| Compound Name | Backbone | Primary Sequence (5' to 3') | Modified Sequence (5' to 3') |
| R5-190 | RNA | GGGAGGGCAAGAGACAGAU GAUGACGGUAGAUUAUGGG UUGAGUGACCGCAUCUCUA UGUGGAAAUGGCGCUGU (SEQ ID NO: 207) | GGGAGGGCAAGAGACAGAUGAU GACGGUAGAUUAUGGGUUGAGU GACCGCAUCUCUAUGUGGAAAUG GCGCUGU (SEQ ID NO: 207), where G is 2'F; and A, C, and U are 2'OMe modified RNA. |
| R5-193 | RNA | GGGAGGGCAAGAGACAGAU GCUGACGGUAGAUUACGGG UAGAGUGACCGCAGCUCUA UGUGGAAAUGGCGCUGU (SEQ ID NO: 208) | GGGAGGGCAAGAGACAGAUGCUG ACGGUAGAUUACGGGUAGAGUG ACCGCAGCUCUAUGUGGAAAUGG CGCUGU (SEQ ID NO: 208), where G is 2'F; and A, C, and U are 2'OMe modified RNA. |
| R5-194 | RNA | GGGAGGGCAAGAGACAGAU GAUGACGGUAGAUUAAGGG UUGUGUGACCGCAUCUCUA UGUGGAAAUGGCGCUGU (SEQ ID NO: 209) | GGGAGGGCAAGAGACAGAUGAU GACGGUAGAUUAAGGGUUGUGU GACCGCAUCUCUAUGUGGAAAUG GCGCUGU (SEQ ID NO: 209), where G is 2'F; and A, C, and U are 2'OMe modified RNA. |
| R5-195 | RNA | GGGAGGGCAAGAGACAGAU GAUGACGGUAGAUGACGGG UAGUGUGACCGCAUCUCUA UGUGGAAAUGGCGCUGU (SEQ ID NO: 210) | GGGAGGGCAAGAGACAGAUGAU GACGGUAGAUGACGGGUAGUGU GACCGCAUCUCUAUGUGGAAAUG GCGCUGU (SEQ ID NO: 210), where G is 2'F; and A, C, and U are 2'OMe modified RNA. |
| R5-196 | RNA | GGGAGGGCAAGAGACAGAU GAUGACGGUAGAUGUCGGG UAGUGUGACCGCAUCUCUA UGUGGAAAUGGCGCUGU (SEQ ID NO: 211) | GGGAGGGCAAGAGACAGAUGAU GACGGUAGAUGUCGGGUAGUGU GACCGCAUCUCUAUGUGGAAAUG GCGCUGU (SEQ ID NO: 211), where G is 2'F; and A, C, and U are 2'OMe modified RNA. |
| R5-199 | RNA | GGGAGGGCAAGAGACAGAU GAUGACUGUAGAUUUCGGG UAGUGUGACAGCAUCUCUA UGUGGAAAUGGCGCUGU (SEQ ID NO: 212) | GGGAGGGCAAGAGACAGAUGAU GACUGUAGAUUUCGGGUAGUGU GACAGCAUCUCUAUGUGGAAAUG GCGCUGU (SEQ ID NO: 212), where G is 2'F; and A, C, and U are 2'OMe modified RNA. |
| R5-203 | RNA | GGGAGGGCAAGAGACAGAU GAUGACGGUAGAUUUAGGG UAGAGUGACCGCAUCUCUA UGUGGAAAUGGCGCUGU (SEQ ID NO: 213) | GGGAGGGCAAGAGACAGAUGAU GACGGUAGAUUUAGGGUAGAGU GACCGCAUCUCUAUGUGGAAAUG GCGCUGU (SEQ ID NO: 213), where G is 2'F; and A, C, and U are 2'OMe modified RNA. |
| R5-206 | RNA | GGGAGGGCAAGAGACAGAU GAUGACGGCAGAUUUCGGG UAGUGUGGCCGCAUCUCUA UGUGGAAAUGGCGCUGU (SEQ ID NO: 214) | GGGAGGGCAAGAGACAGAUGAU GACGGCAGAUUUCGGGUAGUGUG GCCGCAUCUCUAUGUGGAAAUGG CGCUGU (SEQ ID NO: 214), where G is 2'F; and A, C, and U are 2'OMe modified RNA. |
| R5-209 | RNA | GGGAGGGCAAGAGACAGAU GAUGACGGUAGAUUUGGGG UAGUGUGACCGCAUCUCUA UGUGGAAAUGGCGCUGU (SEQ ID NO: 215) | GGGAGGGCAAGAGACAGAUGAU GACGGUAGAUUUGGGGUAGUGU GACCGCAUCUCUAUGUGGAAAUG GCGCUGU (SEQ ID NO: 215), where G is 2'F; and A, C, and U are 2'OMe modified RNA. |
| R5-215 | RNA | GGGAGGGCAAGAGACAGAU GAUGACGGUAGAUUUCAGG UAGUGUGACCGCAUCUCUA UGUGGAAAUGGCGCUGU (SEQ ID NO: 216) | GGGAGGGCAAGAGACAGAUGAU GACGGUAGAUUUCAGGUAGUGU GACCGCAUCUCUAUGUGGAAAUG GCGCUGU (SEQ ID NO: 216), where G is 2'F; and A, C, and U are 2'OMe modified RNA. |

TABLE 2-continued

| Aptamer 3 Family | | | |
|---|---|---|---|
| Compound Name | Backbone | Primary Sequence (5' to 3') | Modified Sequence (5' to 3') |
| R5-217 | RNA | GGGAGGGCAAGAGACAGAU GAUGACGGUAGAUUUUGGG CAGAGUGACCGCAUCUCUA UGUGGAAAUGGCGCUGU (SEQ ID NO: 217) | GGGAGGGCAAGAGACAGAUGAU GACGGUAGAUUUUGGGCAGAGU GACCGCAUCUCUAUGUGGAAAUG GCGCUGU (SEQ ID NO: 217), where G is 2'F; and A, C, and U are 2'OMe modified RNA. |
| R5-218 | RNA | GGGAGGGCAAGAGACAGAU GAUGACGGUAGAUUACGGG GCGUGUGACCGCAUCUCUA UGUGGAAAUGGCGCUGU (SEQ ID NO: 218) | GGGAGGGCAAGAGACAGAUGAU GACGGUAGAUUACGGGGCGUGUG ACCGCAUCUCUAUGUGGAAAUGG CGCUGU (SEQ ID NO: 218), where G is 2'F; and A, C, and U are 2'OMe modified RNA. |
| R5-221 | RNA | GGGAGGGCAAGAGACAGAU GAUGACGGUAGAUAACGGG GAGAGUGACCGCAUCUCUA UGUGGAAAUGGCGCUGU (SEQ ID NO: 219) | GGGAGGGCAAGAGACAGAUGAU GACGGUAGAUAACGGGGAGAGU GACCGCAUCUCUAUGUGGAAAUG GCGCUGU (SEQ ID NO: 219), where G is 2'F; and A, C, and U are 2'OMe modified RNA. |
| R5-230 | RNA | GGGAGGGCAAGAGACAGAU CAUGACGGUAGAUUAUGGG CUGUGUGACCGCAUGUCUA UGUGGAAAUGGCGCUGU (SEQ ID NO: 220) | GGGAGGGCAAGAGACAGAUCAUG ACGGUAGAUUAUGGGCUGUGUG ACCGCAUGUCUAUGUGGAAAUGG CGCUGU (SEQ ID NO: 220), where G is 2'F; and A, C, and U are 2'OMe modified RNA. |
| R5-237 | RNA | GGGAGGGCAAGAGACAGAU GAUGACGGUAGAUACGGGU AGAGUGACCGCAUCUCUAU GUGGAAAUGGCGCUGU (SEQ ID NO: 221) | GGGAGGGCAAGAGACAGAUGAU GACGGUAGAUACGGGUAGAGUG ACCGCAUCUCUAUGUGGAAAUGG CGCUGU (SEQ ID NO: 221), where G is 2'F; and A, C, and U are 2'OMe modified RNA. |
| R5-240 | RNA | GGGAGGGCAAGAGACAGAU GAUGACGGUAGAUAACGGG UUGUGUGACCGCAUCUCUA UGUGGAAAUGGCGCUGU (SEQ ID NO: 222) | GGGAGGGCAAGAGACAGAUGAU GACGGUAGAUAACGGGUUGUGU GACCGCAUCUCUAUGUGGAAAUG GCGCUGU (SEQ ID NO: 222), where G is 2'F; and A, C, and U are 2'OMe modified RNA. |
| R6-68 | RNA | GGGAGAGUCGGUAGCAGUC UGAUGACGGUAGAUUAUGG GUAGAGUGACCGCAUCUCU AUGUGGAAAUGGCGCUGU (SEQ ID NO: 223) | GGGAGAGUCGGUAGCAGUCUGAU GACGGUAGAUUAUGGGUAGAGU GACCGCAUCUCUAUGUGGAAAUG GCGCUGU (SEQ ID NO: 223), where G is 2'F; and A, C, and U are 2'OMe modified RNA. |
| R6-93 | RNA | GGGAGAGUCGGUAGCAGUC UGAUGACGGUAGAUUACGG GUAGUGUGACCGCAUCUCU AUGUGGAAAUGGCGCUGU (SEQ ID NO: 224) | GGGAGAGUCGGUAGCAGUCUGAU GACGGUAGAUUACGGGUAGUGU GACCGCAUCUCUAUGUGGAAAUG GCGCUGU (SEQ ID NO: 224), where G is 2'F; and A, C, and U are 2'OMe modified RNA. |
| R6-126 | RNA | GGGAGAGUCGGUAGCAGUC UUAAACAAAGGAGAUUUCG GUGCGUGUGCCUUGUUUCU AUGUGGAAAUGGCGCUGU (SEQ ID NO: 225) | GGGAGAGUCGGUAGCAGUCUUAA ACAAAGGAGAUUUCGGUGCGUGU GCCUUGUUUCUAUGUGGAAAUGG CGCUGU (SEQ ID NO: 225), where G is 2'F; and A, C, and U are 2'OMe modified RNA. |
| R6-161 | RNA | GGGAGAGUCGGUAGCAGUC UCUAGUUACGGGAGAUUAU GGUGUGUGUGCCCGAACUC UAUGUGGAAAUGGCGCUGU (SEQ ID NO: 226) | GGGAGAGUCGGUAGCAGUCUCUA GUUACGGGAGAUUAUGGUGUGU GUGCCCGAACUCUAUGUGGAAAU GGCGCUGU (SEQ ID NO: 226), where G is 2'F; and A, C, and U are 2'OMe modified RNA. |

TABLE 2-continued

Aptamer 3 Family

| Compound Name | Backbone | Primary Sequence (5' to 3') | Modified Sequence (5' to 3') |
|---|---|---|---|
| R6-234 | RNA | GGGAGAGUCGGUAGCAGUC UGAUGACGGUAGAUUAUGG GUAGUGUGACCGCAUCUCU AUGUGGAAAUGGCGCUGU (SEQ ID NO: 227) | GGGAGAGUCGGUAGCAGUCUGAU GACGGUAGAUUAUGGGUAGUGU GACCGCAUCUCUAUGUGGAAAUG GCGCUGU (SEQ ID NO: 227), where G is 2'F; and A, C, and U are 2'OMe modified RNA. |
| R6-389 | RNA | GGGAGAGUCGGUAGCAGUC UGAUGACGGUAGAUUACGG GUUGAGUGACCGCAUCUCU AUGUGGAAAUGGCGCUGU (SEQ ID NO: 228) | GGGAGAGUCGGUAGCAGUCUGAU GACGGUAGAUUACGGGUUGAGU GACCGCAUCUCUAUGUGGAAAUG GCGCUGU (SEQ ID NO: 228), where G is 2'F; and A, C, and U are 2'OMe modified RNA. |
| R6-426 | RNA | GGGAGAGUCGGUAGCAGUC UGAUGACGGUAGAUUACGG GUAGAGUGACCGCAUCCCU AUGUGGAAAUGGCGCUGU (SEQ ID NO: 229) | GGGAGAGUCGGUAGCAGUCUGAU GACGGUAGAUUACGGGUAGAGU GACCGCAUCCCUAUGUGGAAAUG GCGCUGU (SEQ ID NO: 229), where G is 2'F; and A, C, and U are 2'OMe modified RNA. |
| R6-460 | RNA | GGGAGAGUCGGUAGCAGUC CGAUGACGGUAGAUUACGG GUAGAGUGACCGCAUCUCU AUGUGGAAAUGGCGCUGU (SEQ ID NO: 230) | GGGAGAGUCGGUAGCAGUCCGAU GACGGUAGAUUACGGGUAGAGU GACCGCAUCUCUAUGUGGAAAUG GCGCUGU (SEQ ID NO: 230), where G is 2'F; and A, C, and U are 2'OMe modified RNA. |
| R6-478 | RNA | GGGAGAGUCGGUAGCAGUC UUGGCCACAGUAGAUUUCG GUGCGUGUGACUGGGCCCU AUGUGGAAAUGGCGCUGU (SEQ ID NO: 231) | GGGAGAGUCGGUAGCAGUCUUGG CCACAGUAGAUUUCGGUGCGUGU GACUGGGCCCUAUGUGGAAAUGG CGCUGU (SEQ ID NO: 231), where G is 2'F; and A, C, and U are 2'OMe modified RNA. |
| R6-486 | RNA | GGGAGAGUCGGUAGCAGUC UUGGCCACUGUAGAUUUCG GUGCGUGUGACUGGGCUCU AUGUGGAAAUGGCGCUGU (SEQ ID NO: 232) | GGGAGAGUCGGUAGCAGUCUUGG CCACUGUAGAUUUCGGUGCGUGU GACUGGGCUCUAUGUGGAAAUGG CGCUGU (SEQ ID NO: 232), where G is 2'F; and A, C, and U are 2'OMe modified RNA. |
| R6-506 | RNA | GGGAGAGUCGGUAGCAGUC UGAUGACGGUAGAUUACGG GUAGAGUGACCGCAUCGCU AUGUGGAAAUGGCGCUGU (SEQ ID NO: 233) | GGGAGAGUCGGUAGCAGUCUGAU GACGGUAGAUUACGGGUAGAGU GACCGCAUCGCUAUGUGGAAAUG GCGCUGU (SEQ ID NO: 233), where G is 2'F; and A, C, and U are 2'OMe modified RNA. |
| R6-520 | RNA | GGGAGAGUCGGUAGCAGUC UGAUGACGGUAGAUUACGG GGAGAGUGACCGCAUCUCU AUGUGGAAAUGGCGCUGU (SEQ ID NO: 234) | GGGAGAGUCGGUAGCAGUCUGAU GACGGUAGAUUACGGGGAGAGU GACCGCAUCUCUAUGUGGAAAUG GCGCUGU (SEQ ID NO: 234), where G is 2'F; and A, C, and U are 2'OMe modified RNA. |
| R6-555 | RNA | GGGAGAGUCGGUAGCAGUC UGAUGACGGUAGAUUACGG GUAGAGUGACCGCAUCACU AUGUGGAAAUGGCGCUGU (SEQ ID NO: 235) | GGGAGAGUCGGUAGCAGUCUGAU GACGGUAGAUUACGGGUAGAGU GACCGCAUCACUAUGUGGAAAUG GCGCUGU (SEQ ID NO: 235), where G is 2'F; and A, C, and U are 2'OMe modified RNA. |
| R6-561 | RNA | GGGAGAGUCGGUAGCAGUC UGGGCCACAGUAGAUUUCG GUGCGUGUGACUGGGCUCU AUGUGGAAAUGGCGCUGU (SEQ ID NO: 236) | GGGAGAGUCGGUAGCAGUCUGGG CCACAGUAGAUUUCGGUGCGUGU GACUGGGCUCUAUGUGGAAAUGG CGCUGU (SEQ ID NO: 236), where G is 2'F; and A, C, and U are 2'OMe modified RNA. |

TABLE 2-continued

| Aptamer 3 Family | | | |
|---|---|---|---|
| Compound Name | Backbone | Primary Sequence (5' to 3') | Modified Sequence (5' to 3') |
| R6-600 | RNA | GGGAGAGUCGGUAGCAGUC UGAUGACGGUAGAUUUCGG GUAGAGUGACCGCAUCUCU AUGUGGAAAUGGCGCUGU (SEQ ID NO: 237) | GGGAGAGUCGGUAGCAGUCUGAU GACGGUAGAUUUCGGGUAGAGU GACCGCAUCUCUAUGUGGAAAUG GCGCUGU (SEQ ID NO: 237), where G is 2'F; and A, C, and U are 2'OMe modified RNA. |
| R6-648 | RNA | GGGAGAGUCGGUAGCAGUC UGAUGACGGUAGAUUACGG GCAGAGUGACCGCAUCUCU AUGUGGAAAUGGCGCUGU (SEQ ID NO: 238) | GGGAGAGUCGGUAGCAGUCUGAU GACGGUAGAUUACGGGCAGAGUG ACCGCAUCUCUAUGUGGAAAUGG CGCUGU (SEQ ID NO: 238), where G is 2'F; and A, C, and U are 2'OMe modified RNA. |
| R6-653 | RNA | GGGAGAGUCGGUAGCAGUC UUGACCACAGUAGAUUUCG GUGCGUGUGACUGGGCUCU AUGUGGAAAUGGCGCUGU (SEQ ID NO: 239) | GGGAGAGUCGGUAGCAGUCUUGA CCACAGUAGAUUUCGGUGCGUGU GACUGGGCUCUAUGUGGAAAUGG CGCUGU (SEQ ID NO: 239), where G is 2'F; and A, C, and U are 2'OMe modified RNA. |
| R6-697 | RNA | GGGAGAGUCGGUAGCAGUC AGAUGACGGUAGAUUACGG GUAGAGUGACCGCAUCUCU AUGUGGAAAUGGCGCUGU (SEQ ID NO: 240) | GGGAGAGUCGGUAGCAGUCAGAU GACGGUAGAUUACGGGUAGAGU GACCGCAUCUCUAUGUGGAAAUG GCGCUGU (SEQ ID NO: 240), where G is 2'F; and A, C, and U are 2'OMe modified RNA. |
| R6-766 | RNA | GGGAGAGUCGGUAGCAGUC UGAUGACGGUAGAUUACGG GUAGAGUGACCGCACCUCU AUGUGGAAAUGGCGCUGU (SEQ ID NO: 241) | GGGAGAGUCGGUAGCAGUCUGAU GACGGUAGAUUACGGGUAGAGU GACCGCACCUCUAUGUGGAAAUG GCGCUGU (SEQ ID NO: 241), where G is 2'F; and A, C, and U are 2'OMe modified RNA. |
| R6-797 | RNA | GGGAGAGUCGGUAGCAGUC UUGGCCACAGUAGAUUUCG GUGCGUGUGACGGGGCUCU AUGUGGAAAUGGCGCUGU (SEQ ID NO: 242) | GGGAGAGUCGGUAGCAGUCUUGG CCACAGUAGAUUUCGGUGCGUGU GACGGGGCUCUAUGUGGAAAUGG CGCUGU (SEQ ID NO: 242), where G is 2'F; and A, C, and U are 2'OMe modified RNA. |
| R6-811 | RNA | GGGAGAGUCGGUAGCAGUC UUGGCCACAGUAGAUUUCG GUGUGUGUGACUGGGCUCU AUGUGGAAAUGGCGCUGU (SEQ ID NO: 243) | GGGAGAGUCGGUAGCAGUCUUGG CCACAGUAGAUUUCGGUGUGUGU GACUGGGCUCUAUGUGGAAAUGG CGCUGU (SEQ ID NO: 243), where G is 2'F; and A, C, and U are 2'OMe modified RNA. |
| R6-858 | RNA | GGGAGAGUCGGUAGCAGUC UUGGCCACAGUAGAUUUCG GUGCGUGUGACUGGGUUCU AUGUGGAAAUGGCGCUGU (SEQ ID NO: 244) | GGGAGAGUCGGUAGCAGUCUUGG CCACAGUAGAUUUCGGUGCGUGU GACUGGGUUCUAUGUGGAAAUG GCGCUGU (SEQ ID NO: 244), where G is 2'F; and A, C, and U are 2'OMe modified RNA. |
| R6-859 | RNA | GGGAGAGUCGGUAGCAGUC UUGGCCACGGUAGAUUUCG GUGCGUGUGACUGGGCUCU AUGUGGAAAUGGCGCUGU (SEQ ID NO: 245) | GGGAGAGUCGGUAGCAGUCUUGG CCACGGUAGAUUUCGGUGCGUGU GACUGGGCUCUAUGUGGAAAUGG CGCUGU (SEQ ID NO: 245), where G is 2'F; and A, C, and U are 2'OMe modified RNA. |
| R6-889 | RNA | GGGAGAGUCGGUAGCAGUC UGAUGACGGUAGAUUACGG GUAGAGUGACUGCAUCUCU AUGUGGAAAUGGCGCUGU (SEQ ID NO: 246) | GGGAGAGUCGGUAGCAGUCUGAU GACGGUAGAUUACGGGUAGAGU GACUGCAUCUCUAUGUGGAAAUG GCGCUGU (SEQ ID NO: 246), where G is 2'F; and A, C, and U are 2'OMe modified RNA. |

TABLE 2-continued

Aptamer 3 Family

| Compound Name | Backbone | Primary Sequence (5' to 3') | Modified Sequence (5' to 3') |
|---|---|---|---|
| R6-890 | RNA | GGGAGAGUCGGUAGCAGUC UGAUGACGGUAGAUAACGG GUAGAGUGACCGCAUCUCU AUGUGGAAAUGGCGCUGU (SEQ ID NO: 247) | GGGAGAGUCGGUAGCAGUCUGAU GACGGUAGAUAACGGGUAGAGU GACCGCAUCUCUAUGUGGAAAUG GCGCUGU (SEQ ID NO: 247), where G is 2'F; and A, C, and U are 2'OMe modified RNA. |
| R6-932 | RNA | GGGAGAGUCGGUAGCAGUC UGAUGACGGUUGAUUACGG GUAGAGUGACCGCAUCUCU AUGUGGAAAUGGCGCUGU (SEQ ID NO: 248) | GGGAGAGUCGGUAGCAGUCUGAU GACGGUUGAUUACGGGUAGAGU GACCGCAUCUCUAUGUGGAAAUG GCGCUGU (SEQ ID NO: 248), where G is 2'F; and A, C, and U are 2'OMe modified RNA. |
| R6-939 | RNA | GGGAGAGUCGGUAGCAGUC UGAUGACGGUAGAUUACGG GUAGAGUGGCCGCAUCUCU AUGUGGAAAUGGCGCUGU (SEQ ID NO: 249) | GGGAGAGUCGGUAGCAGUCUGAU GACGGUAGAUUACGGGUAGAGU GGCCGCAUCUCUAUGUGGAAAUG GCGCUGU (SEQ ID NO: 249), where G is 2'F; and A, C, and U are 2'OMe modified RNA. |
| R6-971 | RNA | GGGAGAGUCGGUAGCAGUC UGAUGACGGUAGUUUACGG GUAGAGUGACCGCAUCUCU AUGUGGAAAUGGCGCUGU (SEQ ID NO: 250) | GGGAGAGUCGGUAGCAGUCUGAU GACGGUAGUUUACGGGUAGAGU GACCGCAUCUCUAUGUGGAAAUG GCGCUGU (SEQ ID NO: 250), where G is 2'F; and A, C, and U are 2'OMe modified RNA. |
| R6-978 | RNA | GGGAGAGUCGGUAGCAGUC UGAUGACGGUAGAUUACGG GAAGAGUGACCGCAUCUCU AUGUGGAAAUGGCGCUGU (SEQ ID NO: 251) | GGGAGAGUCGGUAGCAGUCUGAU GACGGUAGAUUACGGGAAGAGU GACCGCAUCUCUAUGUGGAAAUG GCGCUGU (SEQ ID NO: 251), where G is 2'F; and A, C, and U are 2'OMe modified RNA. |
| R6-989 | RNA | GGGAGAGUCGGUAGCAGUC UGACGACGGUAGAUUACGG GUAGAGUGACCGCAUCUCU AUGUGGAAAUGGCGCUGU (SEQ ID NO: 252) | GGGAGAGUCGGUAGCAGUCUGAC GACGGUAGAUUACGGGUAGAGU GACCGCAUCUCUAUGUGGAAAUG GCGCUGU (SEQ ID NO: 252), where G is 2'F; and A, C, and U are 2'OMe modified RNA. |
| Aptamer 38 | RNA | GAUGACGGUAGAUUACGGG UAGAGUGACCGCAUC (SEQ ID NO: 253) | $C6NH_2$- GAUGACGGUAGAUUACGGGUAG AGUGACCGCAUC-idT (SEQ ID NO: 399), where G is 2'F; A, C, and U are 2'OMe modified RNA; $C6NH_2$ is a hexylamine linker; and idT is a deoxythymidine residue. |
| Aptamer 40 | RNA | GAUGCGGUAGAUUACGGGU AGAGUGACCGCAUC (SEQ ID NO: 254) | $C6NH_2$- GAUGCGGUAGAUUACGGGUAGA GUGACCGCAUC-idT (SEQ ID NO: 400), where G is 2'F; A, C, and U are 2'OMe modified RNA; $C6NH_2$ is a hexylamine linker; and idT is a deoxythymidine residue. |
| Aptamer 41 | RNA | GAUGUCGGUAGAUUACGGG UAGAGUGACCGCAUC (SEQ ID NO: 255) | $C6NH_2$- GAUGUCGGUAGAUUACGGGUAG AGUGACCGCAUC-idT (SEQ ID NO: 401), where G is 2'F; A, C, and U are 2'OMe modified RNA; $C6NH_2$ is a hexylamine linker; and idT is a deoxythymidine residue. |

TABLE 2-continued

| Aptamer 3 Family | | | |
|---|---|---|---|
| Compound Name | Backbone | Primary Sequence (5' to 3') | Modified Sequence (5' to 3') |
| Aptamer 42 | RNA | GCGACGGUAGAUUACGGGU AGAGUGACCGCGC (SEQ ID NO: 256) | $C6NH_2$-GCGACGGUAGAUUACGGGUAGAG UGACCGCGC-idT (SEQ ID NO: 402), where G is 2'F; A, C, and U are 2'OMe modified RNA; $C6NH_2$ is a hexylamine linker; and idT is a deoxythymidine residue. |
| Aptamer 43 | RNA | GCGACGGCAGAUUACGGGU AGAGUGGCCGCGC (SEQ ID NO: 257) | $C6NH_2$-GCGACGGCAGAUUACGGGUAGAG UGGCCGCGC-idT (SEQ ID NO: 403), where G is 2'F; A, C, and U are 2'OMe modified RNA; $C6NH_2$ is a hexylamine linker; and idT is a deoxythymidine residue. |
| Aptamer 44 | RNA | GCGACGUAGAUUACGGGUA GAGUGACGCGC (SEQ ID NO: 258) | $C6NH_2$-GCGACGUAGAUUACGGGUAGAGU GACGCGC-idT (SEQ ID NO: 404), where G is 2'F; A, C, and U are 2'OMe modified RNA; $C6NH_2$ is a hexylamine linker; and idT is a deoxythymidine residue. |
| Aptamer 45 | RNA | GCGACGCAGAUUACGGGUA GAGUGGCGCGC (SEQ ID NO: 259) | $C6NH_2$-GCGACGCAGAUUACGGGUAGAGU GGCGCGC-idT (SEQ ID NO: 405), where G is 2'F; A, C, and U are 2'OMe modified RNA; $C6NH_2$ is a hexylamine linker; and idT is a deoxythymidine residue. |
| Aptamer 69 | RNA | CUGAUGACGGU (SEQ ID NO: 260)-(Sp3)-GAUUACGGGUAGAGUGACC GCAUCU (SEQ ID NO: 261), where Sp3 is a 3-carbon spacer. | $C6NH_2$-UGAUGACGGU (SEQ ID NO: 406)-(Sp3)-GAUUACGGGUAGAGUGACCGCAU CU-idT (SEQ ID NO: 407), where G is 2'F; A, C, and U are 2'OMe modified RNA; $C6NH_2$ is a hexylamine linker; idT is a deoxythymidine residue; and Sp3 is a 3-carbon spacer. |
| Aptamer 70 | RNA | UGAUGACGGUA (SEQ ID NO: 262)-(Sp3)-AUUACGGGUAGAGUGACCG CAUCU (SEQ ID NO: 263) where Sp3 is a 3-carbon spacer. | $C6NH_2$-UGAUGACGGUA (SEQ ID NO: 408)-(Sp3)-AUUACGGGUAGAGUGACCGCAUC U-idT (SEQ ID NO: 409), where G is 2'F; A, C, and U are 2'OMe modified RNA; $C6NH_2$ is a hexylamine linker; idT is a deoxythymidine residue; and Sp3 is a 3-carbon spacer. |
| Aptamer 71 | RNA | UGAUGACGGUAG (SEQ ID NO: 264)-(Sp3)-UUACGGGUAGAGUGACCGC AUCU (SEQ ID NO: 265) where Sp3 is a 3-carbon spacer. | $C6NH_2$-UGAUGACGGUAG (SEQ ID NO: 410)-(Sp3)-UUACGGGUAGAGUGACCGCAUCU-idT (SEQ ID NO: 411), where G is 2'F; A, C, and U are 2'OMe modified RNA; $C6NH_2$ is a hexylamine linker; idT is a deoxythymidine residue; and Sp3 is a 3-carbon spacer. |
| Aptamer 72 | RNA | UGAUGACGGUAGA (SEQ ID NO: 266)-(Sp3)-UACGGGUAGAGUGACCGCA UCU-idT (SEQ ID NO: 267) where Sp3 is a 3-carbon spacer. | $C6NH_2$-UGAUGACGGUAGA (SEQ ID NO: 412)-(Sp3)-UACGGGUAGAGUGACCGCAUCU-idT (SEQ ID NO: 413), where G is 2'F; A, C, and U are 2'OMe modified RNA; $C6NH_2$ is a hexylamine linker; idT is a deoxythymidine residue; and Sp3 is a 3-carbon spacer. |

TABLE 2-continued

| Aptamer 3 Family | | | |
|---|---|---|---|
| Compound Name | Backbone | Primary Sequence (5' to 3') | Modified Sequence (5' to 3') |
| Aptamer 73 | RNA | UGAUGACGGUAGAU (SEQ ID NO: 268)-(Sp3)-ACGGGUAGAGUGACCGCAUCU (SEQ ID NO: 269) where Sp3 is a 3-carbon spacer. | $C6NH_2$-UGAUGACGGUAGAU (SEQ ID NO: 414)-(Sp3)-ACGGGUAGAGUGACCGCAUCU-idT (SEQ ID NO: 415), where G is 2'F; A, C, and U are 2'OMe modified RNA; $C6NH_2$ is a hexylamine linker; idT is a deoxythymidine residue; and Sp3 is a 3-carbon spacer. |
| Aptamer 74 | RNA | UGAUGACGGUAGAUU (SEQ ID NO: 270)-(Sp3)-CGGGUAGAGUGACCGCAUCU (SEQ ID NO: 271) where Sp3 is a 3-carbon spacer. | $C6NH_2$-UGAUGACGGUAGAUU (SEQ ID NO: 416)-(Sp3)-CGGGUAGAGUGACCGCAUCU-idT (SEQ ID NO: 417), where G is 2'F; A, C, and U are 2'OMe modified RNA; $C6NH_2$ is a hexylamine linker; idT is a deoxythymidine residue; and Sp3 is a 3-carbon spacer. |
| Aptamer 75 | RNA | UGAUGACGGUAGAUUA (SEQ ID NO: 272)-(Sp3)-GGGUAGAGUGACCGCAUCU (SEQ ID NO: 273) where Sp3 is a 3-carbon spacer. | $C6NH_2$-UGAUGACGGUAGAUUA (SEQ ID NO: 418)-(Sp3)-GGGUAGAGUGACCGCAUCU-idT (SEQ ID NO: 419), where G is 2'F; A, C, and U are 2'OMe modified RNA; $C6NH_2$ is a hexylamine linker; idT is a deoxythymidine residue; and Sp3 is a 3-carbon spacer. |
| Aptamer 76 | RNA | UGAUGACGGUAGAUUAC (SEQ ID NO: 274)-(Sp3)-GGUAGAGUGACCGCAUCU (SEQ ID NO: 275) where Sp3 is a 3-carbon spacer. | $C6NH_2$-UGAUGACGGUAGAUUAC (SEQ ID NO: 420)-(Sp3)-GGUAGAGUGACCGCAUCU-idT (SEQ ID NO: 421), where G is 2'F; A, C, and U are 2'OMe modified RNA; $C6NH_2$ is a hexylamine linker; idT is a deoxythymidine residue; and Sp3 is a 3-carbon spacer. |
| Aptamer 77 | RNA | UGAUGACGGUAGAUUACG (SEQ ID NO: 276)-(Sp3)-GUAGAGUGACCGCAUCU (SEQ ID NO: 277) where Sp3 is a 3-carbon spacer. | $C6NH_2$-UGAUGACGGUAGAUUACG (SEQ ID NO: 422)-(Sp3)-GUAGAGUGACCGCAUCU-idT (SEQ ID NO: 423), where G is 2'F; A, C, and U are 2'OMe modified RNA; $C6NH_2$ is a hexylamine linker; idT is a deoxythymidine residue; and Sp3 is a 3-carbon spacer. |
| Aptamer 78 | RNA | UGAUGACGGUAGAUUACGG (SEQ ID NO: 278)-(Sp3)-UAGAGUGACCGCAUCU (SEQ ID NO: 279) where Sp3 is a 3-carbon spacer. | $C6NH_2$-UGAUGACGGUAGAUUACGG (SEQ ID NO: 424)-(Sp3)-UAGAGUGACCGCAUCU-idT (SEQ ID NO: 425), where G is 2'F; A, C, and U are 2'OMe modified RNA; $C6NH_2$ is a hexylamine linker; idT is a deoxythymidine residue; and Sp3 is a 3-carbon spacer. |
| Aptamer 79 | RNA | UGAUGACGGUAGAUUACGGG (SEQ ID NO: 280)-(Sp3)-AGAGUGACCGCAUCU (SEQ ID NO: 281) where Sp3 is a 3-carbon spacer. | $C6NH_2$-UGAUGACGGUAGAUUACGGG (SEQ ID NO: 426)-(Sp3)-AGAGUGACCGCAUCU-idT (SEQ ID NO: 427), where G is 2'F; A, C, and U are 2'OMe modified RNA; $C6NH_2$ is a hexylamine linker; idT is a deoxythymidine residue; and Sp3 is a 3-carbon spacer. |
| Aptamer 80 | RNA | UGAUGACGGUAGAUUACGGGU (SEQ ID NO: 282)-(Sp3)-GAGUGACCGCAUCU (SEQ ID NO: 283) where Sp3 is a 3-carbon spacer. | $C6NH_2$-UGAUGACGGUAGAUUACGGGU (SEQ ID NO: 428)-(Sp3)-GAGUGACCGCAUCU-idT (SEQ ID NO: 429), where G is 2'F; A, C, and U are 2'OMe modified RNA; $C6NH_2$ is a hexylamine linker; idT is a deoxythymidine residue; and Sp3 is a 3-carbon spacer. |

TABLE 2-continued

| Aptamer 3 Family | | | |
|---|---|---|---|
| Compound Name | Backbone | Primary Sequence (5' to 3') | Modified Sequence (5' to 3') |
| Aptamer 81 | RNA | UGAUGACGGUAGAUUACGG GUA (SEQ ID NO: 284)-(Sp3)-AGUGACCGCAUCU (SEQ ID NO: 285), where Sp3 is a 3-carbon spacer. | $C6NH_2$-UGAUGACGGUAGAUUACGGGUA (SEQ ID NO: 430)-(Sp3)-AGUGACCGCAUCU-idT (SEQ ID NO: 431), where G is 2'F; A, C, and U are 2'OMe modified RNA; $C6NH_2$ is a hexylamine linker; idT is a deoxythymidine residue; and Sp3 is a 3-carbon spacer. |
| Aptamer 82 | RNA | UGAUGACGGUAGAUUACGG GUAG (SEQ ID NO: 286)-(Sp3)-GUGACCGCAUCU (SEQ ID NO: 287), where Sp3 is a 3-carbon spacer. | $C6NH_2$-UGAUGACGGUAGAUUACGGGUA G (SEQ ID NO: 432)-(Sp3)-GUGACCGCAUCU-idT (SEQ ID NO: 433), where G is 2'F; A, C, and U are 2'OMe modified RNA; $C6NH_2$ is a hexylamine linker; idT is a deoxythymidine residue; and Sp3 is a 3-carbon spacer. |
| Aptamer 83 | RNA | UGAUGACGGUAGAUUACGG GUAGA (SEQ ID NO: 288)-(Sp3)-UGACCGCAUCU (SEQ ID NO: 289) where Sp3 is a 3-carbon spacer. | $C6NH_2$-UGAUGACGGUAGAUUACGGGUA GA (SEQ ID NO: 434)-(Sp3)-UGACCGCAUCU-idT (SEQ ID NO: 435), where G is 2'F; A, C, and U are 2'OMe modified RNA; $C6NH_2$ is a hexylamine linker; idT is a deoxythymidine residue; and Sp3 is a 3-carbon spacer. |
| Aptamer 84 | RNA | UGAUGACGGUAGAUUACGG GUAGAG (SEQ ID NO: 290)-(Sp3)-GACCGCAUCU (SEQ ID NO: 291) where Sp3 is a 3-carbon spacer. | $C6NH_2$-UGAUGACGGUAGAUUACGGGUA GAG (SEQ ID NO: 436)-(Sp3)-GACCGCAUCU-idT (SEQ ID NO: 437), where G is 2'F; A, C, and U are 2'OMe modified RNA; $C6NH_2$ is a hexylamine linker; idT is a deoxythymidine residue; and Sp3 is a 3-carbon spacer. |
| Aptamer 85 | RNA | UGAUGACGGUAGAUUACGG GUAGAGU (SEQ ID NO: 292)-(Sp3)-ACCGCAUCU where Sp3 is a 3-carbon spacer. | $C6NH_2$-UGAUGACGGUAGAUUACGGGUA GAGU (SEQ ID NO: 438)-(Sp3)-ACCGCAUCU-idT (SEQ ID NO: 439), where G is 2'F; A, C, and U are 2'OMe modified RNA; $C6NH_2$ is a hexylamine linker; idT is a deoxythymidine residue; and Sp3 is a 3-carbon spacer. |
| Aptamer 87 | RNA | GCGACGGUAGAUUAC (SEQ ID NO: 293)-(Sp3)-GGUAGAGUGACCGCGC (SEQ ID NO: 294) where Sp3 is a 3-carbon spacer. | $C6NH_2$-GCGACGGUAGAUUAC (SEQ ID NO: 440)-(Sp3)-GGUAGAGUGACCGCGC-idT (SEQ ID NO: 441), where G is 2'F; A, C, and U are 2'OMe modified RNA; $C6NH_2$ is a hexylamine linker; idT is a deoxythymidine residue; and Sp3 is a 3-carbon spacer. |
| Aptamer 89 | RNA | GGCGACGGUAGACUACGGG UAGAGUGACCGCGCC (SEQ ID NO: 295) | $C6NH_2$-GGCGACGGUAGACUACGGGUAGA GUGACCGCGCC-idT (SEQ ID NO: 442), where G is 2'F; A, C, and U are 2'OMe modified RNA; $C6NH_2$ is a hexylamine linker; and idT is a deoxythymidine residue. |

TABLE 2-continued

| Aptamer 3 Family | | | |
|---|---|---|---|
| Compound Name | Backbone | Primary Sequence (5' to 3') | Modified Sequence (5' to 3') |
| Aptamer 90 | RNA | GGCGACGGUAGAUCACGGG UAGGGUGACCGCGCC (SEQ ID NO: 296) | $C6NH_2$-GGCGACGGUAGAUCACGGGUAGG GUGACCGCGCC-idT (SEQ ID NO: 443), where G is 2'F; A, C, and U are 2'OMe modified RNA; $C6NH_2$ is a hexylamine linker; and idT is a deoxythymidine residue. |
| Aptamer 92 | RNA | GGCGACGGUAGAUUACGGG UAGAGUGACCGCGCC (SEQ ID NO: 297) | $C6NH_2$-GGCGACGGUAGAUUACGGGUAGA GUGACCGCGCC-idT (SEQ ID NO: 444), where G is 2'F; A, C, and U are 2'OMe modified RNA; $C6NH_2$ is a hexylamine linker; and idT is a deoxythymidine residue. |
| Aptamer 94 | RNA | UGAUGACGGUAGAUUUCGG GUAGUGUGACCGCAUCU (SEQ ID NO: 298) | $C6NH_2$-UGAUGACGGUAGAUUUCGGGUA GUGUGACCGCAUCU-idT (SEQ ID NO: 445), where G is 2'F; A, C, and U are 2'OMe modified RNA; $C6NH_2$ is a hexylamine linker; and idT is a deoxythymidine residue. |
| Aptamer 95 | RNA | UGAUGACGGUAGAUUCCGG GUAGUGUGACCGCAUCU (SEQ ID NO: 299) | $C6NH_2$-UGAUGACGGUAGAUUCCGGGUAG UGUGACCGCAUCU-idT (SEQ ID NO: 446), where G is 2'F; A, C, and U are 2'OMe modified RNA; $C6NH_2$ is a hexylamine linker; and idT is a deoxythymidine residue. |
| Aptamer 96 | RNA | UGAUGACGGUAGAUUACGG GCAGUGUGACCGCAUCU (SEQ ID NO: 300) | $C6NH_2$-UGAUGACGGUAGAUUACGGGCAG UGUGACCGCAUCU-idT (SEQ ID NO: 447), where G is 2'F; A, C, and U are 2'OMe modified RNA; $C6NH_2$ is a hexylamine linker; and idT is a deoxythymidine residue. |
| Aptamer 97 | RNA | UGAUGACGGUAGAUUACGG GGAGUGUGACCGCAUCU (SEQ ID NO: 301) | $C6NH_2$-UGAUGACGGUAGAUUACGGGGA GUGUGACCGCAUCU-idT (SEQ ID NO: 448), where G is 2'F; A, C, and U are 2'OMe modified RNA; $C6NH_2$ is a hexylamine linker; and idT is a deoxythymidine residue. |
| Aptamer 98 | RNA | UGAUGACGGUAGAUUACGG GAAGUGUGACCGCAUCU (SEQ ID NO: 302) | $C6NH_2$-UGAUGACGGUAGAUUACGGGAA GUGUGACCGCAUCU-idT (SEQ ID NO: 449), where G is 2'F; A, C, and U are 2'OMe modified RNA; $C6NH_2$ is a hexylamine linker; and idT is a deoxythymidine residue. |
| Aptamer 99 | RNA | UGAUGACGGUAGAUUAUGG GCAGUGUGACCGCAUCU (SEQ ID NO: 303) | $C6NH_2$-UGAUGACGGUAGAUUAUGGGCA GUGUGACCGCAUCU-idT (SEQ ID NO: 450), where G is 2'F; A, C, and U are 2'OMe modified RNA; $C6NH_2$ is a hexylamine linker; and idT is a deoxythymidine residue. |

TABLE 2-continued

| Aptamer 3 Family | | | |
|---|---|---|---|
| Compound Name | Backbone | Primary Sequence (5' to 3') | Modified Sequence (5' to 3') |
| Aptamer 100 | RNA | UGAUGACGGUAGAUUAUGG GAAGUGUGACCGCAUCU (SEQ ID NO: 304) | $C6NH_2$- UGAUGACGGUAGAUUAUGGGAA GUGUGACCGCAUCU-idT (SEQ ID NO: 451), where G is 2'F; A, C, and U are 2'OMe modified RNA; $C6NH_2$ is a hexylamine linker; and idT is a deoxythymidine residue. |
| Aptamer 101 | RNA | UCAUGACGGUAGAUUUCGG GUAGUGUGACCGCAUGU (SEQ ID NO: 305) | $C6NH_2$- UCAUGACGGUAGAUUUCGGGUAG UGUGACCGCAUGU-idT (SEQ ID NO: 452), where G is 2'F; A, C, and U are 2'OMe modified RNA; $C6NH_2$ is a hexylamine linker; and idT is a deoxythymidine residue. |
| Aptamer 102 | RNA | UCAUGACGGUAGAUUACGG GUAGAGUGACCGCAUGU (SEQ ID NO: 306) | $C6NH_2$- UCAUGACGGUAGAUUACGGGUAG AGUGACCGCAUGU-idT (SEQ ID NO: 453), where G is 2'F; A, C, and U are 2'OMe modified RNA; $C6NH_2$ is a hexylamine linker; and idT is a deoxythymidine residue. |
| Aptamer 103 | RNA | UGAUGACGGUAGAUUACGG GAAGAGUGACCGCAUCU (SEQ ID NO: 307) | $C6NH_2$- UGAUGACGGUAGAUUACGGGAA GAGUGACCGCAUCU-idT (SEQ ID NO: 454), where G is 2'F; A, C, and U are 2'OMe modified RNA; $C6NH_2$ is a hexylamine linker; and idT is a deoxythymidine residue. |
| Aptamer 104 | RNA | UGAUGACGGUAGAUUAAGG GUAGUGUGACCGCAUCU (SEQ ID NO: 308) | $C6NH_2$- UGAUGACGGUAGAUUAAGGGUA GUGUGACCGCAUCU-idT (SEQ ID NO: 455), where G is 2'F; A, C, and U are 2'OMe modified RNA; $C6NH_2$ is a hexylamine linker; and idT is a deoxythymidine residue. |
| Aptamer 105 | RNA | UGAUGACGGUAGAUUACGG GUUGUGUGACCGCAUCU (SEQ ID NO: 309) | $C6NH_2$- UGAUGACGGUAGAUUACGGGUU GUGUGACCGCAUCU-idT (SEQ ID NO: 456), where G is 2'F; A, C, and U are 2'OMe modified RNA; $C6NH_2$ is a hexylamine linker; and idT is a deoxythymidine residue. |
| Aptamer 106 | RNA | UGAUGACGAUAGAUUUCGG GUAGUGUGAUCGCAUCU (SEQ ID NO: 310) | $C6NH_2$- UGAUGACGAUAGAUUUCGGGUA GUGUGAUCGCAUCU-idT (SEQ ID NO: 457), where G is 2'F; A, C, and U are 2'OMe modified RNA; $C6NH_2$ is a hexylamine linker; and idT is a deoxythymidine residue. |
| Aptamer 107 | RNA | UGAUGACGGUAGAUUUGGG UAGAGUGACCGCAUCU (SEQ ID NO: 311) | $C6NH_2$- UGAUGACGGUAGAUUUGGGUAG AGUGACCGCAUCU-idT (SEQ ID NO: 458), where G is 2'F; A, C, and U are 2'OMe modified RNA; $C6NH_2$ is a hexylamine linker; and idT is a deoxythymidine residue. |

TABLE 2-continued

| Aptamer 3 Family | | | |
|---|---|---|---|
| Compound Name | Backbone | Primary Sequence (5' to 3') | Modified Sequence (5' to 3') |
| Aptamer 108 | RNA | UGAUGACGGUAGAUAACGG GUAGAGUGACCGCAUCU (SEQ ID NO: 312) | $C6NH_2$-UGAUGACGGUAGAUAACGGGUA GAGUGACCGCAUCU-idT (SEQ ID NO: 459), where G is 2'F; A, C, and U are 2'OMe modified RNA; $C6NH_2$ is a hexylamine linker; and idT is a deoxythymidine residue. |
| Aptamer 109 | RNA | UGAUGACGGUAGAUAACGG GUAGUGUGACCGCAUCU (SEQ ID NO: 313) | $C6NH_2$-UGAUGACGGUAGAUAACGGGUA GUGUGACCGCAUCU-idT (SEQ ID NO: 460), where G is 2'F; A, C, and U are 2'OMe modified RNA; $C6NH_2$ is a hexylamine linker; and idT is a deoxythymidine residue. |
| Aptamer 110 | RNA | UGAUGACGGUAGAUUUCGG GAAGUGUGACCGCAUCU (SEQ ID NO: 314) | $C6NH_2$-UGAUGACGGUAGAUUUCGGGAA GUGUGACCGCAUCU-idT (SEQ ID NO: 461), where G is 2'F; A, C, and U are 2'OMe modified RNA; $C6NH_2$ is a hexylamine linker; and idT is a deoxythymidine residue. |
| Aptamer 111 | RNA | UGAUGACGGUAGAUUAUGG GUAGUGUGACCGCAUCU (SEQ ID NO: 315) | $C6NH_2$-UGAUGACGGUAGAUUAUGGGUA GUGUGACCGCAUCU-idT (SEQ ID NO: 462), where G is 2'F; A, C, and U are 2'OMe modified RNA; $C6NH_2$ is a hexylamine linker; and idT is a deoxythymidine residue. |
| Aptamer 134 | RNA | GAUGACGGUAGAU (SEQ ID NO: 316)-(Sp3)-(Sp3)-(Sp3)-(Sp3)-GGUAGAGUGACCGCAUC (SEQ ID NO: 317), where Sp3 is a 3-carbon spacer. | $C6NH_2$-GAUGACGGUAGAU (SEQ ID NO: 463)-(Sp3)-(Sp3)-(Sp3)-(Sp3)-GGUAGAGUGACCGCAUC-idT (SEQ ID NO: 464), where G is 2'F; A, C, and U are 2'OMe modified RNA; $C6NH_2$ is a hexylamine linker; idT is a deoxythymidine residue; and Sp3 is a 3-carbon spacer. |
| Aptamer 135 | RNA | GGCGACGGUAGAU (SEQ ID NO: 318)-(Sp3)-(Sp3)-(Sp3)-(Sp3)-GGUAGAGUGACCGCGCC (SEQ ID NO: 319), where Sp3 is a 3-carbon spacer. | $C6NH_2$-GGCGACGGUAGAU (SEQ ID NO: 465)-(Sp3)-(Sp3)-(Sp3)-(Sp3)-GGUAGAGUGACCGCGCC-idT (SEQ ID NO: 466), where G is 2'F; A, C, and U are 2'OMe modified RNA; $C6NH_2$ is a hexylamine linker; idT is a deoxythymidine residue; and Sp3 is a 3-carbon spacer. |
| Aptamer 136 | RNA | GAUGACGGUAGAU (SEQ ID NO: 320)-(Sp3)-GGUAGAGUGACCGCAUC (SEQ ID NO: 321), where Sp3 is a 3-carbon spacer. | $C6NH_2$-GAUGACGGUAGAU (SEQ ID NO: 467)-(Sp3)-GGUAGAGUGACCGCAUC-idT (SEQ ID NO: 468), where G is 2'F; A, C, and U are 2'OMe modified RNA; $C6NH_2$ is a hexylamine linker; idT is a deoxythymidine residue; and Sp3 is a 3-carbon spacer. |
| Aptamer 137 | RNA | GAUGACGGUAGAU (SEQ ID NO: 322)-(Sp3)-(Sp3)-GGUAGAGUGACCGCAUC (SEQ ID NO: 323), where Sp3 is a 3-carbon spacer. | $C6NH_2$-GAUGACGGUAGAU (SEQ ID NO: 469)-(Sp3)-(Sp3)-GGUAGAGUGACCGCAUC-idT (SEQ ID NO: 470) where G is 2'F; A, C, and U are 2'OMe modified RNA; $C6NH_2$ is a hexylamine linker; idT is a deoxythymidine residue; and Sp3 is a 3-carbon spacer. |

TABLE 2-continued

| Aptamer 3 Family | | | |
|---|---|---|---|
| Compound Name | Backbone | Primary Sequence (5' to 3') | Modified Sequence (5' to 3') |
| Aptamer 138 | RNA | GAUGACGGUAGAU (SEQ ID NO: 324)-(Sp3)-(Sp3)-(Sp3)-GGUAGAGUGACCGCAUC (SEQ ID NO: 325), where Sp3 is a 3-carbon spacer. | $C6NH_2$-GAUGACGGUAGAU (SEQ ID NO: 471)-(Sp3)-(Sp3)-(Sp3)-GGUAGAGUGACCGCAUC-idT (SEQ ID NO: 472), where G is 2'F; A, C, and U are 2'OMe modified RNA; $C6NH_2$ is a hexylamine linker; idT is a deoxythymidine residue; and Sp3 is a 3-carbon spacer. |
| Aptamer 139 | RNA | GAUGACGGUAGAU (SEQ ID NO: 326)-(L6)-GGUAGAGUGACCGCAUC (SEQ ID NO: 327), where L6 is a 6-carbon spacer. | $C6NH_2$-GAUGACGGUAGAU (SEQ ID NO: 473)-(L6)-GGUAGAGUGACCGCAUC-idT (SEQ ID NO: 474), where G is 2'F; A, C, and U are 2'OMe modified RNA; $C6NH_2$ is a hexylamine linker; idT is a deoxythymidine residue; and L6 is a 6-carbon spacer. |
| Aptamer 140 | RNA | GAUGACGGUAGAU (SEQ ID NO: 328)-(Sp9)-GGUAGAGUGACCGCAUC (SEQ ID NO: 329), where Sp9 is a 9-atom PEG spacer. | $C6NH_2$-GAUGACGGUAGAU (SEQ ID NO: 475)-(Sp9)-GGUAGAGUGACCGCAUC-idT (SEQ ID NO: 476), where G is 2'F; A, C, and U are 2'OMe modified RNA; $C6NH_2$ is a hexylamine linker; idT is a deoxythymidine residue; and Sp9 is a 9-atom PEG spacer. |
| Aptamer 141 | RNA | GAUGACGGUAGAU (SEQ ID NO: 330)-(Sp18)-GGUAGAGUGACCGCAUC (SEQ ID NO: 331), where Sp18 is an 18-atom PEG spacer. | $C6NH_2$-GAUGACGGUAGAU (SEQ ID NO: 477)-(Sp18)-GGUAGAGUGACCGCAUC-idT (SEQ ID NO: 478), where G is 2'F; A, C, and U are 2'OMe modified RNA; $C6NH_2$ is a hexylamine linker; idT is a deoxythymidine residue; and Sp18 is an 18-atom PEG spacer. |
| Aptamer 142 | RNA | GAUGACGGUAGAUUUCGGGUAGUGUGACCGCAUC (SEQ ID NO: 332) | $C6NH_2$-GAUGACGGUAGAUUUCGGGUAGUGUGACCGCAUC-idT (SEQ ID NO: 479), where G is 2'F; A, C, and U are 2'OMe modified RNA; $C6NH_2$ is a hexylamine linker; and idT is a deoxythymidine residue. |
| Aptamer 143 | RNA | GGCGACGGUAGAUUUCGGGUAGUGUGACCGCGCC (SEQ ID NO: 333) | $C6NH_2$-GGCGACGGUAGAUUUCGGGUAGUGUGACCGCGCC-idT (SEQ ID NO: 480), where G is 2'F; A, C, and U are 2'OMe modified RNA; $C6NH_2$ is a hexylamine linker; and idT is a deoxythymidine residue. |
| Aptamer 144 | RNA | GCGACGGUAGAUUUCGGGUAGUGUGACCGCGC (SEQ ID NO: 334) | $C6NH_2$-GCGACGGUAGAUUUCGGGUAGUGUGACCGCGC-idT (SEQ ID NO: 481), where G is 2'F; A, C, and U are 2'OMe modified RNA; $C6NH_2$ is a hexylamine linker; and idT is a deoxythymidine residue. |
| Aptamer 145 | RNA | GAUGACGGUAGAUUUC (SEQ ID NO: 335)-(Sp3)-GGUAGUGUGACCGCAUC (SEQ ID NO: 336), where Sp3 is a 3-carbon spacer. | $C6NH_2$-GAUGACGGUAGAUUUC (SEQ ID NO: 482)-(Sp3)-GGUAGUGUGACCGCAUC-idT (SEQ ID NO: 483), where G is 2'F; A, C, and U are 2'OMe modified RNA; $C6NH_2$ is a hexylamine linker; idT is a deoxythymidine residue; and Sp3 is a 3-carbon spacer. |

TABLE 2-continued

| Aptamer 3 Family | | | |
|---|---|---|---|
| Compound Name | Backbone | Primary Sequence (5' to 3') | Modified Sequence (5' to 3') |
| Aptamer 146 | RNA | GAUGACGGUAGAUUAUGGG CAGUGUGACCGCAUC (SEQ ID NO: 337) | $C6NH_2$-GAUGACGGUAGAUUAUGGGCAG UGUGACCGCAUC-idT (SEQ ID NO: 484), where G is 2'F; A, C, and U are 2'OMe modified RNA; $C6NH_2$ is a hexylamine linker; and idT is a deoxythymidine residue. |
| Aptamer 147 | RNA | GGCGACGGUAGAUUAUGGG CAGUGUGACCGCGCC (SEQ ID NO: 338) | $C6NH_2$-GGCGACGGUAGAUUAUGGGCAGU GUGACCGCGCC-idT (SEQ ID NO: 485) where G is 2'F; A, C, and U are 2'OMe modified RNA; $C6NH_2$ is a hexylamine linker; and idT is a deoxythymidine residue. |
| Aptamer 148 | RNA | GCGACGGUAGAUUAUGGGC AGUGUGACCGCGC (SEQ ID NO: 339) | $C6NH_2$-GCGACGGUAGAUUAUGGGCAGUG UGACCGCGC-idT (SEQ ID NO: 486), where G is 2'F; A, C, and U are 2'OMe modified RNA; $C6NH_2$ is a hexylamine linker; and idT is a deoxythymidine residue. |
| Aptamer 149 | RNA | GAUGACGGUAGAUUAU (SEQ ID NO: 340)-(Sp3)-GGCAGUGUGACCGCAUC (SEQ ID NO: 341), where Sp3 is a 3-carbon spacer. | $C6NH_2$-GAUGACGGUAGAUUAU (SEQ ID NO: 487)-(Sp3)-GGCAGUGUGACCGCAUC-idT (SEQ ID NO: 488), where G is 2'F; A, C, and U are 2'OMe modified RNA; $C6NH_2$ is a hexylamine linker; idT is a deoxythymidine residue; and Sp3 is a 3-carbon spacer. |
| Aptamer 150 | RNA | GAUGACGGUAGAUUAUGGG AAGUGUGACCGCAUC (SEQ ID NO: 342) | $C6NH_2$-GAUGACGGUAGAUUAUGGGAAG UGUGACCGCAUC-idT (SEQ ID NO: 489) where G is 2'F; A, C, and U are 2'OMe modified RNA; $C6NH_2$ is a hexylamine linker; and idT is a deoxythymidine residue. |
| Aptamer 151 | RNA | GGCGACGGUAGAUUAUGGG AAGUGUGACCGCGCC (SEQ ID NO: 343) | $C6NH_2$-GGCGACGGUAGAUUAUGGGAAG UGUGACCGCGCC-idT (SEQ ID NO: 490), where G is 2'F; A, C, and U are 2'OMe modified RNA; $C6NH_2$ is a hexylamine linker; and idT is a deoxythymidine residue. |
| Aptamer 152 | RNA | GCGACGGUAGAUUAUGGGA AGUGUGACCGCGC (SEQ ID NO: 344) | $C6NH_2$-GCGACGGUAGAUUAUGGGAAGU GUGACCGCGC-idT (SEQ ID NO: 491), where G is 2'F; A, C, and U are 2'OMe modified RNA; $C6NH_2$ is a hexylamine linker; and idT is a deoxythymidine residue. |
| Aptamer 153 | RNA | GAUGACGGUAGAUUAU (SEQ ID NO: 345)-(Sp3)-GGAAGUGUGACCGCAUC (SEQ ID NO: 346), where Sp3 is a 3-carbon spacer. | $C6NH_2$-GAUGACGGUAGAUUAU (SEQ ID NO: 492)-(Sp3)-GGAAGUGUGACCGCAUC-idT (SEQ ID NO: 493), where G is 2'F; A, C, and U are 2'OMe modified RNA; $C6NH_2$ is a hexylamine linker; idT is a deoxythymidine residue; and Sp3 is a 3-carbon spacer. |

TABLE 2-continued

| Aptamer 3 Family | | | |
|---|---|---|---|
| Compound Name | Backbone | Primary Sequence (5' to 3') | Modified Sequence (5' to 3') |
| Aptamer 183 | RNA | UCAUGACGGUAGAUUACGG GUAGAGUGACCGCAUGU (SEQ ID NO: 347) | $C6NH_2$-UCAUGACGGUAGAUUACGGGUAG AGUGACCGCAUGU-idT (SEQ ID NO: 494), where G is 2'F; A, C, and U are 2'OMe modified RNA; $C6NH_2$ is a hexylamine linker; and idT is a deoxythymidine residue. |
| Aptamer 184 | RNA | UGAUCACGGUAGAUUACGG GUAGAGUGACCGGAUCU (SEQ ID NO: 348) | $C6NH_2$-UGAUCACGGUAGAUUACGGGUAG AGUGACCGGAUCU-idT (SEQ ID NO: 495), where G is 2'F; A, C, and U are 2'OMe modified RNA; $C6NH_2$ is a hexylamine linker; and idT is a deoxythymidine residue. |
| Aptamer 185 | RNA | UGAUGACAGUAGAUUACGG GUAGAGUGACUGCAUCU (SEQ ID NO: 349) | $C6NH_2$-UGAUGACAGUAGAUUACGGGUA GAGUGACUGCAUCU-idT (SEQ ID NO: 496), where G is 2'F; A, C, and U are 2'OMe modified RNA; $C6NH_2$ is a hexylamine linker; and idT is a deoxythymidine residue. |
| Aptamer 186 | RNA | UGAUGACGAUAGAUUACGG GUAGAGUGAUCGCAUCU (SEQ ID NO: 350) | $C6NH_2$-UGAUGACGAUAGAUUACGGGUA GAGUGAUCGCAUCU-idT (SEQ ID NO: 497), where G is 2'F; A, C, and U are 2'OMe modified RNA; $C6NH_2$ is a hexylamine linker; and idT is a deoxythymidine residue. |
| Aptamer 187 | RNA | UCUUGACGGUAGAUUACGG GUAGAGUGACCGCAUCU (SEQ ID NO: 351) | $C6NH_2$-UCUUGACGGUAGAUUACGGGUAG AGUGACCGCAUCU-idT (SEQ ID NO: 498), where G is 2'F; A, C, and U are 2'OMe modified RNA; $C6NH_2$ is a hexylamine linker; and idT is a deoxythymidine residue. |
| Aptamer 188 | RNA | UGAUGACCCUAGAUUACGG GUAGAGUGACCGCAUCU (SEQ ID NO: 352) | $C6NH_2$-UGAUGACCCUAGAUUACGGGUAG AGUGACCGCAUCU-idT (SEQ ID NO: 499), where G is 2'F; A, C, and U are 2'OMe modified RNA; $C6NH_2$ is a hexylamine linker; and idT is a deoxythymidine residue. |
| Aptamer 189 | RNA | GAUGACGGUAGAU (SEQ ID NO: 353)-(Sp9)-(Sp9)-GGUAGAGUGACCGCAUC (SEQ ID NO: 354), where Sp9 is a 9-atom PEG spacer. | $C6NH_2$-GAUGACGGUAGAU (SEQ ID NO: 500)-(Sp9)-(Sp9)-GGUAGAGUGACCGCAUC-idT (SEQ ID NO: 501), where G is 2'F; A, C, and U are 2'OMe modified RNA; $C6NH_2$ is a hexylamine linker; idT is a deoxythymidine residue; and Sp9 is a 9-atom PEG spacer. |
| Aptamer 190 | RNA | GAUGACGGUAGAU (SEQ ID NO: 355)-(Sp3)-(Sp9)-GGUAGAGUGACCGCAUC (SEQ ID NO: 356), where Sp3 is a 3-carbon spacer; and Sp9 is a 9-atom PEG spacer. | $C6NH_2$-GAUGACGGUAGAU (SEQ ID NO: 502)-(Sp3)-(Sp9)-GGUAGAGUGACCGCAUC-idT (SEQ ID NO: 503), where G is 2'F; A, C, and U are 2'OMe modified RNA; $C6NH_2$ is a hexylamine linker; idT is a deoxythymidine residue; Sp3 is a 3-carbon spacer; and Sp9 is a 9-atom PEG spacer. |

TABLE 2-continued

| Aptamer 3 Family | | | |
|---|---|---|---|
| Compound Name | Backbone | Primary Sequence (5' to 3') | Modified Sequence (5' to 3') |
| Aptamer 193 | RNA | GGCGACGGUAGAUUUUGGG UAGUGUGACCGCGCC (SEQ ID NO: 357) | $C6NH_2$-GGCGACGGUAGAUUUUGGGUAG UGUGACCGCGCC-idT (SEQ ID NO: 504), where G is 2'F; A, C, and U are 2'OMe modified RNA; $C6NH_2$ is a hexylamine linker; and idT is a deoxythymidine residue. |
| Aptamer 197 | RNA | GGCGACGGUAGAUUUUGGG CAGUGUGACCGCGCC (SEQ ID NO: 358) | $C6NH_2$-GGCGACGGUAGAUUUUGGGCAGU GUGACCGCGCC-idT (SEQ ID NO: 505), where G is 2'F; A, C, and U are 2'OMe modified RNA; $C6NH_2$ is a hexylamine linker; and idT is a deoxythymidine residue. |
| Aptamer 199 | RNA | UGAUGACGGUAGAUUACUG GUAGAGUGACCGCAUCU (SEQ ID NO: 359) | $C6NH_2$-UGAUGACGGUAGAUUACUGGUA GAGUGACCGCAUCU-idT (SEQ ID NO: 506), where G is 2'F; A, C, and U are 2'OMe modified RNA; $C6NH_2$ is a hexylamine linker; and idT is a deoxythymidine residue. |
| Aptamer 200 | RNA | UGAUGACGGUAGAUUACCG GUAGAGUGACCGCAUCU (SEQ ID NO: 360) | $C6NH_2$-UGAUGACGGUAGAUUACCGGUAG AGUGACCGCAUCU-idT (SEQ ID NO: 507), where G is 2'F; A, C, and U are 2'OMe modified RNA; $C6NH_2$ is a hexylamine linker; and idT is a deoxythymidine residue. |
| Aptamer 201 | RNA | UGAUGACGGUAGAUUACAG GUAGAGUGACCGCAUCU-idT (SEQ ID NO: 361) | $C6NH_2$-UGAUGACGGUAGAUUACAGGUA GAGUGACCGCAUCU-idT (SEQ ID NO: 508), where G is 2'F; A, C, and U are 2'OMe modified RNA; $C6NH_2$ is a hexylamine linker; and idT is a deoxythymidine residue. |
| Aptamer 206 | RNA | UGCGGACGGUAGAUUACGG GUAGAGUGACCGCCGCU (SEQ ID NO: 362) | $C6NH_2$-UGCGGACGGUAGAUUACGGGUAG AGUGACCGCCGCU-idT (SEQ ID NO: 509), where G is 2'F; A, C, and U are 2'OMe modified RNA; $C6NH_2$ is a hexylamine linker; and idT is a deoxythymidine residue. |
| Aptamer 207 | RNA | UGGAGACGGUAGAUUACGG GUAGAGUGACCGCUCCU (SEQ ID NO: 363) | $C6NH_2$-UGGAGACGGUAGAUUACGGGUA GAGUGACCGCUCCU-idT (SEQ ID NO: 510), where G is 2'F; A, C, and U are 2'OMe modified RNA; $C6NH_2$ is a hexylamine linker; and idT is a deoxythymidine residue. |
| Aptamer 208 | RNA | UGCCGACGGUAGAUUACGG GUAGAGUGACCGCGGCU (SEQ ID NO: 364) | $C6NH_2$-UGCCGACGGUAGAUUACGGGUAG AGUGACCGCGGCU-idT (SEQ ID NO: 511), where G is 2'F; A, C, and U are 2'OMe modified RNA; $C6NH_2$ is a hexylamine linker; and idT is a deoxythymidine residue. |

TABLE 2-continued

| Aptamer 3 Family | | | |
|---|---|---|---|
| Compound Name | Backbone | Primary Sequence (5' to 3') | Modified Sequence (5' to 3') |
| Aptamer 209 | RNA | UGCUGACGGUAGAUUACGG<br>GUAGAGUGACCGCAGCU<br>(SEQ ID NO: 365) | $C6NH_2$-<br>UGCUGACGGUAGAUUACGGGUAG<br>AGUGACCGCAGCU-idT (SEQ ID<br>NO: 512),<br>where G is 2'F; A, C, and U are 2'OMe modified RNA; $C6NH_2$ is a hexylamine linker; and idT is a deoxythymidine residue. |
| Aptamer 210 | RNA | UGGCGACGGUAGAUUACGG<br>GUAGAGUGACCGCGCCU<br>(SEQ ID NO: 366) | $C6NH_2$-<br>UGGCGACGGUAGAUUACGGGUAG<br>AGUGACCGCGCCU-idT (SEQ ID<br>NO: 513),<br>where G is 2'F; A, C, and U are 2'OMe modified RNA; $C6NH_2$ is a hexylamine linker; and idT is a deoxythymidine residue. |
| Aptamer 221 | RNA | GGCGACGGUAGAUUAUGGG<br>CAGUGUGACCGCGCC (SEQ<br>ID NO: 367) | $C6NH_2$-<br>**G**GCGACGGUAGAUUAUGGGCAG<br>UGUGACCGCGCC-idT (SEQ ID NO:<br>514),<br>where G is 2'F; A, C, U, and **G** (bolded, underlined) are 2'OMe modified RNA; $C6NH_2$ is a hexylamine linker; and idT is a deoxythymidine residue. |
| Aptamer 222 | RNA | GGCGACGGUAGAUUAUGGG<br>CAGUGUGACCGCGCC (SEQ<br>ID NO: 368) | $C6NH_2$-<br>G**G**CGACGGUAGAUUAUGGGCAG<br>UGUGACCGCGCC-idT (SEQ ID NO:<br>515),<br>where G is 2'F; A, C, U, and **G** (bolded, underlined) are 2'OMe modified RNA; $C6NH_2$ is a hexylamine linker; and idT is a deoxythymidine residue. |
| Aptamer 223 | RNA | GGCGACGGUAGAUUAUGGG<br>CAGUGUGACCGCGCC (SEQ<br>ID NO: 369) | $C6NH_2$-<br>GGC**G**ACGGUAGAUUAUGGGCAG<br>UGUGACCGCGCC-idT (SEQ ID NO:<br>516),<br>where G is 2'F; A, C, U, and **G** (bolded, underlined) are 2'OMe modified RNA; $C6NH_2$ is a hexylamine linker; and idT is a deoxythymidine residue. |
| Aptamer 224 | RNA | GGCGACGGUAGAUUAUGGG<br>CAGUGUGACCGCGCC (SEQ<br>ID NO: 370) | $C6NH_2$-<br>GGCGACGGUAGAUUAUGGGCAGU<br>GUGACCGC**G**CC-idT (SEQ ID NO:<br>517),<br>where G is 2'F; A, C, U, and **G** (bolded, underlined) are 2'OMe modified RNA; $C6NH_2$ is a hexylamine linker; and idT is a deoxythymidine residue. |
| Aptamer 225 | RNA | GGCGACGGUAGAUUAUGGG<br>CAGUGUGACCGCGCC (SEQ<br>ID NO: 371) | $C6NH_2$-<br>**GG**CGACGGUAGAUUAUGGGCAG<br>UGUGACCGC**G**CC-idT (SEQ ID NO:<br>518),<br>where G is 2'F; A, C, U, and **G** (bolded, underlined) are 2'OMe modified RNA; $C6NH_2$ is a hexylamine linker; and idT is a deoxythymidine residue. |
| Aptamer 226 | RNA | GGCGACGGUAGAUUAUGGG<br>CAGUGUGACCGCGCC (SEQ<br>ID NO: 372) | $C6NH_2$-<br>**GG**C**G**ACGGUAGAUUAUGGGCAG<br>UGUGACCGC**G**CC-idT (SEQ ID NO:<br>519),<br>where G is 2'F; A, C, U, and **G** (bolded, underlined) are 2'OMe modified RNA; $C6NH_2$ is a hexylamine linker; and idT is a deoxythymidine residue. |

TABLE 2-continued

| Aptamer 3 Family | | | |
|---|---|---|---|
| Compound Name | Backbone | Primary Sequence (5' to 3') | Modified Sequence (5' to 3') |
| Aptamer 227 | RNA | GGCGACGGUAGAUUAUGGG CAGUGUGACCGCGCC (SEQ ID NO: 373) | C6NH$_2$-GGCGAC**G**GUAGAUUAUGGGCAG UGUGACCGCGCC-idT (SEQ ID NO: 520), where G is 2'F; A, C, U, and **G** (bolded, underlined) are 2'OMe modified RNA; C6NH$_2$ is a hexylamine linker; and idT is a deoxythymidine residue. |
| Aptamer 228 | RNA | GGCGACGGUAGAUUAUGGG CAGUGUGACCGCGCC (SEQ ID NO: 374) | C6NH$_2$-GGCGACG**G**UAGAUUAUGGGCAG UGUGACCGCGCC-idT (SEQ ID NO: 521), where G is 2'F; A, C, U, and **G** (bolded, underlined) are 2'OMe modified RNA; C6NH$_2$ is a hexylamine linker; and idT is a deoxythymidine residue. |
| Aptamer 229 | RNA | GGCGACGGUAGAUUAUGGG CAGUGUGACCGCGCC (SEQ ID NO: 375) | C6NH$_2$-GGCGACGGUAGAUUAUGGGCAGU GUGACC**G**CGCC-idT (SEQ ID NO: 522), where G is 2'F; A, C, U, and **G** (bolded, underlined) are 2'OMe modified RNA; C6NH$_2$ is a hexylamine linker; and idT is a deoxythymidine residue. |
| Aptamer 230 | RNA | GGCGACGGUAGAUUAUGGG CAGUGUGACCGCGCC (SEQ ID NO: 376) | C6NH$_2$-GGCGAC**GG**UAGAUUAUGGGCAG UGUGACCGCGCC-idT (SEQ ID NO: 523), where G is 2'F; A, C, U, and **G** (bolded, underlined) are 2'OMe modified RNA; C6NH$_2$ is a hexylamine linker; and idT is a deoxythymidine residue. |
| Aptamer 231 | RNA | GGCGACGGUAGAUUAUGGG CAGUGUGACCGCGCC (SEQ ID NO: 377) | C6NH$_2$-GGCGAC**GG**UAGAUUAUGGGCAG UGUGACC**G**CGCC-idT (SEQ ID NO: 524), where G is 2'F; A, C, U, and **G** (bolded, underlined) are 2'OMe modified RNA; C6NH$_2$ is a hexylamine linker; and idT is a deoxythymidine residue. |
| Aptamer 232 | RNA | GGCGACGGUAGAUUAUGGG CAGUGUGACCGCGCC (SEQ ID NO: 378) | C6NH$_2$-GGCGACGGUA**G**AUUAUGGGCAG UGUGACCGCGCC-idT (SEQ ID NO: 525) where G is 2'F; A, C, U, and **G** (bolded, underlined) are 2'OMe modified RNA; C6NH$_2$ is a hexylamine linker; and idT is a deoxythymidine residue. |
| Aptamer 233 | RNA | GGCGACGGUAGAUUAUGGG CAGUGUGACCGCGCC (SEQ ID NO: 379), | C6NH$_2$-GGCGACGGUAGAUUAU**G**GGCAG UGUGACCGCGCC-idT (SEQ ID NO: 526), where G is 2'F; A, C, U, and **G** (bolded, underlined) are 2'OMe modified RNA; C6NH$_2$ is a hexylamine linker; and idT is a deoxythymidine residue. |
| Aptamer 234 | RNA | GGCGACGGUAGAUUAUGGG CAGUGUGACCGCGCC (SEQ ID NO: 380) | C6NH$_2$-GGCGACGGUAGAUUAUG**G**GCAG UGUGACCGCGCC-idT (SEQ ID NO: 527), where G is 2'F; A, C, U, and **G** (bolded, underlined) are 2'OMe modified RNA; C6NH$_2$ is a hexylamine linker; and idT is a deoxythymidine residue. |

TABLE 2-continued

| Aptamer 3 Family | | | |
|---|---|---|---|
| Compound Name | Backbone | Primary Sequence (5' to 3') | Modified Sequence (5' to 3') |
| Aptamer 235 | RNA | GGCGACGGUAGAUUAUGGG CAGUGUGACCGCGCC (SEQ ID NO: 381) | $C6NH_2$-<br>GGCGACGGUAGAUUAUGG**G**CAG<br>UGUGACCGCGCC-idT (SEQ ID NO: 528),<br>where G is 2'F; A, C, U, and **G** (bolded, underlined) are 2'OMe modified RNA; $C6NH_2$ is a hexylamine linker; and idT is a deoxythymidine residue. |
| Aptamer 236 | RNA | GGCGACGGUAGAUUAUGGG CAGUGUGACCGCGCC (SEQ ID NO: 382) | $C6NH_2$-<br>GGCGACGGUAGAUUAUGGGCA**G**<br>UGUGACCGCGCC-idT (SEQ ID NO: 529),<br>where G is 2'F; A, C, U, and **G** (bolded, underlined) are 2'OMe modified RNA; $C6NH_2$ is a hexylamine linker; and idT is a deoxythymidine residue. |
| Aptamer 237 | RNA | GGCGACGGUAGAUUAUGGG CAGUGUGACCGCGCC (SEQ ID NO: 383) | $C6NH_2$-<br>GGCGACGGUAGAUUAU**GGG**CA**G**<br>UGUGACCGCGCC-idT (SEQ ID NO: 530),<br>where G is 2'F; A, C, U, and **G** (bolded, underlined) are 2'OMe modified RNA; $C6NH_2$ is a hexylamine linker; and idT is a deoxythymidine residue. |
| Aptamer 238 | RNA | GGCGACGGUAGAUUAUGGG CAGUGUGACCGCGCC (SEQ ID NO: 384) | $C6NH_2$-<br>GGCGACGGUAGAUUAUGGGCAGU<br>**G**UGACCGCGCC-idT (SEQ ID NO: 531),<br>where G is 2'F; A, C, U, and **G** (bolded, underlined) are 2'OMe modified RNA; $C6NH_2$ is a hexylamine linker; and idT is a deoxythymidine residue. |
| Aptamer 239 | RNA | GGCGACGGUAGAUUAUGGG CAGUGUGACCGCGCC (SEQ ID NO: 385) | $C6NH_2$-<br>GGCGACGGUAGAUUAUGGGCAGU<br>GU**G**ACCGCGCC-idT (SEQ ID NO: 532),<br>where G is 2'F; A, C, U, and **G** (bolded, underlined) are 2'OMe modified RNA; $C6NH_2$ is a hexylamine linker; and idT is a deoxythymidine residue. |
| Aptamer 240 | RNA | GGCGACGGUAGAUUAUGGG CAGUGUGACCGCGCC (SEQ ID NO: 386) | $C6NH_2$-<br>**GG**CGAC**GG**UAGAUUAUGGGCAG<br>UGUGACCGC**G**CC-idT (SEQ ID NO: 533),<br>where G is 2'F; A, C, U, and **G** (bolded, underlined) are 2'OMe modified RNA; $C6NH_2$ is a hexylamine linker; and idT is a deoxythymidine residue. |
| Aptamer 241 | RNA | GGCGACGGUAGAUUAUGGG CAGUGUGACCGCGCC (SEQ ID NO: 387) | $C6NH_2$-<br>**GG**C**G**AC**GG**UAGAUUAUGGGCAG<br>UGUGACC**G**C**G**CC-idT (SEQ ID NO: 534),<br>where G is 2'F; A, C, U, and **G** (bolded, underlined) are 2'OMe modified RNA; $C6NH_2$ is a hexylamine linker; and idT is a deoxythymidine residue. |
| Aptamer 269 | RNA | GGCGACGGUAGAUUAUGGG CAGUGUGACCGCGCC (SEQ ID NO: 388) | $C6NH_2$-<br>**GG**C**G**AC**GG**UA**G**AUUAUGGGCAG<br>UGUGACC**G**C**G**CC-idT (SEQ ID NO: 535),<br>where G is 2'F; A, C, U, and **G** (bolded, underlined) are 2'OMe modified RNA; $C6NH_2$ is a hexylamine linker; and idT is a deoxythymidine residue. |

TABLE 2-continued

| Aptamer 3 Family | | | |
|---|---|---|---|
| Compound Name | Backbone | Primary Sequence (5' to 3') | Modified Sequence (5' to 3') |
| Aptamer 270 | RNA | GGCGACGGUAGAUUAUGGGCAGUGUGACCGCGCC (SEQ ID NO: 389) | C6NH$_2$-GGCGACGGUAGAUUAUGGGCAGUGUGACCGCGCC-idT (SEQ ID NO: 536), where G is 2'F; A, C, U, and G (bolded, underlined) are 2'OMe modified RNA; C6NH$_2$ is a hexylamine linker; and idT is a deoxythymidine residue. |
| Aptamer 271 | RNA | GGCGACGGUAGAUUAUGGGCAGUGUGACCGCGCC (SEQ ID NO: 390) | C6NH$_2$-GGCGACGGUAGAUUAUGGGCAGUGUGACCGCGCC-idT (SEQ ID NO: 537), where G is 2'F; A, C, U, and G (bolded, underlined) are 2'OMe modified RNA; C6NH$_2$ is a hexylamine linker; and idT is a deoxythymidine residue. |
| Aptamer 272 | RNA | GCGACGGUAGAUUAUGGGCAGUGUGACCGCGC (SEQ ID NO: 391) | C6NH$_2$-GCGACGGUAGAUUAUGGGCAGUGUGACCGCGC-idT (SEQ ID NO: 538), where G is 2'F; A, C, U, and G (bolded, underlined) are 2'OMe modified RNA; C6NH$_2$ is a hexylamine linker; and idT is a deoxythymidine residue. |
| Aptamer 273 | RNA | GCGACGGUAGAUUAUGGGCAGUGUGACCGCGC (SEQ ID NO: 392) | C6NH$_2$-GCGACGGUAGAUUAUGGGCAGUGUGACCGCGC-idT (SEQ ID NO: 539), where G is 2'F; A, C, U, and G (bolded, underlined) are 2'OMe modified RNA; C6NH$_2$ is a hexylamine linker; and idT is a deoxythymidine residue. |
| Aptamer 274 | RNA | GGCGACGGUAGAUUUCGGGUAGUGUGACCGCGCC (SEQ ID NO: 393) | C6NH$_2$-GGCGACGGUAGAUUUCGGGUAGUGUGACCGCGCC-idT (SEQ ID NO: 540), where G is 2'F; A, C, U, and G (bolded, underlined) are 2'OMe modified RNA; C6NH$_2$ is a hexylamine linker; and idT is a deoxythymidine residue. |
| Aptamer 275 | RNA | GGCGACGGUAGAUUUCGGGUAGUGUGACCGCGCC (SEQ ID NO: 394) | C6NH$_2$-GGCGACGGUAGAUUUCGGGUAGUGUGACCGCGCC-idT (SEQ ID NO: 541), where G is 2'F; A, C, U, and G (bolded, underlined) are 2'OMe modified RNA; C6NH$_2$ is a hexylamine linker; and idT is a deoxythymidine residue. |
| Aptamer 276 | RNA | GGCGACGGUAGAUUUCGGGUAGUGUGACCGCGCC (SEQ ID NO: 395) | C6NH$_2$-GGCGACGGUAGAUUUCGGGUAGUGUGACCGCGCC-idT (SEQ ID NO: 542), where G is 2'F; A, C, U, and G (bolded, underlined) are 2'OMe modified RNA; C6NH$_2$ is a hexylamine linker; and idT is a deoxythymidine residue. |
| Aptamer 277 | RNA | GGCGACGGUAGAUUUCGGGUAGUGUGACCGCGCC (SEQ ID NO: 396) | C6NH$_2$-GGCGACGGUAGAUUUCGGGUAGUGUGACCGCGCC-idT (SEQ ID NO: 543), where G is 2'F; A, C, U, and G (bolded, underlined) are 2'OMe modified RNA; C6NH$_2$ is a hexylamine linker; and idT is a deoxythymidine residue. |

TABLE 2-continued

| Aptamer 3 Family | | | |
|---|---|---|---|
| Compound Name | Backbone | Primary Sequence (5' to 3') | Modified Sequence (5' to 3') |
| Aptamer 278 | RNA | GCGACGGUAGAUUUCGGGU AGUGUGACCGCGC (SEQ ID NO: 397) | C6NH$_2$-**G**C**G**AC**GG**UA**G**AUUUCGGGUA**G**U GU**G**ACC**G**C**G**C-idT (SEQ ID NO: 544), where G is 2'F; A, C, U, and G (bolded, underlined) are 2'OMe modified RNA; C6NH$_2$ is a hexylamine linker; and idT is a deoxythymidine residue. |
| Aptamer 279 | RNA | GCGACGGUAGAUUUCGGGU AGUGUGACCGCGC (SEQ ID NO: 398) | C6NH$_2$-**G**C**G**AC**GG**UA**G**AUUUCGGGUAGU GUGACC**G**C**G**C-idT (SEQ ID NO: 545), where G is 2'F; A, C, U, and G (bolded, underlined) are 2'OMe modified RNA; C6NH$_2$ is a hexylamine linker; and idT is a deoxythymidine residue. |

TABLE 3

| Aptamer 8 Family | | | |
|---|---|---|---|
| Compound Name | Backbone | Primary Sequence (5' to 3') | Modified Sequence (5' to 3') |
| R6-34 truncated | RNA | UAAUCGCUGGGAAAUGGGAG AUGGGUUGGCGAUUAU (SEQ ID NO: 546) | UAAUCGCUGGGAAAUGGGAGAUGGGUU GGCGAUUAU (SEQ ID NO: 546), where G is 2'F; and A, C, & U are 2'OMe modified RNA. |
| R6-35 truncated | RNA | UGGGCAUGGGAAAUGUGAGA UGGGUUGUGCUCAAGU (SEQ ID NO: 547) | UGGGCAUGGGAAAUGUGAGAUGGGUUG UGCUCAAGU (SEQ ID NO: 547), where G is 2'F; and A, C, & U are 2'OMe modified RNA. |
| R6-39 truncated | RNA | UGAUAGCAAGUGGGAAAUGU GAGAUGGGUUACUUGU (SEQ ID NO: 548) | UGAUAGCAAGUGGGAAAUGUGAGAUGG GUUACUUGU (SEQ ID NO: 548), where G is 2'F; and A, C, & U are 2'OMe modified RNA. |
| R6-50 truncated | RNA | UAGUCACGGGAAAAGUGAGA UGGGUGUGACGUGUUU (SEQ ID NO: 549) | UAGUCACGGGAAAAGUGAGAUGGGUGU GACGUGUUU (SEQ ID NO: 549), where G is 2'F; and A, C, & U are 2'OMe modified RNA. |
| R6-98 truncated | RNA | UAAUCACCGGUGGGAAAUGU GAGAAGGGUGGCCGGU (SEQ ID NO: 550) | UAAUCACCGGUGGGAAAUGUGAGAAGG GUGGCCGGU (SEQ ID NO: 550), where G is 2'F; and A, C, & U are 2'OMe modified RNA. |
| R6-103 truncated | RNA | UACGGUGGGAAAUGUGAGAU GGGUUGCCGTATTTTT (SEQ ID NO: 551) | UACGGUGGGAAAUGUGAGAUGGGUUGC CGTATTTTT (SEQ ID NO: 551), where G is 2'F; and A, C, & U are 2'OMe modified RNA. |
| R6-170 truncated | RNA | UUGUGCCAUGGGAAAUGUGA GAUGGGUUAUGUCACU (SEQ ID NO: 552) | UUGUGCCAUGGGAAAUGUGAGAUGGGU UAUGUCACU (SEQ ID NO: 552), where G is 2'F; and A, C, & U are 2'OMe modified RNA. |
| R6-183 truncated | RNA | UGACCGGGAAAUGUGAGAUG GGUGGUCAGCAUAAAU (SEQ ID NO: 553) | UGACCGGGAAAUGUGAGAUGGGUGGUC AGCAUAAAU (SEQ ID NO: 553), where G is 2'F; and A, C, & U are 2'OMe modified RNA. |
| R6-209 truncated | RNA | UAAUUAGCUGCGGGAAAUGG GAGAUGGGUUGCGGCU (SEQ ID NO: 554) | UAAUUAGCUGCGGGAAAUGGGAGAUGG GUUGCGGCU (SEQ ID NO: 554), where G is 2'F; and A, C, & U are 2'OMe modified RNA. |

TABLE 3-continued

| Aptamer 8 Family | | | |
|---|---|---|---|
| Compound Name | Backbone | Primary Sequence (5' to 3') | Modified Sequence (5' to 3') |
| R6-311 truncated | RNA | UACGGUGGGAUAUGUGAGAU GGGUUGCCGUAUUUU (SEQ ID NO: 555) | UACGGUGGGAUAUGUGAGAUGGGUUGC CGUAUUUU (SEQ ID NO: 555), where G is 2'F; and A, C, & U are 2'OMe modified RNA. |
| R6-313 truncated | RNA | UAACAUACGGGAAACGUGAG AAGGGUGUAUGUUAUU (SEQ ID NO: 556) | UAACAUACGGGAAACGUGAGAAGGGUG UAUGUUAUU (SEQ ID NO: 556), where G is 2'F; and A, C, & U are 2'OMe modified RNA. |
| R6-317 truncated | RNA | UACGGUGGGAAAUGUGAGAU GGGUUGCCGUUUUUU (SEQ ID NO: 557) | UACGGUGGGAAAUGUGAGAUGGGUUGC CGUUUUUU (SEQ ID NO: 557), where G is 2'F; and A, C, & U are 2'OMe modified RNA. |
| R6-320 truncated | RNA | UUUGAGAGCAGCGGGAAAUG UGAGAUGGGUGUUGCU (SEQ ID NO: 558) | UUUGAGAGCAGCGGGAAAUGUGAGAUG GGUGUUGCU (SEQ ID NO: 558), where G is 2'F; and A, C, & U are 2'OMe modified RNA. |
| R6-345 truncated | RNA | UACGGUGGGAAAUGUGAGAU GGGUUGCCGUAUUUC (SEQ ID NO: 559) | UACGGUGGGAAAUGUGAGAUGGGUUGC CGUAUUUC (SEQ ID NO: 559), where G is 2'F; and A, C, & U are 2'OMe modified RNA. |
| R6-399 truncated | RNA | UACGGUGGGAAAUGCGAGAU GGGUUGCCGUAUUUU (SEQ ID NO: 560) | UACGGUGGGAAAUGCGAGAUGGGUUGC CGUAUUUU (SEQ ID NO: 560), where G is 2'F; and A, C, & U are 2'OMe modified RNA. |
| R6-439 truncated | RNA | UACGGCGGGAAAUGUGAGAU GGGUUGCCGUAUUUU (SEQ ID NO: 561) | UACGGCGGGAAAUGUGAGAUGGGUUGC CGUAUUUU (SEQ ID NO: 561), where G is 2'F; and A, C, & U are 2'OMe modified RNA. |
| R6-471 truncated | RNA | UUGGCCUGGGAAAUGUGAGA AGGGUUAGGCUAUUAU (SEQ ID NO: 562) | UUGGCCUGGGAAAUGUGAGAAGGGUUA GGCUAUUAU (SEQ ID NO: 562), where G is 2'F; and A, C, & U are 2'OMe modified RNA. |
| R6-483 truncated | RNA | UACGGUGGGAAAUGUGAGAU GGGUUGCCGUAUUCU (SEQ ID NO: 563) | UACGGUGGGAAAUGUGAGAUGGGUUGC CGUAUUCU (SEQ ID NO: 563), where G is 2'F; and A, C, & U are 2'OMe modified RNA. |
| R6-502 truncated | RNA | UCGUUUCGGGAAAUGUGAGA UGGGUGAAGCGAUAAU (SEQ ID NO: 564) | UCGUUUCGGGAAAUGUGAGAUGGGUGA AGCGAUAAU (SEQ ID NO: 564), where G is 2'F; and A, C, & U are 2'OMe modified RNA. |
| R6-503 truncated | RNA | UACGGUGGGAAAUGUGAGGU GGGUUGCCGUAUUUU (SEQ ID NO: 565) | UACGGUGGGAAAUGUGAGGUGGGUUGC CGUAUUUU (SEQ ID NO: 565), where G is 2'F; and A, C, & U are 2'OMe modified RNA. |
| R6-505 truncated | RNA | UACGGUGGGAAACGUGAGAU GGGUUGCCGUAUUUU (SEQ ID NO: 566) | UACGGUGGGAAACGUGAGAUGGGUUGC CGUAUUUU (SEQ ID NO: 566), where G is 2'F; and A, C, & U are 2'OMe modified RNA. |
| R6-530 truncated | RNA | UCUUUGGGUGGGAAAUGUGA GACGGGUUGCCCAAAU (SEQ ID NO: 567) | UCUUUGGGUGGGAAAUGUGAGACGGGU UGCCCAAAU (SEQ ID NO: 567), where G is 2'F; and A, C, & U are 2'OMe modified RNA. |
| R6-539 truncated | RNA | UUCGGUGGGAAAUGUGAGAU GGGUUGCCGUAUUUU (SEQ ID NO: 568) | UUCGGUGGGAAAUGUGAGAUGGGUUGC CGUAUUUU (SEQ ID NO: 568), where G is 2'F; and A, C, & U are 2'OMe modified RNA. |
| R6-541 truncated | RNA | UACGGUGGGAAAUGUGGGAU GGGUUGCCGUAUUUU (SEQ ID NO: 569) | UACGGUGGGAAAUGUGGGAUGGGUUGC CGUAUUUU (SEQ ID NO: 569), where G is 2'F; and A, C, & U are 2'OMe modified RNA. |

TABLE 3-continued

| Aptamer 8 Family | | | |
|---|---|---|---|
| Compound Name | Backbone | Primary Sequence (5' to 3') | Modified Sequence (5' to 3') |
| R6-558 truncated | RNA | UACGGUGGGAAUUGUGAGAU GGGUUGCCGUAUUUU (SEQ ID NO: 570) | UACGGUGGGAAUUGUGAGAUGGGUUGC CGUAUUUU (SEQ ID NO: 570), where G is 2'F; and A, C, & U are 2'OMe modified RNA. |
| R6-562 truncated | RNA | UACGGUGGGAAAUGUGUGAU GGGUUGCCGUAUUUU (SEQ ID NO: 571) | UACGGUGGGAAAUGUGUGAUGGGUUGC CGUAUUUU (SEQ ID NO: 571), where G is 2'F; and A, C, & U are 2'OMe modified RNA. |
| R6-571 truncated | RNA | UGCGGUGGGAAAUGUGAGAU GGGUUGCCGUAUUUU (SEQ ID NO: 572) | UGCGGUGGGAAAUGUGAGAUGGGUUGC CGUAUUUU (SEQ ID NO: 572), where G is 2'F; and A, C, & U are 2'OMe modified RNA. |
| R6-576 truncated | RNA | UACGGUGGGAAAUGUGAGAU GGGUUGCCGUAUUUUUU (SEQ ID NO: 573) | UACGGUGGGAAAUGUGAGAUGGGUUGC CGUAUUUUUU (SEQ ID NO: 573), where G is 2'F; and A, C, & U are 2'OMe modified RNA. |
| R6-579 truncated | RNA | UACGGUGGGAAAUGUGAGAU GGGUUGCCGUAUUUG (SEQ ID NO: 574) | UACGGUGGGAAAUGUGAGAUGGGUUGC CGUAUUUG (SEQ ID NO: 574), where G is 2'F; and A, C, & U are 2'OMe modified RNA. |
| R6-601 truncated | RNA | UACGGUGGGAAAGGUGAGAU GGGUUGCCGUAUUUU (SEQ ID NO: 575) | UACGGUGGGAAAGGUGAGAUGGGUUGC CGUAUUUU (SEQ ID NO: 575), where G is 2'F; and A, C, & U are 2'OMe modified RNA. |
| R6-602 truncated | RNA | UACGGUGGGAAAUGGGAGAU GGGUUGCCGUAUUUU (SEQ ID NO: 576) | UACGGUGGGAAAUGGGAGAUGGGUUGC CGUAUUUU (SEQ ID NO: 576), where G is 2'F; and A, C, & U are 2'OMe modified RNA. |
| R6-636 truncated | RNA | UACGGUGGGAAAUGUGAGAU GGGUUGCCGUAUUAU (SEQ ID NO: 577) | UACGGUGGGAAAUGUGAGAUGGGUUGC CGUAUUAU (SEQ ID NO: 577), where G is 2'F; and A, C, & U are 2'OMe modified RNA. |
| R6-640 truncated | RNA | UACGGGGGGAAAUGUGAGAU GGGUUGCCGUAUUUU (SEQ ID NO: 578) | UACGGGGGGAAAUGUGAGAUGGGUUGC CGUAUUUU (SEQ ID NO: 578), where G is 2'F; and A, C, & U are 2'OMe modified RNA. |
| R6-646 truncated | RNA | UUCCAGCGGGAAAUGUGAGA UGGGUUGCUGGGUCUA (SEQ ID NO: 579) | UUCCAGCGGGAAAUGUGAGAUGGGUUG CUGGGUCUA (SEQ ID NO: 579), where G is 2'F; and A, C, & U are 2'OMe modified RNA. |
| R6-654 truncated | RNA | UGAGCAUGGGAAAUGUGAGA UGGGUUGUGCUCAAGU (SEQ ID NO: 580) | UGAGCAUGGGAAAUGUGAGAUGGGUUG UGCUCAAGU (SEQ ID NO: 580), where G is 2'F; and A, C, & U are 2'OMe modified RNA. |
| R6-661 truncated | RNA | UAUGGUGGGAAAUGUGAGAU GGGUUGCCGUAUUUU (SEQ ID NO: 581) | UAUGGUGGGAAAUGUGAGAUGGGUUGC CGUAUUUU (SEQ ID NO: 581), where G is 2'F; and A, C, & U are 2'OMe modified RNA. |
| R6-666 truncated | RNA | UACGGUGGGAAAUGUGAGAU GGGUUGCCGUAUCUU (SEQ ID NO: 582) | UACGGUGGGAAAUGUGAGAUGGGUUGC CGUAUCUU (SEQ ID NO: 582), where G is 2'F; and A, C, & U are 2'OMe modified RNA. |
| R6-682 truncated | RNA | UACGGUGGGAAAUGUGAGAU GGGUUGCCGUAUUGU (SEQ ID NO: 583) | UACGGUGGGAAAUGUGAGAUGGGUUGC CGUAUUGU (SEQ ID NO: 583), where G is 2'F; and A, C, & U are 2'OMe modified RNA. |
| R6-695 truncated | RNA | UACGGUGGGAAAUGUGAGAU GGGUUGCCGUACUUU (SEQ ID NO: 584) | UACGGUGGGAAAUGUGAGAUGGGUUGC CGUACUUU (SEQ ID NO: 584), where G is 2'F; and A, C, & U are 2'OMe modified RNA. |

TABLE 3-continued

| Aptamer 8 Family | | | |
|---|---|---|---|
| Compound Name | Backbone | Primary Sequence (5' to 3') | Modified Sequence (5' to 3') |
| R6-703 truncated | RNA | UACGGUGGGAAAUGUGAGUU GGGUUGCCGUAUUUU (SEQ ID NO: 585) | UACGGUGGGAAAUGUGAGUUGGGUUGC CGUAUUUU (SEQ ID NO: 585), where G is 2'F; and A, C, & U are 2'OMe modified RNA. |
| R6-706 truncated | RNA | UACGAUGGGAAAUGUGAGAU GGGUUGCCGUAUUUU (SEQ ID NO: 586) | UACGAUGGGAAAUGUGAGAUGGGUUGC CGUAUUUU (SEQ ID NO: 586), where G is 2'F; and A, C, & U are 2'OMe modified RNA. |
| R6-707 truncated | RNA | UUUCGUUCGGCGGGAAAAGU GAGAUGGGUGCCGAUU (SEQ ID NO: 587) | UUUCGUUCGGCGGGAAAAGUGAGAUGG GUGCCGAUU (SEQ ID NO: 587), where G is 2'F; and A, C, & U are 2'OMe modified RNA. |
| R6-710 truncated | RNA | UACGGUGGGGAAUGUGAGAU GGGUUGCCGUAUUUU (SEQ ID NO: 588) | UACGGUGGGGAAUGUGAGAUGGGUUGC CGUAUUUU (SEQ ID NO: 588), where G is 2'F; and A, C, & U are 2'OMe modified RNA. |
| R6-749 truncated | RNA | UACGGUGGGAAGUGUGAGAU GGGUUGCCGUAUUUU (SEQ ID NO: 589) | UACGGUGGGAAGUGUGAGAUGGGUUGC CGUAUUUU (SEQ ID NO: 589), where G is 2'F; and A, C, & U are 2'OMe modified RNA. |
| R6-788 truncated | RNA | UACGGUGGGUAAUGUGAGAU GGGUUGCCGUAUUUU (SEQ ID NO: 590) | UACGGUGGGUAAUGUGAGAUGGGUUGC CGUAUUUU (SEQ ID NO: 590), where G is 2'F; and A, C, & U are 2'OMe modified RNA. |
| R6-793 truncated | RNA | UACAGUGGGAAAUGUGAGAU GGGUUGCCGUAUUUU (SEQ ID NO: 591) | UACAGUGGGAAAUGUGAGAUGGGUUGC CGUAUUUU (SEQ ID NO: 591), where G is 2'F; and A, C, & U are 2'OMe modified RNA. |
| R6-803 truncated | RNA | UGCCCGGGAAAUGUGAGAUG GGUUGGGCAAAUCAUU (SEQ ID NO: 592) | UGCCCGGGAAAUGUGAGAUGGGUUGGG CAAAUCAUU (SEQ ID NO: 592), where G is 2'F; and A, C, & U are 2'OMe modified RNA. |
| R6-815 truncated | RNA | UACGGUGGGAAAUGUGAGAU GGGUUGCCGUGUUUU (SEQ ID NO: 593) | UACGGUGGGAAAUGUGAGAUGGGUUGC CGUGUUUU (SEQ ID NO: 593), where G is 2'F; and A, C, & U are 2'OMe modified RNA. |
| R6-825 truncated | RNA | UACGGUGGGAAAUGUGAGAG GGGUUGCCGUAUUUU (SEQ ID NO: 594) | UACGGUGGGAAAUGUGAGAGGGGUUGC CGUAUUUU (SEQ ID NO: 594), where G is 2'F; and A, C, & U are 2'OMe modified RNA. |
| R6-866 truncated | RNA | UACGGUGGGAGAUGUGAGAU GGGUUGCCGUAUUUU (SEQ ID NO: 595) | UACGGUGGGAGAUGUGAGAUGGGUUGC CGUAUUUU (SEQ ID NO: 595), where G is 2'F; and A, C, & U are 2'OMe modified RNA. |
| R6-877 truncated | RNA | UGGGCAUGGGAAAUGUGAGA UGGGUUGUGCUCAUGU (SEQ ID NO: 596) | UGGGCAUGGGAAAUGUGAGAUGGGUUG UGCUCAUGU (SEQ ID NO: 596), where G is 2'F; and A, C, & U are 2'OMe modified RNA. |
| R6-907 truncated | RNA | UACGGUGGGAAAUGUGAGAC GGGUUGCCGUAUUUU (SEQ ID NO: 597) | UACGGUGGGAAAUGUGAGACGGGUUGC CGUAUUUU (SEQ ID NO: 597), where G is 2'F; and A, C, & U are 2'OMe modified RNA. |
| R6-929 truncated | RNA | UUUCUUCAAGCGGGAAAUGA GAGAUGGGUGCUUGAU (SEQ ID NO: 598) | UUUCUUCAAGCGGGAAAUGAGAGAUGG GUGCUUGAU (SEQ ID NO: 598), where G is 2'F; and A, C, & U are 2'OMe modified RNA. |
| R6-943 truncated | RNA | UACGGUGGGAAAUGUGAGAU GGGUGGCCGUAUUUU (SEQ ID NO: 599) | UACGGUGGGAAAUGUGAGAUGGGUGGC CGUAUUUU (SEQ ID NO: 599), where G is 2'F; and A, C, & U are 2'OMe modified RNA. |

TABLE 3-continued

| Aptamer 8 Family | | | |
|---|---|---|---|
| Compound Name | Backbone | Primary Sequence (5' to 3') | Modified Sequence (5' to 3') |
| R6-957 truncated | RNA | UACGGUGGGAAAUGUGAGAU GGGUUGCCGCAUUUU (SEQ ID NO: 600) | UACGGUGGGAAAUGUGAGAUGGGUUGC CGCAUUUU (SEQ ID NO: 600), where G is 2'F; and A, C, & U are 2'OMe modified RNA. |
| R6-982 truncated | RNA | UACGGUGGGAAAAGUGAGAU GGGUUGCCGUAUUUU (SEQ ID NO: 601) | UACGGUGGGAAAAGUGAGAUGGGUUGC CGUAUUUU (SEQ ID NO: 601), where G is 2'F; and A, C, & U are 2'OMe modified RNA. |
| R6-986 truncated | RNA | UACGGUGGGAAAUGUGAGAU GGGUUGCCAUAUUUU (SEQ ID NO: 602) | UACGGUGGGAAAUGUGAGAUGGGUUGC CAUAUUUU (SEQ ID NO: 602), where G is 2'F; and A, C, & U are 2'OMe modified RNA. |
| Aptamer 32 | RNA | CGGUGGGAAAUGUGAGAUGG GUUGCCG (SEQ ID NO: 603) | $C6NH_2$-CGGUGGGAAAUGUGAGAUGGGUUGCCG-idT (SEQ ID NO: 679), where G is 2'F; and A, C, and U are 2'OMe modified RNA; $C6NH_2$ is a hexylamine linker; and idT is an inverted deoxythymidine residue. |
| Aptamer 54 | RNA | CGGUGGGAAAUGUGAGACGG GUUGCCG (SEQ ID NO: 604) | $C6NH_2$-CGGUGGGAAAUGUGAGACGGGUUGCCG-idT (SEQ ID NO: 680), where G is 2'F; and A, C, and U are 2'OMe modified RNA; $C6NH_2$ is a hexylamine linker; and idT is an inverted deoxythymidine residue. |
| Aptamer 59 | RNA | CGGUGGGAAAUGUGAGAAGG GUUGCCG (SEQ ID NO: 605) | $C6NH_2$-CGGUGGGAAAUGUGAGAAGGGUUGCCG-idT (SEQ ID NO: 681), where G is 2'F; and A, C, and U are 2'OMe modified RNA; $C6NH_2$ is a hexylamine linker; and idT is an inverted deoxythymidine residue. |
| Aptamer 61 | RNA | CGGUGGGAAAAGUGAGAUGG GUUGCCG (SEQ ID NO: 606) | $C6NH_2$-CGGUGGGAAAAGUGAGAUGGGUUGCCG-idT (SEQ ID NO: 682), where G is 2'F; and A, C, and U are 2'OMe modified RNA; $C6NH_2$ is a hexylamine linker; and idT is an inverted deoxythymidine residue. |
| Aptamer 112 | RNA | CGGUGGGAAAUCUGAGAUGG GUUGCCG (SEQ ID NO: 607) | $C6NH_2$-CGGUGGGAAAUCUGAGAUGGGUUGCCG-idT (SEQ ID NO: 683), where G is 2'F; and A, C, and U are 2'OMe modified RNA; $C6NH_2$ is a hexylamine linker; and idT is an inverted deoxythymidine residue. |
| Aptamer 113 | RNA | CGGUGGGAAAUAUGAGAUGG GUUGCCG (SEQ ID NO: 608) | $C6NH_2$-CGGUGGGAAAUAUGAGAUGGGUUGCCG-idT (SEQ ID NO: 684), where G is 2'F; and A, C, and U are 2'OMe modified RNA; $C6NH_2$ is a hexylamine linker; and idT is an inverted deoxythymidine residue. |
| Aptamer 114 | RNA | CGGUGGGAAAUUUGAGAUGG GUUGCCG (SEQ ID NO: 609) | $C6NH_2$-CGGUGGGAAAUUUGAGAUGGGUUGCCG-idT (SEQ ID NO: 685), where G is 2'F; and A, C, and U are 2'OMe modified RNA; $C6NH_2$ is a hexylamine linker; and idT is an inverted deoxythymidine residue. |
| Aptamer 115 | RNA | CGGUGGGAAAUGCGAGAUGG GUUGCCG (SEQ ID NO: 610) | $C6NH_2$-CGGUGGGAAAUGCGAGAUGGGUUGCCG-idT (SEQ ID NO: 686), where G is 2'F; and A, C, and U are 2'OMe modified RNA; $C6NH_2$ is a hexylamine linker; and idT is an inverted deoxythymidine residue. |

TABLE 3-continued

| Aptamer 8 Family | | | |
|---|---|---|---|
| Compound Name | Backbone | Primary Sequence (5' to 3') | Modified Sequence (5' to 3') |
| Aptamer 116 | RNA | CGGUGGGAAACGUGAGAUGG GUUGCCG (SEQ ID NO: 611) | $C6NH_2$-CGGUGGGAAACGUGAGAUGGGUUGCCG-idT (SEQ ID NO: 687), where G is 2'F; and A, C, and U are 2'OMe modified RNA; $C6NH_2$ is a hexylamine linker; and idT is an inverted deoxythymidine residue. |
| Aptamer 117 | RNA | CGGUGGGAAACGCGAGAUGG GUUGCCG (SEQ ID NO: 612) | $C6NH_2$-CGGUGGGAAACGCGAGAUGGGUUGCCG-idT (SEQ ID NO: 688), where G is 2'F; and A, C, and U are 2'OMe modified RNA; $C6NH_2$ is a hexylamine linker; and idT is an inverted deoxythymidine residue. |
| Aptamer 118 | RNA | CGGUGGGACACGCGAGAUGG GUGGCCG (SEQ ID NO: 613) | $C6NH_2$-CGGUGGGACACGCGAGAUGGGUGGCCG-idT (SEQ ID NO: 689), where G is 2'F; and A, C, and U are 2'OMe modified RNA; $C6NH_2$ is a hexylamine linker; and idT is an inverted deoxythymidine residue. |
| Aptamer 119 | RNA | CGGUGGGAAACCUGAGAUGG GUUGCCG (SEQ ID NO: 614) | $C6NH_2$-CGGUGGGAAACCUGAGAUGGGUUGCCG-idT (SEQ ID NO: 690), where G is 2'F; and A, C, and U are 2'OMe modified RNA; $C6NH_2$ is a hexylamine linker; and idT is an inverted deoxythymidine residue. |
| Aptamer 120 | RNA | CGGUGGGAAACCCGAGAUGG GUUGCCG (SEQ ID NO: 615) | $C6NH_2$-CGGUGGGAAACCCGAGAUGGGUUGCCG-idT (SEQ ID NO: 691), where G is 2'F; and A, C, and U are 2'OMe modified RNA; $C6NH_2$ is a hexylamine linker; and idT is an inverted deoxythymidine residue. |
| Aptamer 121 | RNA | CGGUGGGACACCCGAGAUGG GUGGCCG (SEQ ID NO: 616) | $C6NH_2$-CGGUGGGACACCCGAGAUGGGUGGCCG-idT (SEQ ID NO: 692), where G is 2'F; and A, C, and U are 2'OMe modified RNA; $C6NH_2$ is a hexylamine linker; and idT is an inverted deoxythymidine residue. |
| Aptamer 122 | RNA | CGGCGGGAAAUGUGAGAUGG GUUGCCG (SEQ ID NO: 617) | $C6NH_2$-CGGCGGGAAAUGUGAGAUGGGUUGCCG-idT (SEQ ID NO: 693), where G is 2'F; and A, C, and U are 2'OMe modified RNA; $C6NH_2$ is a hexylamine linker; and idT is an inverted deoxythymidine residue. |
| Aptamer 154 | RNA | CGGUGGGAACUGUGAGAUGG GGUGCCG (SEQ ID NO: 618) | $C6NH_2$-CGGUGGGAACUGUGAGAUGGGGUGCCG-idT (SEQ ID NO: 694), where G is 2'F; and A, C, and U are 2'OMe modified RNA; $C6NH_2$ is a hexylamine linker; and idT is an inverted deoxythymidine residue. |
| Aptamer 155 | RNA | CGGUGGGAACCGUGAGAUGG GGUGCCG (SEQ ID NO: 619) | $C6NH_2$-CGGUGGGAACCGUGAGAUGGGGUGCCG-idT (SEQ ID NO: 695), where G is 2'F; and A, C, and U are 2'OMe modified RNA; $C6NH_2$ is a hexylamine linker; and idT is an inverted deoxythymidine residue. |
| Aptamer 156 | RNA | CGGUCGGAAAUGUGAGAUGG GUUGCCG (SEQ ID NO: 620) | $C6NH_2$-CGGUCGGAAAUGUGAGAUGGGUUGCCG-idT (SEQ ID NO: 696), where G is 2'F; and A, C, and U are 2'OMe modified RNA; $C6NH_2$ is a hexylamine linker; and idT is an inverted deoxythymidine residue. |

TABLE 3-continued

| Aptamer 8 Family | | | |
|---|---|---|---|
| Compound Name | Backbone | Primary Sequence (5' to 3') | Modified Sequence (5' to 3') |
| Aptamer 157 | RNA | CGGUAGGAAAUGUGAGAUGG GUUGCCG (SEQ ID NO: 621) | $C6NH_2$-CGGUAGGAAAUGUGAGAUGGGUUGCCG-idT (SEQ ID NO: 697), where G is 2'F; and A, C, and U are 2'OMe modified RNA; $C6NH_2$ is a hexylamine linker; and idT is an inverted deoxythymidine residue. |
| Aptamer 158 | RNA | CGGUUGGAAAUGUGAGAUGG GUUGCCG (SEQ ID NO: 622) | $C6NH_2$-CGGUUGGAAAUGUGAGAUGGGUUGCCG-idT (SEQ ID NO: 698), where G is 2'F; and A, C, and U are 2'OMe modified RNA; $C6NH_2$ is a hexylamine linker; and idT is an inverted deoxythymidine residue. |
| Aptamer 159 | RNA | CGGUGCGAAAUGUGAGAUGG GUUGCCG (SEQ ID NO: 623) | $C6NH_2$-CGGUGCGAAAUGUGAGAUGGGUUGCCG-idT (SEQ ID NO: 699), where G is 2'F; and A, C, and U are 2'OMe modified RNA; $C6NH_2$ is a hexylamine linker; and idT is an inverted deoxythymidine residue. |
| Aptamer 160 | RNA | CGGUGAGAAAUGUGAGAUGG GUUGCCG (SEQ ID NO: 624) | $C6NH_2$-CGGUGAGAAAUGUGAGAUGGGUUGCCG-idT (SEQ ID NO: 700), where G is 2'F; and A, C, and U are 2'OMe modified RNA; $C6NH_2$ is a hexylamine linker; and idT is an inverted deoxythymidine residue. |
| Aptamer 161 | RNA | CGGUGUGAAAUGUGAGAUGG GUUGCCG (SEQ ID NO: 625) | $C6NH_2$-CGGUGUGAAAUGUGAGAUGGGUUGCCG-idT (SEQ ID NO: 701), where G is 2'F; and A, C, and U are 2'OMe modified RNA; $C6NH_2$ is a hexylamine linker; and idT is an inverted deoxythymidine residue. |
| Aptamer 162 | RNA | CGGUGGCAAAUGUGAGAUGG GUUGCCG (SEQ ID NO: 626) | $C6NH_2$-CGGUGGCAAAUGUGAGAUGGGUUGCCG-idT (SEQ ID NO: 702), where G is 2'F; and A, C, and U are 2'OMe modified RNA; $C6NH_2$ is a hexylamine linker; and idT is an inverted deoxythymidine residue. |
| Aptamer 163 | RNA | CGGUGGAAAAUGUGAGAUGG GUUGCCG (SEQ ID NO: 627) | $C6NH_2$-CGGUGGAAAAUGUGAGAUGGGUUGCCG-idT (SEQ ID NO: 703), where G is 2'F; and A, C, and U are 2'OMe modified RNA; $C6NH_2$ is a hexylamine linker; and idT is an inverted deoxythymidine residue. |
| Aptamer 164 | RNA | CGGUGGUAAAUGUGAGAUGG GUUGCCG (SEQ ID NO: 628) | $C6NH_2$-CGGUGGUAAAUGUGAGAUGGGUUGCCG-idT (SEQ ID NO: 704), where G is 2'F; and A, C, and U are 2'OMe modified RNA; $C6NH_2$ is a hexylamine linker; and idT is an inverted deoxythymidine residue. |
| Aptamer 165 | RNA | CGGUGGGCAAUGUGAGAUGG GUUGCCG (SEQ ID NO: 629) | $C6NH_2$-CGGUGGGCAAUGUGAGAUGGGUUGCCG-idT (SEQ ID NO: 705), where G is 2'F; and A, C, and U are 2'OMe modified RNA; $C6NH_2$ is a hexylamine linker; and idT is an inverted deoxythymidine residue. |
| Aptamer 166 | RNA | CGGUGGGGAAUGUGAGAUGG GUUGCCG (SEQ ID NO: 630) | $C6NH_2$-CGGUGGGGAAUGUGAGAUGGGUUGCCG-idT (SEQ ID NO: 706), where G is 2'F; and A, C, and U are 2'OMe modified RNA; $C6NH_2$ is a hexylamine linker; and idT is an inverted deoxythymidine residue. |

TABLE 3-continued

| Aptamer 8 Family | | | |
|---|---|---|---|
| Compound Name | Backbone | Primary Sequence (5' to 3') | Modified Sequence (5' to 3') |
| Aptamer 167 | RNA | CGGUGGGUAAUGUGAGAUGG GUUGCCG (SEQ ID NO: 631) | $C6NH_2$-CGGUGGGUAAUGUGAGAUGGGUUGCCG-idT (SEQ ID NO: 707), where G is 2'F; and A, C, and U are 2'OMe modified RNA; $C6NH_2$ is a hexylamine linker; and idT is an inverted deoxythymidine residue. |
| Aptamer 168 | RNA | CGGUGGGAAAUGUCAGAUGG GUUGCCG (SEQ ID NO: 632) | $C6NH_2$-CGGUGGGAAAUGUCAGAUGGGUUGCCG-idT (SEQ ID NO: 708), where G is 2'F; and A, C, and U are 2'OMe modified RNA; $C6NH_2$ is a hexylamine linker; and idT is an inverted deoxythymidine residue. |
| Aptamer 169 | RNA | CGGUGGGAAAUGUAAGAUGG GUUGCCG (SEQ ID NO: 633) | $C6NH_2$-CGGUGGGAAAUGUAAGAUGGGUUGCCG-idT (SEQ ID NO: 709), where G is 2'F; and A, C, and U are 2'OMe modified RNA; $C6NH_2$ is a hexylamine linker; and idT is an inverted deoxythymidine residue. |
| Aptamer 170 | RNA | CGGUGGGAAAUGUUAGAUGG GUUGCCG (SEQ ID NO: 634) | $C6NH_2$-CGGUGGGAAAUGUUAGAUGGGUUGCCG-idT (SEQ ID NO: 710), where G is 2'F; and A, C, and U are 2'OMe modified RNA; $C6NH_2$ is a hexylamine linker; and idT is an inverted deoxythymidine residue. |
| Aptamer 171 | RNA | CGGUGGGAAAUGUGCGAUGG GUUGCCG (SEQ ID NO: 635) | $C6NH_2$-CGGUGGGAAAUGUGCGAUGGGUUGCCG-idT (SEQ ID NO: 711), where G is 2'F; and A, C, and U are 2'OMe modified RNA; $C6NH_2$ is a hexylamine linker; and idT is an inverted deoxythymidine residue. |
| Aptamer 172 | RNA | CGGUGGGAAAUGUGGGAUGG GUUGCCG (SEQ ID NO: 636) | $C6NH_2$-CGGUGGGAAAUGUGGGAUGGGUUGCCG-idT (SEQ ID NO: 712), where G is 2'F; and A, C, and U are 2'OMe modified RNA; $C6NH_2$ is a hexylamine linker; and idT is an inverted deoxythymidine residue. |
| Aptamer 173 | RNA | CGGUGGGAAAUGUGUGAUGG GUUGCCG (SEQ ID NO: 637) | $C6NH_2$-CGGUGGGAAAUGUGUGAUGGGUUGCCG-idT (SEQ ID NO: 713), where G is 2'F; and A, C, and U are 2'OMe modified RNA; $C6NH_2$ is a hexylamine linker; and idT is an inverted deoxythymidine residue. |
| Aptamer 174 | RNA | CGGUGGGAAAUGUGACAUGG GUUGCCG (SEQ ID NO: 638) | $C6NH_2$-CGGUGGGAAAUGUGACAUGGGUUGCCG-idT (SEQ ID NO: 714), where G is 2'F; and A, C, and U are 2'OMe modified RNA; $C6NH_2$ is a hexylamine linker; and idT is an inverted deoxythymidine residue. |
| Aptamer 175 | RNA | CGGUGGGAAAUGUGAAAUGG GUUGCCG (SEQ ID NO: 639) | $C6NH_2$-CGGUGGGAAAUGUGAAAUGGGUUGCCG-idT (SEQ ID NO: 715), where G is 2'F; and A, C, and U are 2'OMe modified RNA; $C6NH_2$ is a hexylamine linker; and idT is an inverted deoxythymidine residue. |
| Aptamer 176 | RNA | CGGUGGGAAAUGUGAUAUGG GUUGCCG (SEQ ID NO: 640) | $C6NH_2$-CGGUGGGAAAUGUGAUAUGGGUUGCCG-idT (SEQ ID NO: 716), where G is 2'F; and A, C, and U are 2'OMe modified RNA; $C6NH_2$ is a hexylamine linker; and idT is an inverted deoxythymidine residue. |

TABLE 3-continued

| Aptamer 8 Family | | | |
|---|---|---|---|
| Compound Name | Backbone | Primary Sequence (5' to 3') | Modified Sequence (5' to 3') |
| Aptamer 177 | RNA | CGGUGGGAAAUGUGAGCUGG GUU (SEQ ID NO: 641) | $C6NH_2$-CGGUGGGAAAUGUGAGCUGGGUU-idT (SEQ ID NO: 717), where G is 2'F; and A, C, and U are 2'OMe modified RNA; $C6NH_2$ is a hexylamine linker; and idT is an inverted deoxythymidine residue. |
| Aptamer 178 | RNA | CGGUGGGAAAUGUGAGGUGG GUUGCCG (SEQ ID NO: 642) | $C6NH_2$-CGGUGGGAAAUGUGAGGUGGGUUGCCG-idT (SEQ ID NO: 718), where G is 2'F; and A, C, and U are 2'OMe modified RNA; $C6NH_2$ is a hexylamine linker; and idT is an inverted deoxythymidine residue. |
| Aptamer 179 | RNA | CGGUGGGAAAUGUGAGUUGG GUUGCCG (SEQ ID NO: 643) | $C6NH_2$-CGGUGGGAAAUGUGAGUUGGGUUGCCG-idT (SEQ ID NO: 719), where G is 2'F; and A, C, and U are 2'OMe modified RNA; $C6NH_2$ is a hexylamine linker; and idT is an inverted deoxythymidine residue. |
| Aptamer 180 | RNA | CGGUGGGAAAUGUGAGAGGG GUUGCCG (SEQ ID NO: 644) | $C6NH_2$-CGGUGGGAAAUGUGAGAGGGGUUGCCG-idT (SEQ ID NO: 720), where G is 2'F; and A, C, and U are 2'OMe modified RNA; $C6NH_2$ is a hexylamine linker; and idT is an inverted deoxythymidine residue. |
| Aptamer 212 | RNA | GCGGUGGGAAAUGUGAGAUG GGUUGCCGC (SEQ ID NO: 645) | $C6NH_2$-GCGGUGGGAAAUGUGAGAUGGGUUGCC GC-idT (SEQ ID NO: 721), where G is 2'F; and A, C, and U are 2'OMe modified RNA; $C6NH_2$ is a hexylamine linker; and idT is an inverted deoxythymidine residue. |
| Aptamer 214 | RNA | CAAUGGGAAAUGUGAGAUGG GUUGCCG (SEQ ID NO: 646) | $C6NH_2$-CAAUGGGAAAUGUGAGAUGGGUUGCCG-idT (SEQ ID NO: 722), where G is 2'F; and A, C, and U are 2'OMe modified RNA; $C6NH_2$ is a hexylamine linker; and idT is an inverted deoxythymidine residue. |
| Aptamer 215 | RNA | CGGUGGGAAAUGUGAGAUGG GAUGCCG (SEQ ID NO: 647) | $C6NH_2$-CGGUGGGAAAUGUGAGAUGGGAUGCCG-idT (SEQ ID NO: 723), where G is 2'F; and A, C, and U are 2'OMe modified RNA; $C6NH_2$ is a hexylamine linker; and idT is an inverted deoxythymidine residue. |
| Aptamer 216 | RNA | CUGUGGGAAAUGUGAGAUGG GUUGCAG (SEQ ID NO: 648) | $C6NH_2$-CUGUGGGAAAUGUGAGAUGGGUUGCAG-idT (SEQ ID NO: 724), where G is 2'F; and A, C, and U are 2'OMe modified RNA; $C6NH_2$ is a hexylamine linker; and idT is an inverted deoxythymidine residue. |
| Aptamer 217 | RNA | CGCUGGGAAAUGUGAGAUGG GUUGGCG (SEQ ID NO: 649) | $C6NH_2$-CGCUGGGAAAUGUGAGAUGGGUUGGCG-idT (SEQ ID NO: 725), where G is 2'F; and A, C, and U are 2'OMe modified RNA; $C6NH_2$ is a hexylamine linker; and idT is an inverted deoxythymidine residue. |
| Aptamer 218 | RNA | CGAUGGGAAAUGUGAGAUGG GUUGUCG (SEQ ID NO: 650) | $C6NH_2$-CGAUGGGAAAUGUGAGAUGGGUUGUCG-idT (SEQ ID NO: 726), where G is 2'F; and A, C, and U are 2'OMe modified RNA; $C6NH_2$ is a hexylamine linker; and idT is an inverted deoxythymidine residue. |

TABLE 3-continued

Aptamer 8 Family

| Compound Name | Backbone | Primary Sequence (5' to 3') | Modified Sequence (5' to 3') |
|---|---|---|---|
| Aptamer 219 | RNA | CGGUGGGAAAUGUGAGAUGG GUUACCG (SEQ ID NO: 651) | $C6NH_2$-<br>CGGUGGGAAAUGUGAGAUGGGUUACCG-idT (SEQ ID NO: 727),<br>where G is 2'F; and A, C, and U are 2'OMe modified RNA; $C6NH_2$ is a hexylamine linker; and idT is an inverted deoxythymidine residue. |
| Aptamer 242 | RNA | GCGGUGGGAAAUGUGAGAUG GGUUGCCGC (SEQ ID NO: 652), | $C6NH_2$-<br>**G**CGGUGGGAAAUGUGAGAUGGGUUGCC GC-idT (SEQ ID NO: 728),<br>where G is 2'F; A, C, U, and **G** (bolded, underlined) are 2'OMe modified RNA; $C6NH_2$ is a hexylamine linker; and idT is a deoxythymidine residue. |
| Aptamer 243 | RNA | GCGGUGGGAAAUGUGAGAUG GGUUGCCGC (SEQ ID NO: 653) | $C6NH_2$-<br>GC**G**GUGGGAAAUGUGAGAUGGGUUGCC GC-idT (SEQ ID NO: 729),<br>where G is 2'F; A, C, U, and **G** (bolded, underlined) are 2'OMe modified RNA; $C6NH_2$ is a hexylamine linker; and idT is a deoxythymidine residue. |
| Aptamer 244 | RNA | GCGGUGGGAAAUGUGAGAUG GGUUGCCGC (SEQ ID NO: 654) | $C6NH_2$-<br>GCG**G**UGGGAAAUGUGAGAUGGGUUGCC GC-idT (SEQ ID NO: 730),<br>where G is 2'F; A, C, U, and **G** (bolded, underlined) are 2'OMe modified RNA; $C6NH_2$ is a hexylamine linker; and idT is a deoxythymidine residue. |
| Aptamer 245 | RNA | GCGGUGGGAAAUGUGAGAUG GGUUGCCGC (SEQ ID NO: 655) | $C6NH_2$-<br>GCGGUGGGAAAUGUGAGAUGGGUUGCC **G**C-idT (SEQ ID NO: 731),<br>where G is 2'F; A, C, U, and **G** (bolded, underlined) are 2'OMe modified RNA; $C6NH_2$ is a hexylamine linker; and idT is a deoxythymidine residue. |
| Aptamer 246 | RNA | GCGGUGGGAAAUGUGAGAUG GGUUGCCGC (SEQ ID NO: 656) | $C6NH_2$-<br>GCGGUGGGAAAUGUGAGAUGGGUU**G**CC GC-idT (SEQ ID NO: 732),<br>where G is 2'F; A, C, U, and **G** (bolded, underlined) are 2'OMe modified RNA; $C6NH_2$ is a hexylamine linker; and idT is a deoxythymidine residue. |
| Aptamer 247 | RNA | GCGGUGGGAAAUGUGAGAUG GGUUGCCGC (SEQ ID NO: 657) | $C6NH_2$-<br>**G**C**GG**UGGGAAAUGUGAGAUGGGUUGCC **G**C-idT (SEQ ID NO: 733),<br>where G is 2'F; A, C, U, and **G** (bolded, underlined) are 2'OMe modified RNA; $C6NH_2$ is a hexylamine linker; and idT is a deoxythymidine residue. |
| Aptamer 248 | RNA | GCGGUGGGAAAUGUGAGAUG GGUUGCCGC (SEQ ID NO: 658) | $C6NH_2$-<br>**G**C**GG**UGGGAAAUGUGAGAUGGGUU**G**CC **G**C-idT (SEQ ID NO: 734),<br>where G is 2'F; A, C, U, and **G** (bolded, underlined) are 2'OMe modified RNA; $C6NH_2$ is a hexylamine linker; and idT is a deoxythymidine residue. |
| Aptamer 249 | RNA | GCGGUGGGAAAUGUGAGAUG GGUUGCCGC (SEQ ID NO: 659) | $C6NH_2$-<br>GCGGUGGGAAAU**G**UGAGAUGGGUUGCC GC-idT (SEQ ID NO: 735),<br>where G is 2'F; A, C, U, and **G** (bolded, underlined) are 2'OMe modified RNA; $C6NH_2$ is a hexylamine linker; and idT is a deoxythymidine residue. |

TABLE 3-continued

Aptamer 8 Family

| Compound Name | Backbone | Primary Sequence (5' to 3') | Modified Sequence (5' to 3') |
|---|---|---|---|
| Aptamer 250 | RNA | GCGGUGGGAAAUGUGAGAUG GGUUGCCGC (SEQ ID NO: 660) | $C6NH_2$-<br>GCGGUGGGAAAUGUGAGAU**G**GGUUGCC<br>GC-idT (SEQ ID NO: 736),<br>where G is 2'F; A, C, U, and **G** (bolded, underlined) are 2'OMe modified RNA; $C6NH_2$ is a hexylamine linker; and idT is a deoxythymidine residue. |
| Aptamer 251 | RNA | GCGGUGGGAAAUGUGAGAUG GGUUGCCGC (SEQ ID NO: 661) | $C6NH_2$-<br>GCGGUGGGAAAUGUGAGAUG**G**GUUGCC<br>GC-idT (SEQ ID NO: 737),<br>where G is 2'F; A, C, U, and **G** (bolded, underlined) are 2'OMe modified RNA; $C6NH_2$ is a hexylamine linker; and idT is a deoxythymidine residue. |
| Aptamer 252 | RNA | GCGGUGGGAAAUGUGAGAUG GGUUGCCGC (SEQ ID NO: 662) | $C6NH_2$-<br>GCGGUGGGAAAUGUGAGAUGG**G**UUGCC<br>GC-idT (SEQ ID NO: 738),<br>where G is 2'F; A, C, U, and **G** (bolded, underlined) are 2'OMe modified RNA; $C6NH_2$ is a hexylamine linker; and idT is a deoxythymidine residue. |
| Aptamer 253 | RNA | GCGGUGGGAAAUGUGAGAUG GGUUGCCGC (SEQ ID NO: 663) | $C6NH_2$-<br>GCGGUGGGAAAU**G**UGAGAUG**G**GUUGCC<br>GC-idT (SEQ ID NO: 739),<br>where G is 2'F; A, C, U, and **G** (bolded, underlined) are 2'OMe modified RNA; $C6NH_2$ is a hexylamine linker; and idT is a deoxythymidine residue. |
| Aptamer 254 | RNA | GCGGUGGGAAAUGUGAGAUG GGUUGCCGC (SEQ ID NO: 664) | $C6NH_2$-<br>GCGGUGGGAAAU**G**UGAGAUG**GG**UUGCC<br>GC-idT (SEQ ID NO: 740),<br>where G is 2'F; A, C, U, and **G** (bolded, underlined) are 2'OMe modified RNA; $C6NH_2$ is a hexylamine linker; and idT is a deoxythymidine residue. |
| Aptamer 255 | RNA | GCGGUGGGAAAUGUGAGAUG GGUUGCCGC (SEQ ID NO: 665) | $C6NH_2$-<br>GCGGUGGGAAAU**G**UGAGAU**GGG**UUGCC<br>GC-idT (SEQ ID NO: 741),<br>where G is 2'F; A, C, U, and **G** (bolded, underlined) are 2'OMe modified RNA; $C6NH_2$ is a hexylamine linker; and idT is a deoxythymidine residue. |
| Aptamer 256 | RNA | GCGGUGGGAAAUGUGAGAUG GGUUGCCGC (SEQ ID NO: 666) | $C6NH_2$-<br>**G**C**GG**UGGGAAAUGUGAGAUG**GG**UUGCC<br>**G**C-idT (SEQ ID NO: 742),<br>where G is 2'F; A, C, U, and **G** (bolded, underlined) are 2'OMe modified RNA; $C6NH_2$ is a hexylamine linker; and idT is a deoxythymidine residue. |
| Aptamer 257 | RNA | GCGGUGGGAAAUGUGAGAUG GGUUGCCGC (SEQ ID NO: 667) | $C6NH_2$-<br>**G**C**GG**UGGGAAAUGUGAGAU**GGG**UUGCC<br>**G**C-idT (SEQ ID NO: 743),<br>where G is 2'F; A, C, U, and **G** (bolded, underlined) are 2'OMe modified RNA; $C6NH_2$ is a hexylamine linker; and idT is a deoxythymidine residue. |
| Aptamer 258 | RNA | GCGGUGGGAAAUGUGAGAUG GGUUGCCGC (SEQ ID NO: 668) | $C6NH_2$-<br>**G**C**GG**UGGGAAAUGUGAGAUG**GG**UU**G**CC<br>**G**C-idT (SEQ ID NO: 744),<br>where G is 2'F; A, C, U, and **G** (bolded, underlined) are 2'OMe modified RNA; $C6NH_2$ is a hexylamine linker; and idT is a deoxythymidine residue. |

TABLE 3-continued

| Aptamer 8 Family | | | |
|---|---|---|---|
| Compound Name | Backbone | Primary Sequence (5' to 3') | Modified Sequence (5' to 3') |
| Aptamer 259 | RNA | GCGGUGGGAAAUGUGAGAUG GGUUGCCGC (SEQ ID NO: 669) | $C6NH_2$- **G**C**GG**UGGGAAAUGUGAGAU**GGG**UU**G**C C**G**C-idT (SEQ ID NO: 745), where G is 2'F; A, C, U, and **G** (bolded, underlined) are 2'OMe modified RNA; $C6NH_2$ is a hexylamine linker; and idT is a deoxythymidine residue. |
| Aptamer 260 | RNA | GCGGUGGGAAAUGUGAGAUG GGUUGCCGC (SEQ ID NO: 670) | $C6NH_2$- GCGGU**G**GGAAAUGUGAGAUGGGUUGCC GC-idT (SEQ ID NO: 746), where G is 2'F; A, C, U, and **G** (bolded, underlined) are 2'OMe modified RNA; $C6NH_2$ is a hexylamine linker; and idT is a deoxythymidine residue. |
| Aptamer 261 | RNA | GCGGUGGGAAAUGUGAGAUG GGUUGCCGC (SEQ ID NO: 671) | $C6NH_2$- GCGGUG**G**GAAAUGUGAGAUGGGUUGCC GC-idT (SEQ ID NO: 747), where G is 2'F; A, C, U, and **G** (bolded, underlined) are 2'OMe modified RNA; $C6NH_2$ is a hexylamine linker; and idT is a deoxythymidine residue. |
| Aptamer 262 | RNA | GCGGUGGGAAAUGUGAGAUG GGUUGCCGC (SEQ ID NO: 672) | $C6NH_2$- GCGGUGG**G**AAAUGUGAGAUGGGUUGCC GC-idT (SEQ ID NO: 748), where G is 2'F; A, C, U, and **G** (bolded, underlined) are 2'OMe modified RNA; $C6NH_2$ is a hexylamine linker; and idT is a deoxythymidine residue. |
| Aptamer 263 | RNA | GCGGUGGGAAAUGUGAGAUG GGUUGCCGC (SEQ ID NO: 673) | $C6NH_2$- GCGGUGGGAAAUGU**G**AGAUGGGUUGCC GC-idT (SEQ ID NO: 749), where G is 2'F; A, C, U, and **G** (bolded, underlined) are 2'OMe modified RNA; $C6NH_2$ is a hexylamine linker; and idT is a deoxythymidine residue. |
| Aptamer 264 | RNA | GCGGUGGGAAAUGUGAGAUG GGUUGCCGC (SEQ ID NO: 674) | $C6NH_2$- GCGGUGGGAAAUGUGA**G**AUGGGUUGCC GC-idT (SEQ ID NO: 750), where G is 2'F; A, C, U, and **G** (bolded, underlined) are 2'OMe modified RNA; $C6NH_2$ is a hexylamine linker; and idT is a deoxythymidine residue. |
| Aptamer 265 | RNA | CGGUGGGAAACGUGAGAUGG GUUGCCG (SEQ ID NO: 675) | $C6NH_2$- CGGUGGGAAAC**G**UGAGAUGGGUUGCCG- idT (SEQ ID NO: 751), where G is 2'F; A, C, U, and **G** (bolded, underlined) are 2'OMe modified RNA; $C6NH_2$ is a hexylamine linker; and idT is a deoxythymidine residue. |
| Aptamer 266 | RNA | CGGUGGGAAACGUGAGAUGG GUUGCCG (SEQ ID NO: 676) | $C6NH_2$- CGGUGGGAAACGUGAGAUGG**G**UUGCCG- idT (SEQ ID NO: 752), where G is 2'F; A, C, U, and **G** (bolded, underlined) are 2'OMe modified RNA; $C6NH_2$ is a hexylamine linker; and idT is a deoxythymidine residue. |
| Aptamer 267 | RNA | CGGUGGGAAACGUGAGAUGG GUUGCCG (SEQ ID NO: 677) | $C6NH_2$- CGGUGGGAAACGUGAGAUG**G**GUUGCCG- idT (SEQ ID NO: 753), where G is 2'F; A, C, U, and **G** (bolded, underlined) are 2'OMe modified RNA; $C6NH_2$ is a hexylamine linker; and idT is a deoxythymidine residue. |

TABLE 3-continued

| Aptamer 8 Family | | | |
|---|---|---|---|
| Compound Name | Backbone | Primary Sequence (5' to 3') | Modified Sequence (5' to 3') |
| Aptamer 268 | RNA | CGGUGGGAAACGUGAGAUGG GUUGCCG (SEQ ID NO: 678) | $C6NH_2$-CGGUGGGAAACGUGAGAU**G**GGUUGCCG-idT (SEQ ID NO: 754), where G is 2'F; A, C, U, and **G** (bolded, underlined) are 2'OMe modified RNA; $C6NH_2$ is a hexylamine linker; and idT is a deoxythymidine residue. |

In some aspects, an aptamer of the disclosure may have a primary nucleic acid sequence according to any one of the aptamer sequences described in Tables 1-3, or may have a primary nucleic acid sequence that shares at least 40% sequence identity to any one of the aptamer sequences described in Tables 1-3. In some aspects, an aptamer of the disclosure may have a primary nucleic acid sequence consisting of any one of the aptamer sequences described in Tables 1-3, or may have a primary nucleic acid sequence that shares at least 40% sequence identity to a primary nucleic acid sequence consisting of any one of the aptamer sequences described in Tables 1-3. In some cases, the nucleic acid sequence may comprise one or more modified nucleotides. In some cases, at least 50% of said nucleic acid sequence may comprise the one or more modified nucleotides. In some cases, the one or more modified nucleotides may comprise a 2'F-modified nucleotide, a 2'OMe-modified nucleotide, or a combination thereof. In some cases, the one or more modified nucleotides may be selected from the group consisting of: 2'F-G, 2'OMe-G, 2'OMe-U, 2'OMe-A, 2'OMe-C, an inverted deoxythymidine at the 3' terminus, and any combination thereof. In some cases, the aptamer may comprise a nucleic acid sequence comprising modified nucleotides (and/or other modifications) of any one of the aptamers described in Tables 1-3. In some cases, the aptamer is any aptamer described in Tables 1-3. In some cases, the aptamer is any aptamer of the Aptamer 3 structural family as described in Table 2. For example, an aptamer of the Aptamer 3 structural family may include any one of Aptamers 3, 38, 40-45, 69-85, 87, 89, 90, 92, 94-111, 134-153, 183-190, 193, 197, 199-201, 206-210, 221-241, and 269-279, as described in Table 2. In some cases, the aptamer is any aptamer of the Aptamer 8 structural family as described in Table 3. For example, an aptamer of the Aptamer 8 structural family may include any one of Aptamers 8, 32, 54, 59, 61, 112-122, 154-180, 212, 214-219, and 242-268, as described in Table 3. In some cases, the aptamer may be conjugated to a polyethylene glycol (PEG) molecule. In some cases, the PEG molecule may have a molecular weight of 80 kDa or less (e.g., 40 kDa).

In some cases, an aptamer of the disclosure may share at least 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% sequence identity with any aptamer described herein. For example, an anti-IL8 aptamer of the disclosure may share at least 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% sequence identity with any aptamer described in Tables 1-3.

In some cases, an anti-IL8 aptamer of the disclosure may be truncated to remove constant regions, or portions thereof. In some cases, an anti-IL8 aptamer of the disclosure may comprise an aptamer sequence according to any aptamer sequence described in Table 1, Table 2, or Table 3, with the constant regions, or portions thereof, removed. In some cases, the constant regions may include the sequences: 5'-GGGAGAGUCGGUAGCAGUC-3' (SEQ ID NO: 755), and 5'-CUAUGUGGAAAUGGCGCUGU-3' (SEQ ID NO: 756), flanking the random region of the aptamer at the 5' end and the 3' end, respectively. In other cases, the constant regions may include the sequences 5'-GGGAGGGCAAGAGACAGA-3' (SEQ ID NO: 757), and 5'-CUAUGUGGAAAUGGCGCUGU-3' (SEQ ID NO: 758), flanking the random region of the aptamer at the 5' end and the 3' end, respectively. In some cases, an anti-IL8 aptamer of the disclosure may comprise a random region of any aptamer sequence described in Table 1, Table 2, or Table 3. In some cases, an anti-IL8 aptamer of the disclosure may share at least 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% sequence identity with a random region of any aptamer sequence described in Table 1, Table 2, or Table 3.

In some cases, an anti-IL8 aptamer of the disclosure may have at least 40% sequence identity with any one of the aptamer sequences described in Tables 1-3. In some cases, an anti-IL8 aptamer of the disclosure may have at least 45% sequence identity with any one of the aptamer sequences described in Tables 1-3. In some cases, an anti-IL8 aptamer of the disclosure may have at least 50% sequence identity with any one of the aptamer sequences described in Tables 1-3. In some cases, an anti-IL8 aptamer of the disclosure may have at least 55% sequence identity with any one of the aptamer sequences described in Tables 1-3. In some cases, an anti-IL8 aptamer of the disclosure may have at least 60% sequence identity with any one of the aptamer sequences described in Tables 1-3. In some cases, an anti-IL8 aptamer of the disclosure may have at least 65% sequence identity with any one of the aptamer sequences described in Tables 1-3. In some cases, an anti-IL8 aptamer of the disclosure may have at least 70% sequence identity with any one of the aptamer sequences described in Tables 1-3. In some cases, an anti-IL8 aptamer of the disclosure may have at least 75% sequence identity with any one of the aptamer sequences described in Tables 1-3. In some cases, an anti-IL8 aptamer of the disclosure may have at least 80% sequence identity with any one of the aptamer sequences described in Tables 1-3. In some cases, an anti-IL8 aptamer of the disclosure may have at least 85% sequence identity with any one of the aptamer sequences described in Tables 1-3. In some cases, an anti-IL8 aptamer of the disclosure may have at least 90% sequence identity with any one of the aptamer sequences described in Tables 1-3. In some cases, an anti-IL8 aptamer of the disclosure may have at least 95% sequence identity with any one of the aptamer sequences described in Tables 1-3.

In some cases, an aptamer of the disclosure may have a primary nucleotide sequence that shares at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, or at least 40 contiguous nucleotides with a nucleotide sequence described in Tables 1-3.

In such cases where specific nucleotide modifications have been recited, it should be understood that any number and type of nucleotide modifications may be substituted. For example, 2'OMe-G may be substituted for 2'F-G. Non-limiting examples of nucleotide modifications have been provided herein. In some instances, all of the nucleotides of an aptamer may be modified. In some instances, at least 50%, 55%, 60%, 65%, 70%, 75%, 80%, 85%, 86%, 87%, 88%, 89%, 90%, 91%, 92%, 93%, 94%, 95%, 96%, 97%, 98%, 99%, or 100% of the nucleotides of an aptamer of the disclosure may be modified. In some aspects, an aptamer of the disclosure has the modified nucleotide sequence of any aptamer sequence described in Tables 1-3.

In some cases, an aptamer of the disclosure may have a modified nucleotide sequence. In some cases, an aptamer of the disclosure may have a modified nucleotide sequence as described in Tables 1-3. In some cases, an aptamer of the disclosure may have a primary nucleotide sequence according to any aptamer described in Tables 1-3, and a modified nucleotide sequence that is different than that described in Tables 1-3. In such cases, an aptamer of the disclosure may have a modified nucleotide sequence that shares at least 10% modification identity with any modified nucleotide sequence described in Tables 1-3. For example, an aptamer of the disclosure may have a modified nucleotide sequence that shares at least 10%, at least 15%, at least 20%, at least 25%, at least 30%, at least 35%, at least 40%, at least 45%, at least 50%, at least 55%, at least 60%, at least 65%, at least 70%, at least 75%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% modification identity with any modified nucleotide sequence described in Tables 1-3.

In some cases, an aptamer of the disclosure may have a primary nucleotide sequence of any aptamer sequence described in Tables 1-3, and a modified nucleotide sequence in which at least 10% of the C nucleotides are modified (e.g., 2'OMe-C). For example, an aptamer of the disclosure may have a modified nucleotide sequence in which at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% of the C nucleotides are modified (e.g., 2'OMe-C). In some cases, an aptamer of the disclosure may have a modified nucleotide sequence wherein at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% of the C nucleotides (C) are modified according to Tables 1-3.

In some cases, an aptamer of the disclosure may have a primary nucleotide sequence of any aptamer sequence described in Tables 1-3, and a modified nucleotide sequence in which at least 10% of the A nucleotides are modified (e.g., 2'OMe-A). For example, an aptamer of the disclosure may have a modified nucleotide sequence in which at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% of the A nucleotides are modified (e.g., 2'OMe-A). In some cases, an aptamer of the disclosure may have a modified nucleotide sequence wherein at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% of the A nucleotides are modified according to Tables 1-3.

In some cases, an aptamer of the disclosure may have a primary nucleotide sequence of any aptamer sequence described in Tables 1-3, and a modified nucleotide sequence in which at least 10% of the U nucleotides are modified (e.g., 2'OMe-U). For example, an aptamer of the disclosure may have a modified nucleotide sequence in which at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% of the U nucleotides are modified (e.g., 2'OMe-U). In some cases, an aptamer of the disclosure may have a modified nucleotide sequence wherein at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% of the U nucleotides are modified according to Tables 1-3.

In some cases, an aptamer of the disclosure may have a primary nucleotide sequence of any aptamer sequence described in Tables 1-3, and a modified nucleotide sequence in which at least 10% of the G nucleotides are modified (e.g., 2'F-G, 2'OMe-G). For example, an aptamer of the disclosure may have a modified nucleotide sequence in which at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% of the G nucleotides are modified (e.g., 2'F-G, 2'OMe-G). In some cases, an aptamer of the disclosure may have a modified nucleotide sequence wherein at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% of the G nucleotides are modified according to Tables 1-3.

In some cases, an aptamer of the disclosure does not comprise any one of SEQ ID NOs: 759-762 as described in Table 4.

TABLE 4

| Aptamer Sequences | |
|---|---|
| Backbone | Sequence 5' to 3' |
| RNA | GGGAGAGCGGAAGCGUGCUGGGCUUA UCAUUCCAUUUAGUGUUAUGAUAACC UUCCCAUCAGACAUAACCCAGAGGUC GAUGGAUCCCGGG (SEQ ID NO: 759) |
| RNA | GGGGGCUUAUCAUUCCAUUUAGUGUU AUGAUAACCUUCCCAUCA (SEQ ID NO: 760) |

TABLE 4-continued

| Aptamer Sequences | |
|---|---|
| Backbone | Sequence 5' to 3' |
| RNA | GGGGGCUUAUCAUUCCAUUUAGUGUU AUGAUAACC (SEQ ID NO: 761) |
| RNA | GGGUUAUCAUUCCAUUUAGUGUUAUG AUAA (SEQ ID NO: 762) |

Aptamer 3 Structural Family

In some cases, an anti-IL8 aptamer of the disclosure may comprise a stem-loop secondary structure. In some cases, the stem-loop secondary structure is as described herein for the Aptamer 3 structural family of aptamers. In some cases, an aptamer of the Aptamer 3 family may have, in a 5' to 3' direction, a first side of a first base paired stem; a first loop; a first side of a second base paired stem; a second loop; a first side of a third base paired stem; a third loop; a second, complementary side of the third base paired stem; a fourth loop; a second, complementary side of the second base paired stem; and a second, complementary side of the first base paired stem.

In some embodiments, each element may be adjacent to each other. For example, an aptamer of the Aptamer 3 family may have, in a 5' to 3' direction, a first side of a first base paired stem. The 3' terminal end of the first side of the first base paired stem may be connected to the 5' terminal end of the first loop. The first loop may be connected at its 5' terminal end to the 3' terminal end of the first side of the first base paired stem, and the first loop may be connected at its 3' terminal end to the 5' terminal end of the first side of the second base paired stem. The first side of the second base paired stem may be connected at its 5' terminal end to the 3' terminal end of the first loop, and the first side of the second base paired stem may be connected at its 3' terminal end to the 5' terminal end of the second loop. The second loop may be connected at its 5' terminal end to the 3' terminal end of the first side of the second base paired stem, and the second loop may be connected at its 3' terminal end to the 5' terminal end of the first side of the third base paired stem. The first side of the third base paired stem may be connected at its 5' terminal end to the 3' terminal end of the second loop, and the first side of the third base paired stem may be connected at its 3' terminal end to the 5' terminal end of the third loop. The third loop may be connected at its 5' terminal end to the 3' terminal end of the first side of the third base paired stem, and the third loop may be connected at its 3' terminal end to the 5' terminal end of the second, complementary side of the third base paired stem. The second, complementary side of the third base paired stem may be connected at its 5' terminal end to the 3' terminal end of the third loop, and the second, complementary side of the third base paired stem may be connected at its 3' terminal end to the 5' terminal end of the fourth loop. The fourth loop may be connected at its 5' terminal end to the 3' terminal end of the second, complementary side of the third base paired stem, and the fourth loop may be connected at its 3' terminal end to the 5' terminal end of the second, complementary side of the second base paired stem. The second, complementary side of the second base paired stem may be connected at its 5' terminal end to the 3' terminal end of the fourth loop, and the second, complementary side of the second based paired stem may be connected at its 3' terminal end to the 5' terminal end of the second, complementary side of the first base paired stem. The second, complementary side of the first base paired stem may be connected at its 5' terminal end to the 3' terminal end of the second, complementary side of the second base paired stem. In some cases, an aptamer of the Aptamer 3 family may comprise a terminal stem. In some cases, the terminal stem may be the first base paired stem. In some cases, an aptamer of the Aptamer 3 family may comprise a terminal loop. In some cases, the terminal loop may be the third loop.

In one aspect, an aptamer of the disclosure may bind to and inhibit IL8, wherein the aptamer comprises a secondary structure comprising at least one terminal loop comprising greater than three nucleotides, wherein the at least one terminal loop participates in binding of said aptamer to IL8. In another aspect, an aptamer of the disclosure may bind to and inhibit IL8, wherein the aptamer comprises a secondary structure comprising at least one asymmetric internal loop pair connected to exactly two stems. In some cases, a first loop sequence of the at least one asymmetric internal loop pair is connected at a 5' end to a first stem sequence and is connected at a 3' end to a second stem sequence, and wherein a second loop sequence of the at least one asymmetric internal loop pair is connected at a 5' end to a third stem sequence that is complementary to the second stem sequence and is connected at a 3' end to a fourth stem sequence that is complementary to the first stem sequence. In another aspect, an aptamer of the disclosure may bind to and inhibit IL8, wherein the aptamer comprises a secondary structure comprising at least two loops, wherein at least two of the at least two loops do not comprise a pyrimidine. In another aspect, an aptamer of the disclosure may bind to and inhibit IL8, wherein the aptamer comprises a secondary structure comprising at least one terminal loop comprising from six to ten nucleotides. In another aspect, an aptamer of the disclosure may bind to and inhibit IL8, wherein the aptamer comprises a secondary structure comprising more than one internal stem, wherein each internal stem of the more than one internal stem has less than six contiguous base pairs.

In a particular aspect, an aptamer of the Aptamer 3 family may have a stem-loop secondary structure comprising: (i) a first side of Stem 1 (S1); (ii) Loop 1 (L1) connected to the 3' terminal end of the first side of S1 and the 5' terminal end of a first side of Stem 2 (S2); (iii) the first side of S2 connected to the 3' terminal end of L1 and the 5' terminal end of Loop 2 (L2); (iv) L2 connected to the 3' terminal end of the first side of S2 and the 5' terminal end of a first side of Stem 3 (S3); (v) S3 connected to the 3' terminal end of L2 and the 5' terminal end of Loop 3 (L3); (vi) L3 connected to the 3' terminal end of the first side of S3 and the 5' terminal end of a second, complementary side of S3; (vii) the second, complementary side of S3 connected to the 3' terminal end of L3 and the 5' terminal end of Loop 4 (L4); (viii) L4 connected to the 3' terminal end of the second, complementary side of S3 and the 5' terminal end of a second, complementary side of S2; (ix) the second, complementary side of S2 connected to the 3' terminal end of L4 and the 5' terminal end of a second, complementary side of S1; and (x) the second, complementary side of S1 connected to the 3' terminal end of the second, complementary side of S2.

In some cases, Stem 1 may have from two to four base pairs. For example, Stem 1 may have two, three, or four base pairs. In some cases, Stem 1 may have more than one, more than two, or more than three base pairs. In some cases, Stem 1 may have less than five, less than four, or less than three base pairs. In some cases, Stem 1 is not highly conserved in sequence identity. In some cases, Stem 1 may comprise an internal mismatch.

In some cases, Loop 1 may have one nucleotide. In some cases, Loop 1 may have less than two nucleotides. In some cases, the sequence of Loop 1 is 5'-A-3'.

In some cases, Stem 2 may have four base pairs. In some cases, Stem 2 may have more than three base pairs. In some cases, Stem 2 may have less than five base pairs. In some cases, Stem 2 is not highly conserved in sequence identity. In some cases, Stem 2 may terminate with a U·A base pair (e.g., the 3' terminal U of the first side of Stem 2 may base pair with the 5' terminal A of the second, complementary side of Stem 2).

In some cases, Loop 2 may have two nucleotides. In some cases, Loop 2 may have more than one nucleotide. In some cases, Loop 2 may have less than three nucleotides. In some cases, the sequence of Loop 2 may be 5'-AG-3'. In some cases, the sequence of Loop 2 may be 5'-WG-3', where W is A or U.

In some cases, Stem 3 may have from one to three base pairs. For example, Stem 3 may have one, two, or three base pairs. In some cases, Stem 3 may have more than one, or more than two base pairs. In some cases, Stem 3 may have less than four, less than three, or less than two base pairs. In some cases, the consensus sequence of the first side of Stem 3 is 5'-WU-3', where W is A or U, and the consensus sequence of the second, complementary side of Stem 3 is 5'-GU-3' (e.g., 5'-WU/GU-3'). In some cases, the consensus sequence of the first side of Stem 3 is 5'-WD-3', where W is A or U; and D is A, G, or U; and the consensus sequence of the second, complementary side of Stem 3 is 5'-GU-3'. In some cases, when Stem 3 has three base pairs, L3 may have eight nucleotides. In some cases, when Stem 3 has three base pairs, the sequence of the first side of Stem 3 may be 5'-AUU-3', and the sequence of the second, complementary side of Stem 3 may be 5'-AGU-3' (e.g., 5'-AUU/AGU-3'). In some cases, when Stem 3 has two base pairs, the sequence of the first side of Stem 3 may be 5'-AU-3', and the sequence of the second, complementary side of Stem 3 may be 5'-GU-3' (e.g., 5'-AU/GU-3'). In some cases, when Stem 3 has one base pair, the sequence of the first side of Stem 3 may be 5'-UU-3', and the sequence of the second, complementary side of Stem 3 may be 5'-GU-3' (e.g., 5'-UU/GU-3'). In some cases, when Stem 3 has one base pair, the sequence of the first side of Stem 3 may be 5'-AA-3' and the sequence of the second, complementary side of Stem 3 may be 5'-GU-3' (e.g., 5'-AA/GU-3'). In some cases, when Stem 3 has one base pair, the sequence of the first side of Stem 3 may be 5'-AG-3' and the sequence of the second, complementary side of Stem 3 may be 5'-GU-3' (e.g., 5'-AG/GU-3').

In some cases, Loop 3 has nine or ten nucleotides. In some cases, Loop 3 may have more than eight nucleotides, or more than nine nucleotides. In some cases, Loop 3 may have less than eleven nucleotides, or less than ten nucleotides. In some cases, Loop 3 may comprise a conserved octamer motif with a sequence of 5'-ACGGGUAG-3'. In some cases, Loop 3 may comprise a conserved octamer motif with a consensus sequence of 5'-WYGGKNDG-3', where W is A or U; Y is Cor U; K is G or U; N is A, C, G, or U; and D is A, G, or U. In some cases, the 5' terminal nucleotide of Loop 3 and the 3' terminal nucleotide of Loop 3 may form a single base pair. In some cases, when the terminal nucleotides of Loop 3 form a single base pair, the sequence of Loop 3 may be 5'-UACGGGUAGA-3' (SEQ ID NO: 763). In some cases, when the terminal nucleotides of Loop 3 form a single base pair, the sequence of Loop 3 may be 5'-UWYGGKNDGA-3' (SEQ ID NO: 764), where W is A or U; Y is C or U; K is G or U; N is A, C, G, or U; and Dis A, G, or U. In some cases, the ends of Loop 3 are single stranded (e.g., the 5' terminal nucleotide of Loop 3 and the 3' terminal nucleotide of Loop 3 do not form a base pair). In some cases, when the ends of Loop 3 are single stranded, the sequence of Loop 3 may be 5'-UACGGGUAGU-3' (SEQ ID NO: 765). In some cases, when the ends of Loop 3 are single stranded, the sequence of Loop 3 may be 5'-UWYGGKNDGU-3' (SEQ ID NO: 766), where W is A or U; Y is C or U: K is G or U; N is A, C, G, or U; and D is A, G, or U. In some cases, when Loop 3 is ten nucleotides long, Loop 3 may have a consensus nucleotide sequence of 5'-DNNRGGNWGH-3 (SEQ ID NO: 767), where D is A, G, or U; Nis A, C, G, or U; R is A or G; W is A or U; and His A, C, or U. In some cases, when Loop 3 is ten nucleotides long, Loop 3 may have a consensus nucleotide sequence of 5'-DNNGGGNWGH-3' (SEQ ID NO: 768), where D is A, G, or U; N is A, C, G, or U; W is A or U; and His A, C, or U. In some cases, when Loop 3 is nine nucleotides long, Loop 3 may have a consensus nucleotide sequence of 5'-HNGGGNAGW-3', where His A, C, or U; N is A, C, G, or U; and W is A or U. In some cases, Loop 3 may comprise one or more non-nucleotidyl spacers. In some cases, one or more nucleotides of Loop 3 may be substituted with one or more non-nucleotidyl linkers.

In some cases, Loop 4 has one nucleotide. In some cases, Loop 4 has less than two nucleotides. In some cases, the sequence of Loop 4 is 5'-G-3'.

In some aspects, when Loop 3 is ten nucleotides long, an aptamer of the disclosure may have a consensus nucleic acid sequence of 5'-NNUSANDDNAGWDDNNRGG-NWGHGUGDHHNSANN-3' (SEQ ID NO: 769), where N is A, C, G, or U; S is Gor C; D is A, G, or U; W is A or U; R is A or G; and His A, C, or U. In some cases, an anti-IL8 aptamer of the disclosure may comprise a consensus nucleic acid sequence of 5' NNUSANDDNAGWDDNNGGG-NWGHGUGDHHNSANN-3' (SEQ ID NO: 770), where N is A, C, G, or U; S is Gor C; D is A, G, or U; W is A or U; R is A or G; and His A, C, or U. In some aspects, when Loop 3 is nine nucleotides long, an aptamer of the disclosure may have a consensus nucleic acid sequence of 5'-NNUSANDD-NAGWDHNGGGNAGWGUGDHHNSANN-3' (SEQ ID NO: 771), where N is A, C, G, or U; S is Gor C; D is A, G, or U; W is A or U; and His A, C, or U. In some aspects, an aptamer of the disclosure may have a consensus nucleic acid sequence of 5'-NNYVANDDNWGWDDNNRG-KNNGHGUGNHHNVRNN-3' (SEQ ID NO: 772), where N is A, C, G, or U; Y is C or U; V is A, C, or G; D is A, G, or U; W is A or U; R is A or G; K is G or U; and H is A, C, or U.

Aptamer 8 Structural Family

In some cases, an anti-IL8 aptamer of the disclosure may comprise a stem-loop secondary structure. In some cases, the stem-loop secondary structure is as described herein for the Aptamer 8 structural family of aptamers. In some cases, an aptamer of the Aptamer 8 family may have, in a 5' to 3' direction, a first side of a first base paired stem; a first loop; a first side of a second base paired stem; a second loop; a second, complementary side of the second base paired stem; and a second, complementary side of the first base paired stem.

In some aspects, each element may be adjacent to each other. For example, an aptamer of the Aptamer 8 family may have, in a 5' to 3' direction, a first side of a first base paired stem. The 3' terminal end of the first side of the first base paired stem may be connected to the 5' terminal end of the first loop. The first loop may be connected at its 5' terminal end to the 3' terminal end of the first side of the first base paired stem, and the first loop may be connected at its 3' terminal end to the 5' terminal end of the first side of the second base paired stem. The first side of the second base paired stem may be connected at its 5' terminal end to the 3' terminal end of the first loop, and the first side of the second base paired stem may be connected at its 3' terminal end to the 5' terminal end of the second loop. The second loop may be connected at its 5' terminal end to the 3' terminal end of the first side of the second base paired stem, and the second loop may be connected at its 3' terminal end to the 5' terminal end of the second, complementary side of the second base paired stem. The second, complementary side of the second base paired stem may be connected at its 5' terminal end to the 3' terminal end of the second loop, and the second, complementary side of the second base paired stem may be connected at its 3' terminal end to the 5' terminal end of the second, complementary side of the first base paired stem. The second, complementary side of the first base paired stem may be connected at its 5' terminal end to the 3' terminal end of the second, complementary side of the second base paired stem. In some cases, an aptamer of the Aptamer 8 family may comprise a terminal stem. In some cases, the terminal stem may be the first base paired stem. In some cases, an aptamer of the Aptamer 8 family may comprise a terminal loop. In some cases, the terminal loop may be the second loop.

In one aspect, an aptamer of the disclosure may bind to and inhibit IL8, wherein the aptamer comprises a secondary structure comprising at least one terminal loop comprising greater than three nucleotides, wherein the at least one terminal loop participates in binding of said aptamer to IL8. In one aspect, an aptamer of the disclosure may bind to and inhibit IL8, wherein the aptamer comprises a secondary structure comprising more than one loop, each loop of the more than one loop having at least four nucleotides. In another aspect, an aptamer of the disclosure may bind to and inhibit IL8, the aptamer comprising a secondary structure comprising a terminal stem comprising from four to six base pairs. In another aspect, an aptamer of the disclosure may bind to and inhibit IL8, wherein the aptamer comprises a secondary structure comprising a single internal loop, wherein the single internal loop comprises at least four nucleotides. In another aspect, an aptamer of the disclosure may bind to and inhibit IL8, wherein the aptamer comprises a secondary structure comprising at least one internal stem having no more than one internal mismatch. In another aspect, an aptamer of the disclosure may bind to and inhibit IL8, wherein the aptamer comprises a secondary structure comprising an internal stem having exactly one internal mismatch.

In a particular aspect, an aptamer of the Aptamer 8 family may have a stem-loop secondary structure comprising: (i) a first side of Stem 1 (S1); (ii) Loop 1 (L1) connected to the 3' terminal end of the first side of S1 and the 5' terminal end of a first side of Stem 2 (S2); (iii) the first side of S2 connected to the 3' terminal end of L1 and the 5' terminal end of Loop 2 (L2); (iv) L2 connected to the 3' terminal end of S2 and the 5' terminal end of a second, complementary side of S2 (S2'); (v) S2' connected to the 3' terminal end of L2 and the 5' terminal end of a second, complementary side of S1 (S1'); and (vi) S1' connected to the 3' terminal end of S2'.

Figure 30A:
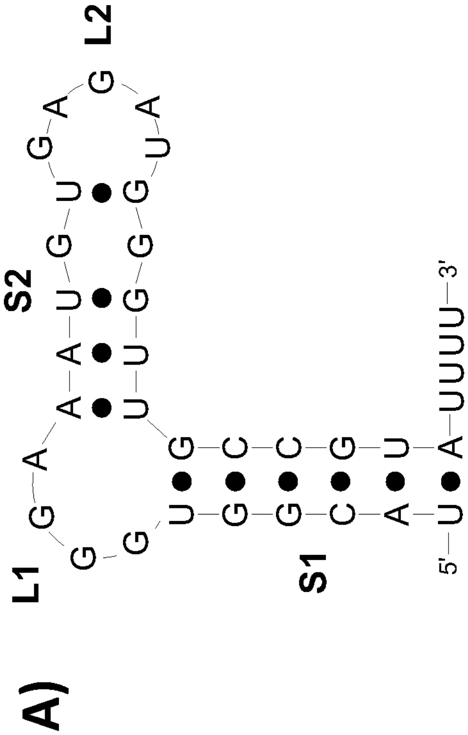
FIG. 30A and FIG. 30B depict a secondary structure of an exemplary anti-IL8 aptamer of the disclosure (SEQ ID NOS: 1238-1239, respectively, in order of appearance).

In some cases, Stem 1 may have from four to six base pairs. For example, Stem 1 may have four, five, or six base pairs. In some cases, Stem 1 may have more than three base pairs, more than four base pairs, or more than five base pairs. In some cases, Stem 1 may have less than seven base pairs, less than six base pairs, or less than five base pairs. In some cases, Stem 1 may not be highly conserved. In some cases, Stem 1 may comprise one or more mismatches (e.g., may be partially complementary). In some cases, Stem 1 may comprise a mismatch at the 3' terminal nucleotide of the first side of Stem 1 (e.g., S1), and the 5' terminal nucleotide of the second, complementary side of Stem 1 (e.g., S1'). In some cases, Stem 1 may comprise a mismatch at positions 6 and 26 (e.g., a wobble base pair) according to the numbering scheme in FIG. 31. In some cases, Stem 1 may comprise a single nucleotide bulge. In some cases, when Stem 1 is six base pairs in length, the first side of Stem 1 (e.g., S1) may comprise a consensus nucleic acid sequence of 5'-HNNNNN-3', and the second, complementary side of Stem 1 (e.g., S1') may comprise a consensus nucleic acid sequence of 5'-NNNNNN-3', where H is A, C, or U; and N is A, C, G, or U. In some cases, when Stem 1 is six base pairs in length, the first side of Stem 1 (e.g., S1) may comprise a consensus nucleic acid sequence of 5'-NDNNNH-3', and the second, complementary side of Stem 1 (e.g., S1') may comprise a consensus nucleic acid sequence of 5'-RNNNHN-3', where N is A, C, G, or U; D is A, G, or U; H is A, C, or U; and R is A or G. In some cases, when Stem 1 is six base pairs in length, the first side of Stem 1 (e.g., S1) may comprise a consensus nucleic acid sequence of 5'-NNNNNN-3', and the second, complementary side of Stem 1 (e.g., S1') may comprise a consensus nucleic acid sequence of 5'-NNNNNN-3', where N is A, C, G, or U. In some cases, when Stem 1 is five base pairs in length, the first side of Stem 1 (e.g., S1) may comprise a consensus nucleic acid sequence of 5'-WSVVB-3', and the second, complementary side of Stem 1 (e.g., S1') may comprise a consensus nucleic acid sequence of 5'-BBBSW-3', where W is A or U; S is G or C; V is A, C, or G; and B is C, G, or U. In some cases, when Stem 1 is five base pairs in length, the first side of Stem 1 (e.g., S1) may comprise a consensus nucleic acid sequence of 5'-DSVVB-3', and the second, complementary side of Stem 1 (e.g., S1') may comprise a consensus nucleic acid sequence of 5'-BBBSW-3', where D is A, G, or U; S is Gor C; Vis A, C, or G; Bis C, G, or U; and W is A or U. In some cases, when Stem 1 is five base pairs in length, the first side of Stem 1 (e.g., S1) may comprise a consensus nucleic acid sequence of 5'-ACGGY-3', and the second, complementary side of Stem 1 (e.g., S1') may comprise a consensus nucleic acid sequence of 5'-GCCGU-3', where Y is C or U. In some cases, when Stem 1 is four base pairs in length, the first side of Stem 1 (e.g., S1) may comprise a nucleic acid sequence of 5'-UGAC-3', and the second, complementary side of Stem 1 (e.g., S1') may comprise a nucleic acid sequence of 5'-GUCA-3'. In some cases, Stem 1 may comprise any sequence configuration described in Table 38 or Table 42. In some cases, the aptamer may comprise one or more unpaired nucleotides at the 5' terminal end of the aptamer, or at the 3' terminal end of the aptamer. In a non-limiting example, an aptamer of the disclosure may comprise one or more U nucleotides at the 3' terminal end of the aptamer (e.g., 5'-UUUU-3' as depicted in FIG. 30A). In some cases, the aptamer does not comprise any unpaired nucleotides at the 5' terminal end or the 3' terminal end of the aptamer.

In some cases, Loop 1 (e.g., L1) may have four or five nucleotides. In some cases, Loop 1 may have more than three nucleotides or more than four nucleotides. In some cases, Loop 1 may have less than six nucleotides or less than five nucleotides. In some cases, when Loop 1 is four nucleotides in length, Loop 1 may comprise a consensus nucleic acid sequence of 5'-GGGD-3', where D is A, G, or U. In some cases, when Loop 1 is five nucleotides in length, Loop 1 may comprise a nucleic acid sequence of 5'-CGGGA-3'. In some cases, Loop 1 may comprise a nucleic acid sequence of 5'-GGGA-3'. In some cases, Loop 1 may comprise any sequence configuration described in Table 39.

In some cases, Stem 2 may be five base pairs in length. In some cases, Stem 2 may comprise a G·G mismatch at positions 14 and 22 according to the numbering scheme in FIG. 31. In addition, Stem 2 may comprise a mismatch at the terminal base pair of positions 15 and 21 according to the numbering scheme in FIG. 31. In some cases, the first side of Stem 2 (e.g., S2) may comprise a consensus nucleic acid sequence of 5'-DDNGN-3', and the second, complementary side of Stem 2 (e.g., S2') may comprise a consensus nucleic acid sequence of 5'-GGGUK-3', where D is A, G, or U; N is A, C, G, or U; K is G or U; and the conserved G:G mismatch is underlined. In some cases, the first side of Stem 2 (e.g., S2) may comprise a nucleic acid sequence of 5'-AAUGU-3', and the second, complementary side of Stem 2 (e.g., S2') may comprise a nucleic acid sequence of 5'-GGGUU-3', where the conserved G:G mismatch is underlined. In some cases, the first side of Stem 2 (e.g., S2) may comprise a consensus nucleic acid sequence of 5'-RANGN-3', and the second, complementary side of Stem 2 (e.g., S2') may comprise a consensus nucleic acid sequence of 5'-GGGUD-3', where R is A or G; N is A, C, G, or U; and D is A, G, or U. In some cases, Stem 2 may comprise any sequence configuration described in Table 40 or Table 43.

In some cases, Loop 2 may be five nucleotides in length. In some cases, Loop 2 may comprise a consensus nucleic acid sequence of 5'-GDGDN-3', where D is A, G, or U; and N is A, C, G, or U. In some cases, Loop 2 may comprise a nucleic acid sequence of 5'-GAGAU-3'. In some cases, Loop 2 may comprise a consensus nucleic acid sequence of 5'-GAGAH-3', where His A, C, or U. In some cases, Loop 2 may comprise a consensus nucleic acid sequence of 5'-GAGAN-3', where N is A, C, G, or U. In some cases, Loop 2 may comprise any sequence configuration described in Table 41 or Table 44.

In some aspects, when the first loop is four nucleotides in length, the aptamer may comprise a consensus nucleic acid sequence of 5'-HNNNNNGGGDDDNGNGDGDNGG-GUKNNNNNN-3' (SEQ ID NO: 773), where H is A, C, or U; Nis A, C, G, or U; D is A, G, or U; and K is Gor U. In some aspects, when the first loop is five nucleotides in length, the aptamer may comprise a consensus nucleic acid sequence of 5'-HNNNNNCGGGADDNGNGDGDNGG-GUKNNNNNN-3' (SEQ ID NO: 774), where H is A, C, or U; N is A, C, G, or U; D is A, G, or U; and K is G or U. In some cases, the aptamer may comprise a consensus nucleic acid sequence of 5'-NDNNNHGGGARANGNGAGANGG-GUDRNNNHN-3' (SEQ ID NO: 775), where N is A, C, G, or U; D is A, G, or U; H is A, C, or U; and R is A or G. In some cases, the aptamer may comprise a consensus nucleic acid sequence of 5'-NNNNNNGGGDDDNGNGDGDNGG-GUDNNNNNN-3' (SEQ ID NO: 776), where N is A, C, G, or U; and D is A, G, or U.

Aptamer Consensus Sequences

In some aspects, an anti-IL8 aptamer of the disclosure may comprise a consensus nucleic acid sequence. In some cases, an anti-IL8 aptamer of the disclosure may comprise a consensus nucleic acid sequence of 5'-ACGGGUAG-3'. In some cases, an anti-IL8 aptamer of the disclosure may comprise a consensus nucleic acid sequence of 5'-UACGG-GUAGA-3' (SEQ ID NO: 777). In some cases, an anti-IL8 aptamer of the disclosure may comprise a consensus nucleic acid sequence of 5'-UACGGGUAGA-3' (SEQ ID NO: 778). In some cases, an anti-IL8 aptamer of the disclosure may comprise a consensus nucleic acid sequence of 5'-UACGG-GUAGU-3' (SEQ ID NO: 779). In some cases, an anti-IL8 aptamer of the disclosure may comprise a consensus nucleic acid sequence of 5'-WYGGKNDG-3', where W is A or U; Y is C or U; K is G or U; N is A, C, G, or U; and D is A, G, or U. In some cases, an anti-IL8 aptamer of the disclosure may comprise a consensus nucleic acid sequence of 5'-UWYGGKNDGA-3' (SEQ ID NO: 780), where W is A or U; Y is C or U; K is G or U; N is A, C, G, or U; and D is A, G, or U. In some cases, an anti-IL8 aptamer of the disclosure may comprise a consensus nucleic acid sequence of 5'-UWYGGKNDGU-3' (SEQ ID NO: 781), where W is A or U; Y is C or U; K is G or U; N is A, C, G, or U; and D is A, G, or U. In some cases, an anti-IL8 aptamer of the disclosure may comprise a consensus nucleic acid sequence of 5'-DNNRGGNWGH-3' (SEQ ID NO: 782), where D is A, G, or U; N is A, C, G, or U; R is A or G; W is A or U; and His A, C, or U. In some cases, an anti-IL8 aptamer of the disclosure may comprise a consensus nucleic acid sequence of 5'-DNNGGGNWGH-3' (SEQ ID NO: 783), where D is A, G, or U; N is A, C, G, or U; W is A or U; and His A, C, or U. In some cases, an anti-IL8 aptamer of the disclosure may comprise a consensus nucleic acid sequence of 5'-HNGGG-NAGW-3', where His A, C, or U; N is A, C, G, or U; and W is A or U. In some cases, an anti-IL8 aptamer of the disclosure may comprise a consensus nucleic acid sequence of 5'-NNUSANDDNAGWDDNNRGGNWGHGUGD-HHNSANN-3' (SEQ ID NO: 784), where N is A, C, G, or U; S is G or C; D is A, G, or U; W is A or U; R is A or G; and His A, C, or U. In some cases, an anti-IL8 aptamer of the disclosure may comprise a consensus nucleic acid sequence of 5'-NNUSANDDNAGWDHNGGG-NAGWGUGDHHNSANN-3' (SEQ ID NO: 785), where N is A, C, G, or U; S is G or C; D is A, G, or U; W is A or U; H is A, C, or U; and S is G or C. In some cases, an anti-IL8 aptamer of the disclosure may comprise a consensus nucleic acid sequence of 5'-NNYVANDDNWGWDDNNRG-KNNGHGUGNHHNVRNN-3' (SEQ ID NO: 786), where Nis A, C, G, or U; Y is C or U; V is A, C, or G; D is A, G, or U; W is A or U; R is A or G; K is G or U; and His A, C, or U.

In some cases, an anti-IL8 aptamer of the disclosure may comprise consensus nucleic acid sequence of 5'-HNNNNNGGGDDDNGNGDGDNGGGUKNNNNHN-3' (SEQ ID NO: 787), where His A, C, or U; N is A, C, G, or U; D is A, G, or U; and K is G or U. In some cases, an anti-IL8 aptamer of the disclosure may comprise a consensus nucleic acid sequence of 5'-HNNNNNCGGGADDNG-NGDGDNGGGUKNNNNHN-3' (SEQ ID NO: 788), where H is A, C, or U; Nis A, C, G, or U; D is A, G, or U; and K is G or U. In some cases, an anti-IL8 aptamer of the disclosure may comprise a consensus nucleic acid sequence of 5'-NDNNNHGGGARANGNGAGANGGGUDRN-NNHN-3' (SEQ ID NO: 789), where N is A, C, G, or U; D is A, G, or U; His A, C, or U; and R is A or G. In some cases, an anti-IL8 aptamer of the disclosure may comprise a consensus nucleic acid sequence of 5'-NNNNNNGGGDDDNGNGDGDNGGGUDNNNNNN-3' (SEQ ID NO: 790), where N is A, C, G, or U; and D is A, G, or U.

Anti-IL8 Compositions

In some aspects, the disclosure provides anti-IL8 compositions that inhibit a function associated with IL8. The anti-IL8 compositions may include one or more anti-IL8 aptamers that bind to specific regions of IL8 with high specificity and high affinity. In some cases, the anti-IL8 compositions may include one or more anti-IL8 aptamers that bind to a region of IL8 that includes the N-terminal domain of IL8, or a portion thereof. The N-terminal domain of IL8 may include any one or more of residues 2-6 of IL8-72 (SEQ ID NO: 2). In some cases, the anti-IL8 compositions may include one or more anti-IL8 aptamers that bind to a region of IL8 that includes the hydrophobic pocket of IL8, or a portion thereof. The hydrophobic pocket of IL8 may include any one or more of residues 12-18, F21, 122, 140, L43, R47, and L49 of IL8-72 (SEQ ID NO: 2). In some cases, the anti-IL8 compositions may include one or more anti-IL8 aptamers that bind to a region of IL8 that includes the N-loop of IL8, or a portion thereof. The N-loop of IL8 may include any one or more of residues 7-11 of IL8-72 (SEQ ID NO: 2). In some cases, the anti-IL8 compositions may include one or more anti-IL8 aptamers that bind to a region of IL8 that includes the GAG binding site of IL8, or a portion thereof. The GAG binding site of IL8 may include any one or more of residues H18, K20, R60, K64, K67, and R68 of IL8-72 (SEQ ID NO: 2). In some cases, the anti-IL8 compositions may include one or more anti-IL8 aptamers that prevent or reduce binding of IL8 with CXCR1, CXCR2, or both. Additionally or alternatively, the anti-IL8 compositions may include one or more anti-IL8 aptamers that bind to a region of IL8 such that a molecule conjugated to the anti-IL8 aptamer (e.g., a polyethylene glycol polymer) is positioned in a manner such that the conjugate itself may prevent or reduce interaction with CXCR1, CXCR2, or both. In such cases, the anti-IL8 aptamer may bind to IL8 at a region that is not itself important for interaction with CXCR1, CXCR2, or both.

Anti-IL8 Aptamers

In some aspects, anti-IL8 aptamers of the disclosure may block the interaction of IL8 with CXCR1, may block the interaction of IL8 with CXCR2, or both. In some aspects, anti-IL8 aptamers of the disclosure may prevent neutrophil activation and chemotaxis. In some cases, anti-IL8 aptamers of the disclosure may target the receptor interaction sites in the N-terminal domain of IL8. In some cases, anti-IL8 aptamers of the disclosure may target the hydrophobic cleft of IL8. In some cases, anti-IL8 aptamers of the disclosure may bind to sites on IL8 that force global conformational changes in the protein, thereby disrupting CXCR1 binding, CXCR2 binding, or both. In some aspects, an aptamer of the disclosure may bind to and inhibit IL8, wherein the aptamer comprises a nucleic acid sequence that selectively binds to an epitope of IL8, wherein the epitope is not a GAG binding site. In some aspects, an aptamer of the disclosure may bind to and inhibit IL8, wherein the aptamer comprises a nucleic acid sequence that selectively binds to an N-terminal domain of IL8, a hydrophobic pocket of IL8, an N-loop of IL8, or any combination thereof. In some aspects, an aptamer of the disclosure may bind to and inhibit IL8, wherein the aptamer comprises a nucleic acid sequence that selectively binds to a GAG binding site of IL8, wherein the nucleic acid sequence does not comprise any one of SEQ ID NOS: 759-762. In some aspects, an aptamer of the disclosure may bind to and inhibit IL8, wherein at least 75% of the aptamer remains bound to IL8 in a presence of 10 μM heparan sulphate.

In some cases, anti-IL8 aptamers of the disclosure may bind the N-terminal domain of IL8, or a portion thereof. The N-terminal may include any one or more of residues 2-6 of IL8-72 (SEQ ID NO: 2). Without wishing to be bound by theory, aptamers that bind to the N-terminal domain of IL8, or a portion thereof, may inhibit or reduce the interaction of the ELR triad of IL8 with the extracellular loops of receptors CXCR1, CXCR2, or both. In some cases, anti-IL8 aptamers that bind to the N-terminal domain of IL8, or a portion thereof, may prevent or reduce the association of IL8 with CXCR1, CXCR2, or both. In some cases, anti-IL8 aptamers that bind the N-terminal domain of IL8, or a portion thereof, may inhibit or reduce IL8-induced $Ca^{2+}$ mobilization in cells expressing CXCR1 receptors, CXCR2 receptors, or both (see, Example 5). In some cases, anti-IL8 aptamers that bind the N-terminal domain of IL8, or a portion thereof, may inhibit or reduce IL8-induced neutrophil migration in a neutrophil migration assay (see, Examples 6 and 18). In some cases, anti-IL8 aptamers that bind the N-terminal domain of IL8, or a portion thereof, may inhibit or reduce IL8-induced angiogenesis as assessed in an endothelial cell tube formation assay (see, Example 19). In some cases, anti-IL8 aptamers that bind the N-terminal domain of IL8, or a portion thereof, may block or reduce association of IL8 with CXCR1, CXCR2, or both, in cell-based receptor binding assays (see, Examples 4 and 17).

In some cases, anti-IL8 aptamers of the disclosure may bind to the hydrophobic pocket of IL8, or a portion thereof. Without wishing to be bound by theory, such aptamers may block the interaction of the CXCR1 N-terminal domain with the IL8 residues surrounding the hydrophobic pocket, may block the interaction of the CXCR2 N-terminal domain with the IL8 residues surrounding the hydrophobic pocket, or both. The hydrophobic pocket of IL8 may include any one or more of residues from the N-loop (residues 12-18) of IL8-72 (SEQ ID NO: 2), F21 from the short turn between the N-loop and the first β-strand of IL8-72 (SEQ ID NO: 2), 122 from the first β-strand of IL8-72 (SEQ ID NO: 2), 140 and L43 from the second β-strand of IL8-72 (SEQ ID NO: 2), R47 from the loop between the second and third β-strand of IL8-72 (SEQ ID NO: 2), and L49 from the third β-strand of IL8-72 (SEQ ID NO: 2). Anti-IL8 aptamers that bind to the hydrophobic pocket of IL8, or a portion thereof, may bind to any one or more of residues 12-18, F21, 122, 140, L43, R47, and L49 of IL8-72 (SEQ ID NO: 2). In some cases, anti-IL8 aptamers that bind to the hydrophobic pocket of IL8, or a portion thereof, may prevent or reduce binding of IL8 to CXCR1, CXCR2, or both, and may prevent or reduce signaling pathways downstream of CXCR1, CXCR2, or both. In some cases, anti-IL8 aptamers that bind to the hydrophobic pocket of IL8, or a portion thereof, may inhibit or reduce IL8-induced $Ca^{2+}$ mobilization in cells expressing CXCR1 receptors, CXCR2 receptors, or both (see, Example 5). In some cases, anti-IL8 aptamers that bind to the hydrophobic pocket of IL8, or a portion thereof, may inhibit or reduce IL8-induced neutrophil migration in a neutrophil migration assay (see, Examples 6 and 18). In some cases, anti-IL8 aptamers that bind to the hydrophobic pocket of IL8, or a portion thereof, may inhibit or reduce IL8-induced angiogenesis as assessed in an endothelial cell tube formation assay (see, Example 19). In some cases, anti-IL8 aptamers that bind to the hydrophobic pocket of IL8, or a portion thereof, may block or reduce the association of IL8 with CXCR1, CXCR2, or both in cell-based receptor binding assays (see Examples 4 and 17). In some cases, anti-IL8 aptamers that bind to the hydrophobic pocket of IL8, or a portion thereof, may compete with N-terminal peptides of CXCR1 (for example: MSNITDPQMWDFDDLNFTGMP-PADEDYSPCMLETETLNK (SEQ ID NO: 791)) or CXCR2 (for example: MESDSFEDFWKGEDLSNYSYS-STLPPFLLDAAPCEPE (SEQ ID NO: 792)), which may occupy this portion of IL8 in a competition binding assay, such as performed using TR-FRET.

In some cases, anti-IL8 aptamers of the disclosure may bind to the N-loop of IL8, or a portion thereof. The N-loop of IL8 may include any one or more of residues 7-11 of IL8-72 (SEQ ID NO: 2). In some cases, these residues may include two Cys residues which may be involved in forming disulfide bonds and may maintain the conformation of IL8. Without wishing to be bound by theory, binding of anti-IL8 aptamers to these residues may change the presentation of the ELR triad and may affect the conformation of the remainder of the N-loop (which forms part of the hydrophobic pocket). In some cases, such aptamers may inhibit the ELR triad from interacting with the extracellular loops of the receptors. In some cases, such aptamers may block the interaction of the CXCR1 N-terminal domain, the CXCR2 N-terminal domain, or both, with the hydrophobic pocket of IL8. In some cases, such aptamers may block or reduce binding of IL8 to CXCR1, CXCR2, or both, and may reduce or prevent downstream signaling of CXCR1, CXCR2, or both. In some cases, anti-IL8 aptamers that bind to the N-loop of IL8, or a portion thereof, may inhibit or reduce IL8-induced $Ca^{2+}$ mobilization in cells expressing CXCR1 receptors, CXCR2 receptors, or both (see, Example 5). In some cases, anti-IL8 aptamers that bind to the N-loop of IL8, or a portion thereof, may inhibit or reduce IL8-induced neutrophil migration in a neutrophil migration assay (see, Examples 6 and 18). In some cases, anti-IL8 aptamers that bind to the N-loop of IL8, or a portion thereof, may inhibit or reduce IL8-induced angiogenesis as assessed in an endothelial cell tube formation assay (see, Example 19). In some cases, anti-IL8 aptamers that bind to the N-loop of IL8, or a portion thereof, may block or reduce association of IL8 with CXCR1, CXCR2, or both in cell-based receptor binding assays (see, Examples 4 and 17). In some cases, anti-IL8 aptamers that bind to the N-loop of IL8, or a portion thereof, may compete with N-terminal peptides of CXCR1 or CXCR2 which may occupy this portion of IL8 in a competition binding assay, such as performed using TR-FRET.

In some cases, anti-IL8 aptamers of the disclosure may bind to the GAG binding site of IL8, or a portion thereof. The GAG binding site may comprise any one or more of the N-loop residue H18, residue K20 between the N-loop and the first β-strand, C-helix residue R60, C-helix residue K64, C-helix residue K67, C-helix residue R68, and any combination thereof, of IL8-72 (SEQ ID NO: 2). Without wishing to be bound by theory, anti-IL8 aptamers that bind to the GAG binding site of IL8, or a portion thereof, may disrupt GAG binding and may cause conformational changes in IL8 to destabilize the hydrophobic pocket and the N terminal domain. In some cases, anti-IL8 aptamers that bind to the GAG binding site of IL8, or a portion thereof, may inhibit or reduce binding of IL8 to CXCR1, CXCR2, or both. In some cases, anti-IL8 aptamers that bind to the GAG binding site of IL8, or a portion thereof, may be detected using a heparinized plate-based IL8 enzyme-linked immunosorbent assay (ELISA), in which case the binding may be reduced as compared to a similar assay format in which non-heparinized plates are used. In some cases, anti-IL8 aptamers that bind to the GAG binding site of IL8, or a portion thereof, may compete with heparan sulfate for binding to IL8 in competition binding assay, such as performed using TR-FRET. In some cases, anti-IL8 aptamers that bind to the GAG binding site of IL8, or a portion thereof, may inhibit or reduce IL8-induced $Ca^{2+}$ mobilization in cells expressing CXCR1 receptors, CXCR2 receptors, or both (see, Example 5). In some cases, anti-IL8 aptamers that bind to the GAG binding site of IL8, or a portion thereof, may inhibit IL8-induced neutrophil migration in a neutrophil migration assay (see, Examples 6 and 18). In some cases, anti-IL8 aptamers that bind to the GAG binding site of IL8, or a portion thereof, may inhibit or reduce IL8-induced angiogenesis as assessed in an endothelial cell tube formation assay (see, Example 19). In some cases, anti-IL8 aptamers that bind to the GAG binding site of IL8, or a portion thereof, may block or reduce the association of IL8 with CXCR1, CXCR2, or both in cell-based receptor binding assays (see, Examples 4 and 17).

In some cases, an anti-IL8 aptamer of the disclosure may bind to a region of IL8 such that a molecule conjugated to the anti-IL8 aptamer (e.g., a polyethylene glycol polymer) is positioned so that the conjugate itself may prevent or reduce interaction with CXCR1, CXCR2, or both. In such cases, the anti-IL8 aptamer may bind to IL8 at a region that is not itself important for interaction with CXCR1, CXCR2, or both.

In some cases, the compositions of the disclosure provide anti-IL8 aptamers that bind near the N-terminus or the N-loop of IL8. In some cases, the compositions of the disclosure include anti-IL8 aptamers that are selected by a process which promotes development of aptamers that bind near the N-terminus or the N-loop of IL8. In one example, such processes may include performing aptamer selection in the presence of heparan sulfate to block the charged C-terminus of IL8. In other examples, aptamer selection may be performed in the presence of any one of the following, without limitation: single-stranded DNA (ssDNA), dextran sulfate, dermatan sulfate, chondroitin sulfate, hyaluronic acid, and tRNA. In some cases, aptamer selection may be performed in the presence of a glycosaminoglycan (GAG). In some cases, aptamer selection may be performed in the presence of IL8 protein immobilized on a GAG-functionalized surface.

In other examples, such processes may include sterically occluding the C-terminus of IL8 during the aptamer selection process. In some cases, an IL8 protein chimera may be used in which a different protein is attached to the C-terminus of IL8, thereby driving selection of aptamers to the N-terminus or the N-loop of IL8. In some cases, the IL8 protein chimera may include a mucin stalk attached to the C-terminus of IL8. In some cases, the IL8 protein chimera may include any one of the following, without limitation: Fc domain, maltose-binding protein (MBP), glutathione S-transferase (GST), thioredoxin (TRX), NUS A, ubiquitin (Ub), and SUMO tag.

Binding Affinity

The dissociation constant ($K_d$) can be used to describe the affinity of an aptamer for a target (or to describe how tightly the aptamer binds to the target) or to describe the affinity of an aptamer for a specific epitope of a target. The dissociation constant may be defined as the molar concentration at which half of the binding sites of a target are occupied by the aptamer. Thus, the smaller the $K_d$, the tighter the binding of the aptamer to its target. In some cases, an anti-IL8 aptamer of the disclosure may have a $K_d$ for IL8 protein of less than about 1000 nM, for example, less than about 500 nM, less than about 100 nM, less than about 50 nM, less than about 10 nM, less than about 5 nM, less than about 1 nM, less than about 0.5 nM, less than about 0.1 nM, or less than about 0.05 nM, as measured by a flow cytometry assay (see, Example 2), a TR-FRET assay (see, Examples 3 and 16), or a competition TR-FRET assay (see, Example 15). In some cases, an anti-IL8 aptamer may have a dissociation constant ($K_d$) for IL8 protein of less than about 50 nM, as measured by a flow cytometry assay (see, Example 2), a TR-FRET assay (see, Examples 3 and 16), or a competition TR-FRET assay (see, Example 15). In some cases, an anti-IL8 aptamer may have a dissociation constant ($K_d$) for IL8 protein of less than about 25 nM, as measured by a flow cytometry assay (see, Example 2), a TR-FRET assay (see, Examples 3 and 16), or a competition TR-FRET assay (see, Example 15). In some cases, an anti-IL8 aptamer may have a dissociation constant ($K_d$) for IL8 protein of less than about 10 nM, as measured by a flow cytometry assay (see, Example 2), a TR-FRET assay (see, Examples 3 and 16), or a competition TR-FRET assay (see, Example 15). In some cases, an anti-IL8 aptamer may have a dissociation constant ($K_d$) for IL8 protein of less than about 5 nM, as measured by a flow cytometry assay (see, Example 2), a TR-FRET assay (see, Examples 3 and 16), or a competition TR-FRET assay (see, Example 15). In some cases, an anti-IL8 aptamer may have a dissociation constant ($K_d$) for IL8 protein of less than about 1 nM, as measured by a flow cytometry assay (see, Example 2), a TR-FRET assay (see, Examples 3 and 16), or a competition TR-FRET assay (see, Example 15). In some cases, an anti-IL8 aptamer may have a dissociation constant ($K_d$) for IL8 protein of less than about 0.5 nM, as measured by a flow cytometry assay (see, Example 2), a TR-FRET assay (see, Examples 3 and 16), or a competition TR-FRET assay (see, Example 15). In some cases, an anti-IL8 aptamer may have a dissociation constant ($K_d$) for IL8 protein of less than about 0.1 nM, as measured by a flow cytometry assay (see, Example 2), a TR-FRET assay (see, Examples 3 and 16), or a competition TR-FRET assay (see, Example 15). In some cases, an anti-IL8 aptamer may have a dissociation constant ($K_d$) for IL8 protein of less than about 0.05 nM, as measured by a flow cytometry assay (see, Example 2), a TR-FRET assay (see, Examples 3 and 16), or a competition TR-FRET assay (see, Example 15). In some cases, the aptamer may bind to any region of IL8 described herein, or a portion thereof, with a $K_d$ of less than about 1000 nM, for example, less than about 500 nM, less than about 100 nM, less than about 50 nM, less than about 25 nM, less than about 10 nM, less than about 5 nM, less than about 1 nM, less than about 0.5 nM, less than about 0.1 nM, or less than about 0.05 nM, as measured by a flow cytometry assay (see, Example 2), a TR-FRET assay (see, Examples 3 and 16), or a competition TR-FRET assay (see, Example 15). In some cases, the aptamer may bind to the N-terminal domain of IL8, the hydrophobic pocket of IL8, the N-loop of IL8, the GAG binding site of IL8, or portions thereof, with a $K_d$ of less than about 1000 nM, for example, less than about 500 nM, less than about 100 nM, less than about 50 nM, less than about 25 nM, less than about 10 nM, less than about 5 nM, less than about 1 nM, less than about 0.5 nM, less than about 0.1 nM, or less than about 0.05 nM, as measured by a flow cytometry assay (see, Example 2), a TR-FRET assay (see, Examples 3 and 16), or a competition TR-FRET assay (see, Example 15). In some cases, the anti-IL8 aptamer may bind to the N-terminal domain of IL8, the hydrophobic pocket of IL8, the N-loop of IL8, the GAG binding site of IL8, or portions thereof, with a $K_d$ from about 0.05 nM to about 5 nM, as measured by a flow cytometry assay (see, Example 2), a TR-FRET assay (see, Examples 3 and 16), or a competition TR-FRET assay (see, Example 15).

In some cases, the aptamers disclosed herein may bind to a region of IL8, such as the N-terminal domain of IL8, the hydrophobic pocket of IL8, the N-loop of IL8, the GAG binding site of IL8, or portions thereof, with a $K_d$ of less than about 50 nM as measured by a flow cytometry assay (see, Example 2), a TR-FRET assay (see, Examples 3 and 16), or a competition TR-FRET assay (see, Example 15), and may have an $IC_{50}$ of less than about 50 nM as measured by an IL8/CXCR1 competition assay (see, Examples 4 and 17), an IL8-mediated intracellular calcium signaling assay (see, Example 5), an IL8-mediated neutrophil migration assay (see, Examples 6 and 18), or an IL8-mediated endothelial cell tube formation assay (see, Example 19). In some cases, the aptamers disclosed herein may bind to a region of IL8, such as the N-terminal domain of IL8, the hydrophobic pocket of IL8, the N-loop of IL8, the GAG binding site of IL8, or portions thereof, with a $K_d$ of less than about 50 nM as measured by a flow cytometry assay (see, Example 2), a TR-FRET assay (see, Examples 3 and 16), or a competition TR-FRET assay (see, Example 15), and may have an $IC_{50}$ of less than about 10 nM as measured by an IL8/CXCR1 competition assay (see, Examples 4 and 17), an IL8-mediated intracellular calcium signaling assay (see, Example 5), an IL8-mediated neutrophil migration assay (see, Examples 6 and 18), or an IL8-mediated endothelial cell tube formation assay (see, Example 19). In some cases, the aptamers disclosed herein may bind to a region of IL8, such as the N-terminal domain of IL8, the hydrophobic pocket of IL8, the N-loop of IL8, the GAG binding site of IL8, or portions thereof, with a $K_d$ of less than about 50 nM as measured by a flow cytometry assay (see, Example 2), a TR-FRET assay (see, Examples 3 and 16), or a competition TR-FRET assay (see, Example 15), and may have an $IC_{50}$ of less than about 5 nM as measured by an IL8/CXCR1 competition assay (see, Examples 4 and 17), an IL8-mediated intracellular calcium signaling assay (see, Example 5), an IL8-mediated neutrophil migration assay (see, Examples 6 and 18), or an IL8-mediated endothelial cell tube formation assay (see, Example 19). In some cases, the aptamers disclosed herein may bind to a region of IL8, such as the N-terminal domain of IL8, the hydrophobic pocket of IL8, the N-loop of IL8, the GAG binding site of IL8, or portions thereof, with a $K_d$ of less than about 50 nM as measured by a flow cytometry assay (see, Example 2), a TR-FRET assay (see, Examples 3 and 16), or a competition TR-FRET assay (see, Example 15), and may have an $IC_{50}$ of less than about 1 nM as measured by an IL8/CXCR1 competition assay (see, Examples 4 and 17), an IL8-mediated intracellular calcium signaling assay (see, Example 5), an IL8-mediated neutrophil migration assay (see, Examples 6 and 18), or an IL8-mediated endothelial cell tube formation assay (see, Example 19). In some cases, the aptamers disclosed herein may bind to a region of IL8, such as the N-terminal domain of IL8, the hydrophobic pocket of IL8, the N-loop of IL8, the GAG binding site of IL8, or portions thereof, with a $K_d$ of less than about 50 nM as measured by a flow cytometry assay (see, Example 2), a TR-FRET assay (see, Examples 3 and 16), or a competition TR-FRET assay (see, Example 15), and may have an $IC_{50}$ of less than about 0.5 nM as measured by an IL8/CXCR1 competition assay (see, Examples 4 and 17), an IL8-mediated intracellular calcium signaling assay (see, Example 5), an IL8-mediated neutrophil migration assay (see, Examples 6 and 18), or an IL8-mediated endothelial cell tube formation assay (see, Example 19). In some cases, the aptamers disclosed herein may bind to a region of IL8, such as the N-terminal domain of IL8, the hydrophobic pocket of IL8, the N-loop of IL8, the GAG binding site of IL8, or portions thereof, with a $K_d$ of less than about 50 nM as measured by a flow cytometry assay (see, Example 2), a TR-FRET assay (see, Examples 3 and 16), or a competition TR-FRET assay (see, Example 15), and may have an $IC_{50}$ of less than about 0.1 nM as measured by an IL8/CXCR1 competition assay (see, Examples 4 and 17), an IL8-mediated intracellular calcium signaling assay (see, Example 5), an IL8-mediated neutrophil migration assay (see, Examples 6 and 18), or an IL8-mediated endothelial cell tube formation assay (see, Example 19).

In some cases, the aptamers disclosed herein may bind to a region of IL8, such as the N-terminal domain of IL8, the hydrophobic pocket of IL8, the N-loop of IL8, the GAG binding site of IL8, or portions thereof, with a $K_d$ of less than about 10 nM as measured by a flow cytometry assay (see, Example 2), a TR-FRET assay (see, Examples 3 and 16), or a competition TR-FRET assay (see, Example 15), and may have an $IC_{50}$ of less than about 50 nM as measured by an IL8/CXCR1 competition assay (see, Examples 4 and 17), an IL8-mediated intracellular calcium signaling assay (see, Example 5), an IL8-mediated neutrophil migration assay (see, Examples 6 and 18), or an IL8-mediated endothelial cell tube formation assay (see, Example 19). In some cases, the aptamers disclosed herein may bind to a region of IL8, such as the N-terminal domain of IL8, the hydrophobic pocket of IL8, the N-loop of IL8, the GAG binding site of IL8, or portions thereof, with a $K_d$ of less than about 10 nM as measured by a flow cytometry assay (see, Example 2), a TR-FRET assay (see, Examples 3 and 16), or a competition TR-FRET assay (see, Example 15), and may have an $IC_{50}$ of less than about 10 nM as measured by an IL8/CXCR1 competition assay (see, Examples 4 and 17), an IL8-mediated intracellular calcium signaling assay (see, Example 5), an IL8-mediated neutrophil migration assay (see, Examples 6 and 18), or an IL8-mediated endothelial cell tube formation assay (see, Example 19). In some cases, the aptamers disclosed herein may bind to a region of IL8, such as the N-terminal loop of IL8, the hydrophobic pocket of IL8, the N-loop of IL8, the GAG binding site of IL8, or portions thereof, with a $K_d$ of less than about 10 nM as measured by a flow cytometry assay (see, Example 2), a TR-FRET assay (see, Examples 3 and 16), or a competition TR-FRET assay (see, Example 15), and may have an $IC_{50}$ of less than about 5 nM as measured by an IL8/CXCR1 competition assay (see, Examples 4 and 17), an IL8-mediated intracellular calcium signaling assay (see, Example 5), an IL8-mediated neutrophil migration assay (see, Examples 6 and 18), or an IL8-mediated endothelial cell tube formation assay (see, Example 19). In some cases, the aptamers disclosed herein may bind to a region of IL8, such as the N-terminal loop of IL8, the hydrophobic pocket of IL8, the N-loop of IL8, the GAG binding site of IL8, or portions thereof, with a $K_d$ of less than about 10 nM as measured by a flow cytometry assay (see, Example 2), a TR-FRET assay (see, Examples 3 and 16), or a competition TR-FRET assay (see, Example 15), and may have an $IC_{50}$ of less than about 1 nM as measured by an IL8/CXCR1 competition assay (see, Examples 4 and 17), an IL8-mediated intracellular calcium signaling assay (see, Example 5), an IL8-mediated neutrophil migration assay (see, Examples 6 and 18), or an IL8-mediated endothelial cell tube formation assay (see, Example 19). In some cases, the aptamers disclosed herein may bind to a region of IL8, such as the N-terminal loop of IL8, the hydrophobic pocket of IL8, the N-loop of IL8, the GAG binding site of IL8, or portions thereof, with a $K_d$ of less than about 10 nM as measured by a flow cytometry assay (see, Example 2), a TR-FRET assay (see, Examples 3 and 16), or a competition TR-FRET assay (see, Example 15), and may have an $IC_{50}$ of less than about 0.5 nM as measured by an IL8/CXCR1 competition assay (see, Examples 4 and 17), an IL8-mediated intracellular calcium signaling assay (see, Example 5), an IL8-mediated neutrophil migration assay (see, Examples 6 and 18), or an IL8-mediated endothelial cell tube formation assay (see, Example 19). In some cases, the aptamers disclosed herein may bind to a region of IL8, such as the N-terminal loop of IL8, the hydrophobic pocket of IL8, the N-loop of IL8, the GAG binding site of IL8, or portions thereof, with a $K_d$ of less than about 10 nM as measured by a flow cytometry assay (see, Example 2), a TR-FRET assay (see, Examples 3 and 16), or a competition TR-FRET assay (see, Example 15), and may have an $IC_{50}$ of less than about 0.1 nM as measured by an IL8/CXCR1 competition assay (see, Examples 4 and 17), an IL8-mediated intracellular calcium signaling assay (see, Example 5), an IL8-mediated neutrophil migration assay (see, Examples 6 and 18), or an IL8-mediated endothelial cell tube formation assay (see, Example 19).

In some cases, the aptamers disclosed herein may bind to a region of IL8, such as the N-terminal domain of IL8, the hydrophobic pocket of IL8, the N-loop of IL8, the GAG binding site of IL8, or portions thereof, with a $K_d$ of less than about 5 nM as measured by a flow cytometry assay (see, Example 2), a TR-FRET assay (see, Examples 3 and 16), or a competition TR-FRET assay (see, Example 15), and may have an $IC_{50}$ of less than about 50 nM as measured by an IL8/CXCR1 competition assay (see, Examples 4 and 17), an IL8-mediated intracellular calcium signaling assay (see, Example 5), an IL8-mediated neutrophil migration assay (see, Examples 6 and 18), or an IL8-mediated endothelial cell tube formation assay (see, Example 19). In some cases, the aptamers disclosed herein may bind to a region of IL8, such as the N-terminal domain of IL8, the hydrophobic pocket of IL8, the N-loop of IL8, the GAG binding site of IL8, or portions thereof, with a $K_d$ of less than about 5 nM as measured by a flow cytometry assay (see, Example 2), a TR-FRET assay (see, Examples 3 and 16), or a competition TR-FRET assay (see, Example 15), and may have an $IC_{50}$ of less than about 10 nM as measured by an IL8/CXCR1 competition assay (see, Examples 4 and 17), an IL8-mediated intracellular calcium signaling assay (see, Example 5), an IL8-mediated neutrophil migration assay (see, Examples 6 and 18), or an IL8-mediated endothelial cell tube formation assay (see, Example 19). In some cases, the aptamers disclosed herein may bind to a region of IL8, such as the N-terminal domain of IL8, the hydrophobic pocket of IL8, the N-loop of IL8, or the GAG binding site of IL8, or portions thereof, with a $K_d$ of less than about 5 nM as measured by a flow cytometry assay (see, Example 2), a TR-FRET assay (see, Examples 3 and 16), or a competition TR-FRET assay (see, Example 15), and may have an $IC_{50}$ of less than about 5 nM as measured by an IL8/CXCR1 competition assay (see, Examples 4 and 17), an IL8-mediated intracellular calcium signaling assay (see, Example 5), an IL8-mediated neutrophil migration assay (see, Examples 6 and 18), or an IL8-mediated endothelial cell tube formation assay (see, Example 19). In some cases, the aptamers disclosed herein may bind to a region of IL8, such as the N-terminal domain of IL8, the hydrophobic pocket of IL8, the N-loop of IL8, or the GAG binding site of IL8, or portions thereof, with a $K_d$ of less than about 5 nM as measured by a flow cytometry assay (see, Example 2), a TR-FRET assay (see, Examples 3 and 16), or a competition TR-FRET assay (see, Example 15), and may have an $IC_{50}$ of less than about 1 nM as measured by an IL8/CXCR1 competition assay (see, Examples 4 and 17), an IL8-mediated intracellular calcium signaling assay (see, Example 5), an IL8-mediated neutrophil migration assay (see, Examples 6 and 18), or an IL8-mediated endothelial cell tube formation assay (see, Example 19). In some cases, the aptamers disclosed herein may bind to a region of IL8, such as the N-terminal domain of IL8, the hydrophobic pocket of IL8, the N-loop of IL8, or the GAG binding site of IL8, or portions thereof, with a $K_d$ of less than about 5 nM as measured by a flow cytometry assay (see, Example 2), a TR-FRET assay (see, Examples 3 and 16), or a competition TR-FRET assay (see, Example 15), and may have an $IC_{50}$ of less than about 0.5 nM as measured by an IL8/CXCR1 competition assay (see, Examples 4 and 17), an IL8-mediated intracellular calcium signaling assay (see, Example 5), an IL8-mediated neutrophil migration assay (see, Examples 6 and 18), or an IL8-mediated endothelial cell tube formation assay (see, Example 19). In some cases, the aptamers disclosed herein may bind to a region of IL8, such as the N-terminal domain of IL8, the hydrophobic pocket of IL8, the N-loop of IL8, or the GAG binding site of IL8, or portions thereof, with a $K_d$ of less than about 5 nM as measured by a flow cytometry assay (see, Example 2), a TR-FRET assay (see, Examples 3 and 16), or a competition TR-FRET assay (see, Example 15), and may have an $IC_{50}$ of less than about 0.1 nM as measured by an IL8/CXCR1 competition assay (see, Examples 4 and 17), an IL8-mediated intracellular calcium signaling assay (see, Example 5), an IL8-mediated neutrophil migration assay (see, Examples 6 and 18), or an IL8-mediated endothelial cell tube formation assay (see, Example 19).

In some cases, the aptamers disclosed herein may bind to a region of IL8, such as the N-terminal domain of IL8, the hydrophobic pocket of IL8, the N-loop of IL8, the GAG binding site of IL8, or portions thereof, with a $K_d$ of less than about 1 nM as measured by a flow cytometry assay (see, Example 2), a TR-FRET assay (see, Examples 3 and 16), or a competition TR-FRET assay (see, Example 15), and may have an $IC_{50}$ of less than about 50 nM as measured by an IL8/CXCR1 competition assay (see, Examples 4 and 17), an IL8-mediated intracellular calcium signaling assay (see, Example 5), an IL8-mediated neutrophil migration assay (see, Examples 6 and 18), or an IL8-mediated endothelial cell tube formation assay (see, Example 19). In some cases, the aptamers disclosed herein may bind to a region of IL8, such as the N-terminal domain of IL8, the hydrophobic pocket of IL8, the N-loop of IL8, the GAG binding site of IL8, or portions thereof, with a $K_d$ of less than about 1 nM as measured by a flow cytometry assay (see, Example 2), a TR-FRET assay (see, Examples 3 and 16), or a competition TR-FRET assay (see, Example 15), and may have an $IC_{50}$ of less than about 10 nM as measured by an IL8/CXCR1 competition assay (see, Examples 4 and 17), an IL8-mediated intracellular calcium signaling assay (see, Example 5), an IL8-mediated neutrophil migration assay (see, Examples 6 and 18), or an IL8-mediated endothelial cell tube formation assay (see, Example 19). In some cases, the aptamers disclosed herein may bind to a region of IL8, such as the N-terminal domain of IL8, the hydrophobic pocket of IL8, the N-loop of IL8, the GAG binding site of IL8, or portions thereof, with a $K_d$ of less than about 1 nM as measured by a flow cytometry assay (see, Example 2), a TR-FRET assay (see, Examples 3 and 16), or a competition TR-FRET assay (see, Example 15), and may have an $IC_{50}$ of less than about 5 nM as measured by an IL8/CXCR1 competition assay (see, Examples 4 and 17), an IL8-mediated intracellular calcium signaling assay (see, Example 5), an IL8-mediated neutrophil migration assay (see, Examples 6 and 18), or an IL8-mediated endothelial cell tube formation assay (see, Example 19). In some cases, the aptamers disclosed herein may bind to a region of IL8, such as the N-terminal domain of IL8, the hydrophobic pocket of IL8, the N-loop of IL8, the GAG binding site of IL8, or portions thereof, with a $K_d$ of less than about 1 nM as measured by a flow cytometry assay (see, Example 2), a TR-FRET assay (see, Examples 3 and 16), or a competition TR-FRET assay (see, Example 15), and may have an $IC_{50}$ of less than about 1 nM as measured by an IL8/CXCR1 competition assay (see, Examples 4 and 17), an IL8-mediated intracellular calcium signaling assay (see, Example 5), an IL8-mediated neutrophil migration assay (see, Examples 6 and 18), or an IL8-mediated endothelial cell tube formation assay (see, Example 19). In some cases, the aptamers disclosed herein may bind to a region of IL8, such as the N-terminal domain of IL8, the hydrophobic pocket of IL8, the N-loop of IL8, the GAG binding site of IL8, or portions thereof, with a $K_d$ of less than about 1 nM as measured by a flow cytometry assay (see, Example 2), a TR-FRET assay (see, Examples 3 and 16), or a competition TR-FRET assay (see, Example 15), and may have an $IC_{50}$ of less than about 0.5 nM as measured by an IL8/CXCR1 competition assay (see, Examples 4 and 17), an IL8-mediated intracellular calcium signaling assay (see, Example 5), an IL8-mediated neutrophil migration assay (see, Examples 6 and 18), or an IL8-mediated endothelial cell tube formation assay (see, Example 19). In some cases, the aptamers disclosed herein may bind to a region of IL8, such as the N-terminal domain of IL8, the hydrophobic pocket of IL8, the N-loop of IL8, the GAG binding site of IL8, or portions thereof, with a $K_d$ of less than about 1 nM as measured by a flow cytometry assay (see, Example 2), a TR-FRET assay (see, Examples 3 and 16), or a competition TR-FRET assay (see, Example 15), and may have an $IC_{50}$ of less than about 0.1 nM as measured by an IL8/CXCR1 competition assay (see, Examples 4 and 17), an IL8-mediated intracellular calcium signaling assay (see, Example 5), an IL8-mediated neutrophil migration assay (see, Examples 6 and 18), or an IL8-mediated endothelial cell tube formation assay (see, Example 19).

In some cases, the aptamers disclosed herein may bind to a region of IL8, such as the N-terminal domain of IL8, the hydrophobic pocket of IL8, the N-loop of IL8, the GAG binding site of IL8, or portions thereof, with a $K_d$ of less than about 0.5 nM as measured by a flow cytometry assay (see, Example 2), a TR-FRET assay (see, Examples 3 and 16), or a competition TR-FRET assay (see, Example 15), and may have an $IC_{50}$ of less than about 50 nM as measured by an IL8/CXCR1 competition assay (see, Examples 4 and 17), an IL8-mediated intracellular calcium signaling assay (see, Example 5), an IL8-mediated neutrophil migration assay (see, Examples 6 and 18), or an IL8-mediated endothelial cell tube formation assay (see, Example 19). In some cases, the aptamers disclosed herein may bind to a region of IL8, such as the N-terminal domain of IL8, the hydrophobic pocket of IL8, the N-loop of IL8, the GAG binding site of IL8, or portions thereof, with a $K_d$ of less than about 0.5 nM as measured by a flow cytometry assay (see, Example 2), a TR-FRET assay (see, Examples 3 and 16), or a competition TR-FRET assay (see, Example 15), and may have an $IC_{50}$ of less than about 10 nM as measured by an IL8/CXCR1 competition assay (see, Examples 4 and 17), an IL8-mediated intracellular calcium signaling assay (see, Example 5), an IL8-mediated neutrophil migration assay (see, Examples 6 and 18), or an IL8-mediated endothelial cell tube formation assay (see, Example 19). In some cases, the aptamers disclosed herein may bind to a region of IL8, such as the N-terminal domain of IL8, the hydrophobic pocket of IL8, the N-loop of IL8, the GAG binding site of IL8, or portions thereof, with a $K_d$ of less than about 0.5 nM as measured by a flow cytometry assay (see, Example 2), a TR-FRET assay (see, Examples 3 and 16), or a competition TR-FRET assay (see, Example 15), and may have an $IC_{50}$ of less than about 5 nM as measured by an IL8/CXCR1 competition assay (see, Examples 4 and 17), an IL8-mediated intracellular calcium signaling assay (see, Example 5), an IL8-mediated neutrophil migration assay (see, Examples 6 and 18), or an IL8-mediated endothelial cell tube formation assay (see, Example 19). In some cases, the aptamers disclosed herein may bind to a region of IL8, such as the N-terminal domain of IL8, the hydrophobic pocket of IL8, the N-loop of IL8, the GAG binding site of IL8, or portions thereof, with a $K_d$ of less than about 0.5 nM as measured by a flow cytometry assay (see, Example 2), a TR-FRET assay (see, Examples 3 and 16), or a competition TR-FRET assay (see, Example 15), and may have an $IC_{50}$ of less than about 1 nM as measured by an IL8/CXCR1 competition assay (see, Examples 4 and 17), an IL8-mediated intracellular calcium signaling assay (see, Example 5), an IL8-mediated neutrophil migration assay (see, Examples 6 and 18), or an IL8-mediated endothelial cell tube formation assay (see, Example 19). In some cases, the aptamers disclosed herein may bind to a region of IL8, such as the N-terminal domain of IL8, the hydrophobic pocket of IL8, the N-loop of IL8, the GAG binding site of IL8, or portions thereof, with a $K_d$ of less than about 0.5 nM as measured by a flow cytometry assay (see, Example 2), a TR-FRET assay (see, Examples 3 and 16), or a competition TR-FRET assay (see, Example 15), and may have an $IC_{50}$ of less than about 0.5 nM as measured by an IL8/CXCR1 competition assay (see, Examples 4 and 17), an IL8-mediated intracellular calcium signaling assay (see, Example 5), an IL8-mediated neutrophil migration assay (see, Examples 6 and 18), or an IL8-mediated endothelial cell tube formation assay (see, Example 19). In some cases, the aptamers disclosed herein may bind to a region of IL8, such as the N-terminal domain of IL8, the hydrophobic pocket of IL8, the N-loop of IL8, the GAG binding site of IL8, or portions thereof, with a $K_d$ of less than about 0.5 nM as measured by a flow cytometry assay (see, Example 2), a TR-FRET assay (see, Examples 3 and 16), or a competition TR-FRET assay (see, Example 15), and may have an $IC_{50}$ of less than about 0.1 nM as measured by an IL8/CXCR1 competition assay (see, Examples 4 and 17), an IL8-mediated intracellular calcium signaling assay (see, Example 5), an IL8-mediated neutrophil migration assay (see, Examples 6 and 18), or an IL8-mediated endothelial cell tube formation assay (see, Example 19).

In some cases, the aptamers disclosed herein may bind to a region of IL8, such as the N-terminal domain of IL8, the hydrophobic pocket of IL8, the N-loop of IL8, the GAG binding site of IL8, or portions thereof, with a $K_d$ of less than about 0.1 nM as measured by a flow cytometry assay (see, Example 2), a TR-FRET assay (see, Examples 3 and 16), or a competition TR-FRET assay (see, Example 15), and may have an $IC_{50}$ of less than about 50 nM as measured by an IL8/CXCR1 competition assay (see, Examples 4 and 17), an IL8-mediated intracellular calcium signaling assay (see, Example 5), an IL8-mediated neutrophil migration assay (see, Examples 6 and 18), or an IL8-mediated endothelial cell tube formation assay (see, Example 19). In some cases, the aptamers disclosed herein may bind to a region of IL8, such as the N-terminal domain of IL8, the hydrophobic pocket of IL8, the N-loop of IL8, the GAG binding site of IL8, or portions thereof, with a $K_d$ of less than about 0.1 nM as measured by a flow cytometry assay (see, Example 2), a TR-FRET assay (see, Examples 3 and 16), or a competition TR-FRET assay (see, Example 15), and may have an $IC_{50}$ of less than about 10 nM as measured by an IL8/CXCR1 competition assay (see, Examples 4 and 17), an IL8-mediated intracellular calcium signaling assay (see, Example 5), an IL8-mediated neutrophil migration assay (see, Examples 6 and 18), or an IL8-mediated endothelial cell tube formation assay (see, Example 19). In some cases, the aptamers disclosed herein may bind to a region of IL8, such as the N-terminal domain of IL8, the hydrophobic pocket of IL8, the N-loop of IL8, the GAG binding site of IL8, or portions thereof, with a $K_d$ of less than about 0.1 nM as measured by a flow cytometry assay (see, Example 2), a TR-FRET assay (see, Examples 3 and 16), or a competition TR-FRET assay (see, Example 15), and may have an $IC_{50}$ of less than about 5 nM as measured by an IL8/CXCR1 competition assay (see, Examples 4 and 17), an IL8-mediated intracellular calcium signaling assay (see, Example 5), an IL8-mediated neutrophil migration assay (see, Examples 6 and 18), or an IL8-mediated endothelial cell tube formation assay (see, Example 19). In some cases, the aptamers disclosed herein may bind to a region of IL8, such as the N-terminal domain of IL8, the hydrophobic pocket of IL8, the N-loop of IL8, the GAG binding site of IL8, or portions thereof, with a $K_d$ of less than about 0.1 nM as measured by a flow cytometry assay (see, Example 2), a TR-FRET assay (see, Examples 3 and 16), or a competition TR-FRET assay (see, Example 15), and may have an $IC_{50}$ of less than about 1 nM as measured by an IL8/CXCR1 competition assay (see, Examples 4 and 17), an IL8-mediated intracellular calcium signaling assay (see, Example 5), an IL8-mediated neutrophil migration assay (see, Examples 6 and 18), or an IL8-mediated endothelial cell tube formation assay (see, Example 19). In some cases, the aptamers disclosed herein may bind to a region of IL8, such as the N-terminal domain of IL8, the hydrophobic pocket of IL8, the N-loop of IL8, the GAG binding site of IL8, or portions thereof, with a $K_d$ of less than about 0.1 nM as measured by a flow cytometry assay (see, Example 2), a TR-FRET assay (see, Examples 3 and 16), or a competition TR-FRET assay (see, Example 15), and may have an $IC_{50}$ of less than about 0.5 nM as measured by an IL8/CXCR1 competition assay (see, Examples 4 and 17), an IL8-mediated intracellular calcium signaling assay (see, Example 5), an IL8-mediated neutrophil migration assay (see, Examples 6 and 18), or an IL8-mediated endothelial cell tube formation assay (see, Example 19). In some cases, the aptamers disclosed herein may bind to a region of IL8, such as the N-terminal domain of IL8, the hydrophobic pocket of IL8, the N-loop of IL8, the GAG binding site of IL8, or portions thereof, with a $K_d$ of less than about 0.1 nM as measured by a flow cytometry assay (see, Example 2), a TR-FRET assay (see, Examples 3 and 16), or a competition TR-FRET assay (see, Example 15), and may have an $IC_{50}$ of less than about 0.1 nM as measured by an IL8/CXCR1 competition assay (see, Examples 4 and 17), an IL8-mediated intracellular calcium signaling assay (see, Example 5), an IL8-mediated neutrophil migration assay (see, Examples 6 and 18), or an IL8-mediated endothelial cell tube formation assay (see, Example 19).

In some cases, the aptamers disclosed herein may bind to a region of IL8, such as the N-terminal domain of IL8, the hydrophobic pocket of IL8, the N-loop of IL8, the GAG binding site of IL8, or portions thereof, with a $K_d$ of less than about 0.05 nM as measured by a flow cytometry assay (see, Example 2), a TR-FRET assay (see, Examples 3 and 16), or a competition TR-FRET assay (see, Example 15), and may have an $IC_{50}$ of less than about 50 nM as measured by an IL8/CXCR1 competition assay (see, Examples 4 and 17), an IL8-mediated intracellular calcium signaling assay (see, Example 5), an IL8-mediated neutrophil migration assay (see, Examples 6 and 18), or an IL8-mediated endothelial cell tube formation assay (see, Example 19). In some cases, the aptamers disclosed herein may bind to a region of IL8, such as the N-terminal domain of IL8, the hydrophobic pocket of IL8, the N-loop of IL8, the GAG binding site of IL8, or portions thereof, with a $K_d$ of less than about 0.05 nM as measured by a flow cytometry assay (see, Example 2), a TR-FRET assay (see, Examples 3 and 16), or a competition TR-FRET assay (see, Example 15), and may have an $IC_{50}$ of less than about 10 nM as measured by an IL8/CXCR1 competition assay (see, Examples 4 and 17), an IL8-mediated intracellular calcium signaling assay (see, Example 5), an IL8-mediated neutrophil migration assay (see, Examples 6 and 18), or an IL8-mediated endothelial cell tube formation assay (see, Example 19). In some cases, the aptamers disclosed herein may bind to a region of IL8, such as the N-terminal domain of IL8, the hydrophobic pocket of IL8, the N-loop of IL8, the GAG binding site of IL8, or portions thereof, with a $K_d$ of less than about 0.05 nM as measured by a flow cytometry assay (see, Example 2), a TR-FRET assay (see, Examples 3 and 16), or a competition TR-FRET assay (see, Example 15), and may have an $IC_{50}$ of less than about 5 nM as measured by an IL8/CXCR1 competition assay (see, Examples 4 and 17), an IL8-mediated intracellular calcium signaling assay (see, Example 5), an IL8-mediated neutrophil migration assay (see, Examples 6 and 18), or an IL8-mediated endothelial cell tube formation assay (see, Example 19). In some cases, the aptamers disclosed herein may bind to a region of IL8, such as the N-terminal domain of IL8, the hydrophobic pocket of IL8, the N-loop of IL8, the GAG binding site of IL8, or portions thereof, with a $K_d$ of less than about 0.05 nM as measured by a flow cytometry assay (see, Example 2), a TR-FRET assay (see, Examples 3 and 16), or a competition TR-FRET assay (see, Example 15), and may have an $IC_{50}$ of less than about 1 nM as measured by an IL8/CXCR1 competition assay (see, Examples 4 and 17), an IL8-mediated intracellular calcium signaling assay (see, Example 5), an IL8-mediated neutrophil migration assay (see, Examples 6 and 18), or an IL8-mediated endothelial cell tube formation assay (see, Example 19). In some cases, the aptamers disclosed herein may bind to a region of IL8, such as the N-terminal domain of IL8, the hydrophobic pocket of IL8, the N-loop of IL8, the GAG binding site of IL8, or portions thereof, with a $K_d$ of less than about 0.05 nM as measured by a flow cytometry assay (see, Example 2), a TR-FRET assay (see, Examples 3 and 16), or a competition TR-FRET assay (see, Example 15), and may have an $IC_{50}$ of less than about 0.5 nM as measured by an IL8/CXCR1 competition assay (see, Examples 4 and 17), an IL8-mediated intracellular calcium signaling assay (see, Example 5), an IL8-mediated neutrophil migration assay (see, Examples 6 and 18), or an IL8-mediated endothelial cell tube formation assay (see, Example 19). In some cases, the aptamers disclosed herein may bind to a region of IL8, such as the N-terminal domain of IL8, the hydrophobic pocket of IL8, the N-loop of IL8, the GAG binding site of IL8, or portions thereof, with a $K_d$ of less than about 0.05 nM as measured by a flow cytometry assay (see, Example 2), a TR-FRET assay (see, Examples 3 and 16), or a competition TR-FRET assay (see, Example 15), and may have an $IC_{50}$ of less than about 0.1 nM as measured by an IL8/CXCR1 competition assay (see, Examples 4 and 17), an IL8-mediated intracellular calcium signaling assay (see, Example 5), an IL8-mediated neutrophil migration assay (see, Examples 6 and 18), or an IL8-mediated endothelial cell tube formation assay (see, Example 19).

In some aspects, the aptamers disclosed herein may have an improved half-life as compared to other therapeutics, including antibodies. In some cases, the aptamers may have an improved half-life in a biological fluid or solution as compared to an antibody. In some cases, the aptamers may have an improved half-life in vivo as compared to an antibody. In one example, the aptamers may have an improved half-life when injected into the eye (intraocular half-life) as compared to an antibody. In some cases, the aptamers may have an improved intraocular half-life when injected into the eye of a human. In some cases, the aptamers may demonstrate improved stability over antibodies under physiological conditions.

In some cases, the aptamers described herein may have an intraocular half-life of at least 7 days in a human as estimated from the intravitreal half-life determined following IVT administration to rabbits (see, Example 22). In some cases, the aptamers described herein may have an intraocular half-life of at least 8 days, at least 9 days, at least 10 days, at least 11 days, at least 12 days, at least 13 days, at least 14 days, at least 15 days, at least 20 days or greater in a human as estimated from the intravitreal half-life determined following IVT administration to rabbits (see, Example 22).

In some cases, the aptamers described herein may have an intraocular half-life of at least 1 day in a non-human animal (e.g., rodent/rabbit/monkey/chimpanzee/pig) as determined by IVT administration and determination of intravitreal concentrations by direct sampling of the vitreous of the treated animals over time (see, Example 22). In some cases, the aptamers described herein may have an intraocular half-life of at least 1 day, at least 2 days, at least 3 days, at least 4 days, at least 5 days, at least 6 days, at least 7 days, at least 8 days, at least 9 days, at least 10 days or greater in a non-human animal such as a rodent, rabbit or monkey as determined by IVT administration and determination of intravitreal concentrations by direct sampling of the vitreous of the treated animals over time (see, Example 22).

In some aspects, the aptamers described herein may have a shorter half-life as compared to other therapeutics. For example, an unmodified or unconjugated aptamer may have a lower half-life as compared to a modified or conjugated aptamer, however, the low molecular weight of the unmodified or unconjugated forms may allow for orders of magnitude greater initial concentrations, thereby achieving greater duration/efficacy. In some examples, the aptamer may have an intraocular half-life of less than about 7 days in a human. In some examples, the aptamers described herein may have an intraocular half-life of less than about 6 days, less than about 5 days or even less than about 4 days in a human.

The aptamers disclosed herein may demonstrate high specificity for IL8 versus other interleukins, chemokine (C-X-C motif) ligand 1 (CXCL1; also known as Gro-α), or chemokine (C-X-C motif) ligand 2 (CXCL2; also known as Gro-β). In some cases, the aptamer may be selected such that the aptamer has high affinity for IL8, but with little to no affinity for other interleukins, Gro-α, or Gro-β. In some cases, the aptamers of the disclosure may bind to IL8 with a specificity of at least 5-fold, at least 10-fold, at least 15-fold, at least 20-fold, at least 50-fold, at least 100-fold, at least 250-fold, at least 500-fold, at least 1,000-fold, at least 5,000-fold, at least 10,000-fold, at least 50,000-fold, or at least 100,000-fold, or greater than 100,000-fold than the aptamers bind to any other interleukin, Gro-α, or Gro-β at relative serum concentrations. In other cases, the aptamers of the disclosure may not exhibit specificity for IL8 over Gro-α, Gro-β, or both (e.g., may bind to IL8, Gro-α, and Gro-β). Such aptamers may, however, exhibit specificity for IL8, Gro-α, and Gro-β over other interleukins, or other proteins.

The activity of a therapeutic agent can be characterized by the half maximal inhibitory concentration ($IC_{50}$). The $IC_{50}$ may be calculated as the concentration of therapeutic agent in nM at which half of the maximum inhibitory effect of the therapeutic agent is achieved. The $IC_{50}$ may be dependent upon the assay utilized to calculate the value. In some examples, the $IC_{50}$ of an aptamer described herein may be less than 100 nM, less than 50 nM, less than 25 nM, less than 10 nM, less than 5 nM, less than 1 nM, less than 0.5 nM, less than 0.1 nM or less than 0.01 nM as measured by an IL8/CXCR1 competition assay (see, Examples 4 and 17). In some examples, the $IC_{50}$ of an aptamer described herein may be less than 100 nM, less than 50 nM, less than 25 nM, less than 10 nM, less than 5 nM, less than 1 nM, less than 0.5 nM, less than 0.1 nM or less than 0.01 nM as measured by an IL8-mediated intracellular calcium signaling assay (see, Example 5). In some examples, the $IC_{50}$ of an aptamer described herein may be less than 100 nM, less than 50 nM, less than 25 nM, less than 10 nM, less than 5 nM, less than 1 nM, less than 0.5 nM, less than 0.1 nM or less than 0.01 nM as measured by an IL8-mediated neutrophil migration assay (see, Examples 6 and 18). In some examples, the $IC_{50}$ of an aptamer described herein may be less than 100 nM, less than 50 nM, less than 25 nM, less than 10 nM, less than 5 nM, less than 1 nM, less than 0.5 nM, less than 0.1 nM, or less than 0.01 nM as measured by an IL8-mediated endothelial cell tube formation assay (see, Example 19).

Aptamers generally have high stability at ambient temperatures for extended periods of time. The aptamers described herein may demonstrate greater than 70%, greater than 75%, greater than 80%, greater than 85%, greater 90%, greater than 91%, greater than 92%, greater than 93%, greater than 94%, greater than 95%, greater than 96%, greater than 97%, greater than 98%, greater than 99%, greater than 99.5%, or greater than 99.9% activity in solution under physiological conditions at 30 days or later.

In some cases, a composition of the disclosure comprises anti-IL8 aptamers, wherein essentially 100% of the anti-IL8 aptamers comprise nucleotides having ribose in the β-D-ribofuranose configuration. In other examples, a composition of the disclosure may comprise anti-IL8 aptamers, wherein at least 50%, at least 60%, at least 70%, at least 80%, at least 90%, or greater than 90% of the anti-IL8 aptamers have ribose in the β-D-ribofuranose configuration.

Indications

In some aspects, the methods and compositions provided herein may be suitable for the treatment of ocular diseases or disorders. In some aspects, the methods and compositions provided herein may be suitable for the prevention of ocular diseases or disorders. In some aspects, the methods and compositions provided herein may be suitable to slow or halt the progression of ocular diseases or disorders. In some cases, the ocular disease or disorder may be age-related macular degeneration. In some cases, the ocular disease or disorder is wet age-related macular degeneration. In some cases, the ocular disease or disorder may be dry age-related macular degeneration. In some cases, the ocular disease or disorder may be geographic atrophy. In some cases, the ocular disease or disorder may be proliferative diabetic retinopathy. In some cases, the ocular disease or disorder may be retinal vein occlusion. In some cases, the ocular disease or disorder may be central retinal vein occlusion. In some cases, the ocular disease or disorder may be diabetic retinopathy. In some cases, the ocular disease or disorder may be diabetic macular edema. In some cases, the ocular disease or disorder may be nonarteritic anterior ischemic optic neuropathy. In some cases, the ocular disease or disorder may be uveitis. Uveitis can be, for example, infectious uveitis or non-infectious uveitis. Uveitis can be, for example, Iritis (anterior uveitis); Cyclitis (intermediate uveitis); Choroiditis and retinitis (posterior uveitis); and/or Diffuse uveitis (panuveitis). In some cases, the ocular disease or disorder may be Behçet's disease. In some cases, the ocular disease or disorder may be Coats' disease. In some cases, the ocular disease or disorder may be retinopathy of prematurity. In some cases, the ocular disease or disorder may be dry eye. In some cases, the ocular disease or disorder may be allergic conjunctivitis. In some cases, the ocular disease or disorder may be pterygium. In some cases, the ocular disease or disorder may be branch retinal vein occlusion. In some cases, the ocular disease or disorder may be central retinal vein occlusion. In some cases, the ocular disease or disorder may be adenovirus keratitis. In some cases, the ocular disease or disorder may be corneal ulcers. In some cases, the ocular disease or disorder may be vernal keratoconjunctivitis. In some cases, the ocular disease or disorder may be Stevens-Johnson syndrome. In some cases, the ocular disease or disorder may be corneal herpetic keratitis. In some cases, the ocular disease or disorder may be rhegmatogenous retinal detachment. In some cases, the ocular disease or disorder may be pseudo-exfoliation syndrome. In some cases, the ocular disease or disorder may be proliferative vitreoretinopathy. In some cases, the ocular disease or disorder may be infectious conjunctivitis. In some cases, the ocular disease or disorder may be Stargardt disease. In some cases, the ocular disease or disorder may be retinitis pigmentosa. In some cases, the ocular disease or disorder may be Contact Lens-Induced Acute Red Eye (CLARE). In some cases, the methods and compositions may be used to treat symptoms associated with conjunctivochalasis. In some cases, the ocular disease or disorder may be an inherited retinal disease. In some cases, the ocular disease or disorder may be a retinal degenerative disease. In some cases, the ocular disease or disorder exhibits elevated levels of IL8. In some cases, the ocular disease or disorder exhibits elevated levels of IL8. In some cases, the ocular disease or disorder exhibits elevated levels of bisretinoids, such as, for example, N-retinylidene-N-retinylethanolamine (A2E).

In some aspects, the methods and compositions provided herein are suitable for the treatment of an ocular disease or disorder that has a partial or incomplete response to anti-VEGF therapy. In some cases, methods and compositions provided herein may be suitable for the treatment of an ocular disease or disorder that has not responded, or has only partially responded, to anti-VEGF therapy. Non-limiting examples of such ocular diseases or disorders may include: wet age-related macular degeneration, dry age-related macular degeneration, geographic atrophy, proliferative diabetic retinopathy, retinal vein occlusion, central retinal vein occlusion, diabetic retinopathy, diabetic macular edema, central serous chorioretinopathy, X-linked retinitis pigmentosa, X-linked retinoschisis, nonarteritic anterior ischemic optic neuropathy, uveitis (including infectious uveitis, non-infectious uveitis, iritis (anterior uveitis), cyclitis (intermediate uveitis), choroiditis and retinitis (posterior uveitis), diffuse uveitis (panuveitis)), scleritis, optic neuritis, optic neuritis secondary to multiple sclerosis, macular pucker, Behçet's disease, Coats' disease, retinopathy of prematurity, open angle glaucoma, neovascular glaucoma, dry eye, allergic conjunctivitis, pterygium, branch retinal vein occlusion, adenovirus keratitis, corneal ulcers, vernal keratoconjunctivitis, blepharitis, epithelial basement membrane dystrophy, Stevens-Johnson syndrome, achromatophasia, corneal herpetic keratitis, keratoconus, rhegmatogenous retinal detachment, pseudo-exfoliation syndrome, proliferative vitreoretinopathy, infectious conjunctivitis, Stargardt disease, retinitis pigmentosa, Contact Lens-Induced Acute Red Eye (CLARE), conjunctivochalasis, inherited retinal disease, a retinal degenerative disease, an ocular disease or disorder exhibiting elevated levels of IL8, and an ocular disease or disorder exhibiting elevated levels of bisretinoids, such as, for example, N-retinylidene-N-retinylethanoloamine (A2E).

Additional examples of ocular diseases or disorders that may be amendable to treatment by the methods and compositions provided herein may include, without limitation, pterygium, inflammatory conjunctivitis, including allergic and giant papillary conjunctivitis, infectious conjunctivitis, vernal keratoconjunctivitis, Stevens-Johnson disease, corneal herpetic keratitis, rhegmatogenous retinal detachment, pseudo-exfoliation syndrome, endophthalmitis, scleritis, corneal ulcers, dry eye syndrome, glaucoma, ischemic retinal disease, corneal transplant rejection, complications related to intraocular surgery such intraocular lens implantation and inflammation associated with cataract surgery, Behcet's disease, Stargardt disease, immune complex vasculitis, Fuch's disease, Vogt-Koyanagi-Harada disease, subretinal fibrosis, keratitis, vitreo-retinal inflammation, ocular parasitic infestation/migration, retinitis pigmentosa, cytomegalovirus retinitis and choroidal inflammation, ectropion, lagophthalmos, blepharochalasis, ptosis, xanthelasma of the eyelid, parasitic infestation of the eyelid, dermatitis of the eyelid, dacryoadenitis, epiphora, dysthyroid exophthalmos, conjunctivitis, scleritis, adenovirus keratitis, corneal ulcer, corneal abrasion, snow blindness, arc eye, Thygeson's superficial punctate keratopathy, corneal neovascularization, Fuchs' dystrophy, keratoconus, keratoconjunctivitis sicca, iritis, sympathetic ophthalmia, cataracts, chorioretinal inflammation, focal chorioretinal inflammation, focal chorioretinitis, focal choroiditis, focal retinitis, focal retinochoroiditis, disseminated chorioretinal inflammation, disseminated chorioretinitis, disseminated choroiditis, disseminated retinitis, disseminated retinochoroiditis, exudative retinopathy, posterior cyclitis, pars planitis, Harada's disease, chorioretinal scars, macula scars of posterior pole, solar retinopathy, choroidal degeneration, choroidal atrophy, choroidal sclerosis, angioid streaks, hereditary choroidal dystrophy, choroideremia, choroidal dystrophy (central arealor), gyrate atrophy (choroid), ornithinaemia, choroidal haemorrhage and rupture, choroidal haemorrhage (not otherwise specified), choroidal haemorrhage (expulsive), choroidal detachment, retinoschisis, retinal artery occlusion, retinal vein occlusion, hypertensive retinopathy, diabetic retinopathy, retinopathy, retinopathy of prematurity, macular degeneration, Bull's Eye maculopathy, epiretinal membrane, peripheral retinal degeneration, hereditary retinal dystrophy, retinitis pigmentosa, retinal haemorrhage, separation of retinal layers, central serous retinopathy, retinal detachment, macular edema, glaucoma—optic neuropathy, glaucoma suspect—ocular hypertension, primary open-angle glaucoma, primary angle-closure glaucoma, floaters, Leber's hereditary optic neuropathy, optic disc drusen, strabismus, ophthalmoparesis, progressive external ophthaloplegia, esotropia, exotropia, disorders of refraction and accommodation, hypermetropia, myopia, astigmatism, anisometropia, presbyopia, internal ophthalmoplegia, amblyopia, Leber's congenital amaurosis, scotoma, anopsia, color blindness, achromatopsia, maskun, nyctalopia, blindness, River blindness, micropthalmia, coloboma, red eye, Argyll Robertson pupil, keratomycosis, xerophthalmia, aniridia, sickle cell retinopathy, ocular neovascularization, retinal neovascularization, subretinal neovascularization; rubeosis iritis inflammatory diseases, chronic posterior and pan uveitis, neoplasms, retinoblastoma, pseudoglioma, neovascular glaucoma; neovascularization resulting following a combined vitrectomy-2 and lensectomy, vascular diseases, retinal ischemia, choroidal vascular insufficiency, choroidal thrombosis, neovascularization of the optic nerve, diabetic macular edema, cystoid macular edema, proliferative vitreoretinopathy, and neovascularization due to penetration of the eye or ocular injury.

In some aspects, the methods and compositions provided herein are suitable for the treatment of diseases that cause one or more ocular symptoms. Non-limiting examples of symptoms which may be amenable to treatment with the methods disclosed herein include, but are not limited to increased drusen volume, reduced reading speed, reduced color vision, increased retinal thickening, increase in central retinal volume and/or, macular sensitivity, loss of retinal cells, increase in area of retinal atrophy, reduced best corrected visual acuity such as measured by Snellen or ETDRS scales, reduced Best Corrected Visual Acuity under low luminance conditions, impaired night vision, impaired light sensitivity, impaired dark adaptation, impaired contrast sensitivity, worsened patient reported outcomes, and any combination thereof. In some cases, the methods and compositions provided herein are suitable for the treatment of symptoms associated with inflammatory eye diseases. Non-limiting examples of symptoms associated with eye diseases may include: redness of the eye, eye pain, dark floating spots in the vision (floaters), vitreous haze, blurred vision, periorbital pain, increased intraocular pressure, photophobia, watery eyes, puffy eyes, feeling of something in the eye, vision loss, neovascular glaucoma, painful blind eye, periorbital pain, eye discomfort, itchiness, watery eyes, and puffy eyes.

In some cases, the methods and compositions provided herein may alleviate or reduce a symptom of a disease. In some cases, treatment with an aptamer provided herein may result in a reduction in the severity of any of the symptoms described herein. In some cases, treatment with an aptamer described herein may slow, halt or reverse the progression of any of the symptoms described herein. In some cases, treatment with an aptamer described herein may prevent the development of any of the symptoms described herein. In some cases, treatment with an aptamer described herein may slow, halt or reverse the progression of a disease, as measured by the number and severity of symptoms experienced. Examples of symptoms and relevant endpoints where the aptamer may have a therapeutic effect include increased drusen volume, reduced reading speed, reduced color vision, increased retinal thickening, increase in central retinal volume and/or, macular sensitivity, loss of retinal cells, increase in area of retinal atrophy, reduced best corrected visual acuity such as measured by Snellen or ETDRS scales, reduced Best Corrected Visual Acuity under low luminance conditions, impaired night vision, impaired light sensitivity, impaired dark adaptation, impaired contrast sensitivity, and worsening patient reported outcomes. In some instances, treatment with an aptamer described herein may have beneficial effects as measured by clinical endpoints including drusen volume, reading speed, retinal thickness as measured by Optical Coherence Tomography or other techniques, central retinal volume, number and density of retinal cells, area of retinal atrophy as measured by Fundus Photography or Fundus Autofluoresence or other techniques, best corrected visual acuity such as measured by Snellen or ETDRS scales, Best Corrected Visual Acuity under low luminance conditions, light sensitivity, dark adaptation, contrast sensitivity, and patient reported outcomes as measured by such tools as the National Eye Institute Visual Function Questionnaire and Health Related Quality of Life Questionnaires.

In some cases, the methods and compositions provided herein may alleviate or reduce a symptom of an inflammatory eye disease. In some cases, treatment with an aptamer provided herein may result in a reduction in the severity of any symptoms associated with an inflammatory eye disease. In some cases, treatment with an aptamer described herein may slow, halt or reverse the progression of any symptom associated with an inflammatory eye disease. In some cases, treatment with an aptamer described herein may prevent the development of any symptom associated with an inflammatory eye disease. In some cases, treatment with an aptamer described herein may slow, halt or reverse the progression of an inflammatory eye disease, as measured by the number and severity of symptoms experienced. Non-limiting examples of symptoms associated with inflammatory eye diseases where the aptamer may have a therapeutic effect include redness of the eye, eye pain, dark floating spots in the vision (floaters), vitreous haze, blurred vision, periorbital pain, increased intraocular pressure, photophobia, watery eyes, puffy eyes, feeling of something in the eye, vision loss, neovascular glaucoma, painful blind eye, periorbital pain, eye discomfort, itchiness, watery eyes, and puffy eyes.

Subjects

The terms "subject" and "patient" are used interchangeably herein to refer to a vertebrate, preferably a mammal, and more preferably a human. Mammals include, but are not limited to, rodents (e.g., mice, rats, rabbits, etc.) simians, humans, research animals (e.g., beagles, etc.), farm animals (e.g., pigs, horses, cows, llamas, alpacas, etc.), sport animals, and pets. In some cases, the methods described herein may be used on tissues or cells derived from a subject and the progeny of such tissues or cells. For example, aptamers described herein may be used to affect some function in tissues or cells of a subject. The tissues or cells may be obtained from a subject in vivo. In some cases, the tissues or cells are cultured in vitro and contacted with a composition provided herein (e.g., an aptamer).

In some aspects, the methods and compositions provided herein are used to treat a subject in need thereof. In some cases, the subject suffers from an ocular disease or disorder. In some cases, the subject is a human. In some cases, the human is a patient at a hospital or a clinic. In some cases, the subject is a non-human animal, for example, a non-human primate, a livestock animal, a domestic pet, or a laboratory animal. For example, a non-human animal can be an ape (e.g., a chimpanzee, a baboon, a gorilla, or an orangutan), an old world monkey (e.g., a rhesus monkey), a new world monkey, a dog, a cat, a bison, a camel, a cow, a deer, a pig, a donkey, a horse, a mule, a lama, a sheep, a goat, a buffalo, a reindeer, a yak, a mouse, a rat, a rabbit, or any other non-human animal.

In cases where the subject is a human, the subject may be of any age. In some cases, the subject has an age-related ocular disease or disorder (e.g., age-related macular degeneration). In some cases, the subject is about 50 years or older. In some cases, the subject is about 55 years or older. In some cases, the subject is about 60 years or older. In some cases, the subject is about 65 years or older. In some cases, the subject is about 70 years or older. In some cases, the subject is about 75 years or older. In some cases, the subject is about 80 years or older. In some cases, the subject is about 85 years or older. In some cases, the subject is about 90 years or older. In some cases, the subject is about 95 years or older. In some cases, the subject is about 100 years or older. In some cases, the subject is about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or greater than 100 years old. In some cases, the subject is about 1, 2, 3, 4, 5, 6, 7, 8, 9, 10, 11, 12, 13, 14, 15, 16, 17, 18, 19, 20 or greater than 20 years old.

In some aspects, the methods and compositions provided herein may be used to treat a subject having, suspected of having, or at risk of developing ocular symptoms as described herein. In some aspects, the methods and compositions provided herein may be used to treat a subject having, suspected of having, or at risk of developing an ocular disease as provided herein. In some cases, the methods and compositions provided herein may be used to treat a subject having, suspected of having, or at risk of developing wet age-related macular degeneration. In some cases, the methods and compositions provided herein may be used to treat a subject having, suspected of having, or at risk of developing dry age-related macular degeneration. In some cases, the methods and compositions provided herein may be used to treat geographic atrophy. In some cases, the methods and compositions provided herein may be used to treat a subject having, suspected of having, or at risk of developing proliferative diabetic retinopathy. In some cases, the methods and compositions provided herein may be used to treat a subject having, suspected of having, or at risk of developing diabetic retinopathy. In some cases, the methods and compositions provided herein may be used to treat a subject having, suspected of having, or at risk of developing diabetic macular edema. In some cases, the methods and compositions provided herein may be used to treat a subject having, suspected of having, or at risk of developing branch retinal vein occlusion. In some cases, the methods and compositions provided herein may be used to treat a subject having, suspected of having, or at risk of developing central retinal vein occlusion. In some cases, the methods and compositions provided herein may be used to treat a subject having, suspected of having, or at risk of developing nonarteritic anterior ischemic optic neuropathy. In some cases, the methods and compositions provided herein may be used to treat a subject having, suspected of having, or at risk of developing uveitis. Uveitis can be, for example, infectious uveitis or non-infectious uveitis. Uveitis can be, for example, Iritis (anterior uveitis); Cyclitis (intermediate uveitis); Choroiditis and retinitis (posterior uveitis); and/or Diffuse uveitis (panuveitis). In some cases, the methods and compositions provided herein may be used to treat a subject having, suspected of having, or at risk of developing Behçet's disease. In some cases, the methods and compositions provided herein may be used to treat a subject having, suspected of having, or at risk of developing Coats' disease. In some cases, the methods and compositions provided herein may be used to treat a subject having, suspected of having, or at risk of developing retinopathy of prematurity. In some cases, the methods and compositions provided herein may be used to treat a subject having, suspected of having, or at risk of developing dry eye. In some cases, the methods and compositions provided herein may be used to treat a subject having, suspected of having, or at risk of developing allergic conjunctivitis. In some cases, the methods and compositions provided herein may be used to treat a subject having, suspected of having, or at risk of developing pterygium. In some cases, the methods and compositions provided herein may be used to treat a subject having, suspected of having, or at risk of developing adenovirus keratitis. In some cases, the methods and compositions provided herein may be used to treat a subject having, suspected of having, or at risk of developing corneal ulcers. In some cases, the methods and compositions provided herein may be used to treat a subject having, suspected of having, or at risk of developing vernal keratoconjunctivitis. In some cases, the methods and compositions provided herein may be used to treat a subject having, suspected of having, or at risk of developing Stevens-Johnson syndrome. In some cases, the methods and compositions provided herein may be used to treat a subject having, suspected of having, or at risk of developing corneal herpetic keratitis. In some cases, the methods and compositions provided herein may be used to treat a subject having, suspected of having, or at risk of developing rhegmatogenous retinal detachment. In some cases, the methods and compositions provided herein may be used to treat a subject having, suspected of having, or at risk of developing pseudo-exfoliation syndrome. In some cases, the methods and compositions provided herein may be used to treat a subject having, suspected of having, or at risk of developing proliferative vitreoretinopathy. In some cases, the methods and compositions provided herein may be used to treat a subject having, suspected of having, or at risk of developing infectious conjunctivitis. In some cases, the methods and compositions provided herein may be used to treat a subject having, suspected of having, or at risk of developing Stargardt disease. In some cases, the methods and composition provided herein may be used to treat a subject having, suspected of having, or at risk of developing retinitis pigmentosa. In some cases, the methods and compositions provided herein may be used to treat a subject having, suspected of having, or at risk of developing Contact Lens-Induced Acute Red Eye (CLARE). In some cases, the methods and compositions provided herein may be used to treat a subject having, suspected of having, or at risk of developing symptoms associated with conjunctivochalasis. In some cases, the methods and compositions provided herein may be used to treat a subject having, suspected of having, or at risk of developing an inherited retinal disease. In some cases, the methods and compositions provided herein may be used to treat a subject having, suspected of having, or at risk of developing a retinal degenerative disease. In some cases, the methods and compositions provided herein may be used to treat a subject having, suspected of having, or at risk of developing an ocular disease or disorder exhibiting elevated levels of IL8. In some cases, the methods and compositions provided herein may be used to treat a subject having, suspected of having, or at risk of developing an ocular disease or disorder exhibiting elevated levels of bisretinoids, such as, for example, N-retinylidene-N-retinylethanolamine (A2E).

In some aspects, the methods and compositions provided herein may be utilized to treat a subject with a highly active immune system. In some cases, the methods and compositions provided herein may be used to treat a subject with an autoimmune disease. In some cases, the methods and compositions provided herein may be used to treat a subject with an inflammatory disease. In some cases, the methods and compositions provided herein may be used to treat a subject undergoing an inflammatory reaction to a disease such as an infectious disease. For example, the aptamers described herein may be used to treat a subject with a fever. In some cases, the aptamers described herein may be used to treat a subject with an allergy. In some cases, the aptamers described herein may be used to treat a subject suffering from an allergic response. In some cases, the aptamers described herein may be particularly useful for treating a subject who has experienced an allergic reaction to an antibody treatment, and/or who has developed neutralizing antibodies against an antibody treatment.

Pharmaceutical Compositions or Medicaments

Disclosed herein are pharmaceutical compositions or medicaments, used interchangeably, for use in a method of therapy, or for use in a method of medical treatment. Such use may be for the treatment of ocular diseases. In some cases, the pharmaceutical compositions can be used for the treatment of wet age-related macular degeneration. In some cases, the pharmaceutical compositions can be used for the treatment of dry age-related macular degeneration. In some cases, the pharmaceutical compositions can be used for the treatment of geographic atrophy. In some cases, the pharmaceutical compositions can be used for the treatment of proliferative diabetic retinopathy. In some cases, the pharmaceutical compositions can be used for the treatment of diabetic retinopathy. In some cases, the pharmaceutical compositions can be used for the treatment of diabetic macular edema. In some cases, the pharmaceutical compositions can be used for the treatment of branch retinal vein occlusion. In some cases, the pharmaceutical compositions can be used for the treatment of central retinal vein occlusion. In some cases, the pharmaceutical compositions can be used for the treatment of nonarteritic anterior ischemic optic neuropathy. In some cases, the pharmaceutical compositions can be used for the treatment of uveitis. Uveitis can be, for example, infectious uveitis or non-infectious uveitis. Uveitis can be, for example, Iritis (anterior uveitis); Cyclitis (intermediate uveitis); Choroiditis and retinitis (posterior uveitis); and/or Diffuse uveitis (panuveitis). In some cases, the pharmaceutical compositions can be used for the treatment of Behçet's disease. In some cases, the pharmaceutical compositions can be used for the treatment of Coats' disease. In some cases, the pharmaceutical compositions can be used for the treatment of retinopathy of prematurity. In some cases, the pharmaceutical compositions can be used for the treatment of dry eye. In some cases, the pharmaceutical compositions can be used for the treatment of allergic conjunctivitis. In some cases, the pharmaceutical compositions can be used for the treatment of pterygium. In some cases, the pharmaceutical compositions can be used for the treatment of adenovirus keratitis. In some cases, the pharmaceutical compositions can be used for the treatment of corneal ulcers. In some cases, the pharmaceutical compositions can be used for the treatment of vernal keratoconjunctivitis. In some cases, the pharmaceutical compositions can be used for the treatment of Stevens-Johnson syndrome. In some cases, the pharmaceutical compositions can be used for the treatment of corneal herpetic keratitis. In some cases, the pharmaceutical compositions can be used for the treatment of rhegmatogenous retinal detachment. In some cases, the pharmaceutical compositions can be used for the treatment of pseudo-exfoliation syndrome. In some cases, the pharmaceutical compositions can be used for the treatment of proliferative vitreoretinopathy. In some cases, the pharmaceutical compositions can be used for the treatment of infectious conjunctivitis. In some cases, the pharmaceutical compositions can be used for the treatment of Stargardt disease. In some cases, the pharmaceutical compositions can be used for the treatment of retinitis pigmentosa. In some cases, the pharmaceutical compositions can be used for the treatment of Contact Lens-Induced Acute Red Eye (CLARE). In some cases, the pharmaceutical compositions can be used for the treatment of symptoms associated with conjunctivochalasis. In some cases, the pharmaceutical compositions can be used for the treatment of an inherited retinal disease. In some cases, the pharmaceutical compositions can be used for the treatment of a retinal degenerative disease. In some cases, the pharmaceutical compositions can be used for the treatment of an ocular disease or disorder that exhibits elevated levels of IL8. In some cases, the pharmaceutical compositions can be used for the treatment of an ocular disease or disorder that exhibits elevated levels of bisretinoids, such as, for example, N-retinylidene-N-retinylethanolamine (A2E).

In some cases, pharmaceutical compositions described herein may include one or more anti-IL8 aptamers for the treatment of wet age-related macular degeneration. In some cases, pharmaceutical compositions described herein may include one or more anti-IL8 aptamers for the treatment of dry age-related macular degeneration. In some cases, pharmaceutical compositions described herein may include one or more anti-IL8 aptamers for the treatment of geographic atrophy. In some cases, pharmaceutical compositions described herein may include one or more anti-IL8 aptamers for the treatment of proliferative diabetic retinopathy. In some cases, pharmaceutical compositions described herein may include one or more anti-IL8 aptamers for the treatment of diabetic retinopathy. In some cases, pharmaceutical compositions described herein may include one or more anti-IL8 aptamers for the treatment of diabetic macular edema. In some cases, pharmaceutical compositions described herein may include one or more anti-IL8 aptamers for the treatment of branch retinal vein occlusion. In some cases, pharmaceutical compositions described herein may include one or more anti-IL8 aptamers for the treatment of central retinal vein occlusion. In some cases, pharmaceutical compositions described herein may include one or more anti-IL8 aptamers for the treatment of nonarteritic anterior ischemic optic neuropathy. In some cases, pharmaceutical compositions described herein may include one or more anti-IL8 aptamers for the treatment of uveitis. Uveitis can be, for example, infectious uveitis or non-infectious uveitis. Uveitis can be, for example, Iritis (anterior uveitis); Cyclitis (intermediate uveitis); Choroiditis and retinitis (posterior uveitis); and/or Diffuse uveitis (panuveitis). In some cases, pharmaceutical compositions described herein may include one or more anti-IL8 aptamers for the treatment of Behçet's disease. In some cases, pharmaceutical compositions described herein may include one or more anti-IL8 aptamers for the treatment of Coats' disease. In some cases, pharmaceutical compositions described herein may include one or more anti-IL8 aptamers for the treatment of retinopathy of prematurity (ROP). In some cases, pharmaceutical compositions described herein may include one or more anti-IL8 aptamers for the treatment of dry eye. In some cases, pharmaceutical compositions described herein may include one or more anti-IL8 aptamers for the treatment of allergic conjunctivitis. In some cases, pharmaceutical compositions described herein may include one or more anti-IL8 aptamers for the treatment of pterygium. In some cases, pharmaceutical compositions described herein may include one or more anti-IL8 aptamers for the treatment of adenovirus keratitis. In some cases, pharmaceutical compositions described herein may include one or more anti-IL8 aptamers for the treatment of corneal ulcers. In some cases, pharmaceutical compositions described herein may include one or more anti-IL8 aptamers for the treatment of vernal keratoconjunctivitis. In some cases, pharmaceutical compositions described herein may include one or more anti-IL8 aptamers for the treatment of Stevens-Johnson syndrome. In some cases, pharmaceutical compositions described herein may include one or more anti-IL8 aptamers for the treatment of corneal herpetic keratitis. In some cases, pharmaceutical compositions described herein may include one or more anti-IL8 aptamers for the treatment of rhegmatogenous retinal detachment. In some cases, pharmaceutical compositions described herein may include one or more anti-IL8 aptamers for the treatment of pseudo-exfoliation syndrome. In some cases, pharmaceutical compositions described herein may include one or more anti-IL8 aptamers for the treatment of proliferative vitreoretinopathy. In some cases, pharmaceutical compositions described herein may include one or more anti-IL8 aptamers for the treatment of infectious conjunctivitis. In some cases, pharmaceutical compositions described herein may include one or more anti-IL8 aptamers for the treatment of Stargardt disease. In some cases, pharmaceutical compositions described herein may include one or more anti-IL8 aptamers for the treatment of retinitis pigmentosa. In some cases, pharmaceutical compositions described herein may include one or more anti-IL8 aptamers for the treatment of Contact Lens-Induced Acute Red Eye (CLARE). In some cases, pharmaceutical compositions described herein may include one or more anti-IL8 aptamers for the treatment of symptoms associated with conjunctivochalasis. In some cases, pharmaceutical compositions described herein may include one or more anti-IL8 aptamers for the treatment of an inherited retinal disease. In some cases, pharmaceutical compositions described herein may include one or more anti-IL8 aptamers for the treatment a retinal degenerative disease. In some cases, pharmaceutical compositions described herein may include one or more anti-IL8 aptamers for the treatment of an ocular disease or disorder which exhibits elevated levels of IL8. In some cases, pharmaceutical compositions described herein may include one or more anti-IL8 aptamers for the treatment of an ocular disease or disorder which exhibits elevated levels of bisretinoids, such as, for example, N-retinylidene-N-retinylethanolamine (A2E).

In some cases, the one or more anti-IL8 aptamers may bind to IL8. In some cases, the one or more anti-IL8 aptamers may bind to the N-terminal domain of IL8, or a portion thereof. The N-terminal domain of IL8 may include any one or more of residues 2-6 of IL8-72 (SEQ ID NO: 2). In some cases, the one or more anti-IL8 aptamers may bind to the hydrophobic pocket of IL8, or a portion thereof. The hydrophobic pocket of IL8 may include any one or more of residues 12-18, F21, 122, 140, L43, R47, and L49 of IL8-72 (SEQ ID NO: 2). In some cases, the one or more anti-IL8 aptamers may bind to the N-loop of IL8, or a portion thereof. The N-loop of IL8 may include any one or more of residues 7-11 of IL8-72 (SEQ ID NO: 2). In some cases, the one or more anti-IL8 aptamers may bind to the GAG binding site of IL8, or a portion thereof. The GAG binding site may include any one or more of residues H18, K20, R60, K64, K67, and R68 of IL8-72 (SEQ ID NO: 2). In some cases the one or more anti-IL8 aptamers may prevent or reduce the binding of IL8 with CXCR1, CXCR2, or both. In some cases, the one or more anti-IL8 aptamers may bind to a region of IL8 such that a molecule conjugated to the anti-IL8 aptamer (e.g., a polyethylene glycol polymer) is positioned in a manner so that the conjugate itself may prevent or reduce interaction with CXCR1, CXCR2, or both. In such cases, the anti-IL8 aptamer may bind to IL8 at a region that is not itself important for interaction with CXCR1, CXCR2, or both. In some cases, the compositions may include, e.g., an effective amount of the aptamer, alone or in combination, with one or more vehicles (e.g., pharmaceutically acceptable compositions or e.g., pharmaceutically acceptable carriers).

In some aspects, the anti-IL8 compositions described herein may be administered in combination with an anti-VEGF or an anti-VEGF Receptor composition, for the treatment of an ocular disease or disorder. An anti-VEGF or an anti-VEGF Receptor composition may include any composition that inhibits a function associated with VEGF or a VEGF receptor. Non-limiting examples of anti-VEGF and or an anti-VEGF Receptor composition that may be used with the anti-IL8 compositions to treat an ocular disease or disorder include: bevacizumab, ranibizumab, pegaptanib, aflibercept, axitinib (N-methyl-2-[3-((E)-2-pyridin-2-yl-vinyl)-1H-indazol-6-ylsulfanyl]-benzamide), Ramucirumab (CYRMZA®;), RTH258/Brolucizumab; RG7716/Faricimab; VGX-100: VEGF-C mAb VGX-100; aflibercept (VEGF-Trap), Pazopanib (5-[[4-[(2,3-dimethyl-2H-indazol-6-yl)methylamino]-2-pyrimidinyl]amino]-2-methyl-benzenesulfonamide); sunitinib (SUTENT®); brivanib (BMS-582664); sorafenib (NEXAVAR®); SU5416; conbercept; abicipar pegol; or any biosimilar thereof.

Formulations

Compositions as described herein may comprise a liquid formulation, a solid formulation or a combination thereof. Non-limiting examples of formulations may include a tablet, a capsule, a gel, a paste, a liquid solution and a cream. The compositions of the present disclosure may further comprise any number of excipients. Excipients may include any and all solvents, coatings, flavorings, colorings, lubricants, disintegrants, preservatives, sweeteners, binders, diluents, and vehicles (or carriers). Generally, the excipient is compatible with the therapeutic compositions of the present disclosure. The pharmaceutical composition may also contain minor amounts of non-toxic auxiliary substances such as wetting or emulsifying agents, pH buffering agents, and other substances such as, for example, sodium acetate, and triethanolamine oleate.

Dosage and Routes of Administration

Therapeutic doses of formulations of the disclosure can be administered to a subject in need thereof. In some cases, a formulation is administered to the eye of a subject for the treatment of an ocular disease as described herein. Administration to the eye can be; b) local ocular delivery; or c) systemic. A topical formulation can be applied directly to the eye (e.g., eye drops, contact lens loaded with the formulation) or to the eyelid (e.g., cream, lotion, gel). In some cases, topical administration can be to a site remote from the eye, for example, to the skin of an extremity. This form of administration may be suitable for targets that are not produced directly by the eye. In some cases, a formulation of the disclosure is administered by local ocular delivery. Non-limiting examples of local ocular delivery include intravitreal (IVT), intracamarel, subconjunctival, subtenon, retrobulbar, posterior juxtascleral, and peribulbar. In some cases, a formulation of the disclosure is delivered by intravitreal administration (IVT). Local ocular delivery may generally involve injection of a liquid formulation. In other cases, a formulation of the disclosure is administered systemically. Systemic administration can involve oral administration. In some cases, systemic administration can be intravenous administration, subcutaneous administration, infusion, implantation, and the like.

Other formulations suitable for delivery of the pharmaceutical compositions described herein may include a sustained release gel or polymer formulations by surgical implantation of a biodegradable microsize polymer system, e.g., microdevice, microparticle, or sponge, or other slow release transscleral devices, implanted during the treatment of an ophthalmic disease, or by an ocular delivery device, e.g., polymer contact lens sustained delivery device. In some cases, the formulation is a polymer gel, a self-assembling gel, a durable implant, an eluting implant, a biodegradable matrix or biodegradable polymers. In some cases, the formulation may be administered by iontophoresis using electric current to drive the composition from the surface to the posterior of the eye. In some cases, the formulation may be administered by a surgically implanted port with an intravitreal reservoir, an extra-vitreal reservoir or a combination thereof. Examples of implantable ocular devices can include, without limitation, the Durasert™ technology developed by Bausch & Lomb, the ODTx device developed by On Demand Therapeutics, the Port Delivery System developed by ForSight VISION4 and the Replenish Micro-Pump™ System developed by Replenish, Inc. In some cases, nanotechnologies can be used to deliver the pharmaceutical compositions including nanospheres, nanoparticles, nanocapsules, liposomes, nanomicelles and dendrimers.

A composition of the disclosure can be administered once or more than once each day. In some cases, the composition is administered as a single dose (i.e., one-time use). In this example, the single dose may be curative. In other cases, the composition may be administered serially (e.g., taken every day without a break for the duration of the treatment regimen). In some cases, the treatment regime can be less than a week, a week, two weeks, three weeks, a month, or greater than a month. In some cases, the composition is administered over a period of at least 12 weeks. In other cases, the composition is administered for a day, at least two consecutive days, at least three consecutive days, at least four consecutive days, at least five consecutive days, at least six consecutive days, at least seven consecutive days, at least eight consecutive days, at least nine consecutive days, at least ten consecutive days, or at least greater than ten consecutive days. In some cases, a therapeutically effective amount can be administered one time per week, two times per week, three times per week, four times per week, five times per week, six times per week, seven times per week, eight times per week, nine times per week, 10 times per week, 11 times per week, 12 times per week, 13 times per week, 14 times per week, 15 times per week, 16 times per week, 17 times per week, 18 times per week, 19 times per week, 20 times per week, 25 times per week, 30 times per week, 35 times per week, 40 times per week, or greater than 40 times per week. In some cases, a therapeutically effective amount can be administered one time per day, two times per day, three times per day, four times per day, five times per day, six times per day, seven times per day, eight times per day, nine times per day, 10 times per day, or greater than 10 times per day. In some cases, the composition is administered at least twice a day. In further cases, the composition is administered at least every hour, at least every two hours, at least every three hours, at least every four hours, at least every five hours, at least every six hours, at least every seven hours, at least every eight hours, at least every nine hours, at least every 10 hours, at least every 11 hours, at least every 12 hours, at least every 13 hours, at least every 14 hours, at least every 15 hours, at least every 16 hours, at least every 17 hours, at least every 18 hours, at least every 19 hours, at least every 20 hours, at least every 21 hours, at least every 22 hours, at least every 23 hours, or at least every day.

Aptamers as described herein may be particularly advantageous over antibodies as they may sustain therapeutic intravitreal concentrations of drug for longer periods of time, thus requiring less frequent administration. The aptamers described herein may have a longer intraocular half-life, and/or sustain therapeutic intravitreal concentrations of drug for longer periods of time than an anti-IL8 antibody therapy and can be dosed less frequently. In some cases, the aptamers of the disclosure are dosed at least once every 4 weeks (q4w), once every 5 weeks (q5w), once every 6 weeks (q6w), once every 7 weeks (q7w), once every 8 weeks (q8w), once every 9 weeks (q9w), once every 10 weeks (q10w), once every 11 weeks (q11w) k once every 12 weeks (q12w), once every 13 weeks (q13w), once every 14 weeks (q14w), once every 15 weeks (q15w), once every 16 weeks (q16w), once every 17 weeks (q17w), once every 18 weeks (q18w), once every 19 weeks (q19w), once every 20 weeks (q20w), once every 21 weeks (q21w), once every 22 weeks (q22w), once every 23 weeks (q23w), once every 24 weeks (q24w), or greater than once every 24 weeks.

In some aspects, a therapeutically effective amount of the aptamer may be administered. A "therapeutically effective amount" or "therapeutically effective dose" are used interchangeably herein and refer to an amount of a therapeutic agent (e.g., an aptamer) that provokes a therapeutic or desired response in a subject. The therapeutically effective amount of the composition may be dependent on the route of administration. In the case of systemic administration, a therapeutically effective amount may be about 10 mg/kg to about 100 mg/kg. In some cases, a therapeutically effective amount may be about 10 μg/kg to about 1000 μg/kg for systemic administration. For intravitreal administration, a therapeutically effective amount can be about 0.01 mg to about 150 mg in about 25 μl to about 100 μl volume per eye.

Methods of Treatment

Disclosed herein are methods for the treatment of ocular diseases or disorders. In some cases, the ocular disease or disorder may be wet age-related macular degeneration. In some cases, the ocular disease or disorder may be dry age-related macular degeneration. In some cases, the ocular disease or disorder may be geographic atrophy. In some cases, the ocular disease or disorder may be proliferative diabetic retinopathy. In some cases, the ocular disease or disorder may be diabetic retinopathy. In some cases, the ocular disease or disorder may be diabetic macular edema. In some cases, the ocular disease or disorder may be branch retinal vein occlusion. In some cases, the ocular disease or disorder may be central retinal vein occlusion. In some cases, the ocular disease or disorder may be nonarteritic anterior ischemic optic neuropathy. In some cases, the ocular disease or disorder may be uveitis. Uveitis can be, for example, infectious uveitis or non-infectious uveitis. Uveitis can be, for example, Iritis (anterior uveitis); Cyclitis (intermediate uveitis); Choroiditis and retinitis (posterior uveitis); and/or Diffuse uveitis (panuveitis). In some cases, the ocular disease or disorder may be Behçet's disease. In some cases, the ocular disease or disorder may be Coats' disease. In some cases, the ocular disease or disorder may be retinopathy of prematurity. In some cases, the ocular disease or disorder may be dry eye. In some cases, the ocular disease or disorder may be allergic conjunctivitis. In some cases, the ocular disease or disorder may be pterygium. In some cases, the ocular disease or disorder may be adenovirus keratitis. In some cases, the ocular disease or disorder may be corneal ulcers. In some cases, the ocular disease or disorder may be vernal keratoconjunctivitis. In some cases, the ocular disease or disorder may be Stevens-Johnson syndrome. In some cases, the ocular disease or disorder may be corneal herpetic keratitis. In some cases, the ocular disease or disorder may be rhegmatogenous retinal detachment. In some cases, the ocular disease or disorder may be pseudo-exfoliation syndrome. In some cases, the ocular disease or disorder may be proliferative vitreoretinopathy. In some cases, the ocular disease or disorder may be infectious conjunctivitis. In some cases, the ocular disease or disorder may be Stargardt disease. In some cases, the ocular disease or disorder may be retinitis pigmentosa. In some cases, the ocular disease or disorder may be Contact Lens-Induced Acute Red Eye (CLARE). In some cases, the methods may involve treatment of symptoms associated with conjunctivochalasis. In some cases, the ocular disease or disorder may be an inherited retinal disease. In some cases, the ocular disease or disorder may be a retinal degenerative disease. In some cases, the ocular disease or disorder may exhibit elevated levels of IL8. In some cases, the ocular disease or disorder may exhibit elevated levels of bisretinoids, such as, for example, N-retinylidene-N-retinylethanolamine (A2E).

In some cases, the method involves administering a therapeutically effective amount of a composition to a subject to treat an ocular disease. In some cases, the composition includes one or more aptamers as described herein. In some cases, the one or more aptamers comprise an aptamer having a stem-loop secondary structure as described herein. In some cases, the one or more aptamers comprise an aptamer from the Aptamer 3 structural family of aptamers. In some cases, the one or more aptamers comprise an aptamer from the Aptamer 8 structural family of aptamers. The aptamers may bind to and inhibit a function associated with IL8 as described herein. Additionally or alternatively, the methods may involve administering a therapeutically effective amount of an anti-IL8 composition described herein in combination with an anti-VEGF composition (e.g., bevacizumab, ranibizumab, aflibercept, pegaptanib, axitinib (N-methyl-2-[3-((E)-2-pyridin-2-yl-vinyl)-1H-indazol-6-ylsulfanyl]-benzamide), Ramucirumab (CYRMZA®;), RTH258/Brolucizumab; RG7716/Faricimab; VGX-100: VEGF-C mAb VGX-100; aflibercept (VEGF-Trap), Pazopanib (5-[[4-[(2,3-dimethyl-2H-indazol-6-yl)methyl-amino]-2-pyrimidinyl]amino]-2-methyl-benzenesulfonamide); sunitinib (SUTENT®); brivanib (BMS-582664); sorafenib (NEXAVAR®); SU5416; conbercept; abicipar pegol; or any biosimilar thereof. In some cases, the anti-IL8 composition and the anti-VEGF composition are administered to a subject separately. In other cases, the anti-IL8 composition and the anti-VEGF composition are co-formulated and administered to a subject at the same time. The methods can be performed at a hospital or a clinic, for example, the pharmaceutical compositions can be administered by a health-care professional. In other cases, the pharmaceutical compositions can be self-administered by the subject. Treatment may commence with the diagnosis of a subject with an ocular disease. In the event that further treatments are necessary, follow-up appointments may be scheduled for the administration of subsequent doses of the composition, for example, administration every 8 weeks.

Further disclosed herein are methods of using an anti-IL8 composition of the disclosure to inhibit a function associated with IL8. For example, the methods may involve administering a composition of the disclosure, including one or more anti-IL8 aptamers, to a biological system (e.g., biological cells, biological tissue, a subject) to inhibit a function associated with IL8. In some cases, the anti-IL8 aptamers may bind to the N-terminal domain of IL8. In some cases, the anti-IL8 aptamers may bind to the hydrophobic pocket of IL8. In some cases, the anti-IL8 aptamers may bind to the N-loop of IL8. In some cases, the anti-IL8 aptamers may bind to the GAG binding site of IL8. In some cases, the methods may be used to prevent or reduce binding of IL8 to CXCR1, CXCR2, or both. In some cases, the methods may be used to inhibit downstream signaling pathways associated with IL8. Additionally or alternatively, the anti-IL8 aptamers may bind to a region of IL8 such that a molecule conjugated to the anti-IL8 aptamer (e.g., a polyethylene glycol polymer) is positioned in a manner so that the conjugate itself may prevent or reduce interaction with CXCR1, CXCR2, or both. In such cases, the anti-IL8 aptamer may bind to IL8 at a region that is not itself important for interaction with CXCR1, CXCR2, or both. Additionally or alternatively, the methods may involve administering an anti-IL8 composition of the disclosure, in combination with an anti-VEGF composition to a biological system.

Methods of Generating Aptamers

The SELEX™ Method

The aptamers described herein can be generated by any method suitable for generating aptamers. In some cases, the aptamers described herein are generated by a process known as Systematic Evolution of Ligands by Exponential Enrichment" ("SELEX™"). The SELEX™ process is described in, e.g., U.S. Pat. No. 5,475,096 entitled "Nucleic Acid Ligands", and U.S. Pat. No. 5,270,163 (see, also WO 91/19813) entitled "Nucleic Acid Ligands", each of which are herein incorporated by reference. By performing iterative cycles of selection and amplification, SELEX™ may be used to obtain aptamers with any desired level of target binding affinity.

The SELEX™ method generally relies as a starting point upon a large library or pool of single stranded oligonucleotides comprising randomized sequences. The oligonucleotides can be modified or unmodified DNA, RNA, or DNA/RNA hybrids. In some examples, the pool comprises 100% random or partially random oligonucleotides. In other examples, the pool comprises random or partially random oligonucleotides containing at least one fixed sequence and/or conserved sequence incorporated within randomized sequence. In other examples, the pool comprises random or partially random oligonucleotides containing at least one fixed sequence and/or conserved sequence at its 5' and/or 3' end which may comprise a sequence shared by all the molecules of the oligonucleotide pool. Fixed sequences are sequences common to oligonucleotides in the pool which are incorporated for a preselected purpose such as, CpG motifs, hybridization sites for PCR primers, promoter sequences for RNA polymerases (e.g., T3, T4, T7, and SP6), sequences to form stems to present the randomized region of the library within a defined terminal stem structure, restriction sites, or homopolymeric sequences, such as poly A or poly T tracts, catalytic cores, sites for selective binding to affinity columns, and other sequences to facilitate cloning and/or sequencing of an oligonucleotide of interest. Conserved sequences are sequences, other than the previously described fixed sequences, shared by a number of aptamers that bind to the same target.

The oligonucleotides of the pool can include a randomized sequence portion as well as fixed sequences necessary for efficient amplification. Typically the oligonucleotides of the starting pool contain fixed 5' and 3' terminal sequences which flank an internal region of 30-50 random nucleotides. The randomized nucleotides can be produced in a number of ways including chemical synthesis and size selection from randomly cleaved cellular nucleic acids. Sequence variation in test nucleic acids can also be introduced or increased by mutagenesis before or during the selection/amplification iterations.

The random sequence portion of the oligonucleotide can be of any length and can comprise ribonucleotides and/or deoxyribonucleotides and can include modified or non-natural nucleotides or nucleotide analogs. Typical syntheses carried out on automated DNA synthesis equipment yield $10^{14}$-$10^{16}$ individual molecules, a number sufficient for most SELEX™ experiments. Sufficiently large regions of random sequence in the sequence design increases the likelihood that each synthesized molecule is likely to represent a unique sequence.

The starting library of oligonucleotides may be generated by automated chemical synthesis on a DNA synthesizer. To synthesize randomized sequences, mixtures of all four nucleotides are added at each nucleotide addition step during the synthesis process, allowing for random incorporation of nucleotides. As stated above, in some cases, random oligonucleotides comprise entirely random sequences; however, in other cases, random oligonucleotides can comprise stretches of nonrandom or partially random sequences. Partially random sequences can be created by adding the four nucleotides in different molar ratios at each addition step.

The starting library of oligonucleotides may be RNA, DNA, substituted RNA or DNA or combinations thereof. In those instances where an RNA library is to be used as the starting library it is typically generated by synthesizing a DNA library, optionally PCR amplifying, then transcribing the DNA library in vitro using a phage RNA polymerase or modified phage RNA polymerase, and purifying the transcribed library. The nucleic acid library is then mixed with the target under conditions favorable for binding and subjected to step-wise iterations of binding, partitioning and amplification, using the same general selection scheme, to achieve virtually any desired criterion of binding affinity and selectivity. More specifically, starting with a mixture containing the starting pool of nucleic acids, the SELEX™ method includes steps of: (a) contacting the mixture with the target under conditions favorable for binding; (b) partitioning unbound nucleic acids from those nucleic acids which have bound specifically to target molecules; (c) dissociating the nucleic acid-target complexes; (d) amplifying the nucleic acids dissociated from the nucleic acid-target complexes to yield a ligand-enriched mixture of nucleic acids; and (e) reiterating the steps of binding, partitioning, dissociating and amplifying through as many cycles as desired to yield highly specific, high affinity nucleic acid ligands to the target molecule. In those instances where RNA aptamers are being selected, the SELEX™ method further comprises the steps of: (i) reverse transcribing the nucleic acids dissociated from the nucleic acid-target complexes before amplification in step (d); and (ii) transcribing the amplified nucleic acids from step (d) before restarting the process.

Within a nucleic acid mixture containing a large number of possible sequences and structures, there is a wide range of binding affinities for a given target. Those which have the higher affinity (lower dissociation constants) for the target are most likely to bind to the target. After partitioning, dissociation and amplification, a second nucleic acid mixture is generated, enriched for the higher binding affinity candidates. Additional rounds of selection progressively favor the best ligands until the resulting nucleic acid mixture is predominantly composed of only one or a few sequences. These can then be cloned, sequenced and individually tested as ligands or aptamers for 1) target binding affinity; and 2) ability to effect target function.

Cycles of selection and amplification are repeated until a desired goal is achieved. In the most general case, selection/amplification is continued until no significant improvement in binding strength is achieved on repetition of the cycle. The method is typically used to sample approximately $10^{14}$ different nucleic acid species but may be used to sample as many as about $10^{18}$ different nucleic acid species. Generally, nucleic acid aptamer molecules are selected in a 3 to 20 cycle procedure.

In some cases, the aptamers of the disclosure are generated using the SELEX™ method as described above. In other cases, the aptamers of the disclosure are generated using any modification or variant of the SELEX™ method.

In some cases, the aptamers described herein have been generated using methodologies to select for specific sites related to activity or function of a target protein. In some cases, the aptamers described herein may be selected using methods that improve the chances of selecting an aptamer with a desired function or desired binding site. In some cases, the aptamers described herein are generated using methods that increase the chances of selecting an aptamer that binds to the N-terminal domain of IL8, the hydrophobic pocket of IL8, the N-loop of IL8, or the GAG binding site of IL8.

In some cases, the methods of the disclosure involve a method of selecting for aptamers that bind near the N-terminal domain or the N-loop of IL8. In some cases, the method may involve selecting for aptamers in the presence of a substance that blocks the charged C-terminus of IL8. In some cases, the substance comprises heparin sulfate or heparan sulfate. In other cases, the method may involve using an IL8 chimera that has a different protein attached to the C-terminus of IL8 to sterically occlude the C-terminus of IL8, thereby driving selection of aptamers towards the N-terminus. In some cases, the IL8 chimera includes a mucin stalk attached to the C-terminus of IL8.

EXAMPLES

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1

A. Selection for Nuclease Stabilized (fGmH) Anti-IL8 Aptamers.

Figure 2C:
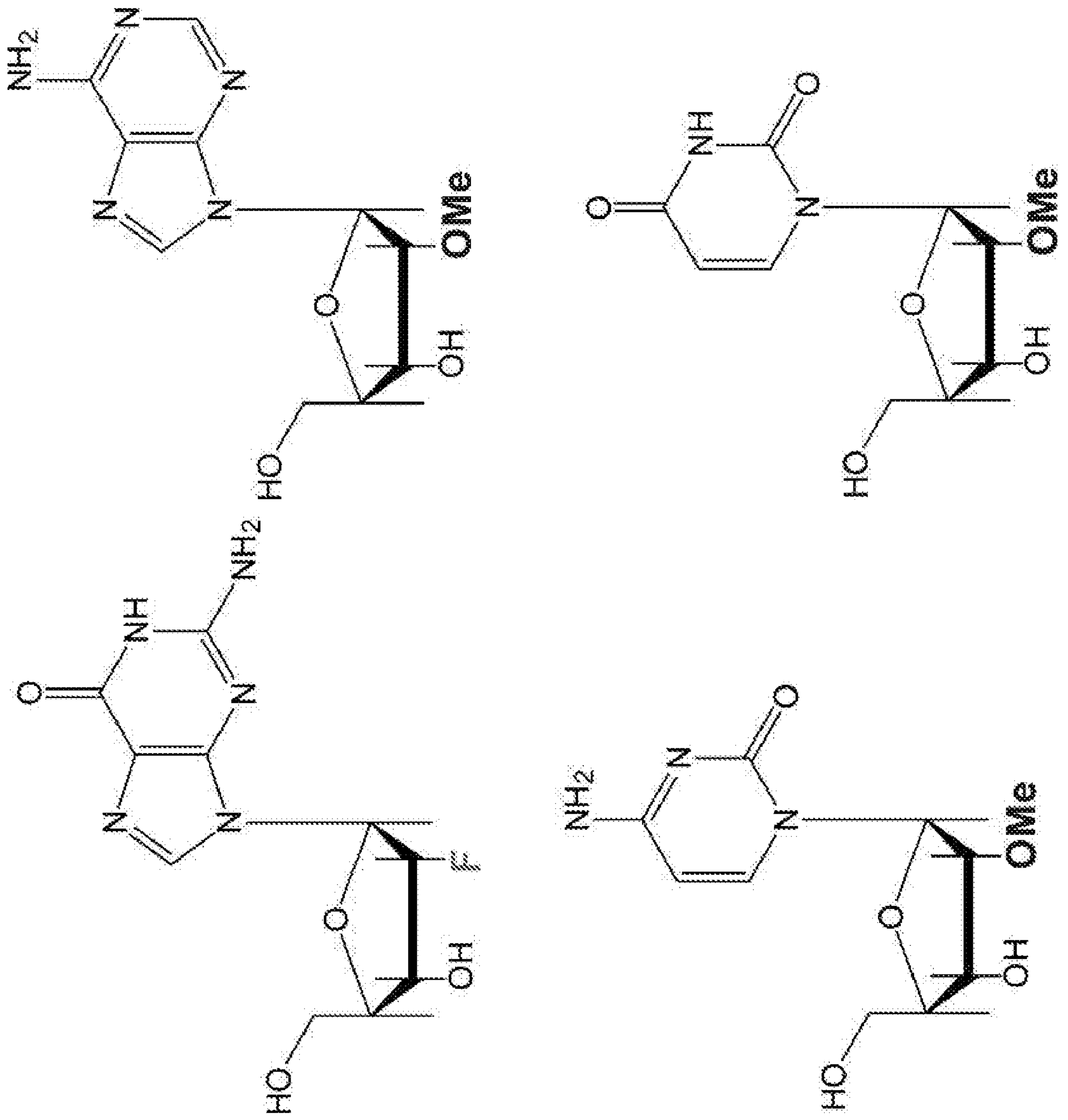
FIG. 2C depicts non-limiting examples of structures of modified nucleotides that may be used to generate an aptamer library suitable for the selection of Interleukin-8 aptamers according to embodiments of the disclosure.

Anti-IL8 aptamers were identified using an N35 library comprised of a 35-nucleotide random region flanked by constant regions at the 5' end (solid underline) and the 3' end (dotted underline) as depicted in FIG. 2A. The sequence in italics represents the forward and reverse primer binding sites. FIG. 2B depicts a representation of the N35 library with the reverse oligo (N35.R. (SEQ ID NO: 795)) hybridized to the 3' constant region. For nuclease stability, the library was composed of 2'-fluoro-G (2'F GTP) and 2'-O-methyl (2'OMe) A/C/U. FIG. 2C depicts structures of modified nucleotides used to generate the N35 library for selection against target IL8. For simplicity, the nucleosides, and not the nucleotide triphosphates are shown. The library sequence and the sequence of oligos used to amplify the library are described in Table 5.

TABLE 5

Library sequence and sequence of oligos used to amplify the library

| SEQ ID NO. | | Sequence (5' to 3') |
|---|---|---|
| SEQ ID NO: 793 | Library sequence (Total library length: 74 bases) | GGGAGAGTCGGTAGCAGTCT-N35-TCTATGTGGAAATGGCGCTGT |
| SEQ ID NO: 794 | N35.F | P-GGGAGAGTCGGTAGCAGTC |
| SEQ ID NO: 795 | N35.R | ACAGCGCCATTTCCACATAG |

where G, A, T and C are deoxyribonucleotides and P-denotes a phage polymerase promoter.

The starting library was transcribed from a pool of ~$10^{14}$ double-stranded DNA (dsDNA) molecules. The dsDNA library was generated by primer extension using Klenow exo (−) DNA polymerase, the pool forward primer (N35.F (SEQ ID NO: 794)) and a synthetic single-stranded DNA (ssDNA) molecule encoding the reverse complement of the library. The dsDNA was subsequently converted to 100% backbone modified RNA via transcription using a mixture of 2'F GTP, 2'OMe ATP/CTP/UTP and a modified phage polymerase in buffer optimized to facilitate efficient transcription. Following transcription, RNAs were treated with DNAse to remove the template dsDNA and purified.

The selection strategy used to isolate the anti-IL8 aptamers described herein was specifically designed to drive the selection for aptamers that bind to the surfaces of IL8 which directly interact with the CXCR1 receptor, the CXCR2 receptor, or both, and away from aptamers that bind to the GAG binding site. Aptamers that bind IL8 at the receptor interaction interface are desirable, as these would directly block IL8 function by preventing association with its cognate receptors. Additionally, an anti-IL8 aptamer that binds to the surfaces of IL8 which interact with the CXCR1 and/or CXCR2 receptor may bind without causing a significant amount of IL8 to be liberated from the cell surface.

For the first round of the selection, a mixture of two variants of recombinant human IL8 was used: one bearing a C-terminal His tag (His-His-His-His-His-His; SEQ ID NO: 796) (C-His-IL8; Sino Biologicals) and the other bearing a C-terminal His-tagged mucin stalk (mucin-stalk-IL8, R&D Systems). Rounds 2 through 6 were carried out using both C-terminal and N-terminal His-tagged IL8 (N-His-IL8; Creative Biomart). Heparan sulfate was included as an additional blocking agent in rounds 6 through 8 to drive selection away from the GAG binding site of IL8. Rounds 7 and 8 were carried out using only the mucin-stalk-IL8 in an effort to drive the selection of aptamers towards molecules which preferentially bind the N-terminus of IL8 because the mucin stalk at the C-terminus of this protein may help in occluding the C-terminus from aptamer binding. The amount of target protein, number of beads, input RNA, blocking agents and washing conditions varied between rounds (Table 6). Briefly, DYNABEADS® His-Tag Isolation and Pulldown beads (Thermofisher) were washed three times with immobilization buffer (50 mM sodium phosphate, pH 8.0, 300 mM NaCl, 0.01% TWEEN®-20) (polyethylene glycol sorbitan monolaurate) and then resuspended in immobilization buffer. His-tagged protein was added to the beads and incubated at room temperature for 30 minutes. The beads were washed three times with binding buffer SB1T (40 mM HEPES, pH 7.5, 125 mM NaCl, 5 mM KCl, 1 mM MgCl2, 1 mM CaCl2, 0.05% TWEEN®-20) to remove any unbound protein and then were re-suspended in 50 pL SB1T buffer without any blocking agent or with 1 µg/ml ssDNA, 0.1% BSA and 1 pg/pl heparin sulphate, depending on the round of selection (Table 6). Protein variants for each round were immobilized separately. After washing, the beads were combined and the mixture of beads was used for selection.

Selection stringency was increased by both decreasing the amount of protein target and increasing the number of washes performed each round (Table 6).

Following the first round of selection, a negative selection step was employed which was included in all the subsequent rounds. For the negative selection, the pool was prepared as described above and then was incubated with beads only (Rounds 2-6) or Gro-A immobilized beads (Rounds 6-8) for 30 minutes at 37° C. in SB1T buffer. The beads were then spun down and the supernatant, containing molecules that did not bind to the unlabeled beads, was utilized for the positive selection step.

TABLE 6

Selection details

| Round | Input (pmoles/ conc.) | Target protein | Protein (pmoles/ conc.) | Blocking agents | Negative selection | washes | # cycles | NGS |
|---|---|---|---|---|---|---|---|---|
| 1 | 1000 pm/ 20 µM | c-his-IL8 and mucin-stalk-IL8 | 100 pm/ 1 µM | none | none | 3 × 5 min. | 12 | no |
| 2 | 25 pm/ 0.5 µM | c-his-IL8 and n-his-IL8 | 25 pm/ 0.25 µM | ssDNA/ BSA | beads | 3 × 5 min. | 16 | no |
| 3 | 25 pm/ 0.5 µM | c-his-IL8 and n-his-IL8 | 25 pm/ 0.25 µM | ssDNA/ BSA | beads | 4 × 5 min. | 26 | no |
| 4 | 25 pm/ 0.5 µM | c-his-IL8 and n-his-IL8 | 20 pm/ 0.20 µM | ssDNA/ BSA | beads | 4 × 5 min. | 23 | no |
| 5 | 25 pm/ 0.5 µM | c-his-IL8 and n-his-IL8 | 10 pm/ 0.1 µM | ssDNA/ BSA | beads | 4 × 5 min. | 15 | yes |
| 6 | 25 pm/ 0.5 µM | c-his-IL8 and n-his-IL8 | 10 pm/ 0.1 µM | ssDNA/ BSA/ heparin | Gro-A-beads | 4 × 5 min. | 16 | yes |
| 7 | 25 pm/ 0.5 µM | Mucin-stalk-IL8 | 10 pm/ 0.1 µM | ssDNA/ BSA/ heparin | Gro-A-beads | 4 × 5 min. | 16 | no |
| 8 | 25 pm/ 0.5 µM | Mucin-stalk-IL8 | 10 pm/ 0.1 µM | ssDNA/ BSA/ heparin | Gro-A-beads | 4 × 5 min. | 16 | yes |

Prior to each round of selection, the modified library was thermally equilibrated by heating at 90° C. for 6 minutes and then cooled at room temperature for 5 minutes in the presence of a 1.5-fold molar excess of reverse primer (N35.R) to allow the library to refold and simultaneously block the 3' end of the pool. Following renaturation, the final volume of the reaction was adjusted to 50 µL in SB1T with or without blocking agents and was incubated with immobilized C-His-IL8 and mucin-stalk-IL8 on beads for 30 minutes at 37° C. The beads were subsequently washed to remove unbound species. The washing conditions varied depending on the round, and are indicated in Table 6. After washing, IL8-bound aptamers were eluted using 200 µL elution buffer (2 M Guanidine-HCl in SB1T buffer) two times (total volume 400 µL). The eluted aptamers, in 400 µL of elution buffer, were precipitated by adding 40 µL 3 M NaOAc, pH 5.2, 1 ml ethanol and 4 µl glycogen and incubating at −80° C. for 15 minutes. The recovered library was converted to DNA by reverse transcription and the ssDNA was subsequently amplified by PCR. The resulting dsDNA library was subsequently converted back into modified RNA via transcription as described above. DNased, purified RNA was used for subsequent rounds.

The first round of selection used 1 nanomole (nM) of RNA (3 copies of ~$2\times10^{14}$ sequences). For subsequent rounds, the input RNA was fixed at 25 picomoles (pM).

B. Assessing the Progress of Selection

Figure 3A:
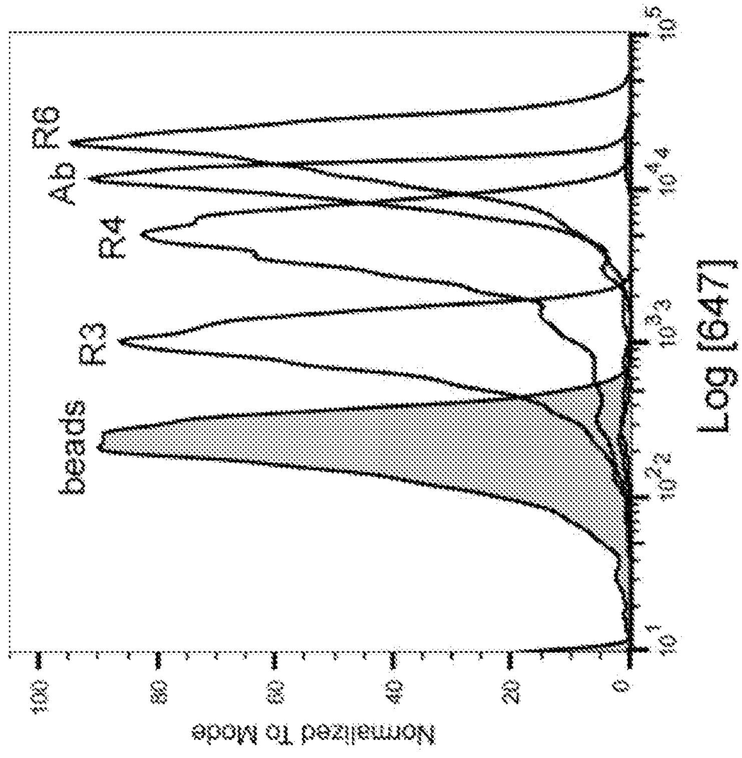
FIG. 3A depicts non-limiting examples of flow cytometry data demonstrating the ability of various aptamer selection rounds to bind to bead-immobilized C terminus His-tagged IL8 according to embodiments of the disclosure.
Figure 3B:
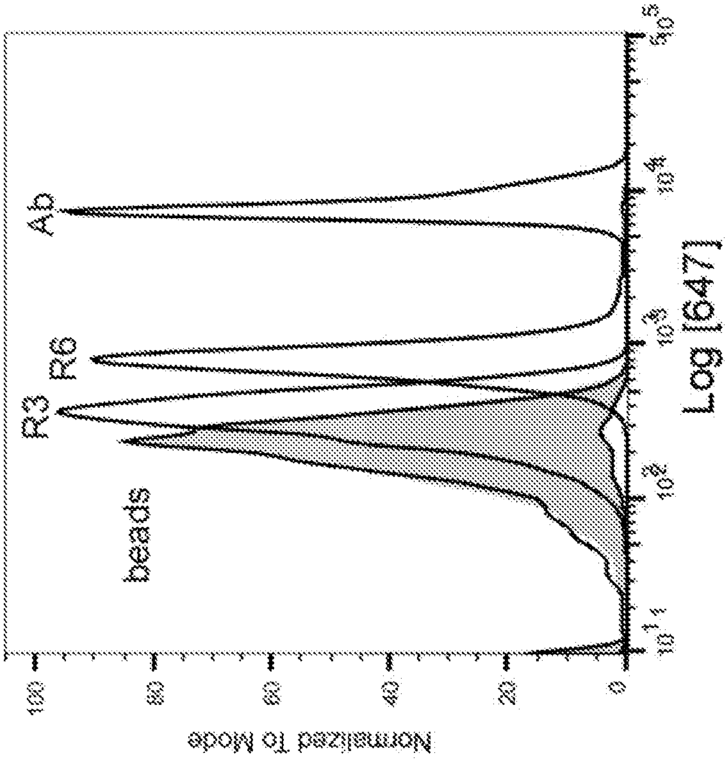
FIG. 3B depicts non-limiting examples of flow cytometry data demonstrating the ability of various aptamer selection rounds to bind to bead-immobilized mucin-stalk-IL8 according to embodiments of the disclosure.
Figure 3C:
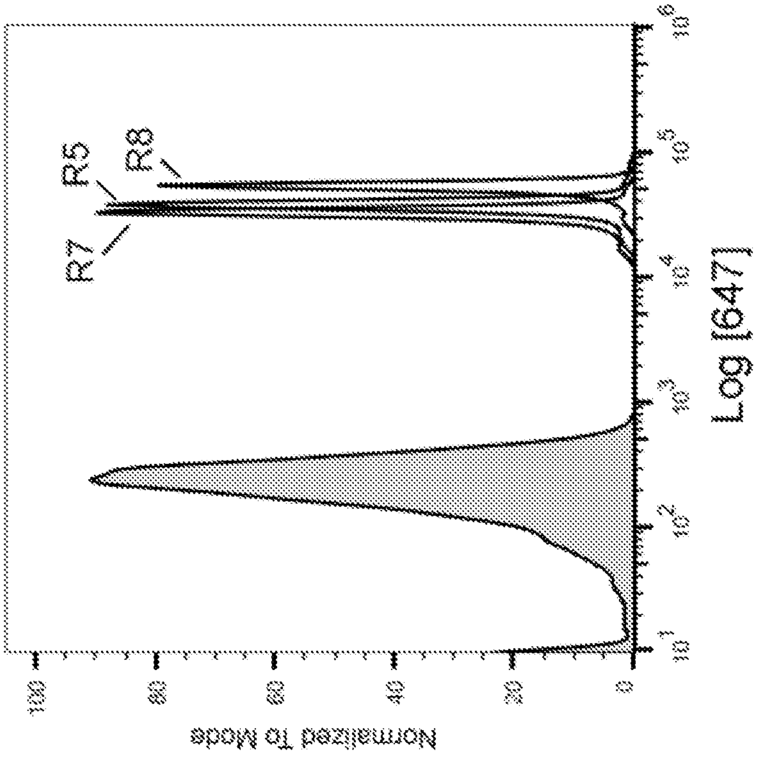
FIG. 3C depicts non-limiting examples of flow cytometry data demonstrating the ability of various aptamer selection rounds to bind to bead-immobilized C-terminus His-tagged IL8 according to embodiments of the disclosure.
Figure 3D:
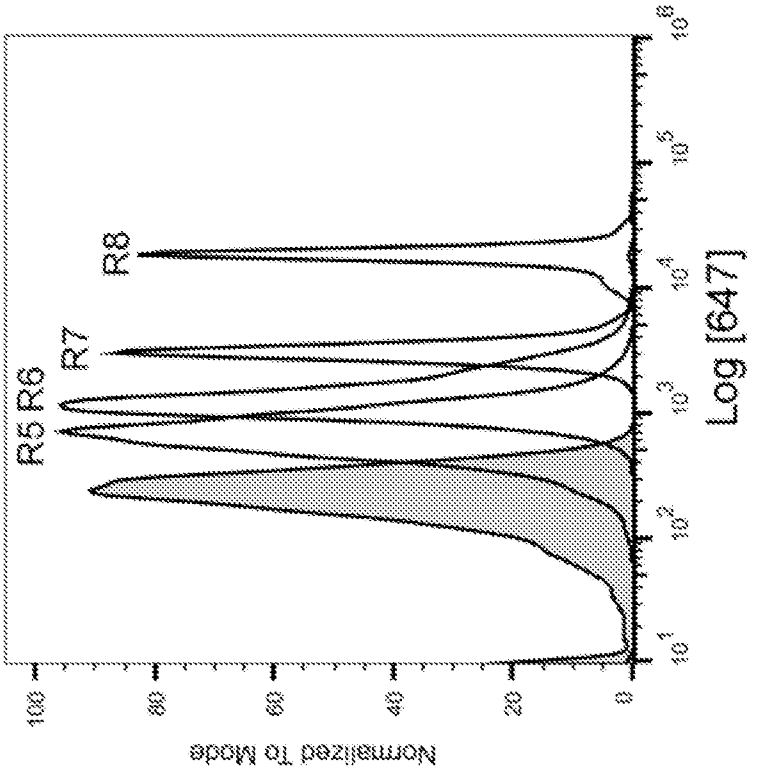
FIG. 3D depicts non-limiting examples of flow cytometry data demonstrating the ability of various aptamer selection rounds to bind to bead-immobilized mucin-stalk-IL8 according to embodiments of the disclosure.

Flow cytometry was used to assess the progress of the selection. For these assays, RNA from each round was first hybridized with reverse complement oligonucleotide composed of 2'OMe RNA labeled with DYLIGHT® 650 (Dy650-N35.R.OMe, sequence identical to N35.R). Briefly, the library was combined with 1.5-fold molar excess of Dy650-N35.R. OMe, heated at 90° C. for 3 minutes and allowed to cool at room temperature for 5 minutes. The libraries were subsequently incubated with bead immobilized IL8 in SB1T buffer containing 0.1% BSA and 1 µg/µl ssDNA. Following incubation for 30 minutes at 37° C., the beads were washed three times with SB1T, re-suspended in SB1T buffer and analyzed by flow cytometry. As shown in FIGS. 3A-D, when binding was assessed using bead immobilized c-his-IL8, an improvement in fluorescent signal with the progressing rounds was observed as early as Round 3 and progressed to Round 5 (FIG. 3A). There was little change in signal between Rounds 5 and 6. Interestingly, when the same analysis was performed on the IL8 mucin stalk fusion protein (mucin-stalk-IL8), significantly weaker binding was observed for the selection rounds, suggesting that the presence of the mucin domain at the C-terminus may sterically occlude IL8 binding of a significant portion of the aptamer population (FIG. 3B). Because of this observation, Round 7 and 8 were performed using this protein as the target in an effort to enrich for molecules which preferentially bind the N-terminus of IL8. Importantly, while the additional rounds of selection had little effect on the ability of the Round 7 and 8 libraries to bind c-his-IL8 (FIG. 3C), a significant improvement in binding for the mucin-stalk-IL8 protein was observed (FIG. 3D).

C. Selection, Purification and Characterization of Clones

The enriched aptamer populations recovered from rounds 5, 6 and 8 of the selection were sequenced using next-generation sequencing (NGS) to identify individual functional clones. Data from greater than 250,000 individual sequences were processed by trimming the flanking constant regions followed by alignment of the random region derived sequences using the ClustalW alignment algorithm. Aptamer sequences were ranked by frequency within each library and organized into families by clustering aptamers with similar sequence elements. All in silico analyses were performed using GENEIOUS® software (Biomatters Inc. Newark NJ, USA). From this analysis, 24 clones were chosen for further testing. A summary of the full-length clones identified for further testing from the selection is shown in Table 7. Aptamers composed of only the portion of the aptamer sequence derived from the random region, as listed in Table 7, were subsequently generated by chemical synthesis. The sequences of the chemically synthesized aptamers are summarized in Table 8.

All aptamers were chemically synthesized on a BioAutomation MerMade 48X using the 2'-fluoro-G and 2'-O-methyl (2'OMe) A/C/U modified phosphoramidites, on an inverted dT-CPG support (idT). To facilitate downstream conjugations, all molecules were synthesized bearing a 5' hexylamine linker ($C6NH_2$). All molecules were purified by anion exchange chromatography and subsequently desalted into nuclease free $H_2O$ via buffer exchange before being used for further analysis. For direct binding assays, synthesized aptamers were labeled with ALEXA FLUOR® 647.

TABLE 7

Sequences of full-length IL8 aptamers

| SEQ ID NO. | Compound Name | Sequence (5' to 3') |
|---|---|---|
| SEQ ID NO: 3 with modifications | rd8-3 | GGGAGAGUCGGUAGCAGUCUAGCGGCCGAAGUU AGCGUACGUUUGCCGGGUACGUCUAUGUGGAAA UGGCGCUGU |
| SEQ ID NO: 4 with modifications | rd6-6 | GGGAGAGUCGGUAGCAGUCUGAUGACGGUAGAU UACGGGUAGAGUGACCGCAUCUCUAUGUGGAAA UGGCGCUGU |
| SEQ ID NO: 5 with modifications | rd6-11 | GGGAGAGUCGGUAGCAGUCUAAUUGCGGUCUACC UUGAAUGACUUGCCGCCCAUUCUAUGUGGAAAUG GCGCUGU |
| SEQ ID NO: 6 with modifications | rd6-4 | GGGAGAGUCGGUAGCAGUCUCGUGAAGGGCGAU UCUGGUGCGUGUUCCCUCGCGUCUAUGUGGAAAU GGCGCUGU |
| SEQ ID NO: 7 with modifications | rd8-4 | GGGAGAGUCGGUAGCAGUCUCAGGCUGAAAAGU GAGCUAUAAUGUCCUGAUUGAUCUAUGUGGAAA UGGCGCUGU |
| SEQ ID NO: 8 with modifications | rd6-10 | GGGAGAGUCGGUAGCAGUCUUAUUGCGGCCCGAU UUACCGAAUUUGCCGUCCGGUCUAUGUGGAAAUG GCGCUGU |
| SEQ ID NO: 9 with modifications | rd6-1 | GGGAGAGUCGGUAGCAGUCUACGGUGGGAAAUG UGAGAUGGGUUGCCGUAUUUUCUAUGUGGAAAU GGCGCUGU |
| SEQ ID NO: 10 with modifications | rd6-3 | GGGAGAGUCGGUAGCAGUCUGCCGACUCACGAAA UCCUCGCGUAGACUGCCUUAUCUAUGUGGAAAUG GCGCUGU |
| SEQ ID NO: 11 with modifications | rd6-19 | GGGAGAGUCGGUAGCAGUCUGAUGAUUUGCGGC AAUACCGUACCUGCCGCCCGGUCUAUGUGGAAAU GGCGCUGU |
| SEQ ID NO: 12 with modifications | rd6-8 | GGGAGAGUCGGUAGCAGUCUCCGGUUGCUGAGA UGUGAGAUUAAUGUCCACCGUUCUAUGUGGAAA UGGCGCUGU |
| SEQ ID NO: 13 with modifications | rd6-9 | GGGAGAGUCGGUAGCAGUCUUGGCCACAGUAGA UUUCGGUGCGUGUGACUGGGCUCUAUGUGGAAA UGGCGCUGU |
| SEQ ID NO: 14 with modifications | rd6-12 | GGGAGAGUCGGUAGCAGUCUCGCUUGUACCUCUG AGAUGUGAGACUAAUGUAGGUCUAUGUGGAAAU GGCGCUGU |
| SEQ ID NO: 15 with modifications | Rd8-7 | GGGAGAGUCGGUAGCAGUCUGCGGCCUCCGUUGA CUGUUGUAAUGCCGGGACAGUCUAUGUGGAAAU GGCGCUGU |

TABLE 7-continued

| Sequences of full-length IL8 aptamers | | |
|---|---|---|
| SEQ ID NO. | Compound Name | Sequence (5' to 3') |
| SEQ ID NO: 16 with modifications | rd6-15 | GGGAGAGUCGGUAGCAGUCUCAGUUGCGGCCCCU GAUACCGAUUUGCCGCCCGGUCUAUGUGGAAAUG GCGCUGU |
| SEQ ID NO: 17 with modifications | rd6-17 | GGGAGAGUCGGUAGCAGUCUGCUGGCGACUCGCA CGGUGUAUUUGUCCCGCACCUCUAUGUGGAAAUG GCGCUGU |
| SEQ ID NO: 18 with modifications | rd6-24 | GGGAGAGUCGGUAGCAGUCUGGAUGACAUUCGG GGGCACCAAUCAUCGUCUGCUCUAUGUGGAAAUG GCGCUGU |
| SEQ ID NO: 19 with modifications | rd6-29 | GGGAGAGUCGGUAGCAGUCUGUCGCCCUACGUAA ACCGCUAUUUGCGACUGCGGUCUAUGUGGAAAUG GCGCUGU |
| SEQ ID NO: 20 with modifications | rd6-30 | GGGAGAGUCGGUAGCAGUCUGACUGCGGUCGCAA GUUACGGAUUUGCCGCCCCGUCUAUGUGGAAAUG GCGCUGU |
| SEQ ID NO: 21 with modifications | rd6-31 | GGGAGAGUCGGUAGCAGUCUUAAGCGCUGAGAC GAGAGAUUAAUGCCGCUUGCCUCUAUGUGGAAA UGGCGCUGU |
| SEQ ID NO: 22 with modifications | rd8-15 | GGGAGAGUCGGUAGCAGUCUCUGAAUCGGCUGA AACGGGAGCAUUAAUGUCCGGUCUAUGUGGAAA UGGCGCUGU |
| SEQ ID NO: 23 with modifications | rd6-40 | GGGAGAGUCGGUAGCAGUCUUAGCCCUGCCAUUG GGGCAUACUUUGGCCGCACUCUAUGUGGAAAUGG CGCUGU |
| SEQ ID NO: 24 with modifications | rd6-63 | GGGAGAGUCGGUAGCAGUCUUGCCCUUUGAUCGU ACCGAGGCGGGGAAGUACGAUCUAUGUGGAAAU GGCGCUGU |
| SEQ ID NO: 25 with modifications | rd6-94 | GGGAGAGUCGGUAGCAGUCUCAUGGGUUGCCAAC CGGCCGUGUAUGUACGUACAUCUAUGUGGAAAU GGCGCUGU |
| SEQ ID NO: 26 with modifications | rd8-3 | GGGAGAGUCGGUAGCAGUCUAGCGGCCGAAGUU AGCGUACGUUUGCCGGGUACGUCUAUGUGGAAA UGGCGCUGU |

where G is 2'F and A, C and U are 2'OMe modified RNA

TABLE 8

| Sequences of truncated IL8 aptamers generated by chemical synthesis | | |
|---|---|---|
| SEQ ID NO: | Aptamer Number | Sequence (5' to 3') |
| SEQ ID NO: 50 with modifications | Aptamer 2 | $C6NH_2$-UAGCGGCCGAAGUUAGCGUACGUUUGCCGG GUACGU-idT |
| SEQ ID NO: 51 with modifications | Aptamer 3 | $C6NH_2$-UGAUGACGGUAGAUUACGGGUAGAGUGACC GCAUCU-idT |
| SEQ ID NO: 52 with modifications | Aptamer 4 | $C6NH_2$-UAAUUGCGGUCUACCUUGAAUGACUUGCCGC CCAUU-idT |
| SEQ ID NO: 53 with modifications | Aptamer 5 | $C6NH_2$-UCGUGAAGGGCGAUUCUGGUGCGUGUUCCC UCGCGU-idT |
| SEQ ID NO: 54 with modifications | Aptamer 6 | $C6NH_2$-UCAGGCUGAAAAGUGAGCUAUAAUGUCCUG AUUGAU-idT |

TABLE 8-continued

| Sequences of truncated IL8 aptamers generated by chemical synthesis | | |
|---|---|---|
| SEQ ID NO: | Aptamer Number | Sequence (5' to 3') |
| SEQ ID NO: 55 with modifications | Aptamer 7 | $C6NH_2$-UUAUUGCGGCCCGAUUUACCGAAUUUGCCGUCCGGU-idT |
| SEQ ID NO: 56 with modifications | Aptamer 8 | $C6NH_2$-UACGGUGGGAAAUGUGAGAUGGGUUGCCGUAUUUU-idT |
| SEQ ID NO: 57 with modifications | Aptamer 9 | $C6NH_2$-UGCCGACUCACGAAAUCCUCGCGUAGACUGCCUUAU-idT |
| SEQ ID NO: 58 with modifications | Aptamer 10 | $C6NH_2$-UGAUGAUUUGCGGCAAUACCGUACCUGCCGCCCGGU-idT |
| SEQ ID NO: 59 with modifications | Aptamer 11 | $C6NH_2$-UCCGGUUGCUGAGAUGUGAGAUUAAUGUCCACCGUU-idT |
| SEQ ID NO: 60 with modifications | Aptamer 12 | $C6NH_2$-UUGGCCACAGUAGAUUUCGGUGCGUGUGACUGGGCU-idT |
| SEQ ID NO: 61 with modifications | Aptamer 13 | $C6NH_2$-UCGCUUGUACCUCUGAGAUGUGAGACUAAUGUAGGU-idT |
| SEQ ID NO: 62 with modifications | Aptamer 14 | $C6NH_2$-UGCGGCCUCCGUUGACUGUUGUAAUGCCGGGACAGU-idT |
| SEQ ID NO: 63 with modifications | Aptamer 15 | $C6NH_2$-UCAGUUGCGGCCCCUGAUACCGAUUUGCCGCCCGGU-idT |
| SEQ ID NO: 64 with modifications | Aptamer 16 | $C6NH_2$-UGCUGGCGACUCGCACGGUGUAUUUGUCCCGCACCU-idT |
| SEQ ID NO: 65 with modifications | Aptamer 18 | $C6NH_2$-UGGAUGACAUUCGGGGGCACCAAUCAUCGUCUGCU-idT |
| SEQ ID NO: 66 with modifications | Aptamer 19 | $C6NH_2$-UGUCGCCCUACGUAAACCGCUAUUUGCGACUGCGGU-idT |
| SEQ ID NO: 67 with modifications | Aptamer 20 | $C6NH_2$-UGACUGCGGUCGCAAGUUACGGAUUUGCCGCCCCGU-idT |
| SEQ ID NO: 68 with modifications | Aptamer 21 | $C6NH_2$-UUAAGCGCUGAGACGAGAGAUUAAUGCCGCUUGCCU-idT |
| SEQ ID NO: 69 with modifications | Aptamer 22 | $C6NH_2$-UCUGAAUCGGCUGAAACGGGAGCAUUAAUGUCCGGU-idT |
| SEQ ID NO: 70 with modifications | Aptamer 23 | $C6NH_2$-UUAGCCCUGCCAUUGGGGCAUACUUUGGCCGCACU-idT |
| SEQ ID NO: 71 with modifications | Aptamer 24 | $C6NH_2$-UUGCCCUUUGAUCGUACCGAGGCGGGGAAGUACGAU-idT |

TABLE 8-continued

| Sequences of truncated IL8 aptamers generated by chemical synthesis | | |
|---|---|---|
| SEQ ID NO: | Aptamer Number | Sequence (5' to 3') |
| SEQ ID NO: 72 with modifications | Aptamer 25 | $C6NH_2$-UCAUGGGUUGCCAACCGGCCGUGUAUGUACGUACAU-idT |

where G is 2'F and A, C and U are 2'OMe modified RNA, $C6NH_2$ is a hexylamine linker, and idT is an inverted deoxythymidine residue.

D. Assaying Individual Synthesized Aptamers for Binding

Figure 4A:
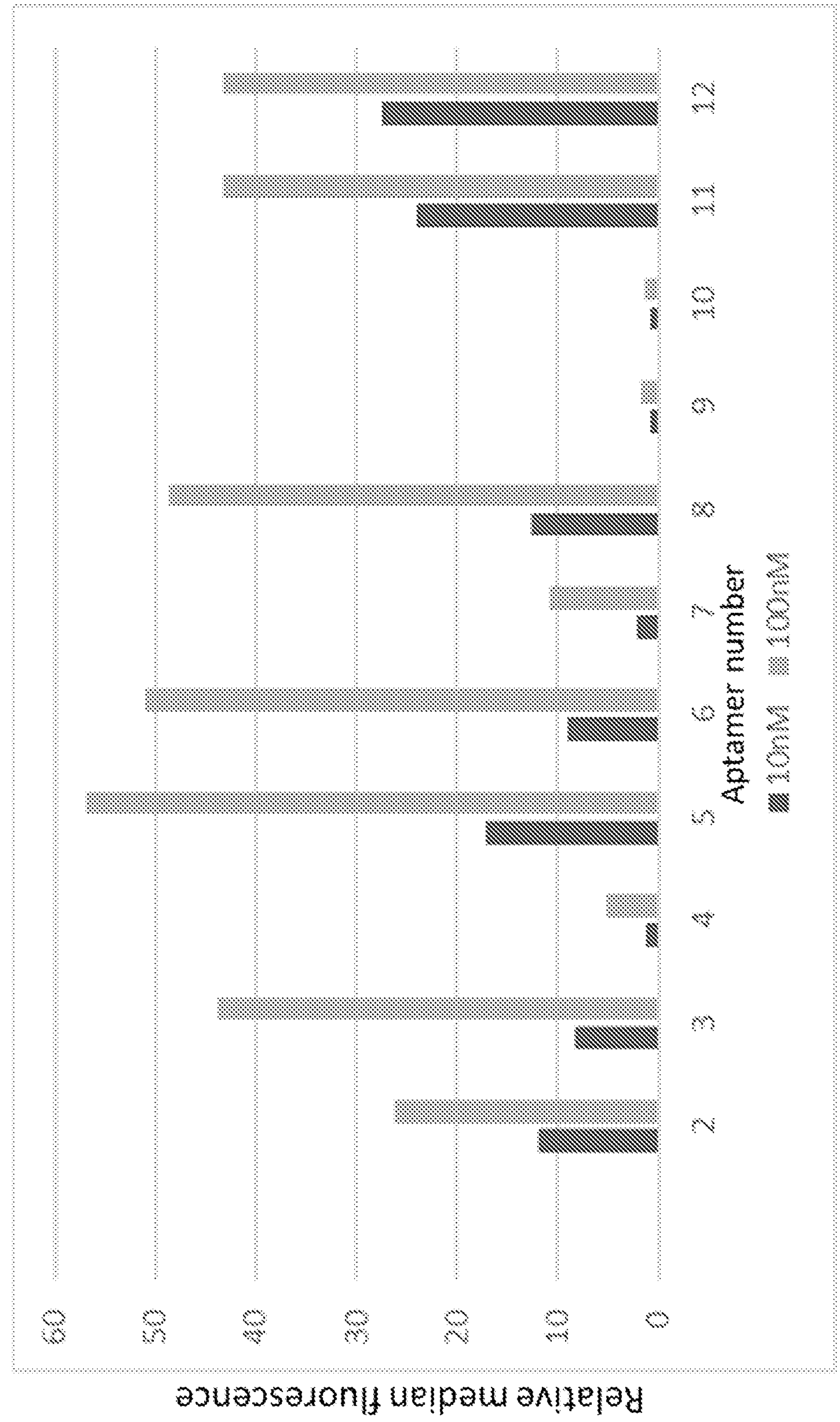
FIG. 4A depicts non-limiting examples of flow cytometry data demonstrating the ability of various aptamers of the disclosure to bind to bead-immobilized C-terminus His-tagged IL8 according to embodiments of the disclosure.
Figure 4B:
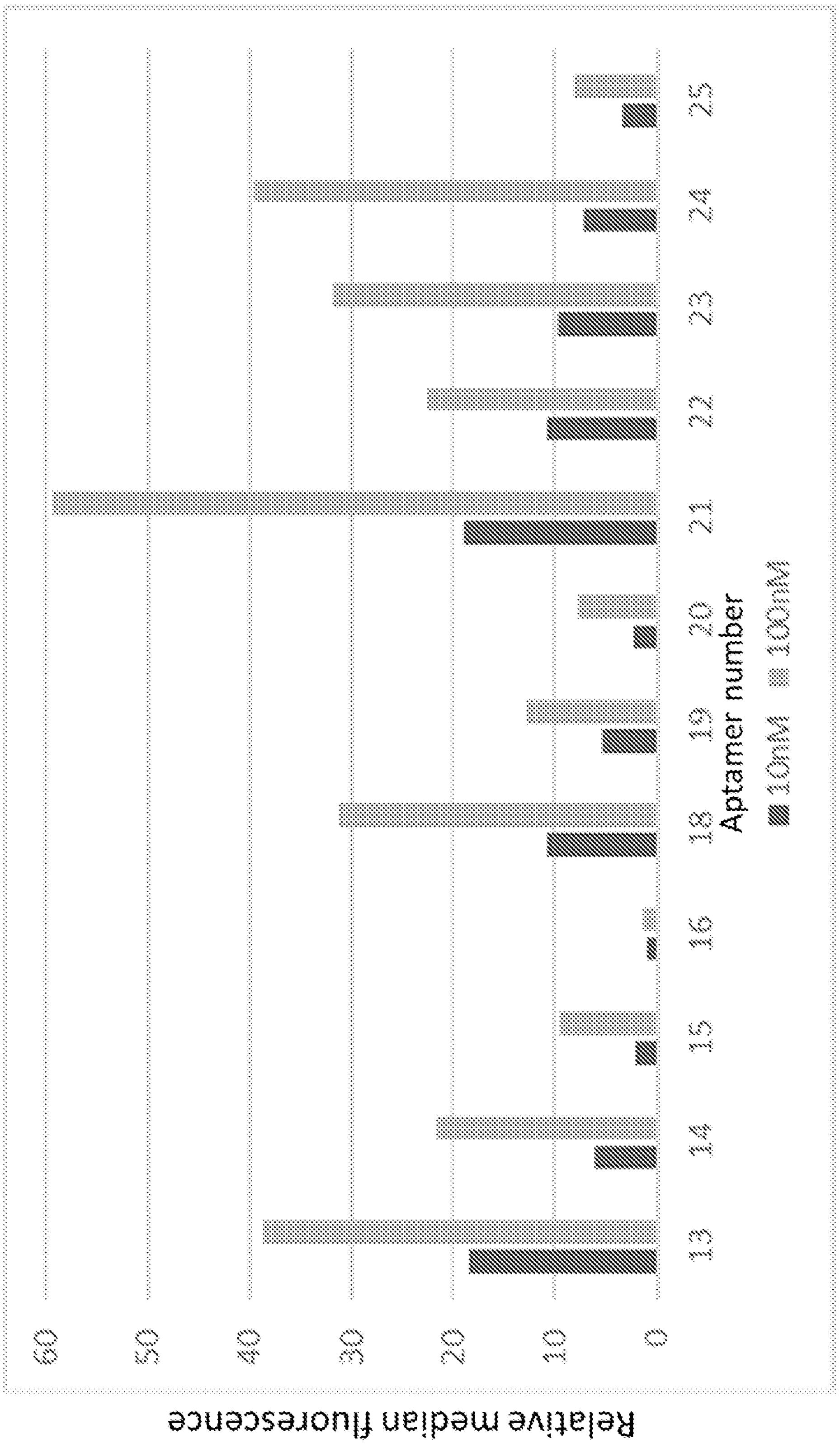
FIG. 4B depicts non-limiting examples of flow cytometry data demonstrating the ability of various aptamers of the disclosure to bind to bead-immobilized C-terminus His-tagged IL8 according to embodiments of the disclosure.

Chemically synthesized aptamers (Table 8) were labeled with ALEXA FLUOR® 647 and were used to test binding to IL8 in a bead based assay using flow cytometry. In brief, fluorescently labeled aptamers were heated at 90° C. for 3 minutes in SB1T and were allowed to cool at room temperature for 5 minutes, after which they were incubated with c-his-IL8, immobilized on DYNABEADS® His-Tag Isolation and Pulldown beads in SB1T buffer containing 0.1% BSA, 1 μg/μl ssDNA and 1 μg/μl heparin sulphate at two different aptamer concentrations: 10 nM and 100 nM. Following incubation for 30 minutes at 37° C., the beads were washed three times with SB1T, re-suspended in SB1T buffer and analyzed by flow cytometry. As shown in FIG. 4A and FIG. 4B, the aptamers showed varying levels of target binding which ranged from very good binding to negligible binding to IL8. Negligible or complete lack of binding seen in cases of some aptamers (e.g., Aptamers 4, 9, 10, and 16) could be due to the removal of the constant regions. No binding was observed when similar experiments were performed in the absence of protein (data not shown). Molecules that demonstrated appreciable binding in this assay (e.g., Aptamer 2, Aptamer 3, Aptamer 5, Aptamer 6, Aptamer 8, Aptamer 11, Aptamer 12, Aptamer 13, Aptamer 14, Aptamer 20, Aptamer 22, Aptamer 23, and Aptamer 25) were subjected to further analysis.

Example 2: Determination of Apparent Binding Constants by Flow Cytometry

Figure 5:
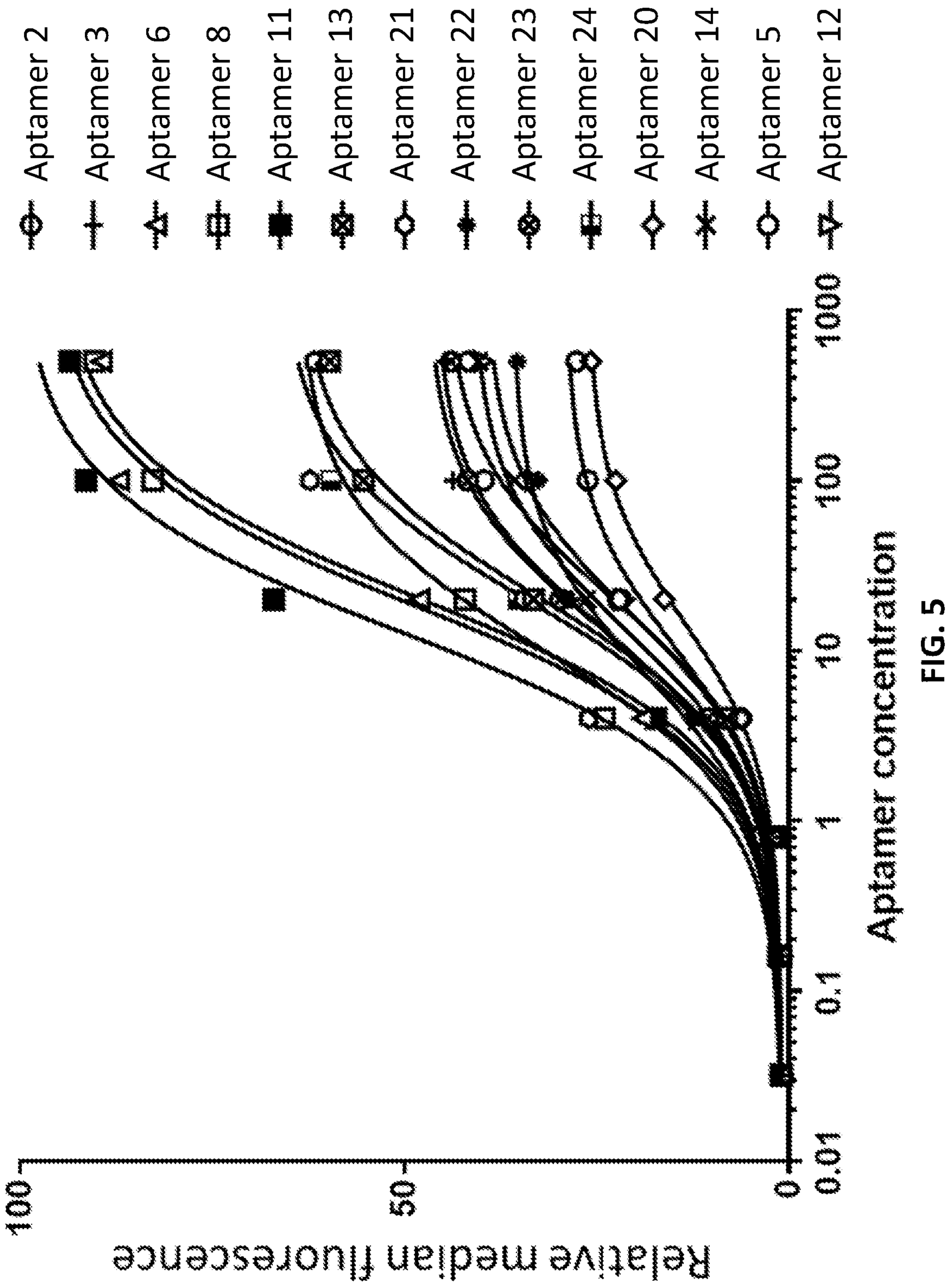
FIG. 5 depicts a non-limiting example of a graph of the median fluorescence intensity versus aptamer concentration in a flow cytometry assay of various aptamers of the disclosure according to embodiments of the disclosure.

Flow cytometry was used to measure the apparent binding affinity for Aptamer 2, Aptamer 3, Aptamer 5, Aptamer 6, Aptamer 8, Aptamer 11, Aptamer 12, Aptamer 13, Aptamer 14, Aptamer 20, Aptamer 22, Aptamer 23, and Aptamer 25 using bead immobilized c-his-IL8. Binding assays were performed as described above, except serial dilutions of each Alexa Fluor® 647-labeled aptamer was used. Following incubation for 30 minutes at 37° C., the beads were washed and fluorescence was measured by flow cytometry. A plot of median fluorescent intensity versus aptamer concentration (FIG. 5) was used to determine the apparent binding constant for each clone. Apparent $K_d$ values were obtained using the equation $Y=B_{max}*X/(K_d+X)$. The apparent binding constants are reported in Table 9.

TABLE 9

| Apparent binding constants of synthesized aptamers by flow cytometry | |
|---|---|
| Aptamer Number | $K_d$ (nM) Bead binding |
| Aptamer 2 | 11 |
| Aptamer 3 | 13 |

TABLE 9-continued

| Apparent binding constants of synthesized aptamers by flow cytometry | |
|---|---|
| Aptamer Number | $K_d$ (nM) Bead binding |
| Aptamer 5 | 20 |
| Aptamer 6 | 18 |
| Aptamer 8 | 20 |
| Aptamer 11 | 13 |
| Aptamer 12 | 16 |
| Aptamer 13 | 21 |
| Aptamer 14 | 13 |
| Aptamer 20 | 15 |
| Aptamer 21 | 10 |
| Aptamer 22 | 7 |
| Aptamer 23 | 13 |
| Aptamer 24 | 19 |

Example 3. Determination of Apparent Binding Constants by TR-FRET

Figure 6:
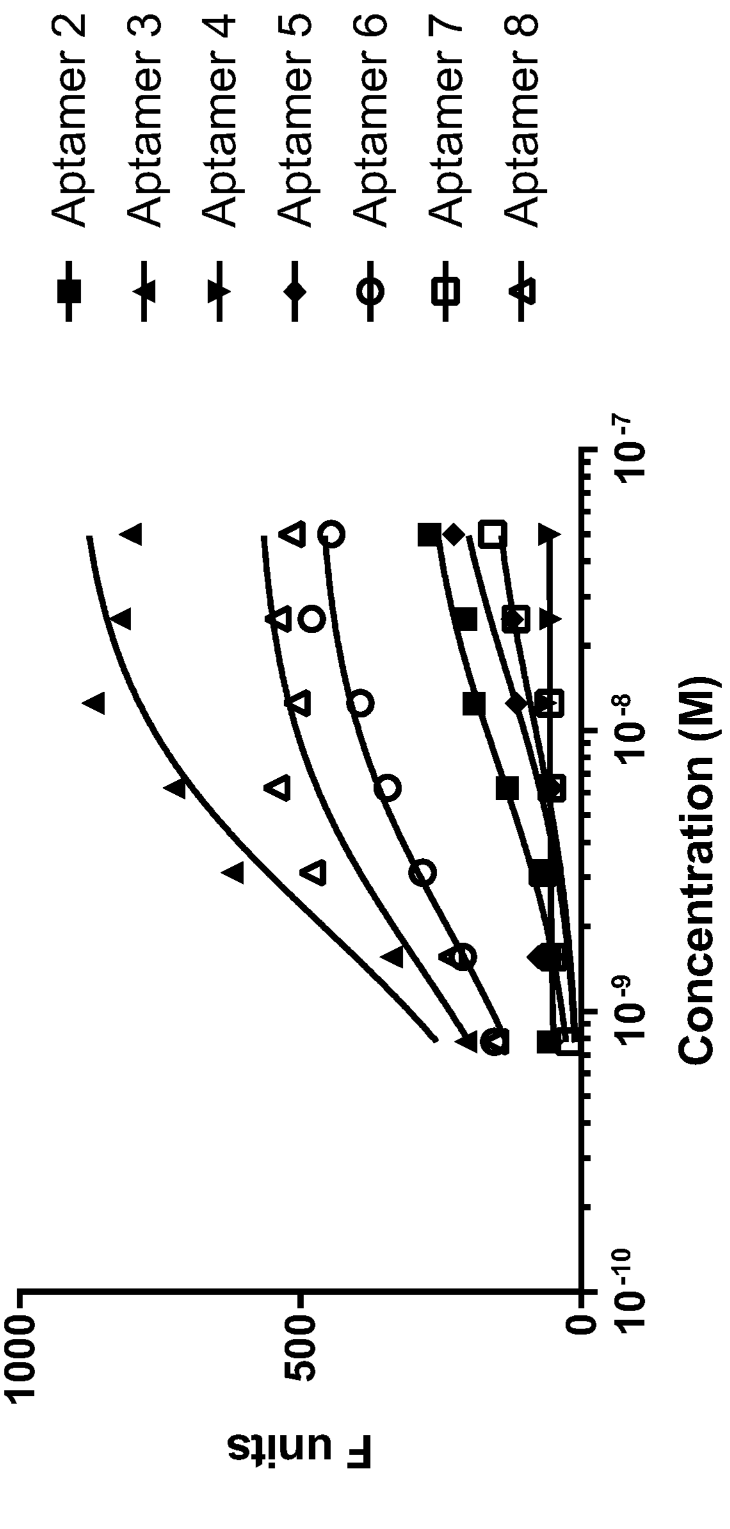
FIG. 6 depicts non-limiting examples of Time-Resolved Fluorescence Resonance Energy Transfer (TR-FRET) data demonstrating the ability of various aptamers of the disclosure to bind to C-terminus His-tagged IL8 according to embodiments of the disclosure.

Aptamers were synthesized and labeled with ALEXA FLUOR® 647, and binding to IL8 was quantified by Time-Resolved Fluorescence Resonance Energy Transfer (TR-FRET). Briefly, 2-fold dilutions of thermally equilibrated aptamers were made in TR-FRET Buffer (50 mM MOPS, pH 7.4, 125 mM NaCl, 5 mM KCl, 50 μM CHAPS, 0.1 mg/mL BSA, 1 mM $CaCl_2$) and 1 mM $MgCl_2$). 10 μL of aptamer or control solution was added to 10 μL of 15 nM C-His-tagged-IL8 (Sino Biological) in a black wall half-area plate (Corning). In the same plate, 10 μl of aptamer solution was added to 10 μl of TR-FRET buffer alone to use for background subtraction. 10 μl of 15 nM anti-His-Eu (Perkin Elmer) was added to each well, the plate was covered with a plate seal and subsequently incubated in the dark for 1 hour at room temperature. The plate was read on a Biotek CYTATION™ 5 plate reader. Samples were excited at 330 nm and fluorescent values were collected at 665 nm. Data analysis was performed by subtracting the background value for each aptamer from the corresponding values obtained from IL8 containing wells. The values were fit by one site specific binding using GraphPad Prism Version 7.0. Apparent $K_d$ values obtained for the fits are calculated as the concentration of half-maximal binding and shown in Table 10, and fit curves as FIG. 6. The final concentration of IL8 in the assay was 5 nM. The measured apparent $K_d$ values ranged from 2 nM to 22 nM. Since the lowest $K_d$ values approximate half the concentration of IL8 (5 nM) in the assay, the apparent $K_d$ values for highest affinity aptamers are likely limited by the IL8 concentration in the assay, while others are expected to be close to their affinity for IL8. Differences between these TR-FRET values (Table 10) and those from the bead binding assay (Table 9) may be due to a different limiting concentration of IL8. For example, if the effective concentration of IL8 in the bead binding assay was ~20 nM, then the lowest calculated $K_d$ values would be 10 nM. It is also possible that differences may arise due to TR-FRET being a homogenous solution binding assay, while bead binding has immobilized ligand and is non-homogenous, so bound aptamers may dissociate during analysis resulting in higher calculated $K_d$ values.

TABLE 10

Apparent $K_d$ values for aptamers binding to IL8 by TR-FRET

| Aptamer Number | $K_d^{app}$ (nM) |
|---|---|
| Aptamer 2 | 9 |
| Aptamer 3 | 2 |
| Aptamer 5 | 10 |
| Aptamer 6 | 2 |
| Aptamer 7 | 2 |
| Aptamer 8 | 2 |
| Aptamer 11 | 2 |
| Aptamer 12 | 12 |
| Aptamer 13 | 7 |
| Aptamer 14 | 6 |
| Aptamer 15 | 22 |
| Aptamer 18 | 13 |
| Aptamer 19 | 4 |
| Aptamer 21 | 7 |
| Aptamer 22 | 15 |
| Aptamer 23 | 12 |
| Aptamer 24 | 9 |

Example 4. Identification of IL8 Inhibiting Aptamers Using IL8/CXCR1 Competition Analysis by Flow Cytometry The ability to inhibit the interaction of IL8 with its cognate receptor, CXCR1, was assessed by flow cytometry using CHEM1 cells stably overexpressing CXCR1 (Eurofins). An IL8 neutralizing antibody (having an amino acid sequence of a heavy chain variable region of: MGWSCIIL-FLVATATGVHSQVQLVESGGGVVQPGRSLRLSCTA-SGFTFSHYGMYWVRQ APGKGLEWVAVIWYDGSY-EYNADSVKGRFTISRDNSKNTLYLQMNSLRAEDTA-VYYC ARDRVGLFDYWGQGTLVTVSSASTKGPSVF-PLAPSSKSTSGGTAALGCLVKDYFPEPVT VSWN-SGALTSGVHTFPAVLQSSGLYSLSSVVTVPSSSL-GTQTYICNVNHKPSNTKVDKK VEPKSCDKTHTCP-PCPAPELLGGPSVFLFPPKPKDTLMISRTPEVTCVVV-DVSHEDPEVK FNWYVDGVEVHNAKTKPREEQYN-STYRVVSVLTVLHQDWLNGKEYKCKVSNKALPA PIEKTISKAKGQPREPQVYTLPPSRDELTKNQVSLT-CLVKGFYPSDIAVEWESNGQPENN YKTTPPVLDS-DGSFFLYSKLTVDKSRWQQGNVFSCSVMHEALHN-HYTQKSLSLSPGK (SEQ ID NO: 797), and an amino acid sequence of light chain variable region of: MGWSCIILFL-VATATGVHSEIVLTQSPGTLSLSPGERATLSCRASQ-SISSSYLAWYQQKPG QAPRLLIYGPSSRATGIPDRFS-GSGSGTDFTLTISRLEPEDFAVYYCQQYAGSLTFG-PGTK VDIKRTVAAPSVFIFPPSDEQLKSGTASVVC-LLNNFYPREAKVQWKVDNALQSGNSQES VTEQD-SKDSTYSLSSTLTLSKADYEKHKVYACEVTHQGLS-SPVTKSFNRGEC (SEQ ID NO: 798)), and a commercially available IL8 blocking antibody (R&D Systems) were used as controls.

Figure 7A:
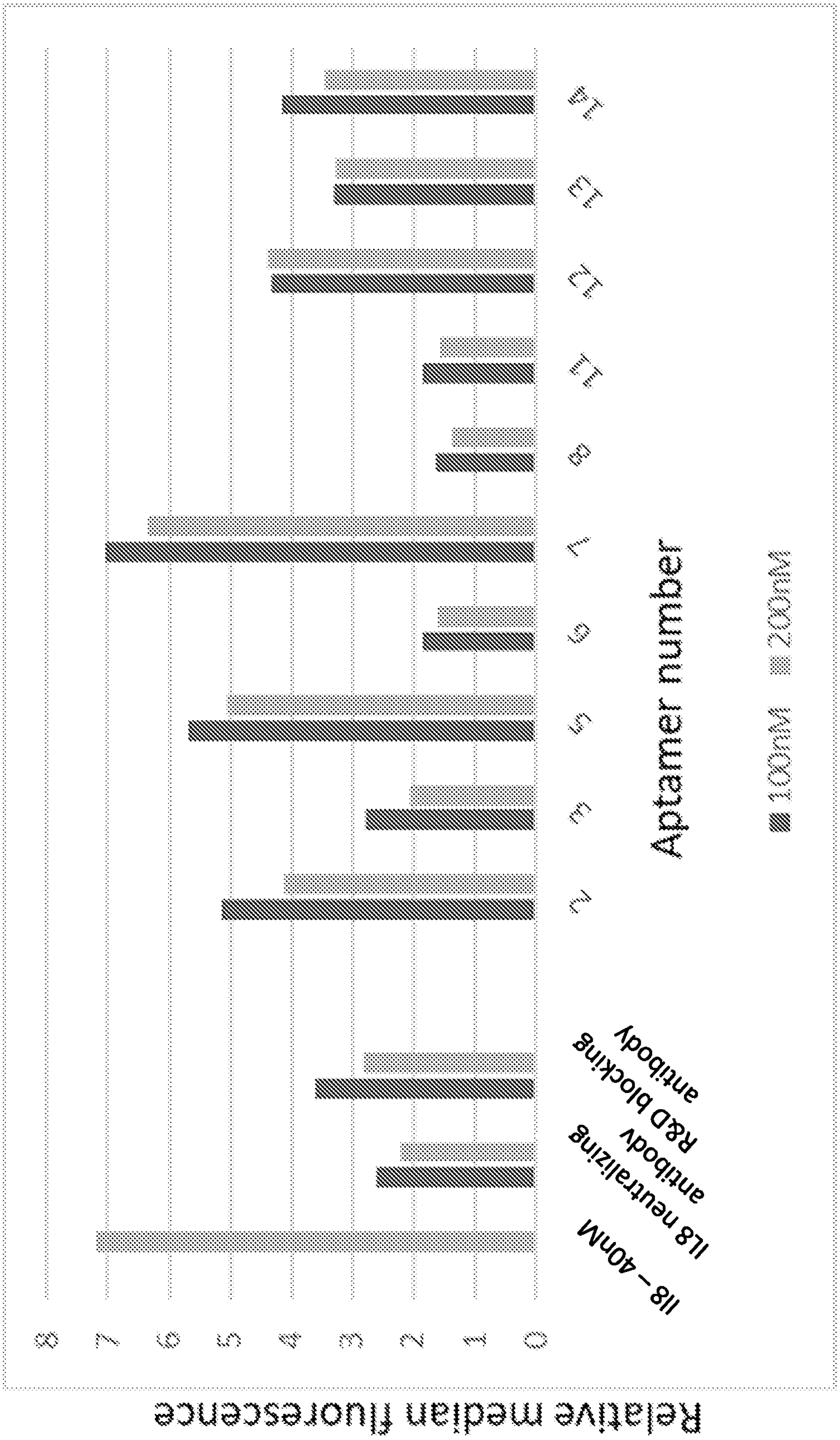
FIG. 7A depicts non-limiting examples of flow cytometry data demonstrating the ability of various aptamers of the disclosure to inhibit IL8 binding to CXCR1 according to embodiments of the disclosure.
Figure 7B:
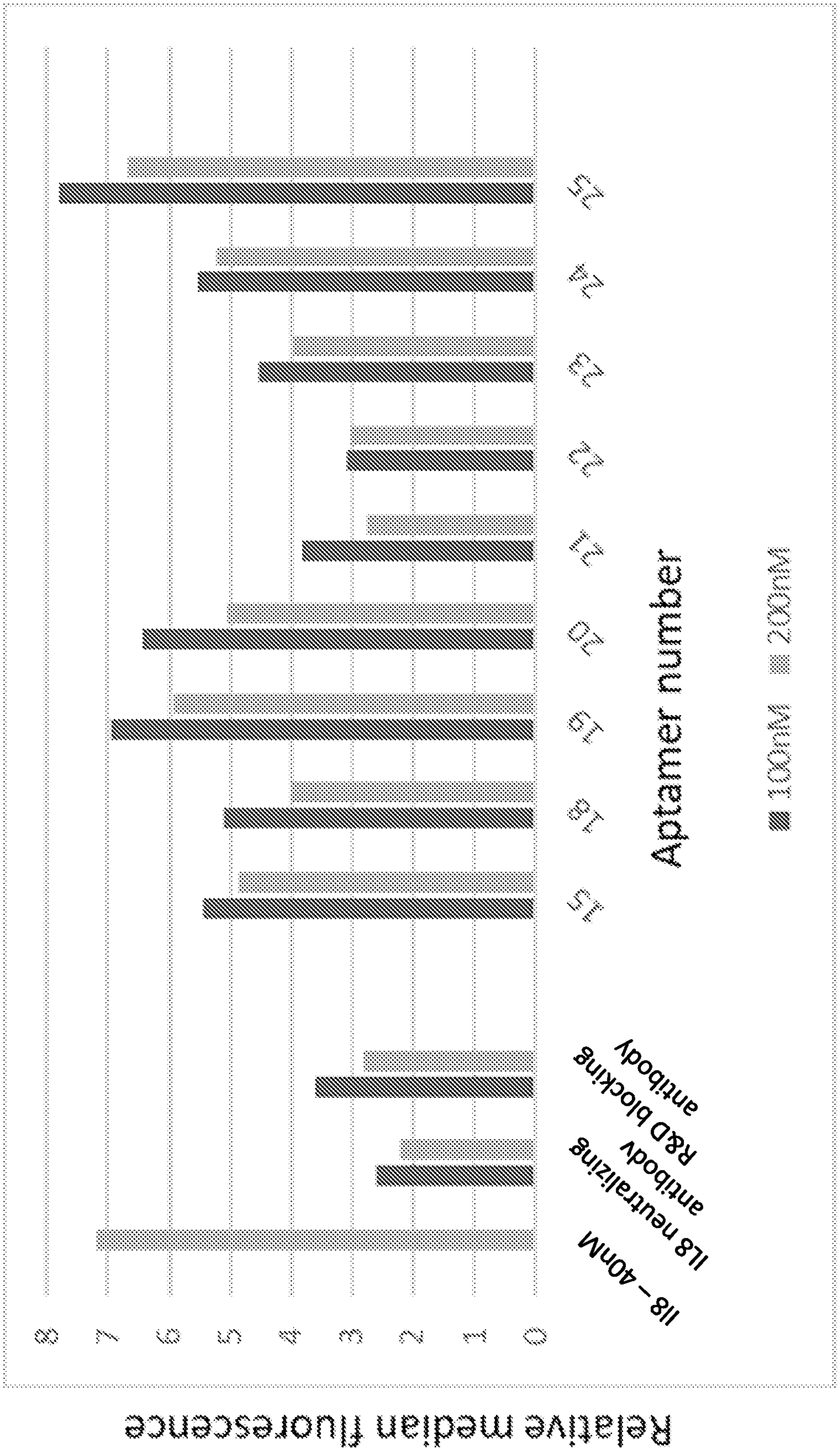
FIG. 7B depicts non-limiting examples of flow cytometry data demonstrating the ability of various aptamers of the disclosure to inhibit IL8 binding to CXCR1 according to embodiments of the disclosure.

To detect binding of IL8 to CXCR1 expressed on the cell surface, 40 nM c-his-IL8 was incubated with the cells (100,000 cells) for 30 minutes at 4° C., after which the cells were washed with PBS+1% BSA twice to remove any unbound IL8. CXCR1-bound IL8 was detected using an APC labeled anti-his antibody (SURELIGHT® anti-6×His (SEQ ID NO: 796)-APC), using flow cytometry. To test the ability of the aptamers or the antibodies to block IL8-CXCR1 interactions, IL8 (40 nM) was pre-incubated with either the chemically synthesized aptamers or control antibodies at two concentrations: 100 nM and 200 nM for 30 minutes at 37° C. Following incubation, the mixture was added to CXCR1 expressing cells (100,000 cells) at 4° C. for 30 minutes. Blocking of the IL8-CXCR1 interaction was detected by measuring the decrease in IL8 signal detected by the anti-His antibody using flow cytometry. Using this approach, the chemically synthesized aptamers which demonstrated IL8 binding in the bead-based assay were screened for the ability to inhibit IL8 binding. As shown in FIG. 7A and FIG. 7B, and summarized in Table 11, all of the molecules tested demonstrated varying levels of IL8 inhibition. Aptamers 3, 6, 8 and 11 showed the highest potency in this assay. Both the antibodies were strongly able to block the association of IL8 with CXCR1.

TABLE 11

Identification of IL8 inhibiting aptamers using CXCR1-expressing cells by flow cytometry

| Aptamer Number | Activity |
|---|---|
| Aptamer 2 | + |
| Aptamer 3 | ++++ |
| Aptamer 5 | + |
| Aptamer 6 | ++++ |
| Aptamer 7 | − |
| Aptamer 8 | ++++ |
| Aptamer 11 | ++++ |
| Aptamer 12 | ++ |
| Aptamer 13 | ++ |
| Aptamer 14 | ++ |
| Aptamer 15 | + |
| Aptamer 18 | + |
| Aptamer 19 | − |
| Aptamer 20 | − |
| Aptamer 21 | +++ |
| Aptamer 22 | +++ |
| Aptamer 23 | + |
| Aptamer 24 | + |
| Aptamer 25 | − |

where ++++ is >90% inhibition of IL8, +++ is~75-90% inhibition of IL8, ++ is~50-75% inhibition of IL8, + is~25-50% inhibition of IL8 and − is <25%

Figure 8A:
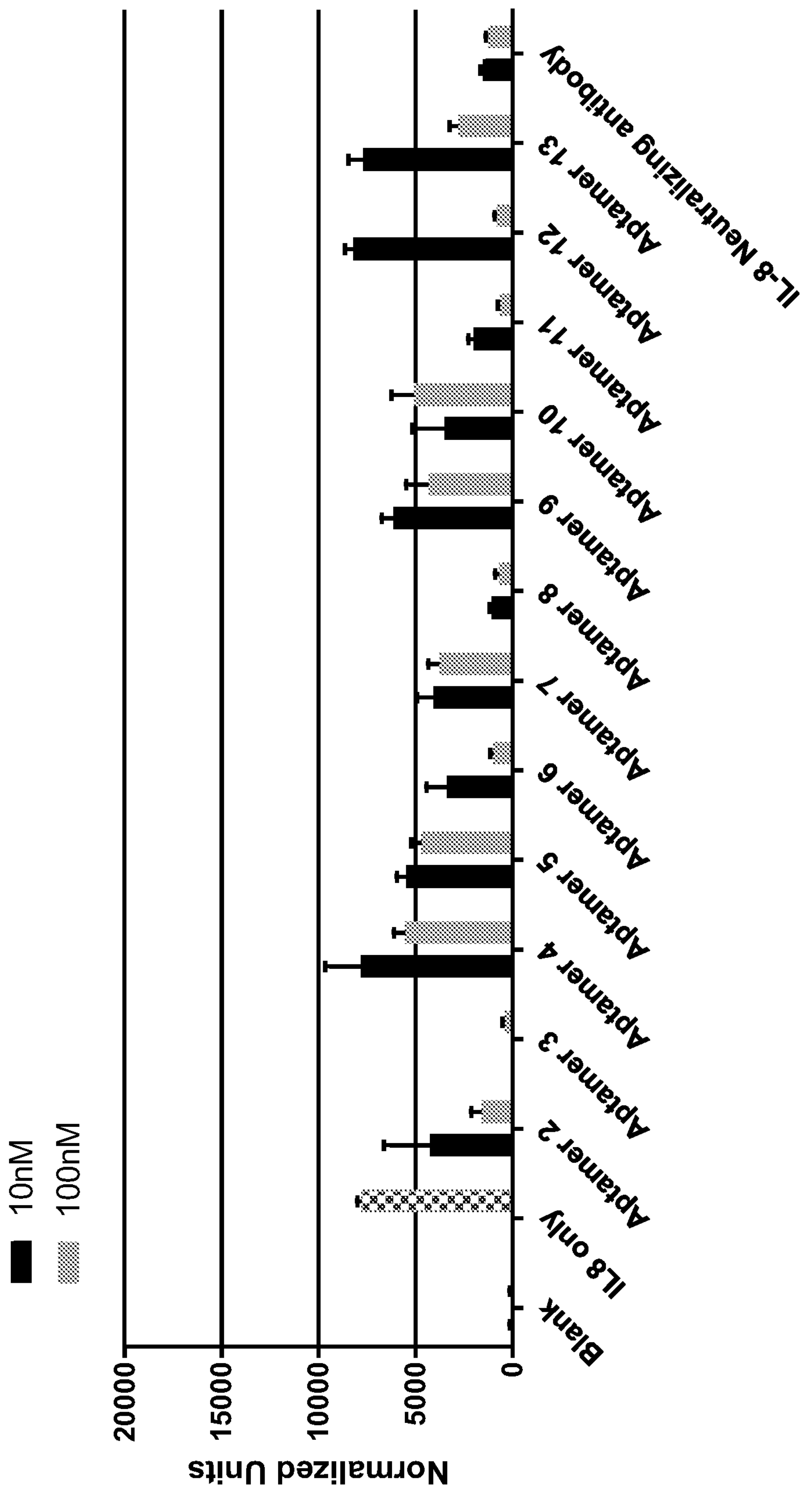
FIG. 8A depicts non-limiting examples of data demonstrating the ability of various aptamers of the disclosure to inhibit IL8-induced calcium mobilization according to embodiments of the disclosure.
Figure 8B:
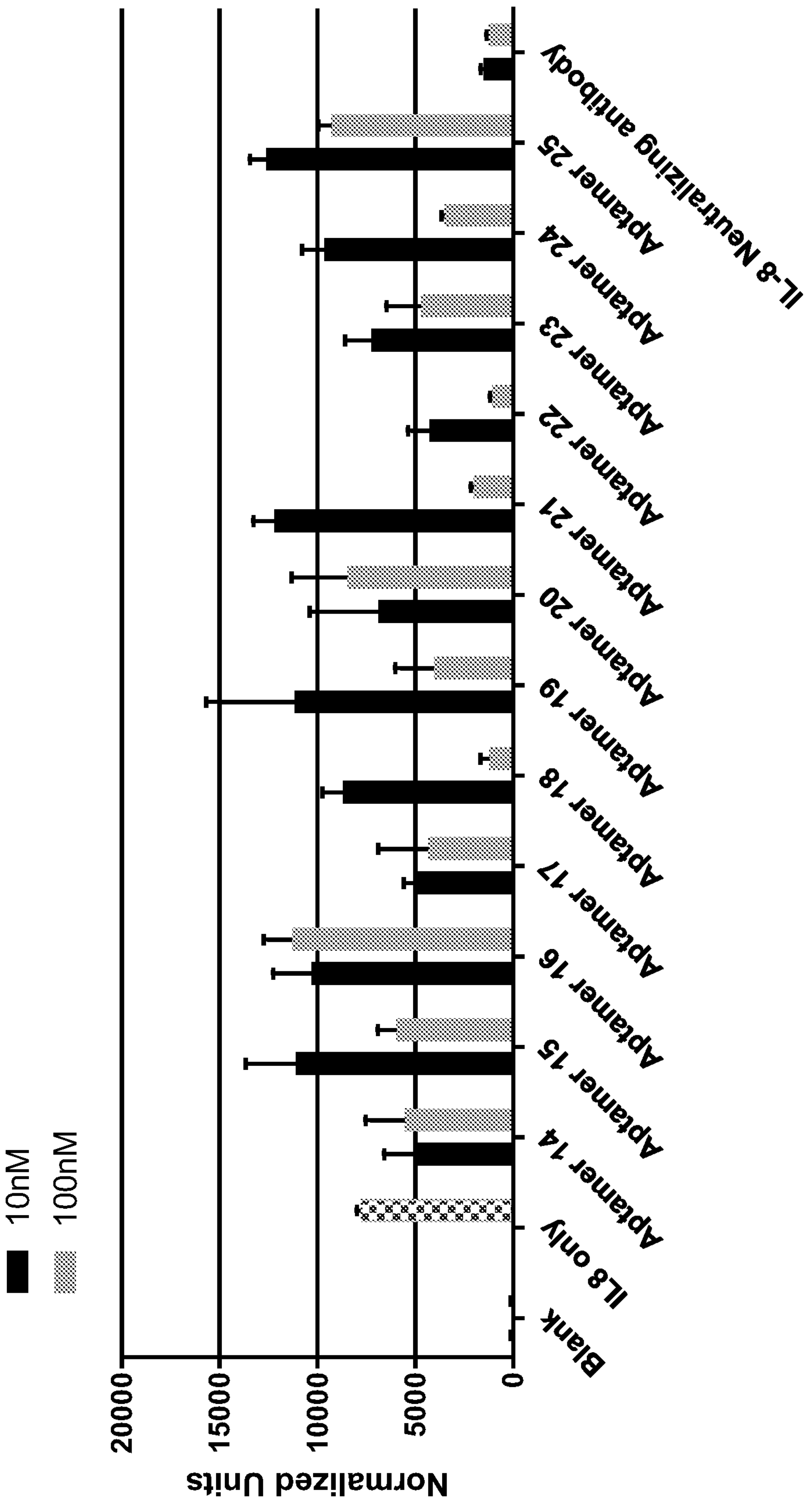
FIG. 8B depicts non-limiting examples of data demonstrating the ability of various aptamers of the disclosure to inhibit IL8-induced calcium mobilization according to embodiments of the disclosure.

Example 5. Inhibition of IL8 Activity as Assessed by Intracellular $Ca^{2+}$ Signaling CHEM1 cells stably overexpressing CXCR1 (Eurofins) were used to measure IL8-induced $Ca^{2+}$ mobilization. 50,000 cells per well were added to a black walled-clear bottom 96 well plate at 100 μl/well and incubated overnight. IL8-induced $Ca^{2+}$ mobilization was measured using the Enzo FLUOROFORTE® Calcium assay per the manufacturer's instructions. Media from cells was aspirated and 1× assay buffer was added to each well for 1 hour. 1 nM IL8 was incubated alone, with an antibody control, or with thermally equilibrated aptamers at a final concentration of 10 nM and 100 nM for 30 minutes. The samples were then added to cells for 1 minute prior to reading on a Biotek CYTATION™ 5 fluorescent plate reader. Data was normalized to the background only negative control and IL8 positive control, and are presented in FIG. 8A and FIG. 8B and as percent inhibition of the IL8 control in Table 12. 1 nM IL8 activity was inhibited by at least 50% with all of these aptamers at 100 nM. At 10 nM aptamers, the inhibition ranged from 0-99% (Table 12). Aptamers that inhibited IL8 activity by at least 50% at 10 nM are consistent with having $IC_{50}$ values of 10 nM or better, consistent with potently inhibiting IL8 activity, as observed for Aptamer 3, Aptamer 5, Aptamer 6, Aptamer 7, Aptamer 8, Aptamer 11, Aptamer 15, Aptamer 18, Aptamer 20, Aptamer 21, Aptamer 22, Aptamer 23, Aptamer 24, and Aptamer 25.

TABLE 12

Inhibition of IL8-induced $Ca^{2+}$ mobilization in CXCR1 overexpressing cells

| Aptamer Number | Inhibition at 10 nM (%) | SEM | Inhibition at 100 nM (%) | SEM |
|---|---|---|---|---|
| Aptamer 2 | 37 | 28 | 78 | 7 |
| Aptamer 3 | 99 | 8 | 98 | 3 |
| Aptamer 5 | 55 | 23 | 54 | 11 |
| Aptamer 6 | 62 | 10 | 80 | 13 |
| Aptamer 7 | 52 | 20 | 75 | 10 |
| Aptamer 8 | 95 | 0 | 102 | 2 |
| Aptamer 11 | 84 | 1 | 94 | 4 |
| Aptamer 12 | 24 | 16 | 81 | 10 |
| Aptamer 13 | 24 | 25 | 71 | 1 |
| Aptamer 14 | 43 | 16 | 65 | 18 |
| Aptamer 15 | 76 | 18 | 81 | 12 |
| Aptamer 17 | 48 | 23 | 63 | 10 |
| Aptamer 18 | 54 | 28 | 95 | 3 |
| Aptamer 19 | 19 | 37 | 82 | 2 |
| Aptamer 20 | 54 | 22 | 71 | 8 |
| Aptamer 21 | 51 | 17 | 98 | 2 |
| Aptamer 22 | 80 | 13 | 104 | 4 |
| Aptamer 23 | 80 | 13 | 56 | 15 |
| Aptamer 24 | 83 | 2 | 69 | 14 |
| Aptamer 25 | 55 | 6 | 55 | 14 |

Example 6. Inhibition of IL8 Mediated Neutrophil Migration

Figure 9:
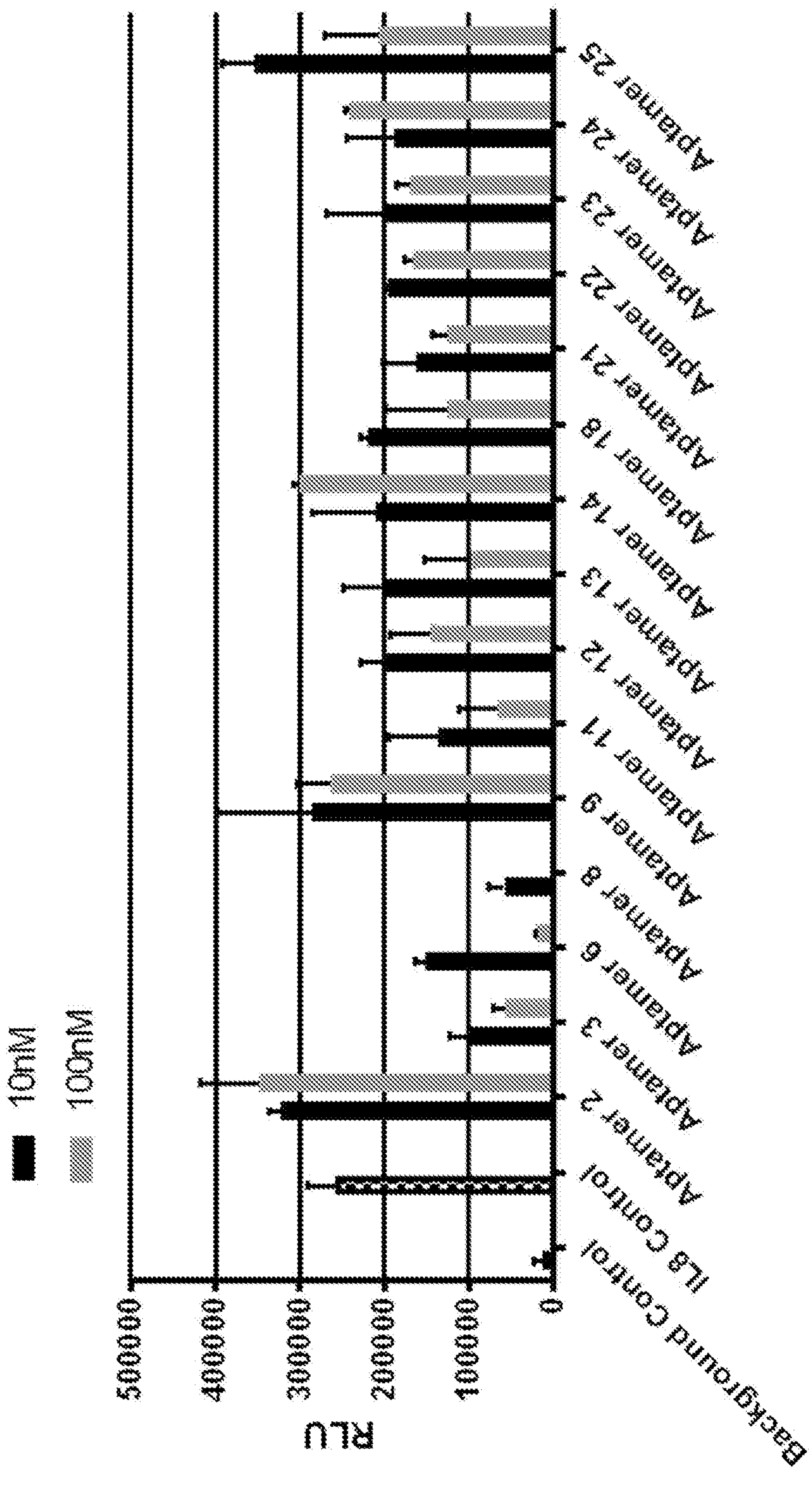
FIG. 9 depicts non-limiting examples of data demonstrating the ability of various aptamers of the disclosure to inhibit IL8-induced neutrophil migration according to embodiments of the disclosure.

Freshly isolated primary human neutrophil migration stimulated by IL8 was measured using a transwell assay. Neutrophils were isolated from fresh whole human blood using Polymorphprep™ (AXIS Shield) and then were re-suspended in assay buffer (RPMI+0.1% Human Serum Albumin) at 10^6 cells/mL. 5 μm Transwell inserts (Corning) were activated with 200 μL assay buffer in the plate and 100 μL of assay buffer in the transwell at 37° C. 3 nM IL8 and aptamers or controls were incubated for 1 hour, then 200 μL of the aptamer/IL8 mix was added to each well and 100 μL of neutrophils was added to the transwell. Aptamer inhibition was tested at two concentrations: 10 nM and 100 nM. After 45 minutes at 37° C., 100 μL from each well was transferred to a white 96-well plate with 50 μL of lysis buffer. The number of cells that migrated from the transwell to the well was quantified by ATPLITE® Luminescence Assay System (Perkin Elmer). A representative experiment is shown in FIG. 9. In Table 13, values are normalized to 3 nM IL8 treatment and average between replicates with standard deviation. 3 nM IL8 activity inhibited by at least 50% at 10 nM aptamer concentration is consistent with aptamers having $IC_{50}$ values of 10 nM or better, as observed for Aptamer 3 and Aptamer 8. All of these aptamers also inhibited IL8-induced $Ca^{2+}$ mobilization at 100 nM (Table 12), demonstrating a persistent inhibition of IL8 activity during the longer 45 minute duration of the neutrophil migration assay.

TABLE 13

IL8 induced migration of primary human neutrophils

| Aptamer Number | Inhibition at 10 nM (%) | SEM | Inhibition at 100 nM (%) | SEM |
|---|---|---|---|---|
| Aptamer 2 | −17 | 5 | −23 | 22 |
| Aptamer 3 | 66 | 2 | 83 | 4 |
| Aptamer 6 | 41 | 6 | 91 | 1 |
| Aptamer 8 | 89 | 2 | 105 | 0 |
| Aptamer 11 | 43 | 8 | 81 | 7 |
| Aptamer 12 | 26 | 0 | 47 | 6 |
| Aptamer 13 | 36 | 5 | 74 | 13 |
| Aptamer 14 | 35 | 19 | 8 | 6 |
| Aptamer 18 | 7 | 4 | 39 | 17 |
| Aptamer 21 | 44 | 11 | 68 | 0 |
| Aptamer 22 | 40 | 4 | 64 | 2 |
| Aptamer 23 | 26 | 18 | 33 | 7 |
| Aptamer 24 | 33 | 16 | 20 | 6 |
| Aptamer 25 | −4 | 1 | 32 | 8 |

Example 7. Isolated Aptamers do not Bind to the GAG Binding Site of IL8

Figure 10:
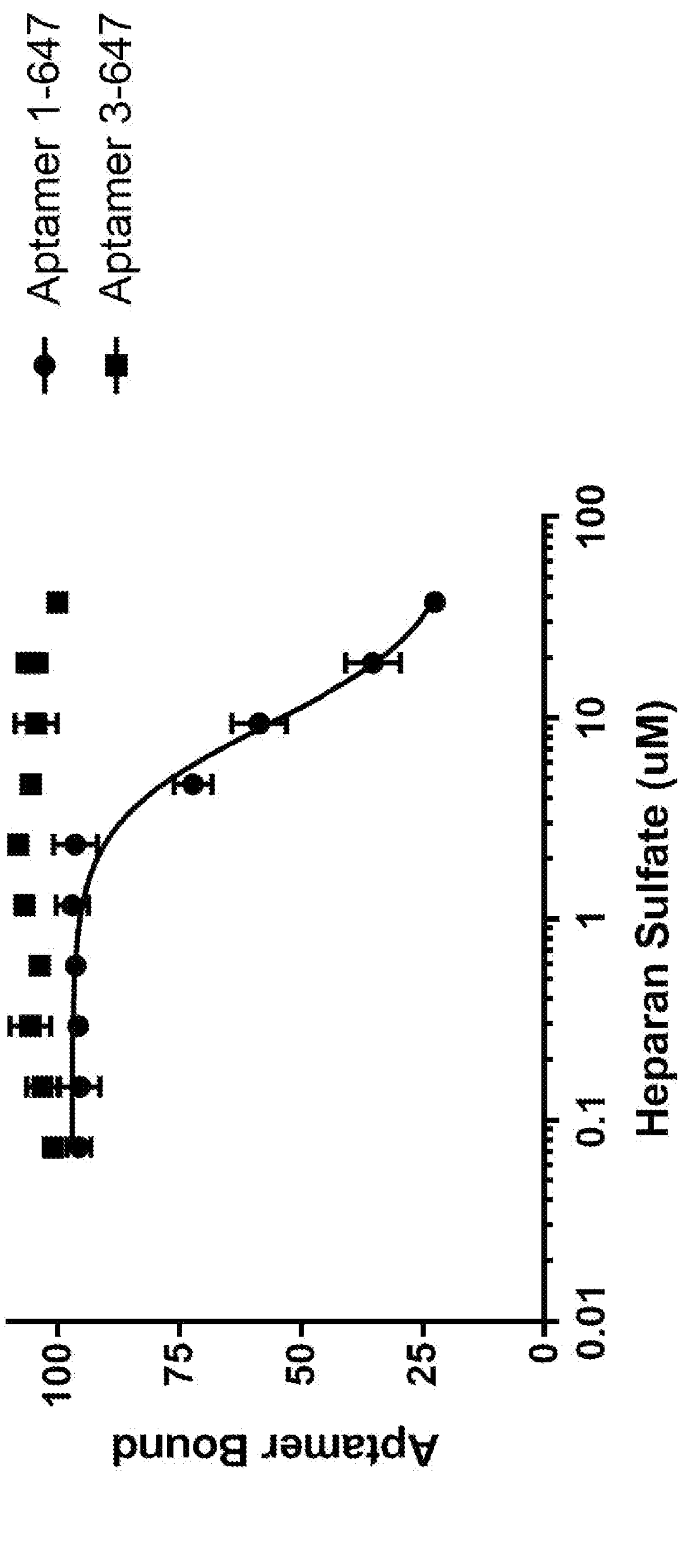
FIG. 10 depicts non-limiting examples of data demonstrating the ability of heparan sulfate to compete with Aptamer 1 for binding to IL8, but not with aptamers isolated according to the current disclosure.

Prior aptamer selections to IL8 (e.g., Sung et al, Biomaterials, 2014; 35 (1): 578-89) isolated aptamers that bind to the GAG binding site of IL8 as demonstrated by NMR spectroscopy. To determine if the selection scheme described in Example 1 led to isolation of aptamers that do not bind to the GAG binding site, competition binding experiments with heparan sulfate were performed. Aptamer 1 ($C6NH_2$-GGGGGCUUAUCAUUCCAUUUAGU-GUUAUGAUAACC-idT, where C and U are 2'F, A and G are 2'OH; $C6NH_2$ is a hexylamino linker; and idT is a 3' inverted deoxythymidine residue (SEQ ID NO: 75 with modifications)) was used as a positive control for an aptamer that binds to the GAG binding site. Aptamers 1, 3, 6, 8 and 11 were labeled with ALEXAFLUOR® 647 as described in Example 3. Binding of Aptamer 1 to C-terminal His-tagged IL8 was confirmed using the TR-FRET assay described in Example 3, and yielded a $K_d^{App}$ of 3 nM, comparable to Aptamer 3. Briefly, 2-fold dilutions of heparan sulfate (Sigma Aldrich) were made in TR-FRET Buffer (50 mM MOPS, pH 7.4, 125 mM NaCl, 5 mM KCl, 50 μM CHAPS, 0.1 mg/mL BSA, 1 mM $CaCl_2$) and 1 mM $MgCl_2$). 5 μL of heparan sulfate or control solution were added to 5 μL of a mixture of 10 nM C-His-tagged-IL8 (Sino Biological), 5 nM anti-His-Eu (Perkin Elmer), and 30 nM AlexaFluor® 647-labeled aptamer in TR-FRET in a black low volume 384-well plate (Greiner). The plate was covered with a plate seal and subsequently incubated in the dark for 1 hour at room temperature. The plate was read on a Biotek CYTATION® 5 plate reader. Samples were excited at 330 nm and fluorescent values were collected at 665 nm. Data analysis was performed by subtracting background from each value and normalizing to aptamer-only control. The values were fit by using a four parameter non-linear fit in GraphPad Prism Version 7.0. $IC_{50}$ values obtained for the fits were calculated as the concentration of half-maximal inhibition. As expected, increasing concentrations of heparan sulfate resulted in loss of binding of Aptamer 1, with an $IC_{50}$ of 9

μM. These data are in agreement with the NMR data reported by Sung et al, the reported affinity of heparan sulfate for IL8 (6 μM; DP Witt and AD Lander. Current Biology 1994; 4:394-400), and a model of direct competition of these two ligands for IL8. In contrast, Aptamers 3, 6, 8, and 11 were not significantly displaced by heparan sulfate, demonstrating that these ligands bind a different epitope, outside of the GAG binding domain. FIG. 10 depicts data demonstrating the ability of heparan sulfate to compete with Aptamer 1, but not with Aptamer 3.

Example 8. Sequence Analysis and Structure Determination of Aptamer 3

Sequence analysis of the aptamers listed in Table 8 revealed a relationship between Aptamers 3 and 12, in that these aptamers adopt a stem-loop secondary structure with highly conserved loop regions (FIG. 11A and FIG. 11B). The stem-loop structure adopted by Aptamers 3 and 12, which is referred to herein as the Aptamer Family 3 structure or Family 3 structure, may comprise (in a 5' to 3' direction), Stem 1 (S1), Loop 1 (L1), Stem 2 (S2), Loop 2 (L2), Stem 3 (S3), Loop 3 (L3), and Loop 4 (L4). As demonstrated in FIGS. 11A-11D, Loop 1 (L1) may be connected to the 3' terminal end of Stem 1 (S1) and the 5' terminal end of Stem 2 (S2). Stem 2 (S2) may be connected to the 3' terminal end of Loop 1 (L1) and the 5' terminal end of Loop 2 (L2). Loop 2 (L2) may be connected to the 3' terminal end of Stem 2 (S2) and the 5' terminal end of Stem 3 (S3). Loop 3 (L3) may be connected to the 3' terminal end of Stem 3 (S3) and the 5' terminal end of the complementary region of Stem 3 (S3). Loop 4 (L4) may connect the 3' terminal end of the complementary region of Stem 3 (S3) with the 5' terminal end of the complementary region of Stem 2 (S2). The complementary region of Stem 2 (S2) may be connected to the 3' terminal end of Loop 4 (L4) and the 5' terminal end of the complementary region of Stem 1 (S1).

As summarized in FIG. 11C, S1 may comprise four base pairs. In some cases, S1 may not be highly conserved in sequence identity. In some cases, L1 may be one nucleotide in length. In some cases, the nucleotide sequence of L1 may be 5'-A-3'. In some cases, S2 may comprise four base pairs. In some cases, S2 may not be highly conserved in sequence identity. In some cases, L2 may be two nucleotides in length. In some cases, the nucleotide sequence of L2 may be 5'-AG-3'. In some cases, S3 may comprise two base pairs. In some cases, a first side of the base-paired Stem 3 (S3) may have a nucleotide sequence of 5'-AU-3'. In some cases, a second, complementary side of the base-paired Stem 3 (S3) may have a nucleotide sequence of 5'-GU-3'. In some cases, L3 may be 10 nucleotides in length. In some cases, L3 may comprise a conserved octamer motif. In some cases, L3 may comprise a conserved octamer motif of 5'-ACGGGUAG-3'. In some cases, the 5' terminal nucleotide and the 3' terminal nucleotide of L3 may form a single base pair (for example, see FIG. 11A). In such cases, the nucleotide sequence of L3 may be 5'-UACGGGUAGA-3' (SEQ ID NO: 799), where the 5' terminal U and the 3' terminal A of L3 form a single base pair (e.g., U.A). In some cases, the 5' terminal end and the 3' terminal end of L3 may be single stranded, e.g., the 5' terminal nucleotide and the 3' terminal nucleotide of L3 may not form a base pair (for example, see FIG. 11B). In such cases, the nucleotide sequence of L3 may be 5'-UACGGGUAGU-3' (SEQ ID NO: 800). In some cases, L4 may be one nucleotide in length. In some cases, the nucleotide sequence of L4 may be 5'-G-3'.

To further refine our understanding of the Aptamer Family 3 structure, the sequence CGGUAGAUUACGGGUAGAGUGACCG (SEQ ID NO: 801) was used to identify molecules related to Aptamers 3 and 12 within the top 1000 stacks from the primary selection. To broaden the search window, up to 5 mutations were allowed to occur within the sequence for this search. The analysis revealed 30 sequences related to Aptamers 3 and 12 (Table 14), which support the common stem-loop secondary structure identified in the analysis of Aptamers 3 and 12, and further define the key sequence and structural features of the Aptamer 3 Family. Together, these data further support a stem-loop structure comprised of Stem 1 (S1), Loop 1 (L1), Stem 2 (S2), Loop 2 (L2), Stem 3 (S3), Loop 3 (L3), and Loop 4 (L4).

TABLE 14

Members of the Aptamer 3 family identified during primary selection against IL8. (Disclosed as SEQ ID NOs: 802-833)

| | S1 L1 S2 L2 S3 L3 S3 L4 S2 S1 |
|---|---|
| (aptamer 03)r5-2: | U--GAUG--A--CGGU--AG--AU--UACGGGUAGA--GU--G--ACCG--CAUC--U |
| (aptamer 12)r6-9: | UU--GGCC--A--CAGU--AG--AU--UUCGGUGCGU--GU--G--ACUG--GGCU |
| r6-68: | U--GAUG--A--CGGU--AG--AU--UAUGGGUAGA--GU--G--ACCG--CAUC--U |
| r6-93: | U--GAUG--A--CGGU--AG--AU--UACGGGUAGU--GU--G--ACCG--CAUC--U |
| r6-126: | UU--AAAC--A--AAGG--AG--AU--UUCGGUGCGU--GU--G--CCUU--GUUU |
| r6-161: | UCU--AGUU--A--CGGG--AG--AU--UAUGGUGUGU--GU--G--CCCG--AACU |
| r6-234: | U--GAUG--A--CGGU--AG--AU--UAUGGGUAGU--GU--G--ACCG--CAUC--U |
| r6-389: | U--GAUG--A--CGGU--AG--AU--UACGGGUUGA--GU--G--ACCG--CAUC--U |
| r6-426: | U--GAUG--A--CGGU--AG--AU--UACGGGUAGA--GU--G--ACCG--CAUC--C |
| r6-460: | C--GAUG--A--CGGU--AG--AU--UACGGGUAGA--GU--G--ACCG--CAUC--U |
| r6-478: | UU--GGCC--A--CAGU--AG--AU--UUCGGUGCGU--GU--G--ACUG--GGCC |
| r6-486: | UU--GGCC--A--CUGU--AG--AU--UUCGGUGCGU--GU--G--ACUG--GGCU |

TABLE 14-continued

Members of the Aptamer 3 family identified during primary selection against IL8. (Disclosed as SEQ ID NOs: 802-833)

| | S1 L1 S2 L2 S3 L3 S3 L4 S2 S1 |
|---|---|
| r6-506: | U--GAUG--A--CGGU--AG--AU--UACGGGUAGA--GU--G--ACCG--CAUC--G |
| r6-520: | U--GAUG--A--CGGU--AG--AU--UACGGGGAGA--GU--G--ACCG--CAUC--U |
| r6-555: | U--GAUG--A--CGGU--AG--AU--UACGGGUAGA--GU--G--ACCG--CAUC--A |
| r6-561: | UG--GGCC--A--CAGU--AG--AU--UUCGGUGCGU--GU--G--ACUG--GGCU |
| r6-600: | U--GAUG--A--CGGU--AG--AU--UUCGGGUAGA--GU--G--ACCG--CAUC--U |
| r6-648: | U--GAUG--A--CGGU--AG--AU--UACGGGCAGA--GU--G--ACCG--CAUC--U |
| r6-653: | UU--GACC--A--CAGU--AG--AU--UUCGGUGCGU--GU--G--ACUG--GGCU |
| r6-697: | A--GAUG--A--CGGU--AG--AU--UACGGGUAGA--GU--G--ACCG--CAUC--U |
| r6-766: | U--GAUG--A--CGGU--AG--AU--UACGGGUAGA--GU--G--ACCG--CACC--U |
| r6-797: | UU--GGCC--A--CAGU--AG--AU--UUCGGUGCGU--GU--G--ACGG--GGCU |
| r6-811: | UU--GGCC--A--CAGU--AG--AU--UUCGGUGUGU--GU--G--ACUG--GGCU |
| r6-859: | UU--GGCC--A--CGGU--AG--AU--UUCGGUGCGU--GU--G--ACUG--GGCU |
| r6-858: | UU--GGCC--A--CAGU--AG--AU--UUCGGUGCGU--GU--G--ACUG--GGUU |
| r6-890: | U--GAUG--A--CGGU--AG--AU--AACGGGUAGA--GU--G--ACCG--CAUC--U |
| r6-889: | U--GAUG--A--CGGU--AG--AU--UACGGGUAGA--GU--G--ACUG--CAUC--U |
| r6-932: | U--GAUG--A--CGGU--UG--AU--UACGGGUAGA--GU--G--ACCG--CAUC--U |
| r6-939: | U--GAUG--A--CGGU--AG--AU--UACGGGUAGA--GU--G--GCCG--CAUC--U |
| r6-971: | U--GAUG--A--CGGU--AG--UU--UACGGGUAGA--GU--G--ACCG--CAUC--U |
| r6-978: | U--GAUG--A--CGGU--AG--AU--UACGGGAAGA--GU--G--ACCG--CAUC--U |
| r6-989: | U--GACG--A--CGGU--AG--AU--UACGGGUAGA--GU--G--ACCG--CAUC--U |

Unpaired regions within stems are underlined. A double dash (--) serves to separate individual structural motifs.

All unique variations identified in S1 from the alignment of the 32 members of the Aptamer 3 Family of molecules found in the primary selection are listed in Table 15 and demonstrate that S1 can be formed using 9 alternative sequence pairing configurations. In combination with Aptamers 3 and 12 and as summarized in FIG. 11D, these additional sequences provide further support of the formation of S1, as indicated by the sequence covariation. They also demonstrate that S1 may be comprised of four base pairs, may include an internal mismatch, and that the sequence may not be highly conserved. The consensus sequence for the first region of S1 may be 5'-RRHB-3', and the sequence of the second, complementary region of S1 may be 5'-VDYY-3' (e.g., 5'-RRHB/CAUC-3'), where R is A or G; His A, C or U; Bis C, G, or U; V is A, C, or G; D is A, G or U; and Y is C or U.

TABLE 15

Sequence pairing configurations for Stem 1 of Aptamer Family 3

| | |
|---|---|
| Aptamer 3 | GAUG/CAUC |
| Aptamer 12 | **GGCC/GGCU** |

TABLE 15-continued

Sequence pairing configurations for Stem 1 of Aptamer Family 3

| | |
|---|---|
| r6-126: | **AAAC/GUUU** |
| r6-161: | **AGUU/AACU** |
| r6-478: | **GGCC/GGCC** |
| r6-653: | **GACC/GGCU** |
| r6-766: | GAUG/CACC |
| r6-858: | **GGCC/GGUU** |
| r6-989: | GACG/CAUC |

Covariations and differences from the parent S1 sequence of Aptamer 3 are denoted by bold letter; mispairings are denoted by underline.

The identity of L1 was found to be 100% conserved in the 32 members of the Aptamer 3 Family found in the primary selection. In some cases, L1 may be one nucleotide in length. In some cases, the nucleotide sequence of L1 may be 5'-A-3'.

All unique variations identified in S2 from the alignment of the 32 members of the Aptamer 3 Family of molecules found in the primary selection are listed in Table 16 and demonstrate that S1 can be formed using 8 alternative sequence pairing configurations. In combination with Aptamers 3 and 12, and as summarized in FIG. 11D, these additional sequences provide further support for the formation of S2, as indicated by the sequence covariation. They also demonstrate that S2 may be comprised of four base pairs, may include an internal mismatch, and that the sequence may not be highly conserved. The consensus sequence for the first region of S2 may be 5'-MDGK-3', and the sequence of the second, complementary region of S2 may be 5'-VCBK-3' (e.g., 5'-MDGK/VCBK-3'), where M is A or C; D is A, G, or U; K is G or U; V is A, C, or G; and B is G, C, or U.

TABLE 16

| Sequence pairing configurations for Stem 2 of Aptamer Family 3 | |
|---|---|
| Aptamer 3: | CGGU/ACCG |
| Aptamer 12 | CAGU/ACUG |
| r6-126: | AAGG/CCUU |
| r6-161: | CGGG/CCCG |
| r6-486: | CUGU/ACUG |
| r6-797: | CAGU/ACGG |
| r6-859: | CGGU/ACUG |
| r6-939: | CGGU/GCCG |

Covariations and differences from the parent S2 sequence of Aptamer 3 are denoted by bold letter; mispairings aredenoted by underline.

All unique variations identified in L2 from the alignment of the 32 members of the Aptamer 3 Family of molecules identified in the primary selection are listed in Table 17 and demonstrate that L2 can be formed using 2 alternative sequences. In some cases, L2 may comprise two nucleotides in length. In some cases, the nucleotide sequence of L2 may be 5'-WG-3', where W is A or U. In some cases, the nucleotide sequence of L2 may be 5'-AG-3'.

TABLE 17

| Sequence configurations for Loop 2 of Aptamer Family 3 | |
|---|---|
| Aptamer 3/12: | AG |
| r6-932: | UG |

Differences from the parent L2 sequence of Aptamer 3 are denoted by bold letter.

All unique variations identified in S3 from the alignment of the 32 members of the Aptamer 3 Family of molecules from the primary selection are listed in Table 18 and demonstrate that S3 can be formed using 2 alternative sequence pairing configurations, as summarized in FIG. 11D. In some cases, S3 may comprise one or two base pairs. In some cases, a first region of S3 may comprise a consensus nucleotide sequence of 5'-WU-3', and a second, complementary region of S3 may comprise a consensus nucleotide sequence of 5'-GU-3' (e.g., 5'-WU/GU-3'; FIG. 11D), where W is A or U. In some cases, when S3 is composed of two base pairs, a first region of S3 may comprise a nucleotide sequence of 5'-AU-3', and a second, complementary region of S3 may comprise a nucleotide sequence of 5'-GU-3' (e.g., 5'-AU/GU-3'; FIG. 11A, FIG. 11B). In some cases, when S3 is composed of one base pair, the sequence of S3 may be 5'-UU/GU-3'.

TABLE 18

| Sequence pairing configurations for Stem 3 of Aptamer Family 3 | |
|---|---|
| Aptamer 3/12: | AU/GU |
| r6-932: | UU/GU |

Differences from the parent S3 sequence of Aptamer 3 are denoted by bold letter; mispairings are denoted by underline.

All unique variations identified in L3 from the alignment of the 32 members of the Aptamer 3 Family of molecules from the primary selection are listed in Table 19 and demonstrate that L3 can be formed using 11 alternative sequences, as summarized in FIG. 11D. In some cases, L3 may be 10 nucleotides in length. In some cases, L3 may comprise a conserved octamer motif. In some cases, L3 may comprise a conserved octamer motif having a nucleotide sequence of 5'-WYGGKNHG-3'; where W is A or U; Y is C or U; K is Gor U; N is A, G, C, or U; and His A, C, or U. In some cases, the 5' terminal nucleotide and the 3' terminal nucleotide of L3 are predicted to form a single base pair. In such cases, the nucleotide sequence of L3 may be 5'-UWYGGKNWGA-3' (SEQ ID NO: 834), where W is A or U; Y is C or U; K is G or U; and N is A, C, G, or U, and where the 5' terminal nucleotide U and the 3' terminal nucleotide A form a single base pair (e.g., U.A). In some cases, the 5' terminal end and the 3' terminal end of L3 are predicted to be single stranded, e.g., the 5' terminal nucleotide and the 3' terminal nucleotide of L3 may not form a base pair. In such cases, the nucleotide sequence of L3 may be 5'-WWYGGKNHGW-3' (SEQ ID NO: 835), where W is A or U; Y is C or U; K is Gor U; Nis A, C, G, or U; and H is A, C, or U.

TABLE 19

| Sequence configurations for Loop 3 of Aptamer Family 3 | | |
|---|---|---|
| Aptamer 3 | UACGGGUAGA | (SEQ ID NO: 836) |
| Aptamer 12: | UUCGGUGCGU | (SEQ ID NO: 837) |
| r6-68: | UAUGGGUAGA | (SEQ ID NO: 838) |
| r6-93: | UACGGGUAGU | (SEQ ID NO: 839) |
| r6-161: | UAUGGUGUGU | (SEQ ID NO: 840) |
| r6-389: | UACGGGUUGA | (SEQ ID NO: 841) |
| r6-600: | UUCGGGUAGA | (SEQ ID NO: 842) |
| r6-648: | UACGGGCAGA | (SEQ ID NO: 843) |
| r6-811: | UUCGGUGUGU | (SEQ ID NO: 844) |
| r6-890: | AACGGGUAGA | (SEQ ID NO: 845) |
| r6-978: | UACGGGAAGA | (SEQ ID NO: 846) |

Differences from the parent L3 sequence of Aptamer 3 are denoted by bold letter.

The identity of L4 was found to be 100% conserved in the 32 members of the Aptamer 3 Family found in the primary selection. In some cases, L4 may be one nucleotide in length. In some cases, the nucleotide sequence of L4 may be 5'-G-3'.

Example 9. Secondary Selection of IL8 Inhibiting Aptamers

To further define the secondary structure of the active aptamers, as well as to potentially identify IL8 aptamers with increased potency, secondary selections were performed utilizing partially randomized libraries including 70% of the parental sequence+10% of the other three nucleotides at each position within the aptamer, flanked by the 5' and 3' constant regions. To avoid potential contamination, the library was designed using an alternate 5' constant region (GGGAGGGCAAGAGACAGA; SEQ ID NO: 847) and amplified using an alternate forward primer (TCTTAATACGACTCACTATAGGGAGGGCAAGAGACAGA; SEQ ID NO: 848). The library 3' constant region and reverse primer used for reverse transcription and amplification were the same as used in the primary selection (SEQ ID NO:81). Degenerate selections were carried out for Aptamer 3. Five rounds of selection against IL8 were conducted using these libraries in independent selections. The progress of the selection was monitored by flow cytometry to ensure the enrichment for function (data not shown). Clones from Round 1 through Round 5 of each selection were barcoded, pooled and sequenced on a MiniSeq high throughput sequencer (Illumina), which yielded approximately ~150,000 sequences per round. Sequences were trimmed to remove constant regions from the 5' and 3' ends, leaving the core 34 nucleotide region from the library with the built-in U spacer on either end. Identical sequences were de-duplicated to form "stacks" of identical sequences. The resultant stacks were then rank ordered based on the total number of sequences within each stack. To a first approximation, the number of times a sequence occurs in a stack directly correlates with molecular function; more functional molecules typically occur more times. Thus, the rank order of each stack can be thought of as a proxy for fitness.

Alignment of the top 250 stacks for Aptamer 3, which contained ~150,000 sequences and corresponded to the top performing ~70% of the selected population from Round 5 of the secondary selections revealed a significant level of conservation in the identity of each nucleotide within each aptamer family. Most positions displayed conservation levels >90% (FIG. 12), with several positions proving to be invariant (conservation=100%). Close examination of these stacks strongly supports the predicted stem loop secondary structures for the two aptamers.

Example 10. Sequence Analysis for Degenerate Selection of Aptamer 3

For the selection using the Aptamer 3 library, comparison of the top 250 sequences revealed that the enriched sequences readily adopted a structure consistent with that reported in FIG. 11A for Aptamer 3 and related molecules identified from the primary selection. Such structure may comprise a terminal Stem 1, that may be connected to the 5' terminal end of Loop 1 (L1). Loop 1 (L1) may be connected to the 3' terminal end of Stem 1 (S1) and the 5' terminal end of Stem 2 (S2). Stem 2 (S2) may be connected to the 3' terminal end of Loop 1 (L1) and the 5' terminal end of Loop 2 (L2). Loop 2 (L2) may be connected to the 3' terminal end of Stem 2 (S2) and the 5' terminal end of Stem 3 (S3). Stem 3 (S3) may be connected to the 3' terminal end of Loop 2 (L2) and the 5' terminal end of Loop 3 (L3). Loop 3 (L3) may be connected to the 3' terminal end of Stem 3 (S3) and the 5' terminal end of the complementary region of Stem 3 (S3). The complementary region of Stem 3 (S3) may be connected to the 3' terminal end of Loop 3 (L3) and the 5' terminal end of Loop 4 (L4). Loop 4 (L4) may be connected to the 3' terminal end of the complementary region of Stem 3 (S3) and the 5' terminal end of the complementary region of Stem 2 (S2). The complementary region of Stem 2 (S2) may be connected to the 3' terminal end of Loop 4 (L4) and the 5' terminal end of the complementary region of Stem 1 (S1). The complementary region of Stem 1 may be connected to the 3' terminal end of the complementary region of Stem 2 (S2).

A comparison of sequences observed in Stem 1 (S1) confirmed that the preferred length of S1 is four base pairs. The identity of S1 was not highly conserved with a consensus sequence of 5'-NNUS/SANN-3', where N is A, C, G, or U; and S is G or C. These data provide additional support of the formation of Stem 1, as indicated by the sequence covariation in this region (Table 20).

TABLE 20

| Sequence variation observed in Stem 1 (S1) of Aptamer Family 3. | |
|---|---|
| Aptamer 3 | 5'-GAUG/CAUC-3' |
| R5-16 | 5'-**C**AUG/CAU**G**-3' |
| R5-39 | 5'-**U**AUG/CAU**A**-3' |
| R5-57 | 5'-GAU**C**/**G**AUC-3' |
| R5-60 | 5'-G**U**UG/CA**A**C-3' |
| R5-80 | 5'-**C**AU**C**/**G**AU**G**-3' |
| R5-97 | 5'-G**G**UG/CA**C**C-3' |
| R5-134 | 5'-**A**AUG/CAU**U**-3' |
| R5-146 | 5'-**C**AUG/CAU**A**-3' |
| R5-193 | 5'-G**C**UG/CA**G**C-3' |

Covariations and differences from the parent stem S1 sequence are denoted by bold letter.

The identity of Loop 1 (L1), which was comprised of a single A in the analysis of the primary selection (Table 14), was found to be 100% conserved across the top 250 stacks of sequences analyzed in the doped selection (FIG. 12). Thus, the nucleotide sequence of L1 may be A.

A comparison of sequences observed in Stem 2 (S2) confirmed that the preferred length of S2 is four base pairs and strongly supports stem formation as indicated by covariation in this region (Table 21). The identity of S2 was not highly conserved with a consensus of 5'-NNDH/DHHN-3', where N is A, C, G, or U; D is A, G, or U; and His A, C, or U.

TABLE 21

| Sequence variation observed in Stem 2 (S2) of Aptamer Family 3. | |
|---|---|
| Aptamer 3 | 5'-CGGU/ACCG-3' |
| R5-199 | 5'-C**U**GU/AC**A**G-3' |
| R5-185 | 5'-**A**GGU/ACC**U**-3' |
| R5-113 | 5'-**U**GGU/ACC**A**-3' |
| R5-206 | 5'-CGG**C**/**G**CCG-3' |
| R5-181 | 5'-**G**GGU/ACC**C**-3' |
| R5-104 | 5'-CGG**A**/**U**CCG-3' |
| R5-141 | 5'-CG**U**U/A**A**CG-3' |

TABLE 21-continued

| Sequence variation observed in Stem 2 (S2) of Aptamer Family 3. | |
|---|---|
| R5-29 | 5'-C**A**GU/AC**U**G-3' |
| R5-22 | 5'-CG**AU**/A**U**CG-3' |

Covariations and differences from the parent stem S2 sequence are denoted by bold letter.

The identity of Loop 2 (L2) was found to be 100% conserved in the top 250 stacks of molecules from the degenerate selection confirming the invariant 5'-AG-3' in these positions (FIG. 12).

The short Stem 3 (S3) was also found to be highly conserved (FIG. 12). In some instances, S3 may be comprised of two base pairs. When S3 is comprised of two base pairs, the nucleotide sequence of the first region of S3 may be 5'-AU-3', and the nucleotide sequence of the second, complementary region of S3 may be 5'-GU-3' (e.g., 5'-AU/GU-3'; see Table 22). In such cases, the two base pairs of S3 may be A·U and U·G. Consistent with the sequences observed from the primary selection (Table 14), in some instances, S3 may be comprised of a single base pair. In some cases, when S3 is comprised of a single base pair, the nucleotide sequence of the first region of S3 may be 5'-AA-3' and the second, complementary region of S3 may be 5'-GU-3' (e.g., 5'-AA/GU-3'; forming A·U base pair). In other cases, when S3 is comprised of a single base pair, the nucleotide sequence of the first region of S3 may be 5'-AG-3', and the second, complementary region of S3 may be 5'-GU-3' (e.g., 5'-AG/GU-3'; forming A·U base pair; see Table 22). In yet other cases, when S3 is comprised of a single base pair, the nucleotide sequence of the first region of S3 may be 5'-UU-3', and the second, complementary region of S3 may be 5'-GU-3' (e.g., 5'-UU/GU-3'; forming G·U wobble base pair; see Table 22). In some cases, the consensus sequence for the first region of S3 may be 5'-WD-3' and the consensus sequence for the second, complementary region of S3 may be 5'-GU-3' (e.g., 5'-WD/GU-3'; see FIG. 13A and FIG. 13B).

TABLE 22

| Sequence variation observed in Stem 3 (S3) of Aptamer Family 3. | |
|---|---|
| Aptamer 3 | 5'-AU/GU-3' |
| R5-75 | 5'-A**A**/GU-3' |
| R5-82 | 5'-A**G**/GU-3' |
| R5-112 | 5'-**U**U/GU-3' |

Covariations and differences from the parent stem S3 sequence are denoted by bold letter.

Figure 13A:
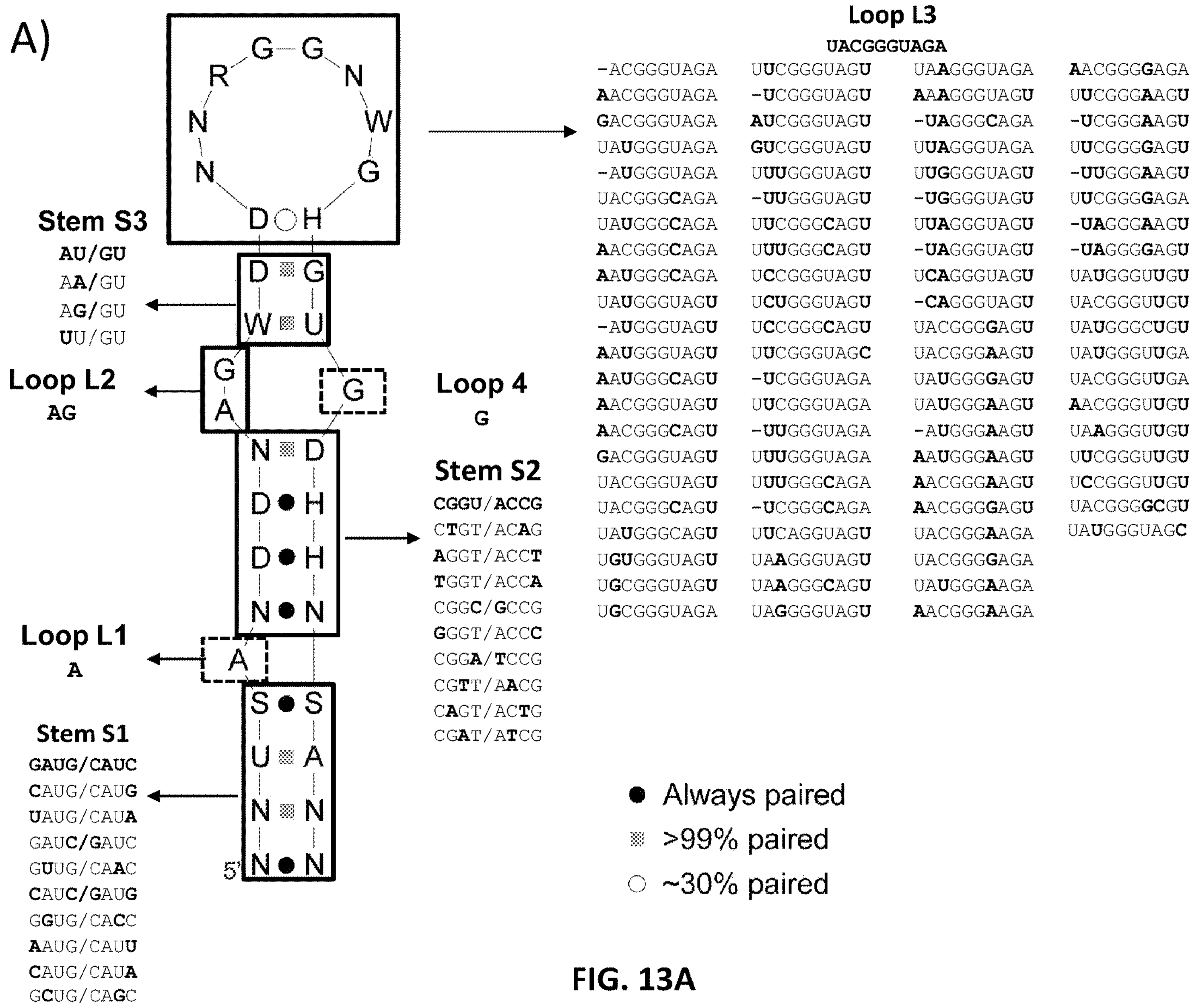
FIG. 13A depicts a representation of an anti-IL8 aptamer secondary structure (SEQ ID NO: 1249) with consensus and motif variations (SEQ ID NOS: 1250-1312 and 1086-1091, respectively, in order of appearance) observed during the secondary selection. The percent base pairing is based on the fraction of sequence stacks, not the total sequence numbers.

In some cases, Loop 3 (L3) may be comprised of nine or ten nucleotides. As depicted in FIG. 12 and Table 23, positions 19, 20, and 23 were 100% conserved, position 18 was 99.6% conserved, position 22 was 94.9% conserved, and position 15 was 84.3% conserved. Other positions varied significantly from the parent sequence with positions 16, 17, and 21 showing essentially no conservation (~57.4%, 65.4%, and 67.9% conservation, respectively, compared with 70% in the starting library). Most strikingly, position 24 demonstrated a preference for conversion from A in the parent sequence to a U in 72% of the selected molecules. Together these data support a preference for the formation of a ten nucleotide Loop 3 in which the 5' terminal nucleotide and the 3' terminal nucleotide of L3 are preferably single stranded, providing further support for a preferred S3 of two base pairs. In some cases, the consensus sequence of L3 may be 5'-DNNRGGNWGH-3' (SEQ ID NO: 849; FIG. 13A). In some cases, the consensus sequence of L3 may be 5'-DNNGGGNWGH-3' (SEQ ID NO: 850). When L3 is nine nucleotides long, the consensus sequence may be 5'-HNGGGNAGW-3'.

TABLE 23

| Sequence variation observed in Loop 3 (L3) of Aptamer Family 3. | | |
|---|---|---|
| Aptamer 3 | 5'-UACGGGUAGA-3' | (SEQ ID NO: 851) |
| R5-2 | 5'-U**U**CGGGUAG**U**-3' | (SEQ ID NO: 852) |
| R5-3 | 5'-UACGGGUAG**U**-3' | (SEQ ID NO: 853) |
| R5-4 | 5'-UA**U**GGGUAG**U**-3' | (SEQ ID NO: 854) |
| R5-5 | 5'-U**C**CGGGUAG**U**-3' | (SEQ ID NO: 855) |
| R5-6 | 5'- **UU**GGGUAGA-3' | |
| R5-7 | 5'-**A**ACGGGUAGA-3' | (SEQ ID NO: 856) |
| R5-8 | 5'-UA**A**GGGUAG**U**-3' | (SEQ ID NO: 857) |
| R5-9 | 5'-UACGGG**A**AG**U**-3' | (SEQ ID NO: 858) |
| R5-10 | 5'-UACGGG**A**AGA-3' | (SEQ ID NO: 859) |
| R5-11 | 5'-**A**ACGGGUAG**U**-3' | (SEQ ID NO: 860) |
| R5-12 | 5'-UACGGG**G**AG**U**-3' | (SEQ ID NO: 861) |
| R5-13 | 5'-U**U**CGGG**A**AG**U**-3' | (SEQ ID NO: 862) |
| R5-14 | 5'-UACGGG**C**AG**U**-3' | (SEQ ID NO: 863) |
| R5-15 | 5'-UA**U**GGG**A**AG**U**-3' | (SEQ ID NO: 864) |

TABLE 23-continued

| Sequence variation observed in Loop 3 (L3) of Aptamer Family 3. | | |
|---|---|---|
| R5-18 | 5'-UAUGGGCAGU-3' | (SEQ ID NO: 865) |
| R5-20 | 5'-UUUGGGUAGU-3' | (SEQ ID NO: 866) |
| R5-21 | 5'-UACGGGCAGA-3' | (SEQ ID NO: 867) |
| R5-23 | 5'-AUCGGGUAGU-3' | (SEQ ID NO: 868) |
| R5-24 | 5'-AAUGGGUAGU-3' | (SEQ ID NO: 869) |
| R5-25 | 5'-UUCGGGCAGU-3' | (SEQ ID NO: 870) |
| R5-27 | 5'-UACGGGUUGU-3' | (SEQ ID NO: 871) |
| R5-28 | 5'-UUCGGGGAGU-3' | (SEQ ID NO: 872) |
| R5-30 | 5'-UUCGGGUUGU-3' | (SEQ ID NO: 873) |
| R5-31 | 5'-UAUGGGCAGA-3' | (SEQ ID NO: 874) |
| R5-32 | 5'-UAAGGGUAGA-3' | (SEQ ID NO: 875) |
| R5-33 | 5'-UUCGGGUAGA-3' | (SEQ ID NO: 876) |
| R5-35 | 5'-UAAGGGCAGU-3' | (SEQ ID NO: 877) |
| R5-36 | 5'-UACGGGGAGA-3' | (SEQ ID NO: 878) |
| R5-40 | 5'-UAUGGGUUGU-3' | (SEQ ID NO: 879) |
| R5-47 | 5'-AACGGGAAGA-3' | (SEQ ID NO: 880) |
| R5-48 | 5'-UUAGGGUAGU-3' | (SEQ ID NO: 881) |
| R5-50 | 5'-UCUGGGUAGU-3' | (SEQ ID NO: 882) |
| R5-52 | 5'-UAUGGGGAGU-3' | (SEQ ID NO: 883) |
| R5-54 | 5'-UUUGGGUAGA-3' | (SEQ ID NO: 884) |
| R5-55 | 5'-UAUGGGAAGA-3' | (SEQ ID NO: 885) |
| R5-56 | 5'- UAGGGAAGU-3' | |
| R5-59 | 5'-UACGGGUUGA-3' | (SEQ ID NO: 886) |
| R5-62 | 5'- AUGGGUAGA-3' | |
| R5-65 | 5'- UCGGGAAGU-3' | |
| R5-69 | 5'-UAUGGGUAGA-3' | (SEQ ID NO: 887) |
| R5-75 | 5'- UCGGGUAGU-3' | |
| R5-77 | 5'-AACGGGAAGU-3' | (SEQ ID NO: 888) |
| R5-78 | 5'-UCAGGGUAGU-3' | (SEQ ID NO: 889) |
| R5-81 | 5'-AACGGGCAGA-3' | (SEQ ID NO: 890) |
| R5-85 | 5'- UCGGGUAGA-3' | |
| R5-90 | 5'-AAAGGGUAGU-3' | (SEQ ID NO: 891) |
| R5-95 | 5'-AACGGGGAGU-3' | (SEQ ID NO: 892) |
| R5-96 | 5'- AUGGGUAGU-3' | |
| R5-100 | 5'-UGUGGGUAGU-3' | (SEQ ID NO: 893) |
| R5-101 | 5'-UAGGGGUAGU-3' | (SEQ ID NO: 894) |
| R5-103 | 5'-UAUGGGUAGC-3' | (SEQ ID NO: 895) |
| R5-106 | 5'-AACGGGCAGU-3' | (SEQ ID NO: 896) |
| R5-115 | 5'-UUUGGGCAGU-3' | (SEQ ID NO: 897) |

TABLE 23-continued

| Sequence variation observed in Loop 3 (L3) of Aptamer Family 3. | | |
|---|---|---|
| R5-116 | 5'-**U**G**C**GGGUAG**U**-3' | (SEQ ID NO: 898) |
| R5-119 | 5'-U**U**CGGG**G**AGA-3' | (SEQ ID NO: 899) |
| R5-127 | 5'-**AAU**GGG**C**AG**U**-3' | (SEQ ID NO: 900) |
| R5-131 | 5'-U**U**CGGGUAG**C**-3' | (SEQ ID NO: 901) |
| R5-133 | 5'- **UA**GGGUAG**U**-3' | |
| R5-132 | 5'-**AAU**GGG**A**AG**U**-3' | (SEQ ID NO: 902) |
| R5-135 | 5'- A**U**GGG**A**AG**U**-3' | |
| R5-137 | 5'- **UU**GGG**A**AG**U**-3' | |
| R5-139 | 5'- **UA**GGG**C**AGA-3' | |
| R5-140 | 5'- **UG**GGGUAG**U**-3' | |
| R5-145 | 5'- **U**CGGG**C**AGA-3' | |
| R5-151 | 5'-U**C**CGGG**C**AG**U**-3' | (SEQ ID NO: 903) |
| R5-160 | 5'-U**C**CGGGU**U**G**U**-3' | (SEQ ID NO: 904) |
| R5-162 | 5'-**G**ACGGGUAGA-3' | (SEQ ID NO: 905) |
| R5-169 | 5'- **CA**GGGUAG**U**-3' | |
| R5-173 | 5'-U**G**CGGGUAGA-3' | (SEQ ID NO: 906) |
| R5-183 | 5'- **UA**GGG**G**AG**U**-3' | |
| R5-190 | 5'-UA**U**GGGU**U**GA-3' | (SEQ ID NO: 907) |
| R5-194 | 5'-UA**A**GGGU**U**G**U**-3' | (SEQ ID NO: 908) |
| R5-195 | 5'-**G**ACGGGUAG**U**-3' | (SEQ ID NO: 909) |
| R5-196 | 5'-**GU**CGGGUAG**U**-3' | (SEQ ID NO: 910) |
| R5-203 | 5'-U**UA**GGGUAGA-3' | (SEQ ID NO: 911) |
| R5-209 | 5'-U**U**G**G**GGUAG**U**-3' | (SEQ ID NO: 912) |
| R5-215 | 5'-U**U**C**A**GGUAG**U**-3' | (SEQ ID NO: 913) |
| R5-217 | 5'-U**UU**GGG**C**AGA-3' | (SEQ ID NO: 914) |
| R5-218 | 5'-UACGGG**GC**G**U**-3' | (SEQ ID NO: 915) |
| R5-221 | 5'-**A**ACGGG**G**AGA-3' | (SEQ ID NO: 916) |
| R5-230 | 5'-UA**U**GGG**CU**G**U**-3' | (SEQ ID NO: 917) |
| R5-237 | 5'- ACGGGUAGA-3' | |
| R5-240 | 5'-**A**ACGGGU**U**G**U**-3' | (SEQ ID NO: 918) |

Differences from the loop L3 parent sequence are denoted by bold letters and deletions are denoted by bold dashes.

Consistent with our previous finding (FIG. 12), L4 is formed from a highly conserved (invariant) G residue.

Using the data from the degenerate selection, when L3 is 10 nucleotides long, the consensus sequence for the Aptamer 3 family of sequence members may be 5'-NNUS-A-NDDN-AG-WD-DNNRGGNWGH-GU-G-DHHN-SANN-3' (SEQ ID NO: 919), where N is A, C, G, or U; S is G or C; D is A, G, or U; W is A or U; R is A or G; and His A, C, or U; and is shown in the context of the predicted secondary structure in FIG. 13A. This figure also depicts the motif variations for each structural element (e.g., S1, L1, S2, L2, S3, L3, L4) observed within the top 250 sequence stacks. Thus, by combining the provided motifs in the proper order for the respective structural elements of this aptamer family, one can assemble extant or novel Aptamer 3-like variants with anti-IL8 activity. When L3 is nine nucleotides long, the consensus sequence for the Aptamer 3 family of sequence members may be 5'-NNUS-A-NDDN-AG-WD-HNGGG-NAGW-GU-G-DHHN-SANN-3' (SEQ ID NO: 920), where N is A, C, G, or U; S is G or C; D is A, G, or U; W is A or U; and His A, C, or U (consensus sequence structure not shown).

Figure 13B:
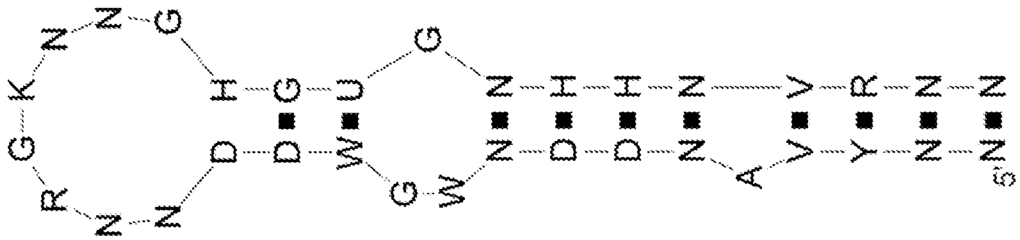
FIG. 13B depicts a representation of an anti-IL8 aptamer secondary structure (SEQ ID NO: 1092) with a consensus sequence compiled from all sequences observed during the primary and secondary selections. The percent base pairing was not determined.

When the sequence data from the degenerate selection is combined with the sequence data for Aptamer 3 family members observed during the primary selection (Table 14), the consensus sequence may be further broadened to 5'-NNYV-A-NDDN-WG-WD-DNNRGKNNGH-GU-G-NHHN-VRNN-3' (SEQ ID NO: 921), where N is A, C, G, or U; Y is Cor U; V is A, C, or G; D is A, G, or U; W is A or U; R is A or G; K is G or U; and His A, C, or U (FIG. 13B).

Figure 14:
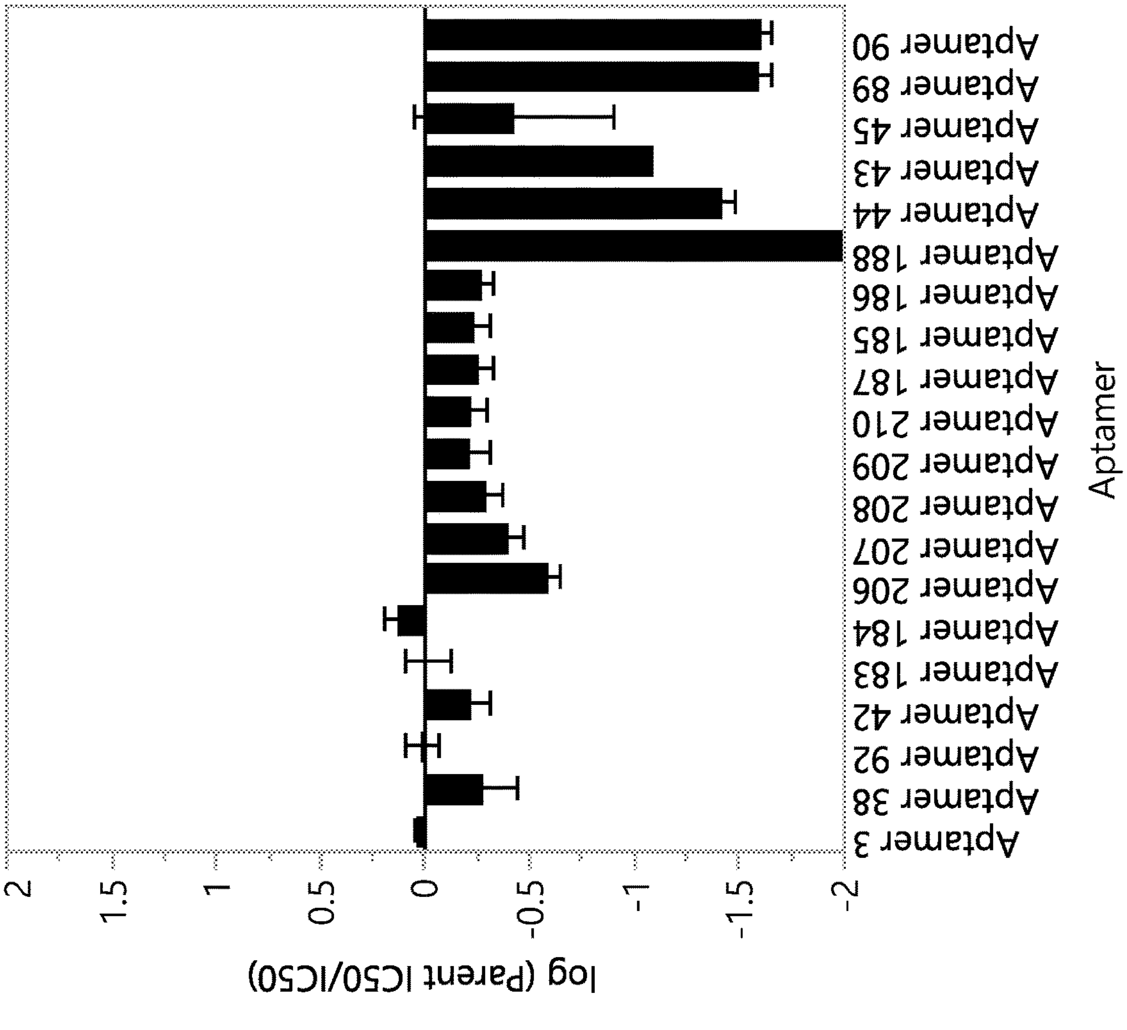
FIG. 14 depicts competitive TR-FRET data demonstrating the relative affinity of doped selection anti-IL8 aptamers according to embodiments of the disclosure. Data is represented as the log of fold change in $IC_{50}$ as compared to parent aptamer.

Example 11. Aptamer 3: Structure Validation and Optimization of Stems by Selective Mutagenesis To better understand the sequence requirements and to confirm the stem structures of members of the Aptamer 3 family as determined from sequence covariation analysis from both the primary and secondary (degenerate) selections, a series of variants which included mutations and deletions to the predicted stems were synthesized and screened (Table 24). Activity of each of these variants were tested using a time resolved competition TR-FRET assay in which the labeled parent Aptamer 3 was competed with increasing concentrations of unlabeled variants for binding to IL8 (FIG. 14). Briefly, 2-fold dilutions of thermally equilibrated aptamers were made in TR-FRET Buffer (50 mM MOPS, pH 7.4, 125 mM NaCl, 5 mM KCl, 50 μM CHAPS, 0.1 mg/mL BSA, 1 mM $CaCl_2$), and 1 mM $MgCl_2$). 5 μL of aptamer or control solution was added to 5 μL mix of 10 nM C-terminal His-tagged-IL8, 60 nM ALEXA FLUOR® 647-labeled Aptamer, and 5 nM anti-His-Eu (Perkin Elmer) in a black wall low volume 384 well plate (Greiner). For control, 5 μl of 1000-fold excess of unlabeled parent aptamer or 5 μl TR-FRET buffer alone was added to the mix of ALEXA FLUOR® 647-labeled aptamer, His-IL8, and anti-His-Eu. The plate was covered with a plate seal and subsequently incubated in the dark for 1 hour at room temperature. The plate was read on a Biotek CYTATION™ 5 plate reader. Samples were excited at 330 nm and fluorescent values were collected at 665 nm. Data analysis was performed by subtracting the background value and plotting as percent inhibition, normalized to baseline in the absence of competitor. The values were fit by [Inhibitor] vs. response-Variable slope (four parameters) using GraphPad Prism Version 7.0 and then normalized to aptamer control to obtain an $IC_{50}$ relative to parent aptamer. Data is presented as log values of relative $IC_{50}$.

Replacing the sequence of Stem 1 (S1) found in Aptamer 3, 5'-GAUG/CAUC-3', with the sequence 5'-GGCG/CGCC-3' did not have any apparent effect on the activity (Table 24; Aptamer 92) and a 3 base pair variant of this molecule, Aptamer 42, showed only a modest decrease in binding affinity (~1.4 fold) compared to the parent. Other covariations within Stem 1 (S1) based on those observed in the degenerate selection (Table 24; Aptamers 183 and 184) or rational design were also tested, altering the sequence of S1 while maintaining pairing (Table 24; Aptamers 206-210). For all the constructs, only a modest (~2-5 fold) loss in activity was observed. Interestingly, in the case of Aptamer 187, unpairing the stem 5'-GA-3' by replacing with 5'-CUUG/CAUC-3' (unpaired residues highlighted) was also well tolerated suggesting that S1 can be shortened to as few as two base pairs. Overall, as indicated by the sequence covariation permitted in this region, these studies provide additional support of the formation of stem S1. Additionally, these data indicated that stem S1 can be from two to four nucleotides in length.

To better understand the identity and requirements for stem S2, the parent aptamer (Aptamer 3) was synthesized with two of the most prevalent covariations seen in the degenerate selection, 5'-CAGU/ACUG-3' (Aptamer 185) and 5'-CGAU/AUCG-3' (Aptamer 186) and observed that both the covariations are tolerated with a modest (~2-fold) effect on binding in the competition TR-FRET assay. In contrast, disrupting the two central G/C pairs in the 4 base pair stem with two unpaired bases (5'-CCCU/ACCG-3', unpaired residues underlined; Aptamer 188) led to a major loss in activity (>10-fold) further confirming requirement for stem formation. Shortening stem S2 to from 4 to 3 base pairs (Aptamer 44 and 45) also led to a significant loss of activity (>10-fold). Finally, consistent with the sequence data observed from the primary selection (Table 14) and degenerate selection (FIG. 12), which demonstrated a preference for the formation of a terminal U/A pair at the junction of S2 and L2/L4, replacement of the terminal base pair in the stem with a C/G pair, (5'-CGGC/GCCG-3'; Aptamer 43) decreased binding affinity (>10-fold). Together these data further support the formation and requirement for an intact 4 base pair stem S2. In a preferred embodiment, S2 terminates in an U/A pair.

The short, two base pair long, stem S3 (5'-AU/GU-3') proved highly conserved during both the primary (Table 14) and degenerate selection (FIG. 12). Consistent with this, changing the terminal base pair at the junction of this stem with L3 from a U/G to a stronger C/G pair (Aptamer 89) led to significant loss of activity, confirming the importance of this pair (FIG. 14).

Sequence analysis from both the primary and secondary (degenerate) selections suggested that in some instances, stem S3 might be extended to three base pairs in length and that when S3 is extended to three base pairs, loop L3 is shortened to eight base pairs (Table 19). When stem S3 was three base pairs in length, the sequence of S3 was 5'-AAU/AGU-3'. To test this, the identity of the 5'U and 3'A residues of the Aptamer 3 loop L3 sequence was altered to 5'G and 3'C, resulting in the stem S3 sequence 5'-AUC/GGU-3'. The resulting molecule, Aptamer 90, lost its ability to effectively compete for binding (>10-fold). Thus, the preferred length of stem S3 is two base pairs long with the sequence 5'-AU/GU-3'.

TABLE 24

Analysis and optimization of stems 1, 2, and 3 of Aptamer Family 3

| SEQ ID NO with modifications : | Aptamer Number | Sequence (5' to 3' ) | STEM | TR-FRET Activity |
|---|---|---|---|---|
| 922 | Aptamer 3 | $C6NH_2$-UGAUG-A-CGGU-AG-AU-UACGGGUAGA-GU-G-ACCG-CAUCU-idT | | parent |
| 923 | Aptamer 38 | $C6NH_2$- GAUG-A-CGGU-AG-AU-UACGGGUAGA-GU-G-ACCG-CAUC -idT | S1 | ~ |
| 924 | Aptamer 92 | $C6NH_2$- G**GC**G-A-CGGU-AG-AU-UACGGGUAGA-GU-G-ACCG-C**GC**C -idT | S1 | ~ |

TABLE 24-continued

| Analysis and optimization of stems 1, 2, and 3 of Aptamer Family 3 | | | | |
|---|---|---|---|---|
| SEQ ID NO with modific ations : | Aptamer Number | Sequence (5' to 3' ) | STEM | TR-FRET Activity |
| 925 | Aptamer 42 | $C6NH_2$- **GC**G-A-CGGU-AG-AU-UACGGGUAGA-GU-G-ACCG-C**GC** -idT | S1 | ~ |
| 926 | Aptamer 183 | $C6NH_2$-U**C**AUG-A-CGGU-AG-AU-UACGGGUAGA-GU-G-ACCG-CAU**G**U-idT | S1 | ~ |
| 927 | Aptamer 184 | $C6NH_2$-UGAU**C**-A-CGGU-AG-AU-UACGGGUAGA-GU-G-ACCG-**G**AUCU-idT | S1 | ~ |
| 928 | Aptamer 206 | $C6NH_2$-UG**CG**G-A-CGGU-AG-AU-UACGGGUAGA-GU-G-ACCG-C**CG**CU-idT | S1 | -- |
| 929 | Aptamer 207 | $C6NH_2$-UG**GA**G-A-CGGU-AG-AU-UACGGGUAGA-GU-G-ACCG-C**UC**CU-idT | S1 | -- |
| 930 | Aptamer 208 | $C6NH_2$-UG**CC**G-A-CGGU-AG-AU-UACGGGUAGA-GU-G-ACCG-C**GG**CU-idT | S1 | ~ |
| 931 | Aptamer 209 | $C6NH_2$-UG**C**UG-A-CGGU-AG-AU-UACGGGUAGA-GU-G-ACCG-CA**G**CU-idT | S1 | ~ |
| 932 | Aptamer 210 | $C6NH_2$-UG**GC**G-A-CGGU-AG-AU-UACGGGUAGA-GU-G-ACCG-C**GC**CU-idT | S1 | ~ |
| 933 | Aptamer 185 | $C6NH_2$-UGAUG-A-C**A**GU-AG-AU-UACGGGUAGA-GU-G-AC**U**G-CAUCU-idT | S2 | ~ |
| 934 | Aptamer 186 | $C6NH_2$-UGAUG-A-CG**A**U-AG-AU-UACGGGUAGA-GU-G-A**U**CG-CAUCU-idT | S2 | ~ |
| 935 | Aptamer 187 | $C6NH_2$-U**CU**UG-A-CGGU-AG-AU-UACGGGUAGA-GU-G-ACCG-CAUCU-idT | S1 | ~ |
| 936 | Aptamer 188 | $C6NH_2$-UGAUG-A-C**CC**U-AG-AU-UACGGGUAGA-GU-G-ACCG-CAUCU-idT | S2 | --- |
| 937 | Aptamer 44 | $C6NH_2$- **GC**G-A-C_GU-AG-AU-UACGGGUAGA-GU-G-AC_G-C**GC** -idT | S1/S2 | --- |
| 938 | Aptamer 43 | $C6NH_2$- **GC**G-A-CGG**C**-AG-AU-UACGGGUAGA-GU-G-**G**CCG-C**GC** -idT | S1/S2 | --- |
| 939 | Aptamer 45 | $C6NH_2$- **GC**G-A-C_G**C**-AG-AU-UACGGGUAGA-GU-G-**G**C_G-C**GC** -idT | S1/S2 | --- |
| 940 | Aptamer 89 | $C6NH_2$- G**GC**G-A-CGGU-AG-A**C**-UACGGGUAGA-GU-G-ACCG-C**GC**C -idT | S1/S3 | --- |
| 941 | Aptamer 90 | $C6NH_2$- G**GC**G-A-CGGU-AG-AU-**C**ACGGGUAG**G**-GU-G-ACCG-C**GC**C -idT | S1/S3 | --- |

where G is 2'F, and A, C, and U are 2'OMe modified RNA; $C6NH_2$ is a hexylamine linker; idT is an inverted deoxythymidine residue. An underscore (_) denotes an internal deleted position. Bold residues indicate the position is different from the parent.
Key: ~ = 2 fold worse to 2 fold better, ++ = 2-10 fold better , +++ = more than 10 fold better, -- = 2-10 fold worse; --- = more than 10 fold worse.

Example 12. Aptamer 3: Structure Validation and Analysis of Loops

Figure 15:
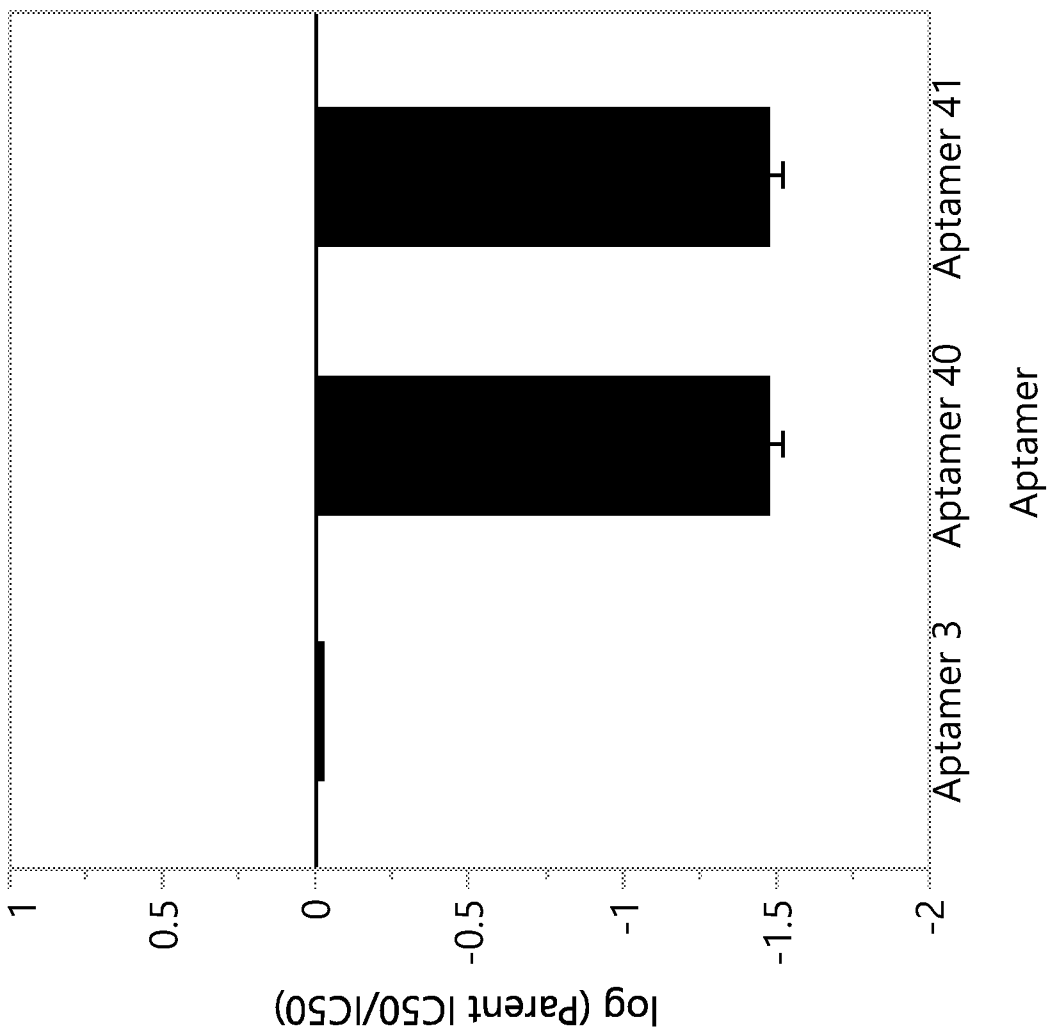
FIG. 15 depicts competitive TR-FRET data demonstrating the relative affinity of doped selection anti-IL8 aptamers according to embodiments of the disclosure. Data is represented as the log of fold change in $IC_{50}$ as compared to parent aptamer.

The short loop L1, composed of a single 2'OMe-A residue located between stem S1 and S2 proved invariant during both the primary (Table 14) and degenerate selections (FIG. 12). To confirm the importance of this residue, molecules were made and tested in which either loop L1 was deleted entirely (Aptamer 40) or was mutated to 5'-U-3' (Aptamer 41). In both cases, there was a complete loss of activity (>10-fold) as determined by competition TR-FRET assay (Table 25 and FIG. 15).

TABLE 25

| Analysis of Loop 1 of Aptamer Family 3. | | | | |
|---|---|---|---|---|
| SEQ ID NO with modifications: | Aptamer Number | Sequence (5' to 3' ) | Loop | TR-FRET Activity |
| 942 | Aptamer 3 | $C6NH_2$-UGAUG-A-CGGU-AG-AU-UACGGGUAGA-GU-G-ACCG-CAUCU-idT | | parent |
| 943 | Aptamer 40 | $C6NH_2$- GAUG-_-CGGU-AG-AU-UACGGGUAGA-GU-G-ACCG-CAUC -idT | L1 | --- |
| 944 | Aptamer 41 | $C6NH_2$- GAUG-**U**-CGGU-AG-AU-UACGGGUAGA-GU-G-ACCG-CAUC -idT | L1 | --- |

where G is 2'F, and A, C, and U are 2'OMe modified RNA; $C6NH_2$ is a hexylamine linker; idT is an inverted deoxythymidine residue. An underscore (_) denotes an internal deleted position. Bold residues indicate the position is different from the parent.

Key: ~ = 2 fold worse to 2 fold better, ++ = 2-10 fold better , +++ = more than 10 fold better, -- = 2-10 fold worse; --- = more than 10 fold worse.

Figure 16:
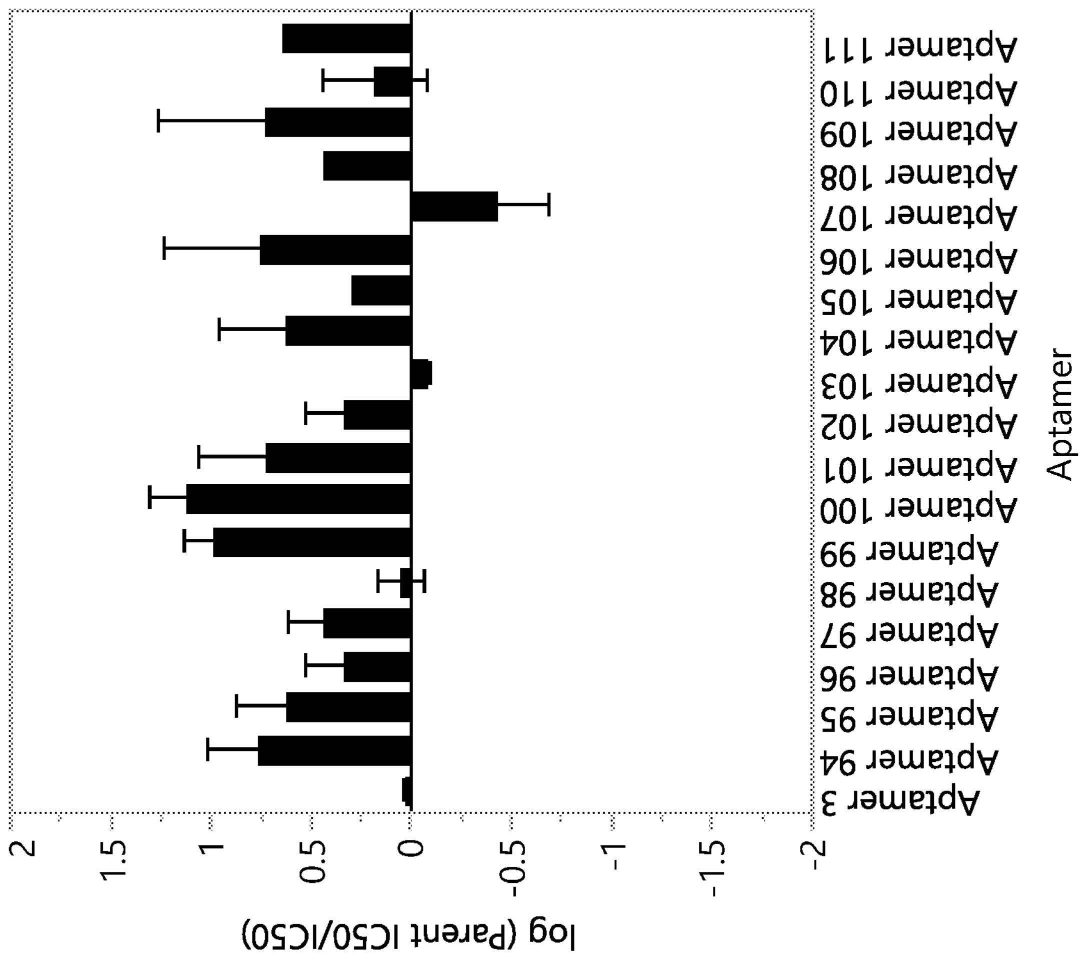
FIG. 16 depicts competitive TR-FRET data demonstrating the relative affinity of doped selection anti-IL8 aptamers according to embodiments of the disclosure. Data is represented as the log of fold change in $IC_{50}$ as compared to parent aptamer.
Figure 17:
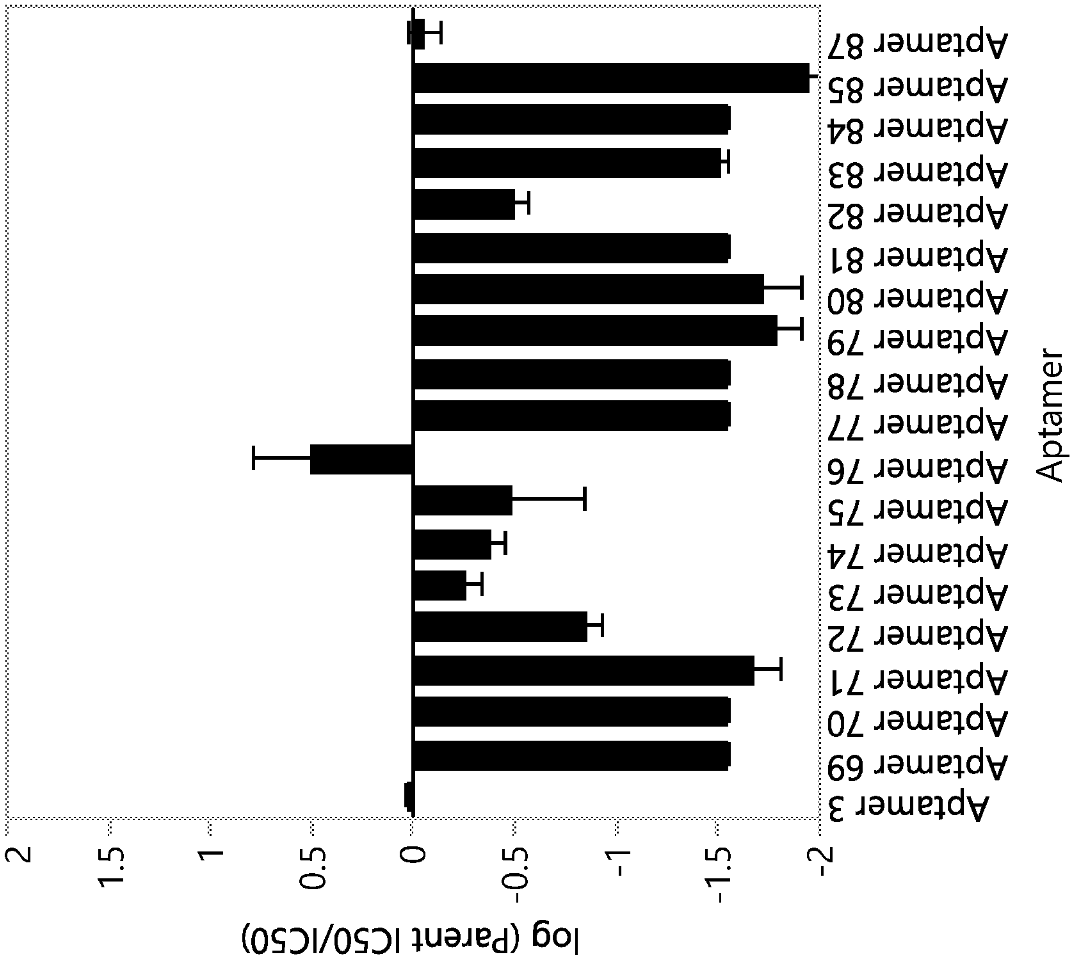
FIG. 17 depicts competitive TR-FRET data demonstrating the relative affinity of doped selection anti-IL8 aptamers according to embodiments of the disclosure. Data is represented as the log of fold change in $I_{C50}$ as compared to parent aptamer.

Unlike loops L1, L2 and L4 which remained nearly invariant in both the primary and degenerate selections, loop L3 showed significant variation in some positions, in particular, positions 15, 16, 17, 21, and 24. To test the effects of variation in this region on aptamer function, aptamer clones from Round 5 of the degenerate selection which had mutations in loop L3 were synthesized (Table 26). All of the compounds were tested in the competition TR-FRET assay. As shown in FIG. 16, with the exception of Aptamer 107, all of the loop L3 variants tested demonstrated similar or better activity than the parent aptamer (Aptamer 3). Aptamer 107, which had a deletion at position 16, was ~5-fold worse than the parent, indicating that the 10 nucleotide length of loop L3 is preferred for optimal activity. Interestingly, the best performing molecules, Aptamers 94, 99, and 100, all contained an A to U mutation at position 24, providing further support that the preferred loop L3 is 10 nucleotides long and that the terminal positions of the loop (positions 15 and 24) remain unpaired.

the competition TR-FRET assay. Sp3 substitutions in loop L2 (Aptamer 69, Aptamer 70) led to significant losses in activity (>10 fold worse) thus confirming the importance of the 5'-AG-3' of loop 2 and further validating the 100% conservation of these residues observed in the degenerate selection sequence analysis (FIG. 17). Similarly, replacing the single G of loop L4 (Aptamer 85) also led to significant loss in activity (>10 fold worse), consistent with the 100% conservation of this residue in the primary and degenerate selections.

Replacement by Sp3 in loop L3 led to some interesting observations (Table 27 and FIG. 17). Consistent with the high level of conservation observed during the degenerate reselection, residues G19, G20, A22 and G23 (Aptamer 77, 78, 80 and 81) could not be replaced with a linker without substantial losses in activity (>10 fold worse). Interestingly, U21, which was only ~70% conserved in the degenerate sequence analysis and could be replaced with any of the other three bases without a significant effect on activity (see

TABLE 26

Analysis of Loop 3 of Aptamer Family 3.

| SEQ ID NO with modifications: | Aptamer Number | Sequence (5' to 3' ) | TR-FRET Activity |
|---|---|---|---|
| 945 | Aptamer 3 | $C6NH_2$-U-GAUG-A-CGGU-AG-AU-UACGGGUAGA-GU-G-ACCG-CAUC-U-idT | Parent |
| 946 | Aptamer 94 | $C6NH_2$-U-GAUG-A-CGGU-AG-AU-U**U**CGGGUAG**U**-GU-G-ACCG-CAUC-U-idT | ++ |
| 947 | Aptamer 95 | $C6NH_2$-U-GAUG-A-CGGU-AG-AU-U**C**CGGGUAG**U**-GU-G-ACCG-CAUC-U-idT | ++ |
| 948 | Aptamer 96 | $C6NH_2$-U-GAUG-A-CGGU-AG-AU-UACGGG**C**AG**U**-GU-G-ACCG-CAUC-U-idT | ++ |
| 949 | Aptamer 97 | $C6NH_2$-U-GAUG-A-CGGU-AG-AU-UACGGG**G**AG**U**-GU-G-ACCG-CAUC-U-idT | ++ |
| 950 | Aptamer 98 | $C6NH_2$-U-GAUG-A-CGGU-AG-AU-UACGGG**A**AG**U**-GU-G-ACCG-CAUC-U-idT | ~ |
| 951 | Aptamer 99 | $C6NH_2$-U-GAUG-A-CGGU-AG-AU-UA**U**GGG**C**AG**U**-GU-G-ACCG-CAUC-U-idT | ++ |
| 952 | Aptamer 100 | $C6NH_2$-U-GAUG-A-CGGU-AG-AU-UA**U**GGG**A**AG**U**-GU-G-ACCG-CAUC-U-idT | +++ |
| 953 | Aptamer 101 | $C6NH_2$-U-CAUG-A-CGGU-AG-AU-U**U**CGGGUAG**U**-GU-G-ACCG-CAU**G**-U-idT | ++ |
| 954 | Aptamer 102 | $C6NH_2$-U-CAUG-A-CGGU-AG-AU-UACGGGUAGA-GU-G-ACCG-CAU**G**-U-idT | ++ |
| 955 | Aptamer 103 | $C6NH_2$-U-GAUG-A-CGGU-AG-AU-UACGGG**A**AGA-GU-G-ACCG-CAUC-U-idT | ~ |
| 956 | Aptamer 104 | $C6NH_2$-U-GAUG-A-CGGU-AG-AU-UA**A**GGGUAG**U**-GU-G-ACCG-CAUC-U-idT | ++ |
| 957 | Aptamer 105 | $C6NH_2$-U-GAUG-A-CGGU-AG-AU-UACGGGU**U**G**U**-GU-G-ACCG-CAUC-U-idT | ~ |
| 958 | Aptamer 106 | $C6NH_2$-U-GAUG-A-CG**A**U-AG-AU-U**U**CGGGUAG**U**-GU-G-A**U**CG-CAUC-U-idT | ++ |
| 959 | Aptamer 107 | $C6NH_2$-U-GAUG-A-CGGU-AG-AU-U_**U**GGGUAGA-GU-G-ACCG-CAUC-U-idT | -- |
| 960 | Aptamer 108 | $C6NH_2$-U-GAUG-A-CGGU-AG-AU-**A**ACGGGUAGA-GU-G-ACCG-CAUC-U-idT | ++ |
| 961 | Aptamer 109 | $C6NH_2$-U-GAUG-A-CGGU-AG-AU-**A**ACGGGUAG**U**-GU-G-ACCG-CAUC-U-idT | ++ |
| 962 | Aptamer 110 | $C6NH_2$-U-GAUG-A-CGGU-AG-AU-U**U**CGGG**A**AG**U**-GU-G-ACCG-CAUC-U-idT | ~ |
| 963 | Aptamer 111 | $C6NH_2$-U-GAUG-A-CGGU-AG-AU-UA**U**GGGUAG**U**-GU-G-ACCG-CAUC-U-idT | ++ |

where G is 2'F, and A, C, and U are 2'OMe modified RNA; $C6NH_2$ is a hexylamine linker; idT is an inverted deoxythymidine residue. An underscore (_) denotes an internal deleted position. Bold indicates the position is different from the parent.
Key: ~ = 2 fold worse to 2 fold better, ++ = 2-10 fold better , +++ = more than 10 fold better, -- = 2-10 fold worse; --- = more than 10 fold worse.

Example 13. Linker Scanning Aptamer 3

To further analyze sequence requirements in loops L2, L3, L4 and stem S3, versions of the parent aptamer, Aptamer 3, were made in which every position from A11 to G27 was replaced, individually, with a non-nucleotide 3-carbon spacer (Sp3; Table 27). All of the compounds were tested in Table 26; Aptamers 96, 97, 98, 103, 110) also displayed substantial losses in activity (>10 fold worse) when replaced by an Sp3 linker (Table 27; Aptamer 79), indicating the importance of a base and/or sugar at this position within loop L3. More surprisingly, replacement of residue G18 with an Sp3 linker led to ~10 fold enhancement of activity even though it was found to be 100% conserved in the degenerate selection (Table 27; Aptamer 76).

TABLE 27

Linker Scan Analysis of Aptamer Family 3.

| SEQ ID NO with modifications: | Aptamer Number | Sequence (5' to 3' ) | TR-FRET Activity |
|---|---|---|---|
| 964 | Aptamer 3 | $C6NH_2$-UGAUG-A-CGGU-AG-AU-UACGGGUAGA-GU-G-ACCG-CAUCU-idT | parent |
| 965-966 | Aptamer 69 | $C6NH_2$-UGAUG-A-CGGU-**X**G-AU-UACGGGUAGA-GU-G-ACCG-CAUCU-idT | --- |
| 967-968 | Aptamer 70 | $C6NH_2$-UGAUG-A-CGGU-A**X**-AU-UACGGGUAGA-GU-G-ACCG-CAUCU-idT | --- |
| 969-970 | Aptamer 71 | $C6NH_2$-UGAUG-A-CGGU-AG-**X**U-UACGGGUAGA-GU-G-ACCG-CAUCU-idT | --- |
| 971-972 | Aptamer 72 | $C6NH_2$-UGAUG-A-CGGU-AG-A**X**-UACGGGUAGA-GU-G-ACCG-CAUCU-idT | -- |
| 973-974 | Aptamer 73 | $C6NH_2$-UGAUG-A-CGGU-AG-AU-**X**ACGGGUAGA-GU-G-ACCG-CAUCU-idT | ~ |
| 975-976 | Aptamer 74 | $C6NH_2$-UGAUG-A-CGGU-AG-AU-U**X**CGGGUAGA-GU-G-ACCG-CAUCU-idT | ~ |
| 977-978 | Aptamer 75 | $C6NH_2$-UGAUG-A-CGGU-AG-AU-UA**X**GGGUAGA-GU-G-ACCG-CAUCU-idT | ~ |
| 979-980 | Aptamer 76 | $C6NH_2$-UGAUG-A-CGGU-AG-AU-UAC**X**GGUAGA-GU-G-ACCG-CAUCU-idT | ++ |
| 981-982 | Aptamer 77 | $C6NH_2$-UGAUG-A-CGGU-AG-AU-UACG**X**GUAGA-GU-G-ACCG-CAUCU-idT | --- |
| 983-984 | Aptamer 78 | $C6NH_2$-UGAUG-A-CGGU-AG-AU-UACGG**X**UAGA-GU-G-ACCG-CAUCU-idT | --- |
| 985-986 | Aptamer 79 | $C6NH_2$-UGAUG-A-CGGU-AG-AU-UACGGG**X**AGA-GU-G-ACCG-CAUCU-idT | --- |
| 987-988 | Aptamer 80 | $C6NH_2$-UGAUG-A-CGGU-AG-AU-UACGGGU**X**GA-GU-G-ACCG-CAUCU-idT | --- |
| 989-990 | Aptamer 81 | $C6NH_2$-UGAUG-A-CGGU-AG-AU-UACGGGUA**X**A-GU-G-ACCG-CAUCU-idT | --- |
| 991-992 | Aptamer 82 | $C6NH_2$-UGAUG-A-CGGU-AG-AU-UACGGGUAG**X**-GU-G-ACCG-CAUCU-idT | -- |
| 993-994 | Aptamer 83 | $C6NH_2$-UGAUG-A-CGGU-AG-AU-UACGGGUAGA-**X**U-G-ACCG-CAUCU-idT | --- |
| 995-996 | Aptamer 84 | $C6NH_2$-UGAUG-A-CGGU-AG-AU-UACGGGUAGA-G**X**-G-ACCG-CAUCU-idT | --- |
| 997-998 | Aptamer 85 | $C6NH_2$-UGAUG-A-CGGU-AG-AU-UACGGGUAGA-GU-**X**-ACCG-CAUCU-idT | --- |
| 999-1000 | Aptamer 87 | $C6NH_2$---GCG-A-CGGU-AG-AU-UAC**X**GGUAGA-GU-G-ACCG-CGC---idT | ~ |

where G is 2'F and A, C, and U are 2'OMe modified RNA; $C6NH_2$ is a hexylamine linker; idT is an inverted deoxythymidine residue; and a bold X is the Sp3 spacer.
Key: ~ = 2 fold worse to 2 fold better, ++ = 2-10 fold better , +++ = more than 10 fold better, -- = 2-10 fold worse; --- = more than 10 fold worse.

Figure 18:
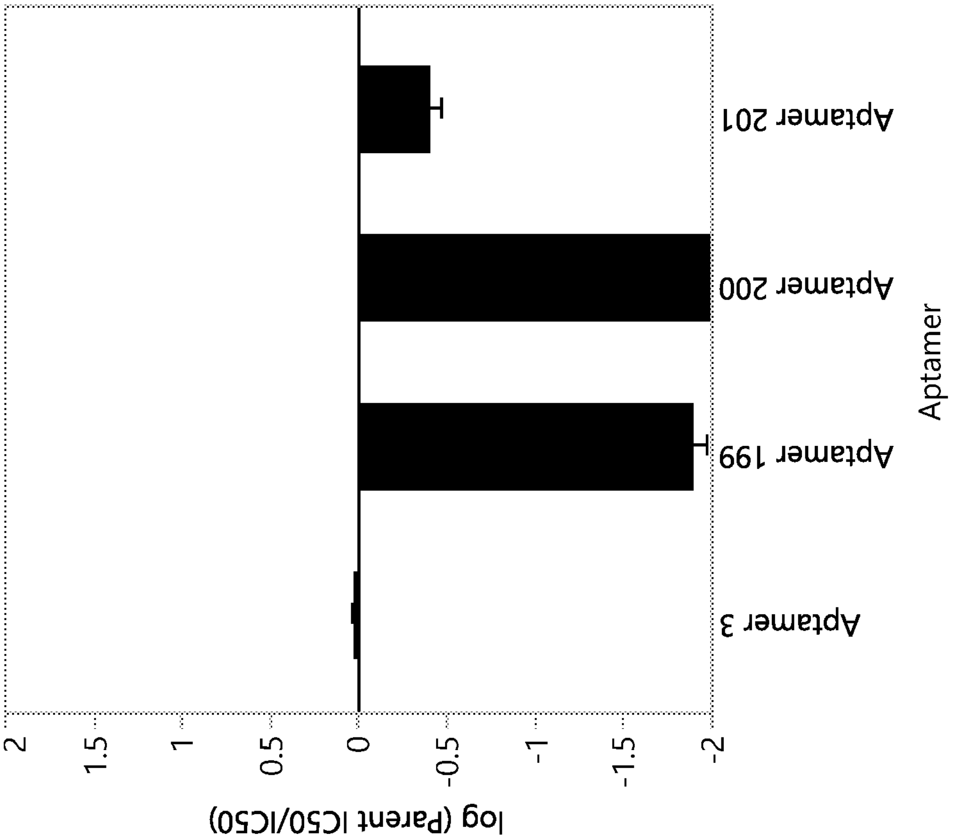
FIG. 18 depicts competitive TR-FRET data demonstrating the relative affinity of doped selection anti-IL8 aptamers according to embodiments of the disclosure. Data is represented as the log of fold change in $IC_{50}$ as compared to parent aptamer.

To further analyze the base requirements at position 18, variants of Aptamer 3 were made where G18 was replaced with a U, a C, or an A, and tested them in competition TR-FRET (Table 28 and FIG. 18). Replacing G18 with U or C led to significant loss in activity (>10 fold worse) whereas replacing it with an A led to only ~5 fold loss in activity. Thus, this position can tolerate an A, but cannot tolerate substitution with a pyrimidine, supporting the rare (0.1%) G to A mutation seen at this position in the degenerate selection.

TABLE 28

Analysis of base identity at position 18 of Aptamer Family 3

| SEQ ID NO with modifications: | Aptamer Number | Sequence (5' to 3' ) | TR-FRET Activity |
|---|---|---|---|
| 1001 | Aptamer 3 | $C6NH_2$-UGAUG-A-CGGU-AG-AU-UACGGGUAGA-GU-G-ACCG-CAUCU-idT | parent |
| 1002 | Aptamer 199 | $C6NH_2$-UGAUG-A-CGGU-AG-AU-UAC**U**GGUAGA-GU-G-ACCG-CAUCU-idT | --- |
| 1003 | Aptamer 200 | $C6NH_2$-UGAUG-A-CGGU-AG-AU-UAC**C**GGUAGA-GU-G-ACCG-CAUCU-idT | --- |
| 1004 | Aptamer 201 | $C6NH_2$-UGAUG-A-CGGU-AG-AU-UAC**A**GGUAGA-GU-G-ACCG-CAUCU-idT | -- |

where G is 2'F and A, C, and U are 2'OMe modified RNA; $C6NH_2$ is a hexylamine linker; idT is an inverted deoxythymidine residue. Positions different from the parent, Aptamer 3, are highlighted in bold.
Key: ~ = 2 fold worse to 2 fold better, ++ = 2-10 fold better , +++ = more than 10 fold better, -- = 2-10 fold worse; --- = more than 10 fold worse.

Figure 19:
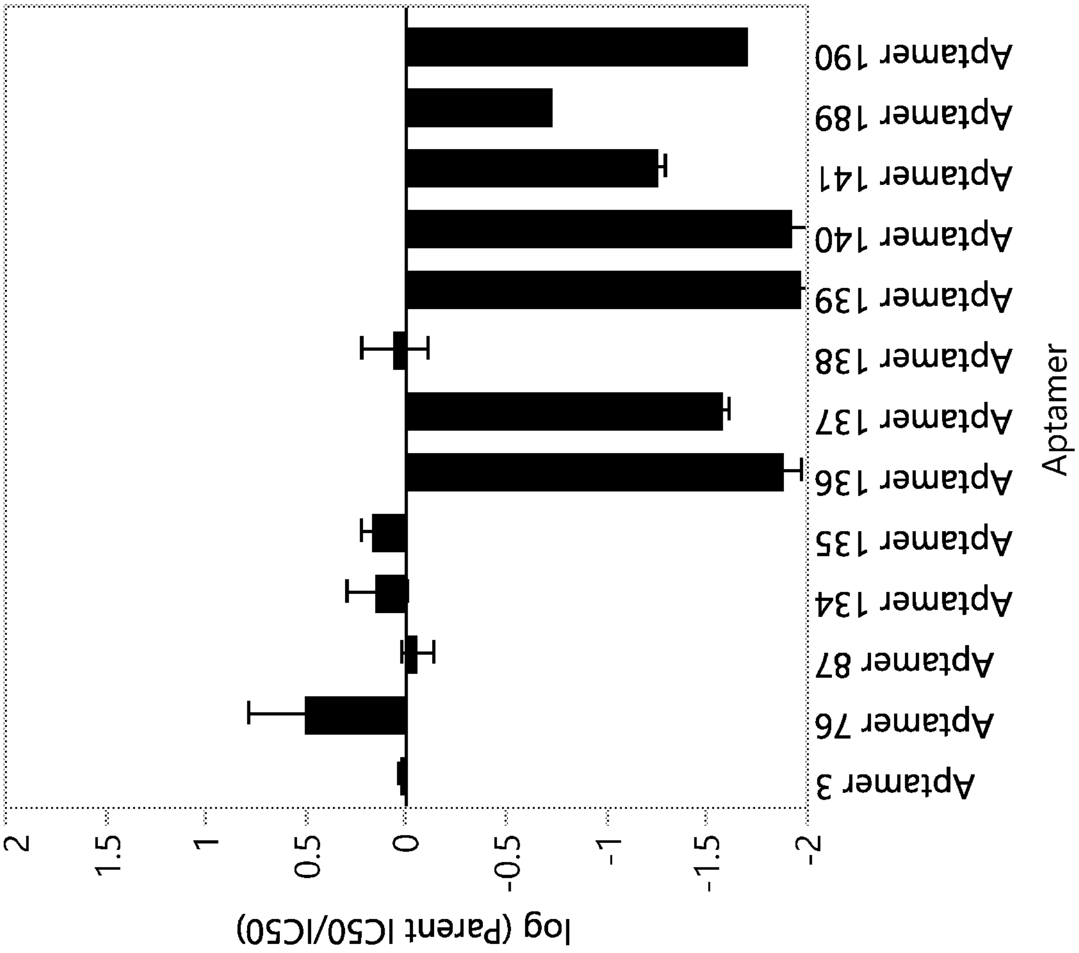
FIG. 19 depicts competitive TR-FRET data demonstrating the relative affinity of doped selection anti-IL8 aptamers according to embodiments of the disclosure. Data is represented as the log of fold change in $IC_{50}$ as compared to parent aptamer.

Linker scanning analysis indicated that replacing each of the residues U15, A16, C17, and G18 with an Sp3 linker was well tolerated by the parent aptamer, Aptamer 3. To explore this further, an additional series of linker variants using linkers of different length, composition and number composition were generated and their function was assessed by competition TR-FRET (Table 29 and FIG. 19).

Replacing all four positions simultaneously with four Sp3 spacers was well tolerated (Aptamers 134, 135), and led to ~5 fold improvement in activity compared to the parent aptamer (Aptamer 3). Replacement with three Sp3 spacers (Aptamer 138) was also well tolerated; the molecules demonstrated activity similar to that of the parent. However, replacing 5'-UACG-3' with one or two Sp3 spacers led to significant loss in activity (Aptamer 136 and Aptamer 137). Similarly, replacement of the 5'-UACG-3' with a 6-carbon linker (L6) (Aptamer 139) or one Sp9 (Aptamer 140), two Sp9 (Aptamer 189), Sp18 (Aptamer 141), or Sp3 followed by Sp9 (Aptamer 190) led to significant losses in activity as well. Overall, loop L3 can tolerate inclusion of a number of non-nucleotidyl spacers with an improvement or only modest loss of activity.

Example 14. Optimization of L3 Aptamer Variants

Figure 20:
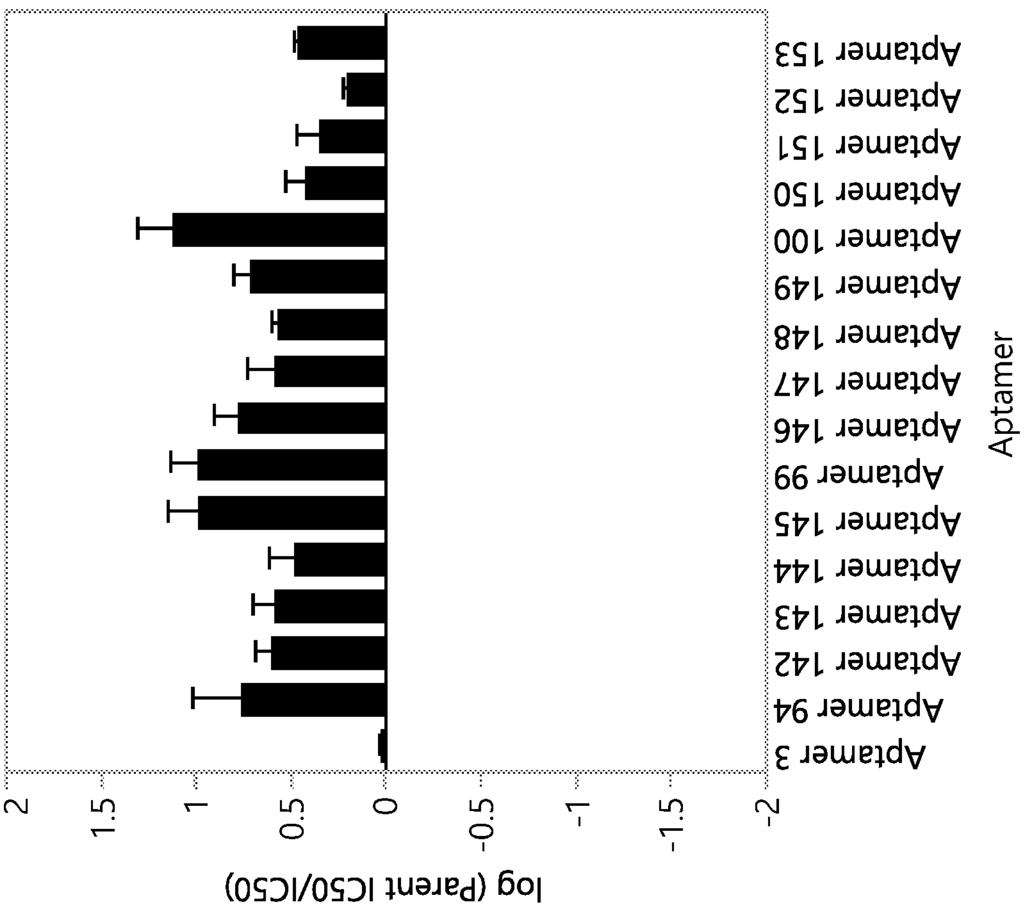
FIG. 20 depicts competitive TR-FRET data demonstrating the relative affinity of doped selection anti-IL8 aptamers according to embodiments of the disclosure. Data is represented as the log of fold change in $IC_{50}$ as compared to parent aptamer.

Loop L3 aptamer variants Aptamers 94, 99, and 100 were among the most potent aptamers tested, with activity 5-10 fold better than the parent, Aptamer 3 (Table 26 and FIG. 16). Variants of Aptamers 94, 99, and 100 were synthesized with an optimized stem S1 and G18 was also replaced with a Sp3 spacer to see if further improvements could be made to these molecules (Table 30 and FIG. 20). While all the stem and linker optimized versions of the mutant clones demonstrated better activity than Aptamer 3, the modifications did not provide further improvement in activity over their respective parent molecules (Aptamers 94, 99, and 100) as determined by competition TR-FRET. Importantly, these experiments yielded aptamer variants with a three and four base pair stem S1 that demonstrated activities 3-10 fold better than the parent molecule Aptamer 3.

TABLE 29

Analysis of base identity at position 18 of Aptamer Family 3.

| SEQ ID NO with modifications: | Aptamer Number | Sequence (5' to 3' ) | TR-FRET Activity |
|---|---|---|---|
| 1005 | Aptamer 3 | $C6NH_2$-UGAUG-A-CGGU-AG-AU-UACGGGUAGA-GU-G-ACCG-CAUCU-idT | parent |
| 1006-1007 | Aptamer 76 | $C6NH_2$-UGAUG-A-CGGU-AG-AU-UAC**X**GGUAGA-GU-G-ACCG-CAUCU-idT | ++ |
| 1008-1009 | Aptamer 87 | $C6NH_2$- GCG-A-CGGU-AG-AU-UAC**X**GGUAGA-GU-G-ACCG-CGC -idT | ~ |
| 1010-1011 | Aptamer 134 | $C6NH_2$- GAUG-A-CGGU-AG-AU-**XXXX**GGUAGA-GU-G-ACCG-CAUC -idT | ~ |
| 1012-1013 | Aptamer 135 | $C6NH_2$- GGCG-A-CGGU-AG-AU-**XXXX**GGUAGA-GU-G-ACCG-CGCC -idT | ~ |
| 1014-1015 | Aptamer 136 | $C6NH_2$- GAUG-A-CGGU-AG-AU-**X**___GGUAGA-GU-G-ACCG-CAUC -idT | --- |
| 1016-1017 | Aptamer 137 | $C6NH_2$- GAUG-A-CGGU-AG-AU-**XX**__GGUAGA-GU-G-ACCG-CAUC -idT | --- |
| 1018-1019 | Aptamer 138 | $C6NH_2$- GAUG-A-CGGU-AG-AU-**XXX**_GGUAGA-GU-G-ACCG-CAUC -idT | ~ |
| 1020-1021 | Aptamer 139 | $C6NH_2$- GAUG-A-CGGU-AG-AU-(**L6**)GGUAGA-GU-G-ACCG-CAUC -idT | --- |
| 1022-1023 | Aptamer 140 | $C6NH_2$- GAUG-A-CGGU-AG-AU-(**Sp9**)GGUAGA-GU-G-ACCG-CAUC -idT | --- |
| 1024-1025 | Aptamer 141 | $C6NH_2$- GAUG-A-CGGU-AG-AU-(**Sp18**)GGUAGA-GU-G-ACCG-CAUC -idT | --- |
| 1026-1027 | Aptamer 189 | $C6NH_2$- GAUG-A-CGGU-AG-AU-(**Sp9**)(**Sp9**)GGUAGA-GU-G-ACCG-CAUC-idT | --- |
| 1028-1029 | Aptamer 190 | $C6NH_2$-GAUG-A-CGGU-AG-AU-X(**Sp9**)GGUAGA-GU-G-ACCG-CAUC-idT | --- |

where G is 2'F, and A, C, and U are 2'OMe modified RNA; $C6NH_2$ is a hexylamine linker; idT is an inverted deoxythymidine residue; a bold X is the Sp3 spacer; bold L6 is a C6 spacer; and bold Sp9 and Sp18 are 9 and 18 atom PEG spacers, respectively; an underscore (_) denotes an internal deleted position.

Key: ~ = 2 fold worse to 2 fold better, ++ = 2-10 fold better , +++ = more than 10 fold better, -- = 2-10 fold worse; --- = more than 10 fold worse.

TABLE 30

Optimization of Aptamer 3 Family variants

| SEQ ID NO with modifications: | Aptamer Number | Sequence (5' to 3') | TR-FRET Activity |
|---|---|---|---|
| 1030 | Aptamer 3 | $C6NH_2$-UGAUG-A-CGGU-AG-AU-UACGGGUAGA-GU-G-ACCG-CAUCU-idT | parent |
| 1031 | Aptamer 94 | $C6NH_2$-UGAUG-A-CGGU-AG-AU-U**U**CGGGUAG**U**-GU-G-ACCG-CAUCU-idT | ++ |
| 1032 | Aptamer 142 | $C6NH_2$- GAUG-A-CGGU-AG-AU-U**U**CGGGUAG**U**-GU-G-ACCG-CAUC -idT | ++ |
| 1033 | Aptamer 143 | $C6NH_2$- G**GC**G-A-CGGU-AG-AU-U**U**CGGGUAG**U**-GU-G-ACCG-C**GC**C -idT | ++ |
| 1034 | Aptamer 144 | $C6NH_2$- **GC**G-A-CGGU-AG-AU-U**U**CGGGUAG**U**-GU-G-ACCG-C**GC** -idT | ++ |
| 1035-1036 | Aptamer 145 | $C6NH_2$- GAUG-A-CGGU-AG-AU-U**U**C**X**GGUAG**U**-GU-G-ACCG-CAUC -idT | ++ |
| 1037 | Aptamer 99 | $C6NH_2$-UGAUG-A-CGGU-AG-AU-UA**U**GGG**C**AG**U**-GU-G-ACCG-CAUCU-idT | ++ |
| 1038 | Aptamer 146 | $C6NH_2$- GAUG-A-CGGU-AG-AU-UA**U**GGG**C**AG**U**-GU-G-ACCG-CAUC -idT | ++ |
| 1039 | Aptamer 147 | $C6NH_2$- G**GC**G-A-CGGU-AG-AU-UA**U**GGG**C**AG**U**-GU-G-ACCG-C**GC**C -idT | ++ |
| 1040 | Aptamer 148 | $C6NH_2$- **GC**G-A-CGGU-AG-AU-UA**U**GGG**C**AG**U**-GU-G-ACCG-C**GC** -idT | ++ |
| 1041-1042 | Aptamer 149 | $C6NH_2$- GAUG-A-CGGU-AG-AU-UA**UX**GG**C**AG**U**-GU-G-ACCG-CAUC -idT | ++ |
| 1043 | Aptamer 100 | $C6NH_2$-UGAUG-A-CGGU-AG-AU-UA**U**GGG**A**AG**U**-GU-G-ACCG-CAUCU-idT | +++ |
| 1044 | Aptamer 150 | $C6NH_2$- GAUG-A-CGGU-AG-AU-UA**U**GGG**A**AG**U**-GU-G-ACCG-CAUC -idT | ++ |
| 1045 | Aptamer 151 | $C6NH_2$- G**GC**G-A-CGGU-AG-AU-UA**U**GGG**A**AG**U**-GU-G-ACCG-C**GC**C -idT | ++ |
| 1046 | Aptamer 152 | $C6NH_2$- **GC**G-A-CGGU-AG-AU-UA**U**GGG**A**AG**U**-GU-G-ACCG-C**GC** -idT | ~ |
| 1047-1048 | Aptamer 153 | $C6NH_2$- GAUG-A-CGGU-AG-AU-UA**UX**GG**A**AG**U**-GU-G-ACCG-CAUC -idT | ++ |

where G is 2'F, and A, C, and U are 2'OMe modified RNA; $C6NH_2$ is a hexylamine linker; idT is an inverted deoxythymidine residue; a bold X is the Sp3 spacer. Differences from the parent (Aptamer 3) are indicated in bold. Key: ~ = 2 fold worse to 2 fold better, ++ = 2-10 fold better, +++ = more than 10 fold better, -- = 2-10 fold worse; --- = more than 10 fold worse.

Analysis of loop L3 mutations observed from the degenerate selection revealed four positions (A16, C17, U21, and A24) with low levels of conservation (less than ~70%). Indeed, mutations at these positions lead to significant improvements (>10-fold) in aptamer activity as observed for Aptamers 94, 99, and 100 and their derivatives with four base pair stem S1 (Aptamers 143, 147; Table 30). More specifically, Aptamer 143 had mutations A16-U and A24-U but did not have C17-U, and Aptamer 147 had mutations C17-U and A24-U but did not have the A16-U mutation.

Figure 21:
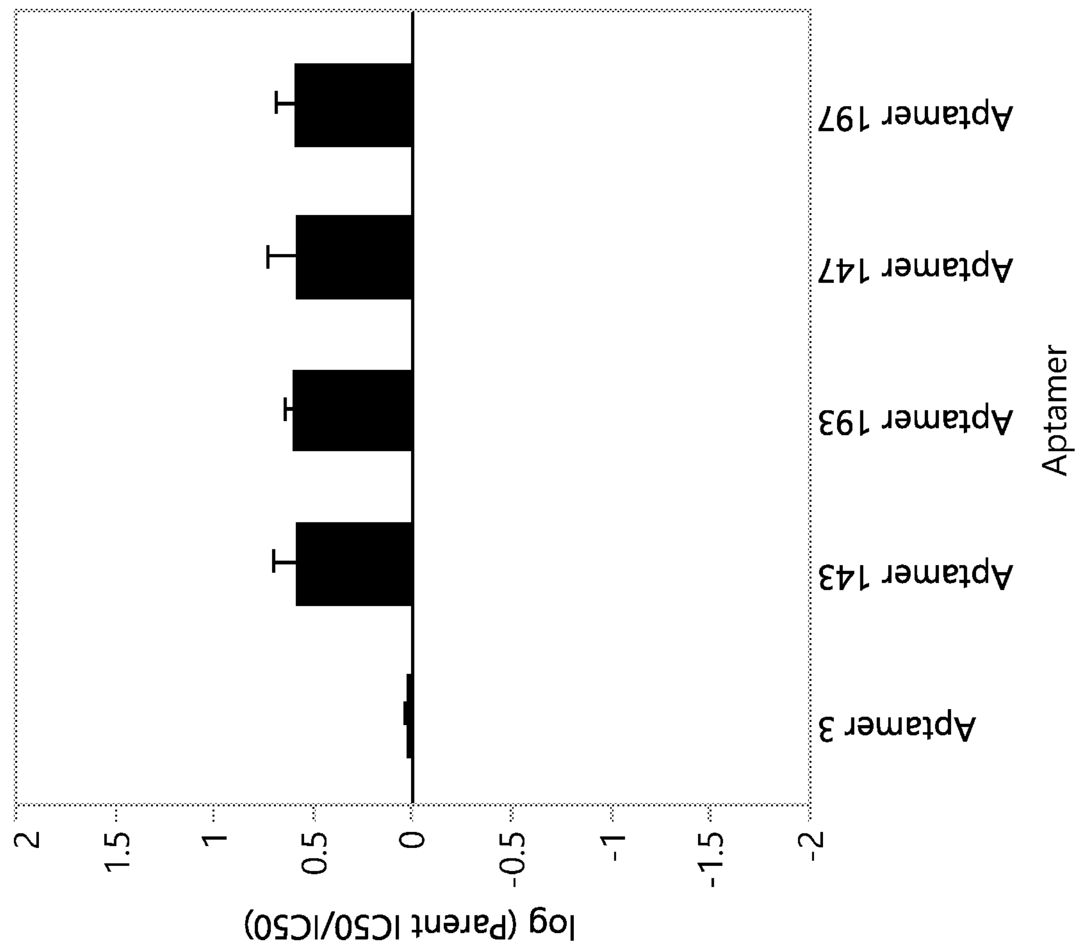
FIG. 21 depicts competitive TR-FRET data demonstrating the relative affinity of doped selection anti-IL8 aptamers according to embodiments of the disclosure. Data is represented as the log of fold change in $IC_{50}$ as compared to parent aptamer.

The C17-U mutation in the loop L3 of Aptamer 143 (Aptamer 193) and A16-U mutation in the loop 3 of Aptamer 147 (Aptamer 197) were added to test the effect of these additional mutations on activity. The mutations had little to no effect on activity (Table 31 and FIG. 21).

TABLE 31

Optimization of Aptamer 3-family variants

| SEQ ID NO with modifications: | Aptamer Number | Sequence (5' to 3') | TR-FRET Activity |
|---|---|---|---|
| 1049 | Aptamer 3 | $C6NH_2$-UGAUG-A-CGGU-AG-AU-UACGGGUAGA-GU-G-ACCG-CAUCU-idT | parent |
| 1050 | Aptamer 143 | $C6NH_2$- GGCG-A-CGGU-AG-AU-U**U**CGGGUAG**U**-GU-G-ACCG-CGCC -idT | ++ |
| 1051 | Aptamer 193 | $C6NH_2$- GGCG-A-CGGU-AG-AU-U**UU**GGGUAG**U**-GU-G-ACCG-CGCC -idT | ++ |
| 1052 | Aptamer 147 | $C6NH_2$- GGCG-A-CGGU-AG-AU-UA**U**GGG**C**AG**U**-GU-G-ACCG-CGCC -idT | ++ |
| 1053 | Aptamer 197 | $C6NH_2$- GGCG-A-CGGU-AG-AU-U**UU**GGG**C**AG**U**-GU-G-ACCG-CGCC -idT | ++ |

where G is 2'F, and A, C, and U are 2'OMe modified RNA; $C6NH_2$ is a hexylamine linker; idT is an inverted deoxythymidine residue.

Differences from the parent (Aptamer 3) are indicated in bold.

Key: ~ = 2 fold worse to 2 fold better, ++ = 2-10 fold better, +++ = more than 10 fold better, -- = 2-10 fold worse; --- = more than 10 fold worse Taken together, the data in Tables 26-31 support the importance of residues G19, G20, A22, and G23 in loop L3. They also demonstrate that positions U15, A16, C17, and G18 can tolerate the observed mutations (Table 12 and FIG. 12 and FIG. 13A). Additionally, replacement of multiple residues with a non-nucleotidyl 3-carbon (Sp3) linker was well tolerated by the parent aptamer, Aptamer 3.

Example 15. Optimization of Aptamer 147 by 2'OMe Sugar Substitutions

Figure 22:
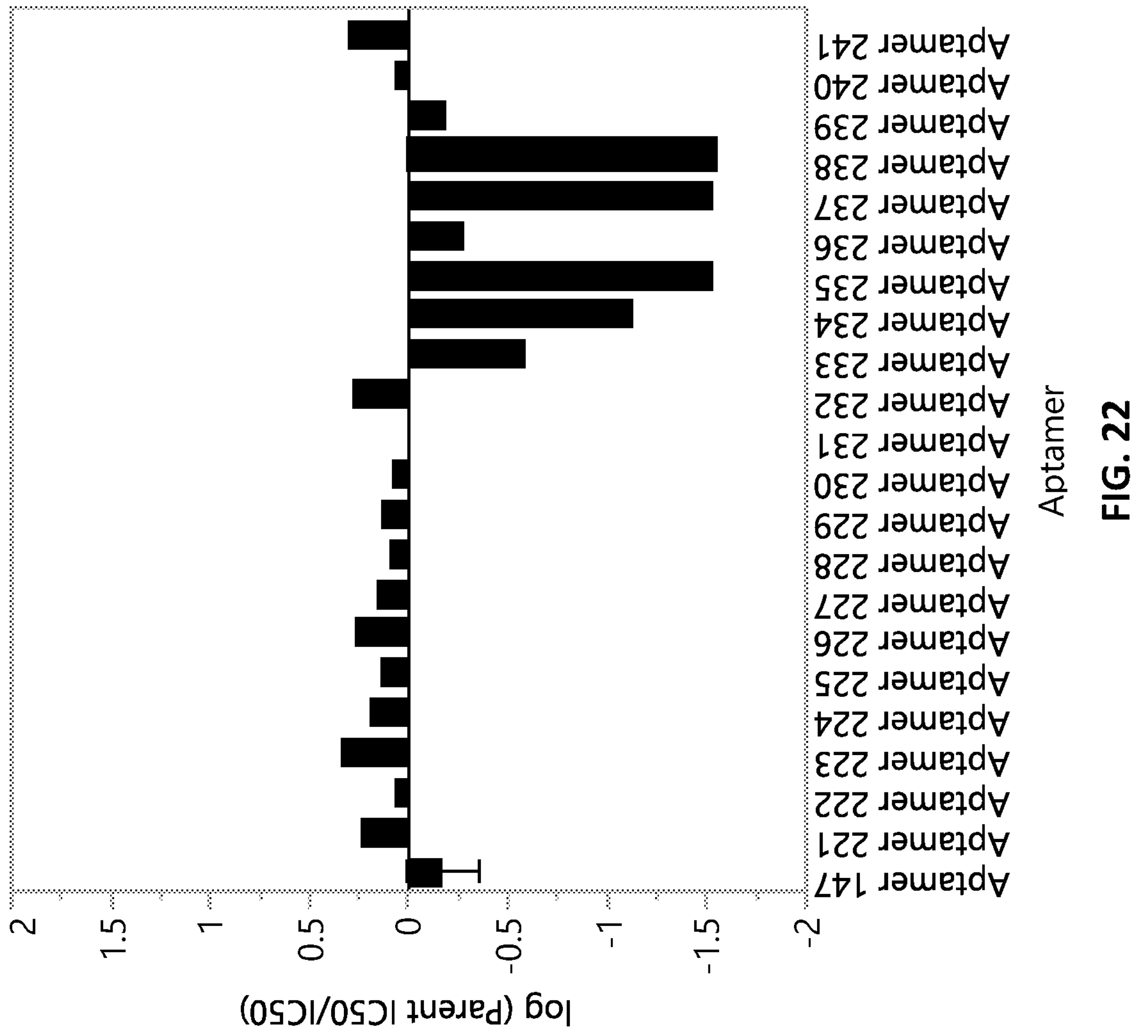
FIG. 22 depicts competitive TR-FRET data demonstrating the relative affinity of anti-IL8 aptamers according to embodiments of the disclosure. Data is represented as the log of fold change in $IC_{50}$ as compared to parent aptamer.
Figure 23:
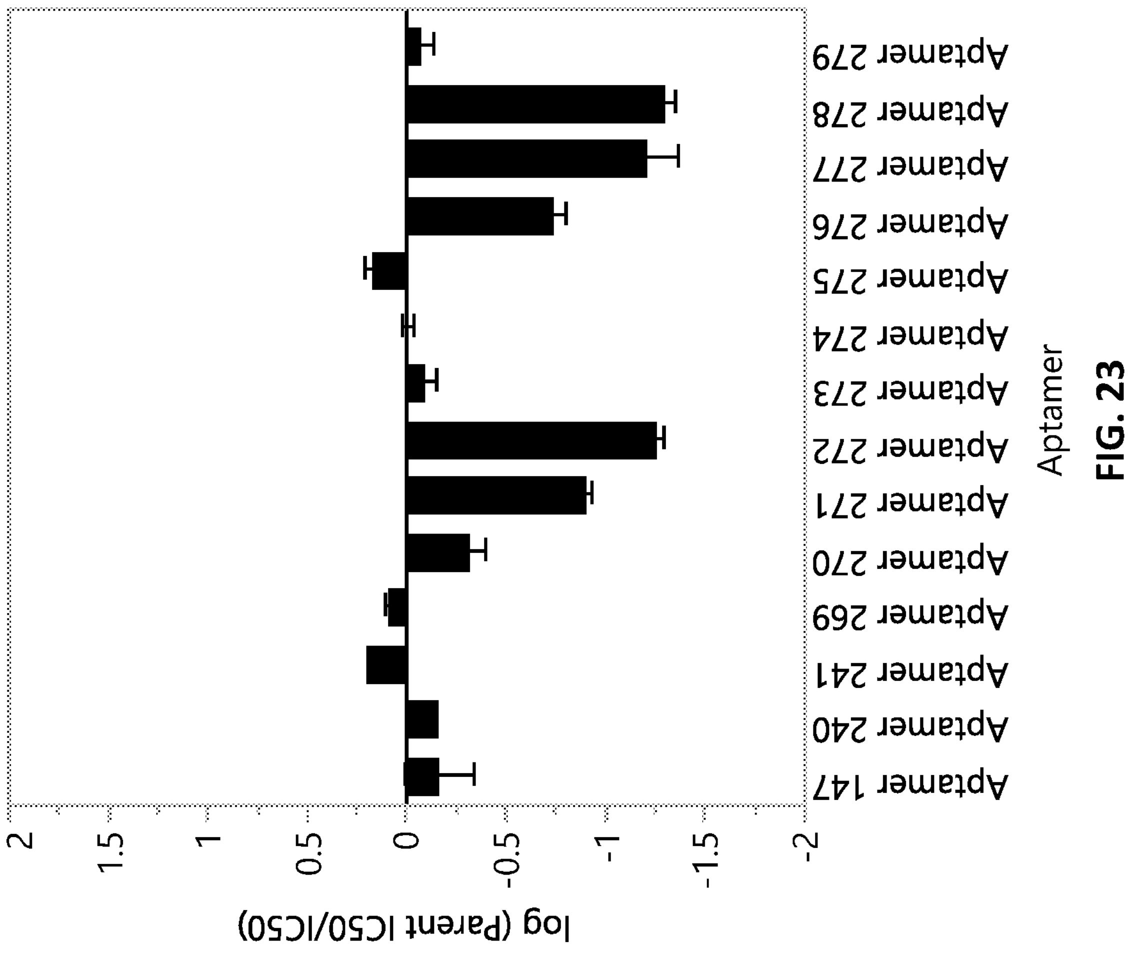
FIG. 23 depicts competitive TR-FRET data demonstrating the relative affinity of anti-IL8 aptamers according to embodiments of the disclosure. Data is represented as the log of fold change in $IC_{50}$ as compared to parent aptamer.

2'OMe modifications may impart higher duplex stability, increased metabolic stability in serum and vitreous, and may have greater coupling efficiency during synthesis compared to 2'F-containing nucleotides. The use of these nucleotides may also avoid the potential loss of the 2'F group during production, which can happen during deprotection steps and exposure to heat. To probe the effect of 2'F-G to 2'OMe-G substitution on target binding, variants of Aptamer 147 were synthesized where 2'F-G was selectively substituted with 2'OMe-G (Table 32) and assayed for activity by competition TR-FRET using ALEXA FLUOR® 647-labeled parent Aptamer 147 (FIG. 22 and FIG. 23). 2'OMe-G replacements were well tolerated in all positions of stem S1 (Aptamers 221-226), stem S2 (Aptamers 227-231), loop L2 (Aptamer 232), and loop L4 (Aptamer 239). In loop L3, only the G23 could be replaced with a 2'OMe-G without adversely affecting the activity (Aptamer 236). Replacement of the 2'F-G at positions 18, 19, and 20 within L3 resulted in a significant loss in activity (Aptamers 233, 234, and 235). Importantly, to a large extent, positions tolerant of 2'F-G to 2'OMe-G substitutions could be combined. For example, combining substitutions in stem S1 and S2 (Aptamers 240 and 241); stem S1, S2 and loop L2 (Aptamer 269); or stem S1, S2 and loop L2 and L4 (Aptamers 270 and 273) all yielded molecules with activity similar to that of the parent, Aptamer 147. However, not all combinations were tolerated. For example, the combination of the loop L3 substitution at position 23, which was well tolerated in isolation (Aptamer 236), but with substitutions in stem S1, S2 and loop L2 and L4 resulted in a more significant loss in activity (Aptamers 271 and 272; >2-fold).

Consistent with these findings, 2'F-G to 2'OMe-G replacements tolerated in Aptamer 147 were also well tolerated in the context of Aptamer 143, which only differs from Aptamer 147 in the identity of loop L3 (Aptamers 274, 275, and 279), although the replacement in L4 was less well tolerated (Aptamer 276). As with Aptamer 147, the addition of the loop L3 substitution at position 23 in combination with substitutions in S1, S2 and loop L2 and L4 resulted in a more significant loss of activity (Aptamers 277 and 278; >10-fold). Taken together, these data indicate that both Aptamers 147 and 143 can be replaced with 2'OMe-Gs in stems S1, S2 and loop L2, and to a lesser extent L4 without any effect on their binding.

TABLE 32

Optimization by 2'OMe sugar substitutions (Disclosed as SEQ ID NOs: 1054-1085, each with modifications) with Aptamer Family 3 variants

| Aptamer Number | Sequence (5' to 3' ) | SEQ ID NOS | Position | TR-FRET Activity |
|---|---|---|---|---|
| Aptamer 221 | C6NH2-**X**GCG-A-CGGU-AG-AU-UAUGGGCAGU-GU-G-ACCG-CGCC-idT | 1054 | S1 | ~ |
| Aptamer 222 | C6NH2-G**X**CG-A-CGGU-AG-AU-UAUGGGCAGU-GU-G-ACCG-CGCC-idT | 1055 | S1 | ~ |
| Aptamer 223 | C6NH2-GGC**X**-A-CGGU-AG-AU-UAUGGGCAGU-GU-G-ACCG-CGCC-idT | 1056 | S1 | ~ |
| Aptamer 224 | C6NH2-GGCG-A-CGGU-AG-AU-UAUGGGCAGU-GU-G-ACCG-C**X**CC-idT | 1057 | S1 | ~ |
| Aptamer 225 | C6NH2-**XX**CG-A-CGGU-AG-AU-UAUGGGCAGU-GU-G-ACCG-C**X**CC-idT | 1058 | S1 | ~ |
| Aptamer 226 | C6NH2-**XX**C**X**-A-CGGU-AG-AU-UAUGGGCAGU-GU-G-ACCG-C**X**CC-idT | 1059 | S1 | ~ |
| Aptamer 227 | C6NH2-GGCG-A-C**X**GU-AG-AU-UAUGGGCAGU-GU-G-ACCG-CGCC-idT | 1060 | S2 | ~ |
| Aptamer 228 | C6NH2-GGCG-A-CG**X**U-AG-AU-UAUGGGCAGU-GU-G-ACCG-CGCC-idT | 1061 | S2 | ~ |
| Aptamer 229 | C6NH2-GGCG-A-CGGU-AG-AU-UAUGGGCAGU-GU-G-ACC**X**-CGCC-idT | 1062 | S2 | ~ |
| Aptamer 230 | C6NH2-GGCG-A-C**XX**U-AG-AU-UAUGGGCAGU-GU-G-ACCG-CGCC-idT | 1063 | S2 | ~ |
| Aptamer 231 | C6NH2-GGCG-A-C**XX**U-AG-AU-UAUGGGCAGU-GU-G-ACC**X**-CGCC-idT | 1064 | S2 | ~ |
| Aptamer 232 | C6NH2-GGCG-A-CGGU-A**X**-AU-UAUGGGCAGU-GU-G-ACCG-CGCC-idT | 1065 | L2 | ~ |
| Aptamer 233 | C6NH2-GGCG-A-CGGU-AG-AU-UAU**X**GGCAGU-GU-G-ACCG-CGCC-idT | 1066 | L3 | -- |

TABLE 32-continued

Optimization by 2'OMe sugar substitutions (Disclosed as SEQ ID NOs: 1054-1085, each with modifications) with Aptamer Family 3 variants

| Aptamer Number | Sequence (5' to 3' ) | SEQ ID NOS | Position | TR-FRET Activity |
|---|---|---|---|---|
| Aptamer 234 | C6NH2-GGCG-A-CGGU-AG-AU-UAUG**X**GCAGU-GU-G-ACCG-CGCC-idT | 1067 | L3 | --- |
| Aptamer 235 | C6NH2-GGCG-A-CGGU-AG-AU-UAUGG**X**CAGU-GU-G-ACCG-CGCC-idT | 1068 | L3 | --- |
| Aptamer 236 | C6NH2-GGCG-A-CGGU-AG-AU-UAUGGGCA**X**U-GU-G-ACCG-CGCC-idT | 1069 | L3 | ~ |
| Aptamer 237 | C6NH2-GGCG-A-CGGU-AG-AU-UAU**XXX**CA**X**U-GU-G-ACCG-CGCC-idT | 1070 | L3 | --- |
| Aptamer 238 | C6NH2-GGCG-A-CGGU-AG-AU-UAUGGGCAGU-**X**U-G-ACCG-CGCC-idT | 1071 | S3 | --- |
| Aptamer 239 | C6NH2-GGCG-A-CGGU-AG-AU-UAUGGGCAGU-GU-**X**-ACCG-CGCC-idT | 1072 | L4 | ~ |
| Aptamer 240 | C6NH2-**XX**CG-A-C**XX**U-AG-AU-UAUGGGCAGU-GU-G-ACCG-C**X**CC-idT | 1073 | S1/S2 | ~ |
| Aptamer 241 | C6NH2-**XX**C**X**-A-C**XX**U-AG-AU-UAUGGGCAGU-GU-G-ACC**X**-C**X**CC-idT | 1074 | S1/S2 | ~ |
| Aptamer 269 | C6NH2-**XX**C**X**-A-C**XX**U-A**X**-AU-UAUGGGCAGU-GU-G-ACC**X**-C**X**CC-idT | 1075 | S1/S2/ L2 | ~ |
| Aptamer 270 | C6NH2-**XX**C**X**-A-C**XX**U-A**X**-AU-UAUGGGCAGU-GU-**X**-ACC**X**-C**X**CC-idT | 1076 | S1/S2/ L2/L4 | ~ |
| Aptamer 271 | C6NH2-**XX**C**X**-A-C**XX**U-A**X**-AU-UAUGGGCA**X**U-GU-**X**-ACC**X**-C**X**CC-idT | 1077 | S1/S2/ L2/L3/ L4 | -- |
| Aptamer 272 | C6NH2- **X**C**X**-A-C**XX**U-A**X**-AU-UAUGGGCA**X**U-GU-**X**-ACC**X**-C**X**C -idT | 1078 | S1/S2/ L2/L3/ L4 | --- |
| Aptamer 273 | C6NH2- **X**C**X**-A-C**XX**U-A**X**-AU-UAUGGGCAGU-GU-G-ACC**X**-C**X**C -idT | 1079 | S1/S2/ L2/L4 | ~ |
| Aptamer 274 | C6NH2-**XX**C**X**-A-C**XX**U-AG-AU-UUCGGGUAGU-GU-G-ACC**X**-C**X**CC-idT | 1080 | S1/S2 | ~ |
| Aptamer 275 | C6NH2-**XX**C**X**-A-C**XX**U-A**X**-AU-UUCGGGUAGU-GU-G-ACC**X**-C**X**CC-idT | 1081 | S1/S2/ L2 | ~ |
| Aptamer 276 | C6NH2-**XX**C**X**-A-C**XX**U-A**X**-AU-UUCGGGUAGU-GU-**X**-ACC**X**-C**X**CC-idT | 1082 | S1/S2/ L2/L4 | -- |
| Aptamer 277 | C6NH2-**XX**C**X**-A-C**XX**U-A**X**-AU-UUCGGGUA**X**U-GU-**X**-ACC**X**-C**X**CC-idT | 1083 | S1/S2/ L2/L3/ L4 | --- |
| Aptamer 278 | C6NH2- **X**C**X**-A-C**XX**U-A**X**-AU-UUCGGGUA**X**U-GU-**X**-ACC**X**-C**X**C -idT | 1084 | S1/S2/ L2/L3/ L4 | --- |
| Aptamer 279 | C6NH2- **X**C**X**-A-C**XX**U-A**X**-AU-UUCGGGUAGU-GU-G-ACC**X**-C**X**C -idT | 1085 | S1/S2/ L2 | ~ |

where G is 2'F-G; a bold X is 2' OMe-G; and A, C and U are 2'OMe modified RNA; $C6NH_2$ is a hexylamine linker; and idT is an inverted deoxythymidine residue. Differences from the parent (Aptamer 3) are indicated in bold. ~ = 2 fold worse to 2 fold better, ++ = 2-10 fold better , +++ = more than 10 fold better, -- = more than 2-10 fold worse; --- = more than 10 fold worse.

Example 16. Affinity of Optimized Aptamer 3 Variants for IL8

In Example 3, the apparent $K_d$ for Aptamer 3 was determined by TR-FRET with a final IL8 concentration of 10 nM. Under these assay conditions, the ability to measure the affinity accurately is limited by the input IL8 protein concentration, and the apparent $K_d$ under these protein-limiting conditions was determined to be 8 nM. To refine the estimate of the affinity of optimized versions of Aptamer 3 for IL8, TR-FRET was conducted using ALEXA FLUOR® 647-labeled Aptamers 3, 147, and 269 in low volume 384 well plates with a final concentration of IL8 of 500 pM. Under these conditions, the apparent $K_d$ for IL8 was approximately 200 pM for Aptamer 3, and approximately 100 pM for Aptamers 147 and 269 (Table 33). When the IL8 concentration in this assay was further reduced to 250 pM, the apparent $K_d$ of Aptamer 3 for IL8 remained approximately 200 pM, indicating this value was not protein limited. In contrast, the apparent $K_d$ of Aptamers 147 and 269 decreased when the IL8 concentration was reduced from 500 pM to 250 pM, indicating that the apparent Kas reported for these aptamers in Table 33 were still protein limited values. The competition TR-FRET data reported for Aptamers 147 and 269 in Table 31 and Table 32, respectively, indicate that these compounds bind to IL8 with an approximate 10-fold greater affinity than Aptamer 3. Therefore, the apparent $K_d$ of Aptamers 147 and 269 for IL8 was estimated to be approximately 20 pM.

TABLE 33

Apparent $K_d$ values of anti-IL8 aptamers by TR-FRET

| Aptamer Number | $K_d$ (pM) |
|---|---|
| Aptamer 3 | 214 ± 15 |
| Aptamer 147 | 110 ± 2 |
| Aptamer 269 | 126 ± 2 |

Example 17. Inhibition of Interaction of IL8 with its Receptor CXCR1

Figure 24:
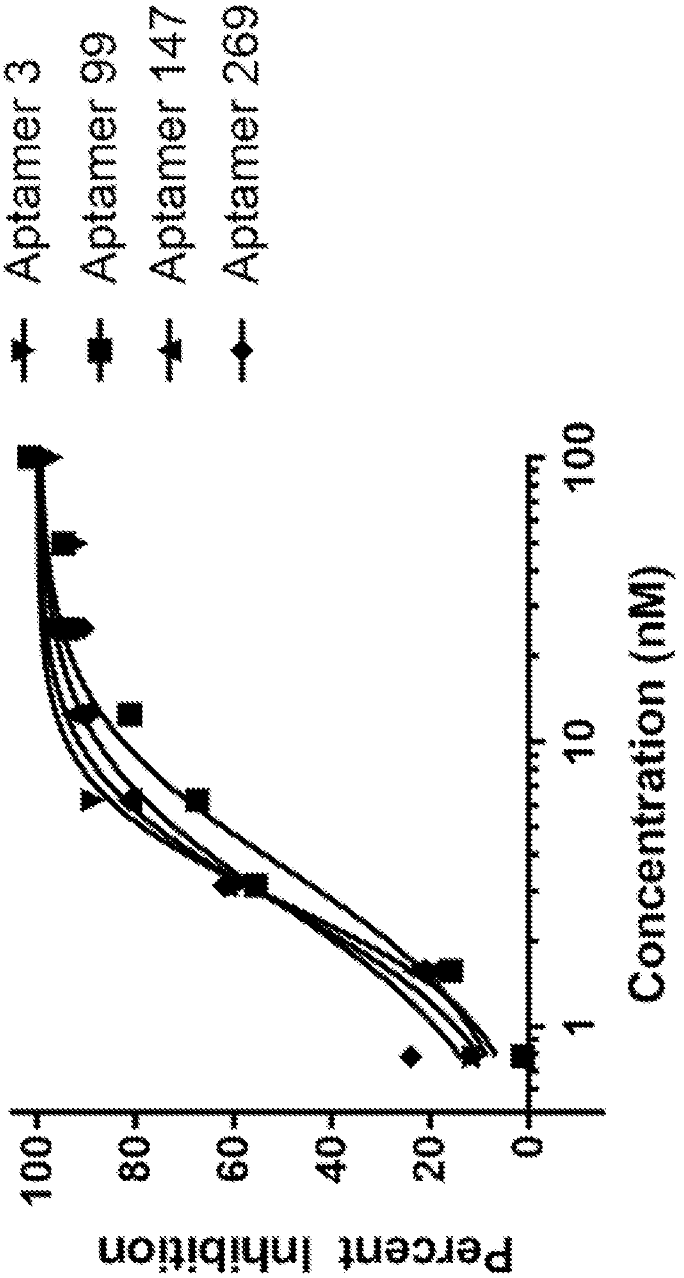
FIG. 24 depicts a non-limiting example of data demonstrating the ability of various aptamers of the disclosure to inhibit IL8 binding to cells expressing the IL8 receptor CXCR1 according to embodiments of the disclosure.

CXCR1 overexpressing cells were used to confirm that aptamers could block IL8 binding to its cognate receptor, CXCR1, in a functional setting. Briefly, CXCR1-overexpressing cells were plated in a 96 well plate and seeded overnight. Serially diluted aptamers and 5 nM IL8 were mixed in cell culture media and applied to cells for 2 hours at 37° C. Media was aspirated, and cells were washed 3× with PBS for 5 minutes. Cells were lysed in Ultra HiBlock Buffer (Perkin Elmer) with gentle agitation. IL8 levels were determined using Ultra TR-FRET (Perkin Elmer). Representative data are shown in FIG. 24 and Table 34. In all cases, the reported potencies were limited by the protein concentration (5 nM) used in the assay.

TABLE 34

$IC_{50}$ values of anti-IL8 aptamers for inhibition of IL8 binding to CXCR1

| Aptamer Number | $IC_{50}$ (nM) |
|---|---|
| Aptamer 3 | 3 |
| Aptamer 99 | 4 |
| Aptamer 147 | 3 |
| Aptamer 269 | 3 |

Figure 25A:
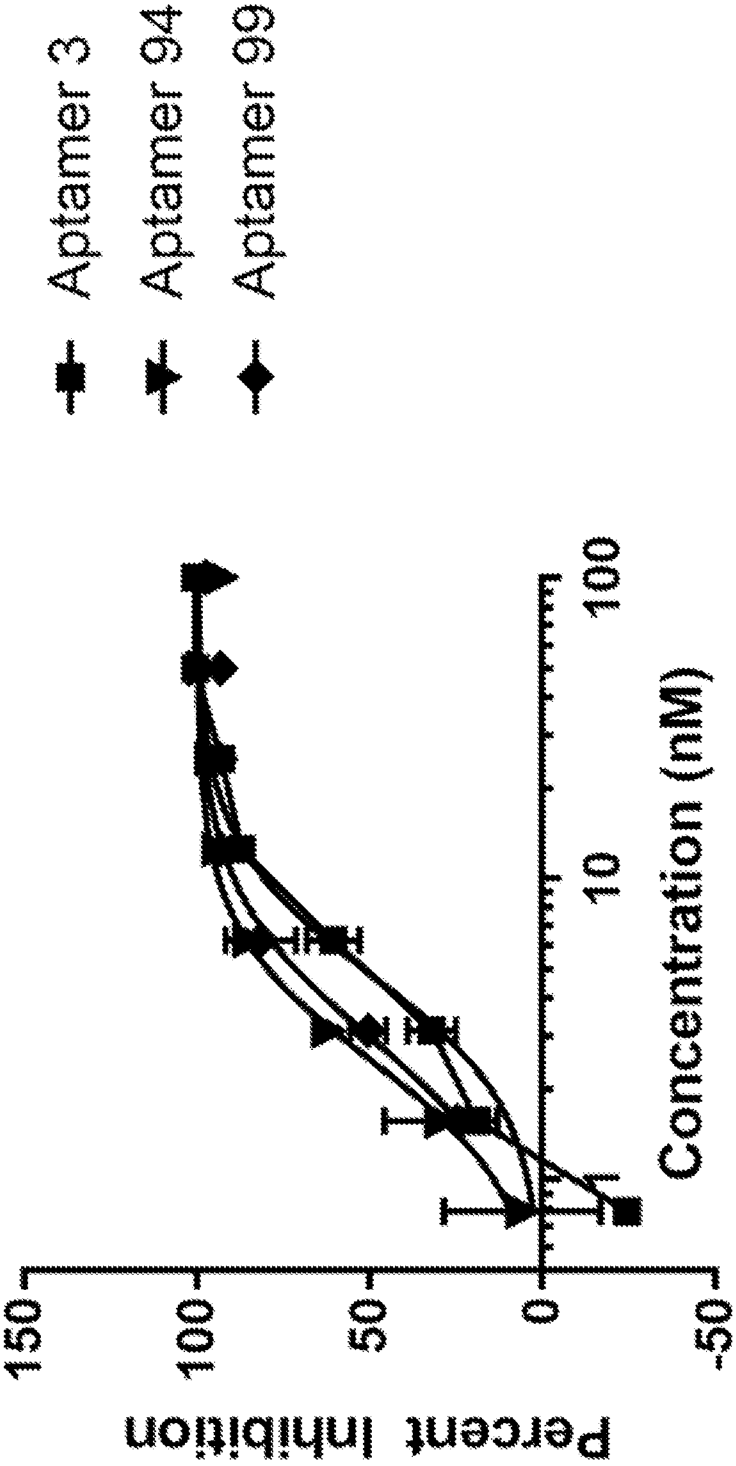
FIG. 25A, FIG. 25B, and FIG. 25C depict non-limiting examples of data demonstrating the ability of various aptamers of the disclosure to inhibit IL8-induced neutrophil migration according to embodiments of the disclosure.
Figure 25B:
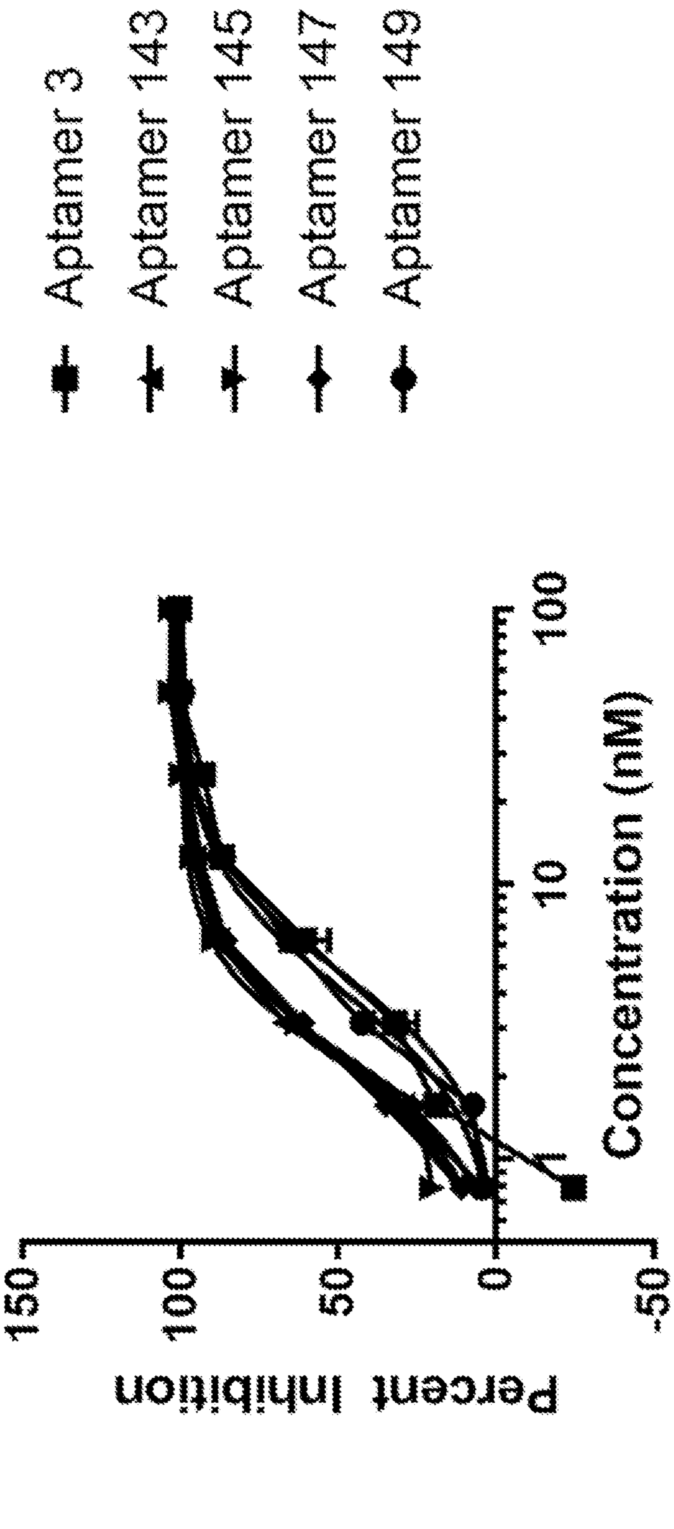
Figure 25C:
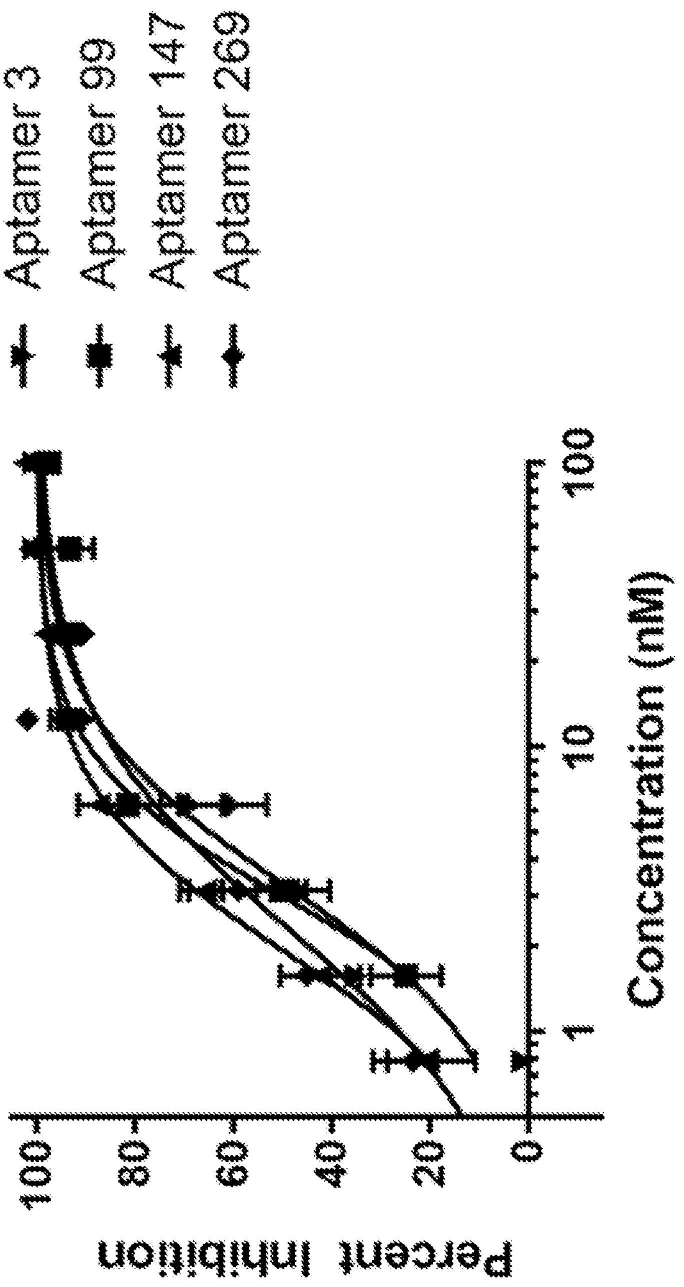

Example 18. Inhibition of IL8 Induced Neutrophil Migration Using Optimized Aptamer 3 Variants The neutrophil migration assay described in Example 6 was used to further characterize optimized variants of Aptamer 3. Serial dilutions of Aptamers 3, 94, 99, 143, 147, and 269 were tested for their ability to inhibit IL8-induced neutrophil migration. Representative data and $IC_{50}$ values are shown in FIG. 25A, FIG. 25B, and FIG. 25C, and Table 35 and demonstrate the ability of each aptamer to inhibit neutrophil migration with high potency. In all cases, the reported potencies were limited by the protein concentration (3 nM) used in the assay.

TABLE 35

$IC_{50}$ values of anti-IL8 aptamers for inhibition of neutrophil migration

| Aptamer Number | $IC_{50}$ (nM) |
|---|---|
| Aptamer 3 | 3 |
| Aptamer 94 | 3 |
| Aptamer 99 | 3 |
| Aptamer 143 | 2 |
| Aptamer 145 | 2 |
| Aptamer 147 | 2 |
| Aptamer 149 | 3 |
| Aptamer 269 | 3 |

Figure 26A:
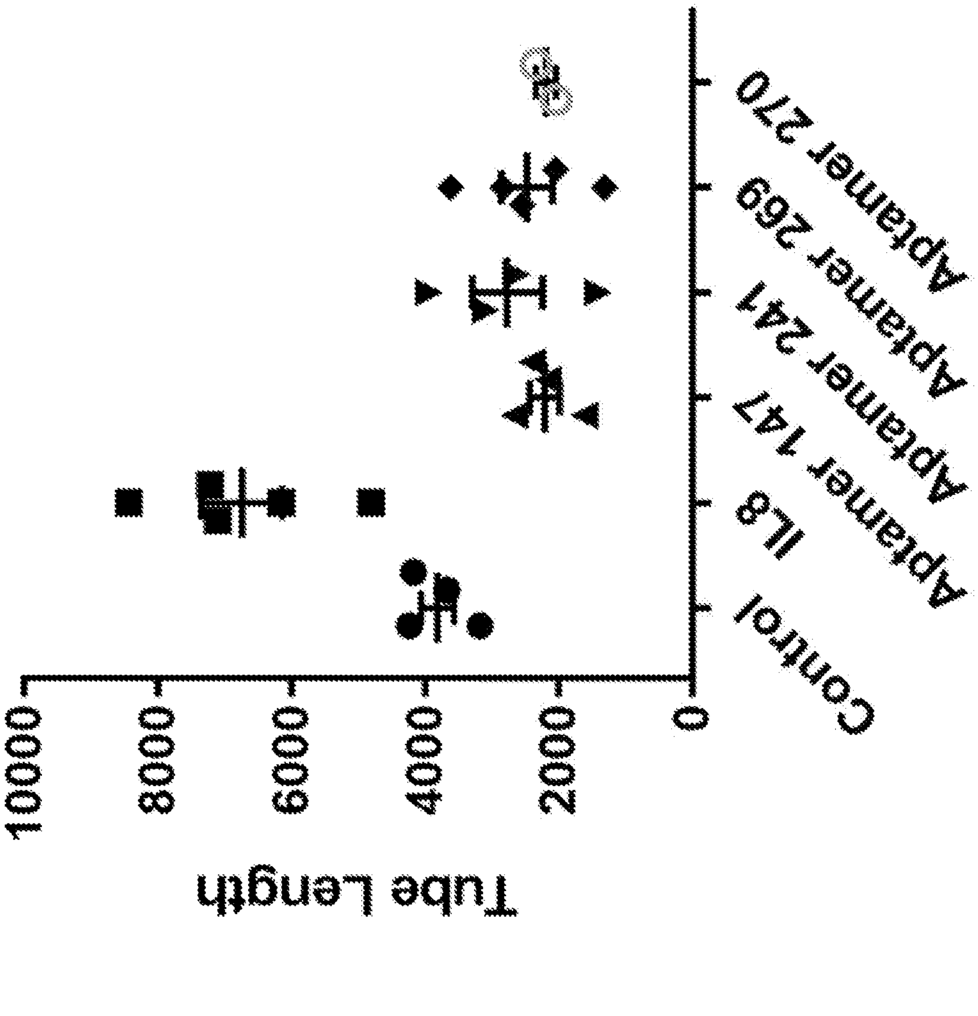
FIG. 26A and FIG. 26B depict non-limiting examples of data demonstrating the ability of various aptamers of the disclosure to inhibit IL8-induced tube formation by human microvascular endothelial cells according to embodiments of the disclosure.
Figure 26B:
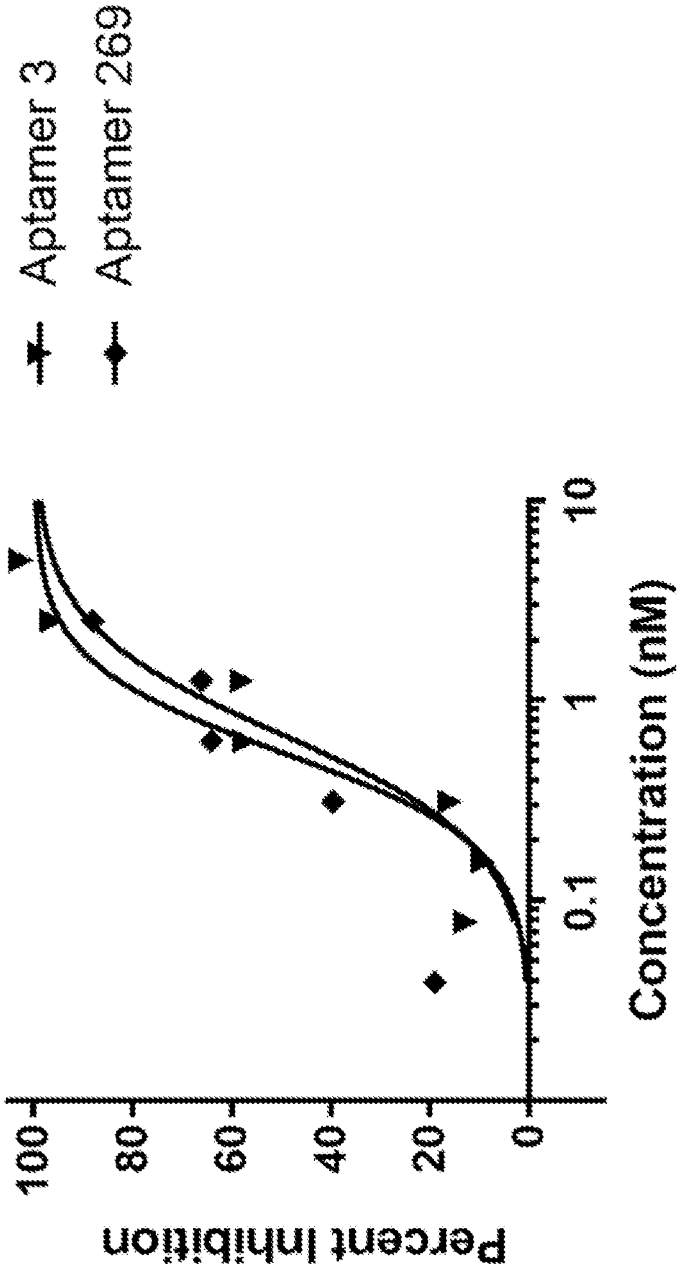

Example 19. Inhibition of IL8 Induced Tube Formation Using Optimized Aptamer 3 Variants IL8 is known to be pro-angiogenic, and some pathologies related to IL8 in retinal diseases may arise from its pro-angiogenic activity. Therefore, the ability of Aptamer 3 and optimized variants were tested for their ability to inhibit tube formation of endothelial cells induced by IL8, as tube formation is a commonly used assay to determine the angiogenic potential of a protein. Human microvascular endothelial cells (HMEC) were chosen for these studies due to high expression of the IL8 receptor CXCR1 (FASEB J. 2000 October; 14 (13): 2055-64). Briefly, HMEC cells were plated on 96 well plates coated with Matrigel Basement Matrix (Corning) in the presence of 1 nM IL8 and diluted Aptamers 3, 147, 241, 269, and 270. Tube formation was imaged at 24 hours and analyzed using Wimasis software. Total length was measured. At 10 nM, all aptamers effectively blocked IL8-induced tube formation (FIG. 26A). Aptamer 3 and Aptamer 269 had a protein limited $IC_{50}$ of 600 pM in a dose response tube formation (FIG. 26B).

Example 20. Aptamer 3 Family Aptamers Tolerate PEG Conjugation

Figure 27A:
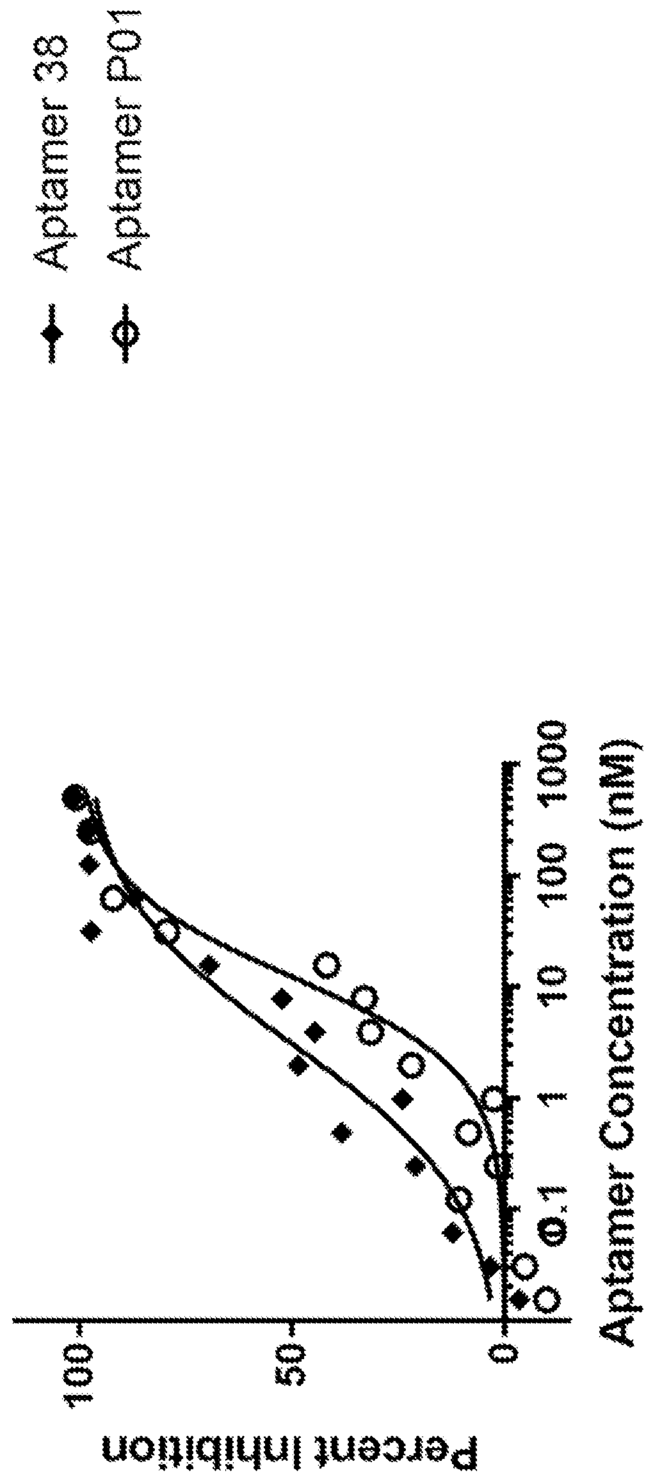
FIG. 27A, FIG. 27B, and FIG. 27C depict competitive TR-FRET data demonstrating the relative affinity of pegylated anti-IL8 aptamers for IL8 as compared to non-pegylated parent aptamers. Data is presented as percent inhibition of binding of a labeled anti-IL8 aptamer to IL8 according to embodiments of the disclosure.
Figure 27B:
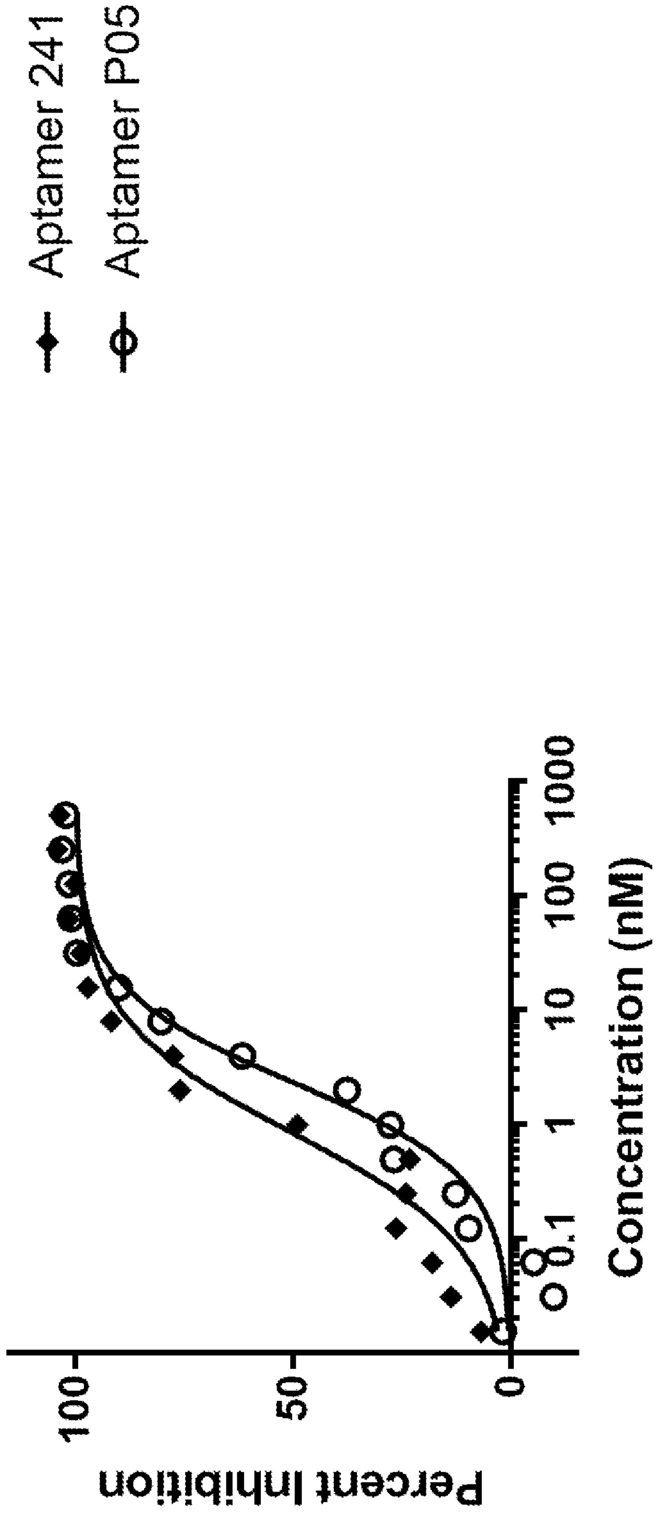
Figure 27C:
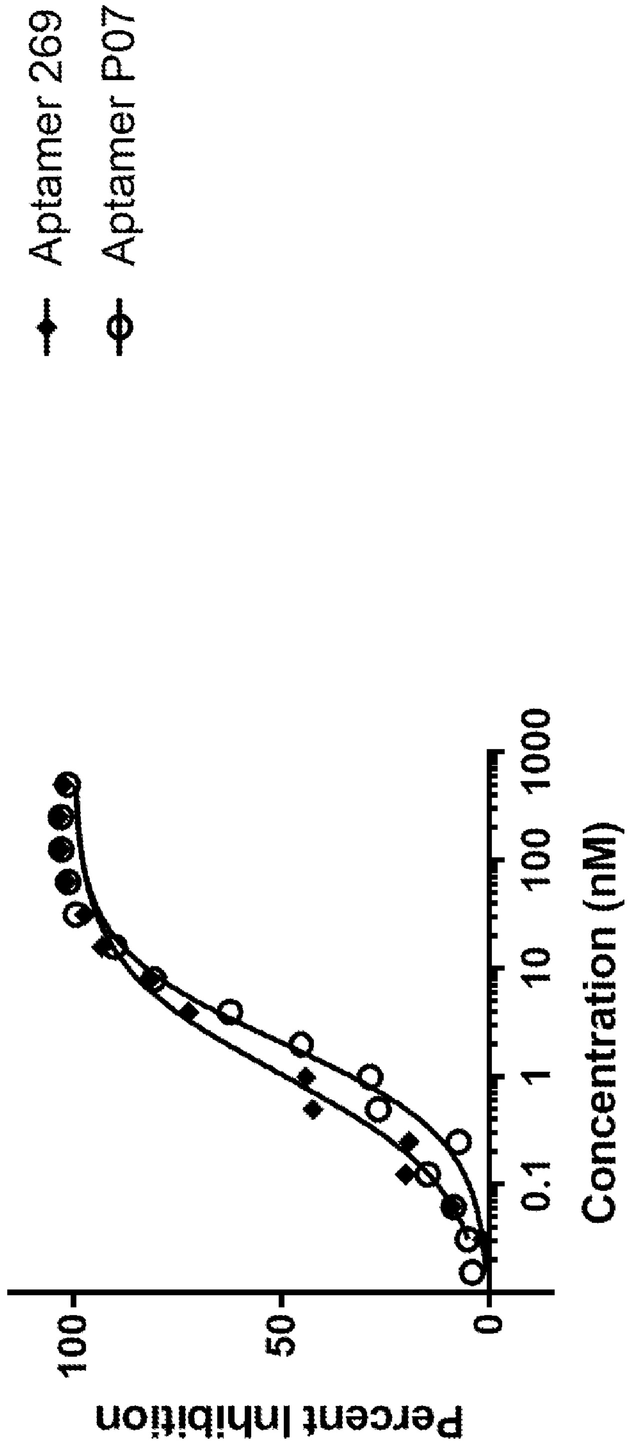

Conjugation of high molecular weight polyethylene glycol (PEG) to nuclease-stabilized aptamers improves their half-life in the vitreous following intravitreal (IVT) administration. Therefore, to assess the impact of PEGylation on the activity of Aptamer 38 (Table 24) and optimized variants, Aptamers 241 and 269, a 40 kDa PEG was conjugated to the 5' terminus of each aptamer. Briefly, a concentrated feed solution consisting of aptamer in DMSO, 16 to 25 mM borate and water was combined with a solution consisting of several equivalents 2,3-Bis(methylpolyoxyethylene-oxy)-1-{3-[(1,5-dioxo-5-succinimidyloxy, pentyl)amino]propyloxy} propane (e.g., SUNBRIGHT® GL2-400GS2) in acetonitrile, and incubated at approximately 35° C. for approximately 1 hour with mixing to effect conjugation of the PEG to the amine moiety of the hexyl amine linker present on the 5' terminus of the aptamer. Following the pegylation reaction, each PEG-aptamer was purified by anion exchange chromatography to collect the pegylated aptamer and remove unreacted PEG and unreacted aptamer. Anion exchange purified PEG-aptamers were desalted by ultrafiltration into water prior to functional characterization. The pegylated versions of Aptamers 3, 241, and 269 were termed Aptamers P01, P05, and P07, respectively. Activity of each pegylated aptamer was tested using the competition TR-FRET assay in which the ALEXA FLUOR® 647-labeled Aptamer 3 was competed with increasing concentrations of PEGylated aptamer variants for binding to IL8 (FIG. 27A, FIG. 27B, and FIG. 27C). The addition of PEG had a modest to no effect on the affinity of the aptamers for IL8, with the calculated Kas for each PEG-aptamer within experimental error of their parent compounds.

Example 21. In Vivo Characterization of PEG-Aptamer P01

Figure 28:
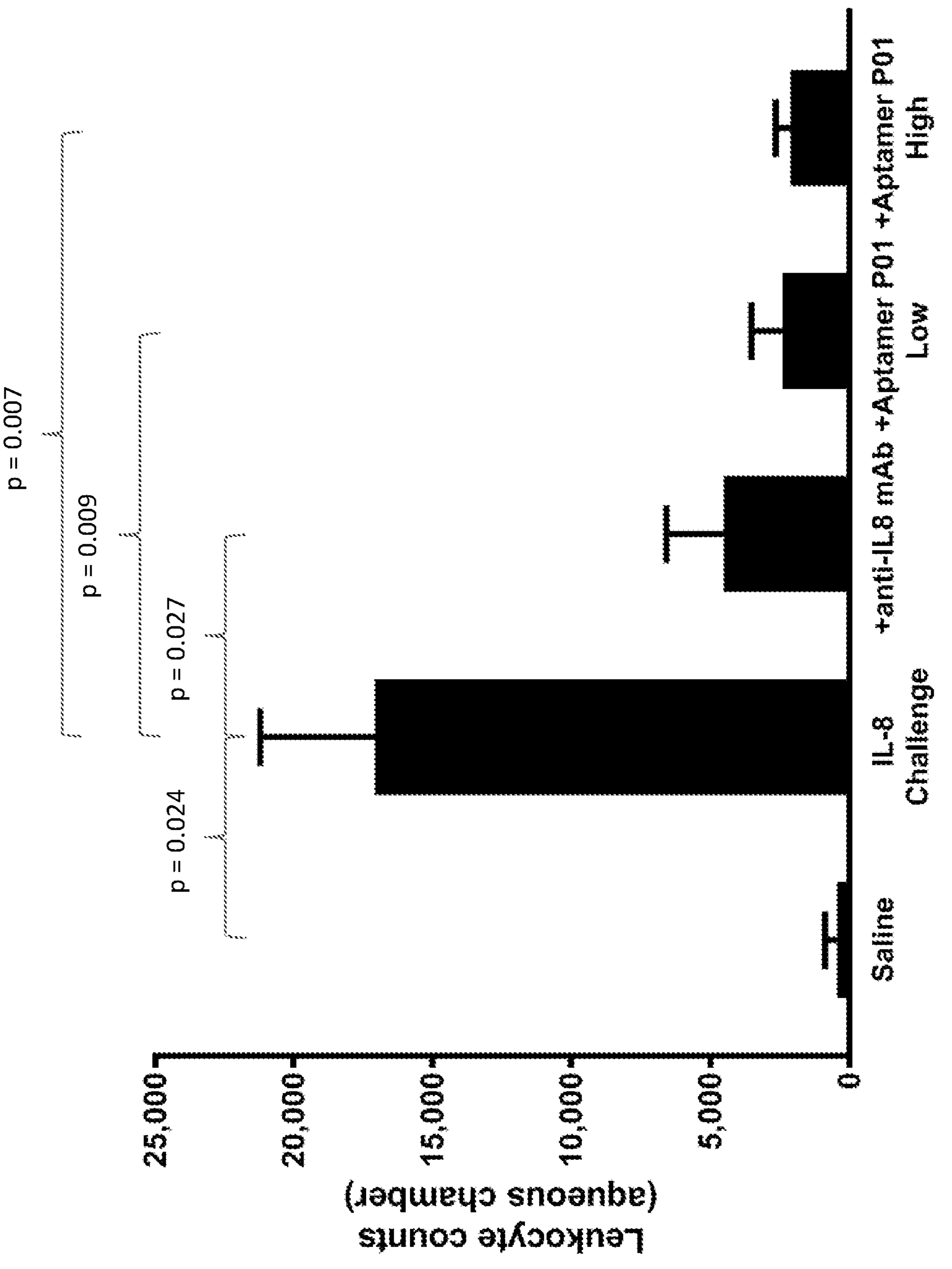
FIG. 28 depicts a non-limiting example demonstrating the ability of Aptamer P01 of the disclosure to inhibit IL8-induced leukocyte migration into the aqueous chamber of rabbit eyes following intravitreal administration to rabbits according to embodiments of the disclosure.

The ability of Aptamer P01 to inhibit the activity of IL8 in vivo was assessed in a rabbit IL8 challenge model. In this acute model of inflammation, IVT administration of IL8 results in migration of leukocytes into the aqueous chamber with a peak infiltration by 24 hours following IL8 administration (Akduman, L, Kaplan HJ, Ataoglu, O, or, M Bilgihan, A, and Hasanreisoglu, B. Comparison of uveitis induced by interleukin-8 (IL-8) and endotoxin in rabbits (1994). Ocular Immunology and Inflammation 2:223-229Add Citation). Briefly, twenty-three New Zealand White rabbits were assigned to 1 of 5 groups: basic saline solution control (n=3); 100 ng/eye IL8 only (n=5); 100 ng/eye IL8 plus 0.25 mg/eye neutralizing anti-IL8 mAb (n=5); 100 ng/eye IL8 plus 0.3 mg/eye Aptamer P01 (n=5); or 100 ng/eye IL8 plus 0.1 mg/eye Aptamer P01 (n=5). Test article or control saline solution was administered at least 30 minutes prior to administration of IL8, with one eye treated per animal. As shown in FIG. 28, administration of IL8 led to a significant increase in leukocyte counts in the aqueous chamber at 24 hours, with cell counts of approximately 17,000 cells per 50 μL of aqueous fluid in the IL8-only treated group as compared to approximately 400 cells per 50 μL of aqueous fluid in the saline control group. Administration of IL8 inhibitors significantly reduced leukocyte infiltration induced by IL8 at 24 hours, with cell counts of approximately 4,500 cells per 50 μL of aqueous fluid in the anti-IL8 mAb group and approximately 2,000 cells per 50 μL of aqueous fluid in the Aptamer P01 treated groups. Therefore, administration of Aptamer Family 3-derived anti-IL8 aptamer P01 inhibited the activity of IL8 in vivo following IVT administration.

Example 22. Characterization of Pharmacokinetic Properties Following IVT Administration Aptamer P01 was selected as a representative pegylated form of the Aptamer Family 3 anti-IL8 aptamers to characterize the duration of action of this class of aptamer following intravitreal administration to rabbits. Seven New Zealand White rabbits, one rabbit providing 2 eyes per timepoint, were treated with 0.3 mg/eye of aptamer P01 administered by IVT injection. Vitreous and plasma samples were taken at 1, 8, 24, 96, 168, 240, and 336 hours post-Aptamer P01 administration with individual samples being obtained from the left and right eye at each timepoint. The concentration of Aptamer P01 was measured in the vitreous over time following administration using a dual hybridization ELISA assay.

The vitreous concentration-time profile of Aptamer POI was multi-phasic. Vitreous Aptamer POI was distributed following a single IVT injection. A maximum Aptamer POI concentration of approximately 270 μg/mL, or approximately 24 μM based on aptamer molecular weight, was observed within I hour of dosing (first sampling time point) and declined over time. At day 14, the vitreous Aptamer POI concentration was approximately ug/mL, or approximately 2 μM based on aptamer molecular weight. Vitreous PK parameters as determined by non-compartmental analysis are provided in Table 36. The estimated vitreous half-life of Aptamer POI was approximately 111 hours, or 4.6 days. By comparison the pegylated aptamer MACUGEN® (pegaptanib sodium injection), which has been well-studied following IVT administration in animals and humans, has a vitreous half-life in rabbits of approximately 80 hours, or 3.3 days, and a vitreous half-life in humans of approximately 10 days MACUGEN®, Drugs at FDA; www.accessdata.fda-.gov/drugsatfda_docs/label/2011/021756s0181bl.pdf). The substantially longer half-life of Aptamer POI, as compared to MACUGEN®, is likely due to the enhanced metabolic stability of the aptamer moiety of Aptamer POI as compared to the aptamer moiety of MACUGEN®.

Based on the comparison of the respective vitreous half-life in rabbits of Aptamer P01 versus Macugen®, in combination with the vitreous half-life of Macugen® in humans, the estimated vitreous half-life of Aptamer P01 in humans following IVT administration would be anticipated to be greater than 10 to about 15 days. In retinal disease states, the concentration of IL8 has been documented to be up to approximately 200 pM. Given the high potency of the optimized variants of Aptamer 3, a vitreous aptamer concentration of approximately 0.4 nM to 4 nM would be sufficient to provide complete to near complete (approximately 90%) occupancy or inhibition of IL8 present in the vitreous or retina in a retinal disease state. With a vitreous half-life of 10 to about 15 days, IVT administration of 1 mg (based on aptamer weight) of Aptamer P01, or a PEGylated optimized variant of Aptamer 3 such as Aptamer P05 or P07, would provide near complete or complete suppression of IL8 activity for approximately 20 to 25 weeks, or 4-6 months (FIG. 29). With these same assumptions, IVT administration of 5 mg (based on aptamer weight) of Aptamer P01, or a PEGylated optimized variant of Aptamer 3 such as Aptamer P05 or P07, would provide near complete or complete suppression of IL8 activity for approximately 26 to 38 weeks, or 6-10 months (FIG. 29).

TABLE 36

Estimated vitreous PK parameters following IVT administration for Aptamer P01

| PK Parameter Estimates | Unit | Value |
|---|---|---|
| $T_{1/2}$ | hr | 110.8 |
| $T_{max}$ | hr | 1 |
| $C_{max}$ | μg/mL | 266.2 |
| $T_{last}$ | hr | 336 |
| $C_{last}$ | μg/mL | 19.3 |
| $MRT_{0\text{-}last}$ | hr | 102.6 |

Example 23. Sequence Analysis and Structure Determination of Aptamer 8

Figure 30B:
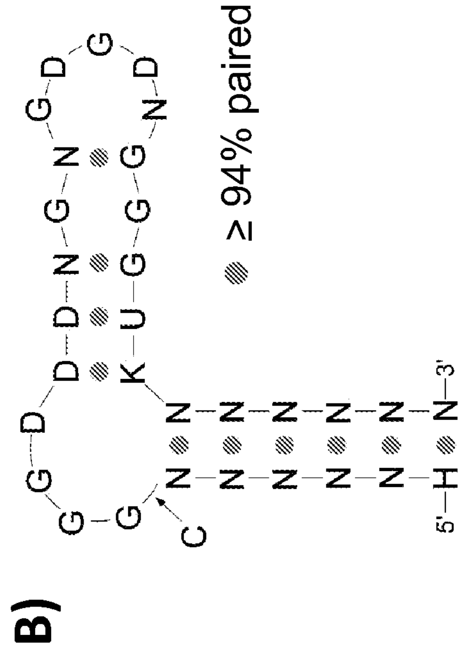

Sequence analysis of Aptamer 8 (Table 8) suggested that this aptamer adopts a stem-loop secondary structure with highly conserved loop regions (FIG. 30A, FIG. 30B). The common stem-loop structure adopted by Aptamer 8, which will be referred to hereafter as the Aptamer Family 8 structure or Family 8 structure, may be comprised of (in a 5' to 3' direction), a first stem (S1), a first loop (L1), a second stem (S2), and a second loop (L2). As demonstrated in FIG. 30A and FIG. 30B, the first loop (L1) may be connected to the 3' terminal end of the first stem (S1) and the 5' terminal end of the second stem (S2). The second stem (S2) may be connected to the 3' terminal end of the first loop (L1) and the 5' terminal end of the second loop (L2). The second loop (L2) may be connected to the 3' terminal end of the second stem (S2) and the 5' terminal end of the complementary region of the second stem (S2). The 5' terminal end of the complementary region of the second stem (S2) may be connected to the 3' terminal end of the second loop (L2) and the 3' end of the complementary region of the second stem (S2) may be connected to the 5' end of the complementary region of the first stem (S1).

The sequence, GGGAAAUGUGAGAUGGGUU (SEQ ID NO: 1093), located within Aptamer 8 was used to identify molecules within the top 1000 stacks from the primary selection related to Aptamer 8. To broaden the search window, as many as 5 mutations were allowed to occur within the last 15 nucleotides of the sequence; the initial GGGA was kept invariant. The analysis revealed 57 sequences related to Aptamer 8 and demonstrated that these molecules conformed to the proposed stem-loop structure (Table 37 and FIG. 30A). The relationship between Aptamer 8 and other members of the family further supported a common stem-loop structure comprised of a first stem (S1), a first loop (L1), a second stem (S2), and a second loop (L2).

TABLE 37

Members of the Aptamer 8 family identified during primary selection against IL8 (SEQ ID NOS: 1094-1151)

| | S1 L1 S2 L2 S2 S1 |
|---|---|
| Aptamer 8: | UACGGU--GGGA--AAUGU--GAGAU--GGGUU--GCCGUA--UUUU-- |
| r6-34: | UA-AUCGCU--GGGA--AAUGG--GAGAU--GGGUU--GGCGAU--UAU--- |
| r6-35: | U-GGGCAU--GGGA--AAUGU--GAGAU--GGGUU--GUGCUC--AAGU-- |
| r6-39: | UGAUA-GCAAGU--GGGA--AAUGU--GAGAU--GGGUU--ACUUGU-------- |
| r6-50: | UAGUCA-CGGGA--AAAGU--GAGAU--GGGUG--UGACG---UGUUU-- |
| r6-98: | UAAUC-ACCGGU--GGGA--AAUGU--GAGAA--GGGUG--GCCGGU-------- |
| r6-103: | UACGGU--GGGA--AAUGU--GAGAU--GGGUU--GCCGTA--TTTTT |
| r6-170: | UUG-UGCCAU--GGGA--AAUGU--GAGAU--GGGUU--AUGUCA--CU---- |
| r6-183: | UGAC-CGGGA--AAUGU--GAGAU--GGGUG--GUCA---- GCAUAAAU |
| r6-209: | UAAUU-AGCUGC--GGGA--AAUGG--GAGAU--GGGUU--GCGGCU-------- |
| r6-311: | UACGGU--GGGA--UAUGU--GAGAU--GGGUU--GCCGUA--UUUU-- |
| r6-313: | U---AACAUA-CGGGA--AACGU--GAGAA--GGGUG--UAUGUU--AUU |
| r6-317: | U---_ACGGU--GGGA--AAUGU--GAGAU--GGGUU--GCCGU_--UUUUU |
| r6-320: | UUUGAG---AGCAG-CGGGA--AAUGU--GAGAU--GGGUG--UUGCU_------ |
| r6-345: | UACGGU--GGGA--AAUGU--GAGAU--GGGUU--GCCGUA--UUUC |
| r6-399: | UACGGU--GGGA--AAUGC--GAGAU--GGGUU--GCCGUA--UUUU |
| r6-439: | UACGGC--GGGA--AAUGU--GAGAU--GGGUU--GCCGUA--UUUU |
| r6-471: | U--UGGCCU--GGGA--AAUGU--GAGAA--GGGUU--AGGCUA--UUAU |
| r6-483: | UACGGU--GGGA--AAUGU--GAGAU--GGGUU--GCCGUA--UUCU |
| r6-502: | UCGUUU-CGGGA--AAUGU--GAGAU--GGGUG--AAGCGA--UAAU |
| r6-503: | UACGGU--GGGA--AAUGU--GAGGU--GGGUU--GCCGUA--UUUU |
| r6-505: | UACGGU--GGGA--AACGU--GAGAU--GGGUU--GCCGUA--UUUU |
| r6-530: | UCU--UUGGGU--GGGA--AAUGU--GAGAC--GGGUU--GCCCAA--AU-- |
| r6-539: | UUCGGU--GGGA--AAUGU--GAGAU--GGGUU--GCCGUA--UUUU |
| r6-541: | UACGGU--GGGA--AAUGU--GGGAU--GGGUU--GCCGUA--UUUU |
| r6-558: | UACGGU--GGGA--AUUGU--GAGAU--GGGUU--GCCGUA--UUUU |
| r6-562: | UACGGU--GGGA--AAUGU--GUGAU--GGGUU--GCCGUA--UUUU |
| r6-571: | UGCGGU--GGGA--AAUGU--GAGAU--GGGUU--GCCGUA--UUUU |

TABLE 37-continued

Members of the Aptamer 8 family identified during primary selection against IL8 (SEQ ID NOS: 1094-1151)

| | S1 L1 S2 L2 S2 S1 |
|---|---|
| r6-576: | UACGGU--GGGA--AAUGU--GAGAU--GGGUU--GCCGUA--UUUUUU |
| r6-579: | UACGGU--GGGA--AAUGU--GAGAU--GGGUU--GCCGUA--UUUG |
| r6-601: | UACGGU--GGGA--AAGGU--GAGAU--GGGUU--GCCGUA--UUUU |
| r6-602: | UACGGU--GGGA--AAUGG--GAGAU--GGGUU--GCCGUA--UUUU |
| r6-636: | UACGGU--GGGA--AAUGU--GAGAU--GGGUU--GCCGUA--UUAU |
| r6-640: | UACGGG--GGGA--AAUGU--GAGAU--GGGUU--GCCGUA--UUUU |
| r6-646: | U--UCCAGC--GGGA--AAUGU--GAGAU--GGGUU--GCUGGG--UCUA |
| r6-654: | U--GAGCAU--GGGA--AAUGU--GAGAU--GGGUU--GUGCUC--AAGU |
| r6-661: | UAUGGU--GGGA--AAUGU--GAGAU--GGGUU--GCCGUA--UUUU |
| r6-666: | UACGGU--GGGA--AAUGU--GAGAU--GGGUU--GCCGUA--UCUU |
| r6-682: | UACGGU--GGGA--AAUGU--GAGAU--GGGUU--GCCGUA--UUGU |
| r6-695: | UACGGU--GGGA--AAUGU--GAGAU--GGGUU--GCCGUA--CUUU |
| r6-703: | UACGGU--GGGA--AAUGU--GAGUU--GGGUU--GCCGUA--UUUU |
| r6-706: | UACGAU--GGGA--AAUGU--GAGAU--GGGUU--GCCGUA--UUUU |
| r6-707: | UUUC--GUUCGG-CGGGA--AAAGU--GAGAU--GGGUG--CCGAUU |
| r6-710: | UACGGU--GGGG--AAUGU--GAGAU--GGGUU--GCCGUA--UUUU |
| r6-749: | UACGGU--GGGA--AGUGU--GAGAU--GGGUU--GCCGUA--UUUU |
| r6-788: | UACGGU--GGGU--AAUGU--GAGAU--GGGUU--GCCGUA--UUUU |
| r6-793: | UACAGU--GGGA--AAUGU--GAGAU--GGGUU--GCCGUA--UUUU |
| r6-803: | UGCCC--GGGA--AAUGU--GAGAU--GGGUU--GGGCAA--AUCAUU |
| r6-815: | UACGGU--GGGA--AAUGU--GAGAU--GGGUU--GCCGUG--UUUU |
| r6-825: | UACGGU--GGGA--AAUGU--GAGAG--GGGUU--GCCGUA--UUUU |
| r6-866: | UACGGU--GGGA--GAUGU--GAGAU--GGGUU--GCCGUA--UUUU |
| r6-877: | U--GGGCAU--GGGA--AAUGU--GAGAU--GGGUU--GUGCUC--AUGU |
| r6-907: | UACGGU--GGGA--AAUGU--GAGAC--GGGUU--GCCGUA--UUUU |
| r6-929: | UUUCU--_UCAAG-CGGGA--AAUGA--GAGAU--GGGUG--CUUGAU |
| r6-943: | UACGGU--GGGA--AAUGU--GAGAU--GGGUG--GCCGUA--UUUU |
| r6-957: | UACGGU--GGGA--AAUGU--GAGAU--GGGUU--GCCGCA--UUUU |
| r6-982: | UACGGU--GGGA--AAAGU--GAGAU--GGGUU--GCCGUA--UUUU |
| r6-986: | UACGGU--GGGA--AAUGU--GAGAU--GGGUU--GCCAUA--UUUU |

Unpaired regions within stems are underlined. Deletions are indicated by (_). Single mismatches within a stem are underline and in italics. A double or single dash (-/--) serve to separate individual structural motifs.

All unique variations identified in S1 from the alignment of the 58 members of the Aptamer 8 family identified in the primary selection are listed in Table 38 and demonstrate that S1 can be formed using 30 alternative sequence pairing configurations. They also demonstrate that S1 contains a significant degree of covariation, is not highly conserved in sequence identity and can contain at least one mismatch or a single nucleotide budge. In some instances, the mismatch may occur at the terminal base pair between positions 6 and 26 (numbering per FIG. 31). The length of S1 may vary from 4 to 6 base pairs. When S1 is 6 base pairs long, the consensus sequence may be 5'-HNNNNN-3' for the 5' side of the stem, and 5'-NNNNNN-3' for the 3' complementary side of the stem, where His A, C, or U; and N is A, C, U, or G. The 6 base pair consensus is shown in the context of the predicted secondary structure in FIG. 30B. When S1 is 5 base pairs long, the consensus sequence may be 5'-WSVVB-3' for the 5' side of the stem, and 5'-BBBSW-3' for the 3' complementary side of the stem, where W is A or U; S is C or G; V is A, C, or G; and B is C, G, or U. When S1 is 4 base pairs long, the sequence of the 5' side of the stem may be 5'-UGAC-3', and 5'-GUCA-3' for the 3' complementary side of the stem. As summarized in FIG. 30B for a 6 base pair long S1, these additional sequences provide further support of the formation of S1, as indicated by the sequence covariation and the conservation of base pairing.

TABLE 38

Sequence pairing configurations for Stem 1 of Aptamer Family 8

| | |
|---|---|
| Aptamer 8 | UACGGU/GCCGUA |
| r6-34: | AUCGCU/GGCGAU |
| r6-35: | GGGCAU/GUGCUC |
| r6-39: | GCAAGU/ACUUGU |
| r6-50: | UAGUCA/UGACG |
| r6-98: | ACCGGU/GCCGGU |
| r6-170: | UGCCAU/AUGUCA |
| r6-183: | UGACC/GUCA |
| r6-209: | AGCUGC/GCGGCU |
| r6-313: | AACAUA/UAUGUU |
| r6-317: | ACGGU/GCCGU |
| r6-320: | AGCAG/UUGCU |
| r6-439: | UACGGC/GCCGUA |
| r6-471: | UGGCCU/AGGCUA |
| r6-502: | UCGUUU/AAGCGA |
| r6-530: | UUGGGU/GCCCAA |
| r6-539: | UUCGGU/GCCGUA |
| r6-571: | UGCGGU/GCCGUA |
| r6-640: | UACGGG/GCCGUA |
| r6-646: | UCCAGC/GCUGGG |
| r6-654: | GAGCAU/GUGCUC |
| r6-661: | UAUGGU/GCCGUA |
| r6-706: | UACGAU/GCCGUA |
| r6-707: | GUUCGG/CCGAUU |
| r6-793: | UACAGU/GCCGUA |
| r6-803: | UGCCC/GGGCA |
| r6-815: | UACGGU/GCCGUG |
| r6-929: | UCAAG/CUUGA |
| r6-957: | UACGGU/GCCGCA |
| r6-986: | UACGGU/GCCAUA |

Covariations and differences from the parent S1 sequence of Aptamer 8 are denoted by bold letter; mispairings are denoted by underline.

All unique variations identified in L1 from the alignment of the 58 members of the Aptamer 8 family identified in the primary selection are listed in Table 39 and demonstrate that L1 can be formed using 4 alternative sequence configurations. Loop L1 was highly conserved across the 58 members of the Family 8 sequence and varied between 4 and 5 nucleotides in length. When loop L1 is 4 nucleotides in length, the sequence of loop L1 may be 5'-GGGD-3', where D is A, G, or U. In a preferred embodiment, the sequence of loop L1 may be 5'-GGGA-3'. When loop L1 is 5 nucleotides in length, the sequence of L1 may be 5'-CGGGA-3'. The consensus sequence when L1 is 4 nucleotides long is shown in the context of the predicted secondary structure in FIG. 30B.

TABLE 39

Sequence configurations for Loop 1 of Aptamer Family 8.

| | |
|---|---|
| Aptamer 8 | GGGA |
| r6-50 | CGGGA |
| r6-707 | GGGG |
| r6-788 | GGGU |

Differences from the parent L1 sequence of Aptamer 8 are denoted by bold letter.

All unique variations identified in stem S2 from the alignment of the 58 members of the Aptamer 8 family identified in the primary selection are listed in Table 40 and demonstrated that S2 can be formed using 14 alternative sequence pairing configurations. Together, they demonstrated that S2 contained a highly conserved G:G mismatch at positions 14 and 22 (numbering per FIG. 31). In some instances, an additional mismatch occurred at the terminal base pair between positions 15 and 21. The consensus sequence of S2 may be 5'-DDNGN-3' for the 5' side of the stem, and 5'-GGGUK-3' for the 3' side of the stem, where D is A, U, or G; N is A, U, G, or C; K is G or U; and the conserved G:G mismatch is underlined. In a preferred embodiment, the sequence of S2 may be 5'-AAUGU-3' for the 5' side of the stem, and 5'-GGGUU-3' for the 3' side of the stem, where the conserved G:G mismatch is underlined. As summarized in FIG. 30B, these additional sequences provide further support of the formation of S2, as indicated by the sequence covariation and the conservation of base pairing.

TABLE 40

Sequence pairing configurations for Stem 2 of Aptamer Family 8

| | | | |
|---|---|---|---|
| Aptamer 8: | AAUGU/GGGUU | r6-313: | AACGU/GGGUG |
| r6-98: | AAUGU/GGGUG | r6-929: | AAUGA/GGGUG |
| r6-34: | AAUGG/GGGUU | r6-749: | AGUGU/GGGUU |
| r6-50: | AAAGU/GGGUG | r6-399: | AAUGC/GGGUU |
| r6-982: | AAAGU/GGGUU | r6-505: | AACGU/GGGUU |
| r6-311: | UAUGU/GGGUU | r6-601: | AAGGU/GGGUU |
| r6-558: | AUUGU/GGGUU | r6-866: | GAUGU/GGGUU |

Covariations and differences from the parent SI sequence of Aptamer 8 aredenoted by bold letter; mispairings are denoted by underline.

All unique variations identified in loop L2 from the alignment of the 58 members of the Aptamer 8 family identified in the primary selection are listed in Table 41 and summarized in FIG. 30B, and demonstrate that L2 can be formed using 8 alternative sequence configurations. The consensus sequence for L2 may be 5'-GDGDN-3', where D is A, U, or G; and N is A, U, G, or C. The consensus sequence is shown in the context of the predicted secondary structure in FIG. 30B.

Using the data from this analysis, when loop L1 is 4 nucleotides long, the consensus sequence for the Aptamer 8 family may be: 5'-HNNNNN-GGGD-DDNGN-GDGDN-GGGUK-NNNNNN-3' (SEQ ID NO: 93), where His A, C, or U; N is A, C, G, or U; D is A, G, or U; and K is Gor U; and is shown in the context of the predicted secondary structure in FIG. 30B. When L1 is 5 nucleotides long, the consensus sequence for the Aptamer 8 family may be: 5'-HNNNNN-CGGGA-DDNGN-GDGDN-GGGUK-NNNNNN-3' (SEQ ID NO: 94), where H is A, C, or U; Nis A, C, G, or U; D is A, G, or U; and K is Gor U.

TABLE 41

| Sequence configurations for Aptamer Family 8 L2 | | | |
|---|---|---|---|
| Aptamer 8: | GAGAU | r6-825: | GAGA**G** |
| r6-98: | GAGA**A** | r6-541: | G**G**GAU |
| r6-530: | GAGA**C** | r6-703: | GAG**U**U |
| r6-503: | GAG**G**U | r6-562: | G**U**GAU |

Differences from the parent L2 sequence of Aptamer 8 are denoted by bold letter.

Example 24. Degenerate Selection of Aptamer Family 8 IL8 Inhibiting Aptamers

To further define the secondary structure of the active aptamers, as well as to potentially identify IL8 aptamers with increased potency, secondary selections were performed utilizing partially randomized libraries consisting of 70% of the parental sequence+10% of the other 3 nucleotides at each position within the aptamer, flanked by the 5' and 3' constant regions. Five rounds of selection against IL8 were conducted using this library. The progress of the selection was monitored by flow cytometry to ensure the enrichment for function (data not shown). Libraries from Round 1 through Round 5 were barcoded, pooled, and sequenced on a Miniseq high throughput sequencer (Illumina), which yielded approximately 200,000 sequences per round. Sequences were trimmed to remove constant regions from the 5' and 3' ends, leaving the core 34 nucleotide region from the library with the built-in U spacer on either end. Identical sequences were de-duplicated to form "stacks" of identical sequences. The resultant stacks were then rank ordered based on the total number of sequences within each stack. To a first approximation, the number of times a sequence occurs in a stack directly correlates with molecular function; more functional molecules typically occur more times. Thus, the rank order of each stack can be thought of as a proxy for fitness.

Alignment of the top 250 stacks for Aptamer 8, which contained ~135,000 sequences and corresponded to the top performing ~70% of the selected population from Round 5 of the secondary selections revealed a significant level of conservation in the identity of each nucleotide within the aptamer family. Most positions displayed conservation levels >90% (FIG. 31), whilst several positions proved to be invariant (conservation=100%). Close examination of these stacks strongly supported the predicted stem loop secondary structures for the two aptamers.

Example 25 Sequence Analysis for Degenerate Selection of Aptamer 8 Family

A comparison of the top 250 sequences revealed that the enriched sequences readily adopted a structure consistent with that reported in FIG. 30A and FIG. 30B for the Aptamer 8 family. The common stem-loop structure may be comprised of (in a 5' to 3' direction), a first stem (S1), a first loop (L1), a second stem (S2), and a second loop (L2). As demonstrated in FIG. 30A and FIG. 30B, the first loop (L1) may be connected to the 3' terminal end of the first stem (S1) and the 5' terminal end of the second stem (S2). The second stem (S2) may be connected to the 3' terminal end of the first loop (L1) and the 5' terminal end of the second loop (L2). The second loop (L2) may be connected to the 3' terminal end of the second stem (S2) and the 5' terminal end of the complementary region of the second stem (S2). The complementary region of the second stem (S2) may be connected to the 3' terminal end of the second loop (L2) and the 5' terminal end of the complementary region of the first stem (S1). The complementary region of the first stem (S1) may be connected to the 3' terminal end of the complementary region of the second stem (S2).

Figure 33:
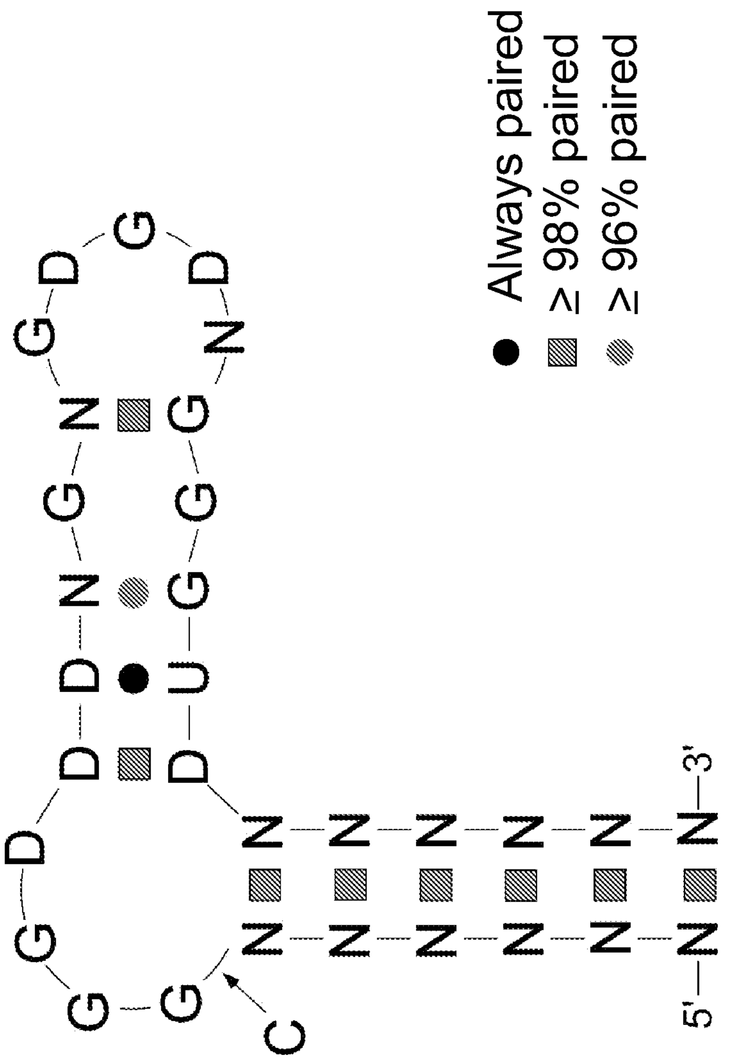
FIG. 33 depicts a representation of an anti-IL8 aptamer secondary structure (SEQ ID NO: 1242) with a consensus sequence compiled from all sequences observed during the primary and secondary selections. The percent base pairing was not determined.

A comparison of sequences observed in stem S1 revealed that this stem can be formed using 40 alternative sequence pairing configurations, may be 5 or 6 nucleotides in length, may not be highly conserved in sequence identity, and may contain at least one mismatch (Table 42). When S1 is 6 base pairs long, the consensus sequence may be 5'-NDNNNH-3' for the 5' side of the stem, and 5'-RNNNHN-3' for the 3' complementary side of the stem, where N is A, U, G, or C; D is A, U, or G; H is A, U, or C; and R is A or G. The 6 base pair consensus is shown in the context of the predicted secondary structure in FIG. 32. When S1 is 5 base pairs long, the consensus sequence may be 5'-ACGGY-3' for the 5' side of the stem, and 5'-GCCGU-3' for the 3' complementary side of the stem, where Y is U or C. When combined with the data from the primary selection (Example 23), these data expand the observed consensus sequences. When S1 is 6 base pairs long, the consensus sequence may be 5'-NNNNNN-3' for the 5' side of the stem, and 5'-NNNNNN-3' for the 3' complementary side of the stem, where Nis A, U, G, or C. The combined consensus is shown in the context of the predicted secondary structure in FIG. 33. When S1 is 5 base pairs long, the consensus sequence may be 5'-DSVVB-3' for the 5' side of the stem, and 5'-BBBSW-3' for the 3' complementary side of the stem, where D is A, U or G; S is G or C; V is A, G, or C; B is G, C, or U; and W is A or U.

TABLE 42

| Sequence variation observed in the degenerate selection of S1 of Aptamer Family 8 | |
|---|---|
| | S1 S1 |
| Aptamer 8- | **UACGGU/GCCGUA** |
| Consensus: | NDNNNH/RNNNHN |
| R5-1 | UACGGU/GCCGUA |
| R5-7 | UACG**A**U/G**U**CGUA |
| R5-13 | UACGG**C**/GCCGUA |
| R5-16 | U**G**CGGU/GCCG**C**A |
| R5-18 | UACG**C**U/G**G**CGUA |

TABLE 42-continued

| Sequence variation observed in the degenerate selection of S1 of Aptamer Family 8 | |
|---|---|
| | S1 S1 |
| R5-19 | UACGGU/ACCGUA |
| R5-20 | UACGGU/GCCGUG |
| R5-22 | CACGGU/GCCGUG |
| R5-25 | UGCGGU/GCCGUA |
| R5-33 | UACUGU/GCAGUA |
| R5-34 | GACGGU/GCCGUC |
| R5-36 | ACGGU/GCCGU |
| R5-42 | UACGUU/GACGUA |
| R5-43 | UUCGGU/GCCGUA |
| R5-54 | UACGAU/AUCGUA |
| R5-61 | UUCGGU/GCCGAA |
| R5-76: | UACAGU/GCUGUA |
| R5-79 | UGCGAU/GUCGCA |
| R5-90 | UACGAU/GCCGUA |
| R5-111 | UAAGGU/GCCUUA |
| R5-126 | UACGGU/GCCGCA |
| R5-131 | UACCGU/GCGGUA |
| R5-135 | UACGGU/GUCGUA |
| R5-137 | UACGGC/GUCGUA |
| R5-160 | UACGGC/GCCGUG |
| R5-163 | UAUGGU/GCCAUA |
| R5-164 | AACGGU/GCCGUU |
| R5-168 | ACGGC/GCCGU |
| R5-193 | CACGAU/GUCGUG |
| R5-206 | UACGUU/AACGUA |
| R5-207 | UGCGGU/GCCGCG |
| R5-208 | UGCGGC/GCCGUA |
| R5-214 | UACGGU/ACCGUG |
| R5-227 | UACGAC/GUCGUA |
| R5-229 | UUCGGC/GCCGUA |
| R5-233 | UGCGGU/ACCGCA |
| R5-246 | UACGGA/GCCGUA |
| R5-220 | UGCGCU/GGCGUA |
| R5-225 | UACGCU/GCCGUA |
| R5-243 | UAGGGU/GCCCUA |
| R5-247 | UGCGUU/GACGCA |

Covariations and differences from the parent S1 sequence of Aptamer 8 are denoted by bold letter; mispairings are denoted by underline.

The identity of loop 1 (L1), which was comprised of the sequence 5'-GGGD-3', where D is A, G, or U, when L1 was 4 nucleotides in length; or was comprised of the sequence 5'-CGGGA-3' when L1 was 5 nucleotides length in the primary selection (Table 37), was found to be four nucleotides in length during the degenerate selection (a likely consequence of library design) and 100% conserved across the top 250 stacks of sequences analyzed in the doped selection (FIG. 31). Thus, the sequence of L1 may be 5'-GGGA-3'.

A comparison of sequences observed in stem S2 from the degenerate selection strongly supported stem formation as indicated by the strong level of co-variation observed in this region (Table 43). Overall, S2 was found to be highly conserved with each position displaying >95% sequence conservation. The mismatch at position 5'-G14-G22-3' was found to be 100% conserved in the stack of top 250 sequences (FIG. 31) indicating that this feature may be critical for target binding. Based on the degenerate selection, stem S2 may be 5 nucleotides long. The consensus sequence for stem S2 may be 5'-RANGN-3' for the 5' side of the stem, and 5'-GGGUD-3' for the 3' complementary side of the stem, where R is A or G; N is A, U, G, or C; and D is A, U, or G. The consensus sequence is shown in the context of the predicted secondary structure in FIG. 32. These data are consistent with the sequence variation observed in the primary selection (Table 40). The combined consensus sequence from the primary and degenerate selections are shown in the context of the secondary structure in FIG. 33.

TABLE 43

| Sequence variation observed in the degenerate selection of S2 of Aptamer family 8 | |
|---|---|
| | S2 S2 |
| Aptamer 8 | AAUGU/GGGUU |
| Consensus: | RANGN/GGGUD |
| R5-1 | AAUGU/GGGUU |
| R5-12 | AAAGU/GGGUU |
| R5-24 | AACGU/GGGUU |
| R5-26 | AAUGC/GGGUU |
| R5-30 | AAUGA/GGGUU |
| R5-35 | AAUGG/GGGUU |
| R5-56 | AAUGU/GGGUG |
| R5-73 | AAGGU/GGGUU |

TABLE 43-continued

| Sequence variation observed in the degenerate selection of S2 of Aptamer family 8 | |
|---|---|
| | S2 S2 |
| R5-138 | **G**AUGU/GGGUU |
| R5-204 | AAUGU/GGGU**A** |

Covariations and differences from the parent S2 sequence of Aptamer 8 are denoted by bold letter; mispairings are denoted by underline.

Most of loop L2, comprising 5'-GAGAU-3', was also found to be ~100% conserved in the top 250 stacks of molecules from the degenerate selection, with only the U20 (numbering per FIG. 31) showing less than 100% conservation (91.8% conserved) (Table 44). The consensus for loop L2 may be 5'-GAGAN-3', where N is A, U, G, or C, and is shown in the context of the secondary structure in FIG. 32. These data are consistent with the sequence variation observed in the primary selection (Table 40). The combined consensus sequence from the primary and degenerate selections are shown in the context of the secondary structure in FIG. 33.

TABLE 44

| Sequence variation observed in the degenerate selection of L2 of Aptamer family 8 | |
|---|---|
| | L2 |
| Aptamer 8 | GAGAU |
| Consensus: | GAGAN |
| R5-1 | GAGAU |
| R5-5 | GAGA**C** |
| R5-10 | GAGA**A** |
| R5-237 | GAGA**G** |

Differences from the parent S2 sequence of Aptamer 8 are denoted by bold letter

Using the data from the degenerate selection, the consensus sequence for the Aptamer 8 family may be: 5'-NDNNNH-GGGA-RANGN-GAGAN-GGGUD-RNNNHN-3' (SEQ ID NO: 1152), where N is A, C, G, or U; D is A, G, or U; H is A, C, or U; and R is A or G; and is shown in the context of the predicted secondary structure in FIG. 32. This figure also depicts the motif variations for each structural element (e.g., S1, L1, S2, L2) observed within the top 250 sequence stacks. Thus, by combining the provided motifs for the respective structural elements of this aptamer family, one can assemble extant or novel Aptamer 8 like variants with anti-IL8 activity.

When the sequence data from the degenerate selection was combined with the sequence data for the Aptamer 8 family members observed during the primary selection (Table 37), the consensus sequence was further broadened to 5'-NNNNNN-GGGD-DDNGN-GDGDN-GGGUD-NNNNNN-3' (SEQ ID NO: 1153), where N is A, C, G, or U; and D is A, G, or U. This sequence is shown in the context of the secondary structure in FIG. 33.

Example 26. Structure Validation and Optimization of Stems by Selective Mutagenesis of Aptamer Family 8

To better understand the sequence requirements and confirm the stem structures of members of the Aptamer 8 family as determined from sequence covariation analysis from both the primary and secondary (degenerate) selections, a series of variants which included mutations and deletions to the predicted stems (Tables 45 and 46) were synthesized and screened. Activity of each of these variants was tested using a competition TR-FRET assay in which the labeled parent Aptamer 8 was competed with increasing concentration of unlabeled variants for binding to IL8 as described in Example 11. Data is summarized in Table 45 and Table 46.

Removing the unpaired 5'-UUUU-3' at the 3' end of the molecule and replacing the 6 base pair sequence of S1 found in Aptamer 8 (5'-UACGGU/GCCGUA-3'), with the 5 base pair sequence 5'-GCGGU/GCCGC-3' (Aptamer 212) or the 4 base pair sequence 5'-CGGU/GCCG-3' (Aptamer 32) did not have a significant effect on the activity (Table 45). Other covaried basepairs within the 4 base pair S1 based on those observed in the degenerate selection were also tested (Table 42). For Aptamer 216, Aptamer 217, and Aptamer 218, the covariation in S1 had negligible effect on binding. Interestingly, in the case of Aptamers 122 and 219, substituting a Watson-Crick basepair for a wobble basepair at the penultimate position within S1 (terminus approaching L1) by mutating U6 to C (Aptamer 122) or G26 to A (Aptamer 219) led to a decrease in activity by ~2.5 fold indicating that the 5'-U6-G26-3' wobble pair is most favored at this position (Table 45). To further confirm the identity of S1, the stem was de-stabilized by mutating 5'-G4-G5-3' to 5'-A-A-3', thereby disrupting the GC pairs (Aptamer 214) which led to a greater than 10-fold loss in activity (Table 45). Overall, these studies provided additional support for the formation of S1. Additionally, these data indicated that S1 can be 6, 5, or 4 base pairs in length. The 4 base pair S1 version (Aptamer 32) was used to carry out further optimization of the Aptamer 8 family.

TABLE 45

| Analysis and optimization of stem 1 of the Aptamer 8 family | | | | |
|---|---|---|---|---|
| SEQ ID NO (+modifications): | Aptamer Number | Sequence (5' to 3') | STEM | TR-FRET Activity |
| 1154 | Aptamer 8 | C6NH2-UACGGU-GGGA-AAUGU-GAGAU-GGGUU-GCCGUA -- UUUU-idT | | parent |
| 1155 | Aptamer 212 | C6NH2-_GCGGU-GGGA-AATGT-GAGAT-GGGTT-GCCGC_--____-idT | S1 | ~ |
| 1156 | Aptamer 32 | C6NH2-__CGGU-GGGA-AAUGU-GAGAU-GGGUU-GCCG__--____-idT | S1 | ~ |

TABLE 45-continued

Analysis and optimization of stem 1 of the Aptamer 8 family

| SEQ ID NO (+modifications): | Aptamer Number | Sequence (5' to 3') | STEM | TR-FRET Activity |
|---|---|---|---|---|
| 1157 | Aptamer 216 | C6NH2-__C**U**GU-GGGA-AAUGU-GAGAU-GGGUU-GC**A**G__--____-idT | S1 | ~ |
| 1158 | Aptamer 217 | C6NH2-__CG**C**U-GGGA-AAUGU-GAGAU-GGGUU-G**G**CG__--____-idT | S1 | ~ |
| 1159 | Aptamer 218 | C6NH2-__CG**A**U-GGGA-AAUGU-GAGAU-GGGUU-G**U**CG__--____-idT | S1 | ~ |
| 1160 | Aptamer 122 | C6NH2-__CGG**C**-GGGA-AAUGU-GAGAU-GGGUU-GCCG__--____-idT | S1 | -- |
| 1161 | Aptamer 219 | C6NH2-__CGGU-GGGA-AAUGU-GAGAU-GGGUU-**A**CCG__--____-idT | S1 | -- |
| 1162 | Aptamer 214 | C6NH2-__C**AA**U-GGGA-AAUGU-GAGAU-GGGUU-GCCG__--____-idT | S1 | --- |

where G is 2'F, and A, C, and U are 2'OMe modified RNA; $C6NH_2$ is a hexylamine linker; idT is an inverted deoxythymidine residue. Bold indicates the position is different from the parent and deletions are indicated by an underline (_). ~ = 2 fold worse to 2 fold better, ++ = 2-10 fold better, +++ = more than 10 fold better, -- = 2-10 fold worse; --- = more than 10 fold worse.

To better understand the identity and requirements for stem S2, covarying basepairs in this stem was tested (Table 46). Consistent with the sequence data observed from the degenerate selection (FIG. 31 and Table 43), most of the mutations in S2 led to significant loss in activity (more than 10 fold) (Table 46), thereby further confirming the high sequence conservation observed in the top 250 stacks of degenerate selection. Surprisingly, while mutating the U13 to C maintained activity (Aptamer 116), so did mutation to an A at this position (Aptamer 61). These data are consistent with the observed variations at position U13 in the top 250 stacks of degenerate selection (FIG. 31) which indicated that it can be an A (3.8%) or a C (1.2%), and suggested that stem S2 can tolerate a second mismatch adjacent to this highly conserved G:G mismatch.

Pairing of the conserved G:G mismatch resulted in >10-fold loss in activity when performed alone (Aptamers 112 and 114) or with other mutations in the stem (Aptamers 119, 120, and 121). An A:G mismatch at this position was also not well tolerated (Aptamer 113). Surprisingly, almost all other substitutions in the stem, even if they maintained pairing consistent with the parent molecule, resulted in significant loss in activity, suggesting a sequence specific dependence on proper folding. Likely, this observation is a consequence of the degenerate library, which was based specifically on the sequence of Aptamer 8.

TABLE 46

Analysis and optimization of stem 2 of the Aptamer 8 family

| SEQ ID NO (+modifications): | Aptamer Number | Sequence (5' to 3') | STEM | TR-FRET Activity |
|---|---|---|---|---|
| 1163 | Aptamer 8 | C6NH2-UACGGU-GGGA-AAUGU-GAGAU-GGGUU-GCCGUA--UUUU -idT | | parent |
| 1164 | Aptamer 32 | C6NH2-__CGGU-GGGA-AAUGU-GAGAU-GGGUU-GCCG__--____-idT | | ~ |
| 1165 | Aptamer 112 | C6NH2-__CGGU-GGGA-AAU**C**U-GAGAU-GGGUU-GCCG__--____-idT | S2 | --- |
| 1166 | Aptamer 113 | C6NH2-__CGGU-GGGA-AAU**A**U-GAGAU-GGGUU-GCCG__--____-idT | S2 | --- |
| 1167 | Aptamer 114 | C6NH2-__CGGU-GGGA-AAU**U**U-GAGAU-GGGUU-GCCG__--____-idT | S2 | --- |
| 1168 | Aptamer 115 | C6NH2-__CGGU-GGGA-AAUG**C**-GAGAU-GGGUU-GCCG__--____-idT | S2 | --- |
| 1169 | Aptamer 116 | C6NH2-__CGGU-GGGA-AA**C**GU-GAGAU-GGGUU-GCCG__--____-idT | S2 | ~ |
| 1170 | Aptamer 61 | C6NH2-__CGGU-GGGA-AA**A**GU-GAGAU-GGGUU-GCCG__--____-idT | S2 | ~ |
| 1171 | Aptamer 117 | C6NH2-__CGGU-GGGA-AA**C**G**C**-GAGAU-GGGUU-GCCG__--____-idT | S2 | --- |
| 1172 | Aptamer 118 | C6NH2-__CGGU-GGGA-**C**A**C**G**C**-GAGAU-GGGU**G**-GCCG__--____-idT | S2 | --- |
| 1173 | Aptamer 119 | C6NH2-__CGGU-GGGA-AA**CC**U-GAGAU-GGGUU-GCCG__--____-idT | S2 | --- |
| 1174 | Aptamer 120 | C6NH2-__CGGU-GGGA-AA**CCC**-GAGAU-GGGUU-GCCG__--____-idT | S2 | --- |

TABLE 46-continued

| Analysis and optimization of stem 2 of the Aptamer 8 family | | | | |
|---|---|---|---|---|
| SEQ ID NO (+modifications): | Aptamer Number | Sequence (5' to 3' ) | STEM | TR-FRET Activity |
| 1175 | Aptamer 121 | C6NH2-__CGGU-GGGA-**C**A**CCC**-GAGAU-GGGU**G**-GCCG__--____-idT | S2 | --- |
| 1176 | Aptamer 154 | C6NH2-__CGGU-GGGA-A**C**UGU-GAGAU-GGG**G**U-GCCG__--____-idT | S2 | --- |
| 1177 | Aptamer 155 | C6NH2-__CGGU-GGGA-A**CC**GU-GAGAU-GGG**G**U-GCCG__--____-idT | S2 | --- |
| 1178 | Aptamer 215 | C6NH2-__CGGU-GGGA-AAUGU-GAGAU-GGG**A**U-GCCG__--____-idT | S2 | --- |

where G is 2'F, and A, C, and U are 2'OMe modified RNA; $C6NH_2$ is a hexylamine linker; idT is an inverted deoxythymidine residue. Bold indicates the position is different from the parent and deletions are indicated by an underline (_).
~ = 2 fold worse to 2 fold better, ++ = 2-10 fold better, +++ = more than 10 fold better, -- = 2-10 fold worse; --- = more than 10 fold worse.

Example 27. Structure Validation and Optimization of Loops by Selective Mutagenesis of Aptamer Family 8

The loop 1 (L1), composed of residues 5'-GGGA-3', proved invariant during the degenerate selections performed on Aptamer family 8 (FIG. 31). To confirm the sequence conservation of this loop, variants of Aptamer 32 were made (4 base pair S1 version of parent Aptamer 8) where each position of L1 was individually replaced with the other 3 bases and tested for binding in the competition TR-FRET assay. Consistent with the 100% conservation of this loop in the degenerate selection, all the L1 mutants showed significant reduction in activity (more than 10-fold) thereby confirming that loop L1 has an invariant sequence of 5'-GGGA-3' (Table 47).

TABLE 47

| Analysis and optimization of loop 1 of the Aptamer 8 family | | | | |
|---|---|---|---|---|
| SEQ ID NO (+modifications): | Aptamer Number | Sequence (5' to 3' ) | Loop | TR-FRET Activity |
| 1179 | Aptamer 8 | C6NH2-UACGGU-GGGA-AAUGU-GAGAU-GGGUU-GCCGUA--UUUU-idT | | parent |
| 1180 | Aptamer 32 | C6NH2-__CGGU-GGGA-AAUGU-GAGAU-GGGUU-GCCG__--____-idT | | ~ |
| 1181 | Aptamer 156 | C6NH2-__CGGU-**C**GGA-AAUGU-GAGAU-GGGUU-GCCG__--____-idT | L1 | --- |
| 1182 | Aptamer 157 | C6NH2-__CGGU-**A**GGA-AAUGU-GAGAU-GGGUU-GCCG__--____-idT | L1 | --- |
| 1183 | Aptamer 158 | C6NH2-__CGGU-**U**GGA-AAUGU-GAGAU-GGGUU-GCCG__--____-idT | L1 | --- |
| 1184 | Aptamer 159 | C6NH2-__CGGU-G**C**GA-AAUGU-GAGAU-GGGUU-GCCG__--____-idT | L1 | --- |
| 1185 | Aptamer 160 | C6NH2-__CGGU-G**A**GA-AAUGU-GAGAU-GGGUU-GCCG__--____-idT | L1 | --- |
| 1186 | Aptamer 161 | C6NH2-__CGGU-G**U**GA-AAUGU-GAGAU-GGGUU-GCCG__--____-idT | L1 | --- |
| 1187 | Aptamer 162 | C6NH2-__CGGU-GG**C**A-AAUGU-GAGAU-GGGUU-GCCG__--____-idT | L1 | --- |
| 1188 | Aptamer 163 | C6NH2-__CGGU-GG**A**A-AAUGU-GAGAU-GGGUU-GCCG__--____-idT | L1 | --- |
| 1189 | Aptamer 164 | C6NH2-__CGGU-GG**U**A-AAUGU-GAGAU-GGGUU-GCCG__--____-idT | L1 | --- |
| 1190 | Aptamer 165 | C6NH2-__CGGU-GGG**C**-AAUGU-GAGAU-GGGUU-GCCG__--____-idT | L1 | --- |

TABLE 47-continued

| Analysis and optimization of loop 1 of the Aptamer 8 family | | | | |
|---|---|---|---|---|
| SEQ ID NO (+modifications): | Aptamer Number | Sequence (5' to 3' ) | Loop | TR-FRET Activity |
| 1191 | Aptamer 166 | C6NH2-__CGGU-GGG**G**-AAUGU-GAGAU-GGGUU-GCCG__--____-idT | L1 | --- |
| 1192 | Aptamer 167 | C6NH2-__CGGU-GGG**U**-AAUGU-GAGAU-GGGUU-GCCG__--____-idT | L1 | --- |

where G is 2'F; and A, C, and U are 2'OMe modified RNA; $C6NH_2$ is a hexylamine linker; idT is an inverted deoxythymidine residue. Bold indicates the position is different from the parent and deletions are indicated by an underline (_). ~ = 2 fold worse to 2 fold better, ++ = 2-10 fold better, +++ = more than 10 fold better, -- = 2-10 fold worse; --- = more than 10 fold worse.

Like L1, most of L2 was also found to be 100% conserved in the degenerate selection, except residue U20, which was ~92% conserved (FIG. 31). To test sequence requirements of L2, variants of Aptamer 32 were made, where each position of L2 was individually replaced with the other 3 bases and tested for binding in the competition TR-FRET assay. All the L2 variants with mutations in 5'-GAGA-3' (Aptamers 168-179) demonstrated significant losses in activity (more than 10 fold) (Table 48), thereby confirming the 100% conservation of 5'-GAGA-3' residues in L2. Interestingly, replacing the U20 with an A (Aptamer 59) or a C (Aptamer 54) led to only a modest decrease in binding (0-2 fold), thus confirming that this position can tolerate an A or C, as observed in the mutation analysis of the top 250 stacks from the degenerate selection. Overall, these data suggest that L2 may comprise 5 bases with the sequence 5'-GAGAU-3'. In some instances, L2 may comprise the sequence 5'-GAGAH-3', where H is A, C, or U.

TABLE 48

| Analysis and optimization of loop 2 of the Aptamer 8 family | | | | |
|---|---|---|---|---|
| SEQ ID NO (+modifications): | Aptamer Number | Sequence (5' to 3' ) | Loop | TR-FRET Activity |
| 1193 | Aptamer 8 | C6NH2- UACGGU-GGGA-AAUGU-GAGAU-GGGUU-GCCGUA--UUUU -idT | | parent |
| 1194 | Aptamer 32 | C6NH2-CGGU-GGGA-AAUGU-GAGAU-GGGUU-GCCG__--____-idT | | ~ |
| 1195 | Aptamer 168 | C6NH2-CGGU-GGGA-AAUGU-**C**AGAU-GGGUU-GCCG__--____-idT | L2 | --- |
| 1196 | Aptamer 169 | C6NH2-CGGU-GGGA-AAUGU-**A**AGAU-GGGUU-GCCG__--____-idT | L2 | --- |
| 1197 | Aptamer 170 | C6NH2-CGGU-GGGA-AAUGU-**U**AGAU-GGGUU-GCCG__--____-idT | L2 | --- |
| 1198 | Aptamer 171 | C6NH2-CGGU-GGGA-AAUGU-G**C**GAU-GGGUU-GCCG__--____-idT | L2 | --- |
| 1199 | Aptamer 172 | C6NH2-CGGU-GGGA-AAUGU-G**G**GAU-GGGUU-GCCG__--____-idT | L2 | --- |
| 1200 | Aptamer 173 | C6NH2-CGGU-GGGA-AAUGU-G**U**GAU-GGGUU-GCCG__--____-idT | L2 | --- |
| 1201 | Aptamer 174 | C6NH2-CGGU-GGGA-AAUGU-GA**C**AU-GGGUU-GCCG__--____-idT | L2 | --- |
| 1202 | Aptamer 175 | C6NH2-CGGU-GGGA-AAUGU-GA**A**AU-GGGUU-GCCG__--____-idT | L2 | --- |
| 1203 | Aptamer 176 | C6NH2-CGGU-GGGA-AAUGU-GA**U**AU-GGGUU-GCCG__--____-idT | L2 | --- |
| 1204 | Aptamer 177 | C6NH2-CGGU-GGGA-AAUGU-GAG**C**U-GGGUU-__--____-idT | L2 | --- |
| 1205 | Aptamer 178 | C6NH2-CGGU-GGGA-AAUGU-GAG**G**U-GGGUU-GCCG__--____-idT | L2 | --- |
| 1206 | Aptamer 179 | C6NH2-CGGU-GGGA-AAUGU-GAG**U**U-GGGUU-GCCG__--____-idT | L2 | --- |

TABLE 48-continued

Analysis and optimization of loop 2 of the Aptamer 8 family

| SEQ ID NO (+modifications): | Aptamer Number | Sequence (5' to 3' ) | Loop | TR-FRET Activity |
|---|---|---|---|---|
| 1207 | Aptamer 180 | C6NH2-CGGU-GGGA-AAUGU-GAGA**G**-GGGUU-GCCG__--____-idT | L2 | --- |
| 1208 | Aptamer 54 | C6NH2-CGGU-GGGA-AAUGU-GAGA**C**-GGGUU-GCCG__--____-idT | L2 | ~ |
| 1209 | Aptamer 59 | C6NH2-CGGU-GGGA-AAUGU-GAGA**A**-GGGUU-GCCG__--____-idT | L2 | ~ |

where G is 2'F, and A, C, and U are 2'OMe modified RNA; $C6NH_2$ is a hexylamine linker; idT is an inverted deoxythymidine residue. Bold indicates the position is different from the parent.
~ = 2 fold worse to 2 fold better, ++ = 2-10 fold better, +++ = more than 10 fold better, -- = 2-10 fold worse; --- = more than 10 fold worse.

Example 28. Optimization of Aptamer Family 8 by 2'OMe Sugar Substitutions

2'OMe modifications may impart higher duplex stability, increased metabolic stability in serum and vitreous, and may have greater coupling efficiency during synthesis compared to 2'F-containing nucleotides. The use of these nucleotides may also avoid the potential loss of the 2'F group during production, which can happen during deprotection steps and exposure to heat. To probe the effect of 2'F-G to 2'OMe-G substitution on target binding, variants of Aptamer 116 and 212 were synthesized where 2'F-G was selectively substituted with 2'OMe-G (Table 49) and assayed for activity by competition TR-FRET using ALEXA FLUOR® 647-labeled parent Aptamer 212. 2'OMe-G replacements were well tolerated in all positions of stem S1 (Aptamers 242-248). However, replacement of positions outside of stem S1 resulted in a significant loss in activity (>10-fold).

TABLE 49

2'OMe sugar substitutions

| SEQ ID NO (+modifications): | Aptamer Number | Sequence (5' to 3' ) | TR-FRET Activity |
|---|---|---|---|
| 1210 | Aptamer 212 | C6NH2-GCGGU-GGGA-AATGT-GAGAT-GGGTT-GCCGC-idT | parent |
| 1211 | Aptamer 242 | C6NH2-**X**CGGU-GGGA-AAUGU-GAGAU-GGGUU-GCCGC-idT | ~ |
| 1212 | Aptamer 243 | C6NH2-GC**X**GU-GGGA-AAUGU-GAGAU-GGGUU-GCCGC-idT | ~ |
| 1213 | Aptamer 244 | C6NH2-GCG**X**U-GGGA-AAUGU-GAGAU-GGGUU-GCCGC-idT | ~ |
| 1214 | Aptamer 245 | C6NH2-GCGGU-GGGA-AAUGU-GAGAU-GGGUU-GCC**X**C-idT | ~ |
| 1215 | Aptamer 246 | C6NH2-GCGGU-GGGA-AAUGU-GAGAU-GGGUU-**X**CCGC-idT | ~ |
| 1216 | Aptamer 247 | C6NH2-**X**C**XX**U-GGGA-AAUGU-GAGAU-GGGUU-GCC**X**C-idT | + |
| 1217 | Aptamer 248 | C6NH2-**X**C**XX**U-GGGA-AAUGU-GAGAU-GGGUU-**X**CC**X**C-idT | ~ |
| 1218 | Aptamer 249 | C6NH2-GCGGU-GGGA-AAU**X**U-GAGAU-GGGUU-GCCGC-idT | --- |
| 1219 | Aptamer 250 | C6NH2-GCGGU-GGGA-AAUGU-GAGAU-**X**GGUU-GCCGC-idT | --- |
| 1220 | Aptamer 251 | C6NH2-GCGGU-GGGA-AAUGU-GAGAU-G**X**GUU-GCCGC-idT | --- |
| 1221 | Aptamer 252 | C6NH2-GCGGU-GGGA-AAUGU-GAGAU-GG**X**UU-GCCGC-idT | --- |
| 1222 | Aptamer 253 | C6NH2-GCGGU-GGGA-AAU**X**U-GAGAU-G**X**GUU-GCCGC-idT | --- |
| 1223 | Aptamer 254 | C6NH2-GCGGU-GGGA-AAU**X**U-GAGAU-G**XX**UU-GCCGC-idT | --- |
| 1224 | Aptamer 255 | C6NH2-GCGGU-GGGA-AAU**X**U-GAGAU-**XXX**UU-GCCGC-idT | --- |
| 1225 | Aptamer 256 | C6NH2-**X**C**XX**U-GGGA-AAUGU-GAGAU-G**XX**UU-GCC**X**C-idT | --- |
| 1226 | Aptamer 257 | C6NH2-**X**C**XX**U-GGGA-AAUGU-GAGAU-**XXX**UU-GCC**X**C-idT | --- |
| 1227 | Aptamer 258 | C6NH2-**X**C**XX**U-GGGA-AAUGU-GAGAU-G**XX**UU-**X**CC**X**C-idT | --- |
| 1228 | Aptamer 259 | C6NH2-**X**C**XX**U-GGGA-AAUGU-GAGAU-**XXX**UU-**X**CC**X**C-idT | --- |
| 1229 | Aptamer 260 | C6NH2-GCGGU-**X**GGA-AAUGU-GAGAU-GGGUU-GCCGC-idT | --- |
| 1230 | Aptamer 261 | C6NH2-GCGGU-G**X**GA-AAUGU-GAGAU-GGGUU-GCCGC-idT | --- |

TABLE 49-continued

| 2'OMe sugar substitutions | | | |
|---|---|---|---|
| SEQ ID NO (+modifications): | Aptamer Number | Sequence (5' to 3' ) | TR-FRET Activity |
| 1231 | Aptamer 262 | C6NH2-GCGGU-GG**X**A-AAUGU-GAGAU-GGGUU-GCCGC-idT | --- |
| 1232 | Aptamer 263 | C6NH2-GCGGU-GGGA-AAUGU-**X**AGAU-GGGUU-GCCGC-idT | --- |
| 1233 | Aptamer 264 | C6NH2-GCGGU-GGGA-AAUGU-GA**X**AU-GGGUU-GCCGC-idT | --- |
| 1234 | Aptamer 265 | C6NH2-CGGU-GGGA-AAC**X**U-GAGAU-GGGUU-GCCG-idT | --- |
| 1235 | Aptamer 266 | C6NH2-CGGU-GGGA-AACGU-GAGAU-GG**X**UU-GCCG-idT | --- |
| 1236 | Aptamer 267 | C6NH2-CGGU-GGGA-AACGU-GAGAU-G**X**GUU-GCCG-idT | --- |
| 1237 | Aptamer 268 | C6NH2-CGGU-GGGA-AACGU-GAGAU-**X**GGUU-GCCG-idT | --- |

where G is 2'F, and A, C, and U are 2'OMe modified RNA; X is 2'OMe-G; C6NH2 is a hexylamine linker, idT is an inverted deoxythymidine residue. Bold indicates the position is different from the parent. ~ = 2 fold worse to 2 fold better, ++ = 2-10 fold better, +++ = more than 10 fold better, -- = 2-10 fold worse; --- = more than 10 fold worse.

Example 29. Inhibition of IL8-Mediated Neutrophil Migration Using Improved Aptamer 8 Variants The neutrophil migration assays described in Examples 6 and 18 were used to confirm the activity of Aptamers 8, 212, and 248. Assays were performed as described in those examples. $IC_{50}$ values are shown in Table 50. In all cases, the reported potencies were limited by the protein concentration (3 nM) used in the assay.

TABLE 50

| $IC_{50}$ values of anti-IL8 aptamers of Aptamer 8 variants tested in a neutrophil migration assay | |
|---|---|
| Aptamer Number | $IC_{50}$ (nM) |
| Aptamer 8 | 2 |
| Aptamer 212 | 1 |
| Aptamer 248 | 2 |

Figure 34:
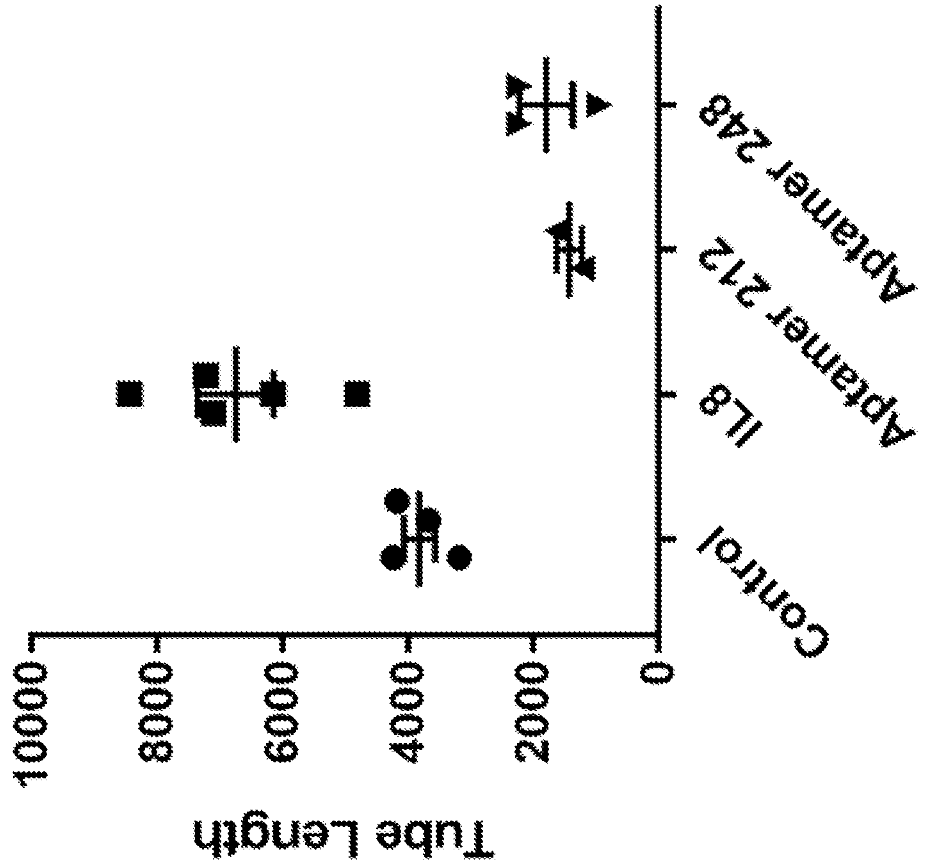
FIG. 34 depicts a non-limiting example of data demonstrating the ability of various aptamers of the disclosure to inhibit IL8-induced tube formation by human microvascular endothelial cells according to embodiments of the disclosure.

Example 30. Inhibition of IL8-Induced Tube Formation Using Aptamer 8 Variants The IL8-induced tube formation assay using HMEC cells described in Example 19 was used to confirm the activity of Aptamers 212 and 248. At 10 nM, the aptamers effectively blocked IL8 induced tube formation (FIG. 34).

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

We claim:

1. An aptamer that binds to and inhibits Interleukin-8 (IL8), comprising a secondary structure comprising at least one terminal loop comprising greater than three nucleotides, wherein said terminal loop selectively binds to an epitope of IL8, wherein said epitope is not a GAG-binding site and wherein the aptamer comprises a consensus nucleic acid sequence of 5'-NNYVANDDNWGWDDNNRG-KNNGHGUGNHHNVRNN-3' (SEQ ID NO:92), where N is A, C, G, or U; Y is Cor U; Vis A, C, or G; D is A, G, or U; W is A or U; R is A or G; K is G or U; and H is A, C, or U.

2. The aptamer of claim 1, wherein said secondary structure further comprises in a 5' to 3' direction: (i) a first base paired stem; (ii) a first loop; (iii) a second base paired stem; and (iv) a second loop.

3. The aptamer of claim 1, wherein said secondary structure comprises in a 5' to 3' direction: (i) a first base paired stem; (ii) a first loop; (iii) a second base paired stem; (iv) a second loop; (v) a third base paired stem; (vi) a third loop; and (vii) a fourth loop.

4. The aptamer of claim 3, wherein said first loop comprises a nucleic acid sequence of 5'-A-3'.

5. The aptamer of claim 3, wherein said second loop comprises a nucleic acid sequence of 5'-AG-3'.

6. The aptamer of claim 3, wherein said fourth loop comprises a nucleic acid sequence of 5'-G-3'.

7. The aptamer of claim 1, wherein said terminal loop comprises a nucleic acid sequence that selectively binds to a N-terminal domain of Interleukin-8 (IL8), a hydrophobic pocket of IL8, a N-loop of IL8, or any combination thereof.

8. The aptamer of claim 1, wherein said aptamer comprises RNA, modified RNA or a combination thereof.

9. The aptamer of claim 1, wherein said aptamer comprises one or more modified nucleotides.

10. The aptamer of claim 1, wherein said aptamer comprises a nuclease-stabilized nucleic acid backbone.

11. The aptamer of claim 1, wherein said aptamer is conjugated to a polyethylene glycol (PEG) molecule.

* * * * *